US011826351B2

(12) United States Patent
Guisot

(10) Patent No.: US 11,826,351 B2
(45) Date of Patent: *Nov. 28, 2023

(54) COMPOUNDS USEFUL AS KINASE INHIBITORS

(71) Applicant: Loxo Oncology, Inc., Indianapolis, IN (US)

(72) Inventor: Nicolas Guisot, Cheshire (GB)

(73) Assignee: Loxo Oncology Inc., Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/525,350

(22) Filed: Nov. 12, 2021

(65) Prior Publication Data

US 2022/0062239 A1 Mar. 3, 2022

Related U.S. Application Data

(63) Continuation of application No. 17/122,103, filed on Dec. 15, 2020, now Pat. No. 11,471,441, which is a continuation of application No. 15/930,657, filed on May 13, 2020, now Pat. No. 10,918,622, which is a continuation of application No. 16/063,542, filed as application No. PCT/GB2016/053968 on Dec. 16, 2016, now Pat. No. 10,695,323.

(30) Foreign Application Priority Data

Dec. 16, 2015 (GB) .................................... 1522245
Aug. 15, 2016 (GB) .................................... 1613945

(51) Int. Cl.
| | |
|---|---|
| A61K 31/415 | (2006.01) |
| C07D 405/14 | (2006.01) |
| C07D 231/14 | (2006.01) |
| C07D 401/04 | (2006.01) |
| C07D 401/06 | (2006.01) |
| C07D 403/04 | (2006.01) |
| C07D 405/04 | (2006.01) |
| C07D 405/08 | (2006.01) |
| C07D 413/06 | (2006.01) |
| A61K 45/06 | (2006.01) |
| C07D 405/06 | (2006.01) |
| A61P 37/02 | (2006.01) |
| A61P 35/02 | (2006.01) |
| C07D 231/38 | (2006.01) |
| A61P 35/00 | (2006.01) |
| A61K 31/4155 | (2006.01) |
| C07D 417/04 | (2006.01) |

(52) U.S. Cl.
CPC ........ *A61K 31/415* (2013.01); *A61K 31/4155* (2013.01); *A61K 45/06* (2013.01); *A61P 35/00* (2018.01); *A61P 35/02* (2018.01); *A61P 37/02* (2018.01); *C07D 231/14* (2013.01); *C07D 231/38* (2013.01); *C07D 401/04* (2013.01); *C07D 401/06* (2013.01); *C07D 403/04* (2013.01); *C07D 405/04* (2013.01); *C07D 405/06* (2013.01); *C07D 405/08* (2013.01); *C07D 405/14* (2013.01); *C07D 413/06* (2013.01); *C07D 417/04* (2013.01)

(58) Field of Classification Search
CPC ...... A61K 31/415; C07D 231/14; A61P 35/00
See application file for complete search history.

(56) References Cited

U.S. PATENT DOCUMENTS

| | | |
|---|---|---|
| 6,660,744 B1 | 12/2003 | Hirst et al. |
| 7,718,662 B1 | 5/2010 | Chen et al. |
| 8,673,925 B1 | 3/2014 | Goldstein |
| 9,090,621 B2 | 7/2015 | Goldstein |
| 9,975,897 B2 | 5/2018 | Calder et al. |
| 2002/0156081 A1 | 10/2002 | Hirst et al. |
| 2003/0225098 A1 | 12/2003 | Hirst et al. |
| 2008/0076921 A1 | 3/2008 | Honiberg et al. |
| 2010/0144705 A1 | 6/2010 | Miller |
| 2010/0254905 A1 | 10/2010 | Honiberg et al. |
| 2011/0144068 A1 | 6/2011 | Pulici et al. |
| 2014/0221333 A1 | 8/2014 | De Man et al. |
| 2017/0129897 A1 | 5/2017 | Calder et al. |
| 2018/0298008 A1 | 10/2018 | Guisot |
| 2018/0362512 A1 | 12/2018 | Guisot |
| 2018/0362533 A1 | 12/2018 | Guisot |
| 2018/0362537 A1 | 12/2018 | Guisot |
| 2019/0000806 A1 | 1/2019 | Guisot |

(Continued)

FOREIGN PATENT DOCUMENTS

| | | |
|---|---|---|
| CN | 102159214 | 8/2011 |
| CN | 105085474 | 11/2015 |
| EP | 2548877 | 1/2013 |

(Continued)

OTHER PUBLICATIONS

Buggy et al., "Bruton Tyrosine Kinase (BTK) and Its Role in B-cell Malignancy," International Reviews of Immunology, Mar. 21, 2012, 31(2):119-132.

(Continued)

*Primary Examiner* — Kamal A Saeed
(74) *Attorney, Agent, or Firm* — Tina M Tyson

(57) ABSTRACT

This invention relates to novel compounds. The compounds of the invention are tyrosine kinase inhibitors. Specifically, the compounds of the invention are useful as inhibitors of Bruton's tyrosine kinase (BTK). The invention also contemplates the use of the compounds for treating conditions treatable by the inhibition of Bruton's tyrosine kinase, for example cancer, lymphoma, leukemia and immunological diseases.

27 Claims, No Drawings

(56) References Cited

U.S. PATENT DOCUMENTS

2019/0119281 A1    4/2019    Calder et al.

FOREIGN PATENT DOCUMENTS

| WO | 0119829 | 3/2001 |
|---|---|---|
| WO | 02080926 | 10/2002 |
| WO | 2008/039218 | 4/2008 |
| WO | 2008/054827 | 5/2008 |
| WO | 2008/121742 | 10/2008 |
| WO | 2009/158571 | 12/2009 |
| WO | 2011/046964 | 4/2011 |
| WO | 2011/090760 | 7/2011 |
| WO | 2011/153514 | 12/2011 |
| WO | 2012/158764 | 11/2012 |
| WO | 2012/158843 | 11/2012 |
| WO | 2013/010136 | 1/2013 |
| WO | 2013/102059 | 7/2013 |
| WO | 2013/191965 | 12/2013 |
| WO | 2014/022569 | 2/2014 |
| WO | 2014/025976 A1 | 2/2014 |
| WO | 2014/068527 | 5/2014 |
| WO | 2014/082598 | 11/2014 |
| WO | 2014/188173 | 4/2015 |
| WO | 2015/048662 | 4/2015 |
| WO | 2015/095099 | 6/2015 |
| WO | 2015/127310 | 8/2015 |
| WO | 2015/140566 | 9/2015 |
| WO | 2015/189620 | 12/2015 |
| WO | 2017/046255 | 3/2017 |
| WO | 2017/046258 | 3/2017 |
| WO | 2017/046604 | 3/2017 |
| WO | 2017/100856 | 6/2017 |
| WO | 2017/103611 | 6/2017 |
| WO | 2017/106396 | 6/2017 |
| WO | 2017/106429 | 6/2017 |
| WO | 2017/106623 | 6/2017 |
| WO | 2016/120196 | 8/2019 |

OTHER PUBLICATIONS

Dubovsky et al., "Ibrutinib is an irreversible molecular inhibitor of ITK driving a Th1-selective gressure in T lymphocytes," Blood, Oct. 10, 2013, 122(15):2539-2549.

Haleblian, "Characterization of habits and crystalline modification of solids and their pharmaceutical applications," J Pharm Sci, Aug. 1975, 64(8):1269-1288.

International Preliminary Report on Patentability in International Application No. PCT/GB2016/053968, dated Jun. 28, 2018, 9 pages.

International Search Report in International Application No. PCT/GB2016/053968, dated Mar. 14, 2017, 13 pages.

Kohrt et al., "Ibrutinib antagonizes rituximab-dependent NK cell-mediated cytotoxicity," Blood, Mar. 20, 2014, 123(12):1957-1960.

Maddocks et al., "Etiology of Ibrutinib Therapy Discontinuation and Outcomes in Patients With Chronic Lymphocytic Leukemia," JAMA Oncol., Apr. 2015, 1(1):80-87.

Whang et al., "Bruton's tyrosine kinase inhibitors for the treatment of rheumatoid arthritis," Drug DiscovToday., Aug. 2014, 19(8): 1200-1204.

Woyach et al., "Resistance mechanisms for the Bruton's tyrosine kinase inhibitor ibrutinib," N Engl J Med, Jun. 12, 2014, 370(24):2286-2294.

Zapf et al. "Covalent Inhibitors of Interleukin-2 Inducible T Cell Kinase (Itk) with Nanomolar Potency in a Whole-Blood Assay ," J. Med. Chem., Nov. 2012, 55(22):10047-10063.

Zhang et al., "Mechanisms of ibrutinib resistance in chronic lymphocytic leukaemia and non-Hodgkin lymphoma," Br J Haematol, Aug. 2015, 170(4):445-456.

Mak, Tak W., and Mary E. Saunders: Excerpt from The Immune Response: Basic and Clinical Principles. Academic Press, 1st Edition, Chapter 30: Hematopoietic Cancers, p. 1058 (2006).

COMPOUNDS USEFUL AS KINASE INHIBITORS

This application is a continuation of U.S. application Ser. No. 17/122,103 filed on Dec. 15, 2020, which is a continuation of U.S. application Ser. No. 15/930,657 filed on May 13, 2020, which is a continuation of U.S. application Ser. No. 16/063,542 filed on Jun. 18, 2018, which is a National Stage application under 35 U.S.C. § 371 of International Application No. PCT/GB2016/053968, filed Dec. 16, 2016, which claims the benefit of priority to GB 1613945.3, filed Aug. 15, 2016 and GB 1522245.8, filed Dec. 16, 2015.

This invention relates to compounds. More specifically, the invention relates to compounds useful as kinase inhibitors, along with processes to prepare the compounds and uses of the compounds. Specifically, the invention relates to inhibitors of Bruton's tyrosine kinase (BTK).

BACKGROUND

Kinases are a class of enzyme that control the transfer of phosphate groups from phosphate donor groups, for example ATP, to specific substrates. Protein kinases are a large subset of kinases that play a central role in the regulation of a wide variety of cellular signalling and processes and BTK is one such protein kinase.

BTK is a member of the src-related Tec family of cytoplasmic tyrosine kinases. BTK plays a key role in the B-cell receptor (BCR) signalling pathway of B-cells, which is required for the development, activation and survival of B-cells. BTK inhibitors have therefore been developed with the aim of treating B-cell malignancies that are dependent on BCR signalling, such as chronic lymphocytic leukemia (CLL) and non-Hodgkin's lymphoma (NHL) (Buggy 2012). BTK is also expressed in specific myeloid cells including, monocytes/macrophages, neutrophils and mast cells. In these myeloid cells, BTK has been indicated in the immune complex mediated activation of FcγR and FcεR, which is believed to contribute to the pathogenesis of rheumatoid arthritis (RA) (Whang 2014). In addition, BTK is required for the maturation of osteoclast cells and so inhibiting BTK could prevent the bone erosion that is associated with RA. The critical role of BTK in both B-cells and myeloid cells has led to BTK becoming an attractive target for the treatment of not only B-cell malignancies but also for the treatment of autoimmune diseases.

Ibrutinib is an irreversible BTK inhibitor that has been approved for the treatment of CLL, mantle cell lymphoma (MCL) and Waldenstrom's macroglobulinemia (WM). Since ibrutinib was first disclosed there have been a number of patent applications concerned with structures closely related to ibrutinib, for example see WO 2012/158843, WO 2012/158764, WO 2011/153514, WO 2011/046964, US 2010/0254905, US 2010/0144705, U.S. Pat. No. 7,718,662, WO, 2008/054827 and WO 2008/121742.

Further BTK inhibitors are disclosed in WO 2013/010136, U.S. Pat. No. 9,090,621, WO 2015/127310, WO 2015/095099 and US 2014/221333. Kinase inhibitors are also disclosed in U.S. Pat. No. 6,660,744, US 2002/0156081, US 2003/0225098 and WO 01/19829.

Ibrutinib also irreversibly binds to interleukin-2 inducible tyrosine kinase (ITK) (Dubovsky 2013). ITK plays a critical role in FcR-stimulated natural killer (NK) cell function that is required for antibody dependent NK cell mediated cytotoxicity (ADCC). ADCC is the mechanism that anti-CD20 antibodies, such as rituximab are believed to activate and ibrutinib has been shown to antagonise this mechanism in vitro (Kohrt 2014). As rituximab-combination chemotherapy is today's standard of care in B-cell malignancies, it would be desirable to have a BTK inhibitor with high selectivity for BTK over ITK.

In the clinic, adverse events have included atrial fibrillation, diarrhea, rash, arthralgia and bleeding (IMBRUVICA package insert 2014). Known BTK inhibitors, e.g. ibrutinib are also known to have gastrointestinal side effects, which are considered to be as a result of a secondary EGFR inhibitory activity. It is therefore desirable to have a BTK inhibitor with high BTK inhibition and low EGFR inhibition to reduce or avoid the gastrointestinal side effects.

Irreversible and covalent reversible BTK inhibitors specifically target a cysteine residue C481 within BTK. Following treatment with ibrutinib, cases of primary and secondary resistance have emerged. Mutations within BTK such as C481S, C481Y, C481R, C481F have been reported in the literature and clearly interfere with drug binding (Woyach 2014; Maddocks 2015). It has been predicted that the incidence of observed resistance will increase as clinical use outside clinical trials expands over time (Zhang 2015).

Therefore, an aim of the present invention is to provide BTK inhibitors with a different binding mode more specifically reversible inhibitors. In addition, the invention aims to provide BTK inhibitors with high selectivity for BTK inhibition over EGFR and ITK inhibition.

Furthermore, it is an aim of certain embodiments of this invention to provide new cancer treatments. In particular, it is an aim of certain embodiments of this invention to provide compounds which have comparable activity to existing cancer treatments but are also effective against mutations. One of the aspects of the invention focuses on providing BTK inhibitors effective against the C481 mutations.

It is an aim of certain embodiments of this invention to provide compounds which exhibit reduced cytotoxicity relative to prior art compounds and existing therapies.

Another aim of certain embodiments of this invention is to provide compounds having a convenient pharmacokinetic profile and a suitable duration of action following dosing. A further aim of certain embodiments of this invention is to provide compounds in which the metabolised fragment or fragments of the drug after absorption are GRAS (Generally Regarded As Safe).

Certain embodiments of the present invention satisfy some or all of the above aims.

BRIEF SUMMARY OF THE DISCLOSURE

In accordance with the present invention there is provided compounds as disclosed below. Furthermore, the invention provides compounds capable of inhibiting Bruton's tyrosine kinase (BTK) and the use of these compounds in inhibiting BTK. In accordance with the invention there is provided a method of treating conditions modulated by BTK. The invention provides compounds for use in treating a condition which is modulated by BTK.

In a first aspect of the invention there is provided a compound according to formula (I) or pharmaceutically acceptable salts thereof:

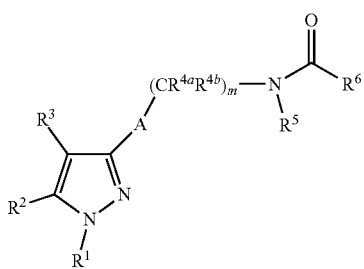

(I)

wherein
A represents a ring selected from unsubstituted or substituted: phenyl, pyridine, pyridazine, pyrimidine, or pyrazine, wherein when substituted A is substituted with from 1 to 4 $R^7$;
$R^1$ represents a group selected from: $C_{1-8}$ alkyl, $C_{1-8}$ haloalkyl, $C_{1-8}$ alkoxy, $C_{2-8}$ alkyl ether, —C(O)$R^A$, $C_{3-10}$ carbocyclic group, 3 to 10 membered heterocyclic group, $C_{1-8}$ alkyl substituted with $C_{3-10}$ carbocyclic group, and $C_{1-8}$ alkyl substituted with 3 to 10 membered heterocyclic group, wherein each of the aforementioned groups are unsubstituted or substituted with 1 to 5 substituents independently selected from: halo, $C_{1-4}$ alkyl, $C_{1-4}$ haloalkyl, $C_{1-4}$ alkoxy, $C_{2-4}$ alkyl ether, —O$R^A$, —N$R^A R^B$, —CN, =O, —OC(O)$R^A$, —C(O)$R^A$, —C(O)O$R^A$, —N$R^A$C(O)$R^B$, —C(O)N$R^A R^B$, —N$R^A$S(O)$_2 R^B$, —S(O)$_2$N$R^A R^B$, benzoyl, a 5 or 6 membered heterocycloaryl, a 3 to 6 membered heterocycloalkyl ring, $C_{1-4}$ alkyl substituted with —O$R^A$ and $C_{1-4}$ alkoxy substituted with —O$R^A$, or a single atom of $R^1$ is substituted twice so as to form a 3 to 6 membered heterocycloalkyl or cycloalkyl ring;
$R^2$ represents a group selected from: —OH, halo, $C_{1-8}$ alkyl, $C_{1-8}$ haloalkyl, $C_{1-8}$ alkoxy, $C_{3-10}$ cycloalkyl, $C_{6-10}$ aryl, 3 to 10 membered heterocyclic group, alkyl substituted with —O$R^C$, $C_{1-8}$ alkyl substituted with $C_{3-10}$ carbocyclic group, alkyl substituted with 3 to 10 membered heterocyclic group, and —N$R^C R^D$;
$R^3$ represents —C(O)N$R^E R^F$, $C_{1-6}$ alkyl substituted with —O$R^G$, or $C_{1-6}$ haloalkyl;
$R^{4a}$ and $R^{4b}$ are independently at each occurrence selected from: H, $C_{1-6}$ alkyl, $C_{1-6}$ haloalkyl, $C_{1-6}$ alkoxy, $C_{3-6}$ cycloalkyl, and $C_{1-6}$ alkyl substituted with —O$R^H$;
$R^5$ is H or $C_{1-4}$ alkyl;
$R^6$ is a group selected from a substituted or unsubstituted: phenyl or a 5 or 6 membered heteroaryl ring, wherein, when substituted, $R^6$ contains from 1 to 5 substituents independently selected at each occurrence from: halo, —O$R^I$, —N$R^I R^J$, —CN, $C_{1-6}$ alkyl, $C_{1-6}$ haloalkyl, and $C_{1-6}$ alkyl substituted with —O$R^I$;
$R^7$ is selected from: H, halo, $C_{1-6}$ alkyl, $C_{1-6}$ haloalkyl, $C_{1-6}$ alkoxy, and $C_{1-6}$ alkyl substituted with —O$R^H$;
m is 1 or 2;
$R^A$ and $R^B$ are, at each occurrence, independently selected from: H, $C_{1-4}$ alkyl, $C_{1-4}$ haloalkyl, $C_{1-4}$ alkoxy, phenyl, benzyl, or $C_{1-4}$ alkyl substituted with —O$R^H$;
$R^C$, $R^D$, $R^E$ and $R^F$ are, at each occurrence, independently selected from: H, $C_{1-4}$ alkyl, $C_{1-4}$ haloalkyl, unsubstituted $C_{3-10}$ carbocyclic group, $C_{1-4}$ alkyl substituted with unsubstituted $C_{3-10}$ carbocyclic group, $C_{1-4}$ alkyl substituted with $C_{3-10}$ carbocyclic group substituted with 1 or 2 $R^H$ or —O$R^H$, and 3 to 10 membered heterocyclic group;
$R^G$, $R^I$, and $R^J$ are independently at each occurrence selected from: H, $C_{1-4}$ alkyl, $C_{1-4}$ haloalkyl, $C_{1-4}$ alkoxy and $C_{1-4}$ alkyl substituted with —O$R^H$; and
$R^H$ is selected from H or $C_{1-4}$ alkyl.

In an embodiment A is unsubstituted phenyl, unsubstituted pyridine, phenyl substituted by from 1 to 4 $R^7$, or pyridine substituted by from 1 to 4 $R^7$.

Preferably, A is unsubstituted phenyl, unsubstituted pyridine, unsubstituted pyridazine, unsubstituted pyrimidine, unsubstituted pyrazine, or phenyl substituted with 1 or 2 $R^7$.

In an embodiment, A is unsubstituted phenyl, unsubstituted pyridine or phenyl substituted with from 1 to 4 $R^7$ (optionally 1 or 2 $R^7$). In an embodiment, A is unsubstituted phenyl or phenyl substituted with from 1 to 4 $R^7$.

As the skilled person will note from the structural formula of formula (I), group "A" is substituted by two groups, shown below (it may also be optionally substituted by from 1 to 4 $R^7$).

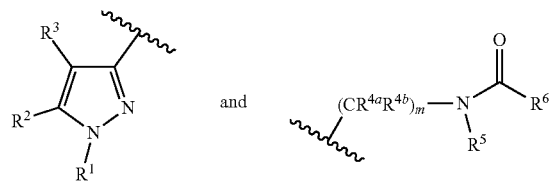

These two groups may be para substituted on A. In other words, the two groups may be 1,4-substituted on A.

In an embodiment, A may be:

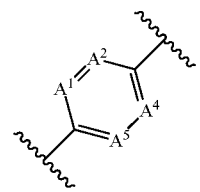

wherein 0, 1 or 2 of $A^1$, $A^2$, $A^4$ and $A^5$ are independently selected from N and the remainder are $CR^7$.

Accordingly, the compounds according to formula (I) may be compounds of formula (II) or pharmaceutically acceptable salts thereof:

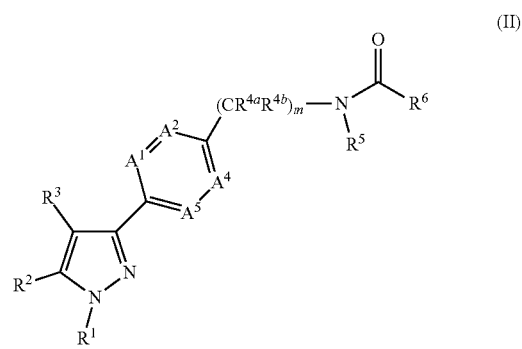

(II)

wherein 0, 1 or 2 of $A^1$, $A^2$, $A^4$ and $A^5$ are independently selected from N and the remainder are $CR^7$.

In embodiments 0 or 1 of $A^1$, $A^2$, $A^4$ and $A^5$ are N, of the remaining $A^1$, $A^2$, $A^4$ and $A^5$ 0 or 1 are $CR^7$ and the remainder are CH.

In embodiments $A^1$, $A^4$ and $A^5$ are CH and $A^2$ is $CR^7$ and $R^7$ is selected from fluoro, methyl, methoxy, or —CH$_2$OH.

In embodiments $A^2$, $A^4$ and $A^5$ are CH and $A^1$ is $CR^7$ and $R^7$ is selected from H, fluoro, methyl, methoxy, or —$CH_2OH$. In embodiments $A^1$, $A^4$ and $A^5$ are CH and $A^2$ is N. In embodiments $A^2$, $A^4$ and $A^5$ are CH and $A^1$ is N. In embodiments $A^1$ and $A^5$ are CH and $A^2$ and $A^4$ are N. In embodiments $A^1$ and $A^5$ are N and $A^2$ and $A^4$ are CH. In embodiments $A^1$ and $A^4$ are CH and $A^2$ and $A^5$ are N. In embodiments $A^1$ and $A^2$ are CH and $A^4$ and $A^5$ are N.

In embodiments $A^1$ and $A^5$ are CH and $A^2$ and $A^4$ are $CR^7$ and $R^7$ is selected from fluoro, methyl, methoxy, or —$CH_2OH$. In embodiments $A^1$ and $A^2$ are CH and $A^4$ and $A^5$ are $CR^7$ and $R^7$ is selected from fluoro, methyl, methoxy, or —$CH_2OH$. In embodiments $A^2$ and $A^4$ are CH and $A^1$ and $A^5$ are $CR^7$ and $R^7$ is selected from fluoro, methyl, methoxy, or —$CH_2OH$. In embodiments $A^1$ and $A^4$ are CH and $A^2$ and $A^5$ are $CR^7$ and $R^7$ is selected from fluoro, methyl, methoxy, or —$CH_2OH$.

Optionally, $R^7$ may be selected from: H, halo, $C_{1-6}$ alkyl, $C_{1-6}$ alkoxy, and $C_{1-6}$ alkyl substituted with —$OR^H$. Preferably, $R^7$ may be selected from: H, fluoro, methyl, methoxy, and —$CH_2OH$. Preferably, $R^7$ is H.

In embodiments A may be selected from:

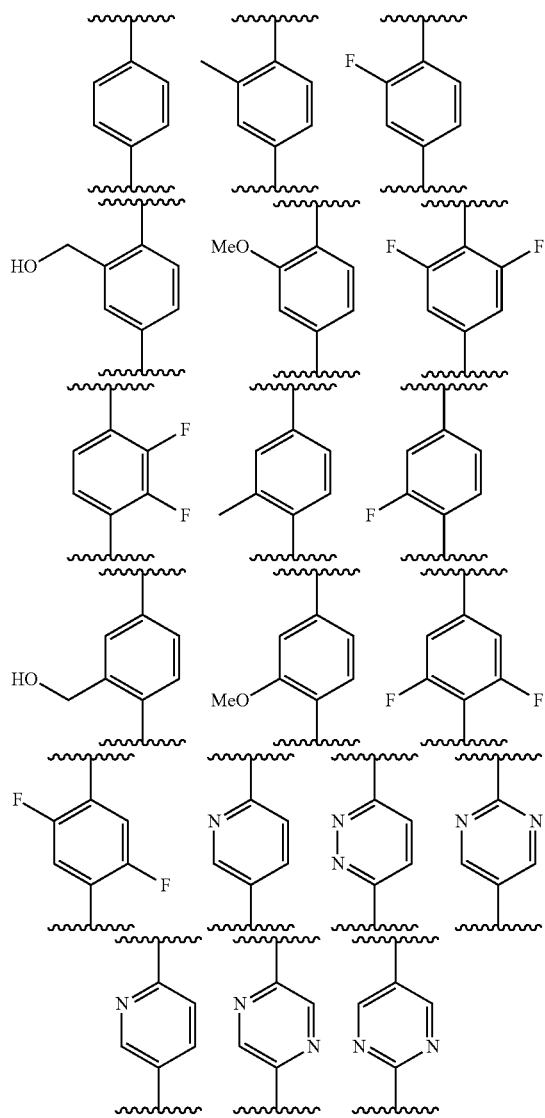

In embodiments A may be selected from:

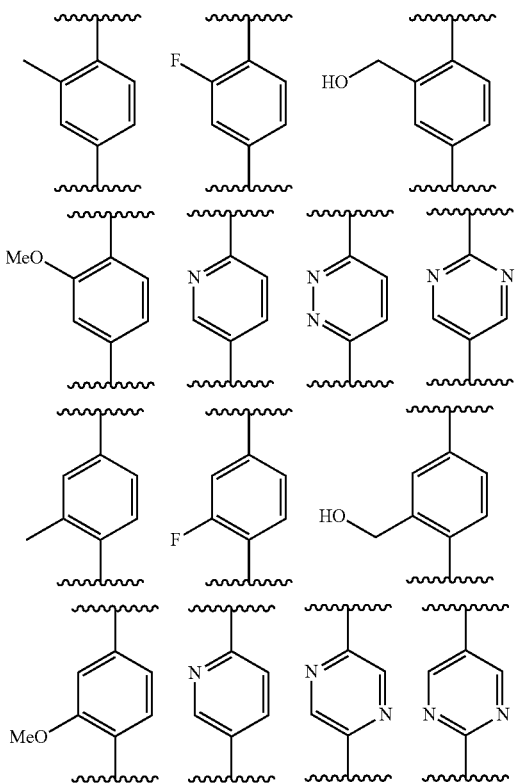

In embodiments A may be selected from:

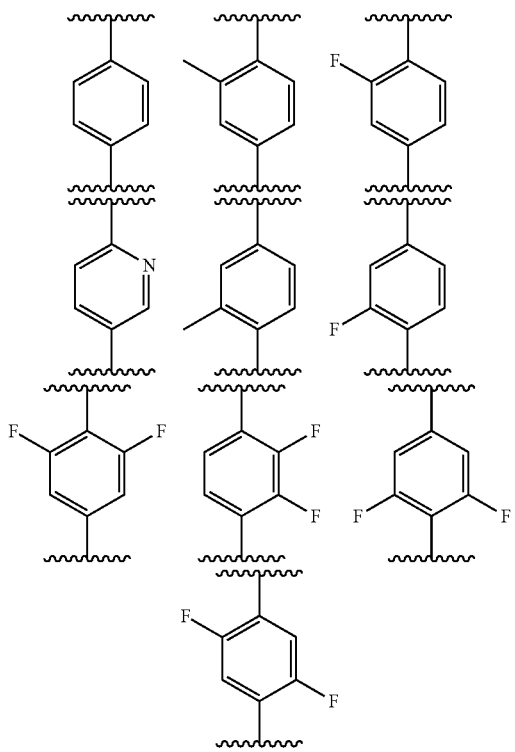

In preferred embodiments, A is selected from:

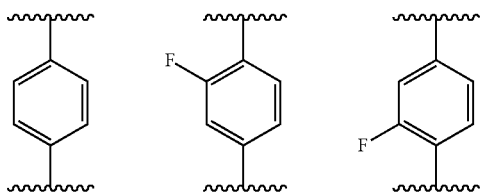 [SMILES: *c1ccc(*)cc1 ; *c1ccc(*)c(F)c1 ; *c1ccc(*)c(F)c1]

In embodiments $R^6$ is a group selected from a substituted or unsubstituted: phenyl or 6 membered heteroaryl ring. Preferably, $R^6$ is a group selected from a substituted: phenyl or 6 membered heteroaryl ring, substituted with 1 or 2 (preferably 1) methoxy (-OMe) group.

In embodiments $R^6$ is a group selected from a substituted or unsubstituted: phenyl, pyridyl, pyridazinyl, pyrazinyl, pyrimidinyl, pyrrolyl, pyrazolyl, imidazolyl, furanyl, thiophenyl, oxazolyl, thiazolyl, isoxazolyl, isothiazolyl, triazolyl, oxadiazolyl, or thiodiazolyl.

Preferably, $R^6$ is a group selected from a substituted: phenyl, pyridyl, pyridazinyl, pyrazinyl, pyrimidinyl, pyrrolyl, pyrazolyl, imidazolyl, furanyl, thiophenyl, oxazolyl, thiazolyl, isoxazolyl, isothiazolyl, triazolyl, oxadiazolyl, or thiodiazolyl, wherein $R^6$ contains from 1, 2 or 3 substituents independently selected at each occurrence from: halo, $-OR^I$, $-CN$, $C_{1-6}$ alkyl, $C_{1-6}$ haloalkyl, and $C_{1-6}$ alkyl substituted with $-OR^I$, optionally $R^I$ is selected from: H, methyl, ethyl, $-CF_3$, $-CH_2-OR^H$ and $-CH_2CH_2-OR^H$. Preferably, $R^I$ is H or methyl.

As the skilled person will be aware, based on the depiction of the structural formula of compounds of the invention, $R^6$ is attached to the remainder of the compound of the invention via a carbonyl ($-C(=O)-$) group. When $R^6$ is substituted by 1, 2 or 3 substituents $R^6$ is substituted by the carbonyl group (connecting $R^6$ to the remainder of the compound) and a further 1, 2 or 3 substituents. In preferred embodiments one of the substituents is substituted adjacent to the $-C(=O)-$. In other words, one of the substituents is substituted ortho to the carbonyl group ($-C(=O)-$). Preferably, the substituent of the 1, 2 or 3 substituents that is substituted on $R^6$ ortho to the carbonyl group is methoxy.

In embodiments $R^6$ is substituted or unsubstituted: phenyl or pyridyl (preferably substituted. In particularly preferred embodiments $R^6$ is substituted phenyl.

Preferably, $R^6$ contains from 1, 2 or 3 substituents independently selected at each occurrence from: fluoro, chloro, methoxy, ethoxy, isopropoxy, $-CN$, methyl, ethyl, trifluoromethyl, trifluoroethyl or $-OCF_3$. In embodiments, $R^6$ contains 1 or 2 substituents independently selected at each occurrence from: fluoro, methoxy or methyl. Preferably, $R^6$ contains 1 methoxy substituent or 2 substituents that are fluoro and methoxy.

A particularly preferred substituent for $R^6$ is methoxy. Accordingly, in preferred embodiments $R^6$ is a group selected from a methoxy substituted: phenyl, pyridyl, pyridazinyl, pyrazinyl, pyrimidinyl, pyrrolyl, pyrazolyl, imidazolyl, furanyl, thiophenyl, oxazolyl, thiazolyl, isoxazolyl, isothiazolyl, triazolyl, oxadiazolyl, or thiodiazolyl. Optionally, $R^6$ is a group selected from a methoxy substituted: phenyl, pyridyl, pyridazinyl, pyrazinyl or pyrimidinyl.

Particularly preferred substituents for $R^6$ are methoxy and fluoro. Accordingly, in preferred embodiments $R^6$ is a group selected from a fluoro and methoxy substituted: phenyl, pyridyl, pyridazinyl, pyrazinyl, pyrimidinyl, pyrrolyl, pyrazolyl, imidazolyl, furanyl, thiophenyl, oxazolyl, thiazolyl, isoxazolyl, isothiazolyl, triazolyl, oxadiazolyl, or thiodiazolyl. Optionally, $R^6$ is a group selected from a fluoro and methoxy substituted: phenyl, pyridyl, pyridazinyl, pyrazinyl or pyrimidinyl.

$R^6$ may be methoxyphenyl or fluoromethoxyphenyl. $R^6$ may be methoxyphenyl. As the skilled person will be aware $R^6$ is attached to the remainder of the compound of the invention via a carbonyl ($-C(=O)-$) group. When $R^6$ is methoxy phenyl the phenyl group of $R^6$ is substituted by the carbonyl group (connecting the phenyl ring to the remainder of the compound) and a methoxy group. In preferred embodiments where $R^6$ is methoxy phenyl, the methoxy group is substituted adjacent to the $-C(=O)-$. In other words, the methoxy group is substituted ortho to the carbonyl group ($-C(=O)-$) Accordingly, in an embodiment compounds according to formula (I) are compounds of formulae (IIIa) and (IIIb):

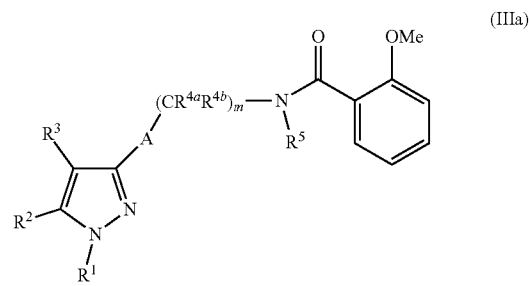

(IIIa)

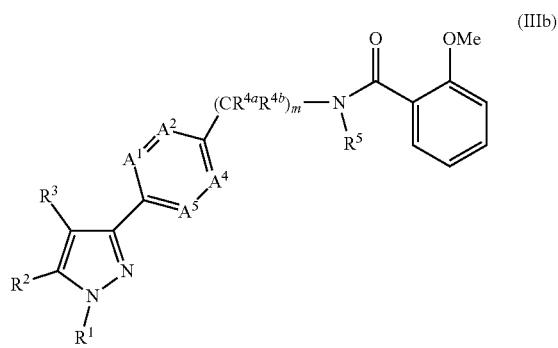

(IIIb)

Hence, in preferred embodiments $R^6$ is 2-methoxyphen-1-yl.

$R^6$ may be fluoromethoxyphenyl. As the skilled person will be aware $R^6$ is attached to the remainder of the compound of the invention via a carbonyl ($-C(=O)-$) group. When $R^6$ is fluoromethoxyphenyl the phenyl group of $R^6$ is substituted by the carbonyl group (connecting the phenyl ring to the remainder of the compound), a fluoro group and a methoxy group. In preferred embodiments where $R^6$ is fluoromethoxyphenyl, the methoxy group is substituted adjacent to the $-C(=O)-$ and the fluoro group is substituted opposite the methoxy group. In other words, the methoy group is substituted ortho to the carbonyl group ($-C(=O)-$) and the fluoro group is attached para to the methoxy group. Accordingly, in an embodiment compounds according to formula (I) are compounds of formulae (IIIc) and (IIId):

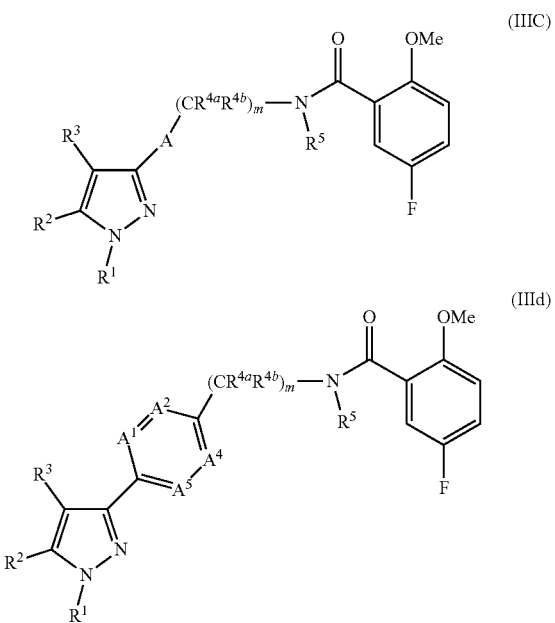

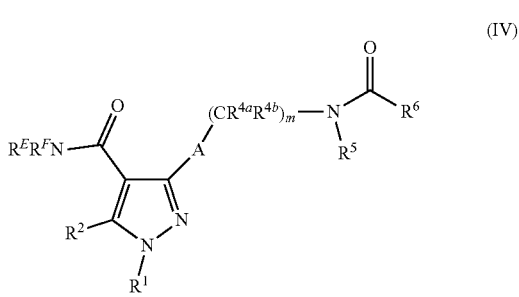

Hence, in preferred embodiments $R^6$ is 5-fluoro-2-methoxyphen-1-yl.

In embodiments $R^6$ is 2-methoxyphen-1-yl or 5-fluoro-2-methoxyphen-1-yl.

$R^5$ may be H or methyl. Preferably, $R^5$ is H.

$R^{4a}$ and $R^{4b}$ may be independently selected at each occurrence from: H, $C_{1-6}$ alkyl, $C_{3-6}$ cycloalkyl, and $C_{1-6}$ alkyl substituted with $-OR^H$. Optionally, $R^{4a}$ and $R^{4b}$ may be independently selected at each occurrence from: H, methyl, ethyl, cyclopropyl, or $-CH_2OH$. Optionally, $R^{4a}$ is H and $R^{4b}$ may be selected from: H, methyl, ethyl, cyclopropyl, or $-CH_2OH$. Optionally, $R^{4a}$ is H and $R^{4b}$ is selected from: H, methyl or $-CH_2OH$. Preferably, $R^{4a}$ is H and $R^{4b}$ is H.

In embodiments m is 1.

In embodiments m is 1 and $R^{4a}$ and $R^{4b}$ are H. In embodiments, m is 1, $R^{4a}$ and $R^{4b}$ are H, and $R^5$ is H. In embodiments, m is 1, $R^{4a}$ and $R^{4b}$ are H, $R^5$ is H, and $R^6$ is fluoromethoxyphenyl or methoxyphenyl. In embodiments m is 1, $R^{4a}$ and $R^{4b}$ are H, and A is unsubstituted phenyl or phenyl substituted by one $R^7$. In embodiments, m is 1, $R^{4a}$ and $R^{4b}$ are H, $R^5$ is H, and A is unsubstituted phenyl or phenyl substituted by one $R^7$. In embodiments, m is 1, $R^{4a}$ and $R^{4b}$ are H, $R^5$ is H, $R^6$ is fluoromethoxyphenyl or methoxyphenyl, and A is unsubstituted phenyl or phenyl substituted by one $R^7$. $R^7$ may be selected from: fluoro, methyl, methoxy, and $-CH_2OH$.

In embodiments m is 1 and $R^{4a}$ and $R^{4b}$ are H. In embodiments, m is 1, $R^{4a}$ and $R^{4b}$ are H, and $R^5$ is H. In embodiments, m is 1, $R^{4a}$ and $R^{4b}$ are H, $R^5$ is H, and $R^6$ is methoxyphenyl. In embodiments m is 1, $R^{4a}$ and $R^{4b}$ are H, and A is unsubstituted phenyl or phenyl substituted by one $R^7$. In embodiments, m is 1, $R^{4a}$ and $R^{4b}$ are H, $R^5$ is H, and A is unsubstituted phenyl or phenyl substituted by one $R^7$. In embodiments, m is 1, $R^{4a}$ and $R^{4b}$ are H, $R^5$ is H, $R^6$ is methoxyphenyl, and A is unsubstituted phenyl or phenyl substituted by one $R^7$. $R^7$ may be selected from: fluoro, methyl, methoxy, and $-CH_2OH$.

In embodiments $R^3$ represents $-C(O)NR^ER^F$. Preferably, $R^3$ represents $-C(O)NHMe$ or $-C(O)NH_2$.

In embodiments the compound according to formula (I) may be compounds of formula (IV) or pharmaceutically acceptable salts thereof:

In embodiments $R^2$ represents a group selected from: halo, $C_{1-8}$ alkyl, $C_{1-8}$ haloalkyl, and $-NR^CR^D$. Preferably, $R^2$ represents Cl, $CHF_2$, $CF_3$, $NH_2$, NHPh, NHMe, NHEt, and $NH^i$-Pr.

In embodiments the compound according to formula (I) may be compounds of formulae (IVa), (IVb), (IVc) or (IVd) or pharmaceutically acceptable salts thereof:

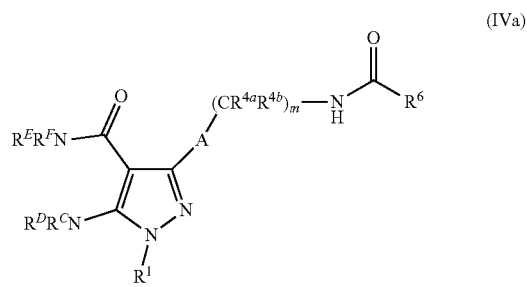

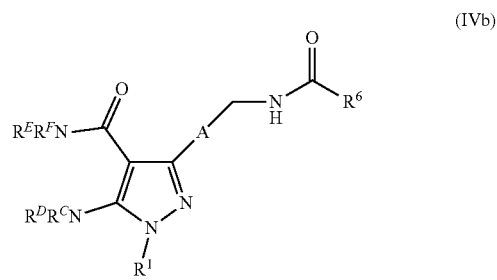

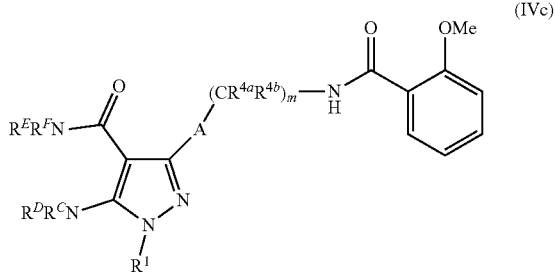

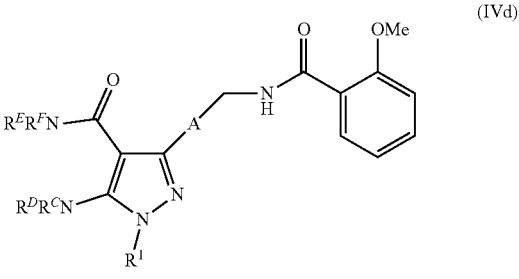

Additionally or alternatively in embodiments the compound according to formula (I) may be compounds of formulae (IVe) or (IVf) or pharmaceutically acceptable salts thereof:

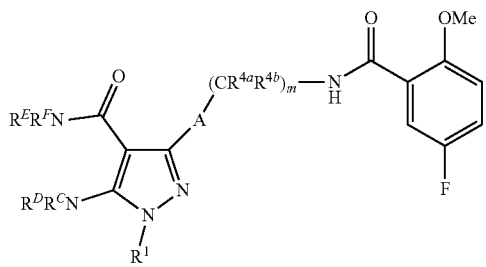

(IVe)

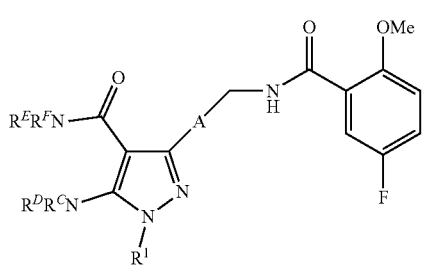

(IVf)

In an embodiment $R^C$ and $R^D$ are, at each occurrence, independently selected from: H, $C_{1-4}$ alkyl, $C_{1-4}$ haloalkyl, unsubstituted $C_{3-10}$ carbocyclic group (optionally $C_{3-6}$ carbocyclic group or phenyl), 3 to 10 membered heterocyclic group (optionally 3 to 6 membered heterocyclic group). Preferably, $R^C$ and $R^D$ are independently selected from: H, methyl, ethyl, isopropyl, difluoromethyl, trifluoromethyl, cyclopropyl, phenyl, pyridyl, and sec-butyl. For example, $R^C$ is H and $R^D$ is selected from: H, methyl, ethyl, isopropyl, difluoromethyl, trifluoromethyl, cyclopropyl, phenyl, pyridyl, and sec-butyl.

In an embodiment $R^C$ and $R^D$ are, at each occurrence, independently selected from: H, $C_{1-4}$ alkyl, $C_{1-4}$ haloalkyl, unsubstituted $C_{3-10}$ carbocyclic group (optionally $C_{3-6}$ carbocyclic group), 3 to 10 membered heterocyclic group (optionally 3 to 6 membered heterocyclic group). Preferably, $R^C$ and $R^D$ are independently selected from: H, methyl, ethyl, isopropyl, trifluoromethyl, cyclopropyl, phenyl, pyridyl, and sec-butyl. Particularly preferred embodiments $R^C$ and $R^D$ are H.

In embodiments $R^E$ and $R^F$ are, at each occurrence, independently selected from: H, $C_{1-4}$ alkyl, $C_{1-4}$ haloalkyl, unsubstituted $C_{3-10}$ carbocyclic group (optionally $C_{3-6}$ carbocyclic group), 3 to 10 membered heterocyclic group (optionally 3 to 6 membered heterocyclic group). In embodiments $R^E$ and $R^F$ are, at each occurrence, independently selected from: H, $C_{1-4}$ alkyl, (preferably $R^E$ and $R^F$ are, at each occurrence, independently selected from: H, methyl, and ethyl). In embodiments $R^E$ and $R^F$ are H.

In embodiments $R^C$, $R^D$, $R^E$ and $R^F$ are H.

In embodiments the compound according to formula (I) may be compounds of formulae (Va) and (Vb) or pharmaceutically acceptable salts thereof:

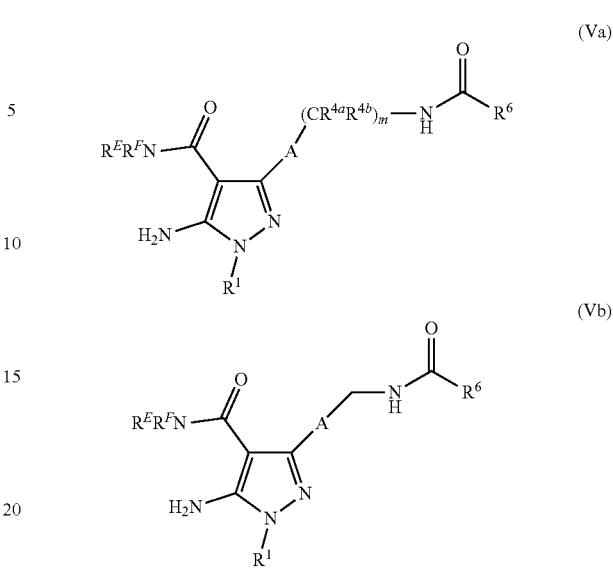

$R^2$ represents a group selected from: —OH, halo, $C_{1-8}$ alkyl, $C_{1-8}$ haloalkyl, $C_{1-8}$ alkoxy, $C_{3-10}$ cycloalkyl, $C_{6-10}$ aryl, 3 to 10 membered heterocyclic group, $C_{1-8}$ alkyl substituted with —$OR^C$, $C_{1-8}$ alkyl substituted with $C_{3-10}$ carbocyclic group, $C_{1-8}$ alkyl substituted with 3 to 10 membered heterocyclic group, and —$NR^CR^D$.

In embodiments $R^2$ represents a group selected from: halo, $C_{1-8}$ alkyl or —$NR^CR^D$, wherein $R^C$ and $R^D$ are, at each occurrence, independently selected from: H or $C_{1-4}$ alkyl.

In embodiments $R^2$ represents a group selected from: fluoro, methyl, ethyl, cyclopropyl, trifluoromethyl, difluoromethyl, morpholinyl, —$CH_2OH$, and —$NR^CR^D$, wherein $R^C$ and $R^D$ are, at each occurrence, independently selected from: H, methyl, ethyl, isopropyl, trifluoromethyl, cyclopropyl, phenyl, pyridyl, and sec-butyl.

Preferably, $R^2$ is $NH_2$ or Me.

In embodiments $R^3$ represents —$C(O)NR^ER^F$, $C_{1-6}$ alkyl substituted with —$OR^G$, or $C_{1-6}$ haloalkyl, optionally wherein $R^E$ and $R^F$ are, at each occurrence, independently selected from: H or $C_{1-4}$ alkyl (preferably $R^E$ and $R^F$ are, at each occurrence, independently selected from: H, methyl, and ethyl, and $R^G$ is selected from: H or $C_{1-4}$ alkyl).

In embodiments one of $R^E$ and $R^F$ are H,

In embodiments $R^3$ represents —$C(O)NH_2$, —$C(O)NHMe$, —$CH_2OH$, $CH(OH)CH_3$, —$CF_3$, or —$CHF_2$.

Preferably, $R^3$ represents —$C(O)NH_2$.

In embodiments $R^2$ is $NH_2$ or Me and $R^3$ is —$C(O)NH_2$. In a particularly preferred embodiment $R^2$ is $NH_2$ and $R^3$ is —$C(O)NH_2$.

In embodiments m is 1, $R^{4a}$ and $R^{4b}$ are H, and $R^2$ is $NH_2$ and $R^3$ is —$C(O)NH_2$. In embodiments, m is 1, $R^{4a}$ and $R^{4b}$ are H, $R^5$ is H, and $R^2$ is $NH_2$ and $R^3$ is —$C(O)NH_2$. In embodiments, m is 1, $R^{4a}$ and $R^{4b}$ are H, $R^5$ is H, $R^6$ is fluoromethoxyphenyl or methoxyphenyl, $R^2$ is $NH_2$, and $R^3$ is —$C(O)NH_2$. In embodiments, m is 1, $R^{4a}$ and $R^{4b}$ are H, $R^5$ is H, $R^6$ is methoxyphenyl, $R^2$ is $NH_2$, and $R^3$ is —$C(O)NH_2$.

$R^1$ represents a group selected from: $C_{1-8}$ alkyl, $C_{1-8}$ haloalkyl, $C_{2-8}$ alkyl ether, —$C(O)R^A$, $C_{3-10}$ carbocyclic group, 3 to 10 membered heterocyclic group, $C_{1-8}$ alkyl substituted with $C_{3-10}$ carbocyclic group, and $C_{1-8}$ alkyl substituted with 3 to 10 membered heterocyclic group, wherein each of the aforementioned groups are unsubstituted or substituted with 1 to 5 substituents selected from: halo, $C_{1-4}$ alkyl, $C_{1-4}$ haloalkyl, $C_{1-4}$ alkoxy, $C_{2-4}$ alkyl ether, —$OR^A$, —CN, =O, —C(O)$OR^A$, —C(O)$NR^AR^B$, a 3 to 6 membered heterocycloalkyl ring, $C_{1-4}$ alkyl substituted with —$OR^A$, $C_{1-4}$ alkoxy substituted with —$OR^A$;

wherein $R^A$ and $R^B$ are independently selected from: H, $C_{1-4}$ alkyl, $C_{1-4}$ haloalkyl, $C_{1-4}$ alkoxy, benzyl or $C_{1-4}$ alkyl substituted with —$OR^H$.

$R^1$ represents a group selected from: $C_{1-8}$ alkyl, $C_{1-8}$ haloalkyl, $C_{2-8}$ alkyl ether, —C(O)$R^A$, $C_{3-10}$ carbocyclic group, 3 to 10 membered heterocyclic group, $C_{1-8}$ alkyl substituted with $C_{3-10}$ carbocyclic group, and $C_{1-8}$ alkyl substituted with 3 to 10 membered heterocyclic group, wherein each of the aforementioned groups are unsubstituted or substituted with 1 to 5 substituents selected from: halo, $C_{1-4}$ alkyl, $C_{1-4}$ haloalkyl, $C_{1-4}$ alkoxy, $C_{2-4}$ alkyl ether, —$OR^A$, —CN, =O, —C(O)$OR^A$, $C_{1-4}$ alkyl substituted with —$OR^A$, $C_{1-4}$ alkoxy substituted with —$OR^A$; wherein $R^A$ is selected from: H, $C_{1-4}$ alkyl, $C_{1-4}$ haloalkyl, benzyl or $C_{1-4}$ alkyl substituted with —$OR^H$.

$R^1$ represents a group selected from: $C_{1-6}$ alkyl, $C_{1-6}$ haloalkyl, $C_{2-6}$ alkyl ether, —C(O)$R^A$, $C_{3-10}$ cycloalkyl (preferably $C_{3-6}$ cycloalkyl), $C_{6-10}$ aryl (preferably phenyl or indanyl), 3 to 10 membered heterocycloalkyl (optionally 3 to 6 membered), 3 to 10 membered heteroaryl (optionally 3 to 6 membered, for example 5 or 6 membered), $C_{1-6}$ alkyl substituted with $C_{3-10}$ cycloalkyl (preferably $C_{3-6}$ cycloalkyl), $C_{1-6}$ alkyl substituted with $C_{6-10}$ aryl (preferably phenyl), $C_{1-6}$ alkyl substituted with 3 to 10 membered heterocycloalkyl (optionally 3 to 6 membered), and $C_{1-6}$ alkyl substituted with 3 to 10 membered heteroaryl (optionally 3 to 6 membered, for example 5 or 6 membered), wherein each of the aforementioned groups are unsubstituted or substituted with 1 to 5 substituents selected from: halo, $C_{1-4}$ alkyl, $C_{1-4}$ haloalkyl, $C_{1-4}$ alkoxy, $C_{2-4}$ alkyl ether, —$OR^A$, —CN, =O, —C(O)$OR^A$, —C(O)$NR^AR^B$, a 3 to 6 membered heterocycloalkyl ring, $C_{1-4}$ alkyl substituted with —$OR^A$, $C_{1-4}$ alkoxy substituted with —$OR^A$, wherein $R^A$ is selected from: H, $C_{1-4}$ alkyl, $C_{1-4}$ haloalkyl, benzyl or $C_{1-4}$ alkyl substituted with —$OR^H$.

In embodiments $R^1$ is selected from substituted or unsubstituted: methyl, ethyl, iso-propyl, propyl, hexyl, tert-hexyl, tert-butyl, trifluoroethyl, trifluoropropyl, trifluorobutyl, difluoropropyl, chloropropyl, propyl ether, cyclopropyl, cyclobutyl, cyclopentyl, cyclopentenyl, cyclohexyl, indanyl, bicyclo[3.1.0]hexyl, oxetane, tetrahydropyranyl, tetrahydrofuranyl, pyrrolidinyl, piperidinyl, phenyl, pyridyl, thiazolyl, $C_{1-8}$ alkyl (preferably methyl or ethyl) substituted with oxetane, $C_{1-8}$ alkyl (preferably methyl or ethyl) substituted with morpholine, $C_{1-8}$ alkyl (preferably methyl or ethyl) substituted with tetrazole, $C_{1-8}$ alkyl (preferably methyl or ethyl) substituted with piperidine, $C_{1-8}$ alkyl (preferably methyl or ethyl) substituted with cyclohexyl, $C_{1-8}$ alkyl (preferably methyl or ethyl) substituted with cyclopentyl, $C_{1-8}$ alkyl (preferably methyl or ethyl) substituted with tetrahydropyranyl, $C_{1-8}$ alkyl (preferably methyl or ethyl) substituted with pyrrolidinyl, $C_{1-8}$ alkyl (preferably methyl or ethyl) substituted with pyridinyl, $C_{1-8}$ alkyl (preferably methyl or ethyl) substituted with phenyl, $C_{1-8}$ alkyl (preferably methyl or ethyl) substituted with tetrohydrofuran, and $C_{1-8}$ alkyl (preferably methyl or ethyl) substituted with cyclopropyl.

In embodiments $R^1$ is selected from substituted or unsubstituted: methyl, ethyl, iso-propyl, tert-hexyl, tert-butyl, trifluoroethyl, propyl ether, cyclopropyl, cyclobutyl, cyclopentyl, cyclohexyl, indanyl, bicyclo[3.1.0]hexyl, oxetane, tetrahydropyranyl, phenyl, pyridyl, $C_{1-8}$ alkyl (preferably methyl or ethyl) substituted with oxetane, $C_{1-8}$ alkyl (preferably methyl or ethyl) substituted with morpholine, $C_{1-8}$ alkyl (preferably methyl or ethyl) substituted with tetrazole, $C_{1-8}$ alkyl (preferably methyl or ethyl) substituted with piperidine, and $C_{1-8}$ alkyl (preferably methyl or ethyl) substituted with cyclohexyl.

Preferably $R^1$ is substituted with 1 to 5 substituents (optionally 1 to 4) selected from: halo, $C_{1-4}$ alkyl, $C_{1-4}$ haloalkyl, $C_{1-4}$ alkoxy, $C_{2-4}$ alkyl ether, —$OR^A$, —CN, =O, —C(O)$OR^A$, —C(O)$NR^AR^B$, 5 or 6 membered heteroaryl, a 3 to 6 membered heterocycloalkyl ring, $C_{1-4}$ alkyl substituted with —$OR^A$, $C_{1-4}$ alkoxy substituted with —$OR^A$ or a single atom of $R^1$ is substituted twice so as to form a 3 to 6 membered heterocycloalkyl or cycloalkyl ring.

In embodiments $R^1$ is substituted with 1 to 4 substituents selected from: —OH, =O, -OMe, —CN, methyl, ethyl, propyl, isopropyl, tert-butyl, $CF_3$, Cl, F, -OBn, —$CO_2H$, —$CO_2Me$, —$CO_2Et$, —C(O)$NH_2$, —C(O)NHMe, —C(O)$NMe_2$, —C(O)NHOMe, pyridinyl, pyrrolidinyl, oxetanyl, tetrahydropyranyl, or tetrahydrofuranyl or a single atom of $R^1$ is substituted twice so as to form a oxirane or oxetane.

Optionally $R^1$ is substituted with 1 to 5 substituents (optionally 1 to 3) selected from: halo, $C_{1-4}$ alkyl, $C_{1-4}$ haloalkyl, $C_{1-4}$ alkoxy, $C_{2-4}$ alkyl ether, —$OR^A$, —CN, =O, —C(O)$OR^A$, $C_{1-4}$ alkyl substituted with —$OR^A$, $C_{1-4}$ alkoxy substituted with —$OR^A$. In embodiments $R^1$ is substituted with 1 to 3 substituents selected from: —OH, =O, -OMe, —CN, methyl, $CF_3$, Cl, F, -OBn, or —$CO_2Et$.

In embodiments $R^1$ is selected from substituted or unsubstituted: methyl, ethyl, iso-propyl, tert-hexyl, tert-butyl, trifluoroethyl, propyl ether, cyclopropyl, cyclobutyl, cyclopentyl, cyclohexyl, indanyl, bicyclo[3.1.0]hexyl, oxetane, tetrahydropyranyl, phenyl, pyridyl, $C_{1-8}$ alkyl (preferably methyl or ethyl) substituted with oxetane, $C_{1-8}$ alkyl (preferably methyl or ethyl) substituted with morpholine, $C_{1-8}$ alkyl (preferably methyl or ethyl) substituted with tetrazole, $C_{1-8}$ alkyl (preferably methyl or ethyl) substituted with piperidine, and $C_{1-8}$ alkyl (preferably methyl or ethyl) substituted with cyclohexyl, wherein $R^1$ is substituted with 1 to 5 substituents selected from: —OH, =O, -OMe, —CN, methyl, $CF_3$, Cl, F, -OBn, or —$CO_2Et$.

In embodiments $R^1$ is selected from substituted or unsubstituted: methyl, ethyl, iso-propyl, tert-hexyl, tert-butyl, trifluoroethyl, wherein $R^1$ is substituted with 1 to 5 substituents selected from: —OH, =O, -OMe, —CN, methyl, $CF_3$, Cl, F, -OBn, or —$CO_2Et$.

$R^1$ may be selected from:

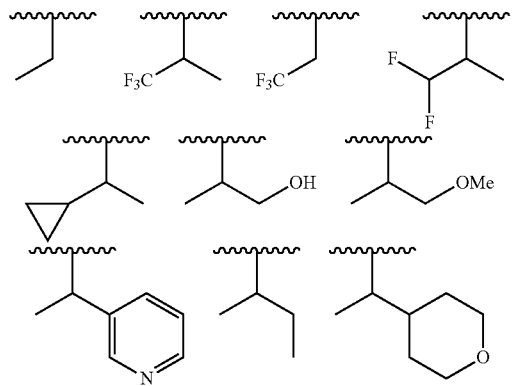

-continued
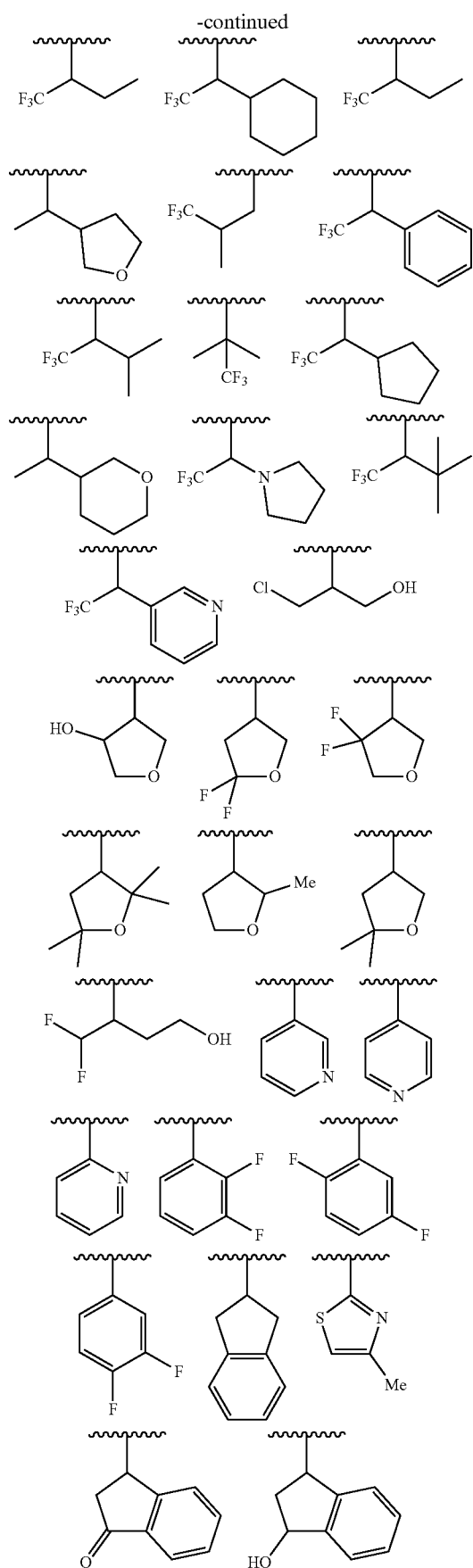
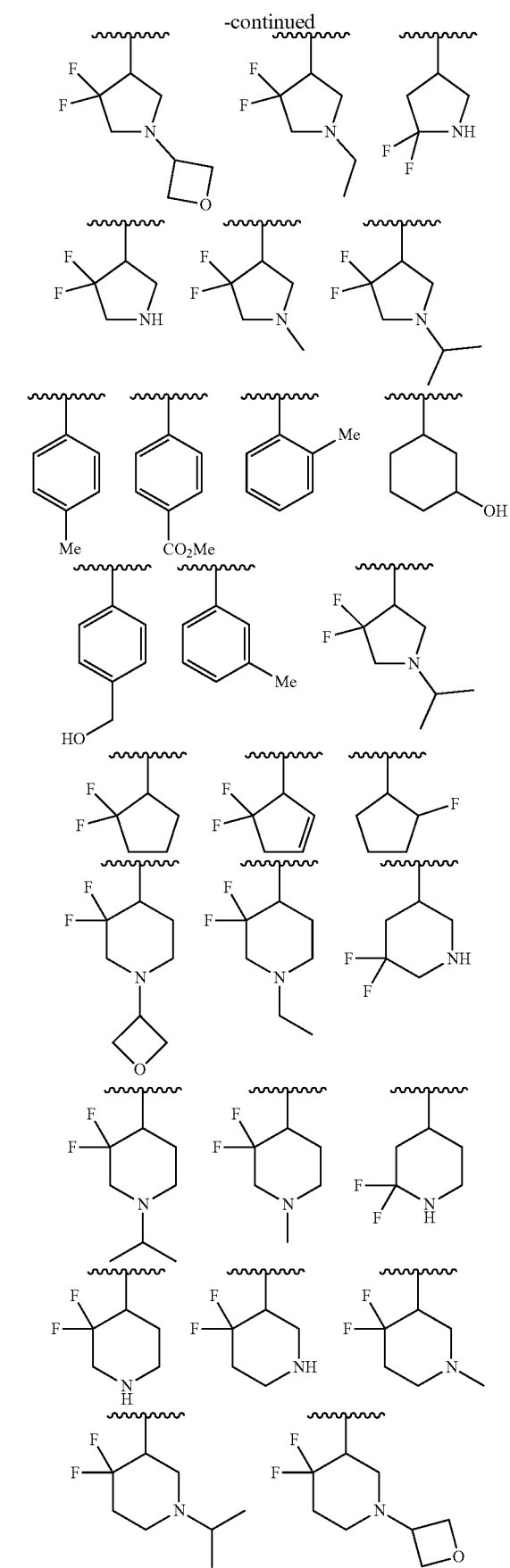

-continued
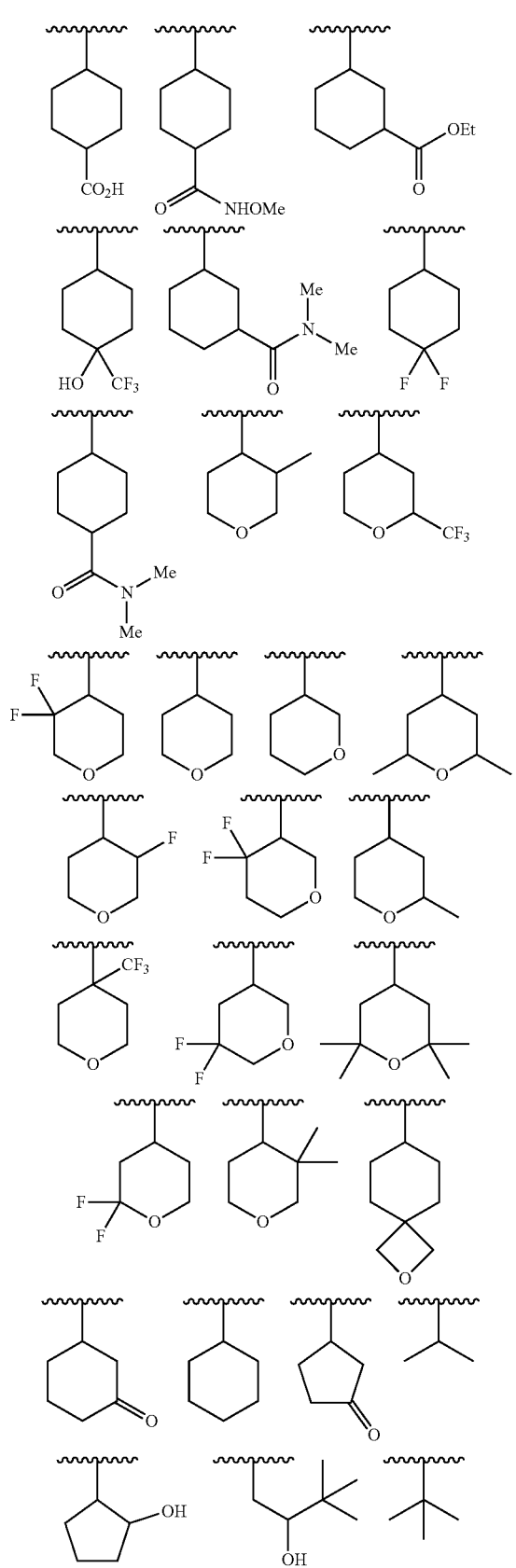
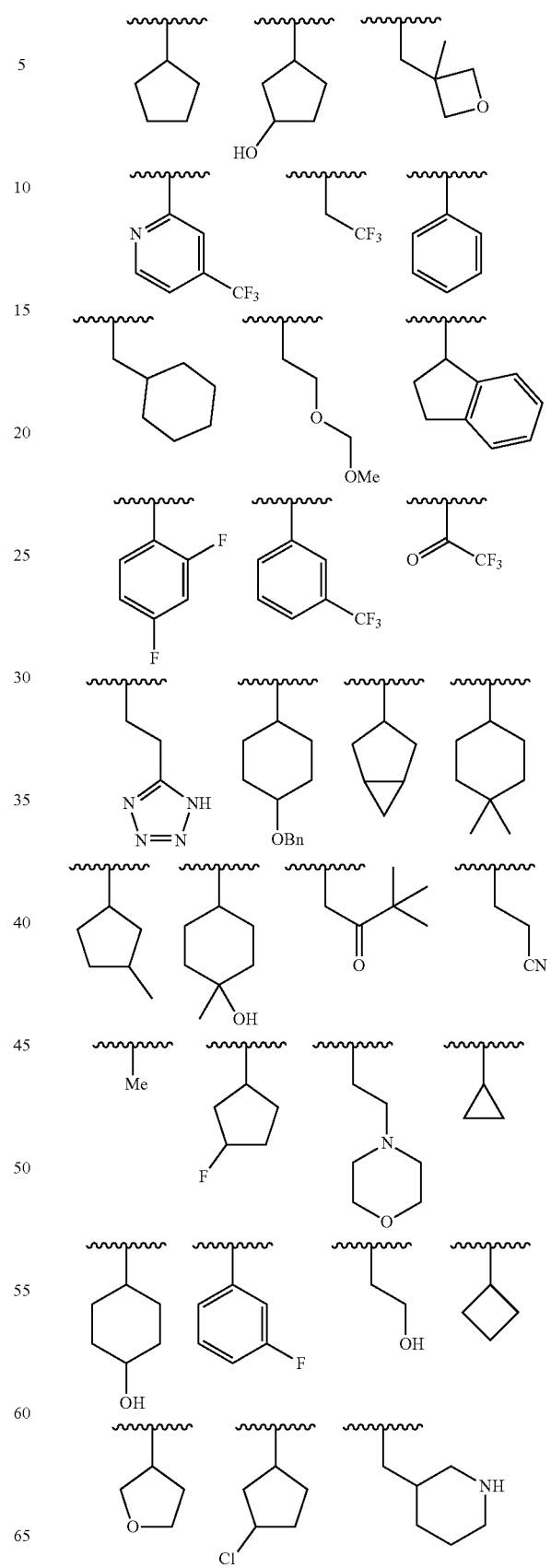

-continued

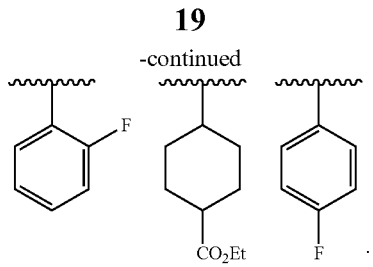

R¹ may be selected from:

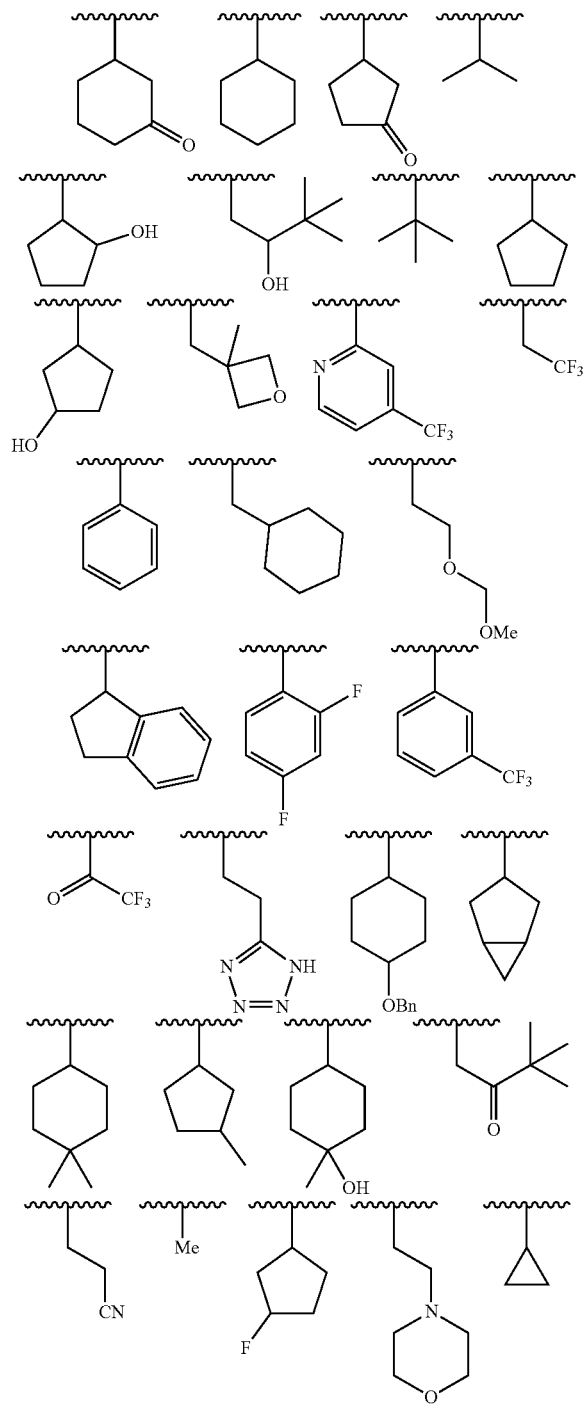

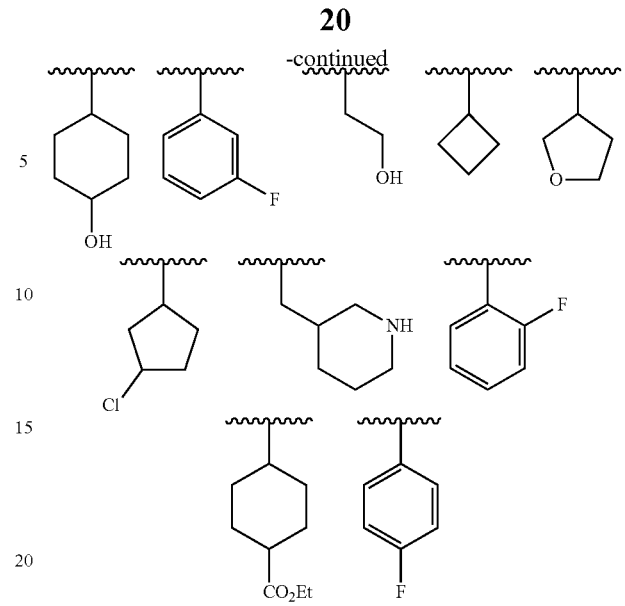

In embodiments R¹ is selected from substituted or unsubstituted: $C_{3-10}$ carbocyclic group, wherein when substituted R¹ is substituted with 1 to 5 substituents selected from: halo, $C_{1-4}$ alkyl, or —$OR^A$, wherein $R^A$ is selected from H or $C_{1-4}$ alkyl.

In embodiments R¹ is selected from substituted or unsubstituted: $C_{3-6}$ cycloalkyl or phenyl, wherein when substituted R¹ is substituted with 1 to 5 substituents selected from: halo, $C_{1-4}$ alkyl, or —$OR^A$, wherein $R^A$ is selected from H or $C_{1-4}$ alkyl.

In preferred embodiments R¹ is selected from substituted or unsubstituted: cyclohexyl, phenyl, cyclobutyl, cyclopentyl, bicyclo[3.1.0]hexyl, piperidinyl, pyrrolidinyl, tetrahydropyranyl, tetrahydrofuranyl, difluoroisopropyl, trifluoroisopropyl, (cyclopropyl)ethyl, or (tetrahydropyranyl)ethyl. Accordingly, R¹ may be selected from:


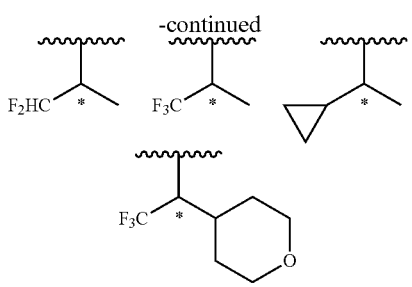

In preferred embodiments R¹ is selected from substituted or unsubstituted: cyclohexyl, phenyl, cyclobutyl, cyclopentyl or bicyclo[3.1.0]hexyl. Preferably, R¹ may be selected from:

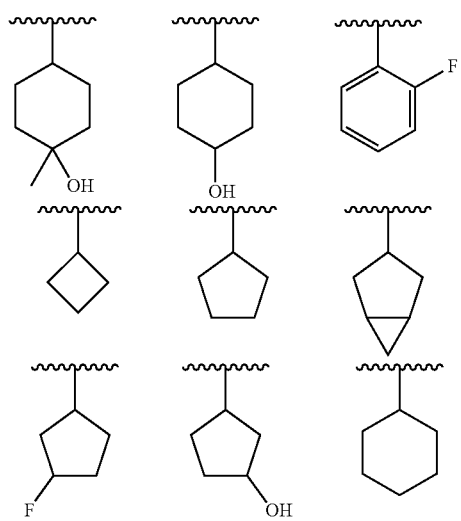

In preferred embodiments R¹ is selected from substituted or unsubstituted: piperidinyl, pyrrolidinyl, tetrahydropyranyl, tetrahydrofuranyl, difluoroisopropyl, trifluoroisopropyl, (cyclopropyl)ethyl, or (tetrahydropyranyl)ethyl. Accordingly, R¹ may be selected from:

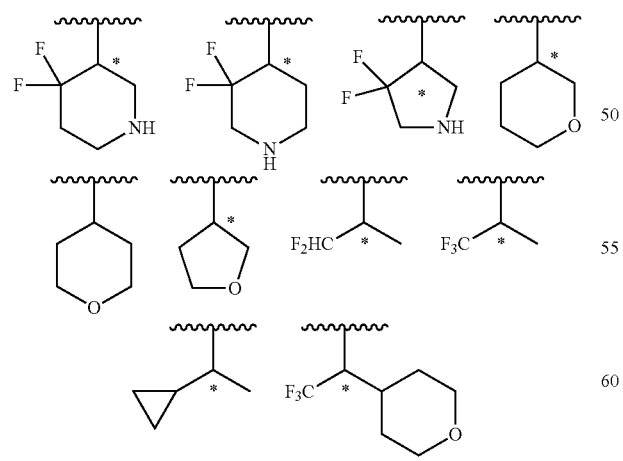

In an embodiment the compound according to formula (I) may be compounds of formulae (VIa) and (VIb) or pharmaceutically acceptable salts thereof:

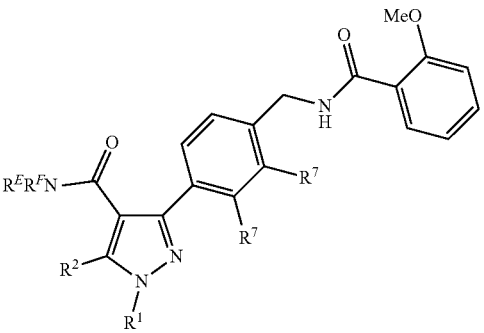

(VIa)

(VIb)

Alternatively, the compound according to formula (I) may be compounds of formulae (VIc) and (VId) or pharmaceutically acceptable salts thereof:

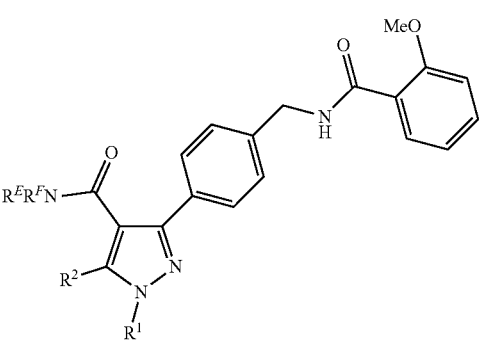

(VIc)

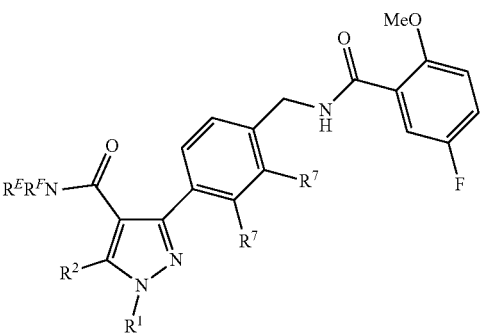

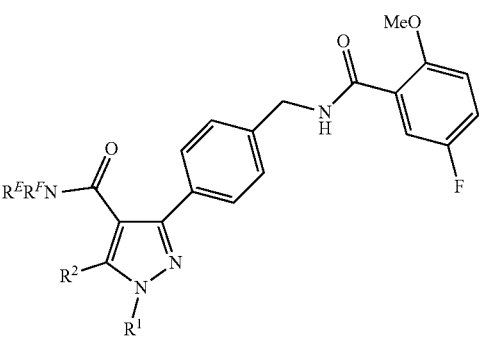

(VId)

In an embodiment the compound according to formula (I) may be compounds of formulae (VIa) and (VIIb) or pharmaceutically acceptable salts thereof:

(VIIa)
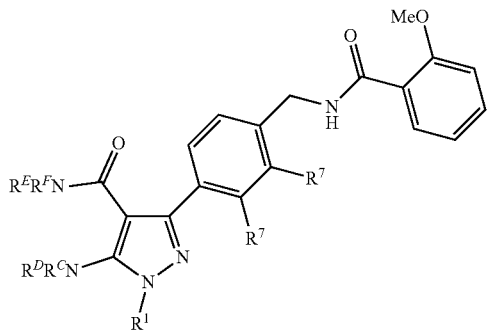

(VIIb)

Alternatively, the compound according to formula (I) may be compounds of formulae (VIIc) and (VIId) or pharmaceutically acceptable salts thereof:

In an embodiment the compound according to formula (I) may be compounds of formulae (VIIIa) and (VIIIb) or pharmaceutically acceptable salts thereof:

(VIIc)

(VIId)
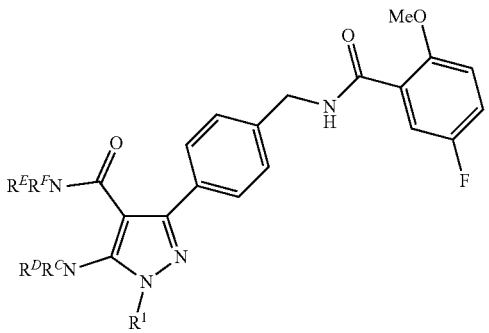

(VIIIa)
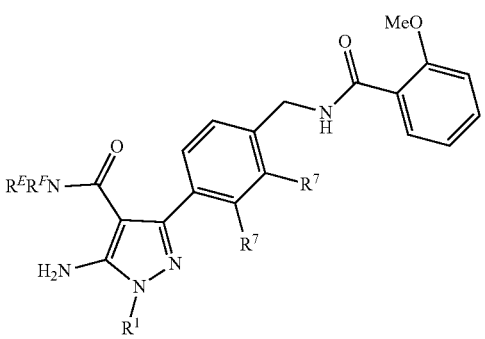

(VIIIb)
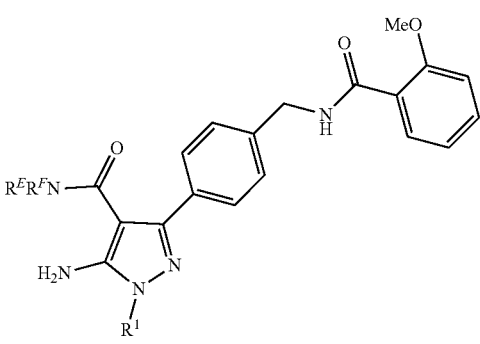

Alternatively, the compound according to formula (I) may be compounds of formulae (VIIIc) and (VIIId) or pharmaceutically acceptable salts thereof:

(VIIIc)
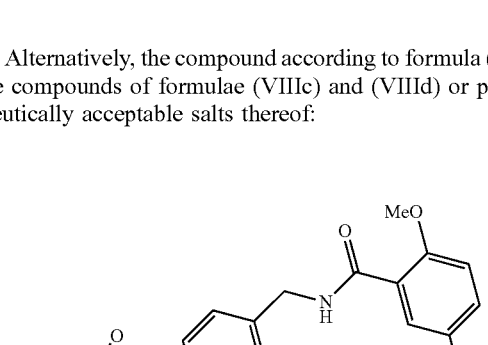

-continued

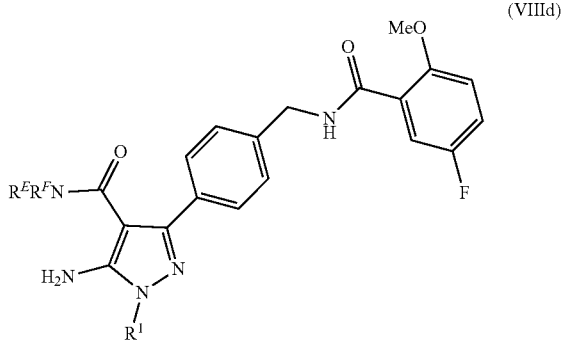

(VIIId)

In an embodiment the compound according to formula (I) may be compounds of formulae (IXa) and (IXb) or pharmaceutically acceptable salts thereof:

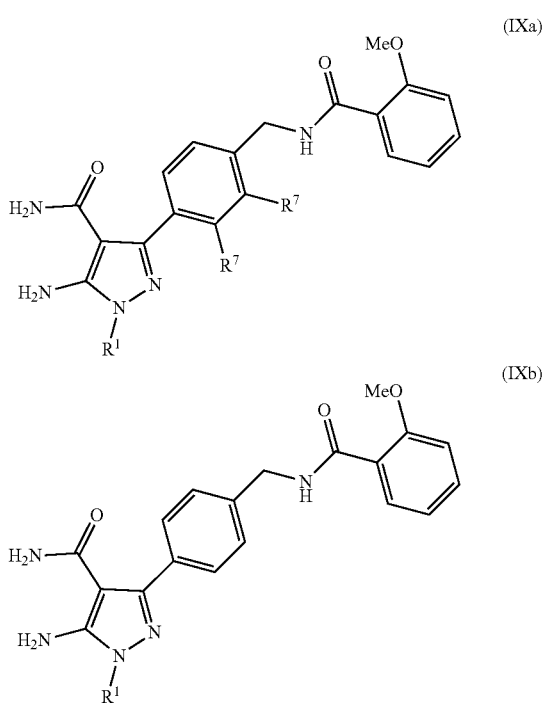

(IXa)

(IXb)

Alternatively, the compound according to formula (I) may be compounds of formulae (IXc) and (IXd) or pharmaceutically acceptable salts thereof:

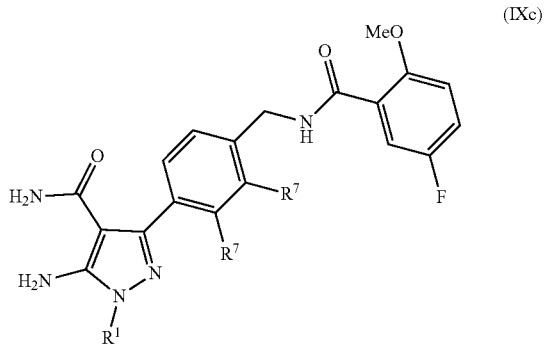

(IXc)

-continued

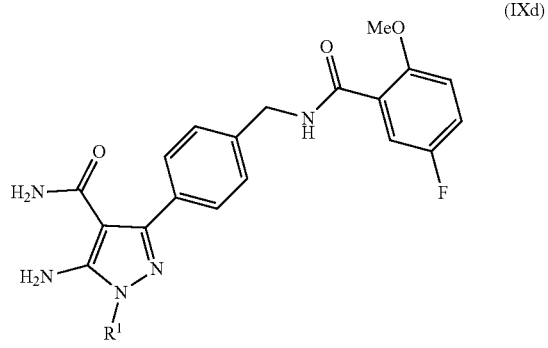

(IXd)

For the compounds of formulae (VIa), (VIIa), (VIIIa), (IXa), (VIc), (VIIc), (VIIIc), and (IXc) $R^7$ may be as defined elsewhere herein, preferably $R^7$ may be selected from: H, fluoro, methyl, methoxy, and —CH$_2$OH.

In a particularly preferred embodiment of the invention $R^1$ is $$\underset{R^{1A} \quad R^{1B}}{\overset{\sim\sim\sim\sim\sim}{\diagup\diagdown}}.$$

Accordingly, the compound according to formula (I) may be a compound of formula (X) or a pharmaceutically acceptable salt thereof:

(X)

wherein $R^{1A}$ is selected from $C_{1-2}$ alkyl or $C_{1-2}$ haloalkyl and $R^B$ is selected from unsubstituted $C_{1-4}$ alkyl, $C_{1-4}$ haloalkyl, $C_{1-4}$ alkyl substituted with OH, $C_{1-4}$ alkyl substituted with OMe, 5 or 6 membered heteroaryl, 3 to 6 membered heterocycloalkyl ring, phenyl, or $C_{3-10}$ carbocyclic group (such as a 3 to 10 membered cycloalkyl ring); provided that when $R^{1A}$ is $C_{1-2}$ alkyl then $R^{1B}$ is not unsubstituted $C_{1-4}$ alkyl.

Preferably, $R^{1A}$ is selected from methyl, difluoromethyl or trifluoromethyl, and $R^{1B}$ is selected from methyl, ethyl, propyl, trifluoromethyl, difluoromethyl, trifluoroethyl, —CH$_2$OH, —CH$_2$CH$_2$OH, —CH$_2$OMe, pyrrolidinyl, piperidinyl, tetrahydrofuranyl, tetrahydropyranyl, pyridyl, phenyl, cyclopropyl, cyclobutyl, cyclopentyl, or cyclohexyl; provided that when $R^{1A}$ is not methyl then $R^{1B}$ is not methyl, ethyl, or propyl. In embodiments, $R^{1A}$ is trifluoromethyl.

Preferably, $R^{1A}$ is selected from methyl or trifluoromethyl, and $R^{1B}$ is selected from methyl, ethyl, propyl, trifluoroethyl, difluoromethyl, trifluoroethyl, —CH$_2$OH, —CH$_2$OMe, pyrrolidinyl, piperidinyl, tetrhydrofuranyl, tetrahydropyranyl, pyridyl, phenyl, cyclopropyl, cyclobutyl, cyclopentyl, or cyclohexyl; provided that when $R^{1A}$ is not methyl then $R^{1B}$ is not methyl, ethyl, or propyl. In embodiments, $R^{1A}$ is trifluoromethyl.

The compounds according to formula (I) may be compounds of formula (II) or pharmaceutically acceptable salts thereof:

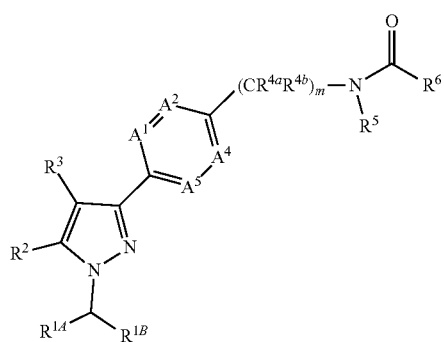
(XI)

wherein 0, 1 or 2 of $A^1$, $A^2$, $A^4$ and $A^5$ are independently selected from N and the remainder are $CR^7$.

In an embodiment compounds according to formula (I) are compounds of formulae (XIIa), (XIIb), (XIIc) and (XIId):

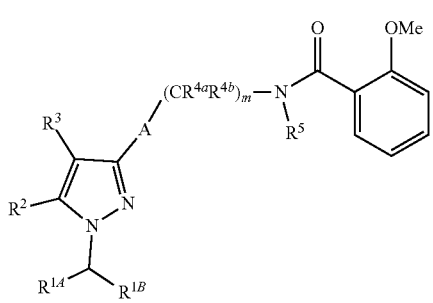
(XIIa)

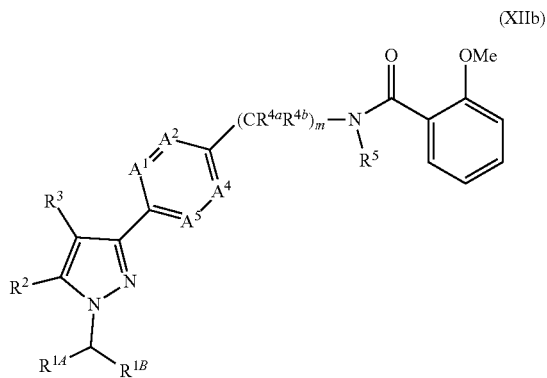
(XIIb)

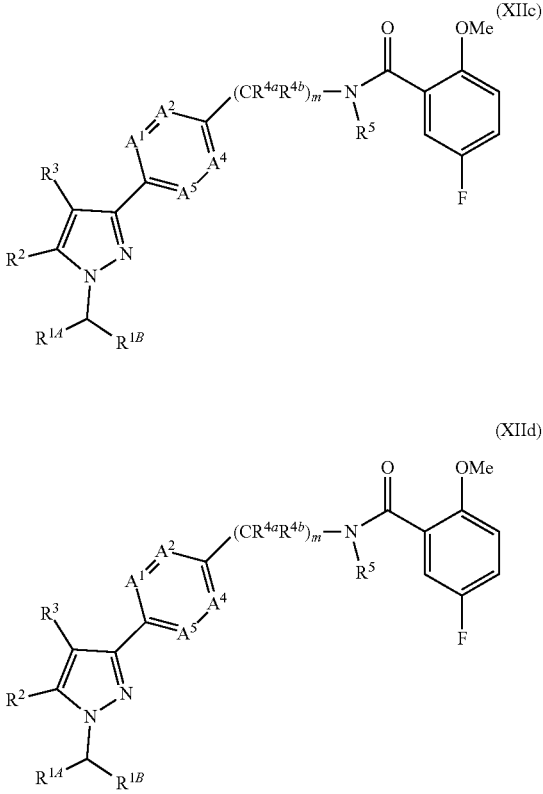
(XIIc)

(XIId)

In embodiments the compound according to formula (I) may be compounds of formulae (XIIIa), (XIIIb), (XIIIc), (XIIId), (XIIIe) or (XIIIf) or pharmaceutically acceptable salts thereof:

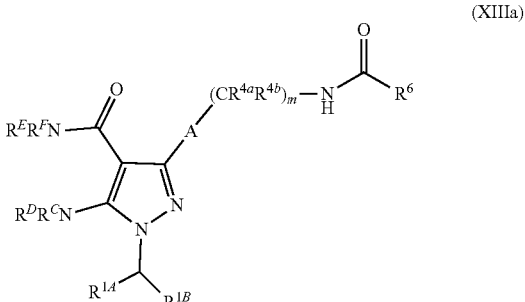
(XIIIa)

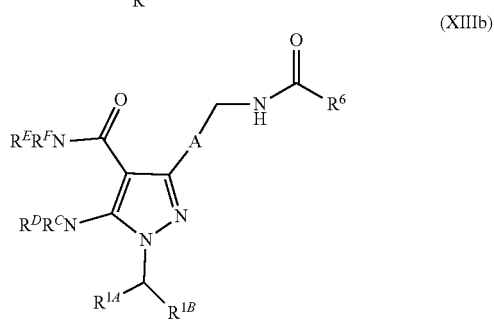
(XIIIb)

In an embodiment the compound according to formula (I) may be compounds of formulae (XIVa), (XIVb), (XIVc) and (XIVd) or pharmaceutically acceptable salts thereof:
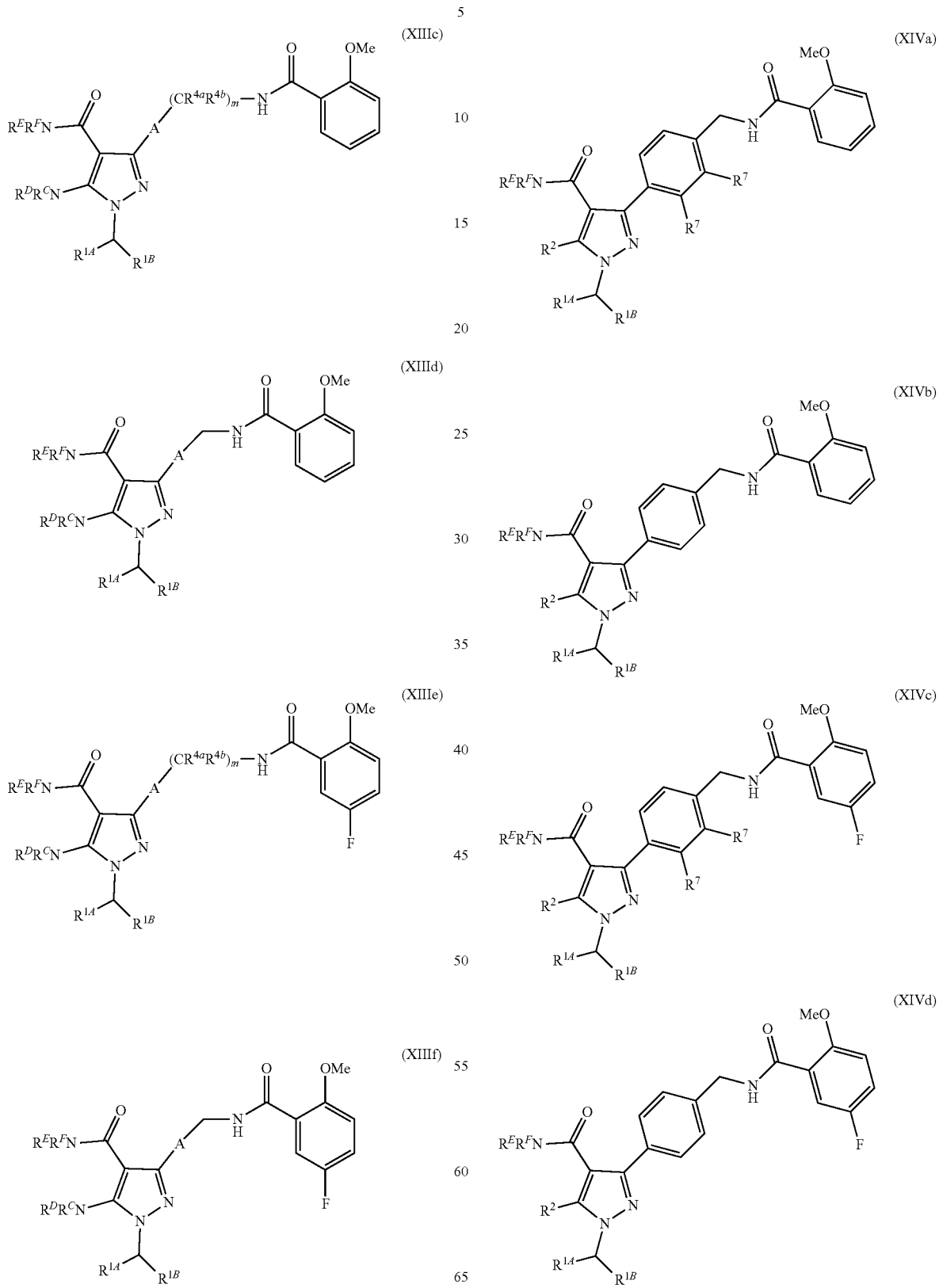

In an embodiment the compound according to formula (I) may be compounds of formulae (XVa), (XVb), (XVc) and (XVd) or pharmaceutically acceptable salts thereof:

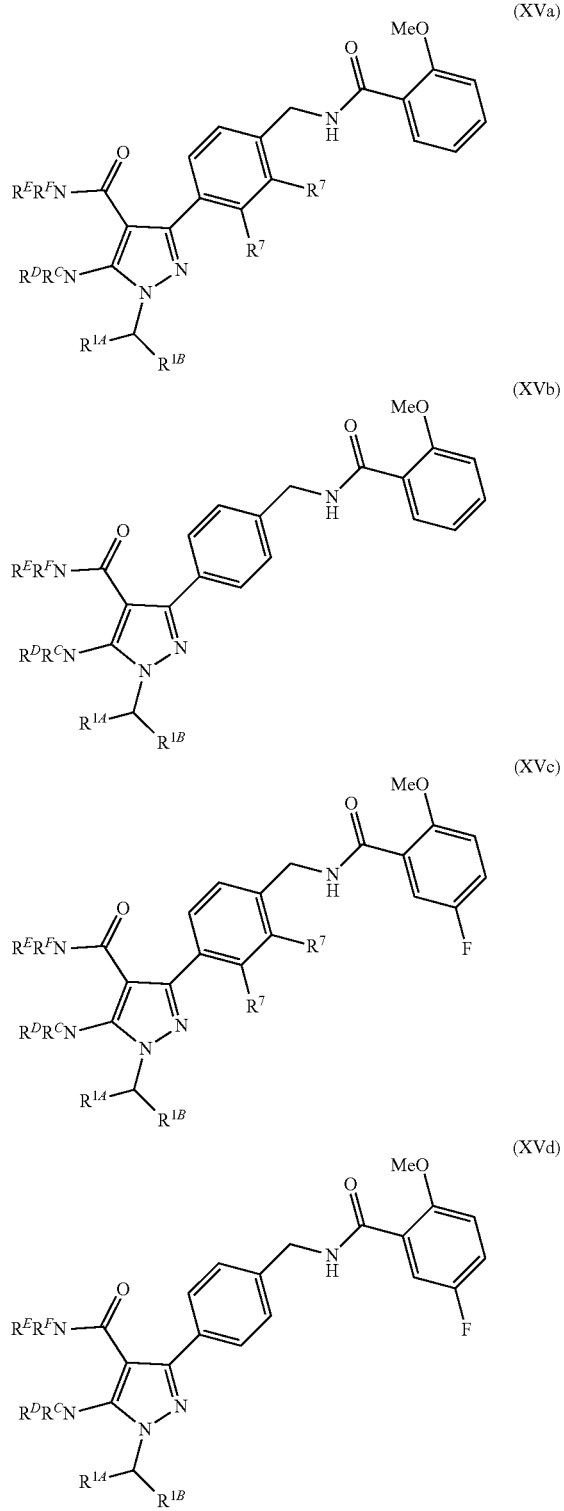

In the compounds of formulae (XVa), (XVb), (XVc) and (XVd) $R^C$ and $R^D$ may be H. In the compounds of formulae (XVa), (XVb), (XVc) and (XVd) $R^E$ and $R^F$ may be H. In the compounds of formulae (XVa), (XVb), (XVc) and (XVd) $R^C$ and $R^D$ may be H and $R^E$ and $R^F$ may be H.

In an embodiment the compound according to formula (I) may be compounds of formulae (XVIa), (XVIb), (XVIc) and (XVId) or pharmaceutically acceptable salts thereof:

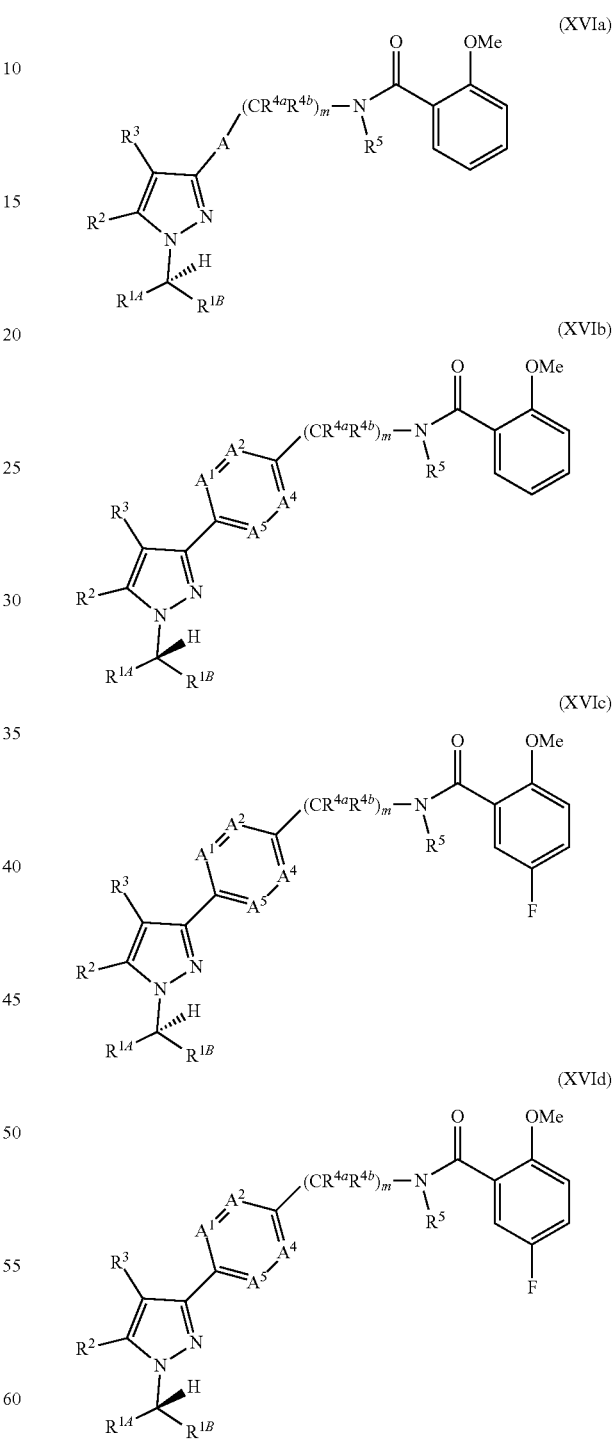

In embodiments of the compounds of formula (XVIa), (XVIb), (XVIc) and (XVId) $A^1$, $A^2$, $A^4$ and $A^5$ are CH, or $A^1$, $A^4$ and $A^5$ are CH and $A^2$ is CH, or $A^2$, $A^4$ and $A^5$ are CH and $A^1$ is CF.

In embodiments of the compounds of formula (XVIa), (XVIb), (XVIc) and (XVId) R² represents —NR^C R^D and R³ represents —C(O)NR^E R^F. Optionally, R^C and R^D are H and R^E and R^F are H.
The genus of compounds represented by formula (X), i.e. where R¹ is —CHR^{1A}R^{1B}, is an active genus.
Preferred compounds of the invention include:
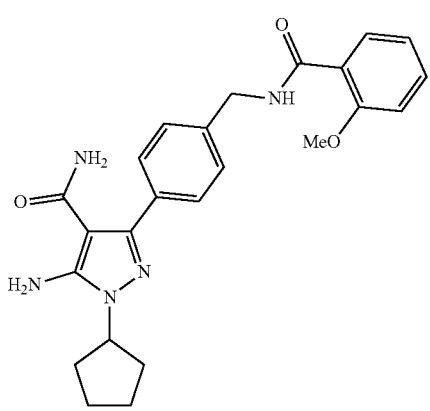
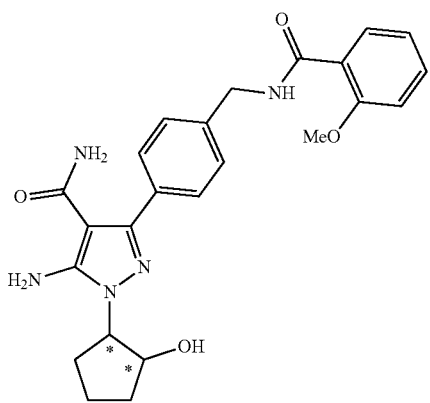
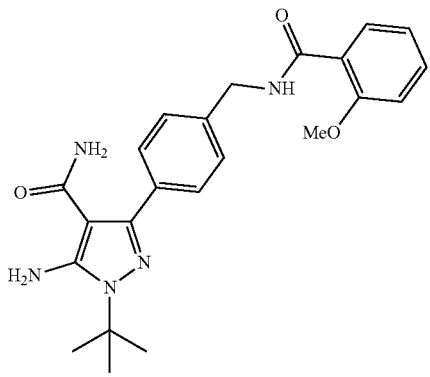
-continued
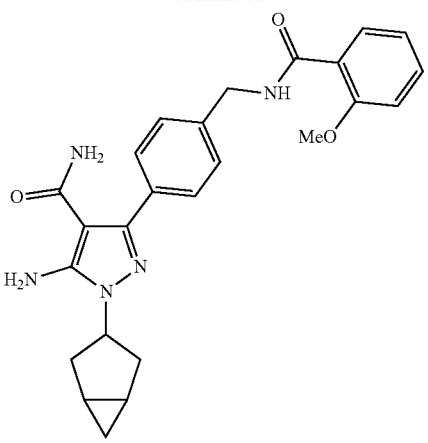
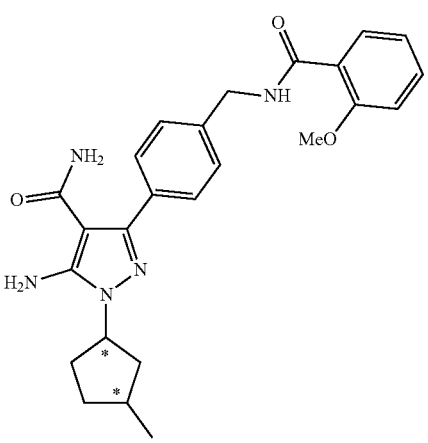
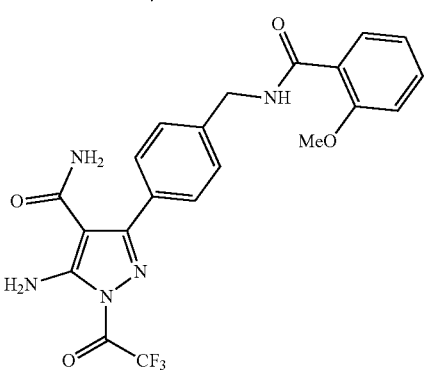
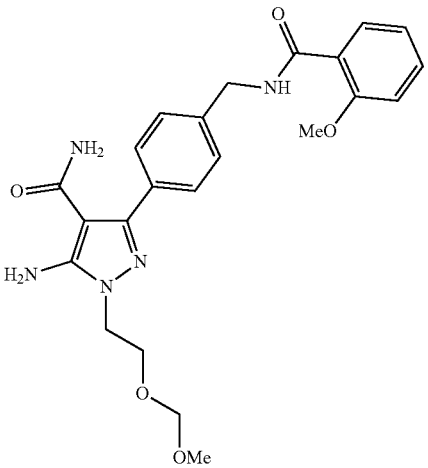

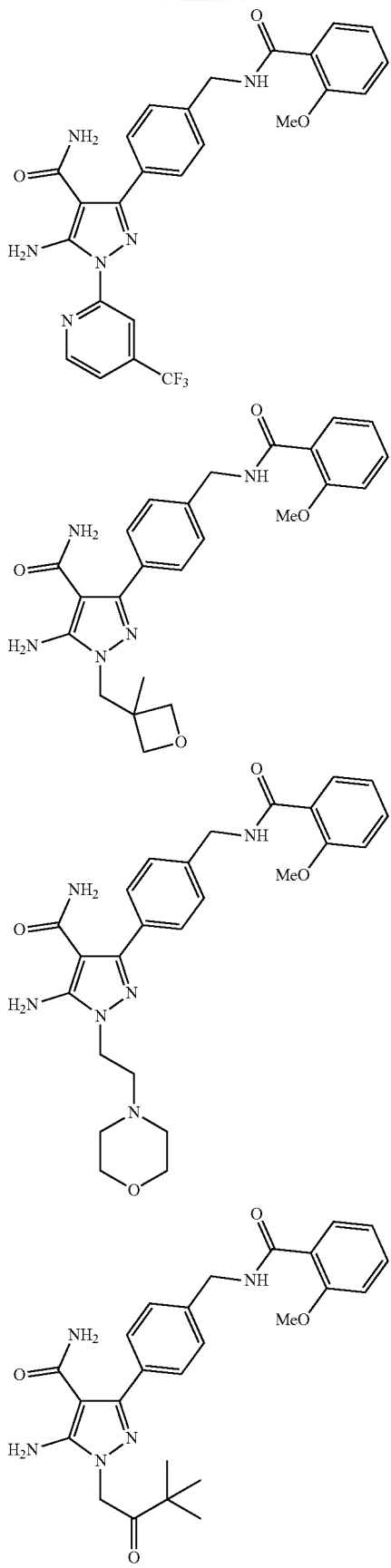
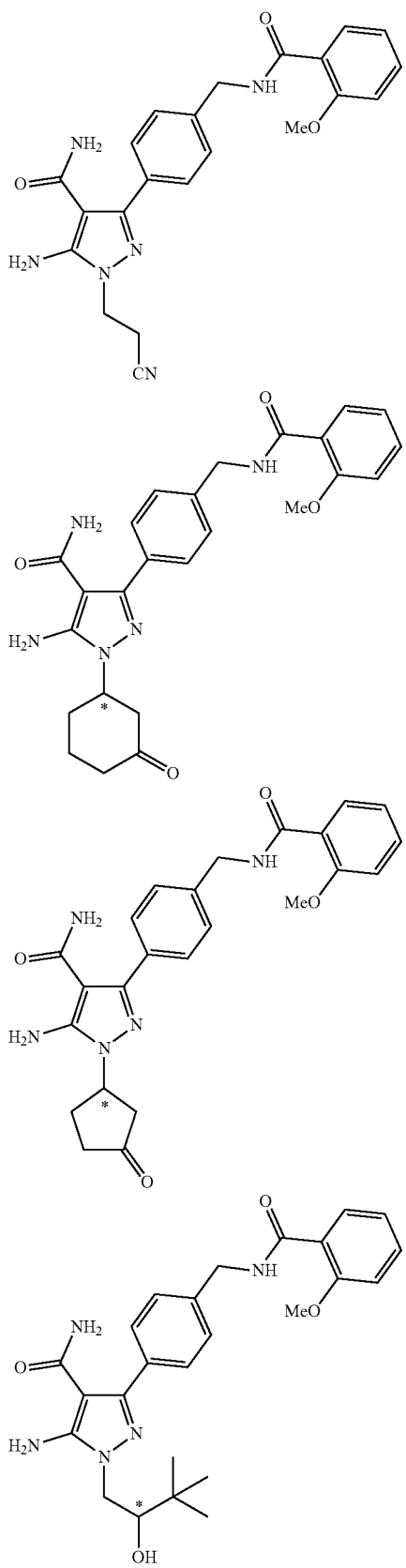

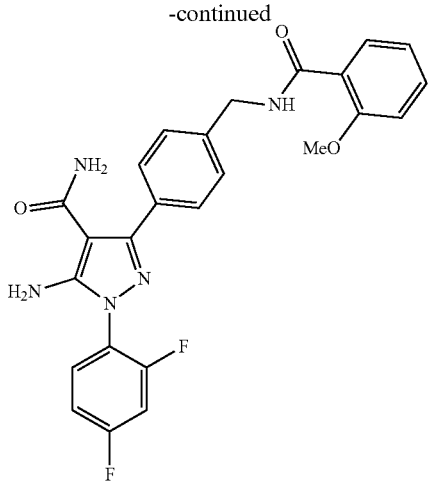
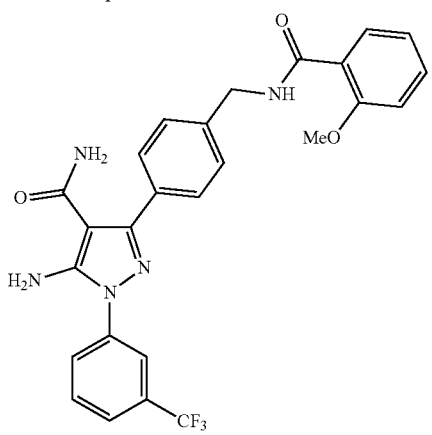
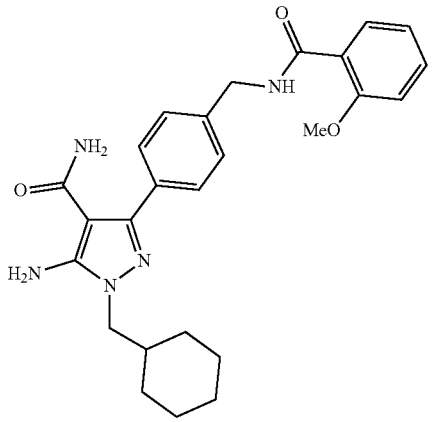
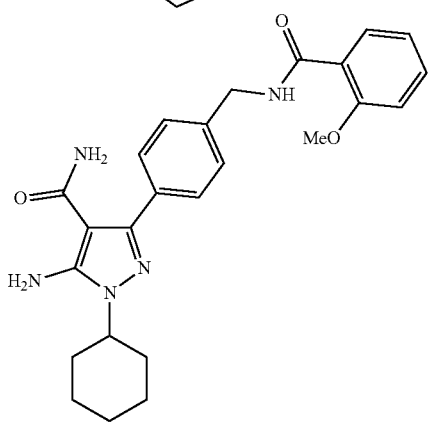
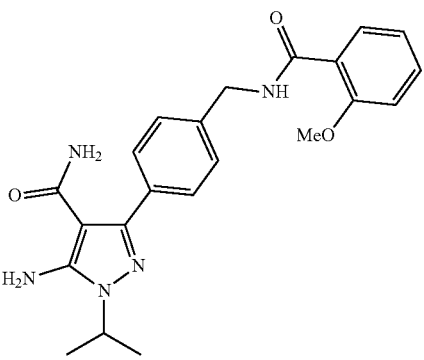
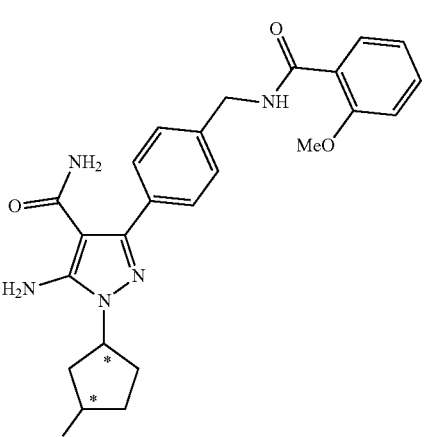
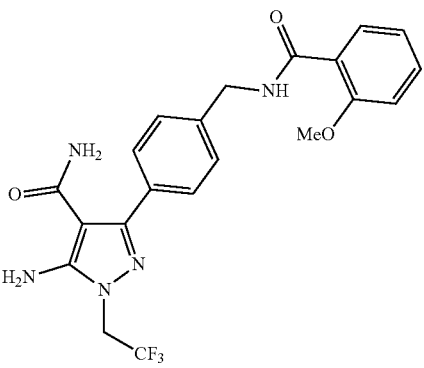
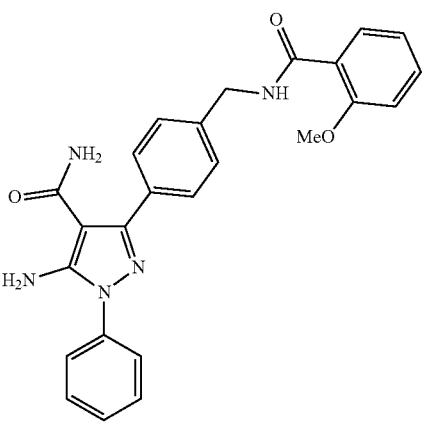

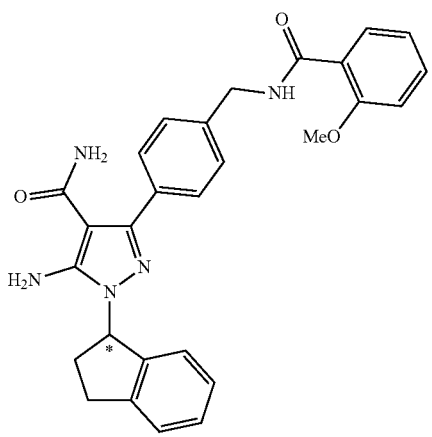
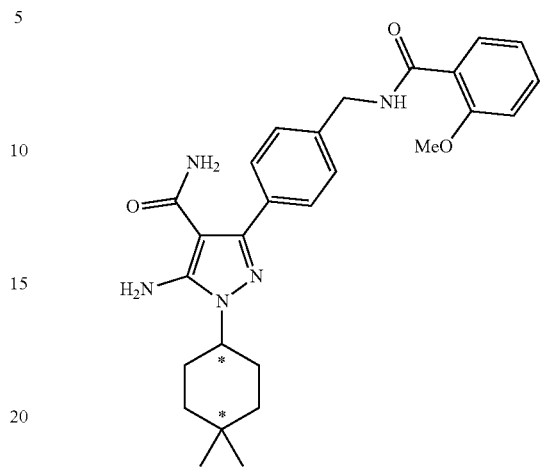
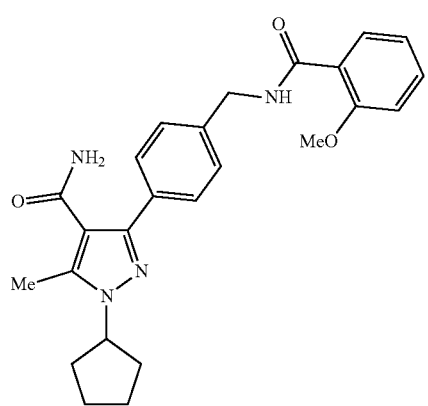
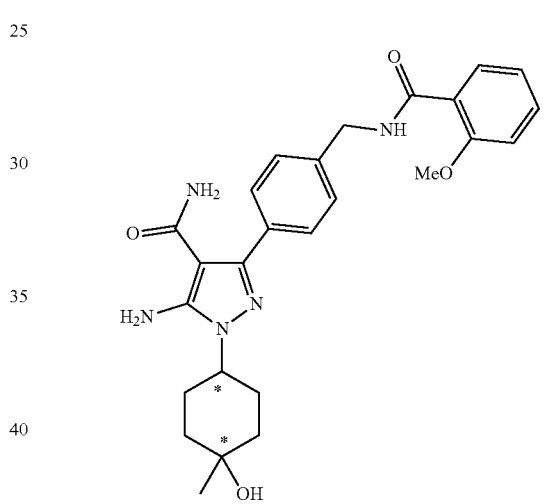
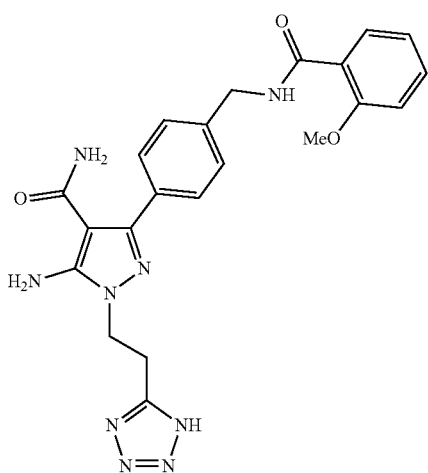
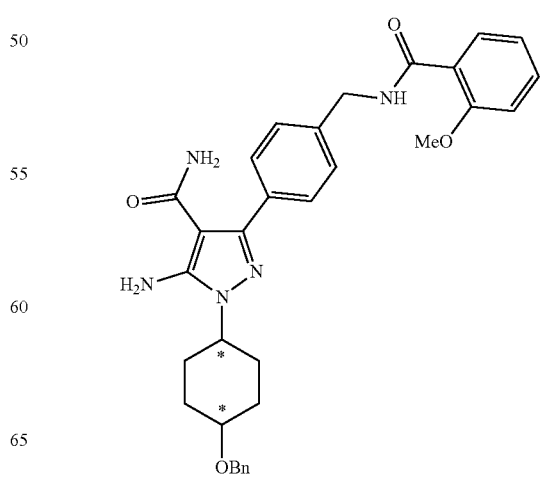

-continued
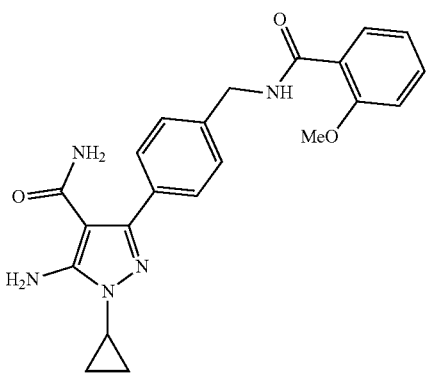
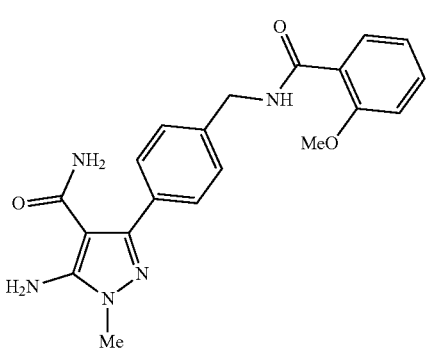
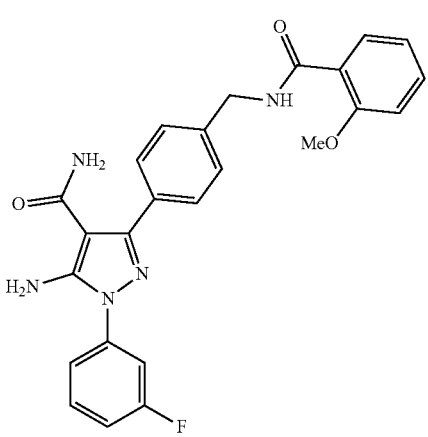
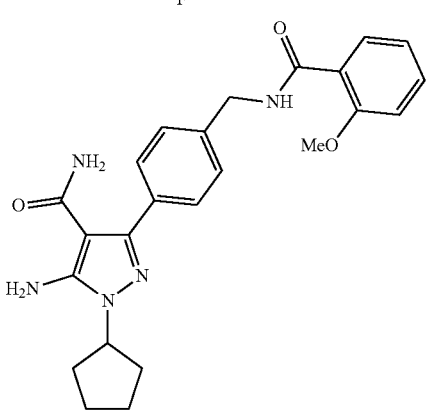
-continued
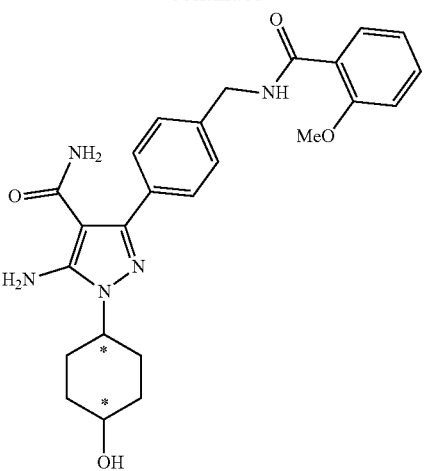
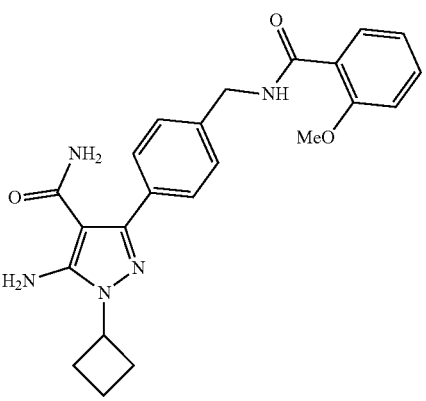
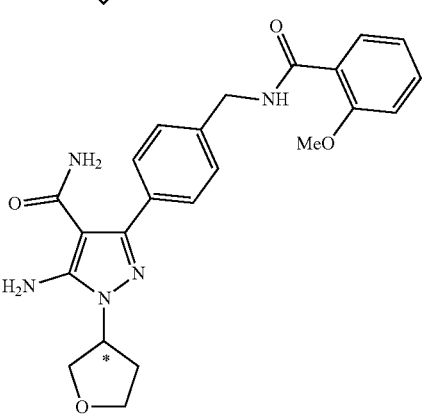
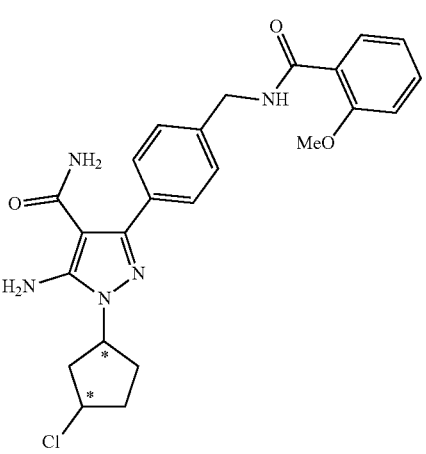

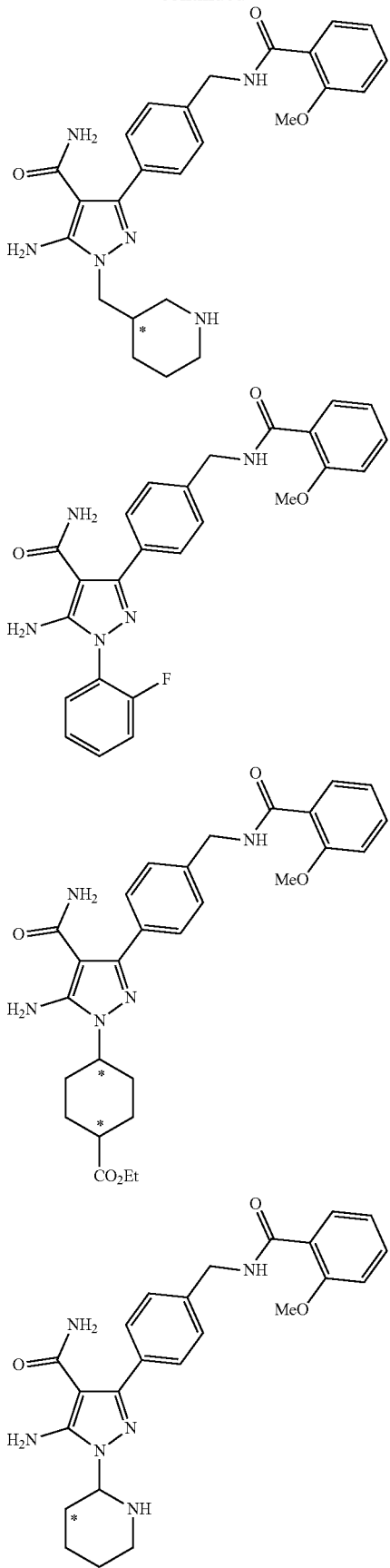

45
-continued
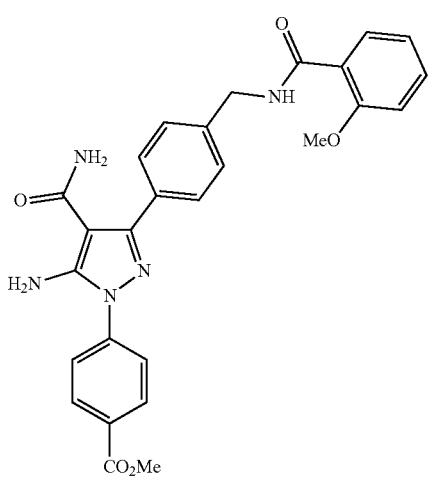
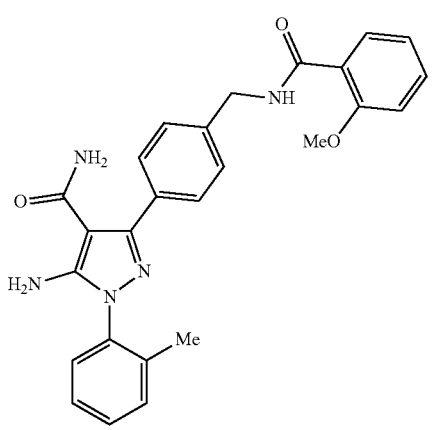
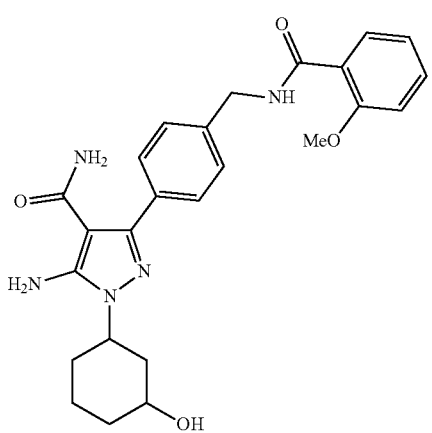
46
-continued
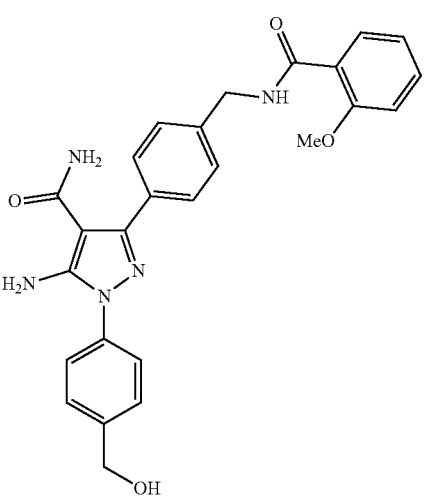
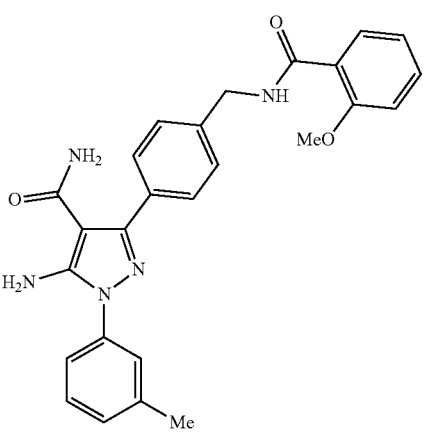
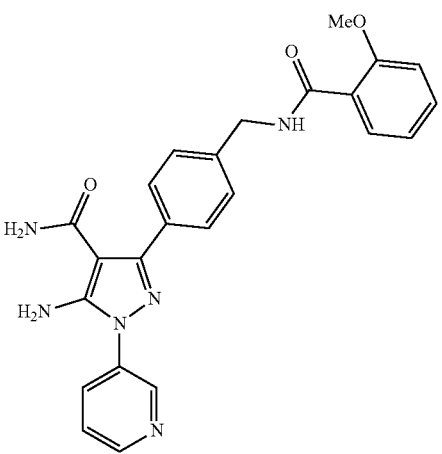

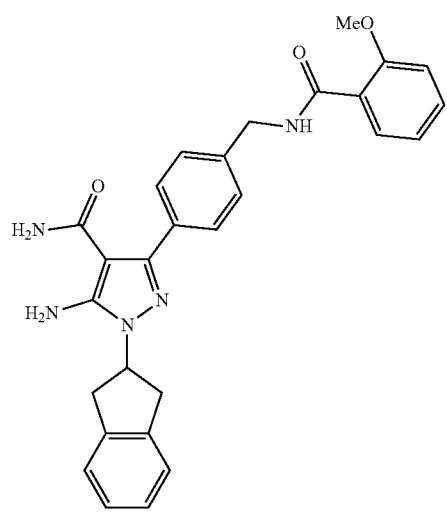
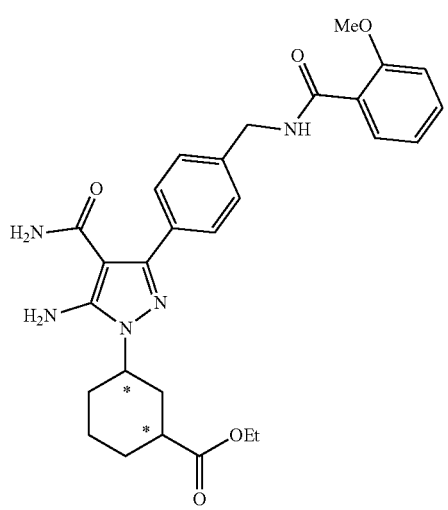
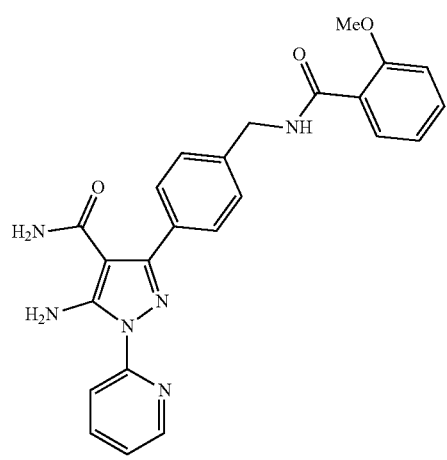
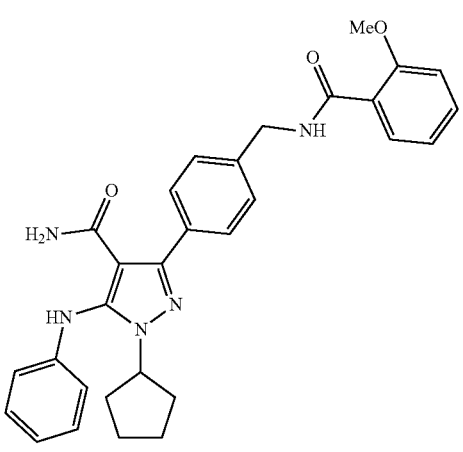
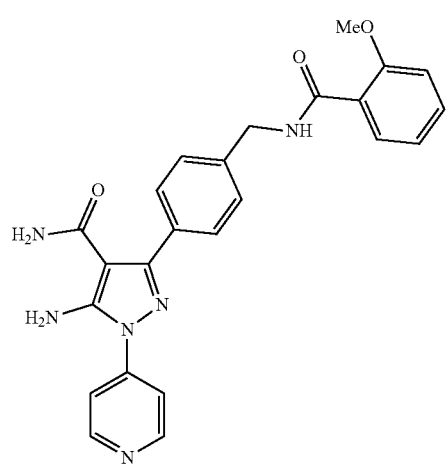
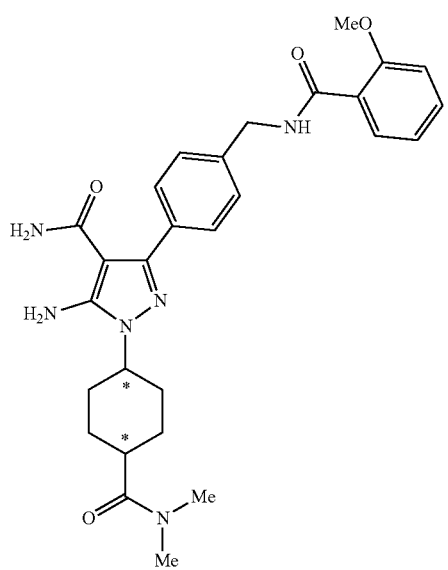

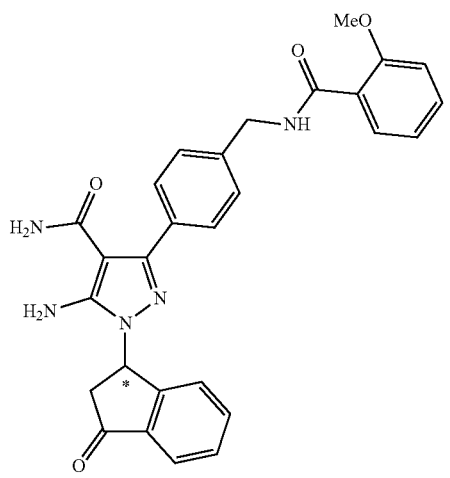
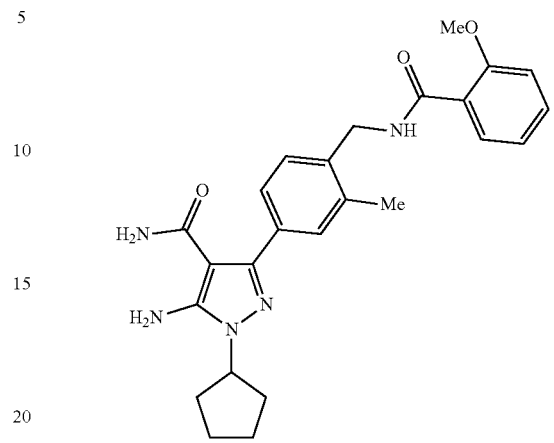
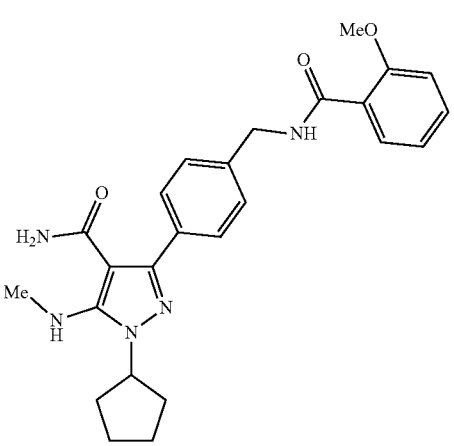
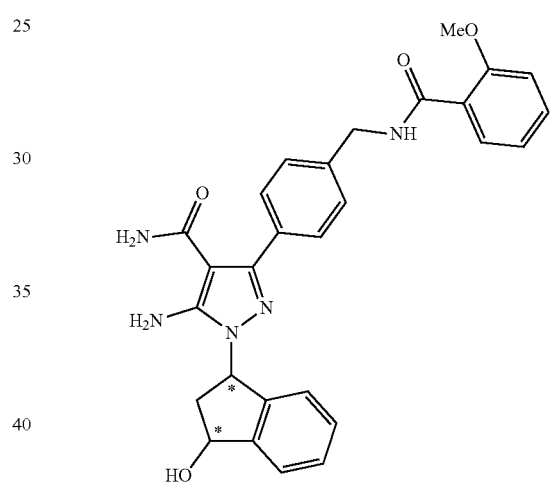
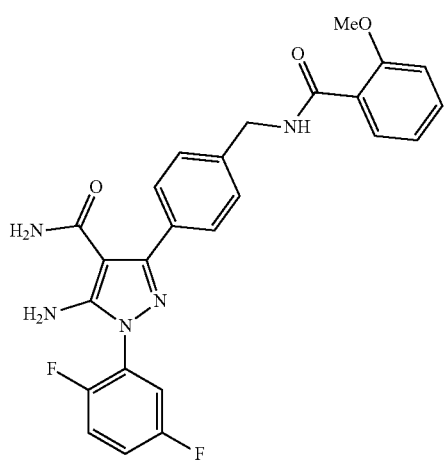
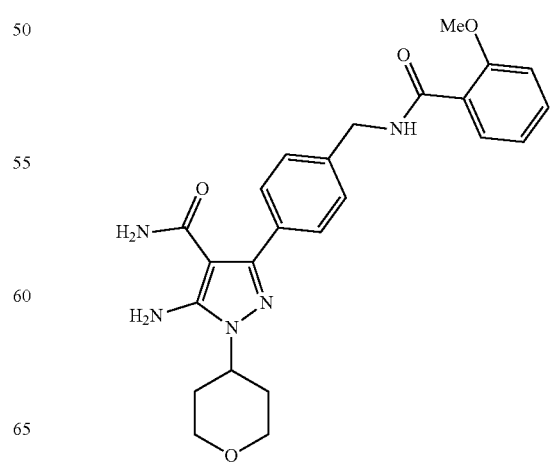

| 51 -continued | 52 -continued |
|---|---|
| 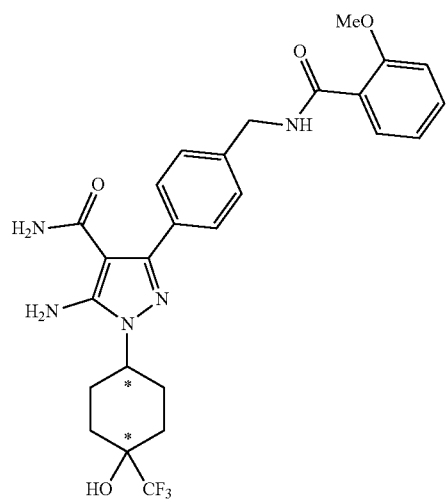 | 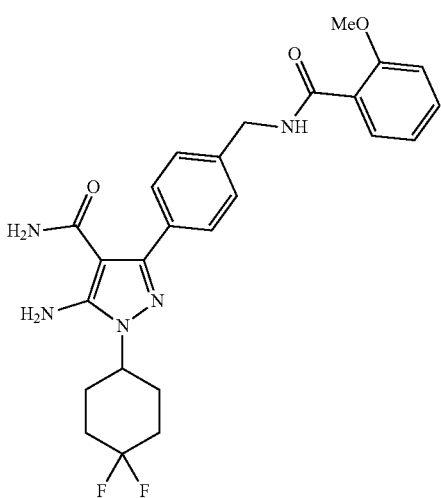 |
| 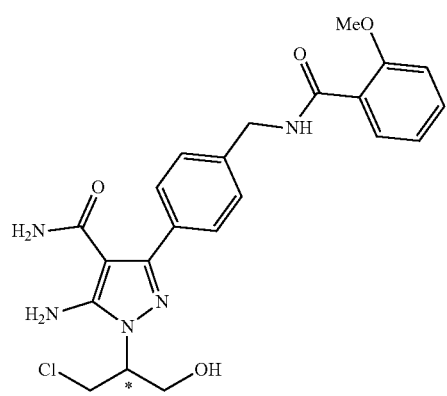 | 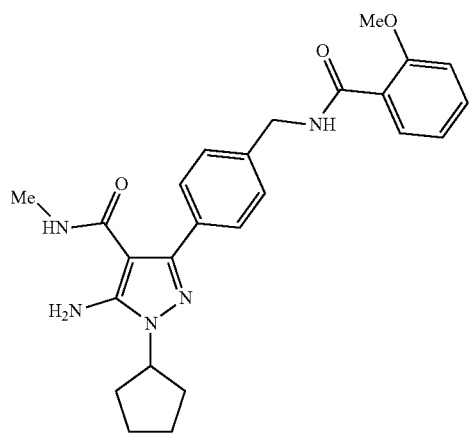 |
| 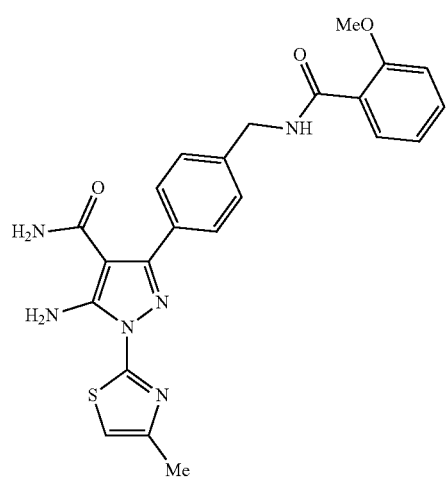 | 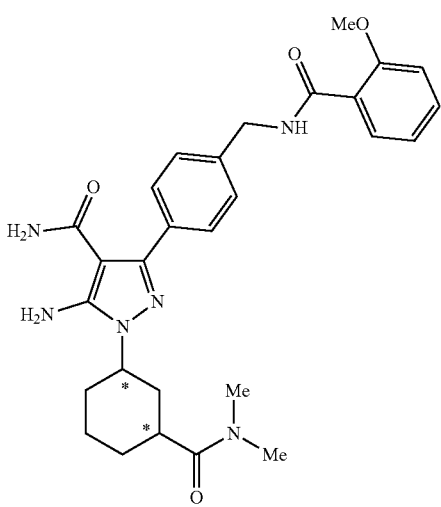 |

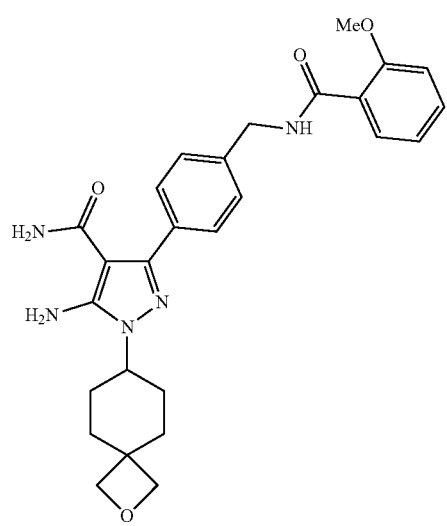
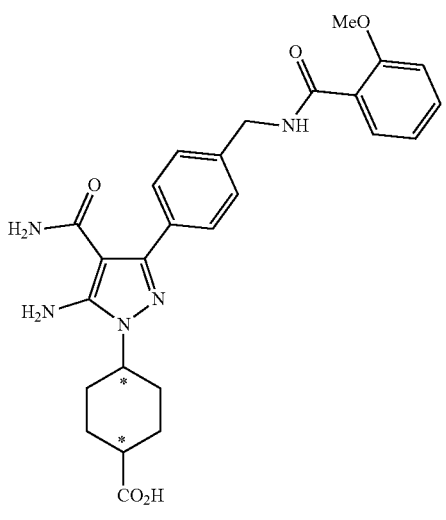
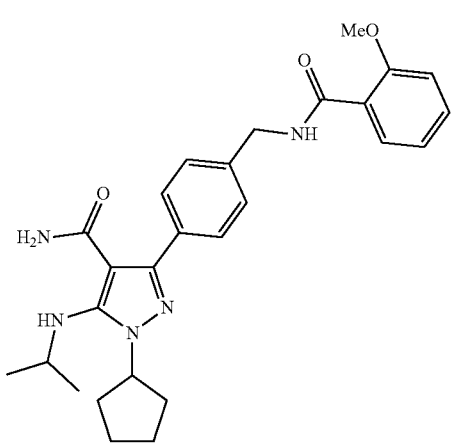
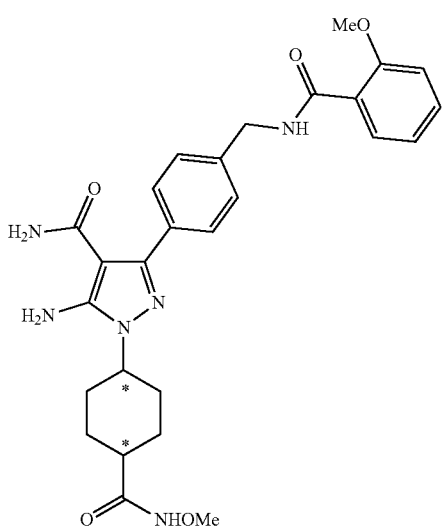
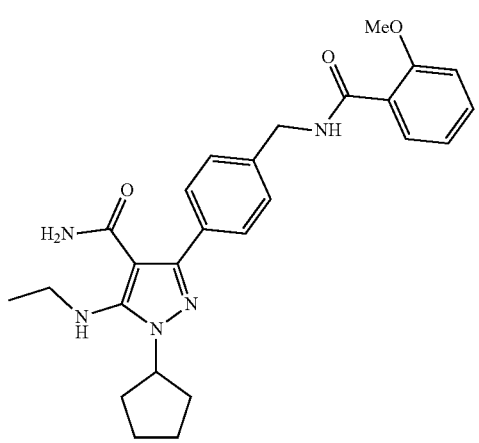
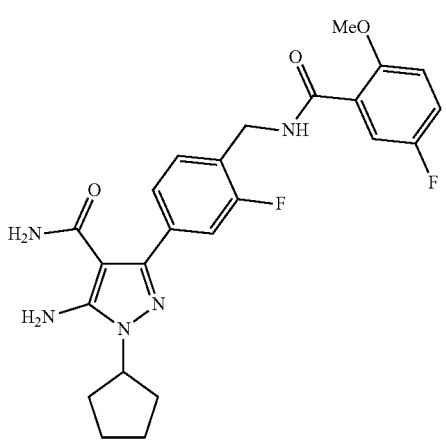

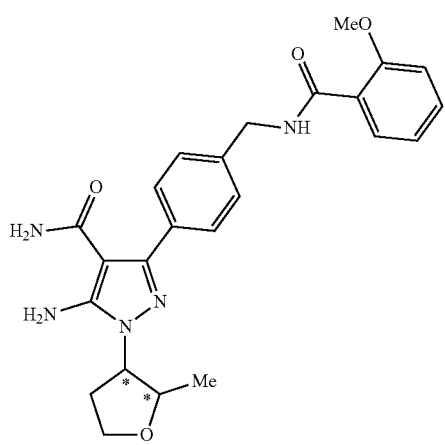
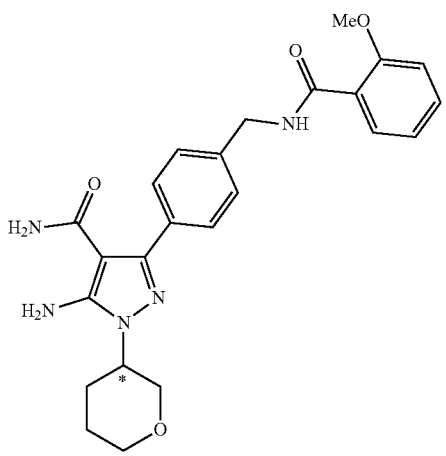
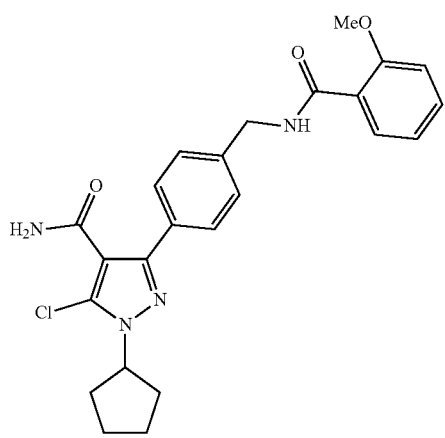
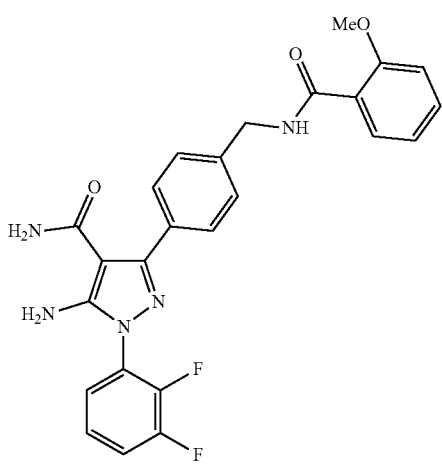
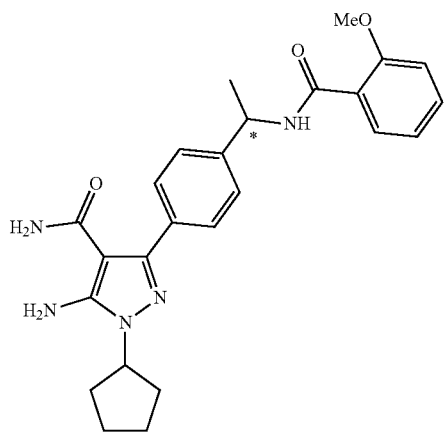
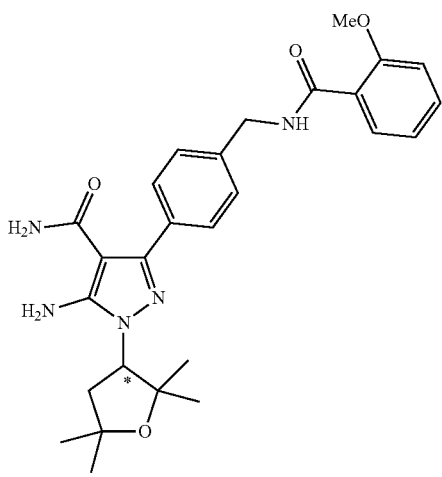

57
-continued
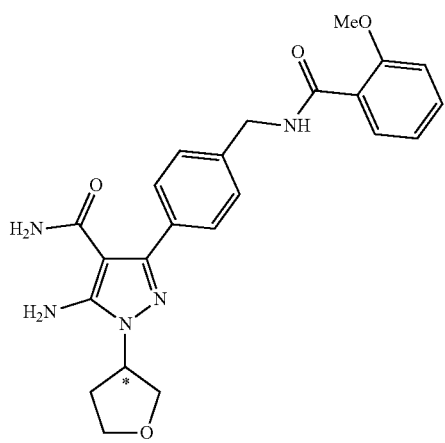
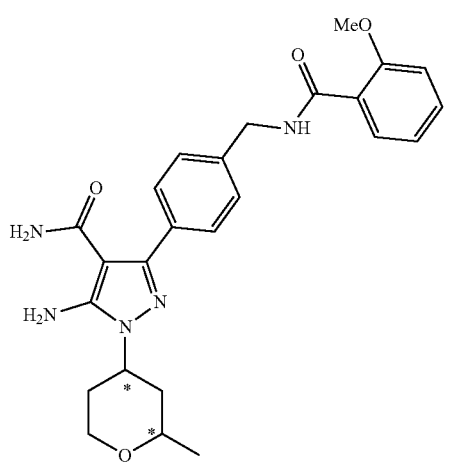
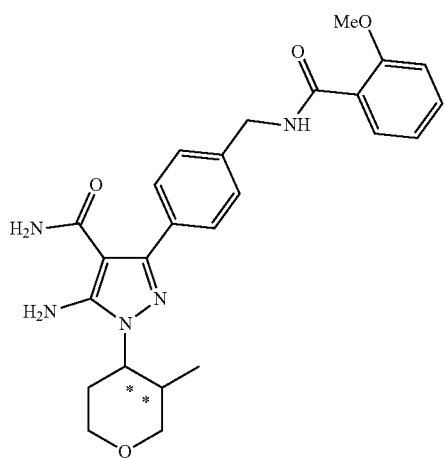
58
-continued
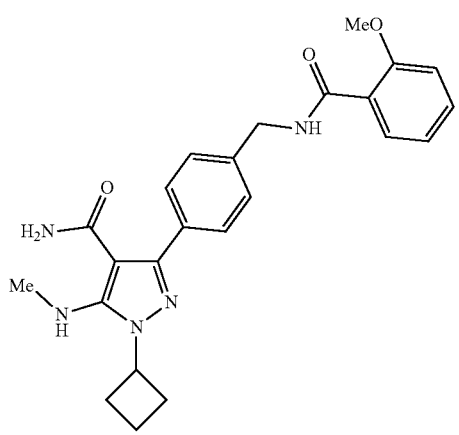
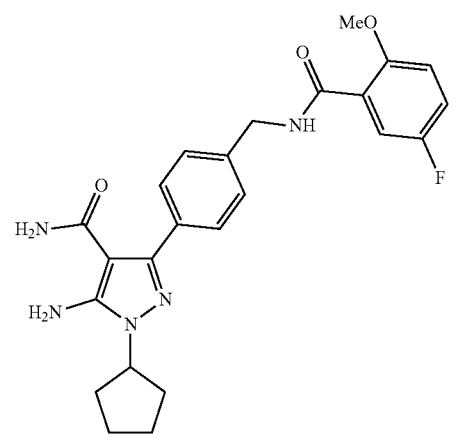
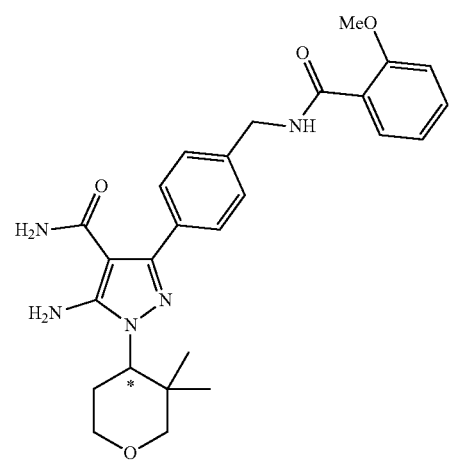

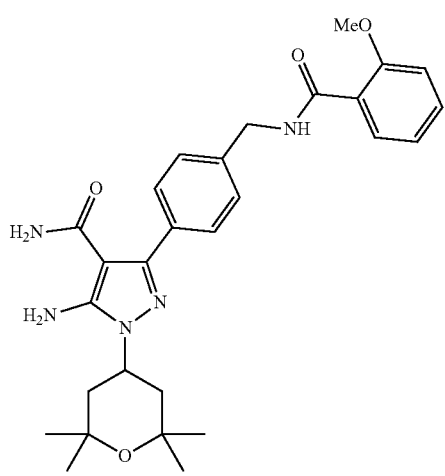
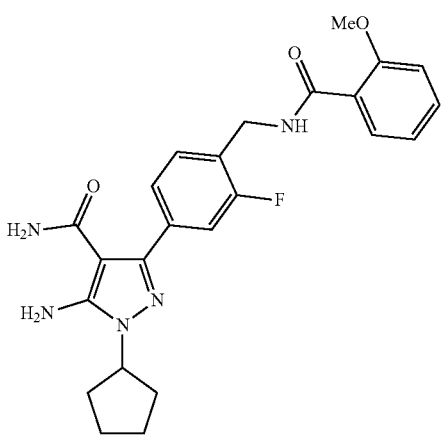
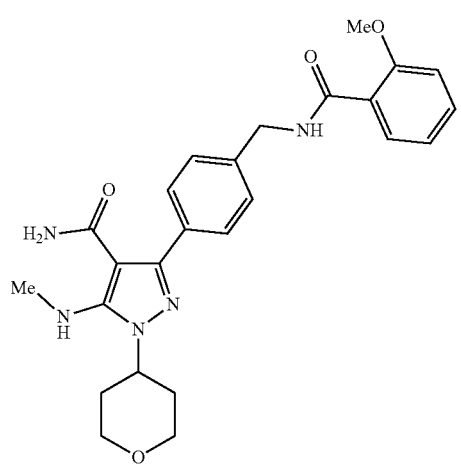
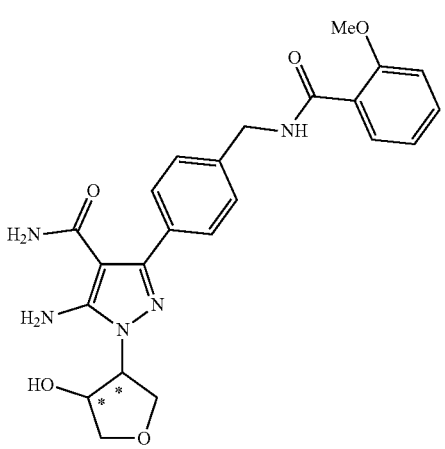
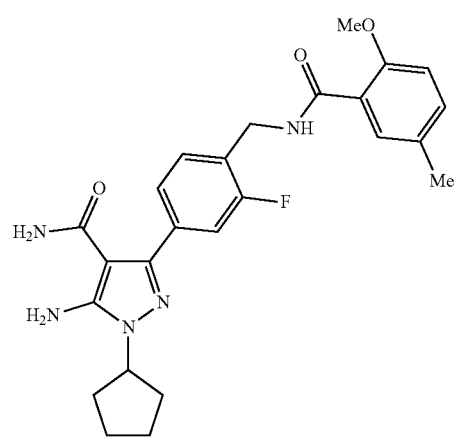
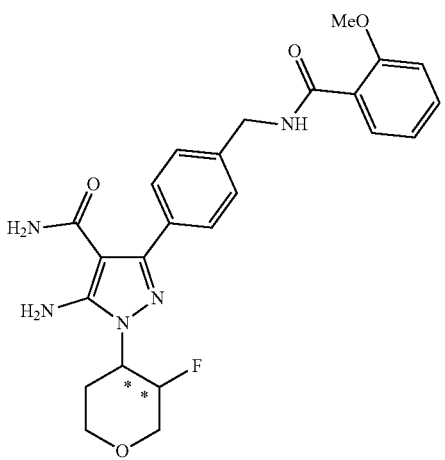

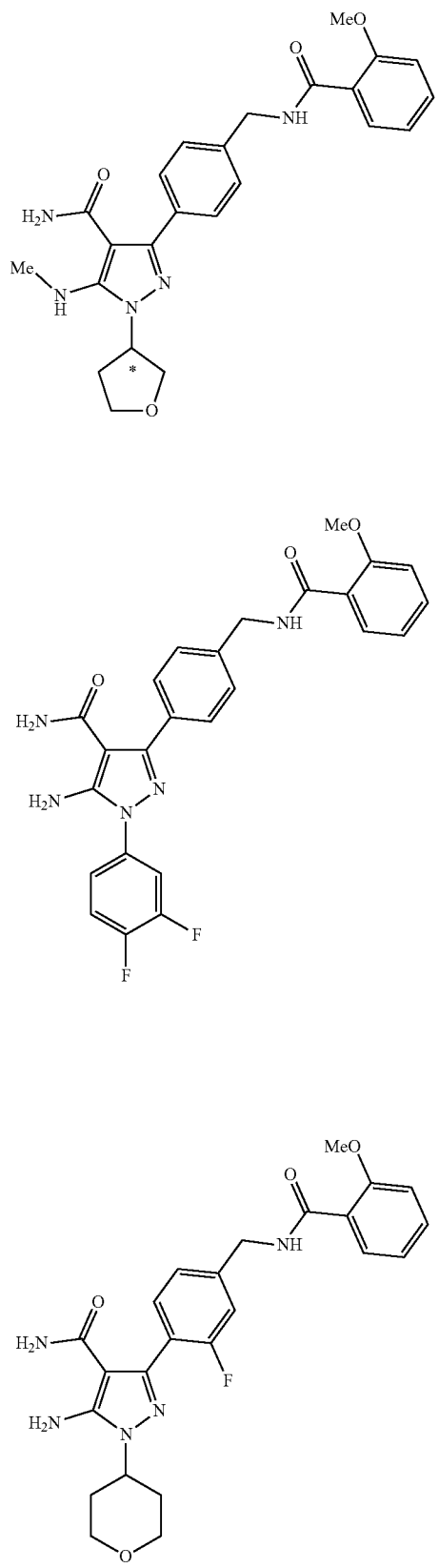
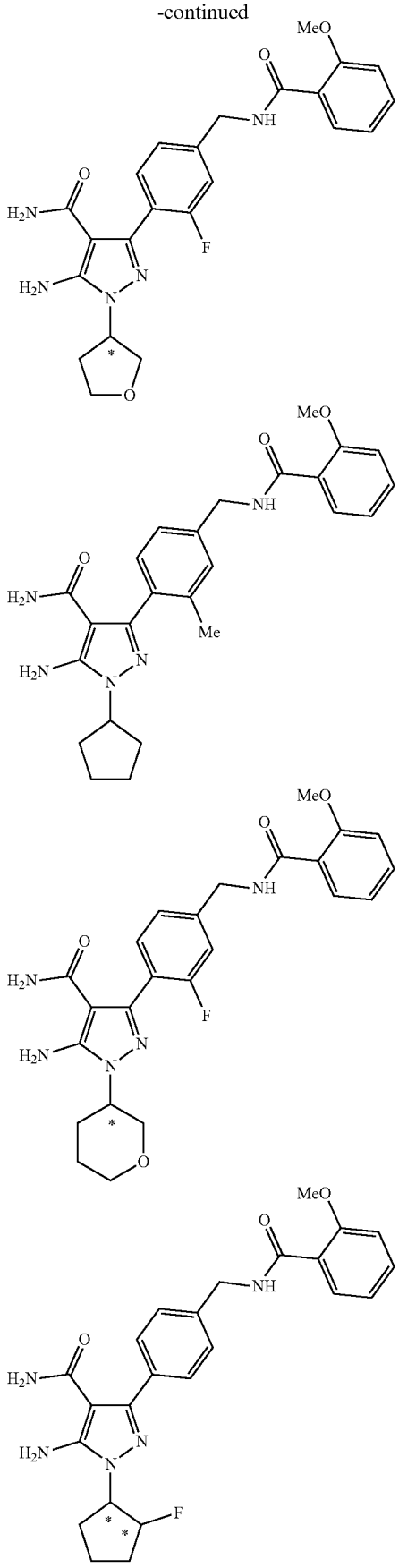

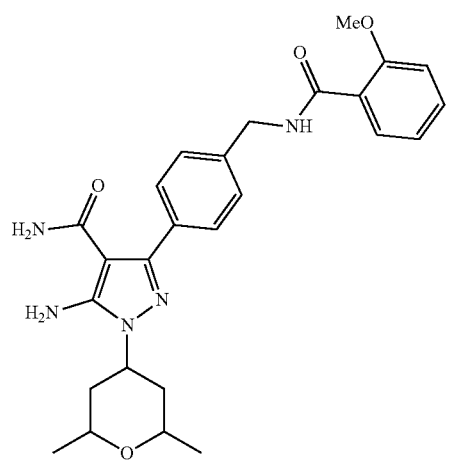
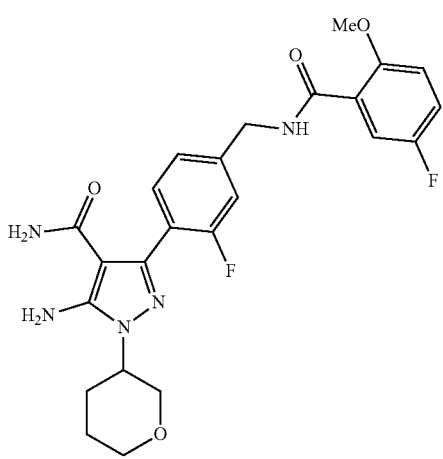
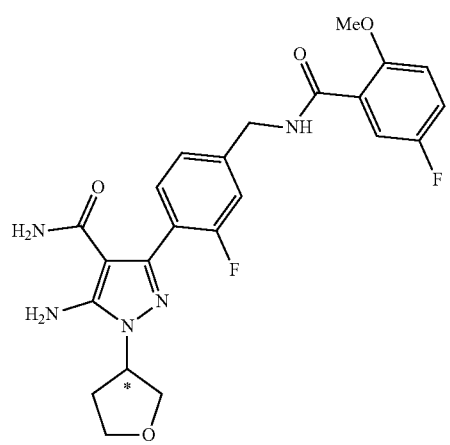
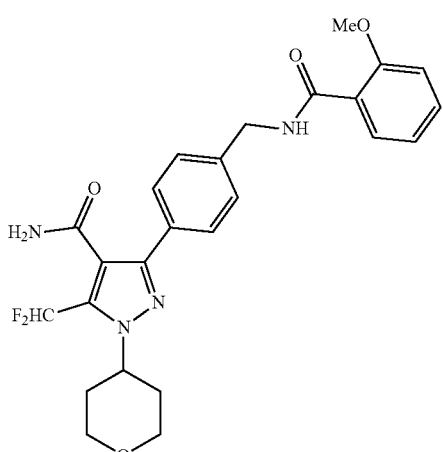
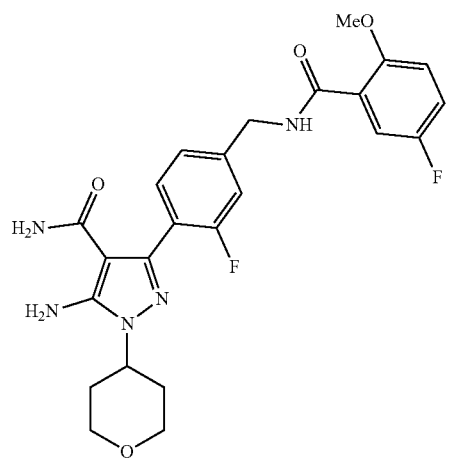
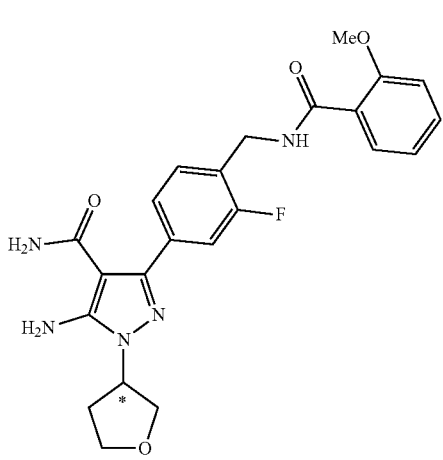

-continued
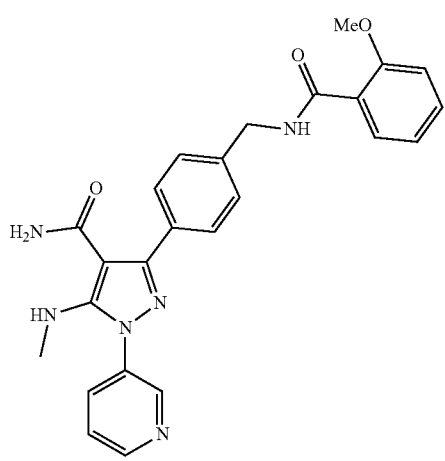
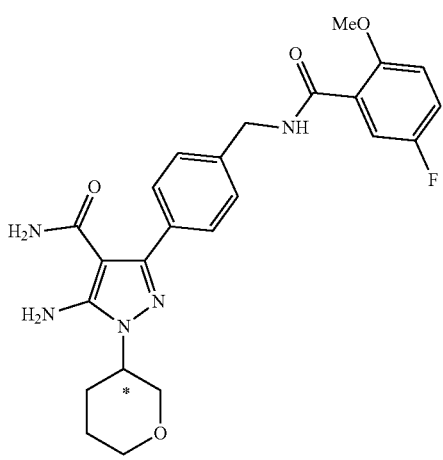
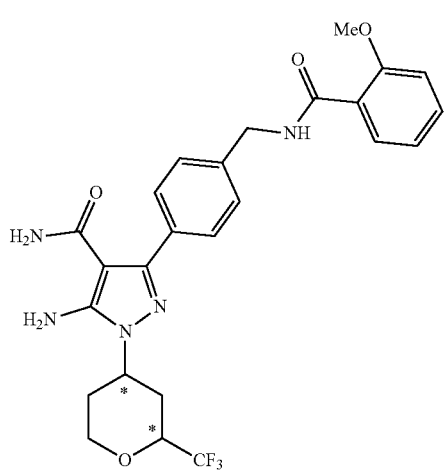
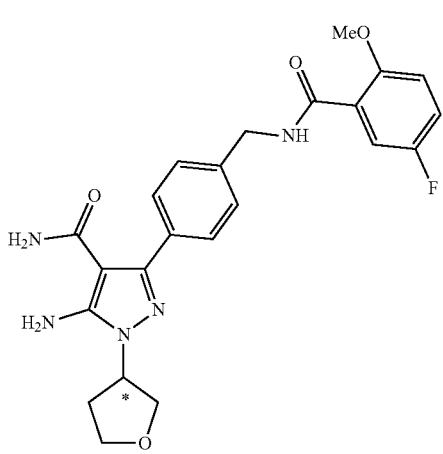
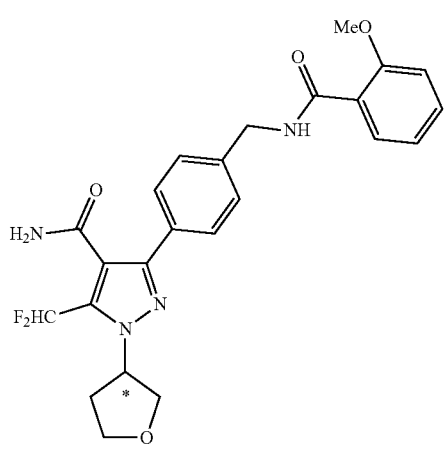
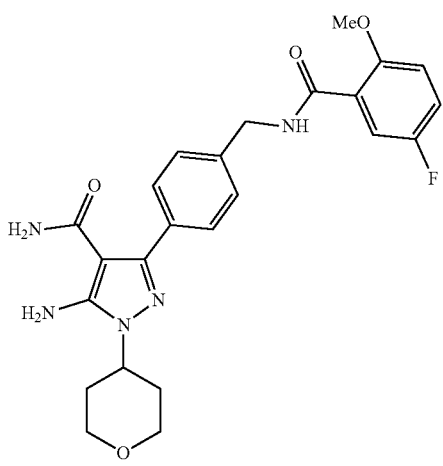

-continued
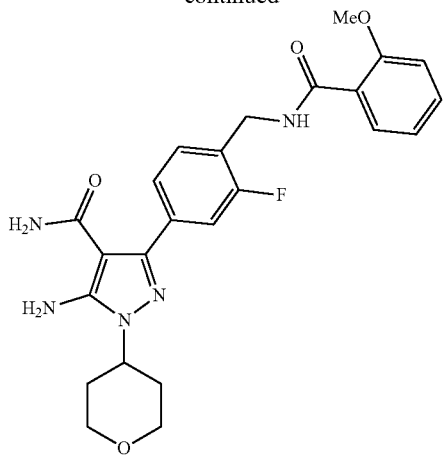
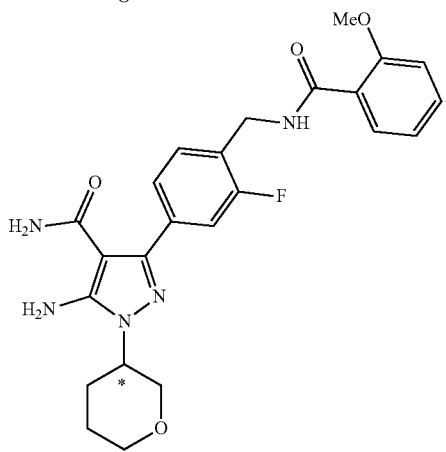
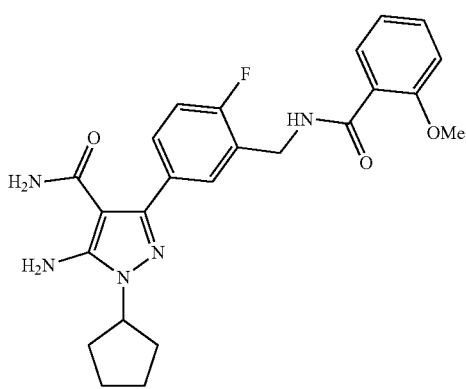
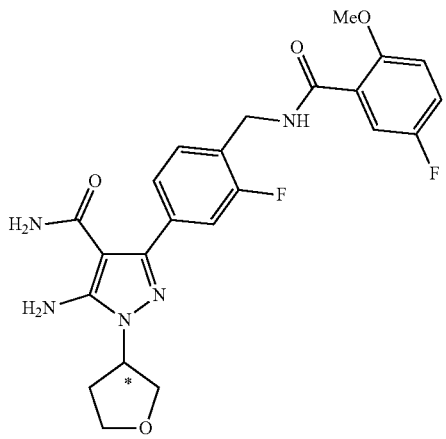
-continued
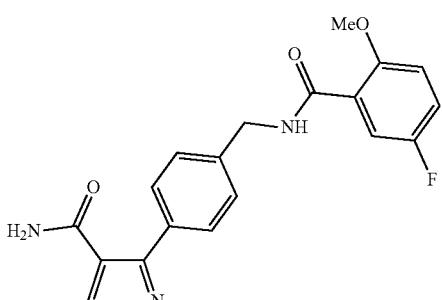
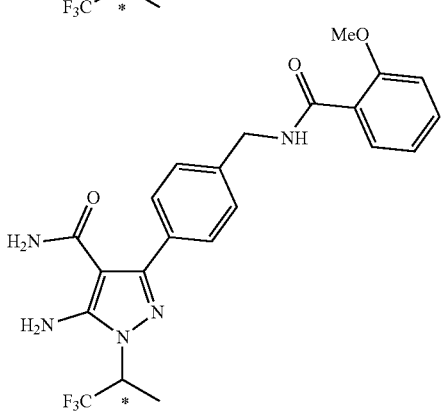
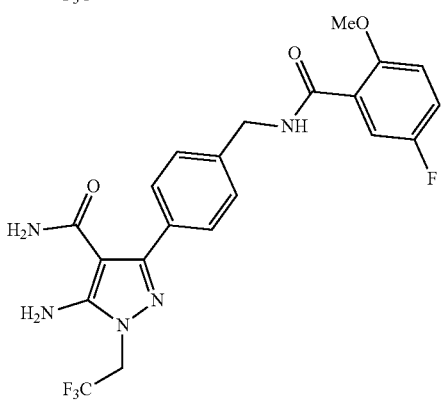
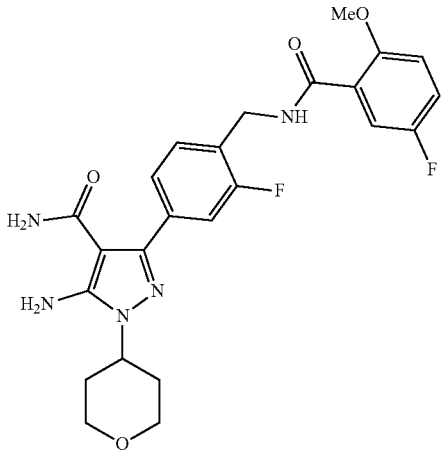

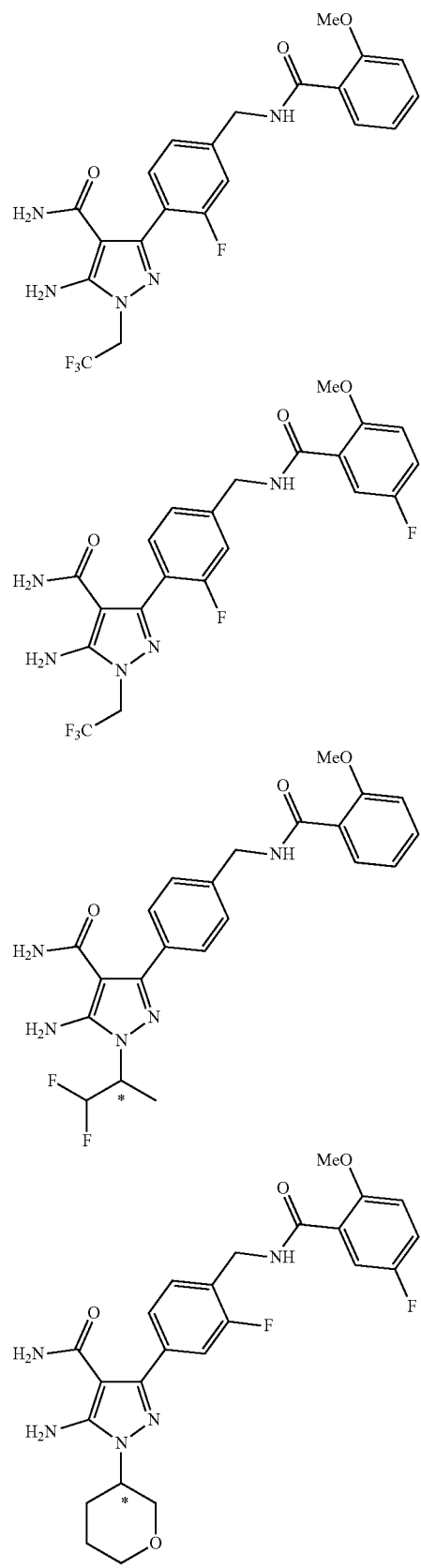
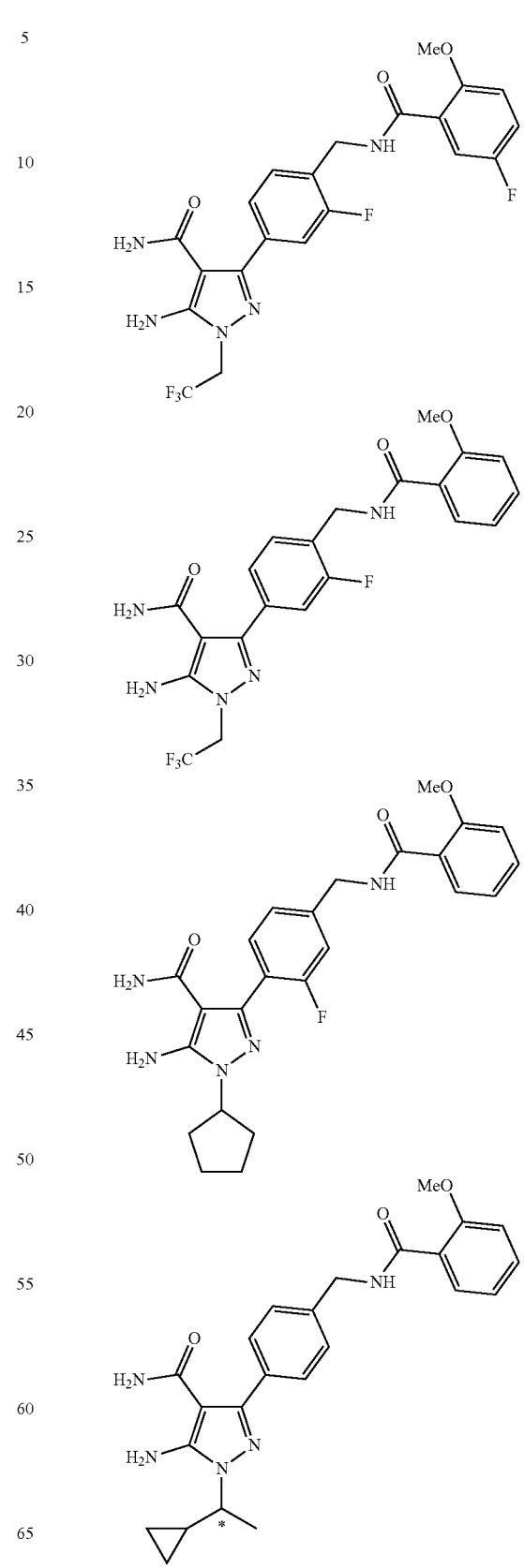

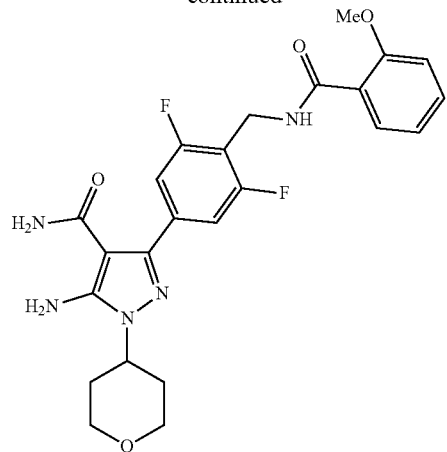
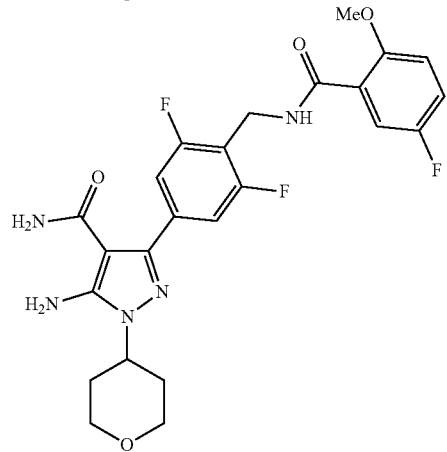
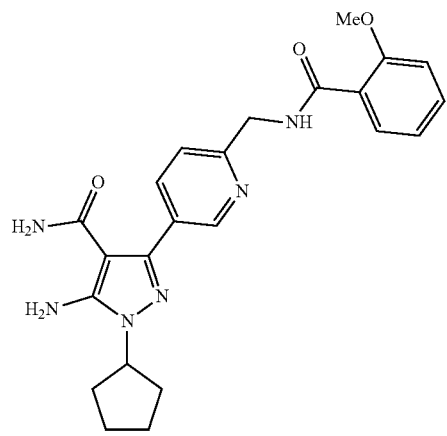
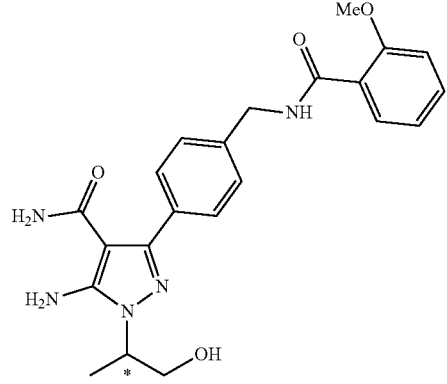
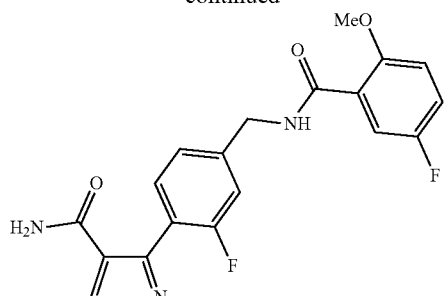
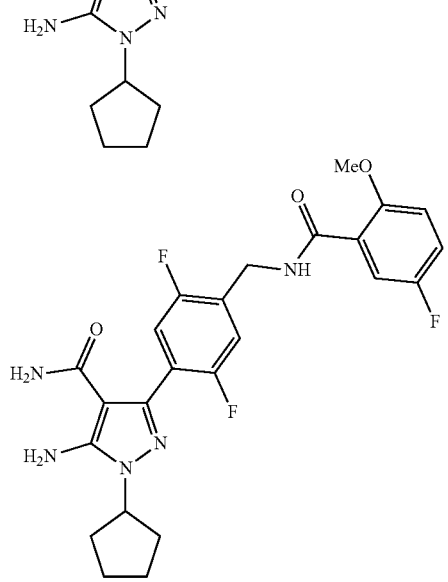
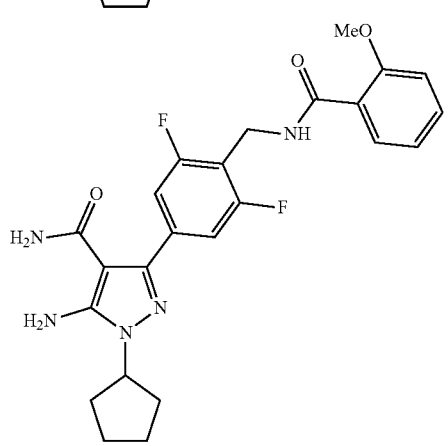
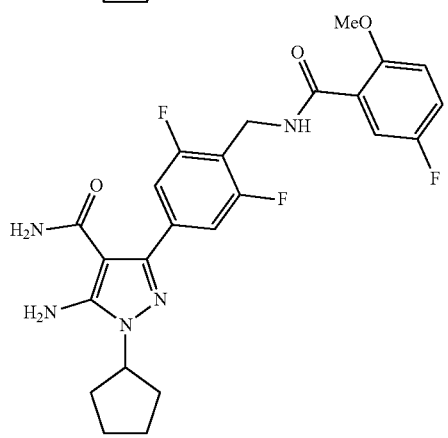

73
-continued
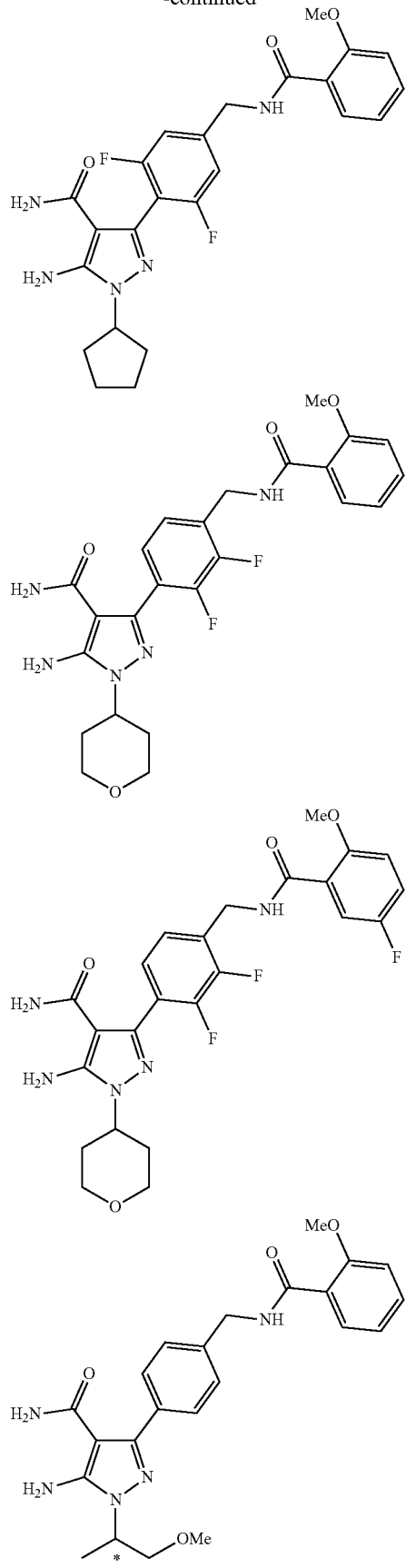
74
-continued
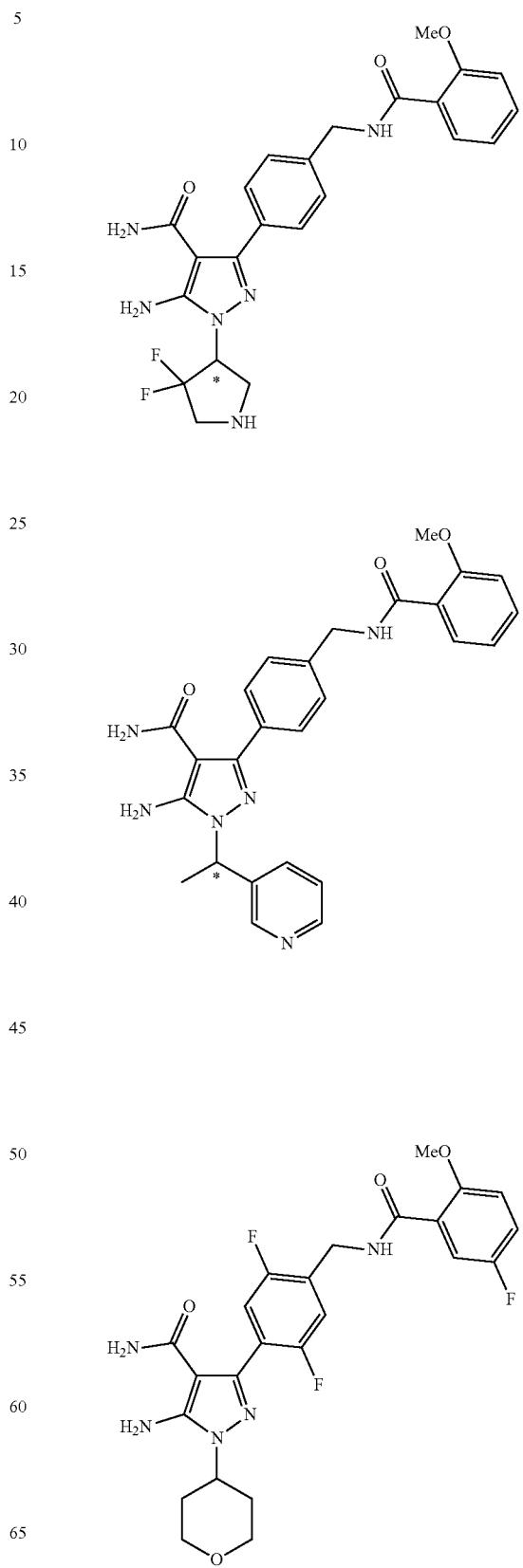

-continued
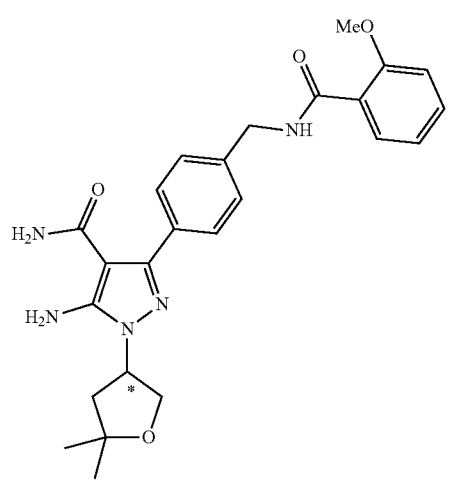
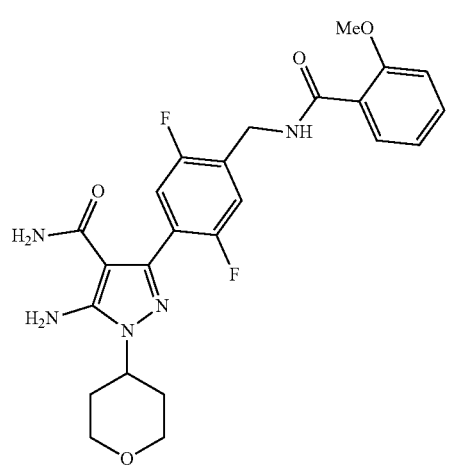
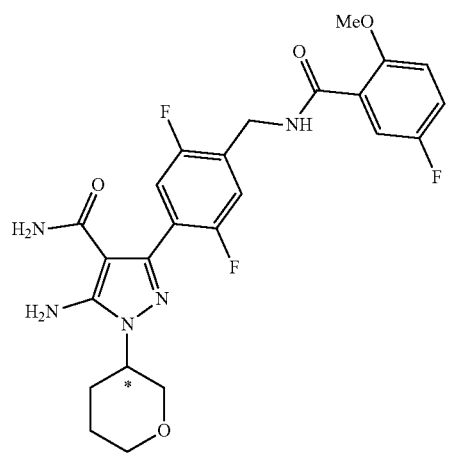
-continued
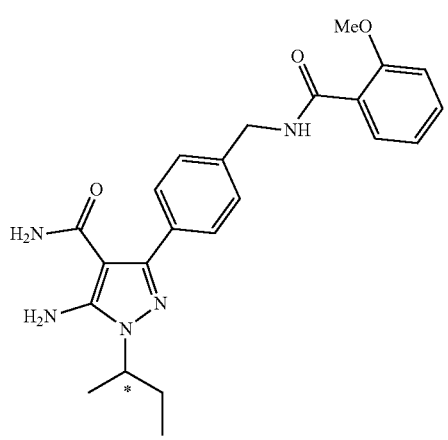
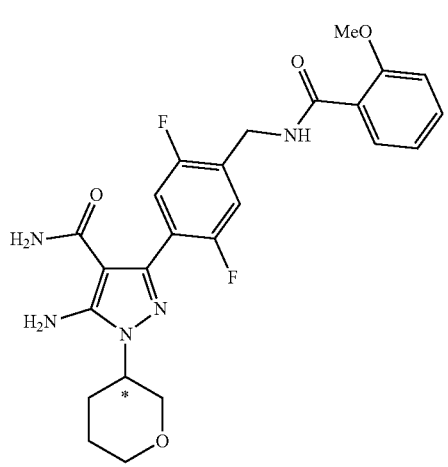
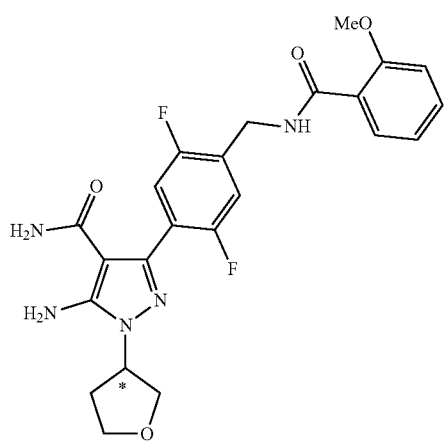

77
-continued
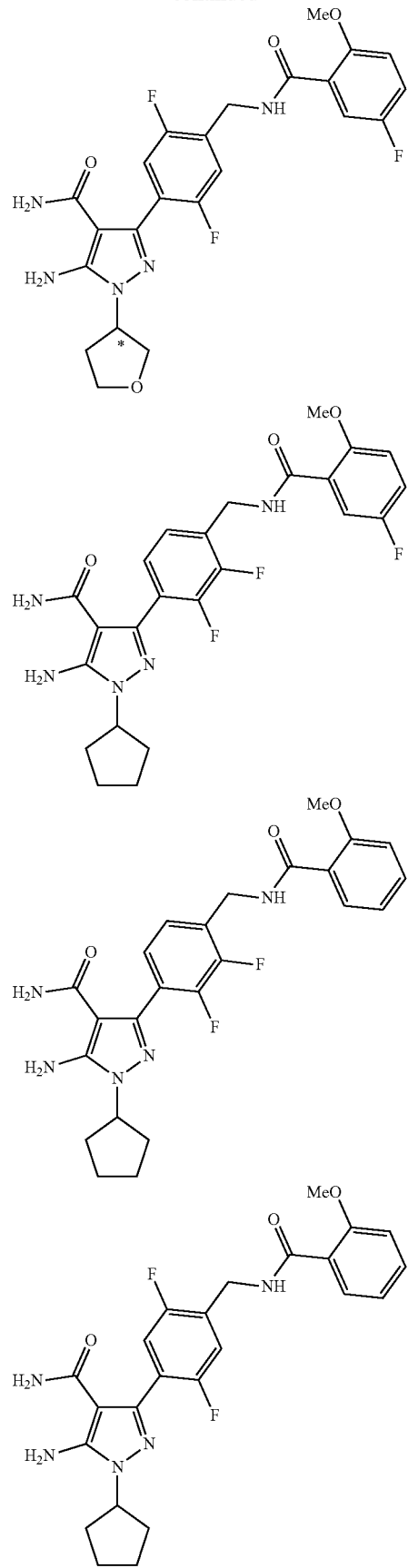 [SMILES: COc1ccccc1C(=O)NCc1ccc(-c2nn(C3CCCC3)c(N)c2C(N)=O)cn1 ; COc1ccccc1C(=O)NCc1ccc(-c2nn(C(C)CO)c(N)c2C(N)=O)cc1 ; COc1ccc(F)cc1C(=O)NCc1ccc(-c2nn(C3CCCC3)c(N)c2C(N)=O)c(F)c1 ; COc1ccc(F)cc1C(=O)NCc1cc(F)c(-c2nn(C3CCCC3)c(N)c2C(N)=O)cc1F]
78
-continued
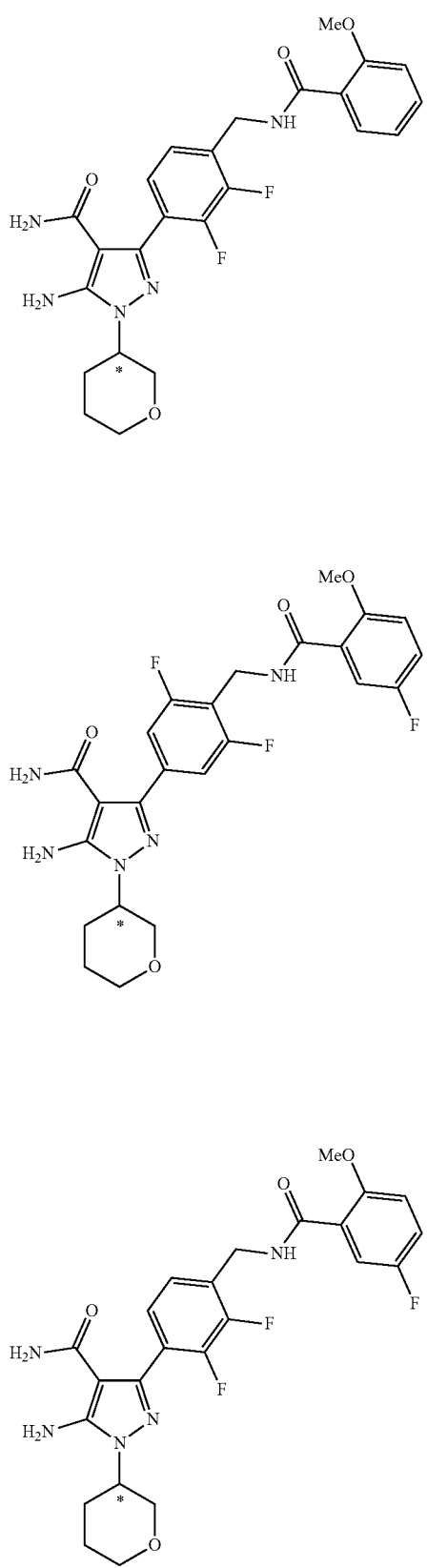

79
-continued
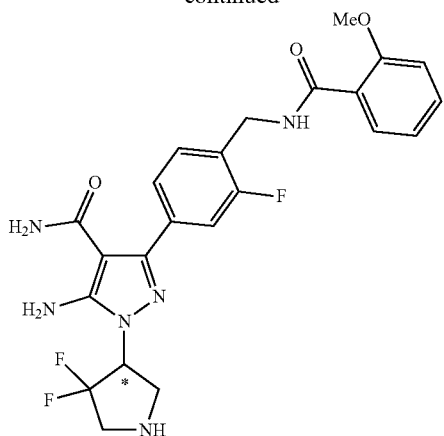
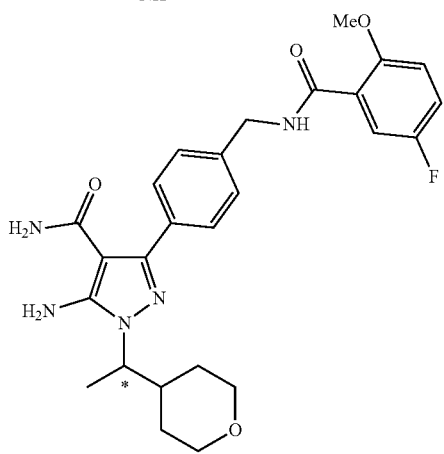
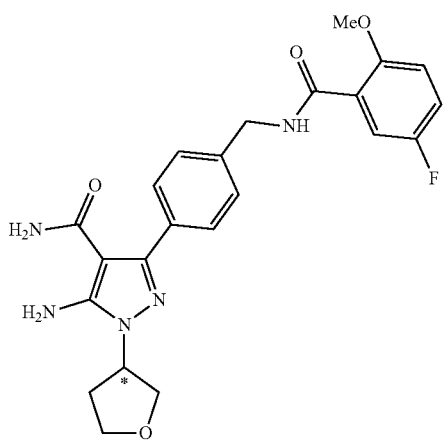
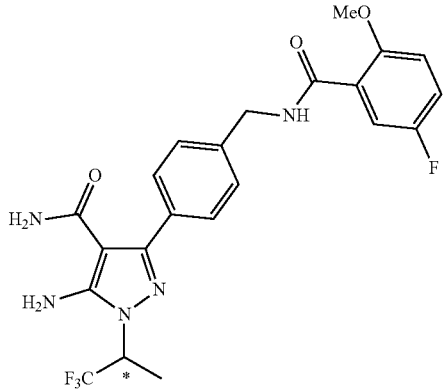
80
-continued
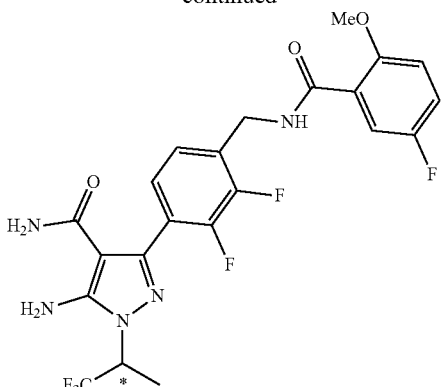
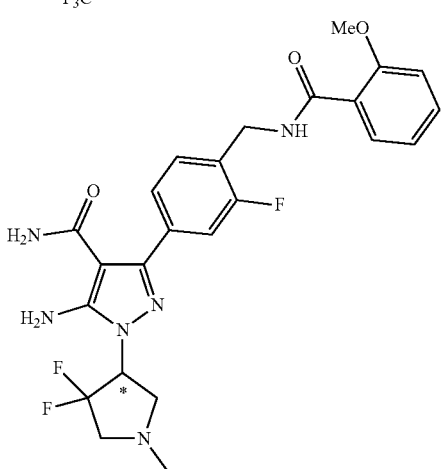
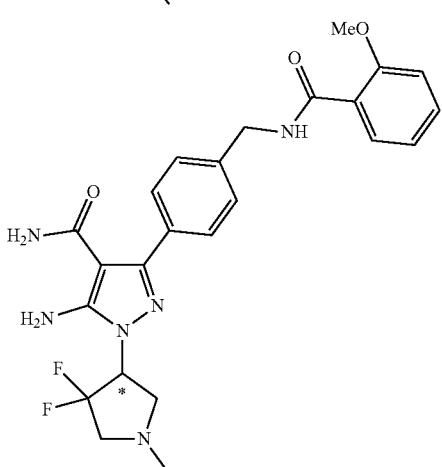
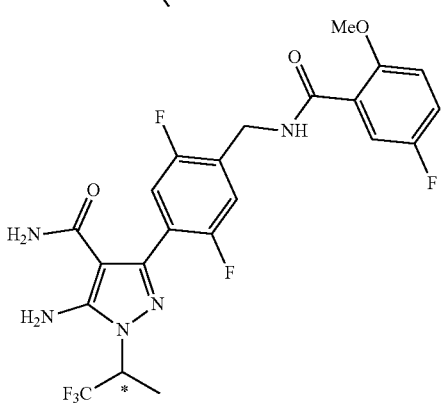

81
-continued
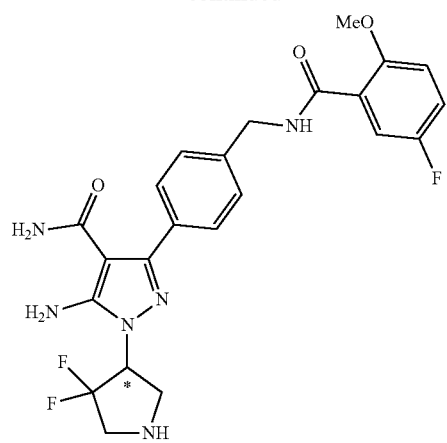
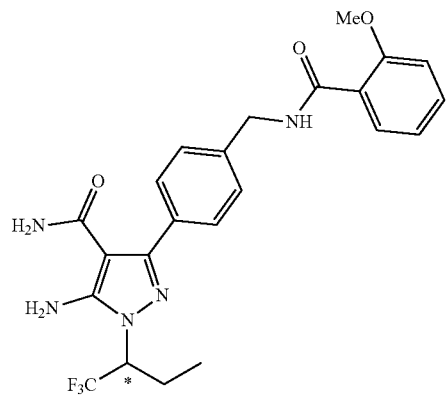
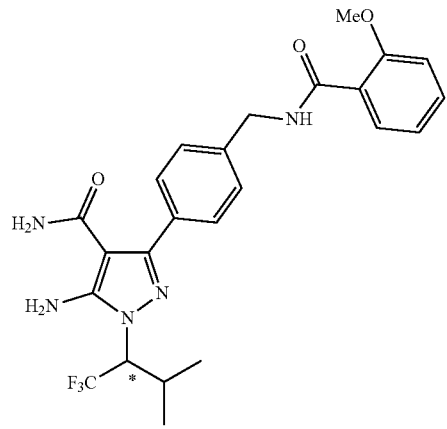
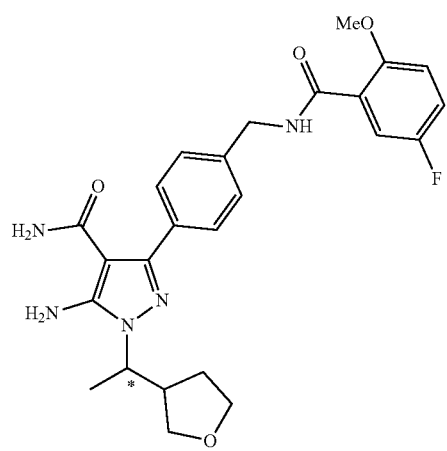
82
-continued
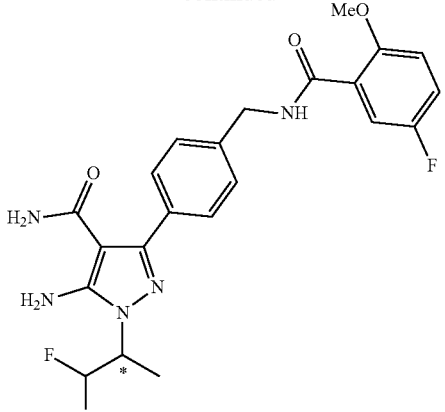
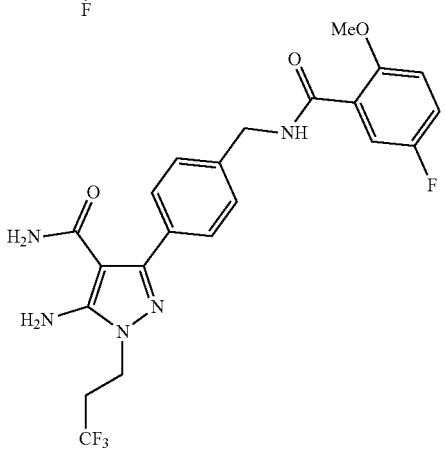
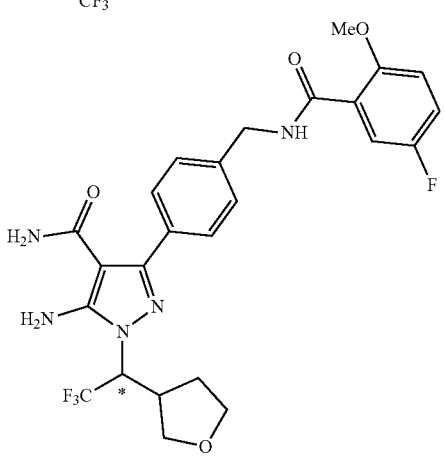
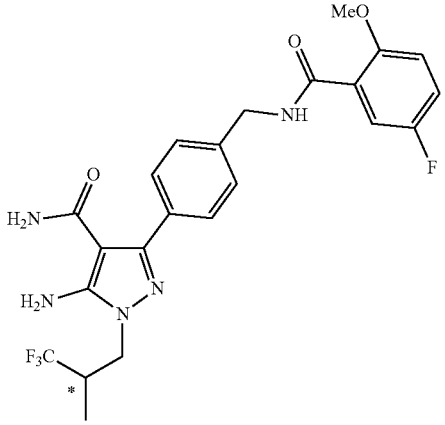

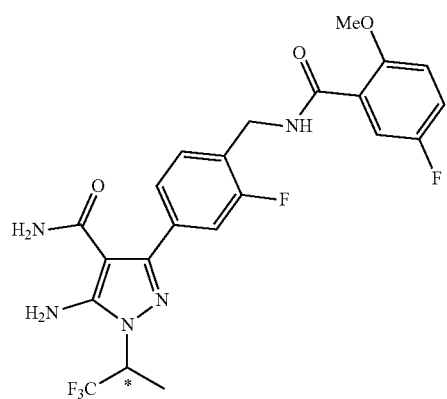
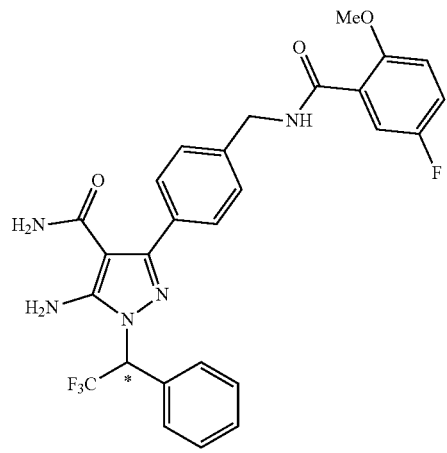
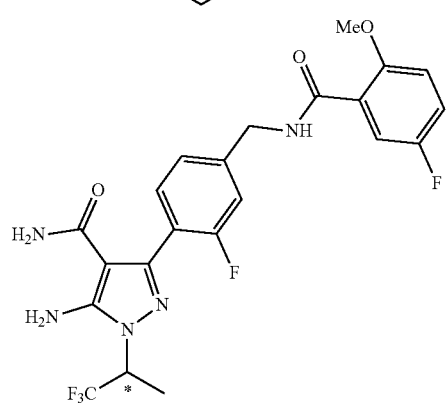
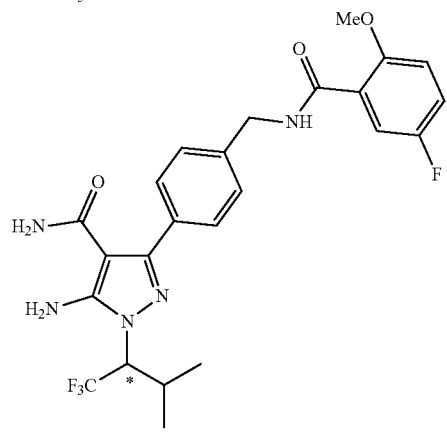
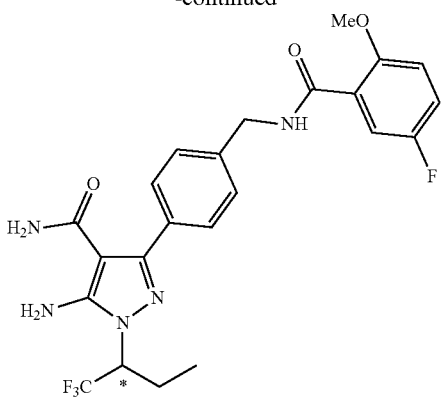
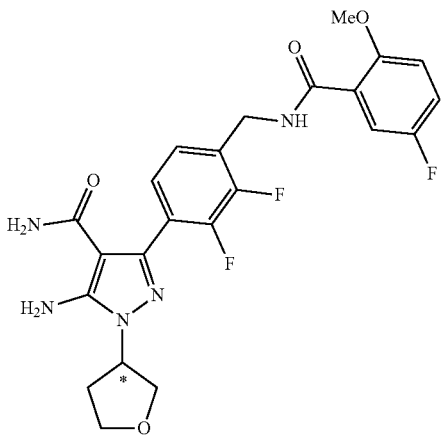
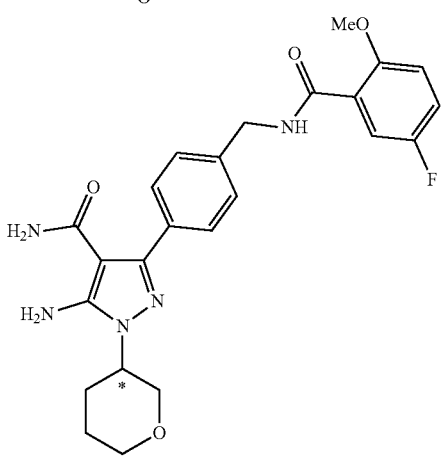
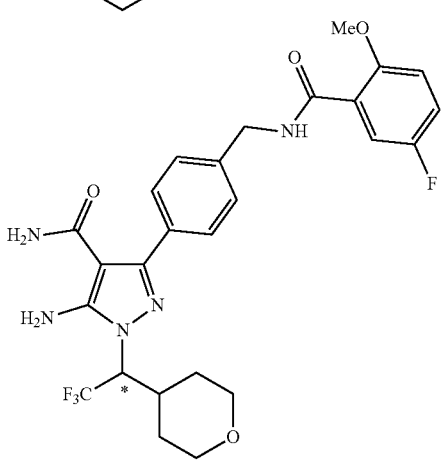

-continued
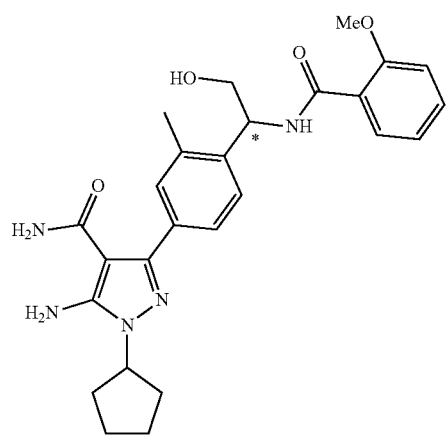
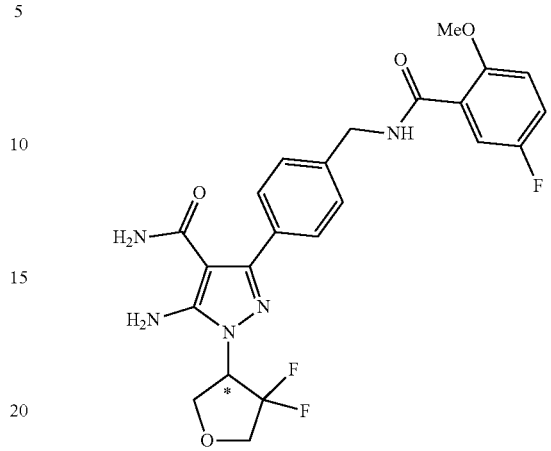
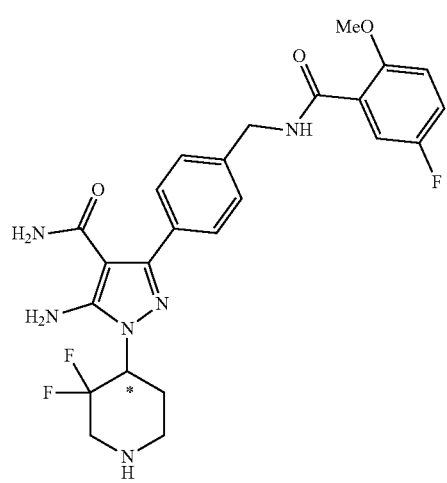
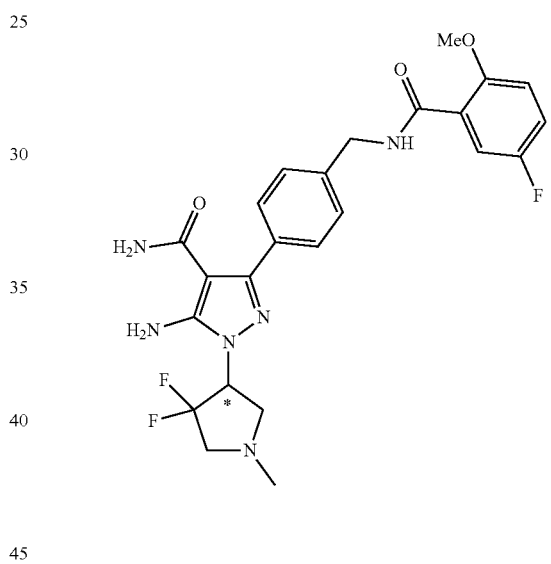
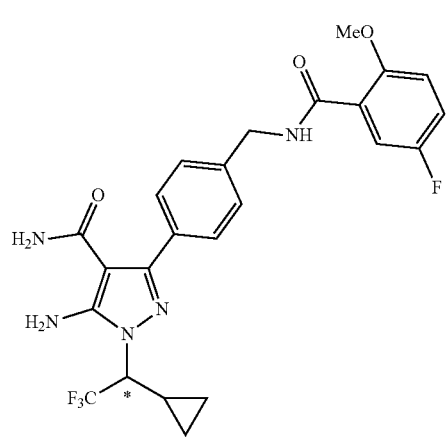
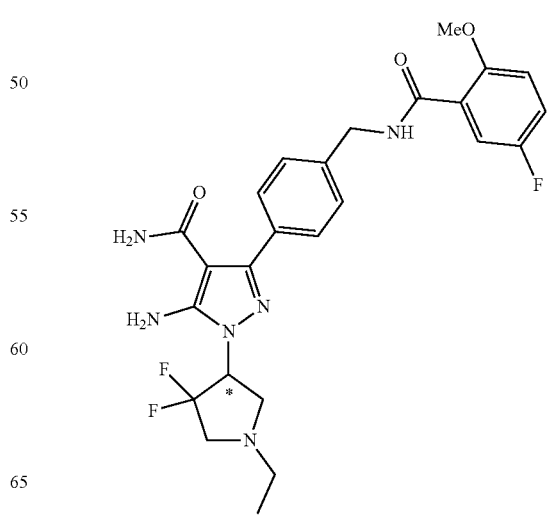

87
-continued
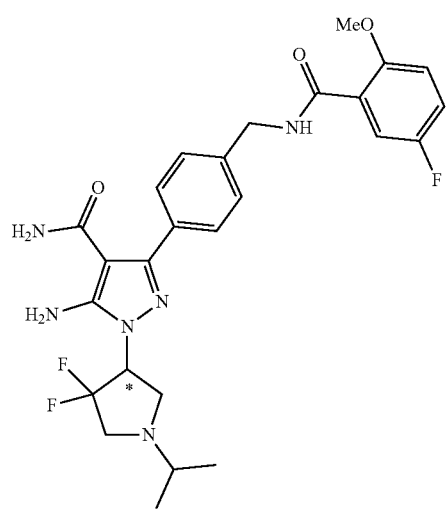
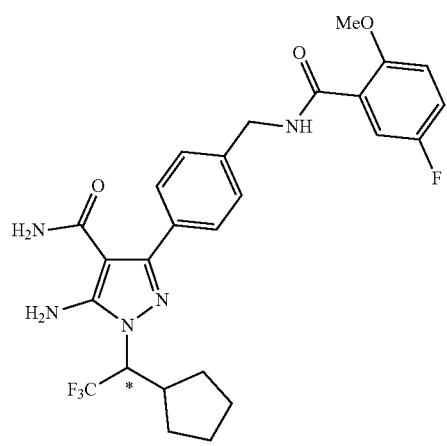
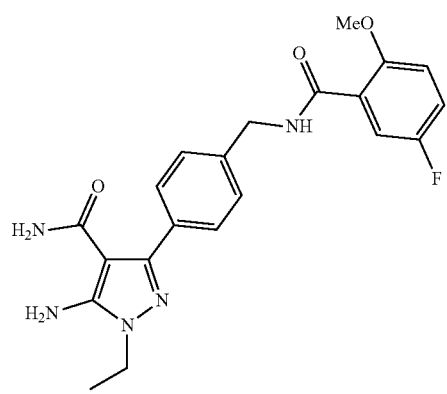
88
-continued
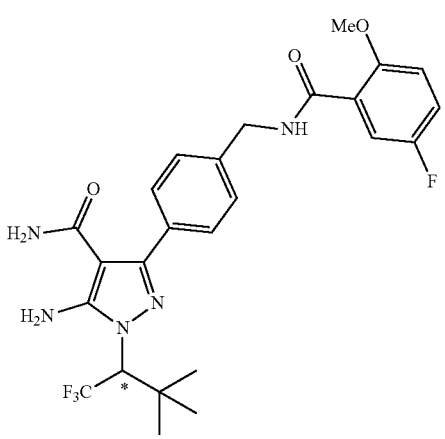
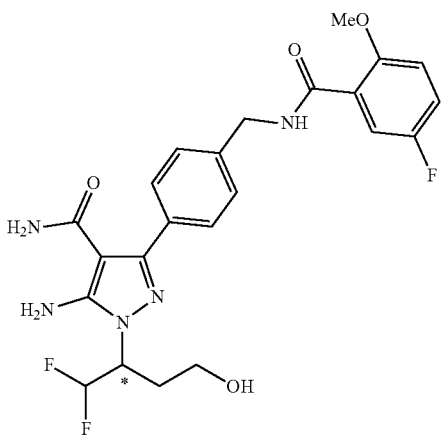
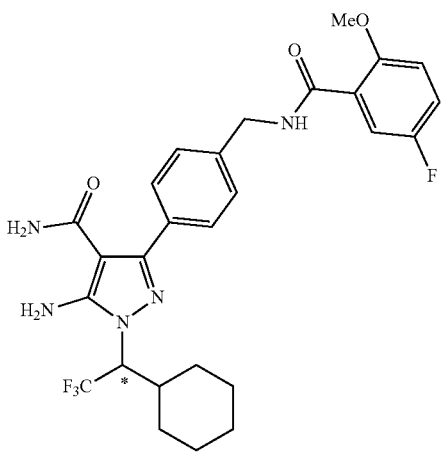

-continued
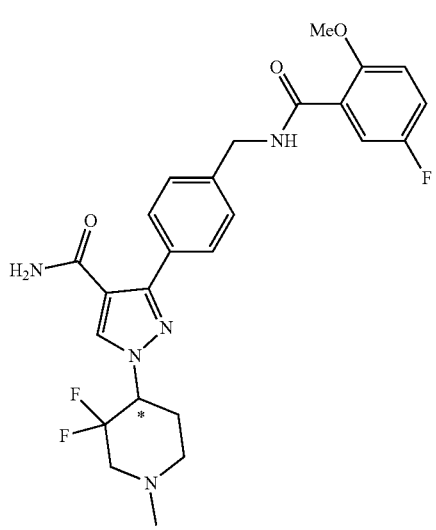
The compound of formula (I) may be a compound selected from:
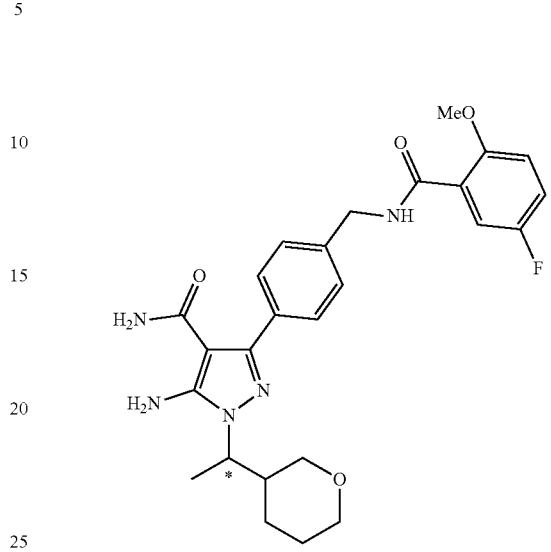
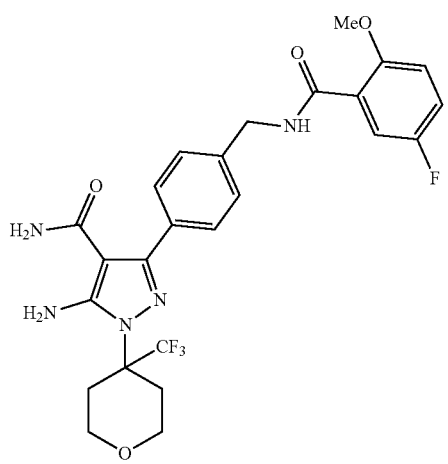
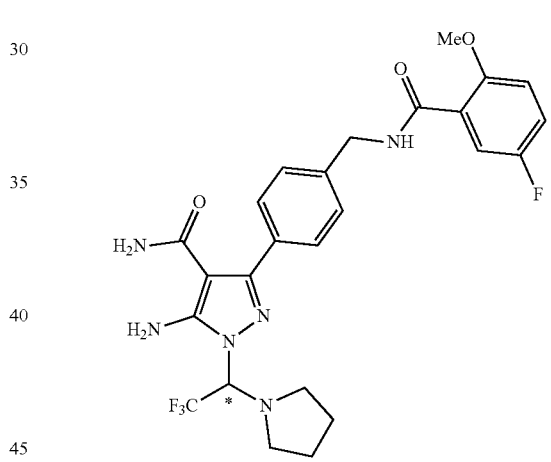
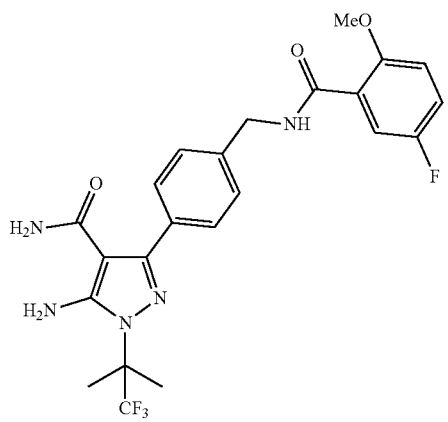
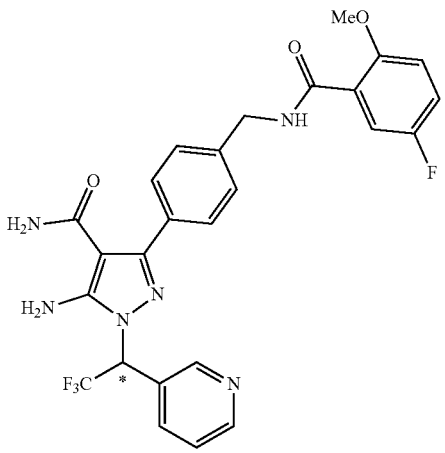

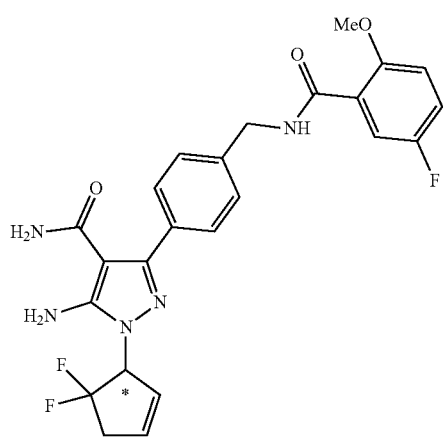
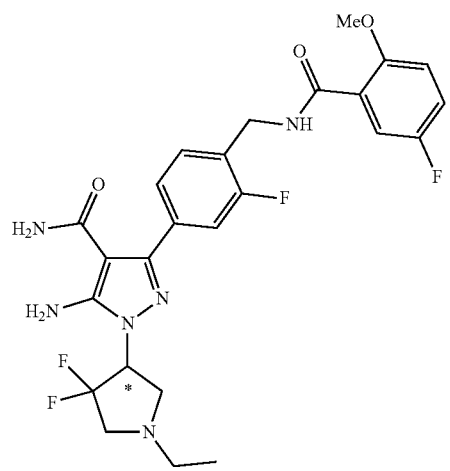
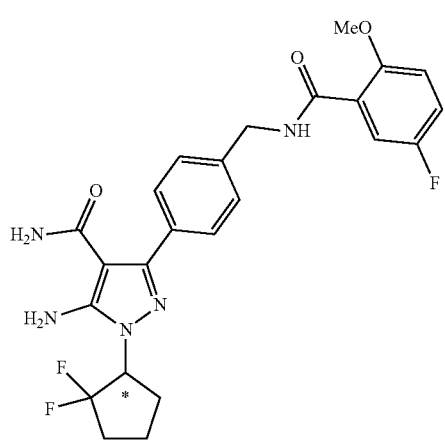 [SMILES: COc1ccc(F)cc1C(=O)NCc1ccc(-c2nn(C3CCCC3(F)F)c(N)c2C(N)=O)cc1]
Compounds of formula (I) may also be selected from:
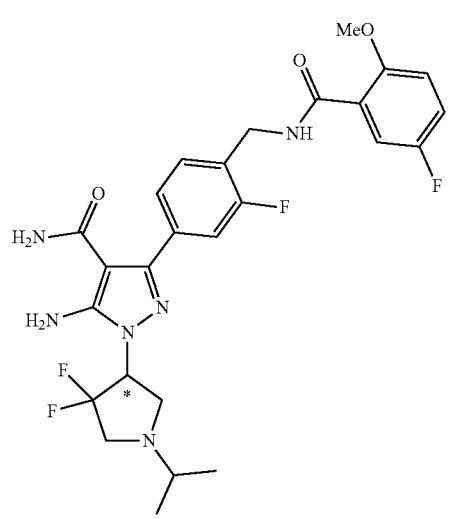
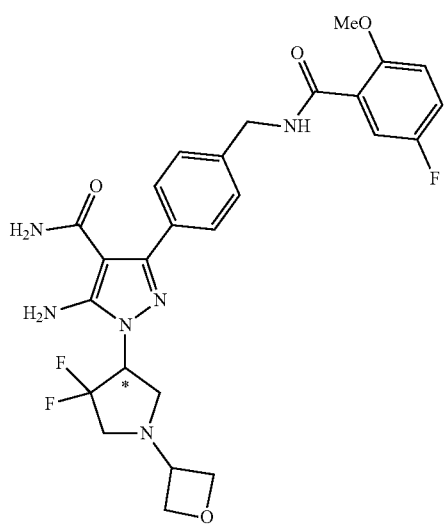
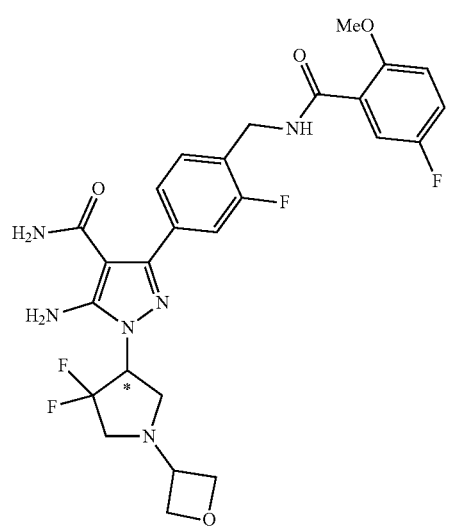

93
-continued
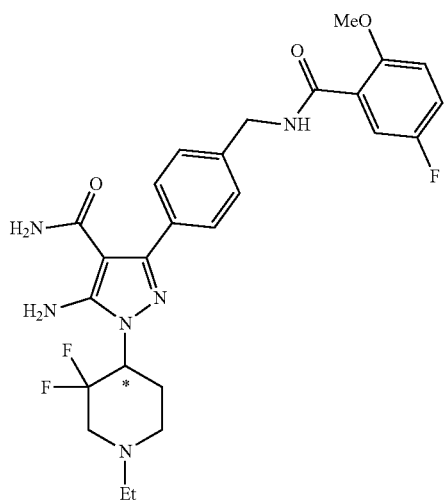
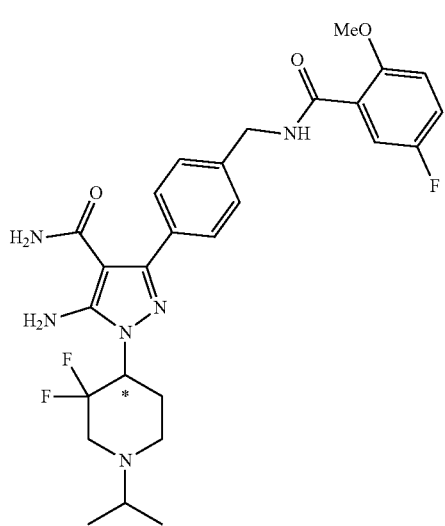
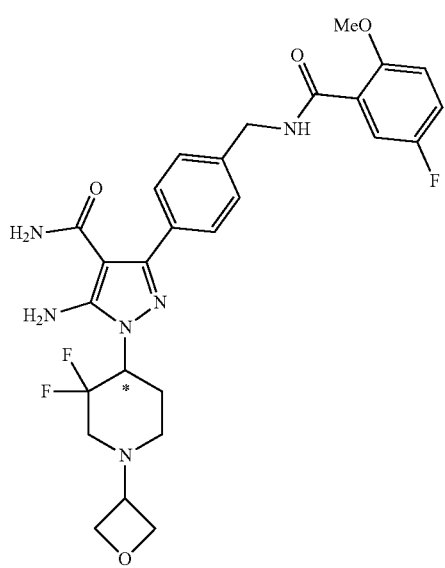
94
-continued
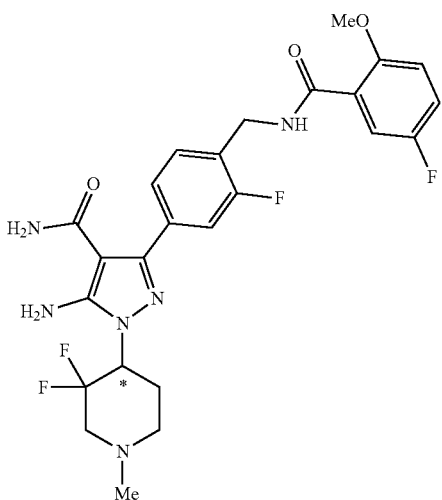
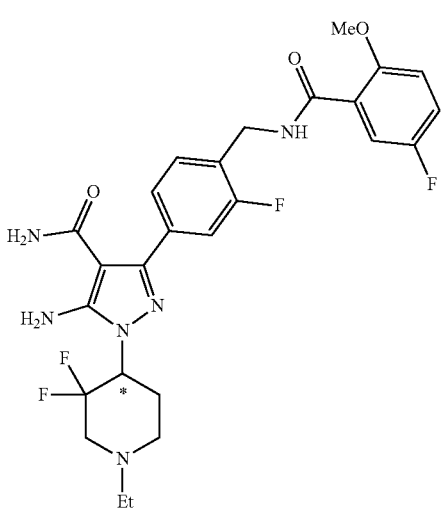
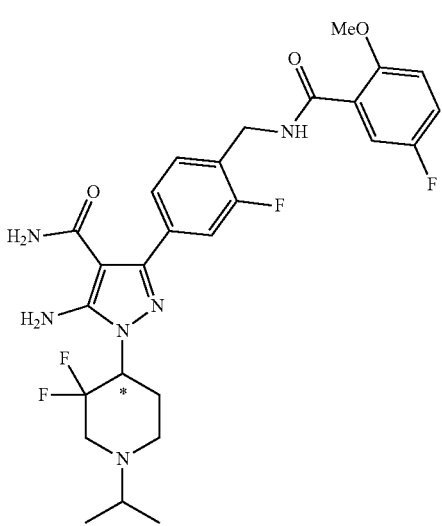

-continued
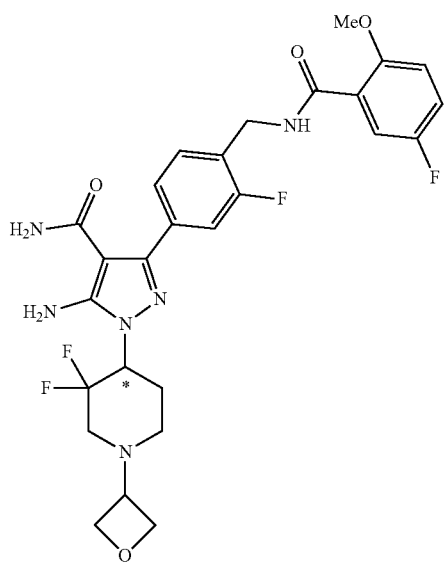
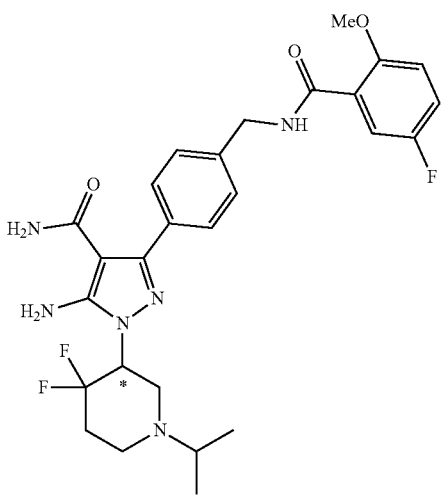
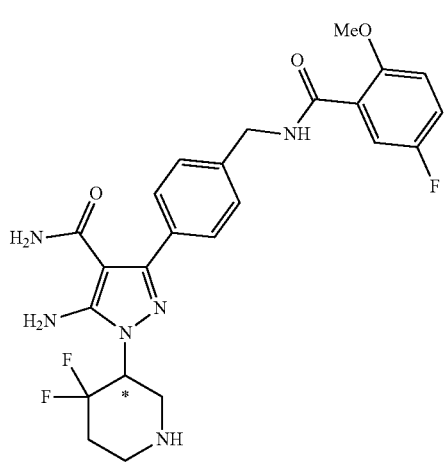
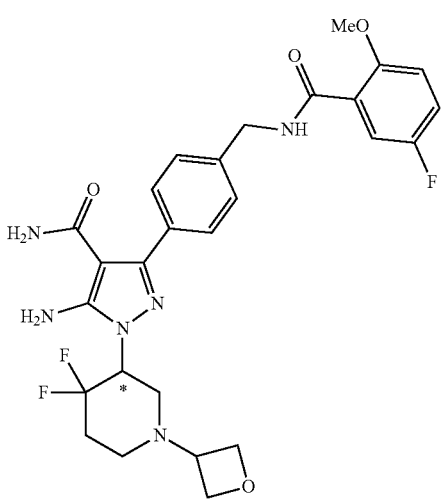
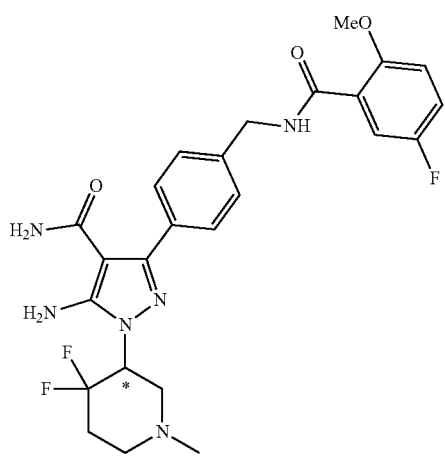
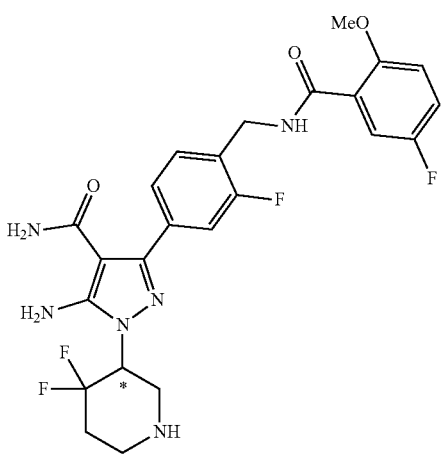

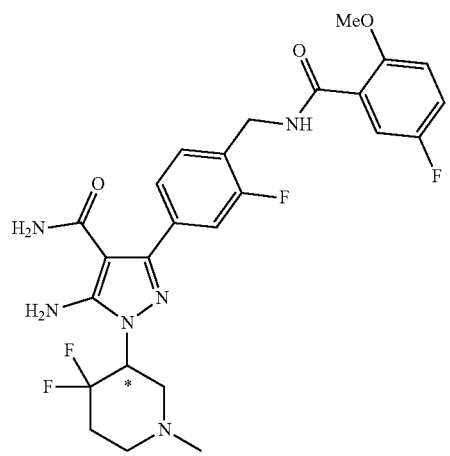
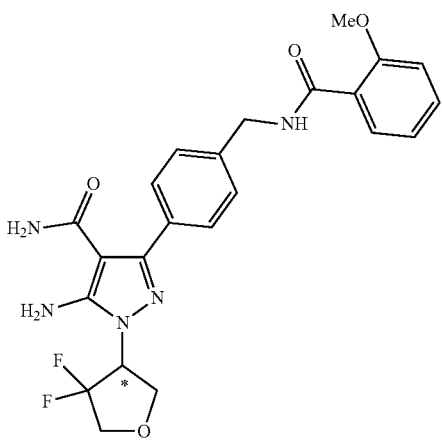
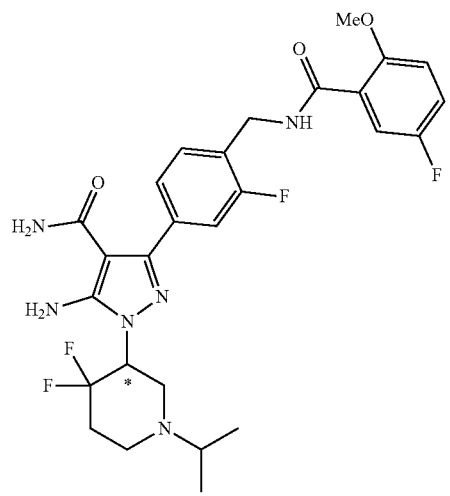
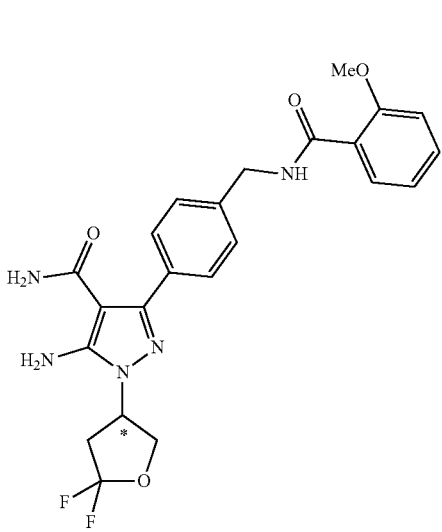
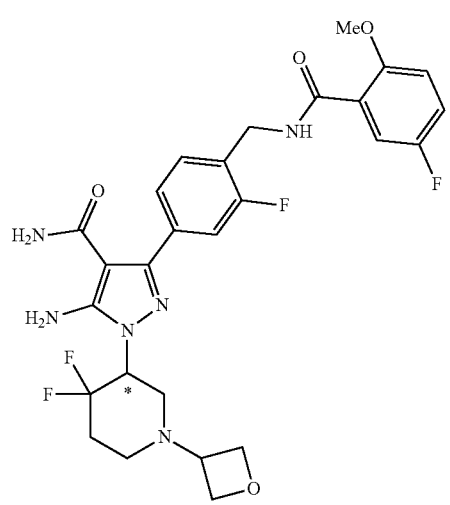
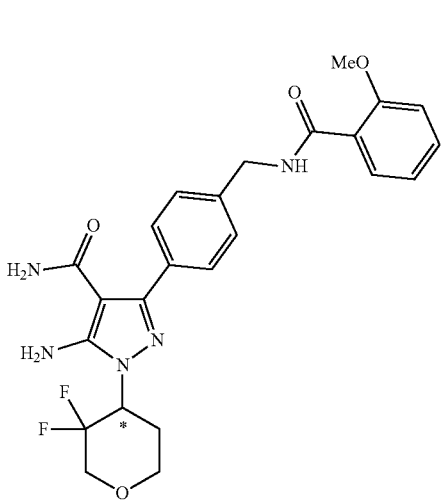

99
-continued
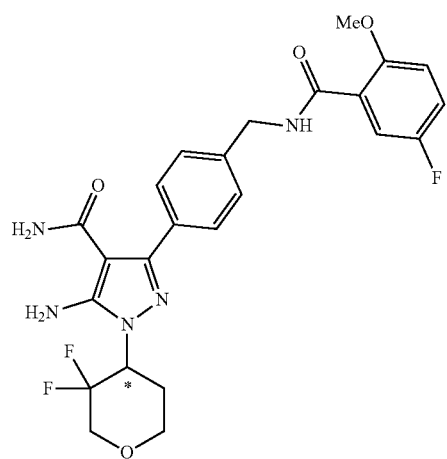
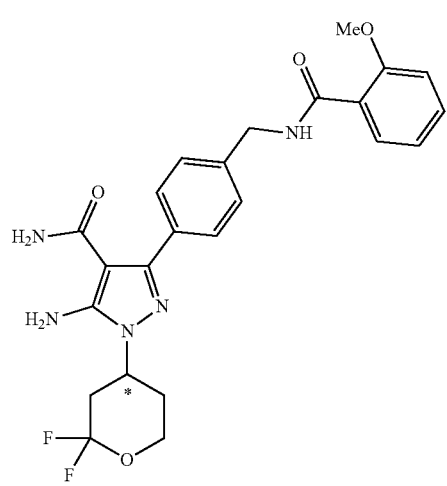
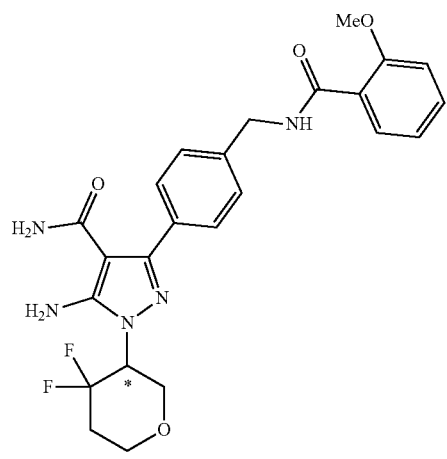
100
-continued
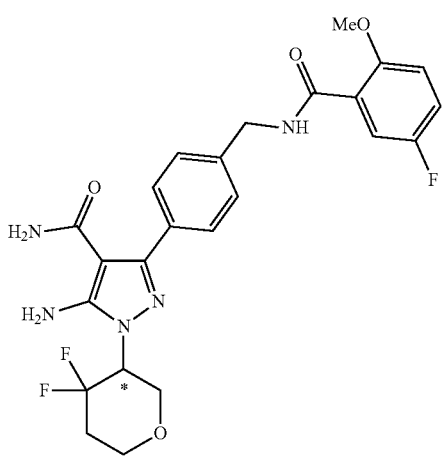
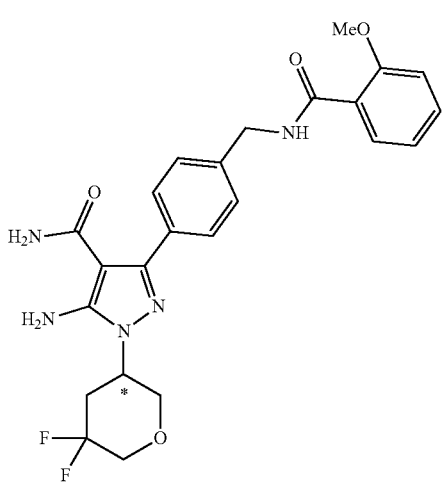
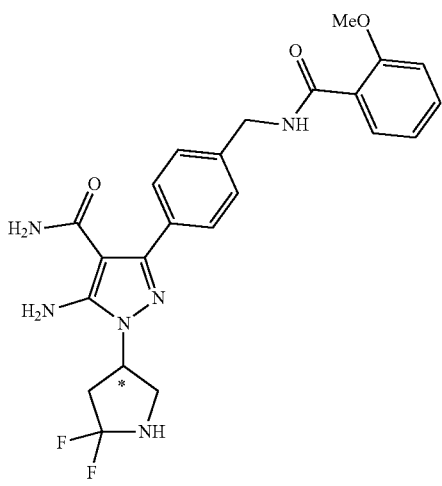

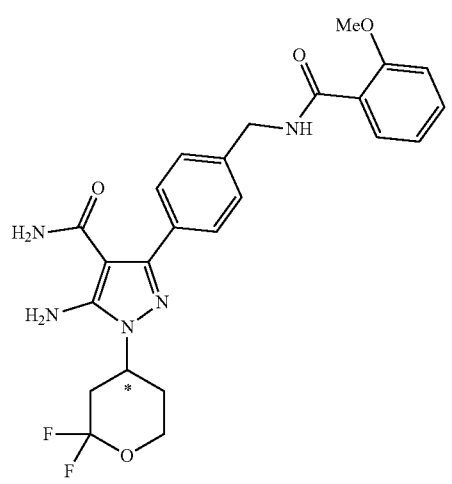
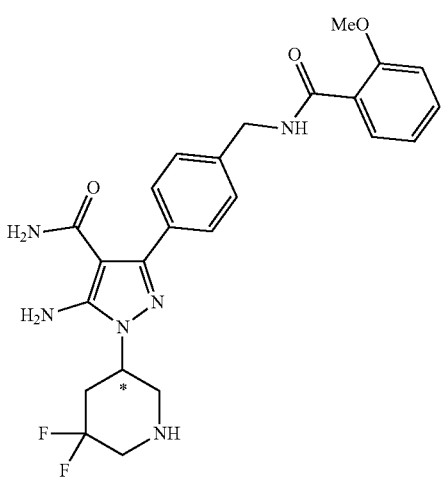
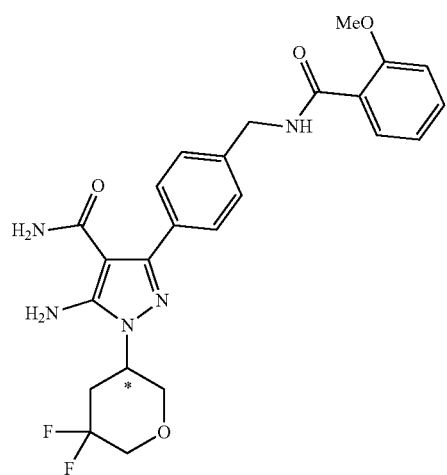
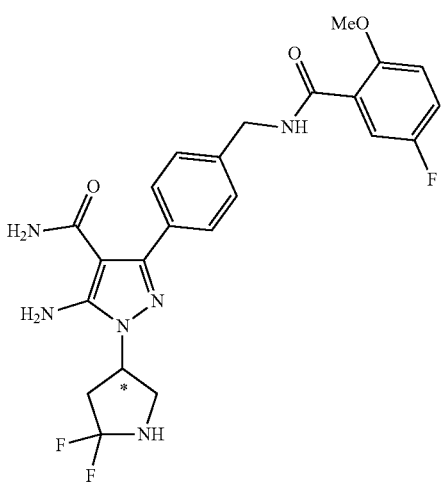
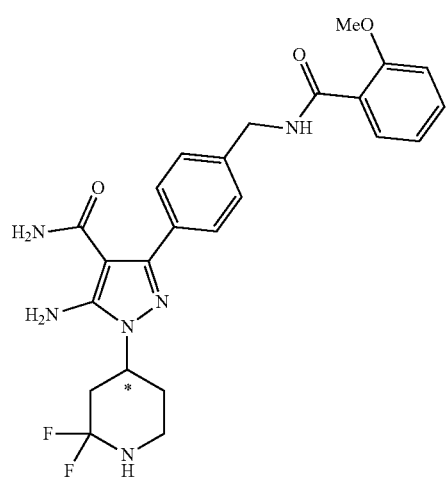
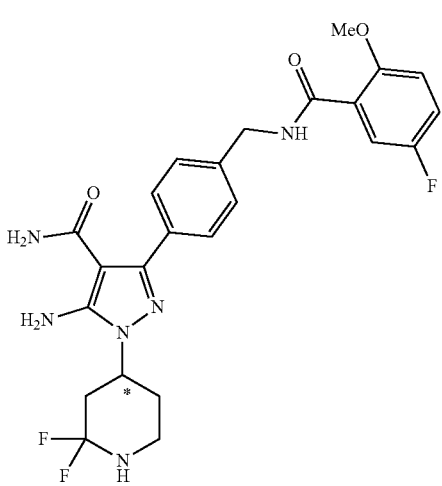

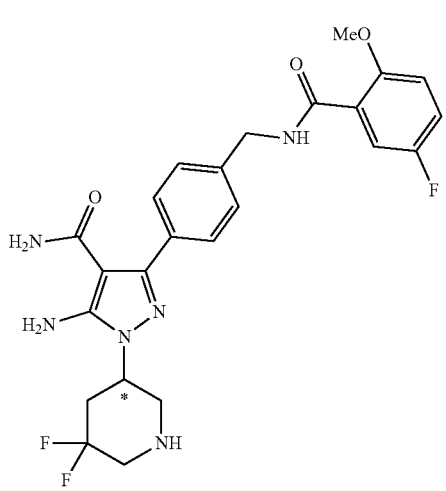

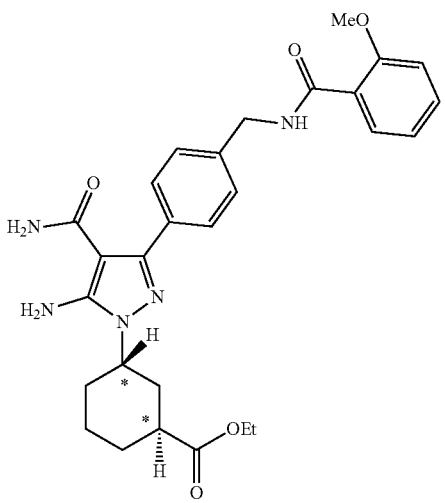

Some of the above compounds have one or more chiral centres, for example one or two chiral centres. All enantiomers and diastereomers of the above compounds are contemplated by the invention. Certain chiral centres are indicated on the compounds above with a * symbol. The compounds may have chiral centres in addition to those indicated with a *. In one embodiment the compounds of the invention have the (R)-configuration at the stereocentre. In an alternative embodiment the compounds of the invention have the (S)-configuration at the stereocentre. Where compounds have two stereocentres the stereocentres may have (R),(R) configuration, (S),(R) configuration, (R),(S) configuration or (S),(S) configuration. The invention also contemplates racemic mixtures of these compounds.

The compounds of formula (I) may be compounds selected from:

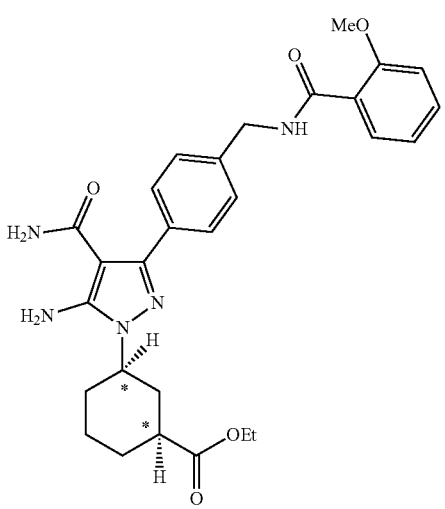

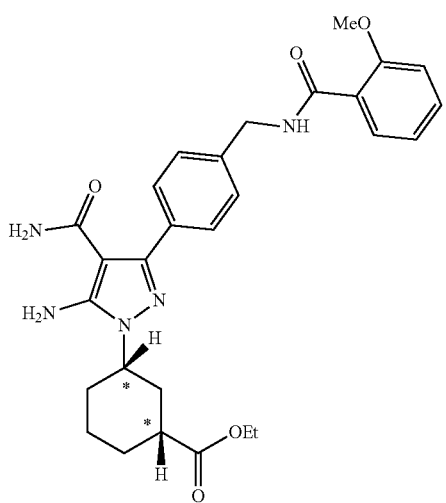

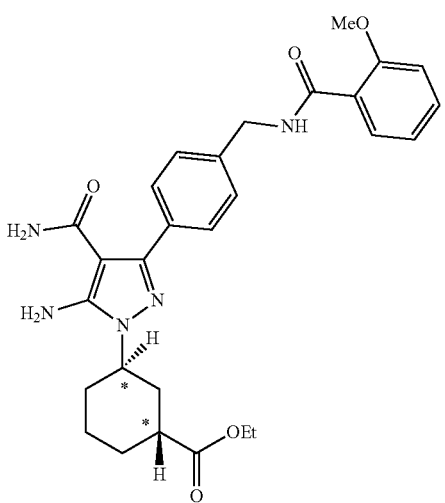

105
-continued
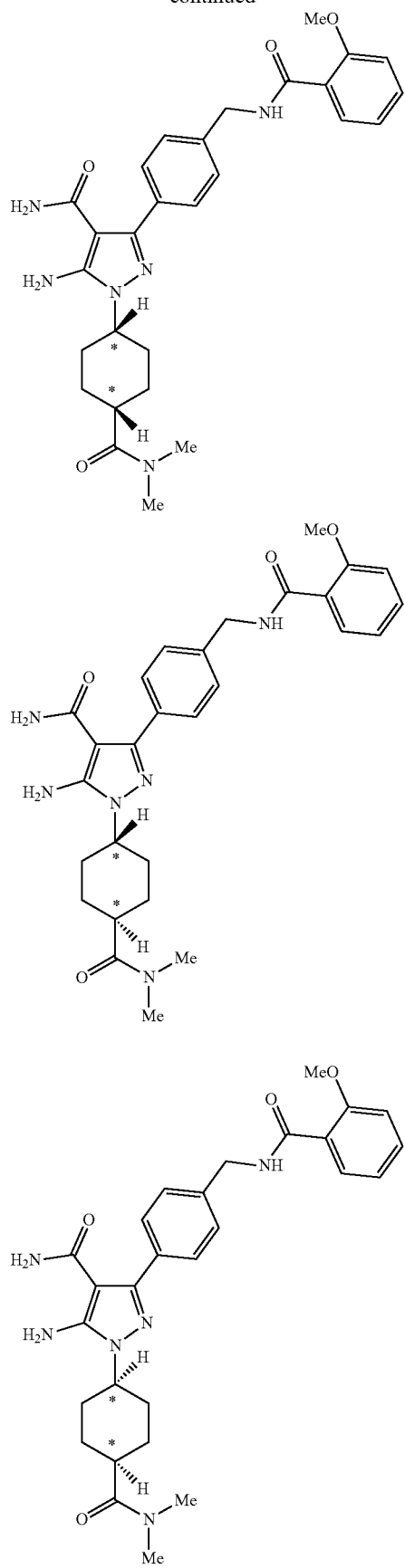
106
-continued
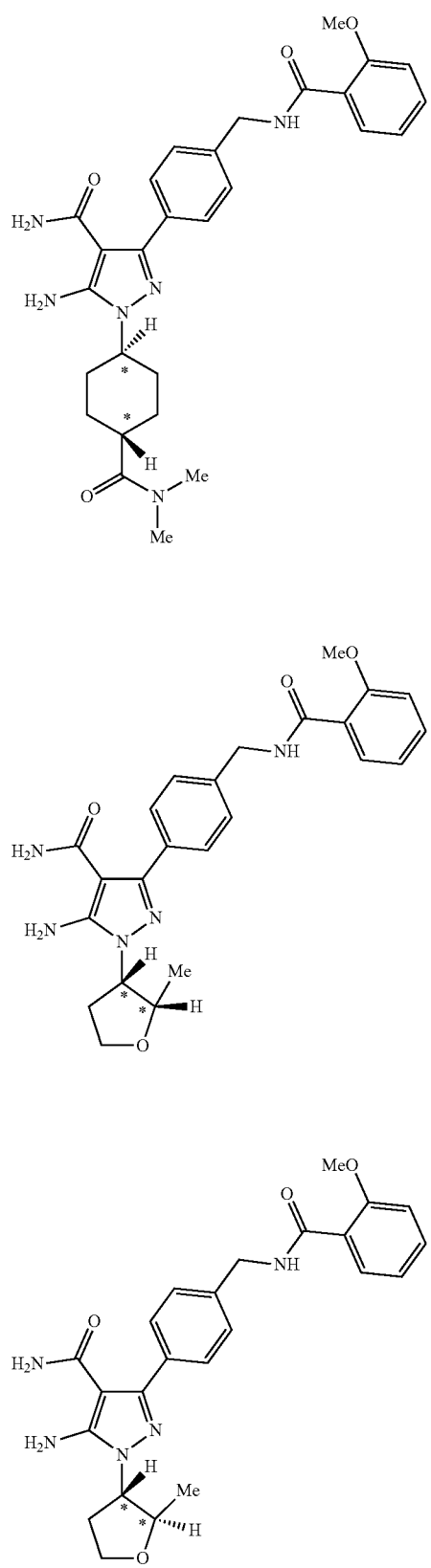

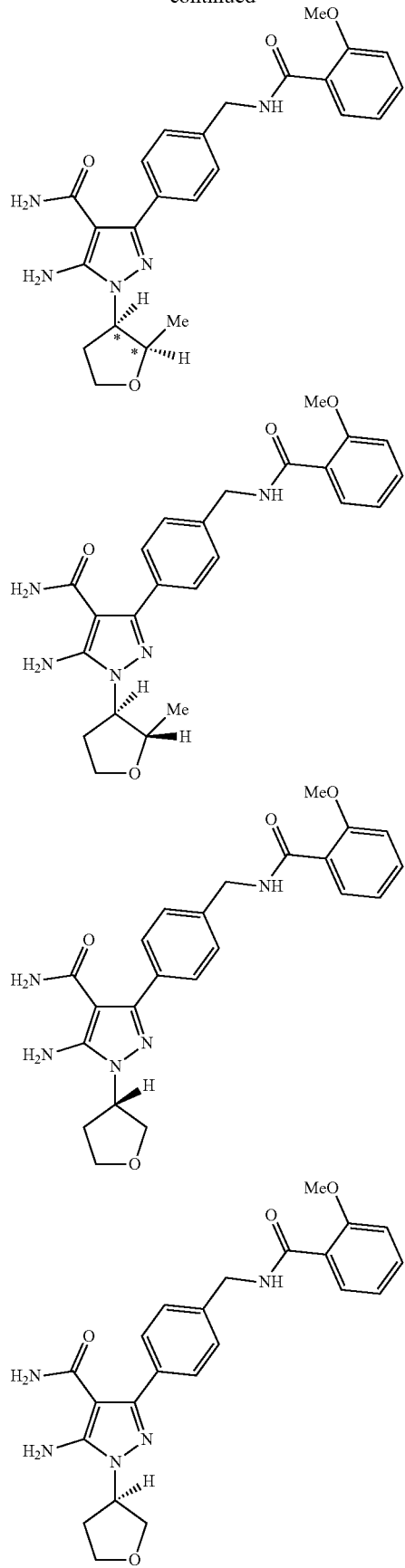
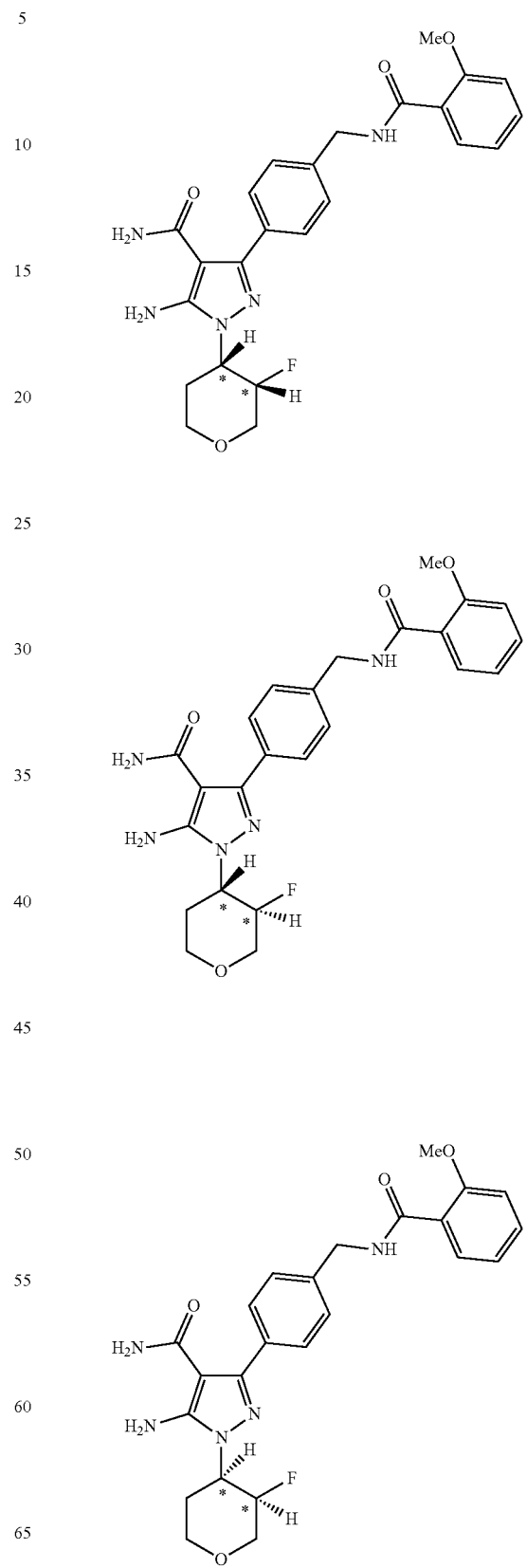

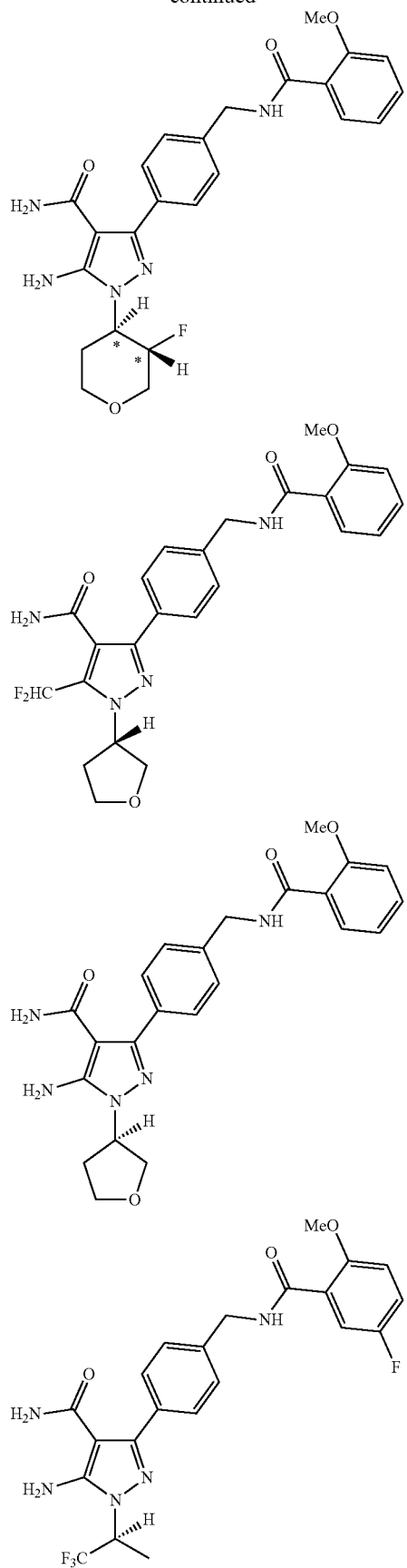
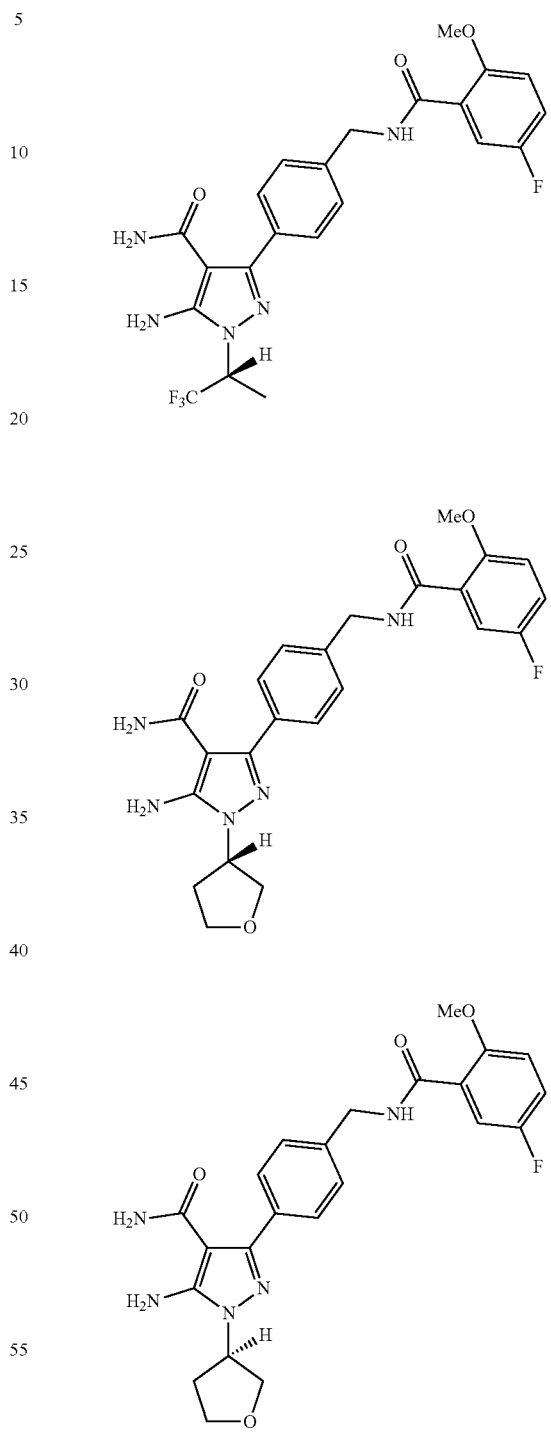

Any compound described in the examples also forms part of the invention. This includes the compounds falling under the scope of formula (I) and in another aspect any and all novel intermediates in the synthesis of the compounds of formula (I).

Less preferred compounds of formula (I) are given below. In certain embodiments the compounds shown below do not form part of the invention.

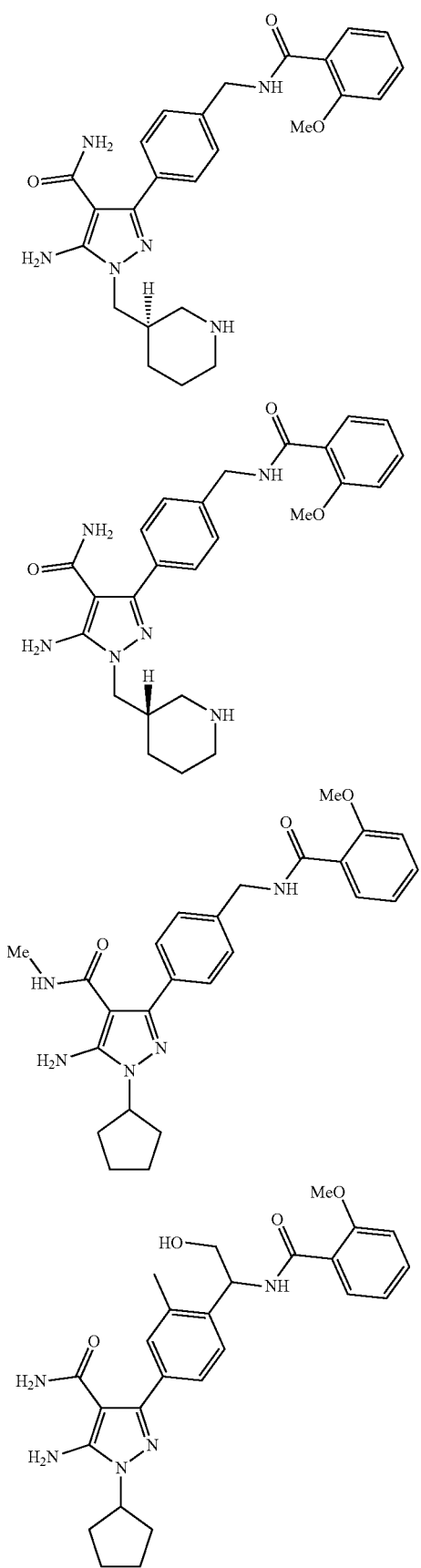

-continued

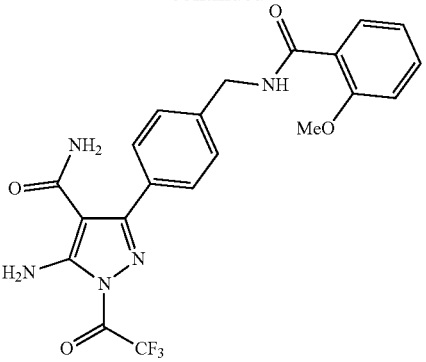 [SMILES: COc1ccccc1C(=O)NCc1ccc(-c2nn(C(=O)C(F)(F)F)c(N)c2C(N)=O)cc1]

In another aspect of the invention there is provided a compound of any formula disclosed herein for use as a medicament.

In another aspect a compound any formula herein is for use in the treatment of a condition which is modulated by Bruton's tyrosine kinase (BTK). Usually conditions that are modulated by BTK are conditions that would be treated by the inhibition of BTK using a compound of the present invention. A compound of any formula disclosed herein may be for use in the treatment of a condition treatable by the inhibition of Bruton's tyrosine kinase (BTK).

BTK inhibition is a novel approach for treating many different human diseases associated with the inappropriate activation of B-cells, including B-cell proliferative disorders, B-cell malignancies, immunological disease for example, autoimmune, heteroimmune conditions, and inflammatory disorders, or fibrosis. In particular, BTK inhibition is a novel approach for treating many different human diseases associated with the inappropriate activation of B-cells, including B-cell malignancies, immunological disease for example, autoimmune and inflammatory disorders.

In embodiments the condition treatable by the inhibition of BTK may be selected from: cancer, lymphoma, leukemia, autoimmune diseases, inflammatory disorders, heteroimmune conditions, or fibrosis. Specific conditions treatable by the inhibition of BTK may be selected from: B-cell malignancy, B-cell lymphoma, diffuse large B cell lymphoma, chronic lymphocytic leukemia, non-Hodgkin lymphoma for example ABC-DLBCL, mantle cell lymphoma, follicular lymphoma, hairy cell leukemia, B-cell non-Hodgkin lymphoma, Waldenstrom's macroglobulinemia, multiple myeloma, bone cancer, bone metastasis, chronic lymphocytic lymphoma, B-cell prolymphocytic leukemia, lymphoplasmacytic lymphoma, splenic marginal zone lymphoma, plasma cell myeloma, plasmacytoma, extranodal marginal zone B-cell lymphoma, nodal marginal zone B-cell lymphoma, mediastinal (thymic) large B-cell lymphoma, intravascular large B-cell lymphoma, primary effusion lymphoma, burkitt lymphoma/leukemia, lymphomatoid granulomatosis, inflammatory bowel disease, arthritis, lupus, rheumatoid arthritis, psoriatic arthritis, osteoarthritis, Still's disease, juvenile arthritis, diabetes, myasthenia gravis, Hashimoto's thyroiditis, Ord's thyroiditis, Graves' disease, Sjogren's syndrome, multiple sclerosis, Guillain-Barre syndrome, acute disseminated encephalomyelitis, Addison's disease, opsoclonus-myoclonus syndrome, ankylosing spondylitisis, antiphospholipid antibody syndrome, aplastic anemia, autoimmune hepatitis, coeliac disease, Goodpasture's syndrome, idiopathic thrombocytopenic purpura, optic neuritis, scleroderma, primary biliary cirrhosis, Reiter's syndrome, Takayasu's arteritis, temporal arteritis, warm autoimmune hemolytic anemia, Wegener's granulomatosis, psoriasis, alopecia universalis, Behcet's disease, chronic fatigue, dysautonomia, endometriosis, interstitial cystitis, neuromyotonia, scleroderma, vulvodynia, graft versus host disease, transplantation, transfusion, anaphylaxis, allergy, type I hypersensitivity, allergic conjunctivitis, allergic rhinitis, atopic dermatitis, asthma, appendicitis, blepharitis, bronchiolitis, bronchitis, bursitis, cervicitis, cholangitis, cholecystitis, colitis, conjunctivitis, cystitis, dacryoadenitis, dermatitis, dermatomyositis, encephalitis, endocarditis, endometritis, enteritis, enterocolitis, epicondylitis, epididymitis, fasciitis, fibrositis, gastritis, gastroenteritis, hepatitis, hidradenitis suppurativa, laryngitis, mastitis, meningitis, myelitis myocarditis, myositis, nephritis, oophoritis, orchitis, osteitis, otitis, pancreatitis, parotitis, pericarditis, peritonitis, pharyngitis, pleuritis, phlebitis, pneumonitis, pneumonia, proctitis, prostatitis, pyelonephritis, rhinitis, salpingitis, sinusitis, stomatitis, synovitis, tendonitis, tonsillitis, uveitis, vaginitis, vasculitis, vulvitis, pulmonary fibrosis, idiopathic pulmonary fibrosis (IPF), usual interstitial pneumonitis (UIP), interstitial lung disease, cryptogenic fibrosing alveolitis (CFA), bronchiolitis obliterans, bronchiectasis, fatty liver disease, steatosis (e.g., nonalcoholic steatohepatitis (NASH), cholestatic liver disease (e.g., primary biliary cirrhosis (PBC), cirrhosis, alcohol-induced liver fibrosis, biliary duct injury, biliary fibrosis, cholestasis or cholangiopathies. In some embodiments, hepatic or liver fibrosis includes, but is not limited to, hepatic fibrosis associated with alcoholism, viral infection, e.g., hepatitis (e.g., hepatitis C, B or D), autoimmune hepatitis, nonalcoholic fatty liver disease (NAFLD), progressive massive fibrosis, exposure to toxins or irritants (e.g., alcohol, pharmaceutical drugs and environmental toxins), renal fibrosis (e.g., chronic kidney fibrosis), nephropathies associated with injury/fibrosis (e.g., chronic nephropathies associated with diabetes (e.g., diabetic nephropathy)), lupus, scleroderma of the kidney, glomerular nephritis, focal segmental glomerular sclerosis, IgA nephropathyrenal fibrosis associated with human chronic kidney disease (CKD), chronic progressive nephropathy (CPN), tubulointerstitial fibrosis, ureteral obstruction, chronic uremia, chronic interstitial nephritis, radiation nephropathy, glomerulosclerosis, progressive glomerulonephrosis (PGN), endothelial/thrombotic microangiopathy injury, HIV-associated nephropathy, or fibrosis associated with exposure to a toxin, an irritant, or a chemotherapeutic agent, fibrosis associated with scleroderma; radiation induced gut fibrosis; fibrosis associated with a foregut inflammatory disorder such as Barrett's esophagus and chronic gastritis, and/or fibrosis associated with a hindgut inflammatory disorder, such as inflammatory bowel disease (IBD), ulcerative colitis and Crohn's disease, age-related macular degeneration, diabetic retinopathy, retinopathy of prematurity and neovascular glaucoma.

B-cell malignancy, B-cell lymphoma, diffuse large B cell lymphoma, chronic lymphocytic leukemia, non-Hodgkin lymphoma for example ABC-DLBCL, mantle cell lymphoma, follicular lymphoma, hairy cell leukemia, B-cell non-Hodgkin lymphoma, Waldenstrom's macroglobulinemia, multiple myeloma, bone cancer, bone metastasis, chronic lymphocytic lymphoma, B-cell prolymphocytic leukemia, lymphoplasmacytic lymphoma, splenic marginal zone lymphoma, plasma cell myeloma, plasmacytoma, extranodal marginal zone B-cell lymphoma, nodal marginal zone B-cell lymphoma, mediastinal (thymic) large B-cell lymphoma, intravascular large B-cell lymphoma, primary effusion lymphoma, burkitt lymphoma/leukemia, and lymphomatoid granulomatosis are examples of cancer, lymphoma and leukemia treatable by BTK inhibition.

B-cell malignancy, B-cell lymphoma, diffuse large B cell lymphoma, chronic lymphocytic leukemia, non-Hodgkin lymphoma for example ABC-DLBCL, mantle cell lymphoma, follicular lymphoma, hairy cell leukemia, B-cell non-Hodgkin lymphoma, Waldenstrom's macroglobulinemia, multiple myeloma, bone cancer and bone metastasis are examples of cancer, lymphoma and leukemia treatable by BTK inhibition.

Arthritis, multiple sclerosis, osteoporosis, irritable bowel syndrome, inflammatory bowel disease, Crohn's disease, lupus, rheumatoid arthritis, psoriatic arthritis, osteoarthritis, Still's disease, juvenile arthritis, diabetes, myasthenia gravis, Hashimoto's thyroiditis, Ord's thyroiditis, Graves' disease, Sjogren's syndrome, Guillain-Barre syndrome, acute disseminated encephalomyelitis, Addison's disease, opsoclonus-myoclonus syndrome, ankylosing spondylitisis, antiphospholipid antibody syndrome, aplastic anemia, autoimmune hepatitis, coeliac disease, Goodpasture's syndrome, idiopathic thrombocytopenic purpura, optic neuritis, scleroderma, primary biliary cirrhosis, Reiter's syndrome, Takayasu's arteritis, temporal arteritis, warm autoimmune hemolytic anemia, Wegener's granulomatosis, psoriasis, alopecia universalis, Behcet's disease, chronic fatigue, dysautonomia, endometriosis, interstitial cystitis, neuromyotonia, scleroderma, vulvodynia, asthma, appendicitis, blepharitis, bronchiolitis, bronchitis, bursitis, cervicitis, cholangitis, cholecystitis, colitis, conjunctivitis, cystitis, dacryoadenitis, dermatitis, dermatomyositis, encephalitis, endocarditis, endometritis, enteritis, enterocolitis, epicondylitis, epididymitis, fasciitis, fibrositis, gastritis, gastroenteritis, hepatitis, hidradenitis suppurativa, laryngitis, mastitis, meningitis, myelitis myocarditis, myositis, nephritis, oophoritis, orchitis, osteitis, otitis, pancreatitis, parotitis, pericarditis, peritonitis, pharyngitis, pleuritis, phlebitis, pneumonitis, pneumonia, proctitis, prostatitis, pyelonephritis, rhinitis, salpingitis, sinusitis, stomatitis, synovitis, tendonitis, tonsillitis, uveitis, vaginitis, vasculitis, vulvitis, graft versus host disease, transplantation, transfusion, anaphylaxis, allergy, type I hypersensitivity, allergic conjunctivitis, allergic rhinitis, and atopic dermatitis are examples of immunological diseases treatable by BTK inhibition.

Arthritis, asthma, appendicitis, blepharitis, bronchiolitis, bronchitis, bursitis, cervicitis, cholangitis, cholecystitis, colitis, conjunctivitis, cystitis, dacryoadenitis, dermatitis, dermatomyositis, encephalitis, endocarditis, endometritis, enteritis, enterocolitis, epicondylitis, epididymitis, fasciitis, fibrositis, gastritis, gastroenteritis, hepatitis, hidradenitis suppurativa, laryngitis, mastitis, meningitis, myelitis myocarditis, myositis, nephritis, oophoritis, orchitis, osteitis, otitis, pancreatitis, parotitis, pericarditis, peritonitis, pharyngitis, pleuritis, phlebitis, pneumonitis, pneumonia, proctitis, prostatitis, pyelonephritis, rhinitis, salpingitis, sinusitis, stomatitis, synovitis, tendonitis, tonsillitis, uveitis, vaginitis, vasculitis, and vulvitis are examples of an inflammatory disorder treatable by BTK inhibition.

Lupus and Sjogren's syndrome, rheumatoid arthritis, psoriatic arthritis, osteoarthritis, Still's disease, juvenile arthritis, diabetes, myasthenia gravis, Hashimoto's thyroiditis, Ord's thyroiditis, Graves' disease, Sjogren's syndrome, Guillain-Barre syndrome, acute disseminated encephalomyelitis, Addison's disease, opsoclonus-myoclonus syndrome, ankylosing spondylitisis, antiphospholipid antibody syndrome, aplastic anemia, autoimmune hepatitis, coeliac disease, Goodpasture's syndrome, idiopathic thrombocytopenic purpura, optic neuritis, scleroderma, primary biliary cirrhosis, Reiter's syndrome, Takayasu's arteritis, temporal arteritis, warm autoimmune hemolytic anemia, Wegener's granulomatosis, psoriasis, alopecia universalis, Behcet's disease, chronic fatigue, dysautonomia, endometriosis, interstitial cystitis, neuromyotonia, scleroderma, and vulvodynia are examples of an autoimmune disease treatable by BTK inhibition.

Graft versus host disease, transplantation, transfusion, anaphylaxis, allergy, type I hypersensitivity, allergic conjunctivitis, allergic rhinitis, and atopic dermatitis are examples of a heteroimmune condition treatable by BTK inhibition.

Pulmonary fibrosis, idiopathic pulmonary fibrosis (IPF), usual interstitial pneumonitis (UIP), interstitial lung disease, cryptogenic fibrosing alveolitis (CFA), bronchiolitis obliterans, bronchiectasis, fatty liver disease, steatosis (e.g., nonalcoholic steatohepatitis (NASH), cholestatic liver disease (e.g., primary biliary cirrhosis (PBC), cirrhosis, alcohol-induced liver fibrosis, biliary duct injury, biliary fibrosis, cholestasis or cholangiopathies. In some embodiments, hepatic or liver fibrosis includes, but is not limited to, hepatic fibrosis associated with alcoholism, viral infection, e.g., hepatitis (e.g., hepatitis C, B or D), autoimmune hepatitis, nonalcoholic fatty liver disease (NAFLD), progressive massive fibrosis, exposure to toxins or irritants (e.g. alcohol, pharmaceutical drugs and environmental toxins), renal fibrosis (e.g. chronic kidney fibrosis), nephropathies associated with injury/fibrosis (e.g., chronic nephropathies associated with diabetes (e.g. diabetic nephropathy)), lupus, scleroderma of the kidney, glomerular nephritis, focal segmental glomerular sclerosis, IgA nephropathyrenal fibrosis associated with human chronic kidney disease (CKD), chronic progressive nephropathy (CPN), tubulointerstitial fibrosis, ureteral obstruction, chronic uremia, chronic interstitial nephritis, radiation nephropathy, glomerulosclerosis, progressive glomerulonephrosis (PGN), endothelial/thrombotic microangiopathy injury, HIV-associated nephropathy, or fibrosis associated with exposure to a toxin, an irritant, a chemotherapeutic agent, fibrosis associated with scleroderma; radiation induced gut fibrosis; fibrosis associated with a foregut inflammatory disorder such as Barrett's esophagus and chronic gastritis, and/or fibrosis associated with a hindgut inflammatory disorder, such as inflammatory bowel disease (IBD), ulcerative colitis and Crohn's disease, age-related macular degeneration, diabetic retinopathy, retinopathy of prematurity and neovascular glaucoma are examples of fibrosis treatable by BTK inhibition.

Arthritis, multiple sclerosis, osteoporosis, irritable bowel syndrome, inflammatory bowel disease, Crohn's disease and lupus are examples of immunological diseases treatable by BTK inhibition. Arthritis is an example of an inflammatory disorder treatable by BTK inhibition. Lupus and Sjogren's syndrome are examples of autoimmune diseases treatable by BTK inhibition.

Any of the conditions disclosed above as being treatable by BTK inhibition may be treated by a compound of the invention, or may be treated in a method comprising administering a compound of the invention, or may be treated by a medicament manufactured through the use of a compound of the present invention.

In embodiments, a compound of the invention may be for use in the treatment of: cancer, lymphoma, leukemia, immunological diseases, autoimmune diseases and inflammatory disorders. The compound of the invention may be for use in the treatment of specific conditions selected from: B-cell malignancy, B-cell lymphoma, diffuse large B cell lymphoma, chronic lymphocytic leukemia, non-Hodgkin lymphoma for example ABC-DLBCL, mantle cell lymphoma, follicular lymphoma, hairy cell leukemia, B-cell non-Hodgkin lymphoma, Waldenstrom's macroglobulinemia, multiple myeloma, bone cancer, bone metastasis, arthritis, multiple sclerosis, osteoporosis, irritable bowel syndrome, inflammatory bowel disease, Crohn's disease, Sjogren's syndrome and lupus. The compounds may also be used for the treatment of disorders associated with renal transplant.

In an embodiment the compound of the invention may be for use in the treatment of specific conditions selected from: B-cell malignancy, B-cell lymphoma, diffuse large B cell lymphoma, chronic lymphocytic leukemia, non-Hodgkin lymphoma for example ABC-DLBCL, mantle cell lymphoma, follicular lymphoma, hairy cell leukemia, B-cell non-Hodgkin lymphoma, Waldenstrom's macroglobulinemia, multiple myeloma, lupus and arthritis.

In an aspect of the invention there is provided a method of treatment of a condition which is modulated by Bruton's tyrosine kinase, wherein the method comprises administering a therapeutic amount of a compound of the invention, to a patient in need thereof.

The method of treatment may be a method of treating a condition treatable by the inhibition of Bruton's tyrosine kinase.

The invention also provides a method of treating a condition selected from: cancer, lymphoma, leukemia, immunological diseases, autoimmune diseases, and inflammatory disorders, wherein the method comprises administering a therapeutic amount of a compound of the invention, to a patient in need thereof. The invention also provides a method of treating a specific condition selected from: B-cell malignancy, B-cell lymphoma, diffuse large B cell lymphoma, chronic lymphocytic leukemia, non-Hodgkin lymphoma for example ABC-DLBCL, mantle cell lymphoma, follicular lymphoma, hairy cell leukemia, B-cell non-Hodgkin lymphoma, Waldenstrom's macroglobulinemia, multiple myeloma, bone cancer, bone metastasis, arthritis, multiple sclerosis, osteoporosis, irritable bowel syndrome, inflammatory bowel disease, Crohn's disease, Sjogren's syndrome and lupus, wherein the method comprises administering a therapeutic amount of a compound of any formula disclosed herein, to a patient in need thereof. The method may also treat disorders associated with renal transplant.

In an embodiment the method may be for treating a specific condition selected from: B-cell malignancy, B-cell lymphoma, diffuse large B cell lymphoma, chronic lymphocytic leukemia, non-Hodgkin lymphoma for example ABC-DLBCL, mantle cell lymphoma, follicular lymphoma, hairy cell leukemia, B-cell non-Hodgkin lymphoma, Waldenstrom's macroglobulinemia, multiple myeloma, arthritis and lupus.

In another aspect of the invention there is provided a pharmaceutical composition, wherein the composition comprises a compound of the invention and pharmaceutically acceptable excipients.

In an embodiment the pharmaceutical composition may be a combination product comprising an additional pharmaceutically active agent. The additional pharmaceutically active agent may be an anti-tumor agent described below.

DETAILED DESCRIPTION

Given below are definitions of terms used in this application. Any term not defined herein takes the normal meaning as the skilled person would understand the term.

The term "halo" refers to one of the halogens, group 17 of the periodic table. In particular the term refers to fluorine, chlorine, bromine and iodine. Preferably, the term refers to fluorine or chlorine.

The term "alkyl" refers to a linear or branched hydrocarbon chain. For example, the terms "$C_{1-8}$ alkyl" or "$C_{1-6}$ alkyl" refer to a linear or branched hydrocarbon chain containing 1, 2, 3, 4, 5 or 6 carbon atoms or 1, 2, 3, 4, 5, 6, 7, or 8 carbon atoms, for example methyl, ethyl, n-propyl, iso-propyl, n-butyl, sec-butyl, tert-butyl, n-pentyl and n-hexyl. Alkylene groups may likewise be linear or branched and may have two places of attachment to the remainder of the molecule. Furthermore, an alkylene group may, for example, correspond to one of those alkyl groups listed in this paragraph. The alkyl and alkylene groups may be unsubstituted or substituted by one or more substituents. Possible substituents are described below. Substituents for the alkyl group may be halogen, e.g. fluorine, chlorine, bromine and iodine, OH, =O, or $C_{1-6}$ alkoxy.

The term "alkoxy" refers to an alkyl group which is attached to a molecule via oxygen. This includes moieties where the alkyl part may be linear or branched. For example, the term "$C_{1-6}$ alkoxy" refers to an alkyl group which is attached to a molecule via oxygen containing 1, 2, 3, 4, 5 or 6 carbon atoms, for example methyl, ethyl, n-propyl, iso-propyl, n-butyl, sec-butyl, tert-butyl, n-pentyl and n-hexyl. Therefore, the alkoxy group may be methoxy, ethoxy, n-propoxy, iso-propoxy, n-butoxy, sec-butoxy, tert-butoxy, n-pentoxy and n-hexoxy. The alkyl part of the alkoxy group may be unsubstituted or substituted by one or more substituents. Possible substituents are described below. Substituents for the alkyl group may be halogen, e.g. fluorine, chlorine, bromine and iodine, OH, $C_{1-6}$ alkoxy.

The term "alkyl ether" refers to a linear or branched alkyl chain that is interrupted by a single oxygen atom to provide an ether. For example, the terms "$C_{2-6}$ alkyl ether" or "$C_{2-4}$ alkyl ether" refer to a linear or branched hydrocarbon chain containing 2, 3, 4, 5 or 6 carbon atoms or 2, 3, or 4 carbon atoms with a single oxygen atom within the chain, for example —$CH_2OCH_3$, —$(CH_2)_2OCH_3$, —$(CH_2)_3OCH_3$, —$CH_2OCH_2CH_3$, —$CH_2O(CH_2)_2CH_3$ or —$(CH_2)_2O(CH_2)_2CH_3$.

The term "haloalkyl" refers to a hydrocarbon chain substituted with at least one halogen atom independently chosen at each occurrence, for example fluorine, chlorine, bromine and iodine. The halogen atom may be present at any position on the hydrocarbon chain. For example, "$C_{1-6}$ haloalkyl" refers to a hydrocarbon chain substituted with at least one halogen atom containing 1, 2, 3, 4, 5 or 6 carbon atoms, for example chloromethyl, fluoromethyl, trifluoromethyl, chloroethyl e.g. 1-chloromethyl and 2-chloroethyl, trichloroethyl e.g. 1,2,2-trichloroethyl, 2,2,2-trichloroethyl, fluoroethyl e.g. 1-fluoromethyl and 2-fluoroethyl, trifluoroethyl e.g. 1,2,2-trifluoroethyl and 2,2,2-trifluoroethyl, chloropropyl, trichloropropyl, fluoropropyl, trifluoropropyl.

The term "alkenyl" refers to a branched or linear hydrocarbon chain containing at least one double bond. For example, the term "$C_{2-6}$ alkenyl" refers to a branched or linear hydrocarbon chain containing at least one double bond having 2, 3, 4, 5 or 6 carbon atoms. The double bond(s) may be present as the E or Z isomer. The double bond may be at any possible position of the hydrocarbon chain. For example, the "$C_{2-6}$ alkenyl" may be ethenyl, propenyl, butenyl, butadienyl, pentenyl, pentadienyl, hexenyl and hexadienyl.

The term "alkynyl" refers to a branded or linear hydrocarbon chain containing at least one triple bond. For example, the term "$C_{2-6}$ alkynyl" refers to a branded or linear hydrocarbon chain containing at least one triple bond having 2, 3, 4, 5 or 6 carbon atoms. The triple bond may be at any possible position of the hydrocarbon chain. For example, the "$C_{2-6}$ alkynyl" may be ethynyl, propynyl, butynyl, pentynyl and hexynyl.

The term "heteroalkyl" refers to a branched or linear hydrocarbon chain at least one heteroatom selected from N, O and S positioned between any carbon in the chain or at an end of the chain. For example, the term "$C_{1-6}$ heteroalkyl" refers to a branded or linear hydrocarbon chain containing 1, 2, 3, 4, 5, or 6 carbon atoms and at least one heteroatom selected from N, O and S positioned between any carbon in the chain or at an end of the chain. For example, the hydrocarbon chain may contain one or two heteroatoms. The $C_{1-6}$ heteroalkyl may be bonded to the rest of the molecule through a carbon or a heteroatom. For example, the "$C_{1-6}$ heteroalkyl" may be $C_{1-6}$ N-alkyl, $C_{1-6}$ N,N-alkyl, or $C_{1-6}$ O-alkyl.

The term "carbocyclic" refers to a saturated or unsaturated carbon containing ring system. A "carbocyclic" system may be monocyclic or a fused polycyclic ring system, for example, bicyclic or tricyclic. A "carbocyclic" moiety may contain from 3 to 14 carbon atoms, for example, 3 to 8 carbon atoms in a monocyclic system and 7 to 14 carbon atoms in a polycyclic system. "Carbocyclic" encompasses cycloalkyl moieties, cycloalkenyl moieties, aryl ring systems and fused ring systems including an aromatic portion.

The term "heterocyclic" refers to a saturated or unsaturated ring system containing at least one heteroatom selected from N, O or S. A "heterocyclic" system may contain 1, 2, 3 or 4 heteroatoms, for example 1 or 2. A "heterocyclic" system may be monocyclic or a fused polycyclic ring system, for example, bicyclic or tricyclic. A "heterocyclic" moiety may contain from 3 to 14 carbon atoms, for example, 3 to 8 carbon atoms in a monocyclic system and 7 to 14 carbon atoms in a polycyclic system. "Heterocyclic" encompasses heterocycloalkyl moieties, heterocycloalkenyl moieties and heteroaromatic moieties. For example, the heterocyclic group may be: oxirane, aziridine, azetidine, oxetane, tetrahydrofuran, pyrrolidine, imidazolidine, succinimide, pyrazolidine, oxazolidine, isoxazolidine, thiazolidine, isothiazolidine, piperidine, morpholine, thiomorpholine, piperazine, and tetrahydropyran.

The term "cycloalkyl" refers to a saturated hydrocarbon ring system. The "cycloalkyl" group may be denoted as a "$C_{3-10}$ cycloalkyl" containing 3, 4, 5, 6, 7, 8, 9 or 10 carbon atoms.

The ring system may be a single ring or a bi-cyclic or tri-cyclic ring system. For example, the "cycloalkyl" may be cyclopropyl, cyclobutyl, cyclopentyl, cyclohexyl, bicyclohexyl, cycloheptyl and cyclooctyl.

The term "cycloalkenyl" refers to an unsaturated hydrocarbon ring system that is not aromatic. The "cycloalkenyl" group may be denoted as a "$C_{3-10}$ cycloalkenyl". A "$C_{3-10}$ cycloalkenyl" is a ring system containing 3, 4, 5, 6, 7, 8, 9 or 10 carbon atoms. The ring may contain more than one double bond provided that the ring system is not aromatic. The ring system may be a single ring or a bi-cyclic or tri-cyclic ring system. For example, the "cycloalkenyl" may be cyclopropenyl, cyclobutenyl, cyclopentenyl, cyclopentadienyl, cyclohexenyl, cyclohexadienly, cycloheptenyl, cycloheptadiene, cyclooctenyl and cycloatadienyl.

The term "heterocycloalkyl" refers to a saturated hydrocarbon ring system with at least one heteroatom within the ring selected from N, O and S. The "heterocycloalkyl" group may be denoted as a "$C_{3-10}$ heterocycloalkyl". A "$C_{3-10}$ heterocycloalkyl" is a ring system containing 3, 4, 5, 6, 7, 8, 9 or 10 atoms at least one being a heteroatom. For example there may be 1, 2 or 3 heteroatoms, optionally 1 or 2. The "heterocycloalkyl" group may also be denoted as a "3 to 10 membered heterocycloalkyl" which is also a ring system containing 3, 4, 5, 6, 7, 8, 9 or 10 atoms at least one being a heteroatom. The ring system may be a single ring or a bi-cyclic or tri-cyclic ring system. Where the ring system is bicyclic one of the rings may be an aromatic ring, for example as in indane. The "heterocycloalkyl" may be bonded to the rest of the molecule through any carbon atom or heteroatom. The "heterocycloalkyl" may have one or more, e.g. one or two, bonds to the rest of the molecule: these bonds may be through any of the atoms in the ring. For example, the "heterocycloalkyl" may be oxirane, aziridine, azetidine, oxetane, tetrahydrofuran, pyrrolidine, imidazolidine, succinimide, pyrazolidine, oxazolidine, isoxazolidine, thiazolidine, isothiazolidine, piperidine, morpholine, thiomorpholine, piperazine, tetrahydropyran, and indane.

The term "heterocycloalkenyl" refers to an unsaturated hydrocarbon ring system, that is not aromatic, having at least one heteroatom within the ring selected from N, O and S. The "heterocycloalkenyl" group may be denoted as a "$C_{3-10}$ heterocycloalkenyl". A "$C_{3-10}$ heterocycloalkenyl" is a ring system containing 3, 4, 5, 6, 7, 8, 9 or 10 atoms at least one being a heteroatom. For example there may be 1, 2 or 3 heteroatoms, optionally 1 or 2. The "heterocycloalkenyl" group may also be denoted as a "3 to 10 membered heterocycloalkenyl" which is also a ring system containing 3, 4, 5, 6, 7, 8, 9 or 10 atoms at least one being a heteroatom. The ring system may be a single ring or a bi-cyclic or tri-cyclic ring system. Where the ring system is bicyclic one of the rings may be an aromatic ring, for example as in indoline and dihydrobenzofuran. The "heterocycloalkenyl" may be bonded to the rest of the molecule through any carbon atom or heteroatom. The "heterocycloalkenyl" may have one or more, e.g. one or two, bonds to the rest of the molecule: these bonds may be through any of the atoms in the ring. For example, the "$C_{3-8}$ heterocycloalkenyl" may be tetrahydropyridine, dihydropyran, dihydrofuran, pyrroline, dihydrobenzofuran, dihydrobenzothiophene and indoline.

The term "aromatic" when applied to a substituent as a whole means a single ring or polycyclic ring system with 4n+2 electrons in a conjugated R system within the ring or ring system where all atoms contributing to the conjugated π system are in the same plane.

The term "aryl" refers to an aromatic hydrocarbon ring system. The ring system has 4n+2 electrons in a conjugated π system within a ring where all atoms contributing to the conjugated π system are in the same plane. The ring system may be a single ring or a bi-cyclic or tri-cyclic ring system. For example, the "aryl" may be phenyl and naphthyl. The aryl system itself may be substituted with other groups.

The term "heteroaryl" refers to an aromatic hydrocarbon ring system with at least one heteroatom within a single ring or within a fused ring system, selected from O, N and S. The ring or ring system has 4n+2 electrons in a conjugated π system where all atoms contributing to the conjugated π system are in the same plane. The ring system may be a single ring or a bi-cyclic or tri-cyclic ring system. For example, the "heteroaryl" may be imidazole, thiene, furane, thianthrene, pyrrole, benzimidazole, pyrazole, pyrazine, pyridine, pyrimidine and indole.

The term "alkaryl" refers to an aryl group, as defined above, bonded to a $C_{1-4}$ alkyl, where the $C_{1-4}$ alkyl group provides attachment to the remainder of the molecule.

The term "alkheteroaryl" refers to a heteroaryl group, as defined above, bonded to a $C_{1-4}$ alkyl, where the alkyl group provides attachment to the remainder of the molecule.

The term "halogen" herein includes reference to F, Cl, Br and I. Halogen may be Cl. Halogen may be F.

A bond terminating in a "⌇" represents that the bond is connected to another atom that is not shown in the structure. A bond terminating inside a cyclic structure and not terminating at an atom of the ring structure represents that the bond may be connected to any of the atoms in the ring structure where allowed by valency.

Where a moiety is substituted, it may be substituted at any point on the moiety where chemically possible and consistent with atomic valency requirements. The moiety may be substituted by one or more substituents, e.g. 1, 2, 3 or 4 substituents; optionally there are 1 or 2 substituents on a group. Where there are two or more substituents, the substituents may be the same or different. The substituent(s) may be selected from: OH, NHR$^9$, amidino, guanidino, hydroxyguanidino, formamidino, isothioureido, ureido, mercapto, C(O)H, acyl, acyloxy, carboxy, sulfo, sulfamoyl, carbamoyl, cyano, azo, nitro, halo, $C_{1-6}$ alkyl, $C_{1-6}$ alkoxy, $C_{1-6}$ haloalkyl, $C_{3-8}$ cycloalkyl, $C_{2-6}$ alkenyl, $C_{2-6}$ alkynyl, aryl, heteroaryl or alkaryl. Where the group to be substituted is an alkyl group the substituent may be =O. Where the moiety is substituted with two or more substituents and two of the substituents are adjacent the adjacent substituents may form a $C_{4-8}$ ring along with the atoms of the moiety on which the substituents are substituted, wherein the $C_{4-8}$ ring is a saturated or unsaturated hydrocarbon ring with 4, 5, 6, 7, or 8 carbon atoms or a saturated or unsaturated hydrocarbon ring with 4, 5, 6, 7, or 8 carbon atoms and 1, 2 or 3 heteroatoms.

If chemically possible to do so, a cyclic substituent may be substituted on a group so as to form a spiro-cycle.

Substituents are only present at positions where they are chemically possible, the person skilled in the art being able to decide (either experimentally or theoretically) without inappropriate effort which substitutions are chemically possible and which are not.

Ortho, meta and para substitution are well understood terms in the art. For the absence of doubt, "ortho" substitution is a substitution pattern where adjacent carbons possess a substituent, whether a simple group, for example the fluoro group in the example below, or other portions of the molecule, as indicated by the bond ending in "⌇".

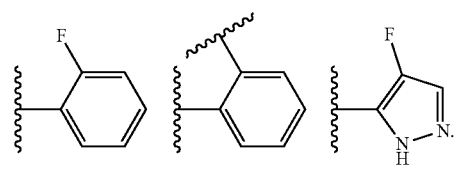

"Meta" substitution is a substitution pattern where two substituents are on carbons one carbon removed from each other, i.e with a single carbon atom between the substituted carbons. In other words there is a substituent on the second atom away from the atom with another substituent. For example the groups below are meta substituted.

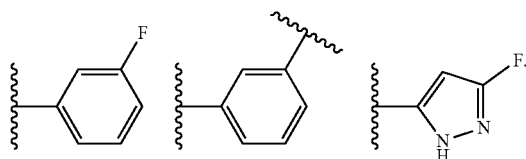

"Para" substitution is a substitution pattern where two substituents are on carbons two carbons removed from each other, i.e with two carbon atoms between the substituted carbons. In other words there is a substituent on the third atom away from the atom with another substituent. For example the groups below are para substituted.

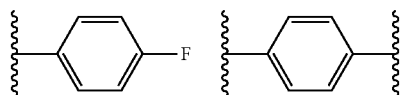

By "acyl" is meant an organic radical derived from, for example, an organic acid by the removal of the hydroxyl group, e.g. a radical having the formula R—C(O)—, where R may be selected from H, $C_{1-6}$ alkyl, $C_{3-8}$ cycloalkyl, phenyl, benzyl or phenethyl group, eg R is H or $C_{1-3}$ alkyl. In one embodiment acyl is alkyl-carbonyl. Examples of acyl groups include, but are not limited to, formyl, acetyl, propionyl and butyryl. A particular acyl group is acetyl.

In embodiments where there is a single enantiomer of the compounds of the invention, the compounds of the invention may have an enantiomeric purity of at least about 90% enantiomeric excess (ee), at least about 95% enantiomeric excess (ee), at least about 98% enantiomeric excess (ee), at least about 99% enantiomeric excess (ee), or 100% enantiomeric excess (ee). In embodiments where there is a mixture of enantiomers of the compounds of the invention, the compounds of the invention may be a racemic mixture or any other mixture of enantiomers, for example the compounds of the invention may have an enantiomeric purity of at least about 50% enantiomeric excess (ee), at least about 60% enantiomeric excess (ee), at least about 70% enantiomeric excess (ee), at least about 80% enantiomeric excess (ee), at least about 90% enantiomeric excess (ee), or at least about 95% enantiomeric excess (ee).

Throughout the description the disclosure of a compound also encompasses pharmaceutically acceptable salts, solvates and stereoisomers thereof. Where a compound has a stereocentre, both (R) and (S) stereoisomers are contemplated by the invention, equally mixtures of stereoisomers or a racemic mixture are completed by the present application. Where a compound of the invention has two or more stereocentres any combination of (R) and (S) stereoisomers is contemplated. The combination of (R) and (S)-stereoisomers may result in a diastereomeric mixture or a single diastereoisomer. The compounds of the invention may be present as a single stereoisomer or may be mixtures of stereoisomers, for example racemic mixtures and other enantiomeric mixtures, and diasteroemeric mixtures. Where the mixture is a mixture of enantiomers the enantiomeric excess may be any of those disclosed above. Where the compound is a single stereoisomer the compounds may still contain other diasteroisomers or enantiomers as impurities. Hence a single stereoisomer does not necessarily have an enantiomeric excess (e.e.) or diastereomeric excess (d.e.) of 100% but could have an e.e. or d.e. of about at least 85%

The invention contemplates pharmaceutically acceptable salts of the compounds of formula (I). These may include the acid addition and base salts of the compounds. These may be acid addition and base salts of the compounds. In addition the invention contemplates solvates of the compounds. These may be hydrates or other solvated forms of the compound.

Suitable acid addition salts are formed from acids which form non-toxic salts. Examples include the acetate, aspartate, benzoate, besylate, bicarbonate/carbonate, bisulfate/sulfate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulfate, naphthylate, 1,5-naphthalenedisulfonate, 2-napsylate, nicotinate, nitrate, orotate, oxalate, palmitate, pamoate, phosphate/hydrogen phosphate/dihydrogen phosphate, saccharate, stearate, succinate, tartrate, tosylate and trifluoroacetate salts.

Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts. Hemisalts of acids and bases may also be formed, for example, hemisulfate and hemicalcium salts. For a review on suitable salts, see "Handbook of Pharmaceutical Salts: Properties, Selection, and Use" by Stahl and Wermuth (Wiley-VCH, Weinheim, Germany, 2002).

Pharmaceutically acceptable salts of compounds of formula (I) may be prepared by one or more of three methods:
(i) by reacting the compound of formula (I) with the desired acid or base;
(ii) by removing an acid- or base-labile protecting group from a suitable precursor of the compound of formula (I) or by ring-opening a suitable cyclic precursor, for example, a lactone or lactam, using the desired acid or base; or
(iii) by converting one salt of the compound of formula (I) to another by reaction with an appropriate acid or base or by means of a suitable ion exchange column.

All three reactions are typically carried out in solution. The resulting salt may precipitate out and be collected by filtration or may be recovered by evaporation of the solvent. The degree of ionisation in the resulting salt may vary from completely ionised to almost non-ionised.

The compounds of the invention may exist in both unsolvated and solvated forms. The term 'solvate' is used herein to describe a molecular complex comprising the compound of the invention and a stoichiometric amount of one or more pharmaceutically acceptable solvent molecules, for example, ethanol. The term 'hydrate' is employed when said solvent is water.

Included within the scope of the invention are complexes such as clathrates, drug-host inclusion complexes wherein, in contrast to the aforementioned solvates, the drug and host are present in stoichiometric or non-stoichiometric amounts. Also included are complexes of the drug containing two or more organic and/or inorganic components which may be in stoichiometric or non-stoichiometric amounts. The resulting complexes may be ionised, partially ionised, or non-ionised. For a review of such complexes, see J Pharm Sci, 64 (8), 1269-1288 by Haleblian (August 1975).

Hereinafter all references to compounds of any formula include references to salts, solvates and complexes thereof and to solvates and complexes of salts thereof.

The compounds of the invention include compounds of a number of formula as herein defined, including all polymorphs and crystal habits thereof, prodrugs and isomers thereof (including optical, geometric and tautomeric isomers) as hereinafter defined and isotopically-labeled compounds of the invention.

Before purification, the compounds of the present invention may exist as a mixture of enantiomers depending on the synthetic procedure used. The enantiomers can be separated by conventional techniques known in the art. Thus the invention covers individual enantiomers as well as mixtures thereof.

For some of the steps of the process of preparation of the compounds of formula (I), it may be necessary to protect potential reactive functions that are not wished to react, and to cleave said protecting groups in consequence. In such a case, any compatible protecting radical can be used. In particular methods of protection and deprotection such as those described by T.W. GREENE (Protective Groups in Organic Synthesis, A. Wiley-lnterscience Publication, 1981) or by P. J. Kocienski (Protecting groups, Georg Thieme Verlag, 1994), can be used. All of the above reactions and the preparations of novel starting materials used in the preceding methods are conventional and appropriate reagents and reaction conditions for their performance or preparation as well as procedures for isolating the desired products will be well-known to those skilled in the art with reference to literature precedents and the examples and preparations hereto.

Also, the compounds of the present invention as well as intermediates for the preparation thereof can be purified according to various well-known methods, such as for example recrystallization or chromatography.

The method of treatment or the compound for use in the treatment of cancer, lymphoma, leukemia or immunological diseases as defined hereinbefore may be applied as a sole therapy or be a combination therapy with an additional active agent.

The method of treatment or the compound for use in the treatment of cancer, lymphoma or leukemia may involve, in addition to the compound of the invention, conventional surgery or radiotherapy or chemotherapy. Such chemotherapy may include one or more of the following categories of anti-tumor agents:

(i) antiproliferative/antineoplastic drugs and combinations thereof, such as alkylating agents (for example cis-platin, oxaliplatin, carboplatin, cyclophosphamide, nitrogen mustard, bendamustin, melphalan, chlorambucil, busulphan, temozolamide and nitrosoureas); antimetabolites (for example gemcitabine and antifolates such as fluoropyrimidines like 5-fluorouracil and tegafur, raltitrexed, methotrexate, pemetrexed, cytosine arabinoside, and hydroxyurea); antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere and polokinase inhibitors); proteasome inhibitors, for example carfilzomib and bortezomib; interferon therapy; and topoisomerase inhibitors (for example epipodophyllotoxins like etoposide and teniposide, amsacrine, topotecan, mitoxantrone and camptothecin);
(ii) cytostatic agents such as antiestrogens (for example tamoxifen, fulvestrant, toremifene, raloxifene, droloxifene and iodoxyfene), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase such as finasteride;
(iii) anti-invasion agents, for example dasatinib and bosutinib (SKI-606), and metalloproteinase inhibitors, inhibitors of urokinase plasminogen activator receptor function or antibodies to Heparanase;
(iv) inhibitors of growth factor function: for example such inhibitors include growth factor antibodies and growth factor receptor antibodies, for example the anti-erbB2 antibody trastuzumab [Herceptin™], the anti-EGFR antibody panitumumab, the anti-erbB1 antibody cetuximab, tyrosine kinase inhibitors, for example inhibitors of the epidermal growth factor family (for example EGFR family tyrosine kinase inhibitors such as gefitinib, erlotinib and 6-acrylamido-N-(3-chloro-4-fluorophenyl)-7-(3-morpholinopropoxy)-quinazolin-4-amine (CI 1033), erbB2 tyrosine kinase inhibitors such as lapatinib); inhibitors of the hepatocyte growth factor family; inhibitors of the insulin growth factor family; modulators of protein regulators of cell apoptosis (for example Bcl-2 inhibitors); inhibitors of the platelet-derived growth factor family such as imatinib and/or nilotinib (AMN107); inhibitors of serine/threonine kinases (for example Ras/Raf signalling inhibitors such as farnesyl transferase inhibitors, for example sorafenib, tipifarnib and lonafarnib), inhibitors of cell signalling through MEK and/or AKT kinases, c-kit inhibitors, abl kinase inhibitors, PI3 kinase inhibitors, Plt3 kinase inhibitors, CSF-1R kinase inhibitors, IGF receptor, kinase inhibitors; aurora kinase inhibitors and cyclin dependent kinase inhibitors such as CDK2 and/or CDK4 inhibitors;
(v) antiangiogenic agents such as those which inhibit the effects of vascular endothelial growth factor, [for example the anti-vascular endothelial cell growth factor antibody bevacizumab (Avastin™); thalidomide; lenalidomide; and for example, a VEGF receptor tyrosine kinase inhibitor such as vandetanib, vatalanib, sunitinib, axitinib and pazopanib;
(vi) gene therapy approaches, including for example approaches to replace aberrant genes such as aberrant p53 or aberrant BRCA1 or BRCA2;
(vii) immunotherapy approaches, including for example antibody therapy such as alemtuzumab, rituximab, ibritumomab tiuxetan (Zevalin®) and ofatumumab; interferons such as interferon α; interleukins such as IL-2 (aldesleukin); interleukin inhibitors for example IRAK4 inhibitors; cancer vaccines including prophylactic and treatment vaccines such as HPV vaccines, for example Gardasil, Cervarix, Oncophage and Sipuleucel-T (Provenge); and toll-like receptor modulators for example TLR-7 or TLR-9 agonists; and
(viii) cytotoxic agents for example fludaribine (fludara), cladribine, pentostatin (Nipent™);
(ix) steroids such as corticosteroids, including glucocorticoids and mineralocorticoids, for example aclometasone, aclometasone dipropionate, aldosterone, amcinonide, beclomethasone, beclomethasone dipropionate, betamethasone, betamethasone dipropionate, betamethasone sodium phosphate, betamethasone valerate, budesonide, clobetasone, clobetasone butyrate, clobetasol propionate, cloprednol, cortisone, cortisone acetate, cortivazol, deoxycortone, desonide, desoximetasone, dexamethasone, dexamethasone sodium phosphate, dexamethasone isonicotinate, difluorocortolone, fluclorolone, flumethasone, flunisolide, fluocinolone, fluocinolone acetonide, fluocinonide, fluocortin butyl, fluorocortisone, fluorocortolone, fluocortolone caproate, fluocortolone pivalate, fluorometholone, fluprednidene, fluprednidene acetate, flurandrenolone, fluticasone, fluticasone propionate, halcinonide, hydrocortisone, hydrocortisone acetate, hydrocortisone butyrate, hydrocortisone aceponate, hydrocortisone buteprate, hydrocortisone valerate, icomethasone, icomethasone enbutate, meprednisone, methylprednisolone, mometasone paramethasone, mometasone furoate monohydrate, prednicarbate, prednisolone, prednisone, tixocortol, tixocortol pivalate, triamcinolone, triamcinolone acetonide, triamcinolone alcohol and their respective pharmaceutically acceptable derivatives. A combination of steroids may be used, for example a combination of two or more steroids mentioned in this paragraph;

(x) targeted therapies, for example PI3Kd inhibitors, for example idelalisib and perifosine.

The method of treatment or the compound for use in the treatment of immunological diseases may involve, in addition to the compound of the invention, additional active agents. The additional active agents may be one or more active agents used to treat the condition being treated by the compound of formula (I) and additional active agent. The additional active agents may include one or more of the following active agents:—

(i) steroids such as corticosteroids, including glucocorticoids and mineralocorticoids, for example aclometasone, aclometasone dipropionate, aldosterone, amcinonide, beclomethasone, beclomethasone dipropionate, betamethasone, betamethasone dipropionate, betamethasone sodium phosphate, betamethasone valerate, budesonide, clobetasone, clobetasone butyrate, clobetasol propionate, cloprednol, cortisone, cortisone acetate, cortivazol, deoxycortone, desonide, desoximetasone, dexamethasone, dexamethasone sodium phosphate, dexamethasone isonicotinate, difluorocortolone, fluclorolone, flumethasone, flunisolide, fluocinolone, fluocinolone acetonide, fluocinonide, fluocortin butyl, fluorocortisone, fluorocortolone, fluocortolone caproate, fluocortolone pivalate, fluorometholone, fluprednidene, fluprednidene acetate, flurandrenolone, fluticasone, fluticasone propionate, halcinonide, hydrocortisone, hydrocortisone acetate, hydrocortisone butyrate, hydrocortisone aceponate, hydrocortisone buteprate, hydrocortisone valerate, icomethasone, icomethasone enbutate, meprednisone, methylprednisolone, mometasone paramethasone, mometasone furoate monohydrate, prednicarbate, prednisolone, prednisone, tixocortol, tixocortol pivalate, triamcinolone, triamcinolone acetonide, triamcinolone alcohol and their respective pharmaceutically acceptable derivatives. A combination of steroids may be used, for example a combination of two or more steroids mentioned in this paragraph;

(ii) TNF inhibitors for example etanercept; monoclonal antibodies (e.g. infliximab (Remicade), adalimumab (Humira), certolizumab pegol (Cimzia), golimumab (Simponi)); fusion proteins (e.g. etanercept (Enbrel)); and 5-HT$_{2A}$ agonists (e.g. 2,5-dimethoxy-4-iodoamphetamine, TCB-2, lysergic acid diethylamide (LSD), lysergic acid dimethylazetidide);

(iii) anti-inflammatory drugs, for example non-steroidal anti-inflammatory drugs;

(iv) dihydrofolate reductase inhibitors/antifolates, for example methotrexate, trimethoprim, brodimoprim, tetroxoprim, iclaprim, pemetrexed, ralitrexed and pralatrexate; and (v) immunosuppressants for example cyclosporins, tacrolimus, sirolimus pimecrolimus, angiotensin II inhibitors (e.g. Valsartan, Telmisartan, Losartan, Irbesatan, Azilsartan, Olmesartan, Candesartan, Eprosartan) and ACE inhibitors e.g. sulfhydryl-containing agents (e.g. Captopril, Zofenopril), dicarboxylate-containing agents (e.g. Enalapril, Ramipril, Quinapril, Perindopril, Lisinopril, Benazepril, Imidapril, Zofenopril, Trandolapril), phosphate-containing agents (e.g. Fosinopril), casokinins, lactokinins and lactotripeptides.

Such combination treatment may be achieved by way of the simultaneous, sequential or separate dosing of the individual components of the treatment. Such combination products employ the compounds of this invention within a therapeutically effective dosage range described hereinbefore and the other pharmaceutically-active agent within its approved dosage range.

According to a further aspect of the invention there is provided a pharmaceutical product comprising a compound of formula (I), or a pharmaceutically acceptable salt thereof as defined hereinbefore and an additional active agent. The additional active agent may be an anti-tumour agent as defined hereinbefore for the combination treatment of a condition modulated by BTK.

According to a further aspect of the invention there is provided a method of treatment a condition modulated by BTK comprising administering a therapeutically effective amount of a compound of formula (I), or a pharmaceutically acceptable salt thereof simultaneously, sequentially or separately with an additional anti-tumor agent, as defined hereinbefore, to a patient in need thereof.

According to a further aspect of the invention there is provided a compound of formula (I), or a pharmaceutically acceptable salt thereof for use simultaneously, sequentially or separately with an additional anti-tumour agent as defined hereinbefore, in the treatment of a condition modulated by BTK.

According to another aspect of the invention there is provided a use of the compound of formula (I) in combination with an anti-tumor agent as hereinbefore described. The compound of formula (I) may be used simultaneously, sequentially or separately with the additional anti-tumor agent. The use may be in a single combination product comprising the compound of formula (I) and the anti-tumor agent.

According to a further aspect there is provided a method of providing a combination product, wherein the method comprises providing a compound of formula (I) simultaneously, sequentially or separately with an anti-tumor agent, as defined herein before. The method may comprise combining the compound of formula (I) and the anti-tumor agent in a single dosage form. Alternatively the method may comprise providing the anti-tumor agent as separate dosage forms.

According to a further aspect there is provided a method of providing a combination product, wherein the method comprises providing a compound of formula (I) simultaneously, sequentially or separately with an anti-tumor agent, as defined hereinbefore. The method may comprise combining the compound of formula (I) and the anti-tumor agent in a single dosage form. Alternatively the method may comprise providing the anti-tumor agent as separate dosage forms.

The condition modulated by BTK described above may be cancer, leukemia or cancer. More specifically the condition modulated by BTK may be selected from: B-cell malignancy, B-cell lymphoma, diffuse large B cell lymphoma, chronic lymphocytic leukemia, non-Hodgkin lymphoma for example ABC-DLBCL, mantle cell lymphoma, follicular lymphoma, hairy cell leukemia, B-cell non-Hodgkin lymphoma, Waldenstrom's macroglobulinemia and multiple myeloma.

Compounds of the invention may exist in a single crystal form or in a mixture of crystal forms or they may be amorphous. Thus, compounds of the invention intended for pharmaceutical use may be administered as crystalline or amorphous products. They may be obtained, for example, as solid plugs, powders, or films by methods such as precipitation, crystallization, freeze drying, or spray drying, or evaporative drying. Microwave or radio frequency drying may be used for this purpose.

For the above-mentioned compounds of the invention the dosage administered will, of course, vary with the compound employed, the mode of administration, the treatment desired and the disorder indicated. For example, if the compound of the invention is administered orally, then the daily dosage of the compound of the invention may be in the range from 0.01 micrograms per kilogram body weight (g/kg) to 100 milligrams per kilogram body weight (mg/kg).

A compound of the invention, or pharmaceutically acceptable salt thereof, may be used on their own but will generally be administered in the form of a pharmaceutical composition in which the compounds of the invention, or pharmaceutically acceptable salt thereof, is in association with a pharmaceutically acceptable adjuvant, diluent or carrier. Conventional procedures for the selection and preparation of suitable pharmaceutical formulations are described in, for example, "Pharmaceuticals—The Science of Dosage Form Designs", M. E. Aulton, Churchill Livingstone, 1988.

Depending on the mode of administration of the compounds of the invention, the pharmaceutical composition which is used to administer the compounds of the invention will preferably comprise from 0.05 to 99% w (percent by weight) compounds of the invention, more preferably from 0.05 to 80% w compounds of the invention, still more preferably from 0.10 to 70% w compounds of the invention, and even more preferably from 0.10 to 50% w compounds of the invention, all percentages by weight being based on total composition.

The pharmaceutical compositions may be administered topically (e.g. to the skin) in the form, e.g., of creams, gels, lotions, solutions, suspensions, or systemically, e.g. by oral administration in the form of tablets, capsules, syrups, powders or granules; or by parenteral administration in the form of a sterile solution, suspension or emulsion for injection (including intravenous, subcutaneous, intramuscular, intravascular or infusion); by rectal administration in the form of suppositories; or by inhalation in the form of an aerosol.

For oral administration the compounds of the invention may be admixed with an adjuvant or a carrier, for example, lactose, saccharose, sorbitol, mannitol; a starch, for example, potato starch, corn starch or amylopectin; a cellulose derivative; a binder, for example, gelatine or polyvinylpyrrolidone; and/or a lubricant, for example, magnesium stearate, calcium stearate, polyethylene glycol, a wax, paraffin, and the like, and then compressed into tablets. If coated tablets are required, the cores, prepared as described above, may be coated with a concentrated sugar solution which may contain, for example, gum arabic, gelatine, talcum and titanium dioxide. Alternatively, the tablet may be coated with a suitable polymer dissolved in a readily volatile organic solvent.

For the preparation of soft gelatine capsules, the compounds of the invention may be admixed with, for example, a vegetable oil or polyethylene glycol. Hard gelatine capsules may contain granules of the compound using the above-mentioned excipients for tablets. Also liquid or semi-solid formulations of the compound of the invention may be filled into hard gelatine capsules. Liquid preparations for oral application may be in the form of syrups or suspensions, for example, solutions containing the compound of the invention, the balance being sugar and a mixture of ethanol, water, glycerol and propylene glycol. Optionally such liquid preparations may contain colouring agents, flavouring agents, sweetening agents (such as saccharine), preservative agents and/or carboxymethylcellulose as a thickening agent or other excipients known to those skilled in art.

For intravenous (parenteral) administration the compounds of the invention may be administered as a sterile aqueous or oily solution.

The size of the dose for therapeutic purposes of compounds of the invention will naturally vary according to the nature and severity of the conditions, the age and sex of the animal or patient and the route of administration, according to well-known principles of medicine.

Dosage levels, dose frequency, and treatment durations of compounds of the invention are expected to differ depending on the formulation and clinical indication, age, and co-morbid medical conditions of the patient. The standard duration of treatment with compounds of the invention is expected to vary between one and seven days for most clinical indications. It may be necessary to extend the duration of treatment beyond seven days in instances of recurrent infections or infections associated with tissues or implanted materials to which there is poor blood supply including bones/joints, respiratory tract, endocardium, and dental tissues.

EXAMPLES AND SYNTHESIS

As used herein the following terms have the meanings given: "Boc" refers to tert-butoxycarbonyl; "DCM" refers to dichloromethane; "DIPEA" refers to N,N-Diisopropylethylamine; "EtOAc" refers to ethyl acetate; "LCMS" refers to liquid chromatography/mass spectrometry; "MIM" refers to monoisotopic mass; "min" refers to minutes; "DMF" refers to N,N-dimethylformamide; "Pet. Ether" refers to petroleum ether; "TLC" refers to thin layer chromatography; "Rf" refers to Retention factor; "RT" refers to room temperature; "SCX" refers to strong cation exchange; "TEA" refers to triethylamine; "TFA" refers to trifluoroacetic acid; "THF" refers to tetrahydrofuran; and "TBME" refers to tert-butyl methyl ether.

Solvents, reagents and starting materials were purchased from commercial vendors and used as received unless otherwise described. All reactions were performed at RT unless otherwise stated.

Compound identity and purity confirmations were performed by LCMS UV using a Waters Acquity SQ Detector 2 (ACQ-SQD2#LCA081). The diode array detector wavelength was 254 nM and the MS was in positive and negative electrospray mode (m z: 150-800). A 2 µL aliquot was injected onto a guard column (0.2 µm×2 mm filters) and UPLC column (C18, 50×2.1 mm, <2 µm) in sequence maintained at 40° C. The samples were eluted at a flow rate of 0.6 mL/min with a mobile phase system composed of A (0.1% (v/v) Formic Acid in Water) and B (0.1% (v/v) Formic Acid in Acetonitrile) according to the gradients outlined in Table 1 below. Retention times are reported in minutes.

TABLE 1

| Time (min) | % A | % B |
|---|---|---|
| Long Acidic | | |
| 0 | 95 | 5 |
| 1.1 | 95 | 5 |
| 6.1 | 5 | 95 |

TABLE 1-continued

| Time (min) | % A | % B |
|---|---|---|
| 7 | 5 | 95 |
| 7.5 | 95 | 5 |
| 8 | 95 | 5 |
| Short Acidic | | |
| 0 | 95 | 5 |
| 0.3 | 95 | 5 |
| 2 | 5 | 95 |
| 2.6 | 95 | 5 |
| 3 | 95 | 5 |

Compound identity confirmations were also performed by LCMS UV using a Waters Alliance 2695 micromass ZQ (K98M4 512M-LAA434). The diode array detector wavelength was 254 nM and the MS was in positive and negative electrospray mode (m/z: 150-650). A 10 µL aliquot was injected onto an HPLC column (C18, 75×4.6 mm, 2.5 µm) at RT which was controlled at 19° C. The samples were eluted at a flow rate of 0.9 mL/min with a mobile phase system composed of A (0.1% (v/v) Formic Acid in 95:5 (v/v) Water: Acetonitrile) and B (0.1% (v/v) Formic Acid in 95:5 (v/v) Acetonitrile: Water) according to the gradients outlined in Table 2 below. Retention times are reported in minutes.

TABLE 2

| Method 1 | | |
|---|---|---|
| Time (min) | % A | % B |
| 0 | 100 | 0 |
| 5.5 | 0 | 100 |
| 6.0 | 5 | 100 |
| 6.5 | 100 | 0 |
| 7 | 100 | 0 |

Compound identity confirmations were also performed by analytical Supercritical Fluid Chromatography (SFC) using an Agilent 1260 analytical SFC (SFC-A). A 10 µL aliquot was injected onto an HPLC column (C18, 75×4.6 mm, 2.5 µm) at RT which was controlled at 19° C. The samples were eluted at a flow rate of 3 mL/min with a mobile phase system composed of A for $CO_2$ and B for methanol (0.05% DEA, V/V) eluting with a gradient of Phase B from 5% to 40% in 3.6 min.

NMR was also used to characterise final compounds. NMR spectra were obtained on a Bruker AVIII 400 Nanobay with 5 mm BBFO probe. Optionally, compound Rf values on silica thin layer chromatography (TLC) plates were measured.

Compound purification was performed by flash column chromatography on silica or by preparative LCMS. LCMS purification was performed using a Waters 3100 Mass detector in positive and negative electrospray mode (m/z: 150-800) with a Waters 2489 UV/Vis detector. Samples were eluted at a flow rate of 20 mL/min on a XBridge™ prep C18 5 µM OBD 19×100 mm column with a mobile phase system composed of A (0.1% (v/v) Formic Acid in Water) and B (0.1% (v/v) Formic Acid in Acetonitrile) according to the gradient outlined in Table 3 below.

TABLE 3

| Time (min) | % A | % B |
|---|---|---|
| 0 | 90 | 10 |
| 1.5 | 90 | 10 |

TABLE 3-continued

| Time (min) | % A | % B |
|---|---|---|
| 11.7 | 5 | 95 |
| 13.7 | 5 | 95 |
| 14 | 90 | 90 |
| 15 | 90 | 90 |

Compound purification was also performed by preparative Supercritical Fluid Chromatography (SFC). SFC purification was performed using a Waters 80Q preparative SFC (SFC-B). Samples were eluted at a flow rate of 50 g/min on a ChiralPak® OJ-H column, 250×30 mm ID. in 5 µm particle size with a mobile phase system composed of A for $CO_2$ and B for Methanol (0.1%$NH_3H_2O$) under isocratic elution (25% phase B).

Chemical names in this document were generated using mol2nam—Structure to Name Conversion by OpenEye Scientific Software. Starting materials were purchased from commercial sources or synthesised according to literature procedures.

General Schemes

Compounds of the invention may be produced by following either of the general schemes shown below, either General Scheme 1 or General Scheme 2.

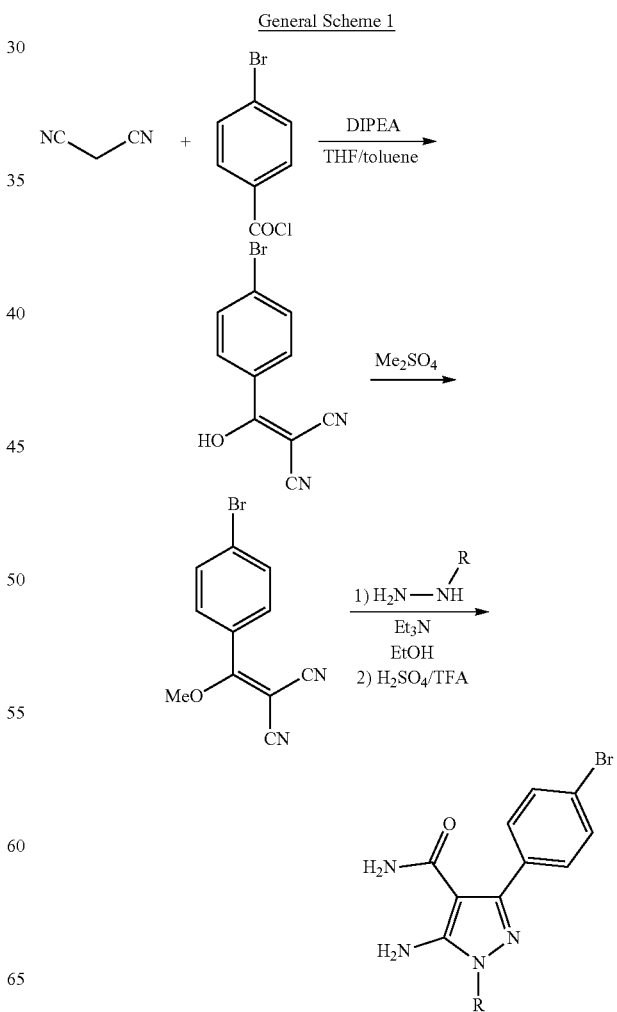

General Scheme 1

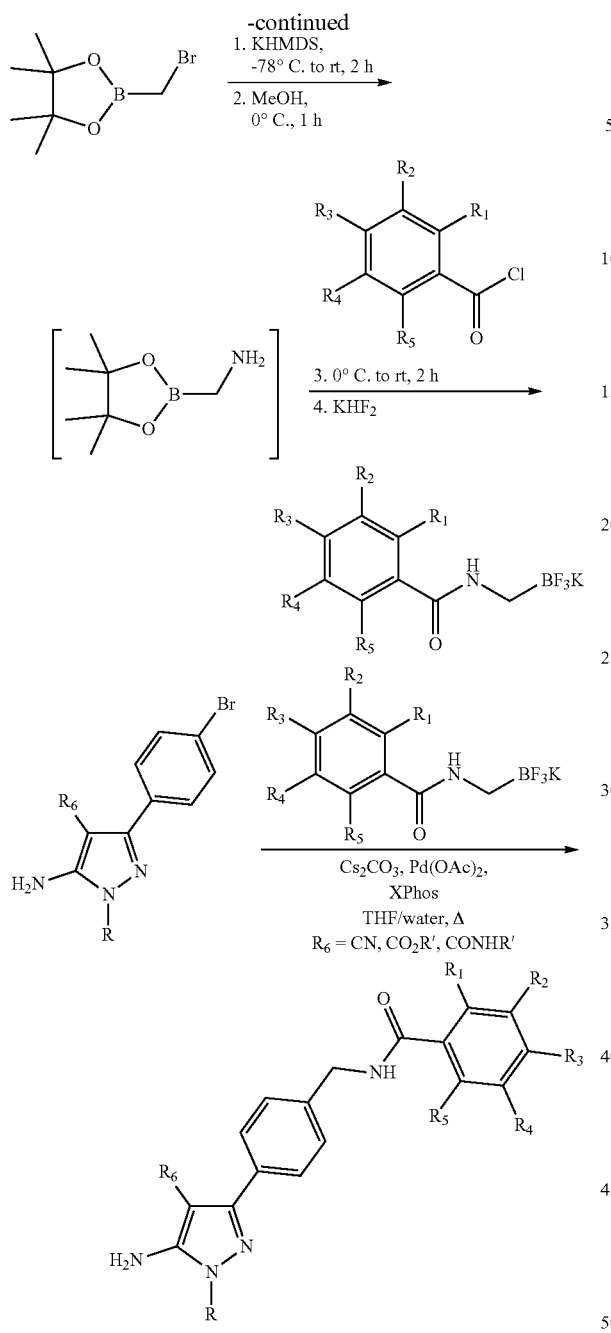

—OR$^I$, —NR$^I$R$^J$, —CN, C$_{1-6}$ alkyl, C$_{1-6}$ haloalkyl, and C$_{1-6}$ alkyl substituted with —OR$^I$;

Y is a halo group, for example fluoro; and

Z is a metal ion, for example a group 1 metal such as potassium or sodium.

In the above aspect of the invention R$^6$ is preferably substituted by a methoxy group and 0 to 4 additional substituents independently selected at each occurrence from: halo, —OR$^I$, —NR$^I$R$^J$, —CN, C$_{1-6}$ alkyl, C$_{1-6}$ haloalkyl, and C$_{1-6}$ alkyl substituted with —OR$^I$.

In a preferred embodiment the compound according to formula (A) is a compound according to formula (B) or (C):

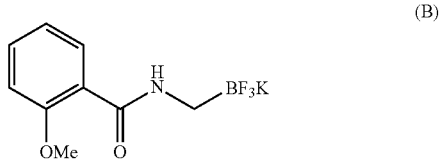

(B)

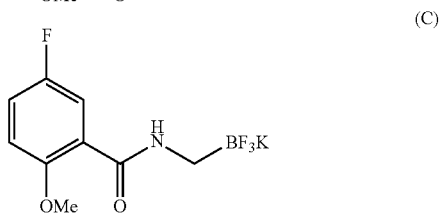

(C)

General Scheme 2

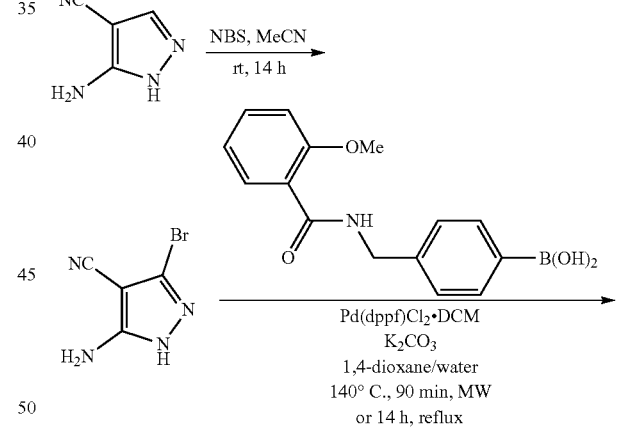

In an aspect of the invention there is provided a compound of formula (A):

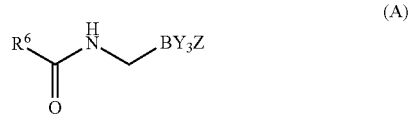

(A)

wherein R$^6$ is as defined elsewhere herein, optionally wherein R$^6$ is a substituted phenyl or a substituted or unsubstituted 5 or 6 membered heteroaryl ring, wherein, when substituted, R$^6$ contains from 1 to 5 substituents independently selected at each occurrence from: halo,

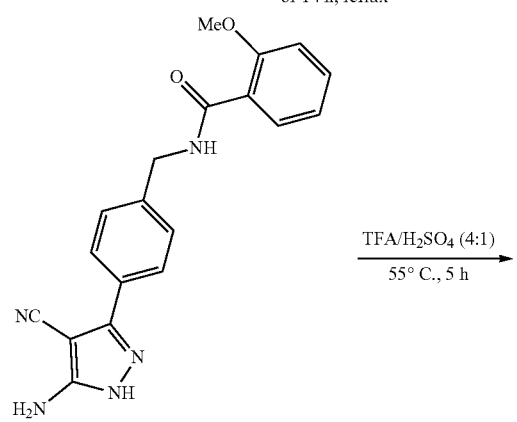

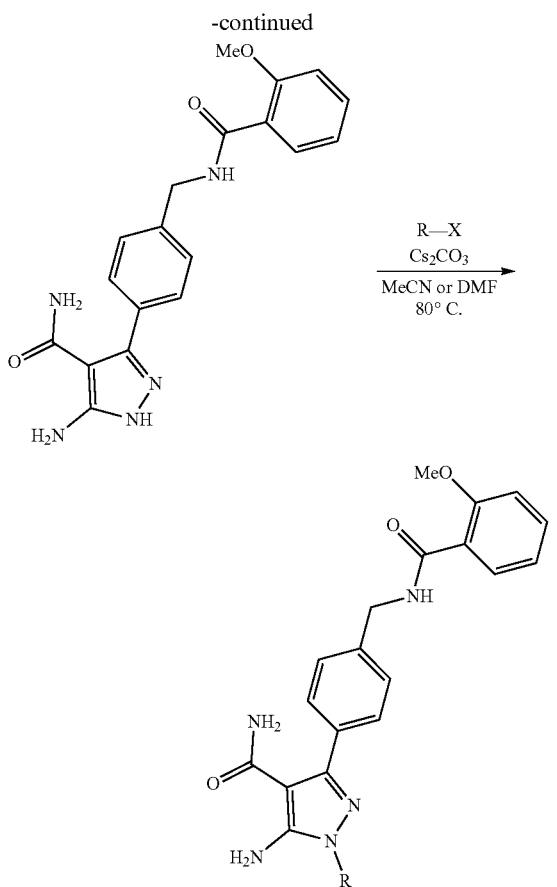

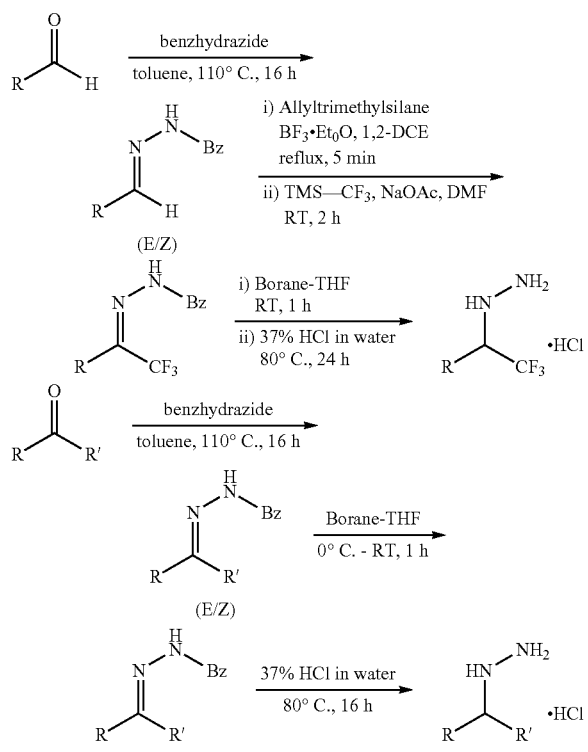

General Scheme 3

General Procedures

General Procedure A

To a suspension of 4-(aminomethyl)phenyl]boronic acid hydrochloride (1.1 eq.) and the corresponding benzoic acid (1.0 eq.) in anhydrous THF (0.49 M), under a nitrogen atmosphere, was added successively, N,N-diisopropylethylamine (5.0 eq.) and a propylphosphonic anhydride solution (50 wt % in EtOAc) (1.5 eq.). The reaction mixture was heated under reflux at 70° C. for 14 h with stirring. The mixture was diluted with water and DCM, then partitioned. The aqueous layer was extracted with DCM (×2). The combined organic extracts were filtered over a phase separator and concentrated under reduced pressure to afford the desired boronic acid. No further purification was attempted and the product was used directly in the next step.

General Procedure B

To a suspension of 4-(aminomethyl)phenyl]boronic acid hydrochloride (1.0 eq.) and DIPEA (3.0 eq.) in anhydrous THF (0.2 M) under a nitrogen atmosphere was added a solution of the corresponding benzoyl chloride derivative (1.1 eq.) in anhydrous THF (0.2 M). The reaction mixture was stirred for 16 h at RT, quenched with a saturated aqueous solution of ammonium chloride and then extracted into ethyl acetate (×3). The combined organics were washed with brine, dried over $Na_2SO_4$ and filtered then concentrated under reduced pressure to afford the desired boronic acid derivative. No further purification was attempted and the product was used directly in the next step.

General Procedure C

A mixture of halide (1.0 eq.), boronic acid or pinacol ester (1.5 eq.) and potassium carbonate (2.0 eq.) in 1,4-dioxane and water (3:1, 0.1 M) was degassed by bubbling nitrogen through it for 25 min. 1,1'-bis(diphenylphosphino)ferrocene-palladium(II) dichloride dichloromethane complex (0.05 eq.) was added and the mixture was degassed again by bubbling nitrogen through it for 30 min. The mixture was then heated at 120° C. for 14 h. The reaction mixture was filtered over Celite®. The cake was rinsed with DCM. Water was added to the filtrate and the layers were partitioned. The aqueous layer was extracted with DCM (×2). The combined organic extracts were filtered over phase separator and then concentrated under reduced pressure to give a dark solid. Further purification by by flash column chromatography on silica gel gave the desired compound.

General Procedure D

A mixture of halide (1.0 eq.), boronic acid or pinacol ester (1.5 eq.) and potassium carbonate (2.0 eq.) in 1,4-dioxane and water (3:1, 0.1 M) was degassed by bubbling nitrogen through it for 15 min. 1,1'-bis(diphenylphosphino)ferrocene-palladium(II) dichloride dichloromethane complex (0.05 eq.) was added and the mixture was degassed again by bubbling nitrogen through it for 15 min. The mixture was then heated under microwave irradiation at 120-140° C. for 60-90 min. The reaction mixture was either purified by SCX SPE cartridge and used as such or purified using the following procedure, unless stated used crude. The mixture was filtered through a pad of Celite®. The cake was rinsed with DCM. Water was added to the filtrate and the layers were partitioned. The aqueous layer was extracted with DCM (×2). The combined organic extracts were filtered over phase separator and then concentrated under reduced pressure to give a dark solid. Further purification by flash column chromatography gave the desired compound.

General Procedure E

To a solution of ketone (1.0 eq.) in MeOH (0.2 M) were added the corresponding hydrazine (1.05 eq.) and the reaction was stirred for 15 h at RT. Volatiles were removed under reduced pressure to provide crude Boc-hydrazone derivative.

General Procedure F

A methanol solution of Boc-hydrazone derivative (1.00 eq.) was treated with 10% palladium on carbon (0.02 eq), acetic acid (0.01 eq.) and purged with $H_2$. The solution was stirred under $H_2$ (1 atm) overnight before being filtered through Celite®. The filtrate was concentrated under reduced to provide the corresponding Boc-protected hydrazine.

General Procedure G

To a solution of Boc-protected hydrazine (1.0 eq.) in MeOH (0.5 M) was added 4 N HCl in 1,4-dioxane (8.0 eq.) and the reaction was stirred at RT for 5 h. Diethyl ether was added and a precipitate formed which was collected by filtration to provide the desired hydrazine intermediate. Alternatively, the mixture was concentrated under reduced pressure and used as such.

General Procedure H

To a solution of 2-[(4-bromophenyl)-methoxy-methylene]propanedinitrile (1.0 eq.) and TEA (3.0 eq.) in EtOH (0.6 M) was added the corresponding hydrazine derivative (1.2 eq.) and the reaction was then stirred for 2-14 h at 100° C. Volatiles were removed under reduced pressure. A saturated aqueous solution of ammonium chloride and ethyl acetate were added to the residue, the organic layer was separated, washed with brine, dried over sodium sulfate, filtered and concentrated under reduced pressure. Further purification by flash column chromatography on silica gel afforded the desired compound.

General Procedure I

To a stirred solution of alcohol (1.0 eq.) in DCM (0.9 M), cooled at 0° C. under a nitrogen atmosphere, was added triethylamine (1.1 eq.). The resulting solution was stirred for 10 min before adding dropwise methanesulfonyl chloride (1.1 eq.). The reaction mixture was stirred at 0° C. for 1 h, quenched with water, and extracted with DCM (×2). The combined organic extracts were filtered over a phase separator and concentrated under reduced pressure to afford the desired mesylated product.

General Procedure J

Hydrochloric acid (1 M, 3.0 eq.) was added to a suspension of 1,3-dioxolane derivative (1.0 eq.) in THF (1 M), cooled at 0° C. The reaction mixture was allowed to return to RT and stirred for 14 h. The mixture was then carefully basified with a saturated solution of sodium carbonate and the aqueous layer was extracted with DCM (×3). The combined organic extracts were filtered over a phase separator and concentrated under reduced pressure to afford crude carbonyl.

General Procedure K

A mixture of halide derivative (1.0 eq.), Molander salt (1.0 eq.), cesium carbonate (3.0 eq.) and XPhos (0.1 eq) in THF and water (10:1, 0.06 M) was degassed by bubbling nitrogen through it for 15 min. Palladium acetate (0.05 eq.) was then added and the mixture was degassed again by bubbling nitrogen through it for 5 min. The mixture was then heated to 85° C. for 16 h, filtered over Celite®. The cake was rinsed with DCM. Water was added to the filtrate and the layers were partitioned. The aqueous layer was extracted with DCM (×2). The combined organic extracts were filtered over phase separator and then concentrated under reduced pressure. Further purification by flash column chromatography on silica gel gave the desired compound.

General Procedure L

To a solution of nitrile derivative (1.0 eq.) in EtOH/water (2:1, 0.8 M) hydrido(dimethylphosphinous acid kP) [hydrogen bis(dimethylphosphinito-kP)]platinum (II) (0.07 g, 0.163 mmol) is added. The mixture is heated at 80° C. overnight then concentrated under reduced pressure. The residue was then partitioned between DCM and water. The aqueous layer was extracted with DCM (×3). The combined organic extracts were filtered over phase separator and then concentrated under reduced pressure to give the desired crude amide.

General Procedure M

A solution of sulfuric acid (10 eq.) and trifluoroacetic acid (40 eq.) was added to the nitrile derivative (1 eq) and the reaction mixture was heated to 55° C. for 5 h. Once cooled, the mixture was poured into an ice-water mixture, carefully neutralized with sodium bicarbonate and then extracted with EtOAc (×3). The combined organic extracts were washed with brine, dried over sodium sulfate and concentrated under reduced pressure. Further purification by flash column chromatography on silica gel gave the desired amide.

General Procedure N

Cesium Carbonate (1.5 eq) was added to a mixture of 5-amino-3-[4-[[(2-methoxybenzoyl)amino]methyl]phenyl]-1H-pyrazole-4-carboxamide (1 eq.) and halide derivative (1.2 eq) in DMF (0.1 M). The reaction mixture was heated to 80° C. for 1.5 h, and then concentrated under reduced pressure. Further purification by either flash column chromatography on silica gel or by mass-directed semi-preparative HPLC afforded the desired product.

General Procedure O

To a solution of hydrazone (1 eq.) in THF (0.5 M) under a nitrogen atmosphere was added a borane tetrahydrofuran complex solution ($BH_3$-THF, 1.0 M in THF, 2 eq.) at 0° C. The reaction mixture was allowed to return to RT, stirred for 14 h, and then quenched with methanol (1 mL) and water. The aqueous layer was extracted with DCM (×3). The combined organic extracts were filtered over a hydrophobic frit and concentrated under reduced pressure. Hydrogen chloride in dioxane (4 M, 10 eq.) was added to the residue and the mixture was stirred for 14 h at RT. The mixture was then concentrated under reduced pressure and the residue taken up with ethanol (0.2 M). 2-[(4-Bromophenyl)-methoxy-methylene]propanedinitrile (0.5-1.0 eq.) and TEA (5 eq.) were added and the reaction was then stirred at RT for 14 h. Volatiles were removed under reduced pressure. Water and DCM were added to the residue and the layers were partitioned. The aqueous layer was extracted with DCM (×2). The combined organic extracts were filtered over a hydrophobic frit and concentrated under reduced pressure. Further purification by flash column chromatography on silica gel afforded the desired product.

General Procedure P

1 M borane THF complex (5.0 eq.) was added dropwise under nitrogen to a stirred solution of nitrile derivative (1.0 eq.) in anhydrous THF (0.10 M). The reaction mixture was then heated at reflux for 4 h before being cooled to RT. Methanol was added carefully dropwise until evolution of gas ceased. The solvent was removed under reduced pressure and the residue was dissolved in methanol and treated with concentrated aqueous HCl. The resulting mixture was heated at reflux for 10 min and then cooled to RT. The solvent was removed under reduced pressure and the residue was treated cautiously with excess aqueous sodium bicarbonate solution. The resultant suspension was extracted with ethyl acetate and the organic layer was dried, filtered and evaporated under reduced pressure to yield the corresponding amine.

General Procedure Q

A solution of acid (1.1 eq.) and 1-hydroxybenzotriazole hydrate (1.1 eq.) and N-(3-dimethylaminopropyl)-N'-ethyl-carbodiimide hydrochloride (1.1 eq.) in DMF (0.5 M) was stirred at RT for 30 min and then treated with the corresponding amine (1.0 eq.), followed by triethylamine (5.0 eq.). The reaction mixture was then stirred at RT for 18 h, poured into brine and extracted with ethyl acetate. The organic layer was washed with 0.2 M aqueous HCl and brine. The organic layer was then dried, filtered and the solvent evaporated under reduced pressure to yield the desired crude amide.

General Procedure R

To a nitrogen degassed solution of potassium acetate (3.0 eq), bis(pinacolato)diboron (1.5 eq) and halide derivative (1.0 eq) in 1,4-dioxane (0.12 M) was added 1,1'-bis(diphenylphosphino)ferrocene-palladium(II) dichloride dichloromethane complex (0.05 eq). The reaction mixture was then degassed with nitrogen for a further 5 min and then the reaction mixture was allowed to stir at 90° C. until completion of the reaction. Once cooled, the mixture was filtered through Celite®. Water was added to the filtrate and the mixture was partitioned. The aqueous layer was extracted with ethyl acetate (×3). The combined organic layers were washed with brine, dried over sodium sulfate, filtered and all volatiles were removed under reduced pressure. The resulting residue was either used crude or further purified by flash column chromatography on silica gel to afford the desired pinacol ester.

General Procedure S

To a solution of benzhydrazide (1 eq) in toluene (0.5 M) was added ketone (1.5 eq). The reaction mixture was heated to 110° C. for 10-18 h, then cooled to RT. The reaction mixture was poured into water and then filtered. The solid was washed with water and further dried to give the desired crude hydrazone.

General Procedure T

To a solution of hydrazone (1 eq.) in THF (0.2-0.4 M), cooled at 0° C., was added borane-THF (1 M, 2 eq.). The reaction was allowed to return to RT and stirred for 3-14 h. The mixture was then cooled to 0° C., quenched with MeOH and allowed to return to RT. The mixture was then concentrated under reduced pressure and the residue was either triturated with a suitable solvent (Pet.Ether, Et$_2$O or EtOAc) to afford the desired hydrazine or purified by flash column chromatography on silica gel.

General Procedure U

To a solution of benzohydrazide (1 eq.) in MeOH (0.7 M) was added hydrogen chloride 37% in water (16 eq). The mixture was heated at 80° C. for 16 h, cooled to RT and concentrated under reduced pressure. EtOAc was added and the precipitate was filtered and washed twice with EtOAc to provide the crude hydrazine salt.

General Procedure W

To a solution of malononitrile (1 eq.) in toluene (0.5 M) and THF (0.5 M) was added the corresponding benzoyl chloride (1 eq.). The reaction mixture was cooled down to −10° C. and then N,N-diisopropylethylamine (2 eq.) was added dropwise whilst maintaining internal temperature below −10° C. Once addition was complete, the reaction mixture was stirred at RT for 14 h, diluted with EtOAc. The layers were partitioned. The organic layer was washed with 1 M HCl then brine, dried with sodium sulfate, filtered and concentrated under reduced pressure to afford the desired compound.

General Procedure X

To a solution of dinitrile (1 eq.) in 1,4-dioxane (0.5 M) was added sodium carbonate (2 eq.) at RT. The reaction was stirred for 10 min then dimethyl sulfate (1.25 eq.) was added dropwise. Once addition was complete, the reaction was heated to reflux for 14 h, cooled and concentrated under reduced pressure. Water was added to the crude residue and the mixture was extracted with EtOAc. The combined organics were dried over sodium sulfate, filtered, and concentrated under reduced pressure. The crude residue was purified by flash column chromatography to afford the desired compound.

General Procedure Y

Allyltrimethylsilane (1.5 eq.) and boron trifluoride diethyl etherate (1.5 eq.) was added to a stirring solution of alkene (1.0 eq.) in DCE (0.5 M). The resulting solution was heated to a reflux for 5 min. The solvent was then removed under reduced pressure, and the mixture was taken up with DMF (0.5 M). Trimethyl(trifluoromethyl)silane (2.0 eq.) and sodium acetate (4.0 eq.) were then added successively. The reaction mixture was left to stir at RT for 2 h, quenched with a saturated solution of Na$_2$CO$_3$ and diluted with water. The aqueous solution was then extracted with diethyl ether (×2), dried over a hydrophobic frit, and concentrated under reduced pressure to afford the desired derivative.

[4-[[(2-Methoxybenzoyl)amino]methyl]phenyl]boronic acid

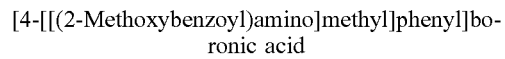

Following general procedure A, 2-methoxybenzoic acid (13.32 mL, 89.45 mmol) and [4-(aminomethyl)phenyl]boronic acid hydrochloride (15.24 g, 81.32 mmol) afforded the titled compound (20.70 g, 72.61 mmol, 89% yield) as an off-white solid.

UPLC-MS (ES$^+$, short acidic): 1.31 min, m/z 286.1 [M+H]$^+$

N-[[4-(5-Amino-4-cyano-1H-pyrazol-3-yl)phenyl]methyl]-2-methoxy-benzamide


Following general procedure C, a mixture of 5-amino-3-bromo-1H-pyrazole-4-carbonitrile (6.04 g, 32.32 mmol) and [4-[[(2-methoxybenzoyl)amino]methyl]phenyl]boronic acid (12.90 g, 45.25 mmol) gave, after purification by flash column chromatography eluting 0-10% with MeOH in DCM, N-[[4-(5-amino-4-cyano-1H-pyrazol-3-yl)phenyl]methyl]-2-methoxy-benzamide (6.45 g, 18.57 mmol, 57% yield) as a light brown solid.

UPLC-MS (ES+, Short acidic): 1.42 min, m/z 348.2 [M+H]+

5-Amino-3-[4-[[(2-methoxybenzoyl)amino]methyl]phenyl]-1-(2,2,2-trifluoroacetyl)pyrazole-4-carboxamide To a degassed solution of N-[[4-(5-amino-4-cyano-1H-pyrazol-3-yl)phenyl]methyl]-2-methoxy-benzamide (6.25 g, 17.99 mmol) was added a solution of sulfuric acid (9.59 mL, 179.92 mmol) and trifluoroacetic acid (55.3 mL, 719.68 mmol). The reaction mixture was heated to 55° C. for 5 h. The reaction mixture was poured into an ice-water mixture, carefully neutralized with sodium bicarbonate and then extracted with EtOAc (×3). The combined organic extracts were washed with brine, dried over sodium sulfate and concentrated under reduced pressure. Further purification by flash column chromatography on silica gel eluting 0-10% MeOH in DCM gave 5-amino-3-[4-[[(2-methoxybenzoyl)amino]methyl]phenyl]-1H-pyrazole-4-carboxamide (5.00 g, 13.68 mmol, 76% yield) as a light brown solid and 5-amino-3-[4-[[(2-methoxybenzoyl)amino]methyl]phenyl]-1-(2,2,2-trifluoroacetyl)pyrazole-4-carboxamide (0.37 g, 0.80 mmol, 4% yield) as a white solid.
UPLC-MS (ES+, Short acidic): 1.26 min, m/z 366.2 [M+H]+
UPLC-MS (ES+, Short acidic): 1.63 min, m/z 462.1 [M+H]+
UPLC-MS (ES+, Long acidic): 3.31 min, m/z 462.2 [M+H]+

Potassium trifluoro-[[(2-methoxybenzoyl)amino]methyl]boranuide

Potassium bis(trimethylsilyl)amide in toluene (0.5 M, 23.8 mL, 11.9 mmol) was added dropwise to a solution of 2-(bromomethyl)-4,4,5,5-tetramethyl-1,3,2-dioxaborolane (2.5 g, 11.3 mmol) in dry THF (25 mL) at −78° C. under nitrogen. After stirring for 25 mins at −78° C., the mixture was allowed to warm to RT and anhydrous methanol (1.3 mL, 32.1 mmol) was added. 2-Methoxybenzoyl chloride (3.4 mL, 22.6 mmol) was slowly added after 1 h and the mixture was stirred overnight. The resulting suspension was filtered and the filtrate concentrated under vacuum. The obtained residue was diluted in methanol (25 mL) followed by addition of an aqueous saturated solution of potassium hydrogen fluoride (3.5 g, 45.3 mmol). After stirring overnight, the mixture was concentrated under reduced pressure. The resulting residue was washed with hot acetone (×4). The acetone phases were filtered and the filtrate was concentrated under reduced pressure until almost all acetone was gone. By subsequent addition of Et$_2$O, the product precipitated and was collected. Potassium trifluoro-[[(2-methoxybenzoyl)amino]methyl]boranuide (1.50 g, 5.53 mmol, 49% yield) was obtained as white solid.
UPLC-MS (ES+, Short acidic): 1.03 min, m/z 232.1 [M−K]+

2-[(4-Bromophenyl)-hydroxy-methylene]propanedinitrile

To a solution of 4-bromobenzoyl chloride (7.00 g, 31.9 mmol) and malononitrile (2.32 g, 35.1 mmol) in toluene (40 mL) and THF (8.6 mL), cooled to −10° C. under a nitrogen atmosphere, was added dropwise a solution of N,N-diisopropylethylamine (11.11 mL, 63.8 mmol) in toluene (30 mL) while maintaining an internal temperature of −10° C. Once the addition was completed, the reaction mixture stirred at 0° C. for 1 h, then at RT for 18 h. Hydrochloric acid (1 M) was added and the reaction mixture partitioned with EtOAc. The aqueous layer was extracted with EtOAc. The combined organic layer was washed with HCl (1 M), brine, dried over sodium sulfate, filtered and then concentrated under dreduced pressure to give 2-[(4-bromophenyl)-hydroxy-methylene]propanedinitrile (7.72 g, 31.0 mmol, 97% yield) as a light brown solid.
$^1$H NMR (400 MHz, DMSO-d$_6$, δ): 7.58 (dt, J=8.7, 2.1 Hz, 2H), 7.52 (dt, J=8.8, 2.1 Hz, 2H).

2-[(4-Bromophenyl)-hydroxy-methylene]propanedinitrile

To a 2 L reactor fitted with a thermometer and under nitrogen was added 4-bromobenzoyl chloride (200 g, 911 mmol), toluene (1000 mL) and THF (200 mL) and malononitrile (63 mL, 1003 mmol). The reaction mixture was cooled down to −10° C. and then N,N-diisopropylethylamine (318 mL, 1823 mmol) was added dropwise to the reaction mixture maintaining an internal temperature below −10° C. (with the cooling fluid at −20° C.) over 45 min. Once the addition was complete the jacket was adjusted to 0° C. for 2 h then 25° C. for 2 h. The reaction mixture transferred to a 7 L separating funnel and the reactor washed out with 1 M aqueous HCl (1.5 L) and EtOAc (1.5 L) consecutively each being transferred to the separating funnel. The layers were partitioned and the organic layer washed with 1 M aqueous HCl (250 mL) then brine (250 mL). The organic layer was dried over magnesium sulfate, filtered and concentrated under reduced pressure down to a slurry. This was then slurried with Pet. Ether (500 mL) and filtered. The solid was washed with cold Pet. Ether (100 mL) to give the product after air-drying crude 2-[(4-bromophenyl)-hydroxy-methylene]propanedinitrile (232 g). This material was slurried with a minimum of cold EtOAc and filtered, washed with minimal EtOAc and diethyl ether to give 2-[(4-bromophenyl)-hydroxy-methylene]propanedinitrile (210 g, 843 mmol, 93% yield) as a a pale yellow solid.

2-[(4-Bromophenyl)-methoxy-methylene]propanedinitrile

A solution of 2-[(4-bromophenyl)-hydroxy-methylene]propanedinitrile (7.00 g, 28.11 mmol) in THF (17 mL) was added dropwise to a suspension of sodium hydride (1.24 g, 30.92 mmol) in THF (20 mL), cooled to 0° C. After 30 min stirring at 0° C., dimethyl sulfate (7.98 mL, 84.32 mmol) was added and the reaction mixture heated to 80° C. and stirred for 14 h. The mixture was cooled to RT, quenched with a saturated solution of ammonium chloride and extracted with EtOAc. The combined organic layers were dried over sodium sulfate and concentrated under reduced pressure. Further purification by flash column chromatography on silica gel eluting with 20-80% DCM in heptane afforded 2-[(4-bromophenyl)-methoxy-methylene]propanedinitrile (3.58 g, 13.61 mmol, 48% yield) as a white crystalline solid.
UPLC-MS (ES+, Short acidic): 1.76 min, m/z 263.4 [M]+

2-[(4-Bromophenyl)-methoxy-methylene]propanedinitrile

To a solution of 2-[(4-bromophenyl)-hydroxy-methylene]propanedinitrile (210 g, 843 mmol) in 1,4-dioxane (1500 mL) was added sodium carbonate (179 g, 1686 mmol) at RT. The mixture was stirred for 10 min then dimethyl sulfate (100 mL, 1054 mmol) was added dropwise over 10 min. The reaction mixture was then heated to reflux for 2 h, cooled and partitioned between water (1.5 L) and DCM (1.5 L). The aqueous layer was then extracted with DCM (1 L) and the combined organic extracts were then washed with water (500 mL) and brine (500 mL), dried over magnesium sulfate, filtered then concentrated under reduced pressure to give an orange solid. Further purification by flash column chromatography on silica gel eluting with 50-100% DCM in Pet. Ether then 25% EtOAc in DCM, gave a pale orange solid, which was then slurried with Pet. Ether (500 mL) and filtered to give 2-[(4-bromophenyl)-methoxy-methylene] propanedinitrile (153 g, 582 mmol, 69% yield) as an off-white solid.

5-Fluoro-2-methoxy-benzoyl chloride

Oxalyl chloride (124 mL, 1469 mmol) was added to a stirred suspension of 5-fluoro-2-methoxybenzoic acid (125 g, 735 mmol) and DMF (2.7 g, 37 mmol) in DCM (1750 mL) at RT. The reaction mixture was then allowed to stir at RT for 16 h, concentrated under reduced pressure to give crude 5-fluoro-2-methoxy-benzoyl chloride (138 g, 732 mmol, assumed quantitative yield) as a yellow oil that rapidly crystallised.
UPLC-MS (ES$^+$, Short acidic): 1.46 min, m/z: 1.46 min [M+H]$^+$ (methyl ester adduct)

Potassium trifluoro-[[(5-fluoro-2-methoxy-benzoyl)amino]methyl]boranuide

Potassium bis(trimethylsilyl)amide 0.7 M in toluene (174 mL, 770 mmol) was added dropwise to a solution of 2-(bromomethyl)-4,4,5,5-tetramethyl-1,3,2-dioxaborolane (170 g, 770 mmol) in dry THF (1200 mL) at −78° C. under a nitrogen atmosphere. After stirring for 25 min at −78° C., the mixture was stirred for a further 10 min at 0° C. then for 30 min at RT. Anhydrous methanol (99 g, 3078 mmol) was added at RT and a precipitate was formed. The mixture was stirred for an additional hour at RT then the reaction mixture was concentrated under reduced pressure while keeping the water bath at 30° C. The mixture was co-evaporated with THF (2×250 mL). The residue was taken up with anhydrous THF (750 mL) and 5-fluoro-2-methoxy-benzoyl chloride (138 g, 731 mol) in THF (250 mL) was then slowly added. The reaction mixture was then stirred at RT for 14 h, and then concentrated under reduced pressure. The resulting residue was taken up with ice-cold MeOH (1000 mL), the mixture was then cooled to 0° C. before the addition of a saturated solution of potassium hydrogen fluoride (264 g, 3386 mmol in water (600 mL). The reaction mixture was warmed to RT and stirred for 15 h, then concentrated under reduced pressure. The residue was azeotroped twice with toluene (3×500 mL) to remove the water. The residue was then washed with cold TBME and filtered. The white solid was washed with cold acetone (750 mL) then hot 25% MeOH in acetone (3×2000 mL). The filtrates were concentrated under reduced pressure. Once most of the solvent was removed TBME (500 mL) was added and the resultant white solid filtered off, washed with cold TBME to give potassium trifluoro-[[(5-fluoro-2-methoxy-benzoyl)amino]methyl]boranuide (198 g, 411 mmol, 53% yield).
$^1$H NMR (400 MHz, DMSO-d$_6$, δ): 7.80-7.71 (m, 1H), 7.64 (dd, J=9.8, 3.4 Hz, 1H), 7.31-7.25 (m, 1H), 7.16 (dd, J=9.2, 4.4 Hz, 1H), 3.88 (s, 3H), 2.17-2.09 (m, 2H).

4-Bromo-2,6-difluoro-benzoyl chloride

To a suspension of 4-bromo-2,6-difluorobenzoic acid (2 g, 8.44 mmol) in DCM (30 mL) was added oxalyl chloride (0.80 mL, 9.28 mmol) and DMF (0.1 mL, 1.30 mmol) at 0° C. The reaction mixture was stirred at RT for 4 h, cooled down to 0° C. More oxalyl chloride (0.79 mL, 9.28 mmol) was added and the reaction mixture was stirred at RT for 16 h, and then concentrated under reduced pressure to give 4-bromo-2,6-difluoro-benzoyl chloride (1.58 g, 6.19 mmol, 73% yield).
UPLC-MS: (ES$^+$, Short acidic): 1.74 min, m/z 250.9 [M]$^+$ (methyl ester adduct)

2-[(4-Bromo-2,6-difluoro-phenyl)-hydroxy-methylene]propanedinitrile

Following general procedure W, malononitrile (450 mg, 6.80 mmol) and 4-bromo-2,6-difluoro-benzoyl chloride (1.58 g, 6.19 mmol) gave 2-[(4-bromo-2,6-difluoro-phenyl)-hydroxy-methylene]propanedinitrile (2 g, 7.05 mmol, assumed quantitative yield) as a thick yellow oil.
UPLC-MS: (ES$^+$, Short acidic): 1.13 min, m/z 286.7 [M+2]$^+$ 2-[(4-Bromo-2,6-difluoro-phenyl)-methoxy-methylene]propanedinitrile Following general procedure X, 2-[(4-bromo-2,6-difluoro-phenyl)-hydroxy-methylene]propanedinitrile (2.01 g, 7.05 mmol) gave, after purification by flash column chromatography on silica gel eluting with 20-80% DCM in heptane, 2-[(4-bromo-2,6-difluoro-phenyl)-methoxy-methylene]propanedinitrile (1.48 g, 4.95 mmol, 70% yield) as a white solid.
UPLC-MS: (ES$^+$, Short acidic): 1.69 min, m/z 300.9 [M+2]$^+$ 2-[(4-Chloro-3,5-difluoro-phenyl)-hydroxy-methylene]propanedinitrile Following general procedure W, 4-chloro-3,5-difluorobenzoyl chloride (2.00 g, 9.48 mmol) gave 2-[(4-chloro-3,5-difluoro-phenyl)-hydroxy-methylene]propanedinitrile (2.48 g, 10.31 mmol, assumed quantitative yield) as a brown thick oil.
UPLC-MS: (ES$^-$, Short acidic): 1.34 min, m/z 238.8 [M−H]$^-$ 2-[(4-Chloro-3,5-difluoro-phenyl)-methoxy-methylene]propanedinitrile Following general procedure X, 2-[(4-chloro-3,5-difluoro-phenyl)-hydroxy-methylene]propanedinitrile (2.48 g, 10.31 mmol) gave, after purification by flash column chromatography on silica gel eluting with 20-80% DCM in heptane, 2-[(4-chloro-3,5-difluoro-phenyl)-methoxy-methylene]propanedinitrile (1.68 g, 6.60 mmol, 64% yield) as a pale yellow solid.
UPLC-MS: (ES$^+$, Short acidic): 1.70 min, m/z 254.9 [M+H]$^+$ 2-[(4-Chloro-2,5-difluoro-phenyl)-hydroxy-methylene]propanedinitrile Following general procedure W, 4-chloro-2,5-difluorobenzoyl chloride (2.00 g, 9.48 mmol) gave 2-[(4-chloro-2,5-difluoro-phenyl)-hydroxy-methylene]propanedinitrile (2.66 g, 11.06 mmol, assumed quantitative yield) as a beige solid.

UPLC-MS: (ES⁻, Short acidic): 1.11 min, m/z 238.8 [M−H]⁻

2-[(4-Chloro-2,5-difluoro-phenyl)-methoxy-methylene]propanedinitrile

Following general procedure X, 2-[(4-chloro-2,5-difluoro-phenyl)-hydroxy-methylene]propanedinitrile (2.66 g, 11.06 mmol) gave, after purification by flash column chromatography on silica gel eluting with 20-80% DCM in heptane, 2-[(4-chloro-2,5-difluoro-phenyl)-methoxy-methylene]propanedinitrile (1.64 g, 6.44 mmol, 58% yield) as a pale yellow oil.

UPLC-MS: (ES⁺, Short acidic): 1.67 min, m/z 254.9 [M+H]⁺

4-Chloro-2,3-difluoro-benzoyl chloride

To a suspension of 4-bromo-2,6-difluorobenzoic acid (2.00 g, 8.44 mmol) in DCM (30 mL) was added oxalyl chloride (0.80 mL, 9.28 mmol) and DMF (0.1 mL, 1.30 mmol) at 0° C. The reaction mixture was stirred at RT for 4 h, cooled again to 0° C. More oxalyl chloride (0.80 mL, 9.28 mmol) was added and the reaction mixture was stirred at RT for 16 h, and then concentrated under reduced pressure to give 4-chloro-2,3-difluoro-benzoyl chloride (2.19 g, 10.38 mmol, assumed quantitative yield).

UPLC-MS: (ES⁺, Short acidic): 1.74 min, m/z 206.8 [M]⁺ (methyl ester adduct)

2-[(4-Chloro-2,3-difluoro-phenyl)-methoxy-methylene]propanedinitrile

Following general procedure W, malononitrile (750 mg, 11.42 mmol) and 4-chloro-2,3-difluoro-benzoyl chloride (2.19 g, 10.38 mmol) gave crude 2-[(4-chloro-2,3-difluoro-phenyl)-hydroxy-methylene]propanedinitrile (2.61 g, 10.85 mmol, assumed quantitative yield) as a brown solid. Following general procedure X, 2-[(4-chloro-2,3-difluoro-phenyl)-methoxy-methylene]propanedinitrile (1.6 g, 6.40 mmol, 59% yield) was obtained as an off-white solid after purification by flash column chromatography on silica gel eluting with 20-80% DCM in heptane, UPLC-MS: (ES⁺, Short acidic): 1.70 min, m/z 254.9 [M+H]⁺

Example 1: 5-amino-1-cyclopentyl-3-[4-[[(2-methoxybenzoyl)amino]methyl]phenyl]pyrazole-4-carboxamide

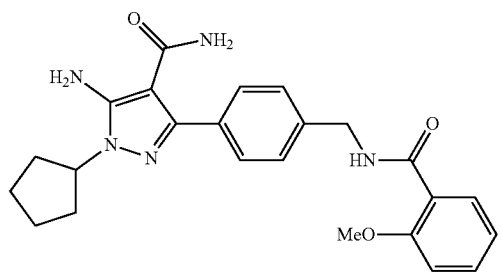 [SMILES: COc1ccccc1C(=O)NCc1ccc(-c2nn(C3CCCC3)c(N)c2C(N)=O)cc1]

5-Amino-3-(4-bromophenyl)-1-cyclopentyl-pyrazole-4-carbonitrile

General procedure H, reacting 2-[(4-bromophenyl)-methoxy-methylene]propanedinitrile (0.76 mmol) and cyclopentylhydrazine hydrochloride (0.91 mmol) to give titled compound (0.83 mmol). UPLC-MS (ES⁺, Short acidic): 2.17 min, m/z 333.2 [M+2]⁺

N-[[4-(5-Amino-4-cyano-1-cyclopentyl-pyrazol-3-yl)phenyl]methyl]-2-methoxy-benzamide General procedure K, reacting 5-amino-3-(4-bromophenyl)-1-cyclopentyl-pyrazole-4-carbonitrile (0.45 mmol) and potassium trifluoro-[[(2-methoxybenzoyl)amino]methyl]boranuide (0.45 mmol) to give titled compound (0.36 mmol) as a yellow solid. UPLC-MS (ES⁺, Short acidic): 1.87 min, m/z 416.2 [M+H]⁺

5-Amino-1-cyclopentyl-3-[4-[[(2-methoxybenzoyl)amino]methyl]phenyl]pyrazole-4-carboxamide General procedure M, reacting N-[[4-(5-amino-4-cyano-1-cyclopentyl-pyrazol-3-yl)phenyl]methyl]-2-methoxy-benzamide (0.36 mmol) to give titled compound (0.23 mmol) as an off-white solid. UPLC-MS (ES⁺, Short acidic): 1.58 min, m/z 434.2 [M+H]⁺ UPLC-MS (ES⁺, Long acidic): 3.59 min, m/z 434.2 [M+H]⁺

¹H NMR (400 MHz, DMSO-d₆, δ): 8.73 (t, J=6.1 Hz, 1H), 7.75 (dd, J=7.7, 1.8 Hz, 1H), 7.51-7.37 (m, 5H), 7.17-7.13 (m, 1H), 7.03 (td, J=7.5, 1.0 Hz, 1H), 6.31 (s, 2H), 4.60 (quint, J=7.3 Hz, 1H), 4.54 (d, J=6.1 Hz, 2H), 3.90 (s, 3H), 2.02-1.86 (m, 4H), 1.83-1.72 (m, 2H), 1.65-1.51 (m, 2H).

The compound of Example 1 can also be made by the process described below.

5-Amino-3-(4-bromophenyl)-1-cyclopentyl-pyrazole-4-carbonitrile

A solution of 2-[(4-bromophenyl)-methoxy-methylene]propanedinitrile (72.2 mmol), cyclopentylhydrazine dihydrochloride (72.2 mmol) and trimethylamine (288.9 mmol) in EtOH (400 mL) was refluxed for 1.5 h. The reaction mixture was heated to reflux for 1.5 h, cooled and concentrated under reduced pressure. Work up and purification produced the titled compound (51.9 mmol) as a pale yellow solid.

N-[[4-(5-Amino-4-cyano-1-cyclopentyl-pyrazol-3-yl)phenyl]methyl]-2-methoxy-benzamide Potassium trifluoro-[[(2-methoxybenzoyl)amino]methyl]boranuide (36.2 mmol), palladium (II) acetate (1.27 mmol), cesium carbonate (108.7 mmol) and 5-amino-3-(4-bromophenyl)-1-cyclopentyl-pyrazole-4-carbonitrile (36.2 mmol) were suspended in THF (250 mL) and water (75 mL). The orange reaction mixture was degassed under vacuum and flushed with nitrogen three times. 2-dicyclohexylphosphino-2',4',6'-triisopropylbiphenyl (2.54 mmol) was added and the mixture was heated to reflux for 4 h. Filteration through Celite®, work up and concentration gave the titled compound (32.01 mmol) as a pale orange solid.

5-Amino-1-cyclopentyl-3-[4-[[(2-methoxybenzoyl)amino]methyl]phenyl]pyrazole-4-carboxamide After heating to 55° C. for 3 h, a solution of N-[[4-(5-amino-4-cyano-1-cyclopentyl-pyrazol-3-yl)phenyl]methyl]-2-methoxy-benzamide (32.0 mmol), sulfuric acid (320.1 mmol) and trifluoroacetic acid (800.3 mmol) was cooled and then carefully added into an ice-cooled solution of sodium bicarbonate (1921 mmol) in water (750 mL) with vigorous stirring. A mixture of heptane/EtOAc (100 mL, 1:1) was added and the mixture was filtered. The solid was suspended in 10% MeOH/DCM (750 mL) and water (100 mL). After work-up and crystalisation from EtOAc and MeOH (200 mL) the titled product was obtained (13.15 mmol) as an off-white solid.

Example 2: 5-Amino-1-[(1R*,2R*)-2-hydroxycyclopentyl]-3-[4-[[(2-methoxybenzoyl)amino]methyl]phenyl]pyrazole-4-carboxamide

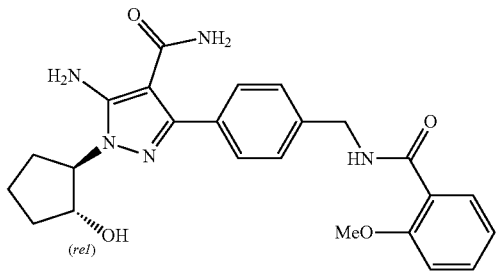 [SMILES: COc1ccccc1C(=O)NCc1ccc(-c2nn([C@@H]3CCC[C@H]3O)c(N)c2C(N)=O)cc1]

5-Amino-3-(4-bromophenyl)-1-[(1R*,2R*)-2-hydroxycyclopentyl]pyrazole-4-carbonitrile General procedure H, reacting 2-[(4-bromophenyl)-methoxy-methylene]propanedinitrile (0.38 mmol) and (1R*,2R*)-2-hydrazinocyclopentanol (0.38 mmol) gave the titled compound (0.38 mmol) as an off-white solid. UPLC-MS (ES+, Short acidic): 1.82 min, m/z 349.1 [M+2]+

N-[[4-[5-Amino-4-cyano-1-[(1R*,2R*)-2-hydroxycyclopentyl]pyrazol-3-yl]phenyl]methyl]-2-methoxy-benzamide Following general procedure C, 5-amino-3-(4-bromophenyl)-1-[(1R*,2R*)-2-hydroxycyclopentyl]pyrazole-4-carbonitrile (0.12 mmol) and potassium trifluoro-[[(2-methoxybenzoyl)amino]methyl]boranuide (0.13 mmol) gave titled compound (0.11 mmol) as a white powder. UPLC-MS (ES+, Short acidic): 1.60 min, m/z 432.2 [M+H]+

5-Amino-1-[(1R*,2R*)-2-hydroxycyclopentyl]-3-[4-[[(2-methoxybenzoyl)amino]methyl]phenyl]pyrazole-4-carboxamide Following general procedure L, N-[[4-[5-amino-4-cyano-1-[(1R*,2R*)-2-hydroxycyclopentyl]pyrazol-3-yl]phenyl]methyl]-2-methoxy-benzamide (0.10 mmol) gave titled compound (0.05 mmol, 49% yield) as a white powder. UPLC-MS (ES+, Short acidic): 1.44 min, m/z 450.3 [M+H]+. UPLC-MS (ES+, Long acidic): 3.16 min, m/z 450.3 [M+H]+

$^1$H NMR (400 MHz, DMSO-d$_6$, δ): 8.74 (t, J=5.9 Hz, 1H), 7.76 (dd, J=7.6, 1.8 Hz, 1H), 7.52-7.38 (m, 5H), 7.18-7.14 (m, 1H), 7.04 (td, J=7.5, 1.0 Hz, 1H), 6.26 (s, 2H), 5.03 (d, J=4.6 Hz, 1H), 4.55 (d, J=6.1 Hz, 2H), 4.36-4.24 (m, 2H), 3.90 (s, 3H), 2.11-2.00 (m, 1H), 2.00-1.85 (m, 2H), 1.79-1.67 (m, 2H), 1.60-1.48 (m, 1H).

Example 3: 5-amino-1-tert-butyl-3-[4-[[(2-methoxybenzoyl)amino]methyl]phenyl]pyrazole-4-carboxamide

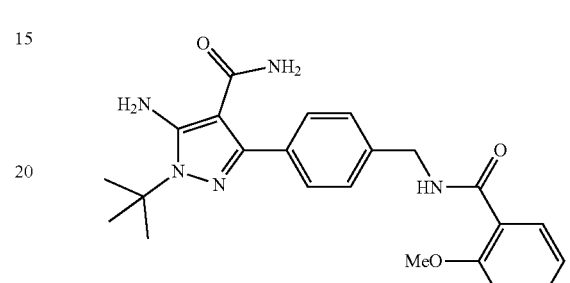

5-Amino-3-(4-bromophenyl)-1-tert-butyl-pyrazole-4-carbonitrile

General procedure H, 2-[(4-bromophenyl)-methoxymethylene]propanedinitrile (0.57 mmol) and tert-butylhydrazine hydrochloride (0.86 mmol) gave, after purification by flash column chromatography on silica gel eluting with 0-5% MeOH in DCM, titled compound (0.52 mmol) as a pale yellow solid. UPLC-MS (ES+, Short acidic): 2.21 min, m/z 321.0 [M+2]+

N-[[4-(5-Amino-1-tert-butyl-4-cyano-pyrazol-3-yl)phenyl]methyl]-2-methoxy-benzamide General procedure K, 5-amino-3-(4-bromophenyl)-1-tert-butyl-pyrazole-4-carbonitrile (0.22 mmol) and potassium trifluoro-[[(2-methoxybenzoyl)amino]methyl]boranuide (0.24 mmol) afforded, after purification by flash column chromatography on silica gel eluting with 0-10% MeOH in DCM, titled compound (0.21 mmol, 98% yield) as a yellow solid. UPLC-MS (ES+, Short acidic): 1.90 min, m/z 404.2 [M+H]+

5-Amino-1-tert-butyl-3-[4-[[(2-methoxybenzoyl)amino]methyl]phenyl]pyrazole-4-carboxamide Following general procedure L, N-[[4-(5-amino-1-tert-butyl-4-cyano-pyrazol-3-yl)phenyl]methyl]-2-methoxy-benzamide (0.74 mmol) gave, after purification by flash column chromatography on silica gel, titled compound (0.03 mmol) as a pale yellow solid. UPLC-MS (ES+, Short acidic): 1.61 min, m/z 422.3 [M+H]+. UPLC-MS (ES+, Long acidic): 3.57 min, m/z 422.3 [M+H]+.

$^1$H NMR (400 MHz, DMSO-d$_6$, δ): 8.73 (t, J=6.1 Hz, 1H), 7.75 (dd, J=7.7, 1.8 Hz, 1H), 7.50-7.37 (m, 5H), 7.17-7.13 (m, 1H), 7.03 (td, J=7.5, 1.1 Hz, 1H), 6.28 (s, 2H), 4.54 (d, J=6.1 Hz, 2H), 3.90 (s, 3H), 1.56 (s, 9H).

Example 4: 5-Amino-1-(3-bicyclo[3.1.0]hexanyl)-3-[4-[[(2-methoxybenzoyl)amino]methyl]phenyl]pyrazole-4-carboxamide

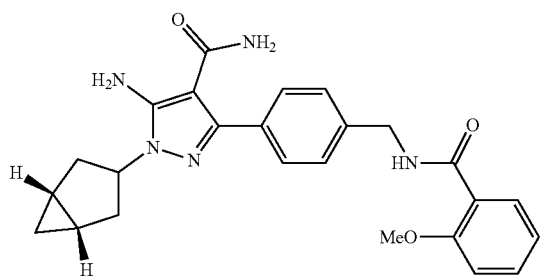 [SMILES: COc1ccccc1C(=O)NCc1ccc(-c2nn(C3C[C@@H]4C[C@@H]4C3)c(N)c2C(N)=O)cc1]

Bicyclo[3.1.0]hexan-3-one

To a solution of pyridine (1.68 mmol) and pyridinium chlorochromate (7.64 mmol) in DCM (6 mL), cooled to 0° C., was added dropwise cis-bicyclo[3.1.0]hexan-3-ol (5.09 mmol). The reaction mixture was then left to warm to RT and left to stir overnight. The reaction mixture was diluted with diethyl ether and the black residue was washed with more diethyl ether (×3). The combined organics were then passed through a pad of florisil and the solvent was removed under reduced pressure to afford titled compound as a crude yellow oil. $^1$H NMR (400 MHz, CDCl$_3$, δ): 2.64-2.54 (m, 2H), 2.20-2.12 (m, 2H), 1.57-1.50 (m, 2H), 0.94-0.86 (m, 1H), −0.03-−0.08 (m, 1H).

tert-Butyl N-(3-bicyclo[3.1.0]hexanylideneamino)carbamate

A mixture of bicyclo[3.1.0]hexan-3-one (5.58 mmol) and tert-butyl carbazate (5.58 mmol) in methanol (20 mL) was stirred at RT for 4 h. The reaction mixture was then concentrated under reduced pressure. The reaction mixture was quenched with water (20 mL), extracted with DCM (3×20 mL). The combined organic extracts were filtered over a hydrophobic frit and then concentrated under reduced pressure. The resulting residue was purified by flash column chromatography on silica gel, eluting with 0-100% EtOAc in heptane, to give titled compound (2.84 mmol) as a clear oil. $^1$H NMR (400 MHz, CDCl$_3$, δ): 2.85-2.77 (m, 1H), 2.63-2.56 (m, 1H), 2.39-2.35 (m, 2H), 1.52-1.35 (m, 12H), 0.74-0.66 (m, 1H), −0.13-−0.18 (m, 1H).

3-Bicyclo[3.1.0]hexanylhydrazine; 2,2,2-trifluoroacetic acid

Sodium cyanoborohydride (4.71 mmol) was added portionwise to a stirred solution of tert-butyl N-(3-bicyclo[3.1.0]hexanylideneamino)carbamate (4.76 mmol) in acetic acid (7 mL) and water (7 mL). The resulting mixture was left to stir at RT for 2 h, neutralised by addition of 1 M NaOH (aq.), and then extracted with DCM (×2). The combined organic extracts were washed with a saturated solution of sodium bicarbonate, dried over sodium sulfate, filtered and concentrated to dryness, to give crude tert-butyl N-(3-bicyclo[3.1.0]hexanylamino)carbamate (4.71 mmol) as a clear oil. The crude product was taken up in DCM (4.5 mL). Trifluoroacetic acid (58.77 mmol) was added dropwise a stirred solution of tert-butyl N-(3-bicyclo[3.1.0]hexanylamino)carbamate (4.71 mmol) in DCM (4.5 mL). The resulting solution was stirred for 2 h and then concentrated under reduced pressure to give crude titled compound (4.42 mmol) as a clear oil.

$^1$H NMR (400 MHz, CDCl$_3$, δ): 3.88-3.78 (m, 1H), 2.43-2.31 (m, 2H), 1.74 (dd, J=14.9, 4.9 Hz, 2H), 1.40-1.24 (m, 2H), 0.83-0.75 (m, 1H), 0.17-0.11 (m, 1H).

5-Amino-1-(3-bicyclo[3.1.0]hexanyl)-3-(4-bromophenyl)pyrazole-4-carbonitrile General procedure H, 2-[(4-bromophenyl)-methoxymethylene]propanedinitrile (0.78 mmol) and 3-bicyclo[3.1.0]hexanylhydrazine; 2,2,2-trifluoroacetic acid (1.17 mmol) gave, after purification by flash column chromatography on silica gel eluting with 0-100% EtOAc in heptane, the titled compound (0.21 mmol) as a colourless oil. UPLC-MS (ES$^+$, Short acidic): 2.15 min, m/z 345.1 [M+2]$^+$

N-[[4-[5-Amino-1-(3-bicyclo[3.1.0]hexanyl)-4-cyano-pyrazol-3-yl]phenyl]methyl]-2-methoxy-benzamide General procedure K, 5-amino-1-(3-bicyclo[3.1.0]hexanyl)-3-(4-bromophenyl)pyrazole-4-carbonitrile (0.21 mmol) and potassium trifluoro-[[(2-methoxybenzoyl)amino]methyl]boranuide (0.21 mmol) afforded the titled compound (0.23 mmol). UPLC-MS (ES$^+$, Short acidic): 1.86 min, m/z 428.2 [M+H]$^+$

5-Amino-1-(3-bicyclo[3.1.0]hexanyl)-3-[4-[[(2-methoxybenzoyl)amino]methyl]phenyl]pyrazole-4-carboxamide General procedure L, N-[[4-[5-amino-1-(3-bicyclo[3.1.0]hexanyl)-4-cyano-pyrazol-3-yl]phenyl]methyl]-2-methoxy-benzamide (0.21 mmol) afforded the titled compound (0.04 mmol) after purification by mass-directed semi-preparative HPLC. UPLC-MS (ES$^+$, Short acidic): 1.68 min, m/z 446.2 [M+H]$^+$. UPLC-MS (ES$^+$, Long acidic): 3.72 min, m/z 446.3 [M+H]$^+$ $^1$H NMR (400 MHz, DMSO-d$_6$, δ): 8.74 (t, J=6.2 Hz, 1H), 7.77 (dd, J=7.7, 1.8 Hz, 1H), 7.54-7.38 (m, 5H), 7.16 (dd, J=8.4, 0.7 Hz, 1H), 7.04 (td, J=7.5, 1.0 Hz, 1H), 6.29 (s, 2H), 5.01-4.83 (m, 1H), 4.55 (d, J=6.1 Hz, 2H), 3.91 (s, 3H), 2.46-2.36 (m, 2H), 1.92 (dd, J=13.8, 4.8 Hz, 2H), 1.35-1.27 (m, 2H), 0.81 (q, J=4.1 Hz, 1H), 0.66-0.54 (m, 1H).

Example 5: 5-Amino-3-[4-[[(2-methoxybenzoyl)amino]methyl]phenyl]-1-(3-methylcyclopentyl)pyrazole-4-carboxamide

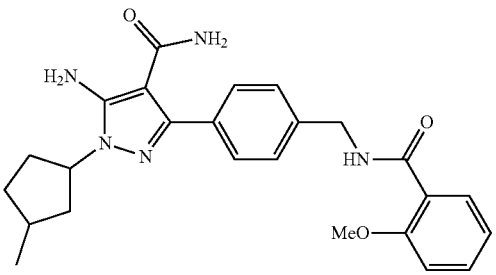 [SMILES: COc1ccccc1C(=O)NCc1ccc(-c2nn(C3CCC(C)C3)c(N)c2C(N)=O)cc1]

tert-Butyl N-[(3-methylcyclopent-2-en-1-ylidene)amino]carbamate

To a solution of 3-methyl-2-cyclopenten-1-one (10.40 mmol) in methanol (59.4 mL) was added tert-butyl carbazate (10.92 mmol) and the reaction was stirred at RT for 16 h. Volatiles were removed under reduced pressure to give the titled compound (12.18 mmol). $^1$H NMR (400 MHz, DMSO-$d_6$, δ): 5.98-5.93 (m, 1H), 3.26-3.05 (br s, 1H), 2.62-2.57 (m, 2H), 2.44-2.41 (m, 2H), 2.15 (s, 3H), 1.47 (s, 9H).

(3-Methylcyclopentyl)hydrazine

To a solution of tert-butyl N-[-(3-methylcyclopent-2-en-1-ylidene)amino]carbamate (10.40 mmol) in THF/MeOH (21 mL, 1:1) was added sodium cyanoborohydride (12.50 mmol) portionwise. The reaction was heated under reflux under a nitrogen atmosphere for 10 min and then cooled to RT. Hydrogen chloride (30.00 mmol) was added and the reaction mixture was heated under reflux for 3 h, cooled to RT and stirred for 16 h. The reaction was filtered to remove inorganic insoluble material and the filtrate was concentrated under reduced pressure and azeotroped (×3) with toluene. The residue was dissolved in hot isopropanol, cooled to RT, diluted with ether and then cooled to 0° C. The precipitate was filtered and the filtrate was concentrated under vacuum to give the titled compound (6.50 mmol). $^1$H NMR (400 MHz, DMSO-$d_6$, δ mixture of diastereoisomers): 3.83-3.62 and 3.56-3.38 (m, 1H), 3.10-2.99 and 2.78-2.68 (m, 2H), 2.26-2.01 (m, 2H), 2.00-1.57 (m, 5H), 1.40-1.02 (m, 1H), 0.99 and 0.93 (d, J=6.5 Hz, 3H).

5-Amino-3-(4-bromophenyl)-1-(3-methylcyclopentyl)pyrazole-4-carbonitrile

General procedure H, 2-[(4-bromophenyl)-methoxymethylene]propanedinitrile (0.38 mmol) and (3-methylcyclopentyl)hydrazine (0.38 mmol) afforded the titled compound (0.07 mmol) after purification by flash column chromatography on silica gel eluting with 0-2% MeOH in DCM. UPLC-MS (ES$^+$, Short acidic): 2.26 min, m/z 345.1 [M]$^+$

N-[[4-[5-Amino-4-cyano-1-(3-methylcyclopentyl)pyrazol-3-yl]phenyl]methyl]-2-methoxy-benzamide General procedure K, 5-amino-3-(4-bromophenyl)-1-(3-methylcyclopentyl)pyrazole-4-carbonitrile (0.08 mmol) and potassium trifluoro-[[(2-methoxybenzoyl)amino]methyl]boranuide (0.08 mmol) afforded the titled compound (0.05 mmol) after purification by flash column chromatography on silica gel eluting with 0-10% MeOH in DCM. UPLC-MS (ES$^+$, Short acidic): 2.03 min, m/z 430.2 [M+H]$^+$

5-Amino-3-[4-[[(2-methoxybenzoyl)amino]methyl]phenyl]-1-(3-methylcyclopentyl)pyrazole-4-carboxamide General procedure L, N-[[4-[5-amino-4-cyano-1-(3-methylcyclopentyl)pyrazol-3-yl]phenyl]methyl]-2-methoxy-benzamide (0.08 mmol) afforded the titled compound (0.01 mmol) after purification by mass-directed semi-preparative HPLC. UPLC-MS (ES$^+$, Short acidic): 1.73 min, m/z 448.3 [M+H]$^+$. UPLC-MS (ES$^+$, Long acidic): 3.86 min, m/z 448.3 [M+H]$^+$ $^1$H NMR (400 MHz, DMSO-$d_6$, δ) (mixture of diastereoisomers): 8.74 (t, J=6.0 Hz, 1H), 7.76 (dd, J=7.6, 1.8 Hz, 1H), 7.53-7.38 (m, 5H), 7.16 (d, J=7.8 Hz, 1H), 7.04 (td, J=7.5, 0.9 Hz, 1H), 6.31 (s, 2H), 4.79-4.58 (m, 1H), 4.55 (d, J=6.0 Hz, 2H), 3.91 (s, 3H), 2.30-2.21 (m, 0.5H), 2.17-2.05 (m, 1.5H), 2.01-1.92 (m, 2.5H), 1.85-1.75 (m, 0.5H), 1.64-1.51 (m, 1H), 1.44-1.33 (m, 0.5H), 1.21-1.11 (m, 0.5H), 1.02 (dd, J=21.0, 6.6 Hz, 3H).

Example 6: 5-Amino-3-[4-[[(2-methoxybenzoyl)amino]methyl]phenyl]-1-[5-(trifluoromethyl)-2-pyridyl]pyrazole-4-carboxamide

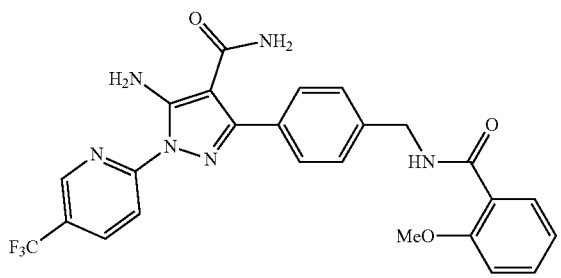 [SMILES: COc1ccccc1C(=O)NCc1ccc(-c2nn(-c3ccc(C(F)(F)F)cn3)c(N)c2C(N)=O)cc1]

5-Amino-3-(4-bromophenyl)-1-[5-(trifluoromethyl)-2-pyridyl]pyrazole-4-carbonitrile Following general procedure H, 2-[(4-bromophenyl)-methoxy-methylene]propanedinitrile (80 mg, 0.30 mmol) and 5-(trifluoromethyl)pyrid-2-ylhydrazine (0.30 mmol) gave the titled compound (0.30 mmol) as an off-white solid. UPLC-MS (ES$^+$, Short acidic): 2.27 min, m/z 408.1 [M]$^+$

N-[[4-[5-Amino-4-cyano-1-[5-(trifluoromethyl)-2-pyridyl]pyrazol-3-yl]phenyl]methyl]-2-methoxy-benzamide General procedure K, 5-amino-3-(4-bromophenyl)-1-[5-(trifluoromethyl)-2-pyridyl]pyrazole-4-carbonitrile (0.10 mmol) and potassium trifluoro-[[(2-methoxybenzoyl)amino]methyl]boranuide (0.12 mmol) gave titled compound (0.06 mmol) as white powder. UPLC-MS (ES$^+$, Short acidic): 2.03 min, m/z 493.3 [M+H]$^+$

5-Amino-3-[4-[[(2-methoxybenzoyl)amino]methyl]phenyl]-1-[5-(trifluoromethyl)-2-pyridyl]pyrazole-4-carboxamide General procedure L, N-[[4-[5-amino-4-cyano-1-[5-(trifluoromethyl)-2-pyridyl]pyrazol-3-yl]phenyl]methyl]-2-methoxy-benzamide (0.06 mmol) gave the titled compound (0.03 mmol) as a white powder. UPLC-MS (ES$^+$, Short acidic): 1.85 min, m/z 511.3 [M+H]$^+$. UPLC-MS (ES$^+$, Long acidic): 4.19 min, m/z 511.3 [M+H]$^+$. $^1$H NMR (400 MHz, DMSO-$d_6$, δ): 8.90-8.86 (m, 1H), 8.79 (t, J=6.1 Hz, 1H), 8.38 (dd, J=8.9, 2.3 Hz, 1H), 8.05 (d, J=8.8 Hz, 1H), 7.83-7.74 (m, 3H), 7.60 (d, J=8.1 Hz, 2H), 7.53-7.45 (m, 3H), 7.17 (d, J=8.3 Hz, 1H), 7.09-7.02 (m, 1H), 4.59 (d, J=6.0 Hz, 2H), 3.92 (s, 3H).

Example 7: 5-amino-3-[4-[[(2-methoxybenzoyl)amino]methyl]phenyl]-1-[2-(methoxymethoxy)ethyl]pyrazole-4-carboxamide

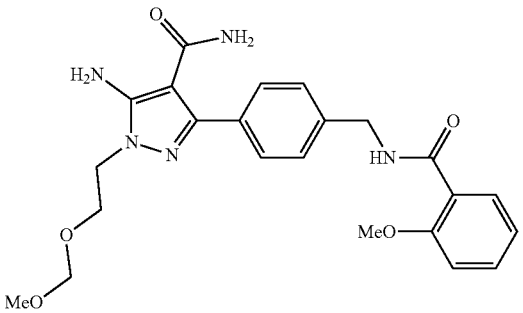 [SMILES: COCOCCn1nc(-c2ccc(CNC(=O)c3ccccc3OC)cc2)c(C(N)=O)c1N]

General procedure N, a mixture of 5-amino-3-[4-[[(2-methoxybenzoyl)amino]methyl]phenyl]-1H-pyrazole-4-carboxamide (0.26 mmol) and 1-bromo-2-(methoxymethoxy)ethane (0.39 mmol) afforded, after purification by mass-directed semi-preparative HPLC (middle method), the titled compound (0.03 mmol). UPLC-MS (ES$^+$, Short acidic): 1.42 min, m/z 454.2 [M+H]$^+$. UPLC-MS (ES$^+$, Long acidic): 3.10 min, m/z 454.3 [M+H]$^+$. $^1$H NMR (400 MHz, DMSO-d$_6$, δ): 8.74 (t, J=6.1 Hz, 1H), 7.75 (dd, J=7.7, 1.8 Hz, 1H), 7.51-7.38 (m, 5H), 7.18-7.13 (m, 1H), 7.04 (td, J=7.5, 1.0 Hz, 1H), 6.30 (s, 2H), 4.57-4.52 (m, 4H), 4.10 (t, J=5.7 Hz, 2H), 3.90 (s, 3H), 3.77 (t, J=5.7 Hz, 2H), 3.19 (s, 3H).

Example 8: 5-amino-3-[4-[[(2-methoxybenzoyl)amino]methyl]phenyl]-1-[(3-methyloxetan-3-yl)methyl]pyrazole-4-carboxamide

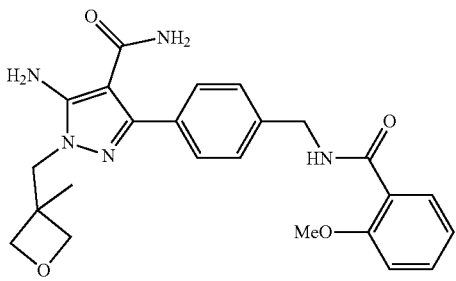 [SMILES: COc1ccccc1C(=O)NCc1ccc(-c2nn(CC3(C)COC3)c(N)c2C(N)=O)cc1]

General procedure N, a mixture of 5-amino-3-[4-[[(2-methoxybenzoyl)amino]methyl]phenyl]-1H-pyrazole-4-carboxamide (0.25 mmol) and 3-(chloromethyl)-3-methyloxetane (0.38 mmol) gave, after purification by mass-directed semi-preparative HPLC, the titled compound (0.07 mmol). UPLC-MS (ES$^+$, Short acidic): 1.42 min, m/z 450.2 [M+H]$^+$. UPLC-MS (ES$^+$, Long acidic): 3.11 min, m/z 450.3 [M+H]$^+$. $^1$H NMR (400 MHz, DMSO-d$_6$, δ): 8.73 (t, J=6.1 Hz, 1H), 7.75 (dd, J=7.7, 1.8 Hz, 1H), 7.51-7.38 (m, 5H), 7.17-7.13 (m, 1H), 7.04 (td, J=7.5, 1.5 Hz, 1H), 6.41 (s, 2H), 4.63 (d, J=5.9 Hz, 2H), 4.54 (d, J=6.1 Hz, 2H), 4.20 (d, J=5.9 Hz, 2H), 4.09 (s, 2H), 3.90 (s, 3H), 1.24 (s, 3H).

Example 9: 5-Amino-3-[4-[[(2-methoxybenzoyl)amino]methyl]phenyl]-1-(2-morpholinoethyl)pyrazole-4-carboxamide

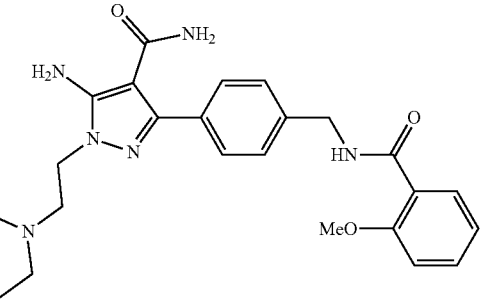

5-Amino-3-[4-[[(2-methoxybenzoyl)amino]methyl]phenyl]-1-(2-morpholinoethyl)pyrazole-4-carboxamide General procedure N, 5-amino-3-[4-[[(2-methoxybenzoyl)amino]methyl]phenyl]-1H-pyrazole-4-carboxamide (0.27 mmol) and N-chloroethylmorpholine hydrochloride (0.41 mmol) afforded the titled compound (0.04 mmol) after purification by flash column chromatography on silica gel eluting with 0-5% MeOH in DCM. UPLC-MS (ES$^+$, Short acidic): 1.20 min, m/z 479.3 [M+H]$^+$. UPLC-MS (ES$^+$, Long acidic): 2.51 min, m/z 479.3 [M+H]$^+$. $^1$H NMR (400 MHz, DMSO-d$_6$, δ): 8.74 (t, J=6.0 Hz, 1H), 7.76 (dd, J=7.7, 1.8 Hz, 1H), 7.53-7.37 (m, 5H), 7.16 (d, J=8.2 Hz, 1H), 7.05 (td, J=7.5, 1.0 Hz, 1H), 6.40 (s, 2H), 4.55 (d, J=6.1 Hz, 2H), 4.04 (t, J=6.7 Hz, 2H), 3.90 (s, 3H), 3.60-3.56 (m, 4H), 2.69-2.65 (m, 2H), 2.47-2.44 (m, 4H).

Example 10: 5-Amino-1-(3,3-dimethyl-2-oxobutyl)-3-[4-[[(2-methoxybenzoyl)amino]methyl]phenyl]pyrazole-4-carboxamide

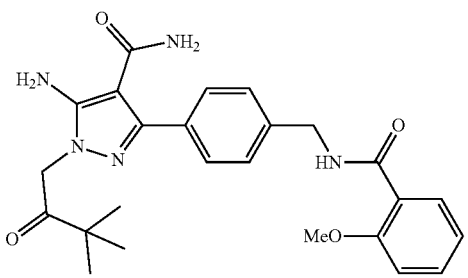 [SMILES: COc1ccccc1C(=O)NCc1ccc(-c2nn(CC(=O)C(C)(C)C)c(N)c2C(N)=O)cc1]

5-Amino-1-(3,3-dimethyl-2-oxo-butyl)-3-[4-[[(2-methoxybenzoyl)amino]methyl]phenyl]pyrazole-4-carboxamide General procedure N, 5-amino-3-[4-[[(2-methoxybenzoyl)amino]methyl]phenyl]-1H-pyrazole-4-carboxamide (0.24 mmol) and 1-bromo-3,3-dimethylbutan-2-one (0.36 mmol) afforded the titled compound (0.03 mmol) after purification by flash column chromatography on silica gel eluting with 0-5% MeOH in DCM. UPLC-MS (ES$^+$, Short acidic): 1.55 min, m/z 464.3 [M+H]$^+$. UPLC-MS (ES$^+$, Long acidic): 3.49 min, m/z 464.3 [M+H]⁺. ¹H NMR (400 MHz, DMSO-d₆, δ): 8.74 (t, J=6.1 Hz, 1H), 7.76 (dd, J=7.6, 1.8 Hz, 1H), 7.53-7.37 (m, 5H), 7.17 (d, J=8.2 Hz, 1H), 7.04 (td, J=7.5, 1.0 Hz, 1H), 6.27 (s, 2H), 5.12 (s, 2H), 4.55 (d, J=6.1 Hz, 2H), 3.90 (s, 3H), 1.18 (s, 9H).

Example 11: 5-Amino-1-(2-cyanoethyl)-3-[4-[[(2-methoxybenzoyl)amino]methyl]phenyl]pyrazole-4-carboxamide

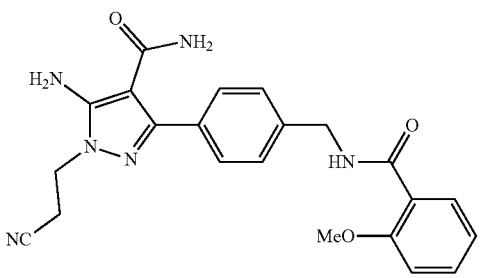 [SMILES: COc1ccccc1C(=O)NCc1ccc(-c2nn(CCC#N)c(N)c2C(N)=O)cc1]

5-Amino-1-(2-cyanoethyl)-3-[4-[[(2-methoxybenzoyl)amino]methyl]phenyl]pyrazole-4-carboxamide General procedure N, 5-amino-3-[4-[[(2-methoxybenzoyl)amino]methyl]phenyl]-1H-pyrazole-4-carboxamide (0.25 mmol) and 3-bromopropionitrile (0.37 mmol) afforded the titled compound (0.07 mmol) after purification by flash column chromatography on silica gel eluting with 0-5% MeOH in DCM.

UPLC-MS (ES⁺, Short acidic): 1.37 min, m/z 419.2 [M+H]⁺. UPLC-MS (ES⁺, Long acidic): 3.02 min, m/z 419.2 [M+H]⁺. ¹H NMR (400 MHz, DMSO-d₆, δ): 8.75 (t, J=6.1 Hz, 1H), 7.76 (dd, J=7.6, 1.8 Hz, 1H), 7.53-7.37 (m, 5H), 7.16 (d, J=7.7 Hz, 1H), 7.04 (td, J=7.5, 1.0 Hz, 1H), 6.49 (s, 2H), 4.56 (d, J=6.1 Hz, 2H), 4.22 (t, J=6.7 Hz, 2H), 3.90 (s, 3H), 2.97 (t, J=6.7 Hz, 2H).

Example 12: 5-amino-3-[4-[[(2-methoxybenzoyl)amino]methyl]phenyl]-1-(3-oxocyclohexyl)pyrazole-4-carboxamide

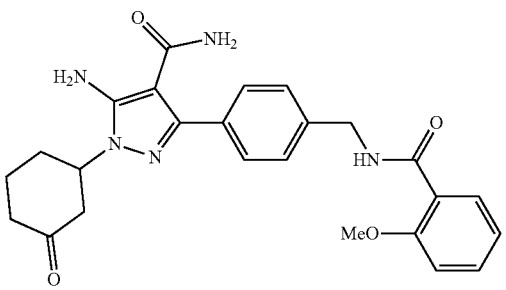 [SMILES: COc1ccccc1C(=O)NCc1ccc(-c2nn(C3CCCC(=O)C3)c(N)c2C(N)=O)cc1]

A solution of 1,8-diazabicyclo[5.4.0]undec-7-ene (0.82 mmol) in MeCN (0.5 mL) was slowly added to a solution of 5-amino-3-[4-[[(2-methoxybenzoyl)amino]methyl]phenyl]-1H-pyrazole-4-carboxamide (0.27 mmol) in MeCN (2 mL). The reaction was stirred at RT for 15 min before cyclohex-2-enone (0.55 mmol) was added. The reaction mixture was stirred for 16 h. Water was added and the reaction mixture extracted with EtOAc. The combined organic layer was dried over sodium sulfate and evaporated in vacuo. Purification by flash column chromatography on silica gel eluting with 0-5% MeOH in DCM gave the titled compound (0.15 mmol) as a pale brown solid. UPLC-MS (ES⁺, Short acidic): 1.42 min, m/z 462.2 [M+H]⁺. UPLC-MS (ES⁺, Long acidic): 3.00 min, m/z 462.3 [M+H]⁺.

¹H NMR (400 MHz, DMSO-d₆, δ): 8.73 (t, J=6.2 Hz, 1H), 7.75 (dd, J=7.7, 1.8 Hz, 1H), 7.51-7.45 (m, 3H), 7.42-7.37 (m, 2H), 7.17-7.13 (m, 1H), 7.04 (td, J=7.6, 1.0 Hz, 1H), 6.38 (d, J=1.8 Hz, 1H), 6.09 (s, 1H), 4.54 (d, J=6.2 Hz, 2H), 4.53-4.49 (m, 1H), 3.89 (s, 3H), 2.13-2.05 (m, 1H), 2.01-1.95 (m, 1H), 1.89-1.79 (m, 2H), 1.78-1.68 (m, 1H), 1.67-1.54 (m, 2H) 1.29-1.06 (m, 1H).

Example 13: 5-Amino-3-[4-[[(2-methoxybenzoyl)amino]methyl]phenyl]-1-(3-oxocyclopentyl)pyrazole-4-carboxamide

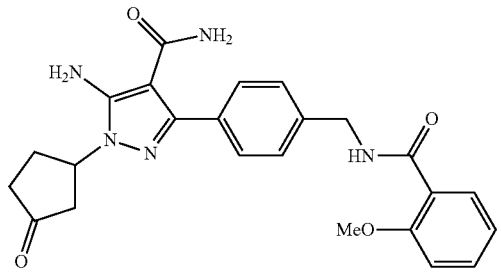 [SMILES: COc1ccccc1C(=O)NCc1ccc(-c2nn(C3CCC(=O)C3)c(N)c2C(N)=O)cc1]

5-Amino-3-[4-[[(2-methoxybenzoyl)amino]methyl]phenyl]-1-(3-oxocyclopentyl)pyrazole-4-carboxamide 1,8-Diazabicyclo[5.4.0]undec-7-ene (0.14 mmol) was added to a mixture of 5-amino-3-[4-[[(2-methoxybenzoyl)amino]methyl]phenyl]-1H-pyrazole-4-carboxamide (0.27 mmol) and 2-cyclopentenone (0.33 mmol) in MeCN (0.54 mL). The reaction mixture was stirred at RT for 2 days and then concentrated under reduced pressure. The resulting residue was purified by flash column chromatography on silica gel eluting with 0-3.5% MeOH in DCM, followed by reverse-phase chromatography eluting with 20-40% MeCN in water containing 0.1% formic acid additive, to give the titled compound (0.04 mmol, 14% yield) as an off-white solid.

UPLC-MS (ES⁺, Short acidic): 1.44 min, m/z 448.2 [M+H]⁺.

UPLC-MS (ES⁺, Long acidic): 3.09 min, m/z 448.2 [M+H]⁺.

¹H NMR (400 MHz, DMSO-d₆, δ): 8.76-8.69 (m, 1H), 7.76 (dd, J=7.6, 1.8 Hz, 1H), 7.52-7.37 (m, 5H), 7.16 (d, J=8.2 Hz, 1H), 7.07-7.00 (m, 1H), 6.42 (s, 2H), 5.05-4.95 (m, 1H), 4.54 (d, J=6.1 Hz, 2H), 3.90 (s, 3H), 2.73-2.61 (m, 1H), 2.60-2.30 (m, 3H), 2.27-2.11 (m, 2H).

Example 14: 5-Amino-1-(2-hydroxy-3,3-dimethyl-butyl)-3-[4-[[(2-methoxybenzoyl)amino]methyl]phenyl]pyrazole-4-carboxamide

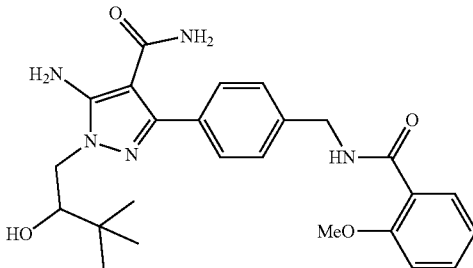 [SMILES: COc1ccccc1C(=O)NCc1ccc(-c2nn(CC(O)C(C)(C)C)c(N)c2C(N)=O)cc1]

5-Amino-1-(2-hydroxy-3,3-dimethyl-butyl)-3-[4-[[(2-methoxybenzoyl)amino]methyl]phenyl]pyrazole-4-carboxamide 5-amino-1-(3,3-dimethyl-2-oxo-butyl)-3-[4-[[(2-methoxybenzoyl)amino]methyl]phenyl]pyrazole-4-carboxamide solution (0.07 mmol) in MeOH (1 mL) was added dropwise to sodium borohydride (0.07 mmol) solution in MeOH (1 mL) at 0° C. The reaction mixture was stirred for 30 min then diluted with DCM. A saturated aq. $Na_2CO_3$ solution was then added and the mixture was extracted with DCM (×3). The combined organic layers were dried over sodium sulfate and concentrated under reduced pressure. The crude material was purified by flash column chromatography on silica gel eluting with 0-5% MeOH in DCM to give the titled compound (0.03 mmol). UPLC-MS (ES+, Short acidic): 1.62 min, m/z 466.3 [M+H]+. UPLC-MS (ES+, Long acidic): 3.49 min, m/z 466.3 [M+H]+. $^1$H NMR (400 MHz, DMSO-$d_6$, δ): 8.74 (t, J=6.1 Hz, 1H), 7.76 (dd, J=7.7, 1.8 Hz, 1H), 7.38-7.54 (m, 5H), 7.16 (d, J=8.1 Hz, 1H), 7.05 (td, J=7.5, 0.9 Hz, 1H), 6.10 (s, 2H), 5.10 (d, J=5.9 Hz, 1H), 4.56 (d, J=6.1 Hz, 2H), 3.99 (dd, J=14.3, 1.7 Hz, 1H), 3.91 (s, 3H), 3.78 (dd, J=14.2, 9.5 Hz, 1H), 3.47-3.59 (m, 1H), 0.92 (s, 9H).

Example 15: 5-Amino-1-(2,4-difluorophenyl)-3-[4-[[(2-methoxybenzoyl)amino]methyl]phenyl]pyrazole-4-carboxamide

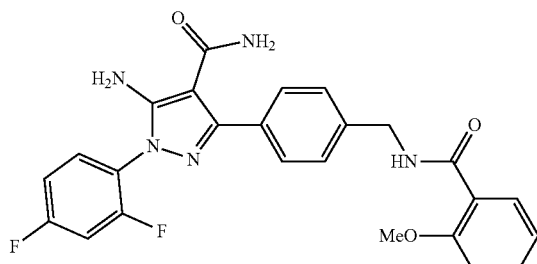

5-Amino-3-(4-bromophenyl)-1-(2,4-difluorophenyl)pyrazole-4-carbonitrile

General procedure H, 2-[(4-bromophenyl)-methoxymethylene]propanedinitrile (0.30 mmol) and 2,4-difluorophenylhydrazine hydrochloride (0.30 mmol) gave the titled compound (0.22 mmol) as an off-white solid. UPLC-MS (ES+, Short acidic): 1.99 min, m/z 375.1 [M]+

N-[[4-[5-Amino-4-cyano-1-(2,4-difluorophenyl)pyrazol-3-yl]phenyl]methyl]-2-methoxy-benzamide General procedure K, 5-amino-3-(4-bromophenyl)-1-(2,4-difluorophenyl)pyrazole-4-carbonitrile (0.11 mmol) and potassium trifluoro-[[(2-methoxybenzoyl)amino]methyl]boranuide (0.19 mmol) gave the titled compound (0.10 mmol) as a white powder. UPLC-MS (ES+, Short acidic): 1.73 min, m/z 460.2 [M+H]+

5-Amino-1-(2,4-difluorophenyl)-3-[4-[[(2-methoxybenzoyl)amino]methyl]phenyl]pyrazole-4-carboxamide General procedure L, N-[[4-[5-amino-4-cyano-1-(2,4-difluorophenyl)pyrazol-3-yl]phenyl]methyl]-2-methoxy-benzamide (0.10 mmol) gave the titled compound (0.05 mmol) as an off-white powder.
UPLC-MS (ES+, Short acidic): 1.57 min, m/z 478.2 [M+H]+. UPLC-MS (ES+, Long acidic): 3.58 min, m/z 478.2 [M+H]+. $^1$H NMR (400 MHz, DMSO-$d_6$, δ): 8.76 (t, J=6.1 Hz, 1H), 7.76 (dd, J=7.6, 1.8 Hz, 1H), 7.69-7.60 (m, 1H), 7.60-7.40 (m, 6H), 7.32-7.23 (m, 1H), 7.16 (d, J=8.3 Hz, 1H), 7.08-7.01 (m, 1H), 6.46 (s, 2H), 4.57 (d, J=6.1 Hz, 2H), 3.90 (s, 3H).

Example 16: 5-Amino-3-[4-[[(2-methoxybenzoyl)amino]methyl]phenyl]-1-[3-(trifluoromethyl)phenyl]pyrazole-4-carboxamide

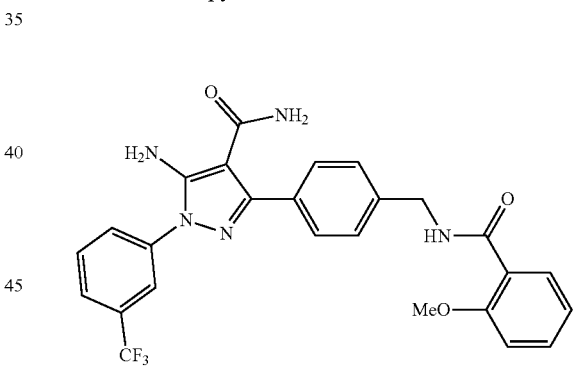

5-Amino-3-(4-bromophenyl)-1-[3-(trifluoromethyl)phenyl]pyrazole-4-carbonitrile

General procedure H, 2-[(4-bromophenyl)-methoxymethylene]propanedinitrile (0.38 mmol) and [3-(trifluoromethyl)phenyl]hydrazine hydrochloride (0.38 mmol) gave the titled compound (0.31 mmol) as an off-white solid. UPLC-MS (ES+, Short acidic): 2.18 min, m/z 407.1 [M]+

5-Amino-3-(4-bromophenyl)-1-[3-(trifluoromethyl)phenyl]pyrazole-4-carboxamide

General procedure nitrile hydrolysis, 5-amino-3-(4-bromophenyl)-1-[3-(trifluoromethyl)phenyl]pyrazole-4-carbonitrile (0.12 mmol) gave the titled compound crude (0.12 mmol) as a clear oil. UPLC-MS (ES+, Short acidic): 1.93 min, m/z 425.0 [M]+

5-Amino-3-[4-[[(2-methoxybenzoyl)amino]methyl]phenyl]-1-[3-(trifluoromethyl)phenyl]pyrazole-4-carboxamide

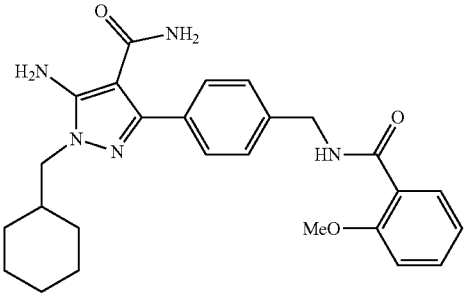 [SMILES: COc1ccccc1C(=O)NCc1ccc(-c2nn(CC3CCCCC3)c(N)c2C(N)=O)cc1]

General procedure K, 5-amino-3-(4-bromophenyl)-1-[3-(trifluoromethyl)phenyl]pyrazole-4-carboxamide (0.12 mmol) and potassium trifluoro-[[(2-methoxybenzoyl)amino]methyl]boranuide (0.18 mmol) gave the titled compound (0.08 mmol) as an off-white powder. UPLC-MS (ES$^+$, Short acidic): 1.79 min, m/z 510.3 [M+H]$^+$. UPLC-MS (ES$^+$, Long acidic): 4.06 min, m/z 510.6 [M+H]$^+$. $^1$H NMR (400 MHz, DMSO-d$_6$, δ): 8.77 (t, J=6.1 Hz, 1H), 8.02-7.92 (m, 2H), 7.83-7.73 (m, 3H), 7.57 (d, J=8.1 Hz, 2H), 7.53-7.43 (m, 3H), 7.16 (d, J=7.2 Hz, 1H), 7.08-7.02 (m, 1H), 6.65 (s, 2H), 4.58 (d, J=6.1 Hz, 2H), 3.91 (s, 3H)

Example 17: 5-amino-1-(cyclohexylmethyl)-3-[4-[[(2-methoxybenzoyl)amino]methyl]phenyl]pyrazole-4-carboxamide General procedure N, a mixture of 5-amino-3-[4-[[(2-methoxybenzoyl)amino]methyl]phenyl]-1H-pyrazole-4-carboxamide (0.26 mmol) and (bromomethyl)cyclohexane (0.39 mmol) afforded, after purification by mass-directed semi-preparative HPLC, titled compound (0.04 mmol). UPLC-MS (ES$^+$, Short acidic): 1.71 min, m/z 462.3 [M+H]$^+$. UPLC-MS (ES$^+$, Long acidic): 3.88 min, m/z 462.3 [M+H]$^+$. $^1$H NMR (400 MHz, DMSO-d$_6$, δ): 8.74 (t, J=6.1 Hz, 1H), 7.76 (dd, J=7.7, 1.8 Hz, 1H), 7.51-7.38 (m, 5H), 7.18-7.14 (m, 1H), 7.04 (td, J=7.5, 1.0 Hz, 1H), 6.31 (s, 2H), 4.55 (d, J=6.1 Hz, 2H), 3.90 (s, 3H), 3.75 (d, J=7.2 Hz, 2H), 1.88-1.75 (m, 1H), 1.73-1.53 (m, 5H), 1.27-1.09 (m, 3H), 1.06-0.91 (m, 2H).

Example 18: 5-amino-1-cyclohexyl-3-[4-[[(2-methoxybenzoyl)amino]methyl]phenyl]pyrazole-4-carboxamide

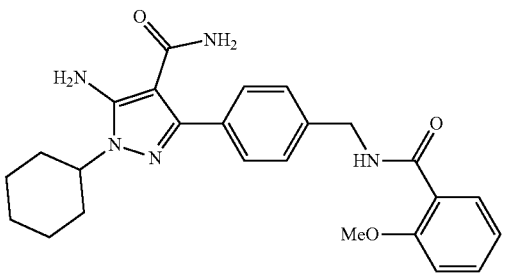 [SMILES: COc1ccccc1C(=O)NCc1ccc(-c2nn(C3CCCCC3)c(N)c2C(N)=O)cc1]

5-Amino-3-(4-bromophenyl)-1-cyclohexyl-pyrazole-4-carbonitrile

General procedure H, 2-[(4-bromophenyl)-methoxymethylene]propanedinitrile (0.76 mmol) and cyclohexylhydrazinehydrochloride (0.91 mmol) gave, after purification by flash column chromatography on silica gel eluting with 0-5% MeOH in DCM, the titled compound (0.65 mmol) as a white solid. UPLC-MS (ES$^+$, Short acidic): 2.11 min, m/z 347.1 [M+2]$^+$ N-[[4-(5-Amino-4-cyano-1-cyclohexyl-pyrazol-3-yl)phenyl]methyl]-2-methoxy-benzamide General procedure K, 5-amino-3-(4-bromophenyl)-1-cyclohexyl-pyrazole-4-carbonitrile (0.64 mmol) and potassium trifluoro-[[(2-methoxybenzoyl)amino]methyl]boranuide (0.70 mmol) gave, after purification by flash column chromatography on silica gel eluting with 0-5% MeOH in DCM, the titled compound (0.59 mmol) as a white solid. UPLC-MS (ES$^+$, Short acidic): 1.81 min, m/z 430.3 [M+H]$^+$ 5-Amino-1-cyclohexyl-3-[4-[[(2-methoxybenzoyl)amino]methyl]phenyl]pyrazole-4-carboxamide General procedure M, N-[[4-(5-amino-4-cyano-1-cyclohexyl-pyrazol-3-yl)phenyl]methyl]-2-methoxy-benzamide (0.58 mmol) gave, after purification by flash column chromatography on silica gel eluting with 0-5% MeOH in DCM, the titled compound (0.32 mmol) as a white solid. UPLC-MS (ES$^+$, Short acidic): 1.59 min, m/z 448.3 [M+H]$^+$. UPLC-MS (ES$^+$, Long acidic): 3.63 min, m/z 448.3 [M+H]$^+$.

$^1$H NMR (400 MHz, DMSO-d$_6$, δ): 8.73 (t, J=6.1 Hz, 1H), 7.76 (dd, J=7.6, 1.7 Hz, 1H), 7.52-7.38 (m, 5H), 7.19-7.14 (m, 1H), 7.04 (td, J=7.6, 0.9 Hz, 1H), 6.32 (s, 2H), 4.55 (d, J=6.1 Hz, 2H), 4.12-4.03 (m, 1H), 3.90 (s, 3H), 1.76-1.60 (m, 8H), 1.45-1.29 (m, 2H).

Example 19: 5-amino-1-isopropyl-3-[4-[[(2-methoxybenzoyl)amino]methyl]phenyl]pyrazole-4-carboxamide

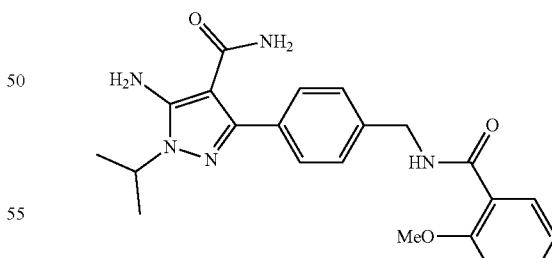

5-Amino-3-(4-bromophenyl)-1-isopropyl-pyrazole-4-carbonitrile

General procedure H, 2-[(4-bromophenyl)-methoxymethylene]propanedinitrile (0.38 mmol) and isopropylhydrazine (0.46 mmol) gave, after purification by flash column chromatography on silica gel eluting with 0-2% MeOH in DCM, the titled compound (0.27 mmol) as a pale yellow solid. UPLC-MS (ES+, Short acidic): 1.96 min, m/z 307.1 [M+2]+

N-[[4-(5-amino-4-cyano-1-isopropyl-pyrazol-3-yl)phenyl]methyl]-2-methoxy-benzamide

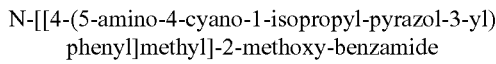

General procedure K, 5-amino-3-(4-bromophenyl)-1-isopropyl-pyrazole-4-carbonitrile (0.27 mmol) and potassium trifluoro-[[(2-methoxybenzoyl)amino]methyl]boranuide (0.27 mmol) gave, after purification by flash column chromatography on silica gel eluting with 0-10% MeOH in DCM, the titled compound (0.19 mmol) as a yellow solid. UPLC-MS (ES+, Short acidic): 1.73 min, m/z 390.2 [M+H]+

5-Amino-1-isopropyl-3-[4-[[(2-methoxybenzoyl)amino]methyl]phenyl]pyrazole-4-carboxamide

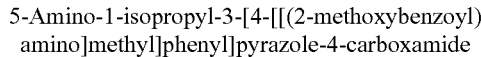

General procedure M, N-[[4-(5-amino-4-cyano-1-isopropyl-pyrazol-3-yl)phenyl]methyl]-2-methoxy-benzamide (0.19 mmol) gave, after purification by flash column chromatography on silica gel eluting with 0-5% MeOH in DCM, the titled compound (0.10 mmol) as a off-white solid. UPLC-MS (ES+, Short acidic): 1.46 min, m/z 408.3 [M+H]+. UPLC-MS (ES+, Long acidic): 3.23 min, m/z 408.3 [M+H]+.
$^1$H NMR (400 MHz, DMSO-$d_6$, δ): 8.73 (t, J=6.1 Hz, 1H), 7.75 (dd, J=7.7, 1.8 Hz, 1H), 7.50-7.38 (m, 5H), 7.18-7.13 (m, 1H), 7.04 (td, J=7.5, 0.9 Hz, 1H), 6.31 (s, 2H), 4.54 (d, J=6.1 Hz, 2H), 4.47 (quint, J=6.6 Hz, 1H), 3.90 (s, 3H), 1.33 (d, J=6.6 Hz, 6H).

Example 20: 5-Amino-1-[(1S*,3R*)-3-hydroxycyclopentyl]-3-[4-[[(2-methoxybenzoyl)amino]methyl]phenyl]pyrazole-4-carboxamide

5-Amino-1-[(1S*,3R*)-3-hydroxycyclopentyl]-3-[4-[[(2-methoxybenzoyl)amino]methyl]phenyl]pyrazole-4-carboxamide

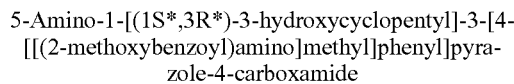

Sodium borohydride (0.20 mmol) was added to a solution of 5-amino-3-[4-[[(2-methoxybenzoyl)amino]methyl]phenyl]-1-(3-oxocyclopentyl)pyrazole-4-carboxamide (0.18 mmol) in methanol (1 mL), cooled to 0° C. The reaction mixture was then stirred at RT for 30 min, quenched with a saturated solution of ammonium chloride and partitioned. The aqueous layer was extracted with DCM (×3). The combined organic extracts were filtered over a hydrophobic frit, and concentrated under reduced pressure. Further purification by reverse-phase chromatography eluting with 20-40% MeCN in water containing 0.1% formic acid additive afforded the titled compound (0.08 mmol) as an off-white solid. UPLC-MS (ES+, Short acidic): 1.38 min, m/z 450.3 [M+H]+. UPLC-MS (ES+, Long acidic): 3.04 min, m/z 450.3 [M+H]+. $^1$H NMR (400 MHz, DMSO-$d_6$, δ): 8.74 (t, J=6.1 Hz, 1H), 7.76 (dd, J=7.5, 1.8 Hz, 1H), 7.55-7.38 (m, 5H), 7.16 (d, J=8.3 Hz, 1H), 7.07-7.01 (m, 1H), 6.40 (s, 2H), 5.07 (d, J=5.7 Hz, 1H), 4.65 (quint, J=7.7 Hz, 1H), 4.55 (d, J=6.1 Hz, 2H), 4.18-4.09 (m, 1H), 3.91 (s, 3H), 2.32-2.21 (m, 1H), 2.08-1.92 (m, 2H), 1.92-1.83 (m, 1H), 1.82-1.62 (m, 2H)

Example 21: 5-Amino-3-[4-[[(2-methoxybenzoyl)amino]methyl]phenyl]-1-(2,2,2-trifluoroethyl)pyrazole-4-carboxamide

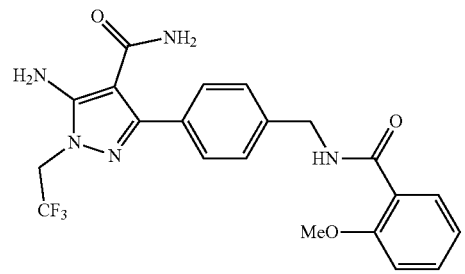 [SMILES: COc1ccccc1C(=O)NCc1ccc(-c2nn(CC(F)(F)F)c(N)c2C(N)=O)cc1]

5-Amino-3-(4-bromophenyl)-1-(2,2,2-trifluoroethyl)pyrazole-4-carbonitrile

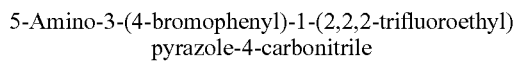

Following general procedure H, 2-[(4-bromophenyl)-methoxy-methylene]propanedinitrile (0.38 mmol) and 2,2,2-trifluoroethyl hydrazine (70% wt in water, 0.46 mmol) gave, after further purification by flash column chromatography on silica gel eluting with 0-10% MeOH in DCM, the titled compound (0.27 mmol) as a light yellow solid. LC-MS (ES+, Method 1): 5.80 min, m/z 345.0 [M]+

N-[[4-[5-Amino-4-cyano-1-(2,2,2-trifluoroethyl)pyrazol-3-yl]phenyl]methyl]-2-methoxy-benzamide

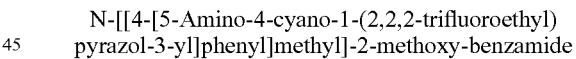

Following general procedure K, 5-amino-3-(4-bromophenyl)-1-(2,2,2-trifluoroethyl)pyrazole-4-carbonitrile (0.29 mmol) and potassium trifluoro-[[(2-methoxybenzoyl)amino]methyl]boranuide (0.38 mmol) gave, after further purification by flash column chromatography on silica gel eluting with 10-100% EtOAc in heptane, the titled compound (0.17 mmol) as an off-white solid. LC-MS (ES+, Method 1): 5.01 min, m/z 430.2 [M+H]+

5-Amino-3-[4-[[(2-methoxybenzoyl)amino]methyl]phenyl]-1-(2,2,2-trifluoroethyl)pyrazole-4-carboxamide

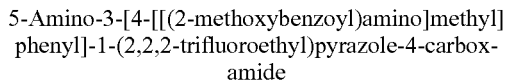

General procedure L, N-[[4-[5-amino-4-cyano-1-(2,2,2-trifluoroethyl)pyrazol-3-yl]phenyl]methyl]-2-methoxy-benzamide (0.16 mmol) gave, after further purification by flash column chromatography on silica gel eluting with 10-100% EtOAc in heptane, the titled compound (0.08 mmol) as a white solid. UPLC-MS (ES+, Short acidic): 1.54 min, m/z 448.2 [M+H]+. UPLC-MS (ES+, Long acidic): 3.22 min, m/z 448.2 [M+H]+. $^1$H NMR (400 MHz, DMSO-$d_6$, δ): 8.75

(t, J=6.0 Hz, 1H), 7.76 (dd, J=7.7, 1.8 Hz, 1H), 7.52-7.40 (m, 5H), 7.16 (d, J=8.1 Hz, 1H), 7.07-7.02 (m, 1H), 6.68 (s, 2H), 4.95 (q, J=9.0 Hz, 2H), 4.56 (d, J=6.1 Hz, 2H), 3.91 (s, 3H)

Example 22: 5-Amino-3-[4-[[(2-methoxybenzoyl)amino]methyl]phenyl]-1-phenyl-pyrazole-4-carboxamide

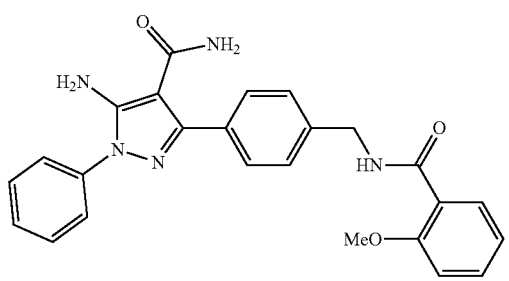 [SMILES: COc1ccccc1C(=O)NCc1ccc(-c2nn(-c3ccccc3)c(N)c2C(N)=O)cc1]

5-Amino-3-(4-bromophenyl)-1-phenyl-pyrazole-4-carbonitrile

General procedure H, 2-[(4-bromophenyl)-methoxymethylene]propanedinitrile (0.35 mmol) and phenylhydrazine (0.42 mmol) gave, after further purification by flash column chromatography on silica gel eluting with 0-10% MeOH in DCM, 5-amino-3-(4-bromophenyl)-1-phenyl-pyrazole-4-carbonitrile (0.28 mmol) as a white solid. UPLC-MS (ES⁺, Short acidic): 2.04 min, m/z 339.1 [M]⁺

N-[[4-(5-amino-4-cyano-1-phenyl-pyrazol-3-yl)phenyl]methyl]-2-methoxy-benzamide

Following general procedure K, 5-amino-3-(4-bromophenyl)-1-phenyl-pyrazole-4-carbonitrile (0.12 mmol) and potassium trifluoro-[[(2-methoxybenzoyl)amino]methyl]boranuide (0.19 mmol) gave, after further purification by flash column chromatography on silica gel eluting with 10-100% EtOAc in heptane, the titled compound (0.09 mmol) as an off-white solid. UPLC-MS (ES⁺, Short acidic): 1.77 min, m/z 424.1 [M+H]⁺

5-Amino-3-[4-[[(2-methoxybenzoyl)amino]methyl]phenyl]-1-phenyl-pyrazole-4-carboxamide General procedure L, N-[[4-(5-amino-4-cyano-1-phenyl-pyrazol-3-yl)phenyl]methyl]-2-methoxy-benzamide (0.07 mmol) gave, after further purification by flash column chromatography on silica gel eluting with 0-10% MeOH in DCM, the titled compound (0.05 mmol) as a white solid. LC-MS (ES+, Method 1): 4.53 min, m/z 442.2 [M+H]⁺. UPLC-MS (ES+, Long acidic): 3.39 min, m/z 442.2 [M+H]⁺

¹H NMR (400 MHz, DMSO-d₆, δ): 8.76 (t, J=6.1 Hz, 1H), 7.76 (dd, J=7.6, 2.0 Hz, 1H), 7.65-7.60 (m, 2H), 7.59-7.38 (m, 8H), 7.16 (d, J=8.1 Hz, 1H), 7.08-7.02 (m, 1H), 6.49 (s, 2H), 4.58 (d, J=6.1 Hz, 2H), 3.91 (s, 3H).

Example 23: 5-Amino-1-[(1R)-indan-1-yl]-3-[4-[[(2-methoxybenzoyl)amino]methyl]phenyl]pyrazole-4-carboxamide

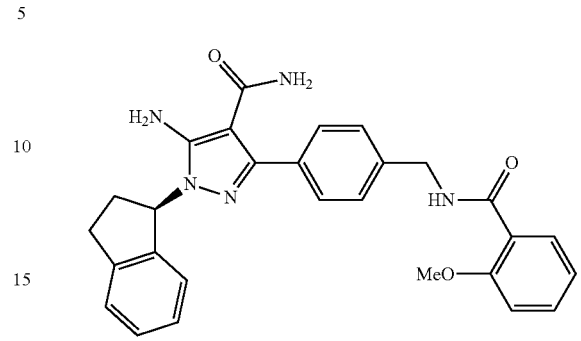

N-[[4-[5-Amino-4-cyano-1-[(1R)-indan-1-yl]pyrazol-3-yl]phenyl]methyl]-2-methoxy-benzamide A suspension of N-[[4-(5-amino-4-cyano-1H-pyrazol-3-yl)phenyl]methyl]-2-methoxy-benzamide (100 mg, 0.29 mmol), (S)-(+)-1-indanol (0.49 mmol) and triphenylphosphine (0.49 mmol) in anhydrous THF (2 mL) was cooled to 0° C. Diisopropyl azodicarboxylate (0.49 mmol) was added dropwise over 5 min and the reaction mixture was allowed to return to RT over 30 min and then stirred for 16 h. The reaction mixture was concentrated under vacuum. Further purification by SPE SCX column eluting with MeOH gave the titled compound (0.17 mmol). UPLC-MS (ES⁺, Short acidic): 1.90 min, m/z 464.3 [M+H]⁺

5-Amino-1-[(1R)-indan-1-yl]-3-[4-[[(2-methoxybenzoyl)amino]methyl]phenyl]pyrazole-4-carboxamide General procedure L, N-[[4-[5-amino-4-cyano-1-[(1R)-indan-1-yl]pyrazol-3-yl]phenyl]methyl]-2-methoxy-benzamide (0.27 mmol) afforded the titled compound (0.03 mmol) after purification by flash column chromatography on silica gel eluting with 0-5% MeOH in DCM. UPLC-MS (ES⁺, Short acidic): 1.74 min, m/z 482.3 [M+H]⁺. UPLC-MS (ES⁺, Long acidic): 3.77 min, m/z 482.3 [M+H]⁺.

¹H NMR (400 MHz, DMSO-d₆, δ): 8.70 (t, J=6.1 Hz, 1H), 7.74 (dd, J=7.6, 1.7 Hz, 1H), 7.52-7.43 (m, 1H), 7.41-7.34 (m, 4H), 7.30 (d, J=7.4 Hz, 1H), 7.24 (t, J=7.1 Hz, 1H), 7.20-7.11 (m, 2H), 7.09-6.98 (m, 2H), 6.56 (s, 2H), 5.91 (t, J=7.5 Hz, 1H), 4.52 (d, J=6.0 Hz, 2H), 3.88 (s, 3H), 3.21-3.06 (m, 1H), 2.97-2.84 (m, 1H), 2.49-2.38 (m, 2H).

Example 24: 1-Cyclopentyl-3-[4-[[(2-methoxybenzoyl)amino]methyl]phenyl]-5-methyl-pyrazole-4-carboxamide

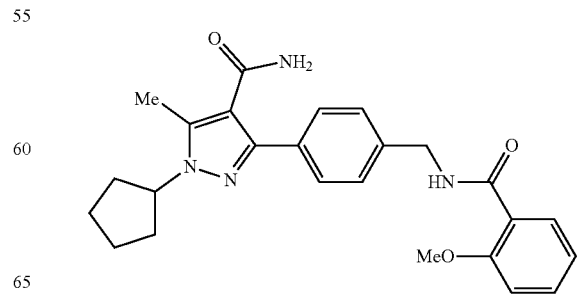

Methyl 2-(4-bromobenzoyl)-3-oxo-butanoate

Under $N_2$, a methylmagnesium bromide solution (2.2 M in THF, 9.27 mmol) was added to a solution of methyl acetoacetate (9.27 mmol) in THF (44 mL) at 0° C. and then allowed to stir at 0° C. for 30 min. Then 4-bromobenzoyl chloride (9.27 mmol) was added and then allowed to stir at RT for 16 h. Afterwards, quenched with a saturated solution of ammonium chloride. Then the aqueous layer was extracted with DCM (×3), organics combined, filtered over a hydrophobic frit and all volatiles were removed under reduced pressure. Purification by flash column chromatography on silica gel eluting with 0-15% EtOAc in heptane afforded the titled compound (4.99 mmol) as a clear oil. UPLC-MS (ES+, Short acidic): 1.88 min, m/z 299.0 [M]+

Methyl 3-(4-bromophenyl)-5-methyl-1H-pyrazole-4-carboxylate

A hydrazine hydrate solution (55-60% in water, 3.99 mmol) was added to a solution of methyl 2-(4-bromobenzoyl)-3-oxo-butanoate (4.99 mmol) in acetic acid (20 mL). Afterwards, allowed to stir at RT for 72 h and then all volatiles were removed under reduced pressure. Afterwards, the residue was basified with a saturated solution of sodium carbonate. Then the aqueous layer was extracted with DCM (×3), extracts combined and filtered over a hydrophobic frit. Afterwards, purification by flash column chromatography on silica gel eluting with 0-6% MeOH in DCM afforded the titled compound (4.21 mmol) as a clear oil. UPLC-MS (ES+, Short acidic): 1.60 min, m/z 296.9 [M+2]+

Methyl 3-(4-bromophenyl)-1-cyclopentyl-5-methyl-pyrazole-4-carboxylate

Cesium carbonate (3.00 mmol) was added to a solution of bromocyclopentane (2.40 mmol) and methyl 3-(4-bromophenyl)-5-methyl-1H-pyrazole-4-carboxylate (1.20 mmol) in DMF (2.5 mL). Afterwards, allowed to stir at 75° C. for 45 min and then all volatiles were removed under reduced pressure. Then the residue was suspended in EtOAc (50 mL). Afterwards, the organic layer was washed with water (×2) and a saturated solution of brine (×1). Then the organic layer was dried over sodium sulphate, filtered and all volatiles were removed under reduced pressure. Purification by flash column chromatography on silica gel eluting with 0-40% EtOAc in heptane afforded the titled compound (0.87 mmol) as a clear oil. UPLC-MS (ES+, Short acidic): 2.27 min, m/z 365.1 [M+2]+

3-(4-Bromophenyl)-1-cyclopentyl-5-methyl-pyrazole-4-carboxylic acid

Lithium hydroxide (2.75 mmol) was added to a solution of methyl 3-(4-bromophenyl)-1-cyclopentyl-5-methyl-pyrazole-4-carboxylate (0.28 mmol) in 1,4-dioxane (0.75 mL) and water (0.75 mL). Afterwards, allowed to stir at 80° C. for 16 h followed by at 100° C. for 16 h. After allowing the reaction mixture to cool back down to RT, the reaction mixture was acidified to pH3 with hydrochloric acid (1M). Then extracted with DCM (×3), filtered over a hydrophobic frit and all volatiles were removed under reduced pressure. Purification by flash column chromatography on silica gel eluting with 0-20% EtOAc in heptane afforded titled compound (0.28 mmol) as a white solid. UPLC-MS (ES+, Short acidic): 2.00 min, m/z 351.1 [M+2]+

3-(4-Bromophenyl)-1-cyclopentyl-N-[(2,4-dimethoxyphenyl)methyl]-5-methyl-pyrazole-4-carboxamide Under $N_2$, 3-(4-bromophenyl)-1-cyclopentyl-5-methyl-pyrazole-4-carboxylic acid (0.28 mmol), 2,4-dimethoxybenzylamine (0.33 mmol) and triethylamine (0.41 mmol) were suspended in THF (1.4 mL). After allowing the reaction mixture to stir at RT for 5 min, a solution of propylphosphonic anhydride (50 wt % in EtOAc, 0.41 mmol) was added and the reaction was stirred at RT for 72 h. Then 2,4-dimethoxybenzylamine (0.33 mmol), triethylamine (0.41 mmol) and a solution of propylphosphonic anhydride (50 wt % in EtOAc, 0.41 mmol) were added. Then the reaction was allowed to stir at RT for 16 h. Then a saturated solution of ammonium chloride (10 mL) and water (10 mL) were added. Afterwards, DCM (×3) was used to extract the aqueous layer. The organic extracts were combined, filtered over a hydrophobic frit, and all volatiles were removed under reduced pressure. Purification by flash column chromatography on silica gel eluting with 0-50% EtOAc in heptane followed by purification by reverse-phase chromatography eluting with 30-70% MeCN in water containing 0.1% formic acid afforded the titled compound (0.07 mmol) as a white solid. UPLC-MS (ES+, Short acidic): 2.18 min, m/z 500.2 [M+2]+

1-Cyclopentyl-N-[(2,4-dimethoxyphenyl)methyl]-3-[4-[[(2-methoxybenzoyl)amino]methyl]phenyl]-5-methyl-pyrazole-4-carboxamide Following general procedure K, 3-(4-bromophenyl)-1-cyclopentyl-N-[(2,4-dimethoxyphenyl)methyl]-5-methyl-pyrazole-4-carboxamide (0.07 mmol) and potassium trifluoro-[[(2-methoxybenzoyl)amino]methyl]boranuide (0.11 mmol) gave, after purification by flash column chromatography on silica gel eluting with 0-2.5% MeOH in DCM followed by reverse-phase chromatography eluting with 20-70% MeCN in water containing 0.1% formic acid, the titled compound (0.05 mmol) as a white solid. UPLC-MS (ES+, Short acidic): 2.04 min, m/z 583.4 [M+H]+

1-Cyclopentyl-3-[4-[[(2-methoxybenzoyl)amino]methyl]phenyl]-5-methyl-pyrazole-4-carboxamide At 0° C., trifluoroacetic acid (0.04 mmol) was added to a solution of 1-cyclopentyl-N-[(2,4-dimethoxyphenyl)methyl]-3-[4-[[(2-methoxybenzoyl)amino]methyl]phenyl]-5-methyl-pyrazole-4-carboxamide (0.04 mmol) in DCM (0.4 mL) and the reaction mixture was stirred for 48 h at RT. Extra portions of trifluoroacetic acid (0.04 mmol) were then added every 24 h for 3 days whilst allowing the reaction mixture to stir at RT. The reaction mixture was then basified with a saturated solution of sodium carbonate. The layers were partitioned and the aqueous layer was extracted with DCM (×3), combined, filtered over a hydrophobic frit and concentrated under reduced pressure. Further purification by flash column chromatography on silica gel eluting with 0-6% MeOH in DCM, followed by reverse-phase chromatography eluting with 20-70% MeCN in water containing 0.1% formic acid additive, afforded the titled compound (0.02 mmol) as an off-white solid. UPLC-MS (ES+, Short acidic): 1.62 min, m/z 433.2 [M+H]+. UPLC-MS (ES+, Long acidic): 3.70 min, m/z 433.2 [M+H]+.
$^1$H NMR (400 MHz, DMSO-$d_6$, δ): 8.70 (t, J=6.0 Hz, 1H), 7.75 (dd, J=7.6, 1.8 Hz, 1H), 7.60 (d, J=8.2 Hz, 2H), 7.51-7.45 (m, 1H), 7.34 (d, J=8.2 Hz, 2H), 7.24-7.17 (m, 2H), 7.16 (d, J=8.3 Hz, 1H), 7.08-7.01 (m, 1H), 4.71 (quint, J=7.3 Hz, 1H), 4.51 (d, J=6.0 Hz, 2H), 3.90 (s, 3H), 2.37 (s, 3H), 2.11-1.91 (m, 4H), 1.91-1.80 (m, 2H), 1.71-1.55 (m, 2H)

Example 25: 5-Amino-3-[4-[[(2-methoxybenzoyl)amino]methyl]phenyl]-1-[2-(1H-tetrazol-5-yl)ethyl]pyrazole-4-carboxamide

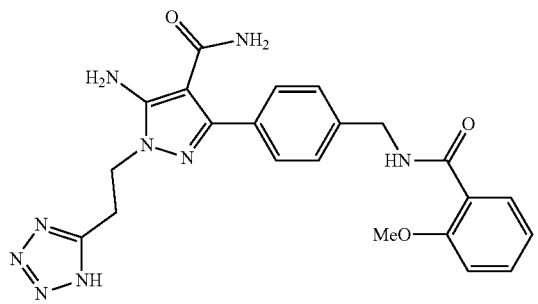 [SMILES: COc1ccccc1C(=O)NCc1ccc(-c2nn(CCc3nnn[nH]3)c(N)c2C(N)=O)cc1]

5-Amino-3-[4-[[(2-methoxybenzoyl)amino]methyl]phenyl]-1-[2-(1H-tetrazol-5-yl)ethyl]pyrazole-4-carboxamide To a solution of 5-amino-1-(2-cyanoethyl)-3-[4-[[(2-methoxybenzoyl)amino]methyl]phenyl]pyrazole-4-carboxamide (0.27 mmol) in DMF (2 mL) was added sodium azide (0.28 mmol) and ammonium chloride (0.30 mmol). The reaction mixture was heated to 110° C. for 16 h. A further sodium azide (0.28 mmol) and ammonium chloride (0.30 mmol) were added and the mixture was heated to 110° C. for 16 h, cooled to RT and concentrated under vacuum. The resulting residue was purified by flash column chromatography on silica gel, eluting with 0-20% MeOH in DCM, to give the titled compound (0.02 mmol). UPLC-MS (ES+, Short acidic): 1.22 min, m/z 462.2 [M+H]+. UPLC-MS (ES+, Long acidic): 2.70 min, m/z 462.2 [M+H]+.

$^1$H NMR (400 MHz, DMSO-$d_6$, –δ): 8.74 (t, J=6.1 Hz, 1H), 8.32 (br s, 1H), 7.76 (dd, J=7.6, 1.9 Hz, 1H), 7.45-7.52 (m, 1H), 7.44-7.38 (m, 4H), 7.16 (d, J=7.7 Hz, 1H), 7.04 (td, J=7.5, 1.0 Hz, 1H), 6.48 (s, 2H), 4.55 (d, J=6.2 Hz, 2H), 4.33 (t, J=7.1 Hz, 2H), 3.90 (s, 3H), 3.27 (t, J=7.2 Hz, 2H).

Example 26: 5-Amino-1-(4,4-dimethylcyclohexyl)-3-[4-[[(2-methoxybenzoyl)amino]methyl]phenyl]pyrazole-4-carboxamide

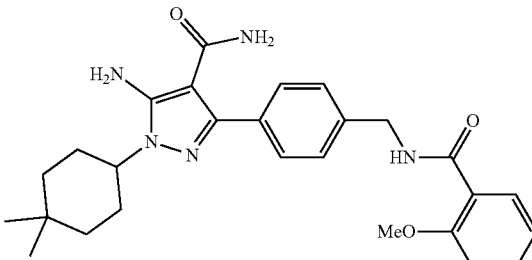

tert-Butyl N-[(4,4-dimethylcyclohexylidene)amino]carbamate

Following general procedure E, 4,4-dimethylcyclohexanone (0.79 mmol) gave the titled compound (0.78 mmol) as an off-white powder. $^1$H NMR (400 MHz, CDCl$_3$, δ): 7.49 (br s, 1H), 2.45-2.39 (m, 2H), 2.26-2.20 (m, 2H), 1.55-1.44 (m, 13H), 1.02 (s, 6H).

5-Amino-3-(4-bromophenyl)-1-(4,4-dimethylcyclohexyl)pyrazole-4-carbonitrile

General procedure O, tert-butyl N-[(4,4-dimethylcyclohexylidene)amino]carbamate (0.78 mmol) and 2-[(4-bromophenyl)-methoxy-methylene]propanedinitrile (0.38 mmol) gave the titled compound (0.36 mmol) as an off-white powder. UPLC-MS (ES+, Short acidic): 2.33 min, m/z 375.1 [M+2]+

N-[[4-[5-Amino-4-cyano-1-(4,4-dimethylcyclohexyl)pyrazol-3-yl]phenyl]methyl]-2-methoxy-benzamide General procedure K, 5-amino-3-(4-bromophenyl)-1-(4,4-dimethylcyclohexyl)pyrazole-4-carbonitrile (0.13 mmol) and potassium trifluoro-[[(2-methoxybenzoyl)amino]methyl]boranuide (0.15 mmol) gave the titled compound (0.13 mmol) as an off-white powder. UPLC-MS (ES+, Short acidic): 1.99 min, m/z 458.3 [M+H]+

5-Amino-1-(4,4-dimethylcyclohexyl)-3-[4-[[(2-methoxybenzoyl)amino]methyl]phenyl]pyrazole-4-carboxamide General procedure M, N-[[4-[5-amino-4-cyano-1-(4,4-dimethylcyclohexyl)pyrazol-3-yl]phenyl]methyl]-2-methoxybenzamide (0.07 mmol) afforded, after further purification by reverse-phase chromatography eluting with 20-60% MeCN in water containing 0.1% formic acid additive, the titled compound (0.02 mmol) as a white solid. UPLC-MS (ES+, Short acidic): 1.74 min, m/z 476.3 [M+H]+. UPLC-MS (ES+, Long acidic): 4.04 min, m/z 476.3 [M+H]+. $^1$H NMR (400 MHz, DMSO-$d_6$, δ): 8.74 (t, J=6.1 Hz, 1H), 7.76 (dd, J=7.6, 1.8 Hz, 1H), 7.52-7.38 (m, 5H), 7.16 (d, J=8.3 Hz, 1H), 7.08-7.01 (m, 1H), 6.31 (s, 2H), 4.55 (d, J=6.1 Hz, 2H), 4.10-3.98 (m, 1H), 3.91 (s, 3H), 2.00-1.86 (m, 2H), 1.71-1.60 (m, 2H), 1.52-1.42 (m, 2H), 1.42-1.29 (m, 2H), 0.95 (s, 6H)

Example 27: 5-Amino-1-(4-hydroxy-4-methyl-cyclohexyl)-3-[4-[[(2-methoxybenzoyl)amino]methyl]phenyl]pyrazole-4-carboxamide

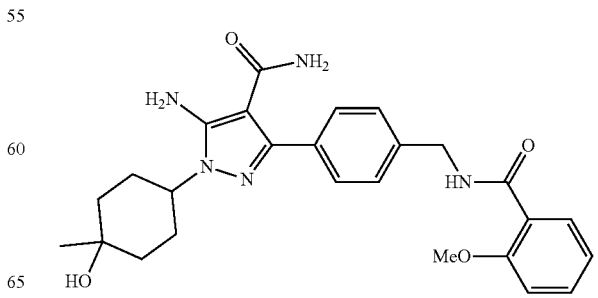

8-Methyl-1,4-dioxaspiro[4.5]decan-8-ol

A solution of methylmagnesium bromide (2.2 M in diethyl ether, 2.82 mmol) was added to a solution of 1,4-cyclohexanedione monoethylene acetal (2.56 mmol) in THF (5 mL), cooled to 0° C. The reaction mixture was stirred at RT for 2 h, and then quenched with a saturated solution of aqueous ammonium chloride. The layers were partitioned between DCM (20 mL) and water (20 mL). The aqueous layer was extracted with DCM (×3). The combined organic extracts were filtered over a phase separator and concentrated under reduced pressure to give crude the titled compound (2.50 mmol,) as a clear oil. $^1$H NMR (400 MHz, CDCl$_3$, δ): 4.02-3.91 (m, 4H), 1.96-1.84 (m, 2H), 1.78-1.65 (m, 4H), 1.65-1.56 (m, 2H), 1.29 (s, 3H), 1.15 (s, 1H)

4-Hydroxy-4-methyl-cyclohexanone

Following general procedure J, 8-methyl-1,4-dioxaspiro[4.5]decan-8-ol (2.50 mmol) in THF (2.5 mL) afforded the titled compound crude (2.50 mmol) as a brown oil. $^1$H NMR (400 MHz, CDCl$_3$, δ): 2.71-2.59 (m, 2H), 2.23-2.12 (m, 2H), 1.96-1.86 (m, 2H), 1.85-1.73 (m, 2H), 1.31 (s, 3H), 1.23 (s, 1H)

tert-Butyl N-[(4-hydroxy-4-methyl-cyclohexylidene)amino]carbamate

Following general procedure E, 4-hydroxy-4-methyl-cyclohexanone (2.50 mmol) gave the titled compound (1.36 mmol) as a clear oil. UPLC-MS (ES$^+$, Short acidic): 1.21 min, m/z 243.1 [M+H]$^+$

5-Amino-3-(4-bromophenyl)-1-(4-hydroxy-4-methyl-cyclohexyl)pyrazole-4-carbonitrile Following general procedure O, tert-butyl N-[(4-hydroxy-4-methyl-cyclohexylidene)amino]carbamate (0.83 mmol) and 2-[(4-bromophenyl)-methoxy-methylene]propanedinitrile (0.68 mmol) gave, after purification by flash column chromatography eluting with 55% EtOAc in heptane followed by 0-8% MeOH in DCM, the titled compound (isomer 1, 0.43 mmol) as an off-white powder and the titled compound (isomer 2, 0.09 mmol) as an off white solid. UPLC-MS (ES$^+$, Short acidic; isomer 1): 1.65 min, m/z 375.0 [M]$^+$. UPLC-MS (ES$^+$, Short acidic; isomer 2): 1.72 min, m/z 375.1 [M]$^+$

5-Amino-3-(4-bromophenyl)-1-(4-hydroxy-4-methyl-cyclohexyl)pyrazole-4-carboxamide Following general procedure L, 5-amino-3-(4-bromophenyl)-1-(4-hydroxy-4-methyl-cyclohexyl)pyrazole-4-carbonitrile (isomer 1) (50 mg, 0.13 mmol) gave 5-amino-3-(4-bromophenyl)-1-(4-hydroxy-4-methyl-cyclohexyl)pyrazole-4-carboxamide (44 mg, 0.11 mmol, 84%) as an off-white powder. UPLC-MS (ES$^+$, Short acidic): 1.35 min, m/z 394.9 [M+2]$^+$

5-Amino-1-(4-hydroxy-4-methyl-cyclohexyl)-3-[4-[[(2-methoxybenzoyl)amino]methyl]phenyl]pyrazole-4-carboxamide General procedure K, 5-amino-3-(4-bromophenyl)-1-(4-hydroxy-4-methyl-cyclohexyl)pyrazole-4-carboxamide (0.11 mmol) and potassium trifluoro-[[(2-methoxybenzoyl)amino]methyl]boranuide (0.12 mmol) gave the titled compound (0.09 mmol) as an off-white powder. UPLC-MS (ES$^+$, Short acidic): 1.33 min, m/z 478.5 [M+H]$^+$. UPLC-MS (ES$^+$, Long acidic): 2.98 min, m/z 478.3 [M+H]$^+$. $^1$H NMR (400 MHz, DMSO-d$_6$, δ): 8.74 (t, J=6.1 Hz, 1H), 7.76 (dd, J=7.7, 1.7 Hz, 1H), 7.52-7.37 (m, 5H), 7.16 (d, J=8.3 Hz, 1H), 7.08-7.01 (m, 1H), 6.29 (s, 2H), 4.55 (d, J=6.2 Hz, 2H), 4.12 (s, 1H), 4.08-3.97 (m, 1H), 3.91 (s, 3H), 2.24-2.07 (m, 2H), 1.70-1.60 (m, 2H), 1.60-1.50 (m, 2H), 1.50-1.37 (m, 2H), 1.15 (s, 3H)

Example 28: 5-Amino-1-(4-benzyloxycyclohexyl)-3-[4-[[(2-methoxybenzoyl)amino]methyl]phenyl]pyrazole-4-carboxamide

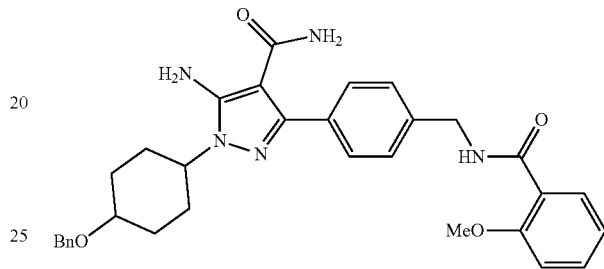

8-Benzyloxy-1,4-dioxaspiro[4.5]decane

Under N$_2$, sodium hydride, (60% dispersed in mineral oil, 1.90 mmol) was added to a solution of 1,4-dioxaspiro[4.5]decan-8-ol (1.26 mmol) in THF (2.4 mL), cooled at 0° C. The reaction mixture was stirred at 0° C. for 30 min, then, benzyl bromide (1.90 mmol) was added. The mixture was allowed to stir at RT overnight, quenched with a saturated solution of ammonium chloride and partitioned. The aqueous layer was extracted with DCM (×3). The combined organic extracts were filtered over a hydrophobic frit and concentrated under reduced pressure. Further purification by flash column chromatography on silica gel eluting with 30% ethyl acetate in heptane afforded the titled compound (0.81 mmol) as a clear oil. UPLC-MS (ES$^+$, Short acidic): 1.76 min, m/z 249.0 [M+H]$^+$

4-Benzyloxycyclohexanone

General procedure J, 8-benzyloxy-1,4-dioxaspiro[4.5]decane (0.81 mmol) gave the titled compound crude (0.81 mmol) as a clear oil. $^1$H NMR (400 MHz, CDCl$_3$, δ): 7.44-7.29 (m, 5H), 4.63 (s, 2H), 3.88-3.82 (m, 1H), 2.71-2.60 (m, 2H), 2.35-2.25 (m, 2H), 2.24-2.12 (m, 2H), 2.05-1.94 (m, 2H)

tert-Butyl N-[(4-benzyloxycyclohexylidene)amino]carbamate

Following general procedure E, 4-benzyloxycyclohexanone (0.81 mmol) gave the titled compound (0.81 mmol) as a clear oil. UPLC-MS (ES$^+$, Short acidic): 1.74 min, m/z 319.2 [M+H]$^+$

5-Amino-1-(4-benzyloxycyclohexyl)-3-(4-bromophenyl)pyrazole-4-carbonitrile

Following general procedure O, tert-butyl N-[(4-benzyloxycyclohexylidene)amino]carbamate (0.81 mmol) and 2-[(4-bromophenyl)-methoxy-methylene]propanedinitrile (0.68 mmol) gave the titled compound (0.68 mmol) as an off-white powder. UPLC-MS (ES+, Short acidic, cis/trans mixture): 2.18 min and 2.20 min, m/z 453.1 [M+2]+

5-Amino-1-(4-benzyloxycyclohexyl)-3-(4-bromophenyl)pyrazole-4-carboxamide

General procedure L, 5-amino-1-(4-benzyloxycyclohexyl)-3-(4-bromophenyl)pyrazole-4-carbonitrile (0.13 mmol) gave the titled compound (0.13 mmol) as a clear oil. UPLC-MS (ES+, Short acidic, cis/trans mixture): 1.91 min, m/z 471.0 [M+2]+

5-Amino-1-(4-benzyloxycyclohexyl)-3-[4-[[(2-methoxybenzoyl)amino]methyl]phenyl]pyrazole-4-carboxamide Following general procedure K, 5-amino-1-(4-benzyloxycyclohexyl)-3-(4-bromophenyl)pyrazole-4-carboxamide (0.13 mmol) and potassium trifluoro-[[(2-methoxybenzoyl)amino]methyl]boranuide (0.15 mmol) gave the titled compound as a mixture of diastereoisomers (0.12 mmol) as a white powder. UPLC-MS (ES+, Short acidic): 1.73 min, m/z 554.5 [M+H]+, 1.77 min, m/z 554.2 [M+H]+. UPLC-MS (ES+, Long acidic): 4.02 min, m/z 554.3 [M+H]+, 4.11 min, m/z 554.3 [M+H]+.
$^1$H NMR (400 MHz, DMSO-$d_6$, δ): 8.73 (t, J=5.9 Hz, 1H), 7.76 (dd, J=7.6, 1.6 Hz, 1H), 7.53-7.31 (m, 9H), 7.31-7.23 (m, 1H), 7.16 (d, J=8.4 Hz, 1H), 7.08-7.01 (m, 1H), 6.34 (s, 1H), 6.32 (s, 1H), 4.59-4.46 (m, 4H), 4.20-4.06 (m, 1H), 3.90 (s, 3H), 3.69-3.62 (m, 0.5), 3.46-3.35 (m, 0.5H), 2.20-1.94 (m, 3H), 1.93-1.73 (m, 2H), 1.68-1.46 (m, 2H), 1.46-1.25 (m, 1H)

Example 29: 5-Amino-1-cyclopropyl-3-[4-[[(2-methoxybenzoyl)amino]methyl]phenyl]pyrazole-4-carboxamide

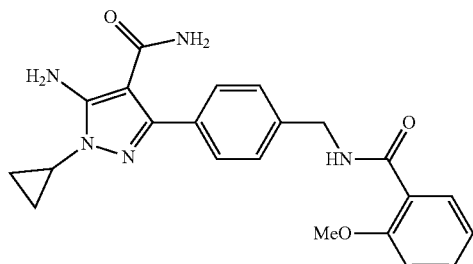

5-Amino-3-(4-bromophenyl)-1-cyclopropyl-pyrazole-4-carbonitrile

Following general procedure H, 2-[(4-bromophenyl)-methoxy-methylene]propanedinitrile (0.46 mmol) and cyclopropylhydrazine hydrochloride (0.55 mmol) gave, after further purification by flash column chromatography on silica gel eluting with 0-10% MeOH in DCM, the titled compound (0.34 mmol) as a white solid. UPLC-MS (ES+, Short acidic): 1.73 min, m/z 303.0 [M]+

N-[[4-(5-amino-4-cyano-1-cyclopropyl-pyrazol-3-yl)phenyl]methyl]-2-methoxy-benzamide General procedure K, 5-amino-3-(4-bromophenyl)-1-cyclopropyl-pyrazole-4-carbonitrile (0.32 mmol) and potassium trifluoro-[[(2-methoxybenzoyl)amino]methyl]boranuide (0.45 mmol) gave, after further purification by flash column chromatography on silica gel eluting with 0-10% MeOH in DCM, the titled compound (0.34 mmol) as crude brown solid. UPLC-MS (ES+, Short acidic): 1.51 min, m/z 388.2 [M+H]+

5-Amino-1-cyclopropyl-3-[4-[[(2-methoxybenzoyl)amino]methyl]phenyl]pyrazole-4-carboxamide General procedure L, N-[[4-(5-amino-4-cyano-1-cyclopropyl-pyrazol-3-yl)phenyl]methyl]-2-methoxy-benzamide (0.32 mmol) gave, after further purification by flash column chromatography on silica gel eluting with 0-10% MeOH in DCM, the titled compound (0.15 mmol) as a white solid. UPLC-MS (ES+, Short acidic): 1.32 min, m/z 406.2 [M+H]+. UPLC-MS (ES+, Long acidic): 2.95 min, m/z 406.3 [M+H]+.
$^1$H NMR (400 MHz, DMSO-$d_6$, δ): 8.75 (t, J=6.0 Hz, 1H), 7.76 (dd, J=7.7, 1.3 Hz, 1H), 7.53-7.34 (m, 5H), 7.16 (d, J=8.3 Hz, 1H), 7.06-7.03 (m, 1H), 6.33 (s, 2H), 4.55 (d, J=6.1 Hz, 2H), 3.90 (s, 3H), 3.32-3.24 (m, 1H), 1.04-0.92 (m, 4H)

Example 30: 5-Amino-3-[4-[[(2-methoxybenzoyl)amino]methyl]phenyl]-1-methyl-pyrazole-4-carboxamide

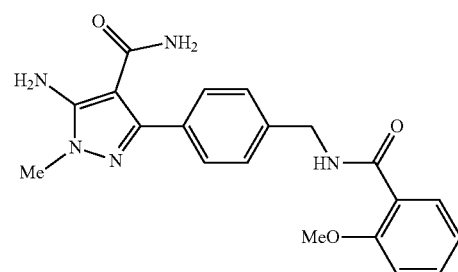

5-Amino-3-(4-bromophenyl)-1-methyl-pyrazole-4-carbonitrile

Following general procedure H, 2-[(4-bromophenyl)-methoxy-methylene]propanedinitrile (1.14 mmol) and methylhydrazine (1.37 mmol) gave, after further purification by flash column chromatography on silica gel eluting with 0-10% MeOH in DCM, an inseparable mixture of regioisomers the titled compound (0.47 mmol) as a white solid. UPLC-MS (ES+, Short acidic): 1.57 min and 1.67 min, m/z 277.0 [M]+

N-[[4-(5-Amino-4-cyano-1-methyl-pyrazol-3-yl)phenyl]methyl]-2-methoxy-benzamide

General procedure K, a mixture of 5-amino-3-(4-bromophenyl)-1-methyl-pyrazole-4-carbonitrile and 3-amino-5-(4-bromophenyl)-1-methyl-pyrazole-4-carbonitrile (0.43 mmol) and potassium trifluoro-[[(2-methoxybenzoyl)amino]methyl]boranuide (1.37 mmol) gave, after further purification by flash column chromatography on silica gel eluting with 10-100% EtOAc in heptane, the titled compound (0.11 mmol) as an white solid. UPLC-MS (ES+, Short acidic): 1.54 min, m/z 362.2 [M+H]+

5-Amino-3-[4-[[(2-methoxybenzoyl)amino]methyl]phenyl]-1-methyl-pyrazole-4-carboxamide General procedure L, N-[[4-(5-amino-4-cyano-1-methyl-pyrazol-3-yl)phenyl]methyl]-2-methoxy-benzamide (0.09 mmol) gave, after further purification by flash column chromatography on silica gel eluting with 0-10% MeOH in DCM, the titled compound (0.05 mmol) as a white solid. UPLC-MS (ES+, Short acidic): 1.24 min, m/z 380.2 [M+H]+. UPLC-MS (ES+, Long acidic): 2.76 min, m/z 380.2 [M+H]+

$^1$H NMR (400 MHz, DMSO-$d_6$, δ): 8.75 (t, J=6.2 Hz, 1H), 7.76 (dd, J=7.8, 1.7 Hz, 1H), 7.51-7.39 (m, 5H), 7.16 (dd, J=8.4, 0.9 Hz, 1H), 7.07-7.03 (m, 1H), 6.28 (s, 2H), 4.55 (d, J=6.2 Hz, 2H), 3.90 (s, 3H), 3.56 (s, 3H)

Example 31: 5-Amino-1-(2-hydroxyethyl)-3-[4-[[(2-methoxybenzoyl)amino]methyl]phenyl]pyrazole-4-carboxamide

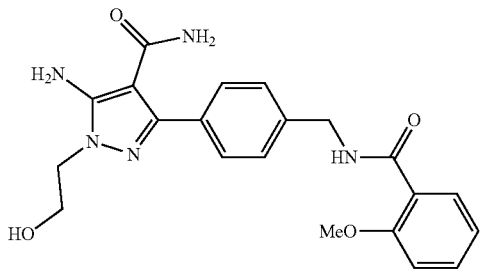 [SMILES: COc1ccccc1C(=O)NCc1ccc(-c2nn(CCO)c(N)c2C(N)=O)cc1]

5-Amino-3-(4-bromophenyl)-1-(2-hydroxyethyl)pyrazole-4-carbonitrile

General procedure H, 2-[(4-bromophenyl)-methoxymethylene]propanedinitrile (1.14 mmol) and 2-hydroxyethylhydrazine (1.37 mmol) gave, after purification by flash column chromatography on silica gel eluting with 10-100% EtOAc in heptane gave the titled compound (0.40 mmol) as a white solid. UPLC-MS (ES+, Short acidic): 1.60 min, m/z 307.0 [M]+

N-[[4-[5-Amino-4-cyano-1-(2-hydroxyethyl)pyrazol-3-yl]phenyl]methyl]-2-methoxy-benzamide General procedure K, 5-amino-3-(4-bromophenyl)-1-(2-hydroxyethyl)pyrazole-4-carbonitrile (0.35 mmol) and potassium trifluoro-[[(2-methoxybenzoyl)amino]methyl]boranuide (0.49 mmol) gave, after further purification by flash column chromatography on silica gel eluting with 0-10% MeOH in DCM, the titled compound (0.22 mmol) as light brown solid. UPLC-MS (ES+, Short acidic): 1.36 min, m/z 392.1 [M+H]+

5-Amino-1-(2-hydroxyethyl)-3-[4-[[(2-methoxybenzoyl)amino]methyl]phenyl]pyrazole-4-carboxamide General procedure L, N-[[4-[5-amino-4-cyano-1-(2-hydroxyethyl)pyrazol-3-yl]phenyl]methyl]-2-methoxy-benzamide (0.21 mmol) gave, after further purification by flash column chromatography on silica gel eluting with 0-10% MeOH in DCM, the titled compound (0.09 mmol) as a white solid. UPLC-MS (ES+, Short acidic): 1.20 min, m/z 410.2 [M+H]+. UPLC-MS (ES+, Long acidic): 2.66 min, m/z 410.2 [M+H]+.

$^1$H NMR (400 MHz, DMSO-$d_6$, δ): 8.74 (t, J=6.2 Hz, 1H), 7.76 (dd, J=7.8, 1.7 Hz, 1H), 7.52-7.39 (m, 5H), 7.16 (m, 1H), 7.05 (m, 1H), 6.21 (s, 2H), 5.00-4.94 (m, 1H), 4.56 (d, J=6.2 Hz, 2H), 3.98 (t, J=5.9 Hz, 2H), 3.90 (s, 3H), 3.71 (q, J=5.71 Hz, 2H).

Example 32: 5-amino-1-(3-fluorophenyl)-3-[4-[[(2-methoxybenzoyl)amino]methyl]phenyl]pyrazole-4-carboxamide

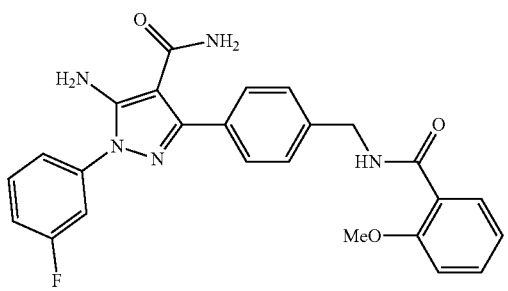 [SMILES: COc1ccccc1C(=O)NCc1ccc(-c2nn(-c3cccc(F)c3)c(N)c2C(N)=O)cc1]

5-Amino-3-(4-bromophenyl)-1-(3-fluorophenyl)pyrazole-4-carbonitrile

General procedure H, (3-fluorophenyl)hydrazinium chloride (0.68 mmol) and 2-[(4-bromophenyl)-methoxy-methylene]propanedinitrile (0.57 mmol) gave, after purification by flash column chromatography on silica gel eluting with 0-100% EtOAc in heptane, the titled compound (0.22 mmol, 38% yield) as a light brown solid. UPLC-MS (ES+, Short acidic): 1.97 min, m/z 357.1 [M]+

N-[[4-[5-Amino-4-cyano-1-(3-fluorophenyl)pyrazol-3-yl]phenyl]methyl]-2-methoxy-benzamide General procedure K, 5-amino-3-(4-bromophenyl)-1-(3-fluorophenyl)pyrazole-4-carbonitrile (0.22 mmol) and potassium trifluoro-[[(2-methoxybenzoyl)amino]methyl]boranuide (0.30 mmol) gave, after further purification by flash column chromatography on silica gel eluting with 0-100% EtOAc in heptane, titled compound (0.05 mmol) as an off-white solid. UPLC-MS (ES+, Short acidic): 1.71 min, m/z 442.2 [M+H]+

5-Amino-1-(3-fluorophenyl)-3-[4-[[(2-methoxybenzoyl)amino]methyl]phenyl]pyrazole-4-carboxamide General procedure L, N-[[4-[5-amino-4-cyano-1-(3-fluorophenyl)pyrazol-3-yl]phenyl]methyl]-2-methoxy-benzamide (0.05 mmol) gave, after further purification by flash column chromatography on silica gel eluting with 0-10% MeOH in DCM, the titled compound (0.03 mmol) was obtained as a white solid. UPLC-MS (ES+, Short acidic): 1.54 min, m/z 460.2 [M+H]+. UPLC-MS (ES+, Long acidic): 3.52 min, m/z 460.2 [M+H]+. $^1$H NMR (400 MHz, DMSO-$d_6$, δ): 8.77 (t, J=6.1 Hz, 1H), 7.76 (dd, J=7.5, 1.6 Hz, 1H), 7.62-7.55 (m, 3H), 7.52-7.45 (m, 5H), 7.26 (t, J=8.6 Hz, 1H), 7.16 (d, J=8.2 Hz, 1H), 7.05 (t, J=7.58 Hz, 1H), 6.62 (s, 2H), 4.57 (d, J=6.1 Hz, 2H), 3.91 (s, 3H).

Example 33: 5-Amino-1-(4-hydroxy-4-methyl-cyclohexyl)-3-[4-[[(2-methoxybenzoyl)amino]methyl]phenyl]pyrazole-4-carboxamide

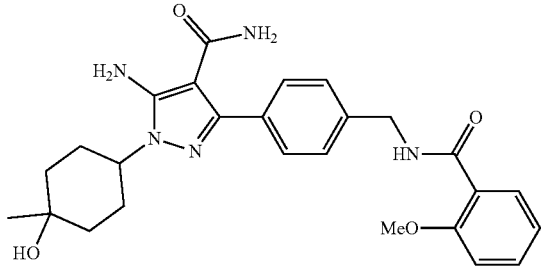

5-Amino-3-(4-bromophenyl)-1-(4-hydroxy-4-methyl-cyclohexyl)pyrazole-4-carboxamide Following general procedure L, 5-amino-3-(4-bromophenyl)-1-(4-hydroxy-4-methyl-cyclohexyl)pyrazole-4-carbonitrile (isomer 2) (0.09 mmol) gave crude the titled compound (0.09 mmol) as an off-white powder. UPLC-MS (ES+, Short acidic): 1.38 min, m/z 395.1 [M+2]+

5-Amino-1-(4-hydroxy-4-methyl-cyclohexyl)-3-[4-[[(2-methoxybenzoyl)amino]methyl]phenyl]pyrazole-4-carboxamide General procedure K, 5-amino-3-(4-bromophenyl)-1-(4-hydroxy-4-methyl-cyclohexyl)pyrazole-4-carboxamide (0.09 mmol) and potassium trifluoro-[[(2-methoxybenzoyl)amino]methyl]boranuide (0.09 mmol) gave the titled compound (0.04 mmol) as an off-white powder. UPLC-MS (ES+, Short acidic): 1.30 min, m/z 478.3 [M+H]+. UPLC-MS (ES+, Long acidic): 2.94 min, m/z 478.3 [M+H]+.

$^1$H NMR (400 MHz, DMSO-$d_6$, δ): 8.74 (t, J=6.0 Hz, 1H), 7.76 (dd, J=7.6, 1.7 Hz, 1H), 7.52-7.37 (m, 5H), 7.16 (d, J=8.3 Hz, 1H), 7.08-7.00 (m, 1H), 6.33 (s, 2H), 4.55 (d, J=6.0 Hz, 2H), 4.42 (s, 1H), 4.18-4.05 (m, 1H), 3.90 (s, 3H), 1.92-1.71 (m, 4H), 1.70-1.60 (m, 2H), 1.60-1.48 (m, 2H), 1.17 (s, 3H).

Example 34a: (Isomer 1) and 34b (Isomer 2): 5-Amino-1-(4-hydroxycyclohexyl)-3-[4-[[(2-methoxybenzoyl)amino]methyl]phenyl]pyrazole-4-carboxamide

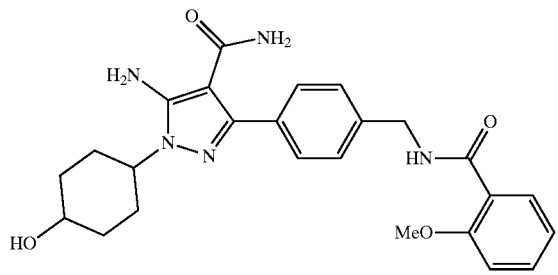

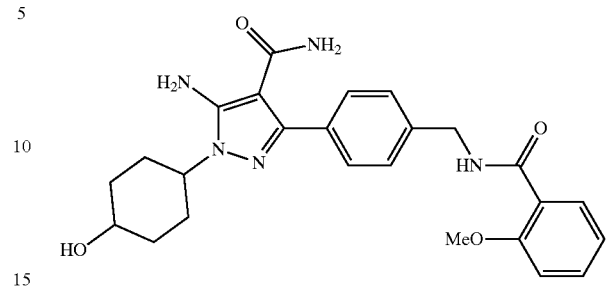

5-Amino-1-(4-hydroxycyclohexyl)-3-[4-[[(2-methoxybenzoyl)amino]methyl]phenyl]pyrazole-4-carboxamide Palladium (10 wt. % on carbon powder, dry) (0.33 mmol) was added to a solution of 5-amino-1-(4-benzyloxycyclohexyl)-3-[4-[[(2-methoxybenzoyl)amino]methyl]phenyl]pyrazole-4-carboxamide (0.13 mmol) in MeOH (1.3 mL) and ammonium formate (0.40 mmol). The reaction mixture was stirred at 60° C. for 2 h then ammonium formate (1.34 mmol) was added and the mixture was stirred at 60° C. for 1 h. Acetic acid (0.5 mL) was added and the reaction mixture was allowed to stir at 60° C. for another 14 h, cooled to RT and filtered over a plug of Celite®. The plug was washed with DCM and the filtrate concentrated under reduced pressure. The residue was basified with a saturated solution of sodium bicarbonate and extracted with DCM (×3). The combined organic extracts were filtered over a hydrophobic frit and concentrated under reduced pressure. Further purification by flash column chromatography on silica gel eluting with 0-10% MeOH in DCM afforded the titled compound (isomer 1, 0.02 mmol) as a white solid and the titled compound (isomer 2, 0.09 mmol) as a brown solid.

UPLC-MS (ES+, Short acidic; isomer 1): 1.27 min, m/z 464.3 [M+H]+. UPLC-MS (ES+, Long acidic; isomer 1): 2.84 min, m/z 464.3 [M+H]+. $^1$H NMR (400 MHz, DMSO-$d_6$, δ) (isomer 1): 8.74 (t, J=6.0 Hz, 1H), 7.76 (dd, J=7.6, 1.7 Hz, 1H), 7.52-7.37 (m, 5H), 7.16 (d, J=8.3 Hz, 1H), 7.08-7.00 (m, 1H), 6.30 (s, 2H), 4.55 (d, J=6.0 Hz, 2H), 4.40 (d, J=2.6 Hz, 1H), 4.13-4.02 (m, 1H), 3.90 (s, 3H), 3.86 (br s, 1H), 2.23-2.07 (m, 2H), 1.84-1.72 (m, 2H), 1.61-1.47 (m, 4H).

UPLC-MS (ES+, Short acidic; isomer 2): 1.26 min, m/z 464.3 [M+H]+. UPLC-MS (ES+, Long acidic; isomer 2): 2.82 min, m/z 464.3 [M+H]+. $^1$H NMR (400 MHz, DMSO-$d_6$, δ) (isomer 2): 8.74 (t, J=6.1 Hz, 1H), 7.76 (dd, J=7.7, 1.7 Hz, 1H), 7.52-7.37 (m, 5H), 7.16 (d, J=8.3 Hz, 1H), 7.08-7.00 (m, 1H), 6.33 (s, 2H), 4.63 (d, J=4.5 Hz, 1H), 4.55 (d, J=6.1 Hz, 2H), 4.13-4.01 (m, 1H), 3.90 (s, 3H), 3.51-3.39 (m, 1H), 1.96-1.86 (m, 2H), 1.86-1.74 (m, 4H), 1.39-1.25 (m, 2H).

Example 35: 5-Amino-1-cyclobutyl-3-[4-[[(2-methoxybenzoyl)amino]methyl]phenyl]pyrazole-4-carboxamide

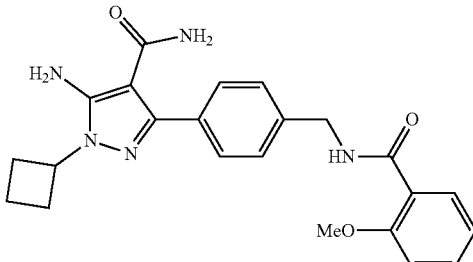

tert-Butyl N-(cyclobutylideneamino)carbamate

To a solution of cyclobutanone (2.0 mmol) in heptane (2 mL) was added tert-butyl carbazate (2.2 mmol) and the reaction was heated to reflux and stirred for 2 h. Volatiles were removed under reduced pressure to give the titled compound (2.0 mmol, 100% yield) as a white solid. UPLC-MS (ES+, Short acidic): 1.61 min, m/z 185.0 [M+H]+

Cyclobutylhydrazine hydrochloride tert-Butyl N-(cyclobutylideneamino)carbamate (0.27 mmol) was dissolved in THF (5 mL) and dimethylsulfide borane (0.46 mmol) was added. The reaction was stirred at RT for 1 h. As TLC showed consumption of the starting material, the solvent was removed in vacuo. The residue was dissolved in hydrogen chloride-methanol solution (7.6 mL), the reaction was heated to reflux and stirred overnight. Evaporation of the solvent afforded the titled compound (0.27 mmol) as a yellowish gum which was used without any further purification. $^1$H NMR (400 MHz, DMSO-$d_6$, δ): 3.66-3.54 (m, 1H), 2.16-1.97 (m, 4H), 1.83-1.64 (m, 2H).

5-Amino-3-(4-bromophenyl)-1-cyclobutyl-pyrazole-4-carbonitrile

General procedure H, cyclobutylhydrazine hydrochloride (0.25 mmol) and 2-[(4-bromophenyl)-methoxy-methylene]propanedinitrile (0.21 mmol) gave, after purification by flash column chromatography on silica gel eluting with 20-80% EtOAc in heptane, the titled compound (0.14 mmol) as a white solid. UPLC-MS (ES+, Short acidic): 1.95 min, m/z 317.0 [M]+

N-[[4-(5-Amino-4-cyano-1-cyclobutyl-pyrazol-3-yl)phenyl]methyl]-2-methoxy-benzamide Following general procedure K, 5-amino-3-(4-bromophenyl)-1-cyclobutyl-pyrazole-4-carbonitrile (0.14 mmol) and potassium trifluoro-[[(2-methoxybenzoyl)amino]methyl]boranuide (0.19 mmol) gave the titled compound (0.13 mmol) as a white powder. UPLC-MS (ES+, Short acidic): 1.67 min, m/z 402.2 [M+H]+

5-Amino-1-cyclobutyl-3-[4-[[(2-methoxybenzoyl)amino]methyl]phenyl]pyrazole-4-carboxamide General procedure L, N-[[4-(5-amino-4-cyano-1-cyclobutyl-pyrazol-3-yl)phenyl]methyl]-2-methoxy-benzamide (0.05 mmol) gave the titled compound (0.03 mmol) as a white powder. UPLC-MS (ES+, Short acidic): 1.46 min, m/z 420.3 [M+H]+. UPLC-MS (ES+, Long acidic): 3.29 min, m/z 420.2 [M+H]+

$^1$H NMR (400 MHz, DMSO-$d_6$, δ): 8.74 (t, J=6.2 Hz, 1H), 7.76 (dd, J=7.9, 2.2 Hz, 1H), 7.50-7.41 (m, 5H), 7.16 (d, J=8.3 Hz, 1H), 7.04 (t, J=7.5 Hz, 1H), 6.30 (s, 2H), 4.81-4.73 (m, 1H), 4.55 (d, J=6.0 Hz, 2H), 3.91 (s, 3H), 2.33-2.26 (m, 4H), 1.78-1.69 (m, 2H).

Example 36: 5-Amino-3-[4-[[(2-methoxybenzoyl)amino]methyl]phenyl]-1-tetrahydrofuran-3-yl-pyrazole-4-carboxamide

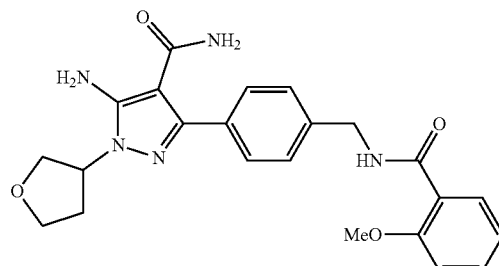

tert-Butyl N-tetrahydrofuran-3-ylideneamino]carbamate

To a solution of dihydro(3(2H)-furanone (1.95 mmol) in ethanol (2 mL) was added tert-butyl carbazate (2.35 mmol) and the reaction was heated to reflux and stirred overnight. Volatiles were removed under reduced pressure to give the titled compound (1.95 mmol) as a white solid. $^1$H NMR (400 MHz, CDCl$_3$, δ, mixture of isomers): 7.25 (s, 0.75H), 7.12 (s, 0.25H), 4.34 (t, J=1.2 Hz, 1.5H), 4.24 (t, J=1.2 Hz, 0.5H), 4.12 (t, J=6.9 Hz, 1.5H), 4.02 (t, J=6.9 Hz, 0.5H), 2.78 (td, J=6.9, 1.2 Hz, 0.5H), 2.48 (td, J=6.9, 1.2 Hz, 1.5H), 1.54 (s, 7.5H), 1.53 (s, 1.5H).

Tetrahydrofuran-3-ylhydrazine hydrochloride tert-Butyl N-[tetrahydrofuran-3-ylideneamino]carbamate (0.25 mmol) was dissolved in THF (5 mL) and dimethylsulfide borane (0.42 mmol) was added. The reaction was stirred at RT for 1 h until TLC showed complete consumption of the starting material. Solvent was removed in vacuo. The residue was dissolved with a hydrogen chloride solution in MeOH (1.25 M, 6.99 mL), and the reaction was heated to reflux and stirred overnight. Evaporation of the solvent afforded the titled compound (0.25 mmol) as a yellowish gum which was used without any further purification. $^1$H NMR (400 MHz, DMSO-$d_6$, δ): 3.86-3.59 (m, 6H), 2.11-1.96 (m, 1H), 1.95-1.84 (m, 1H).

5-Amino-3-(4-bromophenyl)-1-tetrahydrofuran-3-yl-pyrazole-4-carbonitrile

General procedure H, tetrahydrofuran-3-ylhydrazine hydrochloride (0.23 mmol) and 2-[(4-bromophenyl)-methoxy-methylene]propanedinitrile (0.19 mmol) gave, after purification by flash column chromatography on silica gel eluting with 20-80% EtOAc in heptane, the titled compound (0.09 mmol) as a light brown solid. UPLC-MS (ES+, Short acidic): 1.71 min, m/z 333.1 [M]+

N-[[4-(5-Amino-4-cyano-1-tetrahydrofuran-3-yl-pyrazol-3-yl)phenyl]methyl]-2-methoxy-benzamide General procedure K, 5-amino-3-(4-bromophenyl)-1-tetrahydrofuran-3-yl-pyrazole-4-carbonitrile (0.10 mmol) and potassium trifluoro-[[(2-methoxybenzoyl)amino]methyl]boranuide (0.14 mmol) gave the titled compound (0.06 mmol) as a white solid. UPLC-MS (ES+, Short acidic): 1.51 min, 418.2 m/z [M+H]+

5-Amino-3-[4-[[(2-methoxybenzoyl)amino]methyl]phenyl]-1-tetrahydrofuran-3-yl-pyrazole-4-carboxamide General procedure L, N-[[4-(5-amino-4-cyano-1-tetrahydrofuran-3-yl-pyrazol-3-yl)phenyl]methyl]-2-methoxy-benzamide (0.06 mmol) gave the titled compound (0.03 mmol) as a white powder. UPLC-MS (ES+, Short acidic): 1.32 min, m/z 458.2 [M+Na]+. UPLC-MS (ES+, Long acidic): 2.95 min, m/z 436.2 [M+H]+. $^1$H NMR (400 MHz, DMSO-$d_6$, δ): 8.74 (t, J=5.8 Hz, 1H), 7.75 (dd, J=7.4, 1.8 Hz, 1H), 7.50-7.40 (m, 5H), 7.16 (d, J=7.7 Hz, 1H), 7.04 (td, J=7.5, 1.0 Hz, 1H), 6.40 (s, 2H), 4.97-4.90 (m, 1H), 4.55 (d, J=6.0 Hz, 2H), 4.00-3.94 (m, 2H), 3.90 (s, 3H), 3.83-3.78 (m, 2H), 2.28-2.24 (m, 2H)

Example 37: 5-amino-1-[(1S*,3S*)-3-chlorocyclopentyl]-3-[4-[[(2-methoxybenzoyl)amino]methyl]phenyl]pyrazole-4-carboxamide

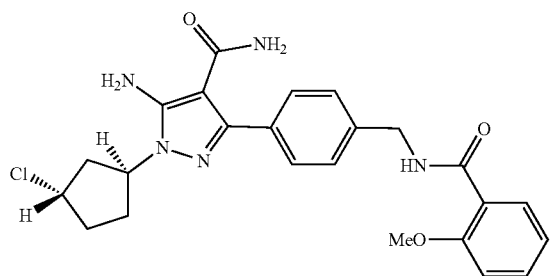 [SMILES: COc1ccccc1C(=O)NCc1ccc(-c2nn([C@H]3CC[C@H](Cl)C3)c(N)c2C(N)=O)cc1]

5-Amino-1-[(1S*,3S*)-3-chlorocyclopentyl]-3-[4-[[(2-methoxybenzoyl)amino]methyl]phenyl]pyrazole-4-carboxamide Thionyl chloride (0.67 mmol) was added to a solution of 5-amino-1-[(1S*,3R*)-3-hydroxycyclopentyl]-3-[4-[[(2-methoxybenzoyl)amino]methyl]phenyl]pyrazole-4-carboxamide (0.22 mmol) in DCM (3 mL), cooled to 0° C. The reaction was allowed to rise to RT and stirred for 48 h at this temperature. The mixture was then concentrated and the resulting residue was then purified by reverse-phase chromatography eluting with 30-80% MeCN in water containing 0.1% formic acid additive to afford the titled compound (0.07 mmol) as a white solid. UPLC-MS (ES+, Short acidic): 1.58 min, m/z 468.1 [M]+. UPLC-MS (ES+, Long acidic): 3.62 min, m/z 468.1 [M]+.

$^1$H NMR (400 MHz, CDCl$_3$, δ): 8.29-8.20 (m, 2H), 7.56-7.42 (m, 5H), 7.15-7.11 (m, 1H), 6.99 (d, J=8.2 Hz, 1H), 5.46 (br.s, 2H), 5.15 (br.s, 2H) 4.80-4.70 (m, 3H), 4.68-4.63 (m, 1H), 3.95 (s, 3H), 2.77-2.67 (m, 1H), 2.55-2.37 (m, 3H), 2.23-2.11 (m, 1H), 2.11-2.01 (m, 1H)

Example 38: 5-amino-3-[4-[[(2-methoxybenzoyl)amino]methyl]phenyl]-1-[[(3R)-3-piperidyl]methyl]pyrazole-4-carboxamide

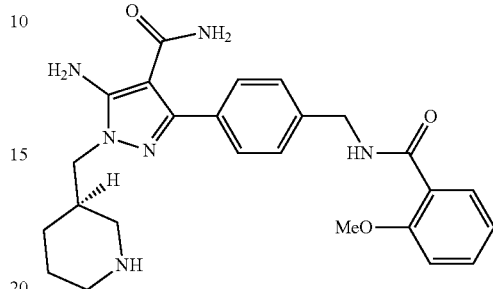

tert-Butyl (3R)-3-(hydroxymethyl)piperidine-1-carboxylate

To a stirred solution of (3R)-1-(tert-Butoxycarbonyl)piperidine-3-carboxylic acid (0.87 mmol) in dry THF (10 mL) at RT was added dropwise borane-tetrahydrofuran (1:1, 2.62 mmol). The reaction was stirred for 4 h, quenched with a saturated NH$_4$Cl solution (2 mL) and partitioned. The aqueous phase was extracted with EtOAc. The combined organic extracts were washed with brine, dried over sodium sulfate and concentrated under reduced pressure. Further purification by flash column chromatography on silica gel eluting with 0-100% EtOAc in heptane afforded the titled compound (0.84 mmol) as a white solid. $^1$H NMR (400 MHz, DMSO-$d_6$, δ): 4.52-4.46 (m, 1H), 4.01-3.86 (m, 1H), 3.83-3.75 (m, 1H), 3.30-3.26 (m, 1H), 3.22-3.16 (m, 1H), 2.75-2.63 (m, 1H), 1.70-1.62 (m, 1H), 1.61-1.53 (m, 1H), 1.50-1.40 (m, 1H), 1.38 (s, 9H), 1.36-1.21 (m, 2H), 1.13-1.01 (m, 1H).

tert-Butyl (3R)-3-(methylsulfonyloxymethyl)piperidine-1-carboxylate

General procedure I, tert-butyl (3R)-3-(hydroxymethyl)piperidine-1-carboxylate (0.84 mmol) and methanesulfonyl chloride (0.88 mmol) gave, after purification by flash column chromatography on silica gel eluting with 0-50% EtOAc in heptane, the titled compound (0.58 mmol) as a colourless oil. UPLC-MS (ES+, Short acidic): 1.71 min, m/z 316.1 [M+Na]+ tert-Butyl (3R)-3-[[5-amino-4-carbamoyl-3-[4-[[(2-methoxybenzoyl)amino]methyl]phenyl]pyrazol-1-yl]methyl]piperidine-1-carboxylate General procedure N, 5-amino-3-[4-[[(2-methoxybenzoyl)amino]methyl]phenyl]-1H-pyrazole-4-carboxamide (0.29 mmol) and tert-butyl (3R)-3-(methylsulfonyloxymethyl)piperidine-1-carboxylate (0.58 mmol) gave, after purification by flash column chromatography on silica gel, the titled compound (0.19 mmol) and tert-butyl (3R)-3-[[5-amino-4-carbamoyl-3-[4-[[(2-methoxybenzoyl)amino]methyl]phenyl]pyrazol-2-yl]methyl]piperidine-1-carboxylate as a mixture of regioisomers. UPLC-MS (ES+, Short acidic): 1.58 and 1.60 min, m/z 563.3 [M+H]+

5-Amino-3-[4-[[(2-methoxybenzoyl)amino]methyl]phenyl]-1-[[(3R)-3-piperidyl]methyl]pyrazole-4-carboxamide A mixture of regioisomers tert-butyl (3R)-3-[[5-amino-4-carbamoyl-3-[4-[[(2-methoxybenzoyl)amino]methyl]phenyl]pyrazol-1-yl]methyl]piperidine-1-carboxylate (0.19 mmol) and tert-butyl (3R)-3-[[5-amino-4-carbamoyl-3-[4-[[(2-methoxybenzoyl)amino]methyl]phenyl]pyrazol-2-yl]methyl]piperidine-1-carboxylate was dissolved in DCM (5 mL) and trifluoroacetic acid (4.7 mmol) was added. The reaction was stirred at RT overnight. The solvent was removed in vacuo. The residue was taken up with MeOH and passed through a SPE SCX cartridge, eluting with 0-100% 1 N ammonia in MeOH. Further purification by mass-directed semi-preparative HPLC gave the titled compound (0.02 mmol). UPLC-MS (ES+, Short acidic): 1.10 min, m/z 463.2 [M+H]+. UPLC-MS (ES+, Long acidic): 2.41 min, m/z 463.3 [M+H]+. $^1$H NMR (400 MHz, DMSO-$d_6$, δ): 8.74 (t, J=6.0 Hz, 1H), 8.38 (s, 2H), 7.76 (dd, J=7.4, 1.5 Hz, 1H), 7.51-7.40 (m, 5H), 7.16 (d, J=8.6 Hz, 1H), 7.04 (t, J=7.5 Hz, 1H), 6.37 (s, 2H), 4.55 (d, J=6.0 Hz, 2H), 3.90 (s, 3H), 3.83 (d, J=7.1 Hz, 2H), 2.95-2.88 (m, 2H), 2.43-2.38 (m, 1H), 2.09-1.99 (m, 1H), 1.70-1.64 (m, 2H), 1.46-1.36 (m, 1H), 1.24-1.15 (m, 1H).

Example 39: 5-amino-1-(2-fluorophenyl)-3-[4-[[(2-methoxybenzoyl)amino]methyl]phenyl]pyrazole-4-carboxamide

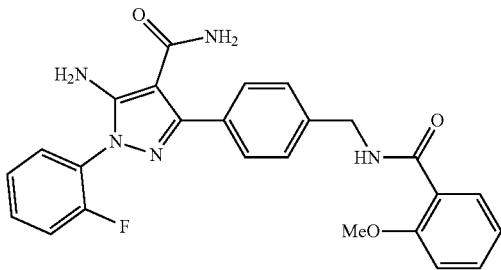 [SMILES: COc1ccccc1C(=O)NCc1ccc(-c2nn(-c3ccccc3F)c(N)c2C(N)=O)cc1]

5-Amino-3-(4-bromophenyl)-1-(2-fluorophenyl)pyrazole-4-carbonitrile

General procedure H, (2-fluorophenyl)hydrazine hydrochloride (0.68 mmol) and 2-[(4-bromophenyl)-methoxy-methylene]propanedinitrile (0.57 mmol) gave, after purification by flash column chromatography on silica gel eluting with 0-100% EtOAc in heptane, the titled compound (0.29 mmol) as a brown solid. UPLC-MS (ES+, Short acidic): 1.88 min, m/z 357.1 [M]+

N-[[4-[5-Amino-4-cyano-1-(2-fluorophenyl)pyrazol-3-yl]phenyl]methyl]-2-methoxy-benzamide General procedure K, 5-amino-3-(4-bromophenyl)-1-(2-fluorophenyl)pyrazole-4-carbonitrile (0.29 mmol) and potassium trifluoro-[[(2-methoxybenzoyl)amino]methyl]boranuide (0.40 mmol) gave, after further purification by flash column chromatography on silica gel eluting with 10-100% EtOAc in heptane, the titled compound (0.23 mmol) as a red solid. UPLC-MS (ES+, Short acidic): 1.62 min, m/z 442.1 [M+H]+

5-Amino-1-(2-fluorophenyl)-3-[4-[[(2-methoxybenzoyl)amino]methyl]phenyl]pyrazole-4-carboxamide General procedure L, N-[[4-[5-amino-4-cyano-1-(2-fluorophenyl)pyrazol-3-yl]phenyl]methyl]-2-methoxy-benzamide (0.23 mmol) gave, after further purification by flash column chromatography on silica gel eluting with 0-10% MeOH in DCM, the titled compound (0.02 mmol) as an off white solid. UPLC-MS (ES+, Short acidic): 1.46 min, m/z 460.2 [M+H]+. UPLC-MS (ES+, Long acidic): 3.32 min, m/z 460.2 [M+H]+. $^1$H NMR (400 MHz, DMSO-$d_6$, δ): 8.76 (t, J=6.0 Hz, 1H), 7.76 (dd, J=7.6, 1.6 Hz, 1H), 7.60-7.53 (m, 4H), 7.50-7.43 (m, 4H), 7.38 (t, J=7.75 Hz, 1H), 7.16 (d, J=8.4 Hz, 1H), 7.05 (t, J=7.4 Hz, 1H), 6.42 (s, 2H), 4.57 (d, J=6.0 Hz, 2H), 3.91 (s, 3H).

Example 40: Ethyl 4-[5-amino-4-carbamoyl-3-[4-[[(2-methoxybenzoyl)amino]methyl]phenyl]pyrazol-1-yl]cyclohexanecarboxylate

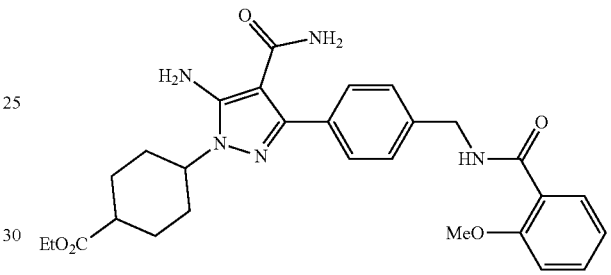

Ethyl 4-(tert-butoxycarbonylhydrazono)cyclohexanecarboxylate

General procedure E, ethyl 4-oxocyclohexanecarboxylate (3.14 mmol) gave the titled compound (2.96 mmol) as a clear oil. UPLC-MS (ES+, Short acidic): 1.52 min, m/z 285.1 [M+H]+

Ethyl 4-[5-amino-3-(4-bromophenyl)-4-cyano-pyrazol-1-yl]cyclohexanecarboxylate General procedure O, ethyl 4-(tert-butoxycarbonylhydrazono)cyclohexanecarboxylate (1.93 mmol) and 2-[(4-bromophenyl)-methoxy-methylene]propanedinitrile (1.63 mmol) gave the titled compound (1.56 mmol, mixture of cis/trans isomers) as a white powder. UPLC-MS (ES+, Short acidic): 2.00 min, m/z 419.1 [M+2]+, 2.06 min, m/z 419.1 [M+2]+

Ethyl 4-[5-amino-3-(4-bromophenyl)-4-carbamoyl-pyrazol-1-yl]cyclohexanecarboxylate General procedure L, ethyl 4-[5-amino-3-(4-bromophenyl)-4-cyano-pyrazol-1-yl]cyclohexanecarboxylate (0.91 mmol) gave the titled compound (0.91 mmol, mixture of cis/trans isomers) as an off-white powder. UPLC-MS (ES+, Short acidic): 1.70 min, m/z 437.1 [M+2]+, 1.72 min, m/z 437.1 [M+2]+

Ethyl 4-[5-amino-4-carbamoyl-3-[4-[[(2-methoxybenzoyl)amino]methyl]phenyl]pyrazol-1-yl]cyclohexanecarboxylate General procedure K, potassium trifluoro-[[(2-methoxybenzoyl)amino]methyl]boranuide (1.00 mmol) and ethyl 4-[5-amino-3-(4-bromophenyl)-4-carbamoyl-pyrazol-1-yl] cyclohexanecarboxylate (0.91 mmol) gave the titled compound (0.68 mmol, mixture of cis/trans isomers) as a white powder. UPLC-MS (ES+, Short acidic): 1.57 min, m/z 520.3 [M+H]+, 1.59 min, m/z 520.3 [M+H]+. UPLC-MS (ES+, Long acidic): 3.63 min, m/z 520.3 [M+H]+, 3.67 min, m/z 520.3 [M+H]+. 1H NMR (400 MHz, DMSO-$d_6$, δ) 8.73 (t, J=6.1 Hz, 1H), 7.79-7.73 (m, 1H), 7.52-7.38 (m, 5H), 7.16 (d, J=8.4 Hz, 1H), 7.08-7.00 (m, 1H), 6.35 (s, 0.8H), 6.33 (s, 1.2H), 4.55 (d, J=6.1 Hz, 2H), 4.18-4.03 (m, 3H), 3.90 (s, 3H), 2.73-2.29 (m, 1H), 2.22-2.11 (m, 1H), 2.06-1.95 (m, 1H), 1.92-1.42 (m, 6H), 1.23-1.15 (m, 3H)

Example 41: 5-amino-1-[(1S*,3S*)-3-fluorocyclopentyl]-3-[4-[[(2-methoxybenzoyl)amino]methyl] phenyl]pyrazole-4-carboxamide

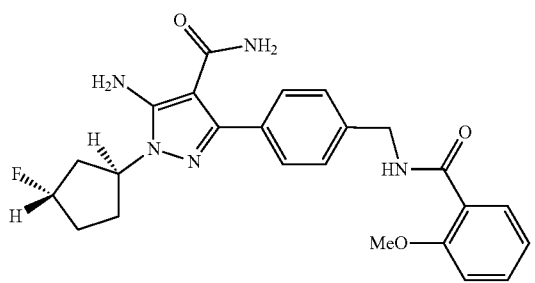 [SMILES: COc1ccccc1C(=O)NCc1ccc(-c2nn([C@H]3CC[C@H](F)C3)c(N)c2C(N)=O)cc1]

5-Amino-1-[(1S*,3S*)-3-fluorocyclopentyl]-3-[4-[[(2-methoxybenzoyl)amino]methyl]phenyl]pyrazole-4-carboxamide (Diethylamino)sulfur trifluoride (0.96 mmol) was added dropwise to a solution of 5-amino-1-[(1S*,3R*)-3-hydroxycyclopentyl]-3-[4-[[(2-methoxybenzoyl)amino]methyl]phenyl]pyrazole-4-carboxamide (0.24 mmol) in DCM (2 mL), cooled to −20° C. The reaction mixture was allowed to return to RT and then stirred for a further 2 h. The mixture was diluted with DCM and then quenched with saturated aqueous $NaHCO_3$. The aqueous layer was extracted with DCM. The organic layers were combined, filtered over a hydrophobic frit and concentrated under reduced pressure. The resulting residue was purified by flash column chromatography on silica gel, eluting with 0-10% MeOH in DCM. Further purification by reverse-phase chromatography eluting with 30-80% MeCN in water containing 0.1% formic acid additive afforded the titled compound (0.02 mmol) as a white solid. UPLC-MS (ES+, Short acidic): 1.49 min, m/z 452.1 [M+H]+. UPLC-MS (ES+, Long acidic): 3.39 min, m/z 452.3 [M+H]+.

1H NMR (400 MHz, DMSO-$d_6$, δ): 8.72 (t, J=6.1 Hz, 1H), 7.74 (dd, J=1.8, 7.7, 1H), 7.50-7.37 (m, 5H), 7.14 (d, J=8 Hz, 1H), 7.03 (td, J=1.0, 7.5 Hz, 1H), 6.39 (br s, 2H), 5.32 (d, J=53.6 Hz, 1H), 4.94-4.83 (m, 1H), 4.53 (d, J=6.1 Hz, 2H), 3.89 (s, 3H), 2.31-1.79 (m, 6H)

Example 42: 5-amino-3-[4-[[(2-methoxybenzoyl)amino]methyl]phenyl]-1-[[(3S)-3-piperidyl]methyl] pyrazole-4-carboxamide

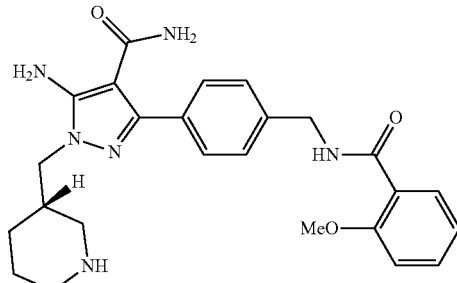

tert-Butyl (3S)-3-(methylsulfonyloxymethyl)piperidine-1-carboxylate

General procedure I, tert-butyl (3S)-3-(hydroxymethyl) piperidine-1-carboxylate (0.82 mmol) and methanesulfonyl chloride (0.86 mmol) gave, after purification by flash column chromatography on silica gel eluting with 0-50% EtOAc in heptane, the titled compound (0.72 mmol) as a colourless oil. UPLC-MS (ES+, Short acidic): 1.71 min, m/z 316.1 [M+Na]+ tert-Butyl (3S)-3-[[5-amino-4-carbamoyl-3-[4-[[(2-methoxybenzoyl)amino]methyl]phenyl]pyrazol-1-yl] methyl]piperidine-1-carboxylate General procedure N, 5-amino-3-[4-[[(2-methoxybenzoyl)amino]methyl]phenyl]-1H-pyrazole-4-carboxamide (0.23 mmol) and tert-butyl (3S)-3-(methylsulfonyloxymethyl)piperidine-1-carboxylate (0.47 mmol) gave, after purification by flash column chromatography on silica gel, the titled compound and tert-butyl (3S)-3-[[5-amino-4-carbamoyl-3-[4-[[(2-methoxybenzoyl)amino]methyl]phenyl]pyrazol-2-yl]methyl]piperidine-1-carboxylate (0.13 mmol) as a beige solid mixture of regioisomers. UPLC-MS (ES+, Short acidic): 1.59 and 1.60 min, m/z 563.3 [M+H]+

3-Amino-5-[4-[[(2-methoxybenzoyl)amino]methyl] phenyl]-1-[[(3S)-3-piperidyl]methyl]pyrazole-4-carboxamide and 5-amino-3-[4-[[(2-methoxybenzoyl)amino]methyl]phenyl]-1-[[(3S)-3-piperidyl] methyl]pyrazole-4-carboxamide tert-Butyl (3S)-3-[[5-amino-4-carbamoyl-3-[4-[[(2-methoxybenzoyl)amino]methyl]phenyl]pyrazol-1-yl] methyl]piperidine-1-carboxylate and tert-butyl (3S)-3-[[5-amino-4-carbamoyl-3-[4-[[(2-methoxybenzoyl)amino] methyl]phenyl]pyrazol-2-yl]methyl]piperidine-1-carboxylate (0.13 mmol) was dissolved in DCM (5 mL) and trifluoroacetic acid (3.3 mmol) was added. The reaction was stirred at RT overnight. The solvent was removed under reduced pressure. The residue was taken up with MeOH and passed through a SPE SCX cartridge, eluting with 0-100% 1 M ammonia in MeOH. The mixture of regioisomers was then purified by mass-directed semi-preparative HPLC to give 5-amino-3-[4-[[(2-methoxybenzoyl)amino]methyl] phenyl]-1-[[(3S)-3-piperidyl]methyl]pyrazole-4-carboxamide (0.01 mmol). UPLC-MS (ES+, Short acidic): 1.09 min, m/z 463.2 [M+H]+. UPLC-MS (ES+, Long acidic): 2.41 min, m/z 463.3 [M+H]+

1H NMR (400 MHz, DMSO-d6, δ): 8.74 (t, J=5.8 Hz, 1H), 8.42 (s, 2H), 7.75 (dd, J=7.5, 1.5 Hz, 1H), 7.50-7.40 (m, 5H), 7.16 (d, J=8.2 Hz, 1H), 7.06-7.03 (m, 1H), 6.36 (s, 2H), 4.55 (d, J=5.8 Hz, 2H), 3.90 (s, 3H), 3.82 (d, J=7.1 Hz, 2H), 2.91-2.86 (m, 2H), 2.40-2.38 (m, 2H), 2.03-1.99 (m, 1H), 1.69-1.62 (m, 2H), 1.40-1.34 (m, 1H), 1.21-1.15 (m, 1H).

Example 43: 5-amino-1-(4-fluorophenyl)-3-[4-[[(2-methoxybenzoyl)amino]methyl]phenyl]pyrazole-4-carboxamide

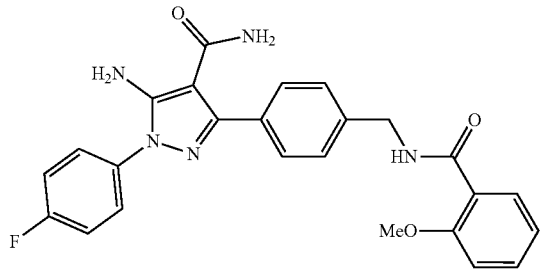 [SMILES: COc1ccccc1C(=O)NCc1ccc(-c2nn(-c3ccc(F)cc3)c(N)c2C(N)=O)cc1]

5-Amino-3-(4-bromophenyl)-1-(4-fluorophenyl)pyrazole-4-carbonitrile

General procedure H, 4-fluorophenyl)hydrazine hydrochloride (0.68 mmol) and 2-[(4-bromophenyl)-methoxy-methylene]propanedinitrile (0.57 mmol) gave, after purification by flash column chromatography on silica gel eluting with 0-100% EtOAc in heptane, the titled compound (0.41 mmol) as a light brown solid. UPLC-MS (ES+, Short acidic): 1.94 min, m/z 359.0 [M+2]+

N-[[4-[5-Amino-4-cyano-1-(4-fluorophenyl)pyrazol-3-yl]phenyl]methyl]-2-methoxy-benzamide General procedure K, 5-amino-3-(4-bromophenyl)-1-(4-fluorophenyl)pyrazole-4-carbonitrile (0.41 mmol) and potassium trifluoro-[[(2-methoxybenzoyl)amino]methyl]boranuide (0.57 mmol) gave, after purification by flash column chromatography on silica gel eluting with 0-100% EtOAc in heptane, the titled compound (0.38 mmol) as a brown solid. UPLC-MS (ES+, Short acidic): 1.69 min, m/z 442.2 [M+H]+

5-Amino-1-(4-fluorophenyl)-3-[4-[[(2-methoxybenzoyl)amino]methyl]phenyl]pyrazole-4-carboxamide General procedure M, N-[[4-[5-amino-4-cyano-1-(4-fluorophenyl)pyrazol-3-yl]phenyl]methyl]-2-methoxy-benzamide (0.33 mmol) gave, after further purification by mass-directed semi-preparative HPLC, the titled compound (0.03 mmol) was obtained as a white solid. UPLC-MS (ES+, Short acidic): 1.52 min, m/z 460.2 [M+H]+. UPLC-MS (ES+, Long acidic): 3.45 min, m/z 460.3 [M+H]+

1H NMR (400 MHz, DMSO-d6, δ): 8.76 (t, J=6.1 Hz, 1H), 7.77 (dd, J=7.7, 1.7 Hz, 1H), 7.66-7.63 (m, 2H), 7.56-7.54 (m, 2H), 7.51-7.44 (m, 3H), 7.41 (m, 2H), 7.16 (d, J=8.1 Hz, 1H), 7.07-7.03 (m, 1H), 6.47 (s, 2H), 4.57 (d, J=6.1 Hz, 2H), 3.91 (s, 3H).

Example 44: 5-amino-3-[4-[[(2-methoxybenzoyl)amino]methyl]phenyl]-1-(p-tolyl)pyrazole-4-carboxamide

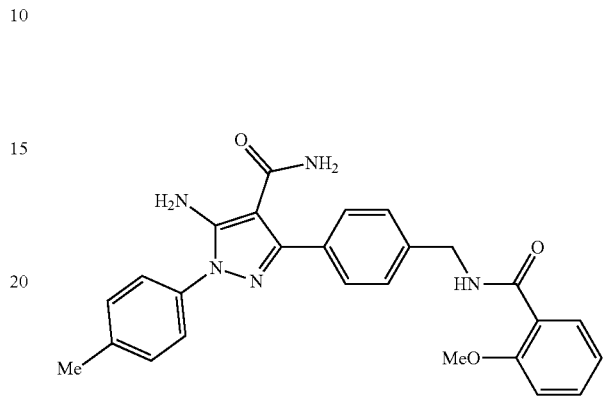

5-Amino-3-(4-bromophenyl)-1-(p-tolyl)pyrazole-4-carbonitrile

General procedure H, p-tolylhydrazine hydrochloride (0.34 mmol) and 2-[(4-bromophenyl)-methoxy-methylene]propanedinitrile (0.29 mmol) gave, after further purification by flash column chromatography on silica gel eluting with 0-100% EtOAc in heptane, the titled compound (0.29 mmol) as an orange solid. UPLC-MS (ES+, Short acidic): 2.00 min, m/z 353.0 [M]+

N-[[4-[5-Amino-4-cyano-1-(p-tolyl)pyrazol-3-yl]phenyl]methyl]-2-methoxy-benzamide General procedure K, potassium trifluoro-[[(2-methoxybenzoyl)amino]methyl]boranuide (0.30 mmol) and 5-amino-3-(4-bromophenyl)-1-(p-tolyl)pyrazole-4-carbonitrile (0.21 mmol) gave, after further purification by flash column chromatography on silica gel eluting with 0-100% EtOAc in heptane, the titled compound (0.09 mmol) as a light brown solid. UPLC-MS (ES+, Short acidic): 1.75 min, m/z 438.3 [M+H]+

5-Amino-3-[4-[[(2-methoxybenzoyl)amino]methyl]phenyl]-1-(p-tolyl)pyrazole-4-carboxamide General procedure M, N-[[4-[5-amino-4-cyano-1-(p-tolyl)pyrazol-3-yl]phenyl]methyl]-2-methoxy-benzamide (0.09 mmol) gave, after further purification by preparative HPLC, the titled compound (0.01 mmol) as an off-white solid. UPLC-MS (ES+, Short acidic): 1.57 min, m/z 456.3 [M+H]+. UPLC-MS (ES+, Long acidic): 3.59 min, m/z 456.3 [M+H]+. 1H NMR (400 MHz, DMSO-d6, δ): 8.76 (t, J=5.9 Hz, 1H), 7.77 (dd, J=7.7, 1.8 Hz, 1H), 7.55-7.53 (m, 2H), 7.51-7.44 (m, 5H), 7.34-7.33 (m, 2H), 7.16 (d, J=8.6 Hz, 1H), 7.07-7.03 (m, 1H), 6.41 (s, 2H), 4.56 (d, J=6.2 Hz, 2H), 3.91 (s, 3H), 2.38 (s, 3H).

Example 45: Methyl 4-[5-amino-4-carbamoyl-3-[4-[[(2-methoxybenzoyl)amino]methyl]phenyl]pyrazol-1-yl]benzoate

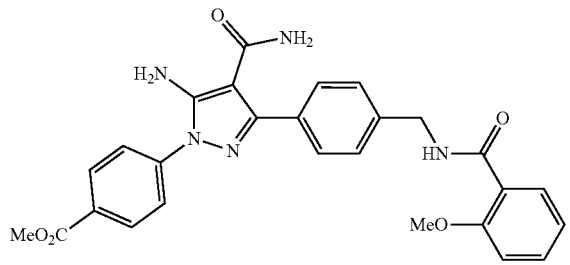 [SMILES: COC(=O)c1ccc(-n2nc(-c3ccc(CNC(=O)c4ccccc4OC)cc3)c(C(N)=O)c2N)cc1]

Methyl 4-[5-amino-3-(4-bromophenyl)-4-cyano-pyrazol-1-yl]benzoate

Following general procedure H, methyl 4-hydrazinylbenzoate hydrochloride (0.55 mmol) and 2-[(4-bromophenyl)-methoxy-methylene]propanedinitrile (0.46 mmol) gave, after further purification by flash column chromatography on silica gel eluting with 0-100% EtOAc in heptane, the titled compound (0.27 mmol) as an orange solid. UPLC-MS (ES+, Short acidic): 1.96 min, m/z 397.1 [M]+

Methyl 4-[5-amino-4-cyano-3-[4-[[(2-methoxybenzoyl)amino]methyl]phenyl]pyrazol-1-yl]benzoate General procedure K, methyl 4-[5-amino-3-(4-bromophenyl)-4-cyano-pyrazol-1-yl]benzoate (0.27 mmol) and potassium trifluoro-[[(2-methoxybenzoyl)amino]methyl]boranuide (0.38 mmol) gave, after further purification by flash column chromatography on silica gel eluting with 0-100% EtOAc in heptane, titled compound (0.20 mmol) as an off-white solid. UPLC-MS (ES+, Short acidic): 1.70 min, 482.3 m/z [M+H]+

Methyl 4-[5-amino-4-carbamoyl-3-[4-[[(2-methoxy-benzoylamino]methyl]phenyl]pyrazol-1-yl]benzoate General procedure M, methyl 4-[5-amino-4-cyano-3-[4-[[(2-methoxybenzoyl)amino]methyl]phenyl]pyrazol-1-yl]benzoate (0.20 mmol) gave, after further purification by mass-directed preparative HPLC, the titled compound (0.01 mmol) as an off-white solid. UPLC-MS (ES+, Short acidic): 1.53 min, m/z 500.3 [M+H]+. UPLC-MS (ES+, Long acidic): 3.52 min, m/z 500.3 [M+H]+. $^1$H NMR (400 MHz, DMSO-$d_6$, δ): 8.76 (t, J=6.3 Hz, 1H), 8.10 (d, J=8.5 Hz, 2H), 7.83 (d, J=8.5 Hz, 2H), 7.76 (dd, J=7.7, 1.7 Hz, 1H), 7.57 (d, J=8.4 Hz, 2H), 7.50-7.45 (m, 3H), 7.16 (d, J=8.4 Hz, 1H), 7.04 (t, J=7.4 Hz, 1H), 6.7 (s, 2H), 4.58 (d, J=6.0 Hz, 2H), 3.90 (s, 3H), 3.89 (s, 3H).

Example 46: 5-amino-1-[(S*,3S*)-3-hydroxycyclopentyl]-3-[4-[[(2-methoxybenzoyl)amino]methyl]phenyl]pyrazole-4-carboxamide

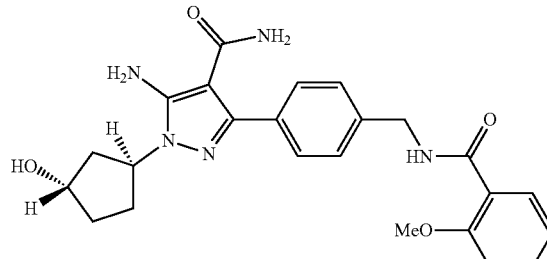

[(1S*)-3-[(1S*)-5-Amino-4-carbamoyl-3-[4-[[(2-methoxybenzoyl)amino]methyl]phenyl]pyrazol-1-yl]cyclopentyl]2,2-dimethylpropanoate To a solution of 5-amino-1-[(1S*,3R*)-3-hydroxycyclopentyl]-3-[4-[[(2-methoxybenzoyl)amino]methyl]phenyl]pyrazole-4-carboxamide (160 mg, 0.36 mmol) in THF (1.8 mL) was added triphenylphosphine (0.71 mmol) and trimethylacetic acid (0.53 mmol) and cooled to 0° C. Diisopropyl azodicarboxylate (0.71 mmol) was then added and the mixture stirred at this temperature for 15 min before allowing to rise to RT and stirring at this temperature for 48 h. The reaction was concentrated and then purified by flash column chromatography on silica gel eluting with 0-100% EtOAc in heptane to give titled compound (0.18 mmol). UPLC-MS (ES+, Short acidic): 1.73 min, 534.3 m/z [M+H]+

5-Amino-1-[(1S*,3S*)-3-hydroxycyclopentyl]-3-[4-[[(2-methoxybenzoyl)amino]methyl]phenyl]pyrazole-4-carboxamide To a solution of [(1S*,3S*)-3-[5-amino-4-carbamoyl-3-[4-[[(2-methoxybenzoyl)amino]methyl]phenyl]pyrazol-1-yl]cyclopentyl] 2,2-dimethylpropanoate (0.22 mmol) in THF (1 mL) was added lithium hydroxide (1.79 mmol). The reaction mixture was then heated to 80° C. for 4 days, cooled and diluted with DCM and partitioned with water. The mixture was passed through a phase separator and the aqueous layer was extracted with DCM several times. The organic layers were combined and concentrated. The resulting residue was purified by flash column chromatography on silica gel eluting with 0-10% MeOH in DCM to give the titled compound (0.05 mmol, 23% yield) as a white solid. UPLC-MS (ES+, Short acidic): 1.28 min, m/z 450.3 [M+H]+. UPLC-MS (ES+, Long acidic): 2.86 min, m/z 450.3 [M+H]+. $^1$H NMR (400 MHz, DMSO-$d_6$, δ): 8.72 (t, J=6.1 Hz, 1H), 7.74 (dd, J=1.8, 7.6 Hz, 1H), 7.50-7.45 (m, 1H), 7.43 (d, J=8.3 Hz, 2H), 7.39 (d, J=8.3 Hz, 2H), 7.15 (d, J=8.5 Hz, 1H), 7.03 (td, J=1.0, 7.5 Hz, 1H), 6.33 (br.s, 2H), 4.82 (quint, J=8.1, 15.3 Hz, 1H), 4.62 (d, J=3.4 Hz, 1H), 4.54 (d, J=6.1 Hz, 2H), 4.35-4.28 (m, 1H), 3.89 (s, 3H), 2.21-2.06 (m, 2H), 2.04-1.86 (m, 2H), 1.85-1.74 (m, 1H), 1.58-1.48 (m, 1H)

Example 47: 5-amino-3-[4-[[(2-methoxybenzoyl)amino]methyl]phenyl]-1-(o-tolyl)pyrazole-4-carboxamide

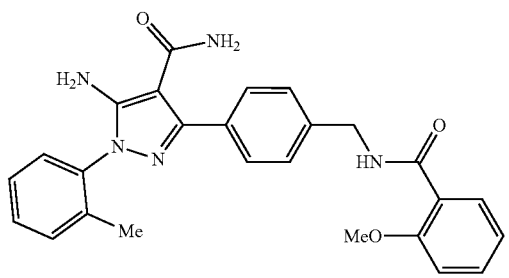 [SMILES: COc1ccccc1C(=O)NCc1ccc(-c2nn(-c3ccccc3C)c(N)c2C(N)=O)cc1]

5-Amino-3-(4-bromophenyl)-1-(o-tolyl)pyrazole-4-carbonitrile

Following general procedure H, o-tolylhydrazine hydrochloride (0.68 mmol) and 2-[(4-bromophenyl)-methoxymethylene]propanedinitrile (0.57 mmol) gave, after further purification by flash column chromatography on silica gel eluting with 0-100% EtOAc in heptane, the titled compound (0.53 mmol) as an orange solid. UPLC-MS (ES+, Short acidic): 1.94 min, m/z 355.0 [M+2]+

N-[[4-[5-Amino-4-cyano-1-(o-tolyl)pyrazol-3-yl]phenyl]methyl]-2-methoxy-benzamide General procedure K, potassium trifluoro-[[(2-methoxybenzoyl)amino]methyl]boranuide (0.30 mmol) and 5-amino-3-(4-bromophenyl)-1-(o-tolyl)pyrazole-4-carbonitrile (0.21 mmol) gave, after further purification by flash column chromatography on silica gel eluting with 0-100% EtOAc in heptane, the titled compound (0.19 mmol) as a white solid. UPLC-MS (ES+, Short acidic): 1.69 min, m/z 438.3 [M+H]+

5-Amino-3-[4-[[(2-methoxybenzoyl)amino]methyl]phenyl]-1-(o-tolyl)pyrazole-4-carboxamide General procedure M, N-[[4-[5-amino-4-cyano-1-(o-tolyl)pyrazol-3-yl]phenyl]methyl]-2-methoxy-benzamide (0.19 mmol) gave, after further purification by flash column chromatography on silica gel eluting with 0-10% MeOH in DCM, the titled compound (0.06 mmol) as a white solid. UPLC-MS (ES+, Short acidic): 1.50 min, m/z 456.3 [M+H]+. UPLC-MS (ES+, Long acidic): 3.42 min, m/z 456.3 [M+H]+.

$^1$H NMR (400 MHz, DMSO-$d_6$, δ): 8.81 (t, J=6.0 Hz, 1H), 7.82 (dd, J=7.4, 1.7 Hz, 1H), 7.60-7.58 (m, 2H), 7.56-7.49 (m, 5H), 7.45-7.40 (m, 2H), 7.21 (d, J=8.2 Hz, 1H), 7.10 (t, J=7.3 Hz, 1H), 6.21 (s, 2H), 4.62 (d, J=6.0 Hz, 2H), 3.96 (s, 3H), 2.19 (s, 3H).

Example 48: 5-amino-1-(3-hydroxycyclohexyl)-3-[4-[[(2-methoxybenzoyl)amino]methyl]phenyl]pyrazole-4-carboxamide

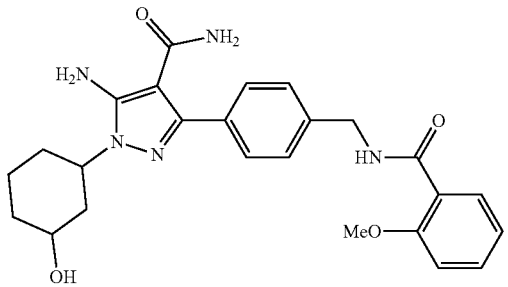 [SMILES: COc1ccccc1C(=O)NCc1ccc(-c2nn(C3CCCC(O)C3)c(N)c2C(N)=O)cc1]

Sodium borohydride (836 mg, 22.10 mmol) was added to a solution of 5-amino-3-[4-[[(2-methoxybenzoyl)amino]methyl]phenyl]-1-(3-oxocyclohexyl)pyrazole-4-carboxamide (0.44 mmol) in MeOH (15 mL), cooled to 0° C. The reaction was allowed to return to RT and then heated to 60° C. for 14 h once the gas evolution stopped. The reaction was cooled back to 0° C. and more sodium borohydride (22.1 mmol) was added and the reaction heated again to 60° C. The mixture was then cooled and quenched with ammonium chloride, and then extracted with EtOAc. The combined organic layer was dried over sodium sulfate and concentrated under reduced pressure. The resulting residue was purified by reverse-phase chromatography to give the titled compound (0.09 mmol) as a white solid. UPLC-MS (ES+, Short acidic): 1.30 min, m/z 464.3 [M+H]+. UPLC-MS (ES+, Long acidic): 2.90 min, m/z 464.3 [M+H]+.

$^1$H NMR (400 MHz, DMSO-$d_6$, δ): 8.73 (t, J=6.0 Hz, 1H), 7.75 (dd, J=7.5, 1.8 Hz, 1H), 7.51-7.37 (m, 5H), 7.17-7.13 (m, 1H), 7.04 (td, J=7.6, 0.9 Hz, 1H), 6.32 (s, 2H), 4.70 (d, J=4.9 Hz, 1H), 4.54 (d, J=6.0 Hz, 2H), 4.17-4.06 (m, 1H), 3.90 (s, 3H), 3.56-3.45 (m, 1H), 2.05-1.96 (m, 1H), 1.88-1.80 (m, 1H), 1.79-1.71 (m, 2H), 1.71-1.61 (m, 1H), 1.61-1.51 (m, 1H), 1.39-1.21 (m, 1H), 1.15-1.01 (m, 1H).

Example 49: 5-amino-1-[4-(hydroxymethyl)phenyl]-3-[4-[[(2-methoxybenzoyl)amino]methyl]phenyl]pyrazole-4-carboxamide

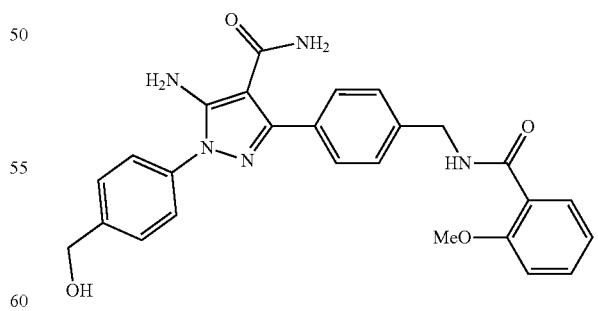

To a solution of 4-[5-amino-4-carbamoyl-3-[4-[[(2-methoxybenzoyl)amino]methyl]phenyl]pyrazol-1-yl]benzoic acid (0.05 mmol) in THF (3 mL) was added borane-dimethylsulfide (0.24 mmol). The reaction mixture was stirred at RT for 5 h, quenched by addition of a saturated solution of ammonium chloride (1 mL) and partitioned. The aqueous layer was extracted with EtOAc. The combined organic extracts were dried over sodium sulfate, and concentrated under reduced pressure. The resulting residue was purified by mass-directed semi-preparative HPLC to give the titled compound (0.01 mmol) as a white solid. UPLC-MS (ES+, Short acidic): 1.31 min, m/z 472.3 [M+H]+. UPLC-MS (ES+, Long acidic): 2.95 min, m/z 472.3 [M+H]+. 1H NMR (400 MHz, DMSO-$d_6$, δ): 8.75 (t, J=6.0 Hz, 1H), 7.78-7.72 (m, 1H), 7.59-7.51 (m, 4H), 7.51-7.41 (m, 5H), 7.18-7.13 (m, 1H), 7.06-7.01 (m, 1H), 6.44 (s, 2H), 5.35-5.27 (m, 1H), 4.60-4.52 (m, 4H), 3.90 (s, 3H).

Example 50: 5-amino-3-[4-[[(2-methoxybenzoyl)amino]methyl]phenyl]-1-(m-tolyl)pyrazole-4-carboxamide

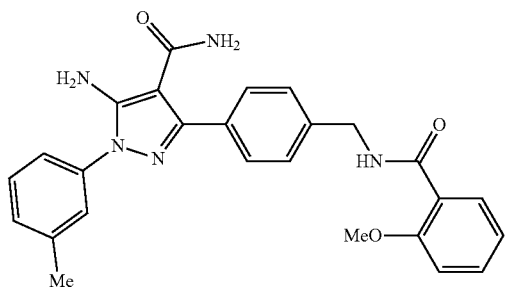 [SMILES: COc1ccccc1C(=O)NCc1ccc(-c2nn(-c3cccc(C)c3)c(N)c2C(N)=O)cc1]

5-Amino-3-(4-bromophenyl)-1-(m-tolyl)pyrazole-4-carbonitrile

General procedure H, 2-[(4-bromophenyl)-methoxy-methylene]propanedinitrile (0.29 mmol) and m-tolylhydrazine (0.34 mmol) gave, after purification by flash column chromatography on silica gel eluting with 0-80% EtOAc in heptane, the titled compound (0.21 mmol) as an orange solid. UPLC-MS (ES+, Short acidic): 2.02 min, m/z 353.0 [M]+

N-[[4-[5-Amino-4-cyano-1-(m-tolyl)pyrazol-3-yl]phenyl]methyl]-2-methoxy-benzamide General procedure K, potassium trifluoro-[[(2-methoxybenzoyl)amino]methyl]boranuide (0.39 mmol) and 5-amino-3-(4-bromophenyl)-1-(m-tolyl)pyrazole-4-carbonitrile (0.20 mmol) gave, after purification by flash column chromatography on silica gel eluting with 10-100% EtOAc in heptane, the titled compound (0.19 mmol) as an off-white solid. UPLC-MS (ES+, Short acidic): 1.76 min, m/z 438.3 [M+H]+

5-Amino-3-[4-[[(2-methoxybenzoyl)amino]methyl]phenyl]-1-(m-tolyl)pyrazole-4-carboxamide General procedure M, N-[[4-[5-amino-4-cyano-1-(m-tolyl)pyrazol-3-yl]phenyl]methyl]-2-methoxy-benzamide (0.19 mmol) gave, after purification by flash column chromatography on silica gel eluting with 0-10% MeOH in DCM, the titled compound (0.02 mmol). UPLC-MS (ES+, Short acidic): 1.57 min, m/z 456.3 [M+H]+. UPLC-MS (ES+, Long acidic): 3.59 min, m/z 456.3 [M+H]+.

1H NMR (400 MHz, DMSO-$d_6$, δ): 8.75 (t, J=6.2 Hz, 1H), 7.75 (dd, J=7.6, 1.7 Hz, 1H), 7.57-7.52 (m, 2H), 7.51-7.37 (m, 6H), 7.24-7.19 (m, 1H), 7.18-7.13 (m, 1H), 7.07-7.01 (m, 1H), 6.46 (s, 2H), 4.56 (d, J=6.2 Hz, 2H), 3.90 (s, 3H), 2.39 (s, 3H).

Example 51: 5-amino-3-[4-[[(2-methoxybenzoyl)amino]methyl]phenyl]-1-(3-pyridyl)pyrazole-4-carboxamide

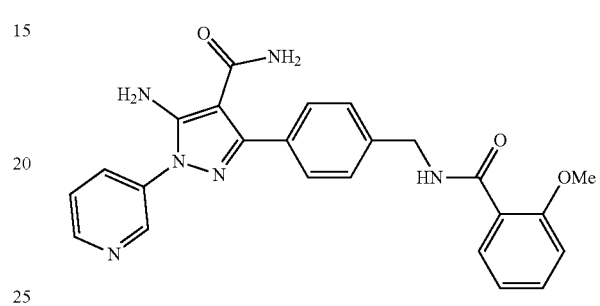

5-Amino-3-(4-bromophenyl)-1-(3-pyridyl)pyrazole-4-carbonitrile

General procedure H without triethylamine, 2-[(4-bromophenyl)-methoxy-methylene]propanedinitrile (0.42 mmol) and 3-pyridylhydrazine (0.46 mmol) gave the titled compound (0.42 mmol) as a white solid. LC-MS (ES+, Short acidic): 5.21 min, m/z 339.9 [M]+

N-[[4-[5-Amino-4-cyano-1-(3-pyridyl)pyrazol-3-yl]phenyl]methyl]-2-methoxy-benzamide General procedure K, 5-amino-3-(4-bromophenyl)-1-(3-pyridyl)pyrazole-4-carbonitrile (0.42 mmol) and potassium trifluoro-[[(2-methoxybenzoyl)amino]methyl]boranuide (0.46 mmol) gave, after purification by flash column chromatography on silica gel eluting with 0-5% MeOH in DCM, the titled compound (0.30 mmol) as an off-white solid. LC-MS (ES+, Short acidic): 4.44 min, m/z 425.1 [M+H]+

5-Amino-3-[4-[[(2-methoxybenzoyl)amino]methyl]phenyl]-1-(3-pyridyl)pyrazole-4-carboxamide General procedure M, N-[[4-[5-amino-4-cyano-1-(3-pyridyl)pyrazol-3-yl]phenyl]methyl]-2-methoxy-benzamide (0.14 mmol) gave, after purification by flash column chromatography on silica gel eluting with 0-10% MeOH in DCM, the titled compound (0.10 mmol) as a white solid. UPLC-MS (ES+, Short acidic): 1.29 min, m/z 443.4 [M+H]+. UPLC-MS (ES+, Long acidic): 2.86 min, m/z 443.1 [M+H]+

1H NMR (400 MHz, DMSO-$d_6$, δ): 8.86 (d, J=2.5 Hz, 1H), 8.76 (t, J=6.2 Hz, 1H), 8.60 (dd, J=4.9, 1.6 Hz, 1H), 8.06-8.03 (m, 1H), 7.75 (dd, J=7.7, 1.8 Hz, 1H), 7.60-7.54 (m, 3H), 7.50-7.44 (m, 3H), 7.17-7.14 (m, 1H) 7.03 (td, J=7.7, 1.1 Hz, 1H), 6.63 (br s, 2H), 4.56 (d, J=6.1 Hz, 2H), 3.90 (s, 3H)

Example 52: 5-amino-1-indan-2-yl-3-[4-[[(2-methoxybenzoyl)amino]methyl]phenyl]pyrazole-4-carboxamide

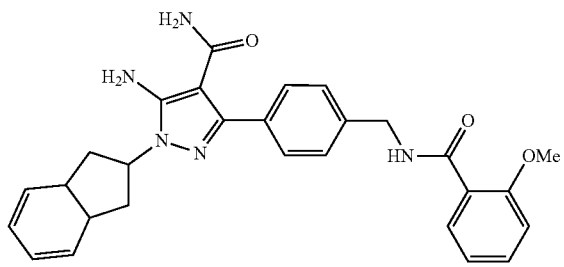 [SMILES: COc1ccccc1C(=O)NCc1ccc(-c2nn(C3CC4C=CC=CC4C3)c(N)c2C(N)=O)cc1]

tert-Butyl N-(indan-2-ylideneamino)carbamate

General procedure E, 2-indanone (1.14 mmol) and tert-butyl carbazate (1.36 mmol) gave, after purification by flash column chromatography on silica gel eluting with 0-80% EtOAc in heptane, the titled compound (0.89 mmol) as a pale yellow solid. $^1$H NMR (400 MHz, DMSO-$d_6$, δ): 9.54 (s, 1H), 7.31-7.26 (m, 2H), 7.23-7.20 (m, 2H), 3.72 (s, 2H), 3.69 (s, 2H), 1.47 (s, 9H).

Indan-2-ylhydrazine hydrochloride tert-Butyl N-(indan-2-ylideneamino)carbamate (0.89 mmol) was dissolved in THF (5 mL) and a borane dimethyl sulfide complex solution (2 M in THF, 1.52 mmol) was added. The reaction was stirred at RT for 2 h until TLC showed complete consumption of the starting material. The reaction was quenched with a saturated aqueous solution of NH$_4$Cl and the layers separated. The aqueous layer was extracted with DCM, and the combined organic extracts dried over sodium sulfate, and concentrated under reduced pressure. The residue was dissolved with a hydrogen chloride solution (1.25 M in MeOH, 9.04 mmol), and the reaction was stirred at RT for 16 h. The reaction was concentrated under reduced pressure to afford crude indan-2-ylhydrazine hydrochloride (0.89 mmol). UPLC-MS: (ES$^+$, Short acidic): 0.83 min, m/z 149.0 [M−HCl+H]$^+$

5-Amino-3-(4-bromophenyl)-1-indan-2-yl-pyrazole-4-carbonitrile

General procedure H, 2-[(4-bromophenyl)-methoxymethylene]propanedinitrile (0.68 mmol) and indan-2-ylhydrazine hydrochloride (0.82 mmol) gave, after purification by flash column chromatography on silica gel eluting with 0-80% EtOAc in heptane, the titled compound (0.45 mol) as an orange solid. UPLC-MS: (ES$^+$, Short acidic): 2.09 min, m/z 381.1 [M+2]$^+$

N-[[4-(5-Amino-4-cyano-1-indan-2-yl-pyrazol-3-yl)phenyl]methyl]-2-methoxy-benzamide General procedure K, 5-amino-3-(4-bromophenyl)-1-indan-2-yl-pyrazole-4-carbonitrile (0.45 mmol) and potassium trifluoro-[[(2-methoxybenzoyl)amino]methyl]boranuide (0.63 mmol) gave, after purification by flash column chromatography on silica gel eluting with 0-100% EtOAc in heptane, the titled compound benzamide (0.34 mol) as an off-white solid. $^1$H NMR (400 MHz, CDCl$_3$, δ): 8.27 (dd, J=7.8, 1.8 Hz, 1H), 8.24-8.19 (m, 1H), 7.91-7.89 (m, 2H), 7.50-7.47 (m, 1H), 7.44-7.41 (m, 2H), 7.28-7.25 (m, 4H), 7.14-7.10 (m, 1H), 7.01-6.99 (m, 1H), 5.09-5.01 (m, 1H), 4.73 (d, J=5.6 Hz, 2H), 4.27 (s, 2H), 3.95 (s, 3H), 3.61 (dd, J=16.1, 7.1 Hz, 2H), 3.45 (dd, J=16.4, 8.7 Hz, 2H).

5-Amino-1-indan-2-yl-3-[4-[[(2-methoxybenzoyl)amino]methyl]phenyl]pyrazole-4-carboxamide General procedure L, N-[[4-(5-amino-4-cyano-1-indan-2-yl-pyrazol-3-yl)phenyl]methyl]-2-methoxy-benzamide (0.11 mmol) gave, after purification by flash column chromatography eluting with 0-10% MeOH in DCM, the titled compound (0.03 mmol) as a white solid. UPLC-MS (ES$^+$, Short acidic): 1.65 min, m/z 482.1 [M+H]$^+$. UPLC-MS (ES$^+$, Long acidic): 3.85 min, m/z 482.1 [M+H]$^+$
$^1$H NMR (400 MHz, DMSO-$d_6$, δ): 8.72 (t, J=6.0 Hz, 1H), 7.74 (dd, J=6.2, 1.7 Hz, 1H), 7.50-7.38 (m, 5H), 7.25-7.23 (m, 2H), 7.19-7.14 (m, 3H), 7.05-7.01 (m, 1H), 6.45 (s, 2H), 5.23-5.15 (m, 1H), 4.53 (d, J=6.0 Hz, 2H), 3.89 (s, 3H), 3.39-3.28 (m, 4H).

Example 53: 5-amino-3-[4-[[(2-methoxybenzoyl)amino]methyl]phenyl]-1-(2-pyridyl)pyrazole-4-carboxamide

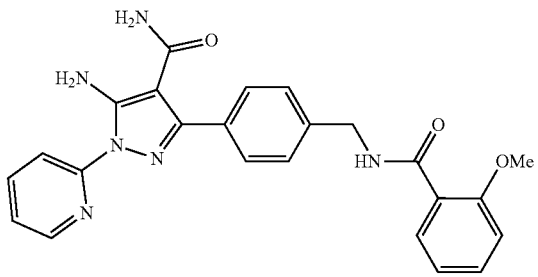 [SMILES: COc1ccccc1C(=O)NCc1ccc(-c2nn(-c3ccccn3)c(N)c2C(N)=O)cc1]

5-Amino-3-(4-bromophenyl)-1-(2-pyridyl)pyrazole-4-carbonitrile

General procedure H without triethylamine, 2-[(4-bromophenyl)-methoxy-methylene]propanedinitrile (1.24 mmol) and 2-hydrazinopyridine (1.36 mmol) gave the titled compound crude (1.24 mmol, assumed quantitative) as a white solid. UPLC-MS (ES$^+$, Short acidic): 2.03 min, m/z 340.1 [M]$^+$

N-[[4-[5-Amino-4-cyano-1-(2-pyridyl)pyrazol-3-yl]phenyl]methyl]-2-methoxy-benzamide General procedure K, 5-amino-3-(4-bromophenyl)-1-(2-pyridyl)pyrazole-4-carbonitrile (0.44 mmol) and potassium trifluoro-[[(2-methoxybenzoyl)amino]methyl]boranuide (0.48 mmol) gave, after purification by flash column chromatography on silica gel eluting with 0-10% MeOH in DCM, the titled compound (0.31 mmol, 70% yield) as an off-white solid. UPLC-MS (ES$^+$, Short acidic): 1.77 min, m/z 425.1 [M+H]$^+$

5-Amino-3-[4-[[(2-methoxybenzoyl)amino]methyl]phenyl]-1-(2-pyridyl)pyrazole-4-carboxamide General procedure M, N-[[4-[5-amino-4-cyano-1-(2-pyridyl)pyrazol-3-yl]phenyl]methyl]-2-methoxy-benzamide (0.31 mmol) gave, after purification by flash column chromatography on silica gel eluting with 0-10% MeOH in DCM, the titled compound (0.10 mmol) as a white solid. UPLC-MS (ES⁺, Short acidic): 1.60 min, m/z 443.1 [M+H]⁺. UPLC-MS (ES⁺, Long acidic): 3.67 min, m/z 443.1 [M+H]⁺

¹H NMR (400 MHz, DMSO-d₆, δ): 8.77 (t, J=6.3 Hz, 1H), 8.49-8.47 (m, 1H), 8.01-7.96 (m, 1H), 7.88-7.86 (m, 1H), 7.76 (dd, J=7.7, 1.9 Hz, 1H), 7.69 (br s, 2H), 7.59-7.56 (m, 2H), 7.51-7.46 (m, 3H), 7.34-7.31 (m, 1H), 7.17-7.15 (m, 1H), 7.04 (td, J=7.6, 0.8 Hz, 1H), 4.58 (d, J=6.0 Hz, 2H), 3.91 (s, 3H).

Example 54: 5-amino-3-[4-[[(2-methoxybenzoyl)amino]methyl]phenyl]-1-(4-pyridyl)pyrazole-4-carboxamide

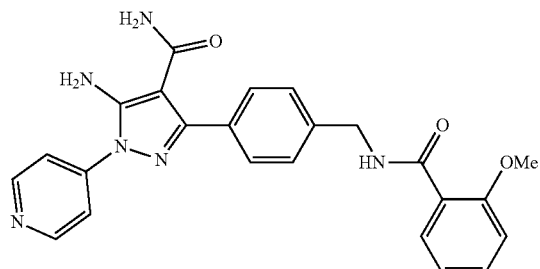

5-Amino-3-(4-bromophenyl)-1-(4-pyridyl)pyrazole-4-carbonitrile

Following general procedure H without triethylamine, 4-pyridylhydrazine (1.44 mmol) and 2-[(4-bromophenyl)-methoxy-methylene]propanedinitrile (1.31 mmol) gave the titled compound crude (1.31 mmol) as a white solid. LC-MS (ES⁺, Short acidic): 4.66 min, m/z 341.9 [M+2]⁺

N-[[4-[5-Amino-4-cyano-1-(4-pyridyl)pyrazol-3-yl]phenyl]methyl]-2-methoxy-benzamide General procedure K, 5-amino-3-(4-bromophenyl)-1-(4-pyridyl)pyrazole-4-carbonitrile (0.44 mmol) and potassium trifluoro-[[(2-methoxybenzoyl)amino]methyl]boranuide (0.48 mmol) gave, after purification by flash column chromatography on silica gel eluting with 0-10% MeOH in DCM, the titled compound (0.36 mmol) as an off-white solid. UPLC-MS (ES⁺, Short acidic): 1.37 min, m/z 425.1 [M+H]⁺

5-Amino-3-[4-[[(2-methoxybenzoyl)amino]methyl]phenyl]-1-(4-pyridyl)pyrazole-4-carboxamide General procedure M, N-[[4-[5-amino-4-cyano-1-(4-pyridyl)pyrazol-3-yl]phenyl]methyl]-2-methoxy-benzamide (0.36 mmol) gave, after purification by flash column chromatography on silica gel eluting with 0-10% MeOH in DCM, the titled compound (0.13 mmol) as a white solid. UPLC-MS (ES⁺, Short acidic): 1.19 min, m/z 443.1 [M+H]⁺. UPLC-MS (ES⁺, Long acidic): 2.67 min, m/z 443.1 [M+H]⁺.

¹H NMR (400 MHz, DMSO-d₆, δ): 8.76 (t, J=6.2 Hz, 1H), 8.69-8.67 (m, 2H), 7.75 (dd, J=7.6, 1.8 Hz, 1H), 7.73-7.71 (m, 2H), 7.58-7.55 (m, 2H), 7.50-7.45 (m, 3H), 7.17-7.14 (m, 1H), 7.03 (td, J=7.6, 1.0 Hz, 1H), 6.81 (br s, 2H), 4.57 (d, J=6.0 Hz, 2H), 3.90 (s, 3H).

Example 55: ethyl 3-[5-amino-4-carbamoyl-3-[4-[[(2-methoxybenzoyl)amino]methyl]phenyl]pyrazol-1-yl]cyclohexanecarboxylate (Isomer 1)

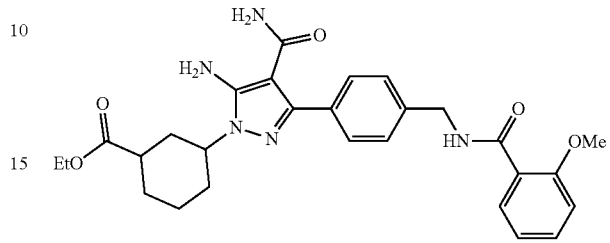

Ethyl 3-(tert-butoxycarbonylhydrazono)cyclohexanecarboxylate

General procedure E, ethyl 3-oxocyclohexanecarboxylate (5.04 mmol) and tert-butyl carbazate (5.30 mmol) was stirred for 3 h at RT. The reaction mixture was quenched with MeOH and then concentrated under reduced pressure. The residue was diluted with DCM and washed with a saturated aqueous solution of NH₄Cl. The organic layer was passed through a phase separator and concentrated under reduced pressure to give the titled compound crude (3.77 mmol). UPLC-MS (ES⁺, Short acidic): 1.55 min, m/z 285.1 [M+H]⁺

Ethyl 3-[5-amino-3-(4-bromophenyl)-4-cyano-pyrazol-1-yl]cyclohexanecarboxylate

General procedure O, ethyl 3-(tert-butoxycarbonylhydrazono)cyclohexanecarboxylate (3.77 mmol) and 2-[(4-bromophenyl)-methoxy-methylene]propanedinitrile (3.04 mmol) gave, after purification by flash column chromatography on silica gel eluting with 0-100% EtOAc in heptane, the titled compound (isomer 1, 1.47 mmol) and the titled compound (isomer 2, 1.21 mmol). UPLC-MS (ES⁺, Short acidic, Isomer 1):2.05 min, m/z 419.1[M+2]⁺. UPLC-MS (ES⁺, Short acidic, Isomer 2):2.11 min, m/z 419.1 [M+2]⁺

Ethyl 3-[5-amino-4-cyano-3-[4-[[(2-methoxybenzoyl)amino]methyl]phenyl]pyrazol-1-yl]cyclohexanecarboxylate (Isomer 1)

General procedure K, potassium trifluoro-[[(2-methoxybenzoyl)amino]methyl]boranuide (1.11 mmol) and ethyl 3-[5-amino-3-(4-bromophenyl)-4-cyano-pyrazol-1-yl]cyclohexanecarboxylate (isomer 1, 0.72 mmol) was stirred at 80° C. for 16 h. The reaction mixture was filtered through a pad of Celite® and washed with DCM. The solution was diluted with water and extracted with DCM (×3). The combined organic layers were passed through a phase separator and concentrated under reduced pressure to give the titled compound crude (isomer 1, 0.72 mmol). UPLC-MS (ES⁺, Short acidic): 1.83 min, m/z 502.3 [M+H]⁺

Ethyl 3-[5-amino-4-carbamoyl-3-[4-[[(2-methoxybenzoyl)amino]methyl]phenyl]pyrazol-1-yl]cyclohexanecarboxylate (Isomer 1)

General procedure L, ethyl 3-[5-amino-4-cyano-3-[4-[[(2-methoxybenzoyl)amino]methyl]phenyl]pyrazol-1-yl]

cyclohexanecarboxylate (isomer 1, 0.30 mmol), gave after purification by flash column chromatography on silica gel eluting with 0-100% EtOAc in heptane, the titled compound (isomer 1, 0.03 mmol, 10%). UPLC-MS (ES+, Short acidic): 1.63 min, m/z 520.4 [M+H]+. UPLC-MS (ES+, Long acidic): 3.76 min, m/z 520.2 [M+H]+. ¹H NMR (400 MHz, DMSO-d₆, δ): 8.73 (t, J=6.1 Hz, 1H), 7.75 (dd, J=7.7, 1.8 Hz, 1H), 7.51-7.39 (m, 5H), 7.17-7.15 (m, 1H), 7.04 (td, J=7.6, 1.0 Hz, 1H), 6.27 (br s, 2H), 4.55 (d, J=6.2 Hz, 2H), 4.34-4.25 (m, 1H), 4.15-4.09 (m, 2H), 3.90 (s, 3H), 3.01-2.94 (m, 1H), 2.11-2.04 (m, 2H), 1.93-1.43 (m, 6H), 1.22 (t, J=6.9 Hz, 3H)

Example 56: 5-anilino-1-cyclopentyl-3-[4-[[(2-methoxybenzoyl)amino]methyl]phenyl]pyrazole-4-carboxamide

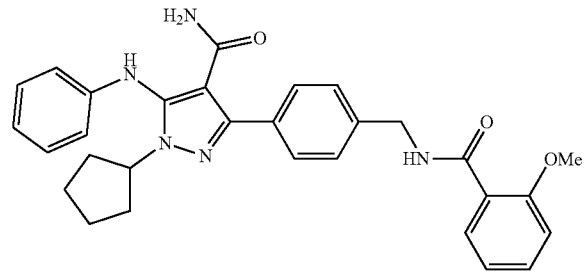 [SMILES: COc1ccccc1C(=O)NCc1ccc(-c2nn(C3CCCC3)c(Nc3ccccc3)c2C(N)=O)cc1]

5-Anilino-3-(4-bromophenyl)-1-cyclopentyl-pyrazole-4-carbonitrile

To a suspension of 5-amino-3-(4-bromophenyl)-1-cyclopentyl-pyrazole-4-carbonitrile (0.15 mmol), phenylboronic acid (0.30 mmol) and copper(II) acetate (0.15 mmol) in DCM (1 mL) was added triethylamine (0.30 mmol). The reaction mixture was stirred at RT for 16 h then concentrated under reduced pressure. Purification by flash column chromatography on silica gel eluting with 20-60% EtOAc in heptane afforded the titled compound (0.10 mmol) as a white solid. UPLC-MS (ES+, Short acidic): 2.30 min, m/z 407.0 [M]+

N-[[4-(5-Anilino-4-cyano-1-cyclopentyl-pyrazol-3-yl)phenyl]methyl]-2-methoxy-benzamide General procedure K, 5-anilino-3-(4-bromophenyl)-1-cyclopentyl-pyrazole-4-carbonitrile (0.10 mmol) gave, after purification by flash column chromatography on silica gel eluting with 20-80% EtOAc in heptane, the titled compound (0.09 mmol) as a white powder. UPLC-MS (ES+, Short acidic): 2.04 min, m/z 492.1 [M+H]+

5-Anilino-1-cyclopentyl-3-[4-[[(2-methoxybenzoyl)amino]methyl]phenyl]pyrazole-4-carboxamide General procedure L, N-[[4-(5-anilino-4-cyano-1-cyclopentyl-pyrazol-3-yl)phenyl]methyl]-2-methoxy-benzamide (0.09 mmol) gave, after purification by flash column chromatography on silica gel eluting with 0-3% MeOH in DCM, the titled compound (0.07 mmol) as a white solid. UPLC-MS (ES+, Short acidic): 1.88 min, m/z 510.2 [M+H]+. UPLC-MS (ES+, Long acidic): 4.47 min, m/z 510.2 [M+H]+.

¹H NMR (400 MHz, DMSO-d₆, δ): 8.71 (t, J=6.0 Hz, 1H), 7.83 (s, 1H), 7.76 (dd, J=7.6, 1.7 Hz, 1H), 7.67 (d, J=8.2 Hz, 2H), 7.52-7.44 (m, 1H), 7.35 (d, J=8.2 Hz, 2H), 7.22-7.09 (m, 4H), 7.08-6.95 (m, 2H), 6.80-6.72 (m, 1H), 6.61 (d, J=7.7 Hz, 2H), 4.67-4.57 (m, 1H), 4.53 (d, J=6.0 Hz, 2H), 3.91 (s, 3H), 2.01-1.76 (m, 6H), 1.63-1.48 (m, 2H).

Example 57:5-amino-1-[4-(dimethylcarbamoyl)cyclohexyl]-3-[4-[[(2-methoxybenzoyl)amino]methyl]phenyl]pyrazole-4-carboxamide (Isomers 1, Example 57a, and 2, Example 57b)

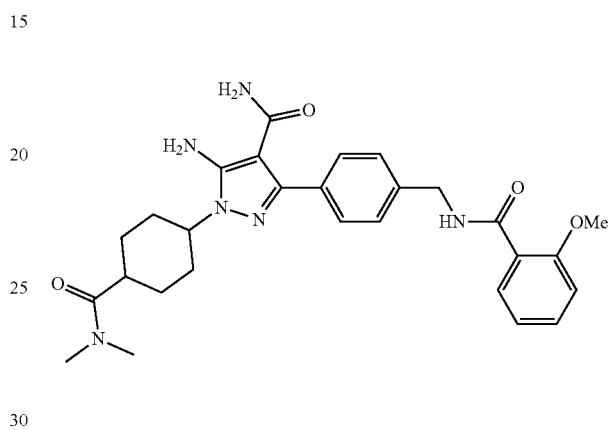

5-Amino-1-[4-(dimethylcarbamoyl)cyclohexyl]-3-[4-[[(2-methoxybenzoyl)amino]methyl]phenyl]pyrazole-4-carboxamide A solution of propylphosphonic anhydride (50 wt % in EtOAc, 0.14 mmol) was added to a solution of dimethylamine (2 M in THF, 0.92 mmol), N,N-diisopropylethylamine (0.27 mmol) and 4-[5-amino-4-carbamoyl-3-[4-[[(2-methoxybenzoyl)amino]methyl]phenyl]pyrazol-1-yl]cyclohexanecarboxylic acid (0.09 mmol) in THF (0.50 mL). The reaction mixture was heated to 40° C. and stirred for 16 h. Additional dimethylamine (2 M in THF, 0.92 mmol), N,N-diisopropylethylamine (0.27 mmol) and a solution of propylphosphonic anhydride (50 wt % in EtOAc, 0.14 mmol) were added sequentially and the reaction mixture was stirred at 40° C. for 48 h, and then cooled to RT. The reaction mixture was partitioned between water and DCM. The aqueous layer was extracted with DCM (×3). The combined organic extracts were filtered over a hydrophobic frit and all volatiles were removed under reduced pressure. Further purification by flash column chromatography on silica gel eluting with 0-8% MeOH in DCM gave the titled compound (isomer 1: 0.04 mmol, 42% yield) and the titled compound (isomer 2: 0.02 mmol) were obtained as white solids. UPLC-MS (ES+, Short acidic; isomer 1): 1.40 min, m/z 519.3 [M+H]+. UPLC-MS (ES+, Long acidic; isomer 1): 3.71 min, m/z 519.2 [M+H]+. ¹H NMR (400 MHz, DMSO-d₆, δ, isomer 1): 8.73 (t, J=6.0 Hz, 1H), 7.76 (dd, J=7.7, 1.7 Hz, 1H), 7.52-7.38 (m, 5H), 7.16 (d, J=8.4 Hz, 1H), 7.08-7.01 (m, 1H), 6.30 (s, 2H), 4.55 (d, J=6.0 Hz, 2H), 4.21-4.10 (m, 1H), 3.91 (s, 3H), 3.00 (s, 3H), 2.90-2.82 (m, 1H), 2.80 (s, 3H), 2.22-2.08 (m, 2H), 2.03-1.90 (m, 2H), 1.74-1.64 (m, 2H), 1.64-1.53 (m, 2H).

UPLC-MS (ES+, Short acidic; isomer 2): 1.37 min, m/z 519.2 [M+H]+. UPLC-MS (ES+, Long acidic; isomer 2): 3.67 min, m/z 519.2 [M+H]+. $^1$H NMR (400 MHz, DMSO-$d_6$, δ, isomer 2): 8.74 (t, J=6.1 Hz, 1H), 7.78-7.73 (m, 1H), 7.52-7.37 (m, 5H), 7.16 (d, J=9.0 Hz, 1H), 7.08-7.01 (m, 1H), 6.35 (s, 2H), 4.55 (d, J=6.0 Hz, 2H), 4.20-4.06 (m, 1H), 3.90 (s, 3H), 3.03 (s, 3H), 2.81 (s, 3H), 2.73-2.61 (m, 1H), 1.96-1.82 (m, 4H), 1.82-1.73 (m, 2H), 1.62-1.44 (m, 2H).

Example 58: ethyl 3-[5-amino-4-carbamoyl-3-[4-[[(2-methoxybenzoyl)amino]methyl]phenyl]pyrazol-1-yl]cyclohexanecarboxylate (Isomer 2)

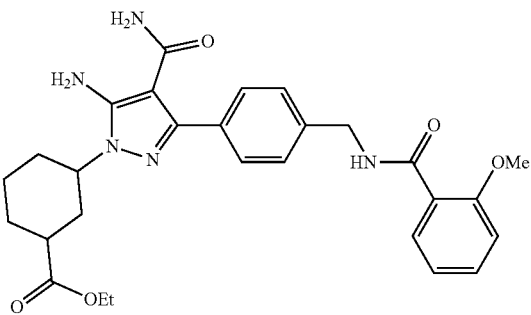 [SMILES: CCOC(=O)C1CCCC(n2nc(-c3ccc(CNC(=O)c4ccccc4OC)cc3)c(C(N)=O)c2N)C1]

Ethyl 3-[5-amino-4-cyano-3-[4-4[[(2-methoxybenzoyl)amino]methyl]phenyl]pyrazol-1-yl]cyclohexanecarboxylate (Isomer 2)

General procedure K, ethyl 3-[5-amino-3-(4-bromophenyl)-4-cyano-pyrazol-1-yl]cyclohexanecarboxylate (isomer 2, 0.72 mmol) and potassium trifluoro-[[(2-methoxybenzoyl)amino]methyl]boranuide (1.11 mmol) gave the titled compound crude (isomer 2, 0.72 mmol, assumed quantitative yield). UPLC-MS (ES+, Short acidic): 1.78 min, m/z 502.3 [M+H]+

Ethyl 3-[5-amino-4-carbamoyl-3-[4-[[(2-methoxybenzoyl)amino]methyl]phenyl]pyrazol-1-yl]cyclohexanecarboxylate (Isomer 2)

General procedure L, ethyl 3-[5-amino-4-cyano-3-[4-[[(2-methoxybenzoyl)amino]methyl]phenyl]pyrazol-1-yl]cyclohexanecarboxylate (isomer 2, 0.30 mmol) gave after purification by flash column chromatography on silica gel eluting with 0-10% MeOH in DCM, the titled compound (isomer 2, 0.02 mmol, 6% yield). UPLC-MS (ES+, Short acidic): 1.78 min, m/z 520.2 [M+H]+. UPLC-MS (ES+, Long acidic): 4.23 min, m/z 520.2 [M+H]+. $^1$H NMR (400 MHz, DMSO-$d_6$, δ): 8.74 (t, J=6.1 Hz, 1H), 7.75 (dd, J=7.7, 1.8 Hz, 1H), 7.52-7.38 (m, 5H), 7.17-7.15 (m, 1H), 7.04 (td, J=7.5, 0.7 Hz, 1H), 6.35 (br s, 2H), 4.55 (d, J=6.1 Hz, 2H), 4.23-4.12 (m, 1H), 4.11-4.02 (m, 2H), 3.90 (s, 3H), 2.49-2.43 (m, 1H), 2.08-1.99 (m, 1H), 1.94-1.66 (m, 5H), 1.51-1.36 (m, 1H), 1.35-1.21 (m, 1H), 1.17 (t, J=7.0 Hz, 3H).

Example 59: 5-amino-3-[4-[[(2-methoxybenzoyl)amino]methyl]phenyl]-1-(3-oxoindan-1-yl)pyrazole-4-carboxamide

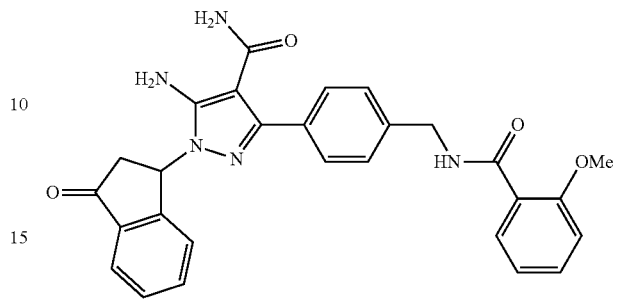

tert-Butyl N-[(3-oxoindan-1-ylidene)amino]carbamate

General procedure E, 1,3-indandione (1.37 mmol) and tert-butyl carbazate (1.44 mmol) gave, after purification by flash column chromatography on silica gel eluting with 10-50% EtOAc in heptane, the titled compound (0.86 mmol, 62% yield) as a yellow solid. $^1$H NMR (400 MHz, DMSO-$d_6$, δ): 10.19 (s, 1H), 7.90-7.88 (m, 1H), 7.81-7.76 (m, 1H), 7.63-7.59 (m, 1H), 7.63-7.59 (m, 1H), 3.41 (s, 2H), 1.50 (s, 9H).

tert-Butyl N-[(3-oxoindan-1-yl)amino]carbamate

General procedure F, tert-butyl N-[(3-oxoindan-1-ylidene)amino]carbamate (0.75 mmol) gave the titled compound crude (0.57 mmol) as a colourless oil. UPLC-MS (ES+, Short acidic): 1.41 min, m/z 285.1 [M+Na]+

[(3-Oxoindan-1-yl)amino]ammonium: 2,2,2-trifluoroacetate

To a solution of tert-butyl N-[(3-oxoindan-1-yl)amino]carbamate (0.57 mmol) in DCM (5 mL) was added TFA (60 mmol). The reaction mixture was stirred at RT for 1 h and concentrated under reduced pressure to afford the titled compound crude (0.57 mmol). $^1$H NMR (400 MHz, DMSO-$d_6$, δ): 7.89-7.35 (m, 4H), 5.21-5.10 (m, 1H), 3.19-3.05 (m, 1H), 2.88-2.75 (m, 1H)

5-Amino-3-(4-bromophenyl)-1-(3-oxoindan-1-yl)pyrazole-4-carbonitrile

Following general procedure H, 2-[(4-bromophenyl)-methoxy-methylene]propanedinitrile (0.46 mmol) and [(3-oxoindan-1-yl)amino]ammonium; 2,2,2-trifluoroacetate (0.10 mmol) gave, after purification by flash column chromatography on silica gel eluting with 0-80% EtOAc in heptane, the titled compound (0.10 mmol) as an orange solid. UPLC-MS (ES+, Short acidic): 1.84 min, m/z 394.9 [M+2]+

N-[[4-[5-Amino-4-cyano-1-(3-oxoindan-1-yl)pyrazol-3-yl]phenyl]methyl]-2-methoxy-benzamide General procedure K, 5-amino-3-(4-bromophenyl)-1-(3-oxoindan-1-yl)pyrazole-4-carbonitrile (0.1 mmol) and potassium trifluoro-[[(2-methoxybenzoyl)amino]methyl]

boranuide (0.13 mmol) gave, after purification by flash column chromatography on silica gel eluting with 0-100% EtOAc in heptane, the titled compound (0.03 mmol) as a brown solid. UPLC-MS (ES+, Short acidic): 1.63 min, m/z 478.1 [M+H]+

5-Amino-3-[4-[[(2-methoxybenzoyl)amino]methyl] phenyl]-1-(3-oxoindan-1-yl)pyrazole-4-carboxamide General procedure L, N-[[4-[5-amino-4-cyano-1-(3-oxoindan-1-yl)pyrazol-3-yl]phenyl]methyl]-2-methoxy-benzamide (0.03 mmol) gave, after purification by mass-directed semi-preparative HPLC, the titled compound (0.02 mmol) as a beige solid. UPLC-CMS (ES+, Short acidic): 1.47 min, m/z 496.1 [M+H]+. UPLC-MS (ES+, Long acidic): 3.74 min, m/z 496.1 [M+H]+. $^1$H NMR (400 MHz, DMSO-$d_6$, δ): 8.69 (t, J=6.0 Hz, 1H), 7.75-7.71 (m, 3H), 7.56 (t, J=7.8 Hz, 1H), 7.49-7.47 (m, 2H), 7.34 (s, 4H), 7.14 (d, J=6.0 Hz, 1H), 7.05-7.00 (m, 1H), 6.72 (s, 2H), 6.20 (dd, J=7.7, 3.5 Hz, 1H), 4.50 (d, J=6.1 Hz, 2H), 3.87 (s, 3H), 3.25 (dd, J=18.5, 7.6 Hz, 1H), 3.03 (dd, J=18.6, 3.4 Hz, 1H).

Example 60: 1-cyclopentyl-3-[4-[[(2-methoxybenzoyl)amino]methyl]phenyl]-5-(methylamino)pyrazole-4-carboxamide

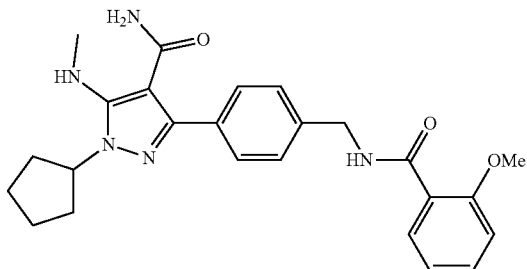

3-(4-Bromophenyl)-1-cyclopentyl-5-(methyleneamino)pyrazole-4-carbonitrile

To a solution of 5-amino-3-(4-bromophenyl)-1-cyclopentyl-pyrazole-4-carbonitrile (0.30 mmol) dissolved in MeOH (3 mL) was added paraformaldehyde (0.91 mmol) and sodium methoxide (25 wt % in MeOH, 1.81 mmol). The reaction mixture was heated at reflux for 16 h. The reaction mixture was cooled to RT and then partitioned between DCM and water. The aqueous layer was extracted with DCM (×3), and the combined organic layers were passed through a hydrophobic frit and concentrated under reduced pressure to afford the titled compound crude (0.30 mmol). UPLC-MS (ES+, Short acidic): 2.09 min, m/z 377.0 [M+MeOH+2]+

3-(4-Bromophenyl)-1-cyclopentyl-5-(methylamino) pyrazole-4-carbonitrile

To a solution of 3-(4-bromophenyl)-1-cyclopentyl-5-(methyleneamino)pyrazole-4-carbonitrile (0.30 mmol) in MeOH (3 mL) was added at 0° C. sodium borohydride (3.02 mmol). The reaction mixture was stirred at RT for 72 h. Then it was carefully quenched with a saturated aqueous solution of NH$_4$Cl. The aqueous layer was then extracted with DCM (×3), and the combined organic layers were passed through a hydrophobic frit and concentrated under reduced pressure. Purification by flash column chromatography on silica gel eluting with 20-60% EtOAc in heptane afforded the titled compound (0.20 mmol,) as a white solid. UPLC-MS (ES+, Short acidic): 2.14 min, m/z 347.0 [M+2]+

N-[[4-[4-Cyano-1-cyclopentyl-5-(methylamino) pyrazol-3-yl]phenyl]methyl]-2-methoxy-benzamide General procedure K, 3-(4-bromophenyl)-1-cyclopentyl-5-(methylamino)pyrazole-4-carbonitrile (0.20 mmol) and potassium trifluoro-[[(2-methoxybenzoyl)amino]methyl] boranuide (0.22 mmol) gave, after purification by column chromatrography on silica gel eluting with 20-60% EtOAc in heptane, the titled compound (0.11 mmol) as a white solid. UPLC-MS (ES+, Short acidic): 1.85 min, m/z 430.1 [M+H]+

1-Cyclopentyl-3-[4-[[(2-methoxybenzoyl)amino] methyl]phenyl]-5-(methylamino)pyrazole-4-carboxamide General procedure L, N-[[4-[4-cyano-1-cyclopentyl-5-(methylamino)pyrazol-3-yl]phenyl]methyl]-2-methoxy-benzamide (0.11 mmol) gave, after purification by flash column chromatography on silica gel eluting with 0-4% MeOH in DCM and reverse phase column chromatography eluting with 20-70% MeCN in water containing 0.1% formic acid, the titled compound (0.05 mmol) as a white solid. UPLC-MS (ES+, Short acidic): 1.67 min, m/z 448.1 [M+H]+. UPLC-MS (ES+, Long acidic): 4.30 min, m/z 448.1 [M+H]+. $^1$H NMR (400 MHz, DMSO-$d_6$, δ): 8.71 (t, J=6.1 Hz, 1H), 7.76 (dd, J=7.7, 1.8 Hz, 1H), 7.54-7.46 (m, 3H), 7.37-7.34 (m, 2H), 7.17-7.15 (m, 1H), 7.07-7.02 (m, 1H), 5.85-5.81 (m, 1H), 4.73-4.64 (m, 1H), 4.52 (d, J=6.0 Hz, 2H), 3.90 (s, 3H), 2.83 (d, J=5.6 Hz, 3H), 2.06-1.89 (m, 4H), 1.89-1.76 (m, 2H), 1.69-1.54 (m, 2H).

Example 61: 5-amino-1-(2,5-difluorophenyl)-3-[4-[[(2-methoxybenzoyl)amino]methyl]phenyl]pyrazole-4-carboxamide

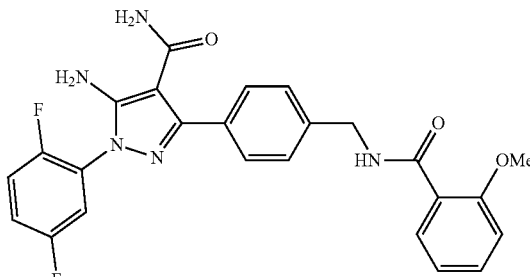

5-Amino-3-(4-bromophenyl)-1-(2,5-difluorophenyl) pyrazole-4-carbonitrile

Following general procedure H at RT, 2-[(4-bromophenyl)-methoxy-methylene]propanedinitrile (0.76 mmol) and (2,5-difluorophenyl)hydrazine (0.76 mmol) afforded, after purification by flash column chromatography on silica gel eluting with 0-60% EtOAc in heptane, the titled compound (0.24 mmol) as a beige solid. UPLC-MS (ES+, Short acidic): 1.92 min, m/z 375.0 [M]+

N-[[4-[5-amino-4-cyano-1-(2,5-difluorophenyl)pyrazol-3-yl]phenyl]methyl]-2-methoxy-benzamide General procedure K, 5-amino-3-(4-bromophenyl)-1-(2,5-difluorophenyl)pyrazole-4-carbonitrile (0.24 mmol) and potassium trifluoro-[[(2-methoxybenzoyl)amino]methyl]boranuide (0.26 mmol) afforded, after purification by flash column chromatography on silica gel eluting with 0-10% MeOH in DCM, the titled compound (0.24 mmol) as a dark yellow gum. UPLC-MS (ES$^+$, Short acidic): 1.68 min, m/z 460.2 [M+H]$^+$

5-Amino-1-(2,5-difluorophenyl)-3-[4-[[(2-methoxybenzoyl)amino]methyl]phenyl]pyrazole-4-carboxamide General procedure M, N-[[4-[5-amino-4-cyano-1-(2,5-difluorophenyl)pyrazol-3-yl]phenyl]methyl]-2-methoxy-benzamide (0.26 mmol) afforded, after purification by flash column chromatography on silica gel eluting with 0-10% MeOH in DCM, the titled compound (0.03 mmol, 10% yield) as a white solid. UPLC-MS (ES$^+$, Short acidic): 1.50 min, m/z 478.2 [M+H]$^+$. UPLC-MS (ES$^+$, Long acidic): 3.42 min, m/z 478.3 [M+H]$^+$.
$^1$H NMR (400 MHz, DMSO-d$_6$, δ): 8.77 (t, J=6.1 Hz, 1H), 7.76 (dd, J=1.8, 7.7 Hz, 1H), 7.57-7.41 (m, 8H), 7.17-7.15 (m, 1H), 7.07-7.01 (m, 1H), 6.54 (s, 2H), 4.57 (d, J=6.1 Hz, 2H), 3.90 (s, 3H).

Example 62: 5-amino-1-cyclopentyl-3-[4-[[(2-methoxybenzoyl)amino]methyl]-3-methyl-phenyl]pyrazole-4-carboxamide

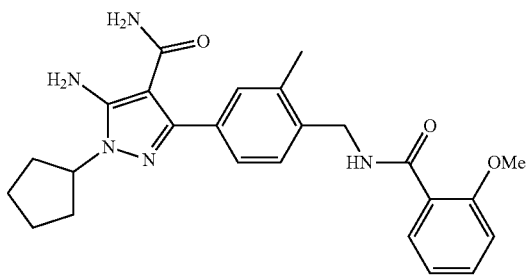 [SMILES: COc1ccccc1C(=O)NCc1ccc(-c2nn(C3CCCC3)c(N)c2C(N)=O)cc1C]

N-[(4-bromo-2-methyl-phenyl)methyl]-2-methoxybenzamide

To a solution of 4-bromo-2-methyl-benzonitrile (5.10 mmol) dissolved in THF (30 mL) was added, at 0° C., a borane tetrahydrofuran complex solution (1 M in THF, 15.30 mmol). The solution was stirred at 0° C. for 30 min before being warmed up to RT and stirred for 18 h. The reaction was quenched dropwise with MeOH. Volatiles were concentrated under reduced pressure and the residue was partitioned with an aqueous solution of NaOH (1 M) and EtOAc. The organic layer was dried over sodium sulfate, and concentrated under reduced pressure to give crude 4-bromo-2-methyl-phenyl)methanamine, which was then dissolved in THF (20 mL) and N,N-diisopropylethylamine (15.29 mmol) was added. The solution was cooled to 0° C. before 2-methoxybenzoyl chloride (5.61 mmol) was added. It was then stirred at 0° C. for 20 min before the reaction was warmed up to RT and stirred for 16 h. The reaction was quenched with a saturated aqueous solution of NH$_4$Cl, worked-up, and purified (column chromatography, 0-30% EtOAc in heptane) to give the titled compound (2.49 mmol). UPLC-MS (ES$^+$, Short acidic): 1.85 min, m/z 336.1 [M+2]$^+$

2-Methoxy-N-[[2-methyl-4-(4,4,5,5-tetramethyl-1,3,2-dioxaborolan-2-yl)phenyl]methyl]benzamide General procedure R, N-[(4-bromo-2-methyl-phenyl)methyl]-2-methoxy-benzamide (2.49 mmol) gave crude the titled compound (2.49 mmol). UPLC-MS (ES$^+$, Short acidic): 1.95 min, m/z 382.2 [M+H]$^+$

N-[[4-(5-Amino-4-cyano-1H-pyrazol-3-yl)-2-methyl-phenyl]methyl]-2-methoxy-benzamide General procedure D, 2-methoxy-N-[[2-methyl-4-(4,4,5,5-tetramethyl-1,3,2-dioxaborolan-2-yl)phenyl]methyl]benzamide (2.04 mmol) gave, after purification (flash column chromatography, 0-100% EtOAc in heptane) the titled compound (0.48 mmol). UPLC-MS (ES$^+$, Short acidic): 1.40 min, m/z 362.3 [M+H]$^+$

N-[[4-(5-Amino-4-cyano-1-cyclopentyl-pyrazol-3-yl)-2-methyl-phenyl]methyl]-2-methoxy-benzamide Cesium carbonate (0.63 mmol) was added to a mixture of N-[[4-(5-amino-4-cyano-1H-pyrazol-3-yl)-2-methyl-phenyl]methyl]-2-methoxy-benzamide (0.48 mmol) and bromocyclopentane (0.53 mmol) in DMF (5 mL). The reaction was heated to 80° C. for 16 h. Following work-up and purification by flash column chromatography eluting with 0-1% MeOH in DCM, the titled compound (0.15 mmol) was obtained. UPLC-MS (ES$^+$, Short acidic): 1.81 min, m/z 430.1 [M+H]$^+$

5-Amino-1-cyclopentyl-3-[4-[[(2-methoxybenzoyl)amino]methyl]-3-methyl-phenyl]pyrazole-4-carboxamide General procedure L, N-[[4-(5-amino-4-cyano-1-cyclopentyl-pyrazol-3-yl)-2-methyl-phenyl]methyl]-2-methoxy-benzamide (0.15 mmol) afforded, after purification by flash column chromatography on silica gel eluting with 25-100% EtOAc in heptane, the titled compound (0.04 mmol). UPLC-MS (ES$^+$, Short acidic): 1.70 min, m/z 448.1 [M+H]$^+$. UPLC-MS (ES$^+$, Long acidic): 4.04 min, m/z 448.1 [M+H]$^+$.
$^1$H NMR (400 MHz, DMSO-d$_6$, δ): 8.61 (t, J=5.8 Hz, 1H), 7.73 (dd, J=7.7, 1.7 Hz, 1H), 7.50-7.46 (m, 1H), 7.35 (d, J=7.6 Hz, 1H), 7.30-7.23 (m, 2H), 7.15 (d, J=8.3 Hz, 1H), 7.06-7.02 (m, 1H), 6.32 (s, 2H), 4.64-4.56 (m, 1H), 4.50 (d, J=5.8 Hz, 2H), 3.89 (s, 3H), 2.36 (s, 3H), 2.03-1.84 (m, 4H), 1.84-1.73 (m, 2H), 1.63-1.54 (m, 2H).

Example 63: 5-amino-1-(3-hydroxyindan-1-yl)-3-[4-[[(2-methoxybenzoyl)amino]methyl]phenyl]pyrazole-4-carboxamide

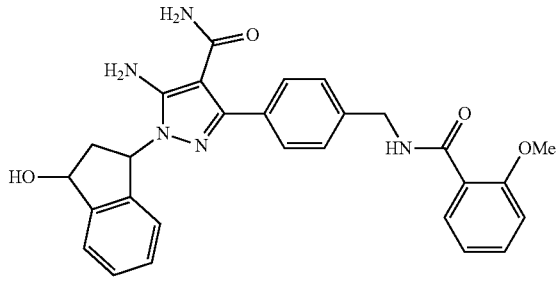 [SMILES: COc1ccccc1C(=O)NCc1ccc(-c2nn(C3CC(O)c4ccccc43)c(N)c2C(N)=O)cc1]

tert-Butyl N-[(3-hydroxyindan-1-yl)amino]carbamate tert-Butyl N-[(3-oxoindan-1-ylidene)amino]carbamate (0.58 mmol) was dissolved in THF (5 mL) and a borane dimethyl sulfide complex solution (2 M in THF, 3.45 mmol) was added. The reaction was stirred at RT for 14 h. A saturated aqueous solution of $NH_4Cl$ was added and following work-up and concentration the titled compound was obtained crude (0.57 mmol) as a pale orange solid. UPLC-MS ($ES^+$, Short acidic): 1.57 min, m/z 287.0 $[M+Na]^+$

[(3-Hydroxyindan-1-yl)amino]ammonium; 2,2,2-trifluoroacetate

To a solution of tert-butyl N-[(3-hydroxyindan-1-yl)amino]carbamate (0.57 mmol) in DCM (5 mL) was added trifluoroacetic acid (57 mmol) and the reaction mixture was stirred at RT for 1 h. Volatiles were concentrated under reduced pressure to afford crude [(3-hydroxyindan-1-yl)amino]ammonium; 2,2,2-trifluoroacetate (0.57 mmol). $^1$H NMR (400 MHz, DMSO-$d_6$, δ): 7.57-7.31 (m, 4H), 5.04-4.99 (m, 1H), 2.83-2.78 (m, 1H), 2.09-1.98 (m, 1H)

5-Amino-3-(4-bromophenyl)-1-(3-hydroxyindan-1-yl)pyrazole-4-carbonitrile

General procedure H, 2-[(4-bromophenyl)-methoxymethylene]propanedinitrile (0.46 mmol) and [(3-hydroxyindan-1-yl)amino]ammonium; 2,2,2-trifluoroacetate (0.55 mmol) gave, after purification by flash column chromatography on silica gel eluting with 0-80% EtOAc in heptane, the titled compound (0.28 mmol) as an orange solid. UPLC-MS ($ES^+$, Short acidic): 1.87 min, 396.9 $[M+2]^+$

N-[[4-[5-Amino-4-cyano-1-(3-hydroxyindan-1-yl)pyrazol-3-yl]phenyl]methyl]-2-methoxy-benzamide General procedure K, 5-amino-3-(4-bromophenyl)-1-(3-hydroxyindan-1-yl)pyrazole-4-carbonitrile (0.28 mmol) and potassium trifluoro-[[(2-methoxybenzoyl)amino]methyl]boranuide (0.39 mmol) gave, after purification by flash column chromatography on silica gel eluting with 0-100% EtOAc in heptane, the titled compound (0.25 mmol) as a yellow solid. UPLC-MS ($ES^+$, Short acidic): 1.75 min, m/z 480.1 $[M+H]^+$

5-Amino-1-(3-hydroxyindan-1-yl)-3-[4-[[(2-methoxybenzoyl)amino]methyl]phenyl]pyrazole-4-carboxamide General procedure L, N-[[4-[5-amino-4-cyano-1-(3-hydroxyindan-1-yl)pyrazol-3-yl]phenyl]methyl]-2-methoxy-benzamide (0.10 mmol) gave, after purification by mass-directed semi-preparative HPLC, the titled compound (0.05 mmol) as a beige solid. UPL-CMS ($ES^+$, Short acidic): 1.60 min, m/z 498.1 $[M+H]^+$. UPLC-MS ($ES^+$, Long acidic): 3.68 min, m/z 498.1 $[M+H]^+$. $^1$H NMR (400 MHz, DMSO-$d_6$, δ): 8.71 (t, J=6.0 Hz, 1H), 7.74 (dd, J=7.7, 1.7 Hz, 1H), 7.50-7.36 (m, 6H), 7.34-7.30 (m, 1H), 7.27-7.24 (m, 1H), 7.14 (d, J=8.3 Hz, 1H), 7.05-7.00 (m, 2H), 6.58 (s, 2H), 5.76-5.71 (m, 1H), 5.68 (d, J=7.4 Hz, 1H), 5.06-5.01 (m, 1H), 4.52 (d, J=6.0 Hz, 2H), 3.88 (s, 3H), 2.89-2.82 (m, 1H), 2.41-2.36 (m, 1H)

Example 64: 5-amino-3-[4-[[(2-methoxybenzoyl)amino]methyl]phenyl]-1-tetrahydropyran-4-yl-pyrazole-4-carboxamide

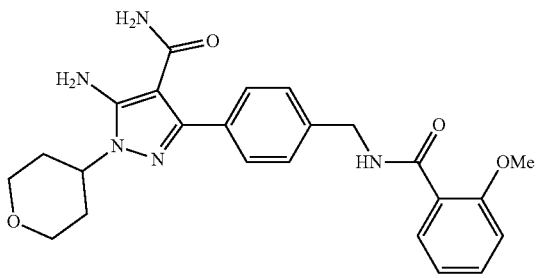

N-[[4-(5-Amino-4-cyano-1-tetrahydropyran-4-yl-pyrazol-3-yl)phenyl]methyl]-2-methoxy-benzamide General procedure K, 5-amino-3-(4-bromophenyl)-1-tetrahydropyran-4-yl-pyrazole-4-carbonitrile (0.27 mmol) and potassium trifluoro-[[(2-methoxybenzoyl)amino]methyl]boranuide (0.30 mmol) afforded, after purification by flash column chromatography on silica gel eluting with 0-10% MeOH in DCM, the titled compound (0.19 mmol, 72% yield) as a dark yellow gum. UPLC-MS ($ES^+$, Short acidic): 1.51 min, m/z 432.3 $[M+H]^+$

5-Amino-3-[4-[[(2-methoxybenzoyl)amino]methyl]phenyl]-1-tetrahydropyran-4-yl-pyrazole-4-carboxamide General procedure M, N-[[4-(5-amino-4-cyano-1-tetrahydropyran-4-yl-pyrazol-3-yl)phenyl]methyl]-2-methoxy-benzamide (0.33 mmol) afforded, after purification by flash column chromatography on silica gel eluting with 0-10% MeOH in DCM followed by purification by SPE SCX cartridge eluting with MeOH, the titled compound (0.15 mmol) as a white solid. UPLC-MS ($ES^+$, Short acidic): 1.56 min, m/z 450.1 $[M+H]^+$. UPLC-MS ($ES^+$, Long acidic): 3.57 min, m/z 450.1 $[M+H]^+$ $^1$H NMR (400 MHz, DMSO-$d_6$, δ): 8.77 (t, J=6.1 Hz, 1H), 7.76 (dd, J=7.7, 1.8 Hz, 1H), 7.50-7.40 (m, 5H), 7.17-7.15 (m, 1H), 7.06-7.02 (m, 1H), 6.38 (s, 2H), 4.55 (d, J=6.0 Hz, 2H), 4.40-4.32 (m, 1H), 3.99-3.95 (m, 2H), 3.90 (s, 3H), 3.46-3.40 (m, 2H), 2.03-1.94 (m, 2H), 1.79-1.76 (m, 2H).

Example 65: 5-amino-1-[4-hydroxy-4-(trifluoromethyl)cyclohexyl]-3-[4-[[(2-methoxybenzoyl)amino]methyl]phenyl]pyrazole-4-carboxamide

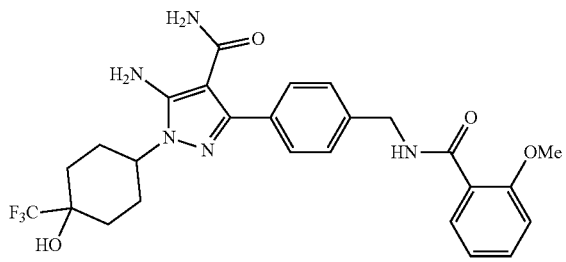 [SMILES: COc1ccccc1C(=O)NCc1ccc(-c2nn(C3CCC(O)(C(F)(F)F)CC3)c(N)c2C(N)=O)cc1]

8-(Trifluoromethyl)-1,4-dioxaspiro[4.5]decan-8-ol

To a solution of 1,4-cyclohexandione monoethylene acetal (6.40 mmol) in anhydrous THF (20 mL) was added, under a nitrogen atmosphere at 0° C., trimethyl(trifluoromethyl)silane (12.8 mmol) followed by tetrabutylammonium fluoride (1.0 M in THF, 13.4 mmol). The reaction mixture was then warmed to 25° C. and stirred for 2 h. A saturated aqueous ammonium chloride solution (10 mL) was then added. The reaction mixture was stirred for 10 min and then concentrated under reduced pressure. work-up and purification gave the titled compound (5.83 mmol) as a pale yellow oil. $^1$H NMR (400 MHz, CDCl$_3$, δ): 4.00-3.92 (m, 4H), 1.97-1.88 (m, 4H), 1.83-1.79 (m, 2H), 1.69-1.67 (m, 2H).

4-Hydroxy-4-(trifluoromethyl)cyclohexanone

To a solution of 8-(trifluoromethyl)-1,4-dioxaspiro[4.5]decan-8-ol (5.84 mmol) in acetone (29 mL) was added hydrochloric acid (4 M, 8.75 mmol). The reaction mixture was stirred for 18 h at RT and, following work-up and purification, gave the titled compound (5.12 mmol) as a white solid. $^1$H NMR (400 MHz, DMSO-d$_6$, δ): 6.26 (br s, 1H), 2.62-2.52 (m, 2H), 2.19-2.15 (m, 2H), 2.04-1.92 (m, 2H), 1.79-1.62 (m, 2H).

tert-Butyl N-[[4-hydroxy-4-(trifluoromethyl)cyclohexylidene]amino]carbamate

General procedure E, 4-hydroxy-4-(trifluoromethyl)cyclohexanone (5.12 mmol) gave the titled compound (2.29 mmol) as a white solid. $^1$H NMR (400 MHz, DMSO-d$_6$, δ): 9.60 (br s, 1H), 6.02 (br s, 1H), 2.83-2.79 (m, 1H), 2.42-2.37 (m, 2H), 2.24-2.20 (m, 1H), 1.85-1.79 (m, 2H), 1.70-1.55 (m, 2H), 1.43 (s, 9H).

5-Amino-3-(4-bromophenyl)-1-[4-hydroxy-4-(trifluoromethyl)cyclohexyl]pyrazole-4-carbonitrile General procedure O, tert-butyl N-[[4-hydroxy-4-(trifluoromethyl)cyclohexylidene]amino]carbamate (2.29 mmol) and 2-[(4-bromophenyl)-methoxy-methylene]propanedinitrile (0.89 mmol) gave the titled compound (0.12 mmol) as a yellow solid. UPLC-MS (ES$^+$, Short acidic): 1.94 min, m/z 430.9 [M+2]$^+$ N-[[4-[5-Amino-4-cyano-1-[4-hydroxy-4-(trifluoromethyl)cyclohexyl]pyrazol-3-yl]phenyl]methyl]-2-methoxy-benzamide General procedure K, 5-amino-3-(4-bromophenyl)-1-[4-hydroxy-4-(trifluoromethyl)cyclohexyl]pyrazole-4-carbonitrile (0.42 mmol) and potassium trifluoro-[[(2-methoxybenzoyl)amino]methyl]boranuide (0.46 mmol) gave the titled compound (0.24 mmol) as an off-white solid. UPLC-MS (ES$^+$, Short acidic): 1.82 min, m/z 514.1 [M+H]$^+$ 5-Amino-1-[4-hydroxy-4-(trifluoromethyl)cyclohexyl]-3-[4-[[(2-methoxybenzoyl)amino]methyl]phenyl]pyrazole-4-carboxamide General procedure L, N-[[4-[5-amino-4-cyano-1-[4-hydroxy-4-(trifluoromethyl)cyclohexyl]pyrazol-3-yl]phenyl]methyl]-2-methoxy-benzamide (0.24 mmol) gave the titled compound (0.095 mmol) as an pale yellow solid. UPLC-MS (ES$^+$, Short acidic): 1.68 min, m/z 532.1 [M+H]$^+$. UPLC-MS (ES$^+$, Long acidic): 3.91 min, m/z 532.1 [M+H]$^+$
$^1$H NMR (400 MHz, DMSO-d$_6$, δ): 8.73 (t, J=6.6 Hz, 1H), 7.75 (dd, J=7.7, 1.8 Hz, 1H), 7.50-7.39 (m, 5H), 7.16-7.14 (m, 1H), 7.04 (td, J=7.5, 1.0 Hz, 1H), 6.34 (br s, 2H), 5.86 (br s, 1H), 4.54 (d, J=6.0 Hz, 2H), 4.18-4.11 (m, 1H), 3.90 (s, 3H), 2.18-2.07 (m, 2H), 1.85-1.83 (m, 2H), 1.73-1.63 (m, 4H).

Example 66: 5-amino-1-[1-(chloromethyl)-2-hydroxy-ethyl]-3-[4-[[(2-methoxybenzoyl)amino]methyl]phenyl]pyrazole-4-carboxamide

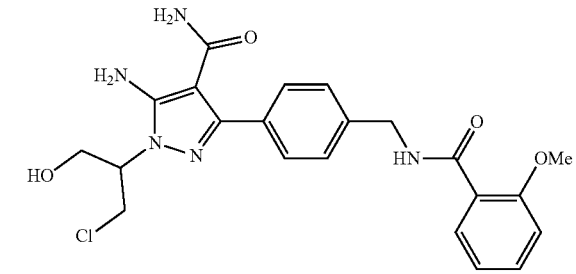 [SMILES: COc1ccccc1C(=O)NCc1ccc(-c2nn(C(CO)CCl)c(N)c2C(N)=O)cc1]

tert-Butyl N-(oxetan-3-ylideneamino)carbamate

Following general procedure E, 3-oxetanone (6.94 mmol) and tert-butyl carbazate (7.29 mmol) gave, after washing the crude with heptane, the titled compound (4.51 mmol) as a white solid. $^1$H NMR (400 MHz, DMSO-d$_6$, δ): 10.25 (s, 1H), 5.19-5.15 (m, 4H), 1.43 (s, 9H)

tert-Butyl N-(oxetan-3-ylamino)carbamate

Following general procedure F, tert-butyl N-(oxetan-3-ylideneamino)carbamate (4.40 mmol) gave after 2 days the titled compound (3.84 mmol) as a colourless oil. $^1$H NMR (400 MHz, DMSO-d$_6$, δ): 8.38 (s, 1H), 4.96-4.94 (m, 1H), 4.51 (t, J=6.8 Hz, 2H), 4.37 (t, J=6.2 Hz, 2H), 4.07-3.99 (m, 1H), 1.40 (s, 9H)

Oxetan-3-ylhydrazine hydrochloride

Following general procedure G, tert-butyl N-(oxetan-3-ylamino)carbamate (3.84 mmol) gave the titled compound (2.88 mmol) as a brown oil. $^1$H NMR (400 MHz, DMSO-d$_6$, δ): 3.81-3.71 (m, 2H), 3.61-3.53 (m, 2H), 3.25-3.19 (m, 1H)

5-Amino-3-(4-bromophenyl)-1-[1-(chloromethyl)-2-hydroxy-ethyl]pyrazole-4-carbonitrile Following general procedure H at 85° C. for 2 h, 2-[(4-bromophenyl)-methoxy-methylene]propanedinitrile (0.38 mmol) and oxetan-3-ylhydrazine hydrochloride (0.46 mmol) gave the titled compound (0.21 mmol) as a white solid. UPLC-MS (ES$^+$, Short acidic): 1.76 min, m/z 357.1 [M+2]$^+$ N-[[4-[5-Amino-1-[1-(chloromethyl)-2-hydroxy-ethyl]-4-cyano-pyrazol-3-yl]phenyl]methyl]-2-methoxy-benzamide General procedure K, 5-amino-3-(4-bromophenyl)-1-[1-(chloromethyl)-2-hydroxy-ethyl]pyrazole-4-carbonitrile (0.20 mmol) and potassium trifluoro-[[(2-methoxybenzoyl)amino]methyl]boranuide (0.28 mmol) gave the titled compound (0.13 mmol) as a white solid. UPLC-MS (ES+, Short acidic): 1.50 min, m/z 440.2 [M]$^+$ 5-Amino-1-[1-(chloromethyl)-2-hydroxy-ethyl]-3-[4-[[(2-methoxybenzoyl)amino]methyl]phenyl]pyrazole-4-carboxamide General procedure L, N-[[4-[5-amino-1-[1-(chloromethyl)-2-hydroxy-ethyl]-4-cyano-pyrazol-3-yl]phenyl]methyl]-2-methoxy-benzamide (0.11 mmol) gave the titled compound (0.03 mmol) as a white solid. UPLC-MS (ES+, Short acidic): 1.33 min, m/z 458.2 [M]$^+$. UPLC-MS (ES+, Long acidic): 2.98 min, m/z 458.2 [M]$^+$. $^1$H NMR (400 MHz, DMSO-d$_6$, δ): 8.74 (t, J=6.1 Hz, 1H), 7.76 (dd, J=7.6, 1.8 Hz, 1H), 7.51-7.41 (m, 5H), 7.16 (d, J=8.0 Hz, 1H), 7.07-7.03 (m, 1H), 6.42 (s, 2H), 5.11 (t, J=5.4 Hz, 1H), 4.59-4.52 (m, 3H), 4.02-3.93 (m, 2H), 3.91 (s, 3H), 3.78-3.67 (m, 2H).

Example 67: 5-amino-3-[4-[[(2-methoxybenzoyl)amino]methyl]phenyl]-1-(4-methylthiazol-2-yl)pyrazole-4-carboxamide

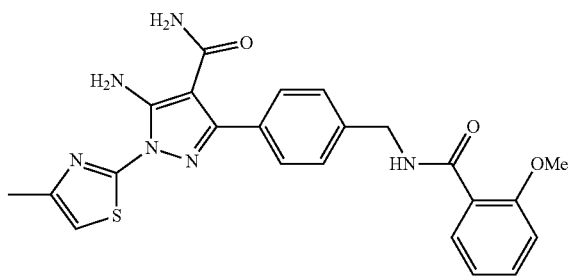 [SMILES: COc1ccccc1C(=O)NCc1ccc(-c2nn(-c3nc(C)cs3)c(N)c2C(N)=O)cc1]

5-Amino-3-(4-bromophenyl)-1-(4-methylthiazol-2-yl)pyrazole-4-carbonitrile

Following general procedure H at 85° C. for 2 h, 2-[(4-bromophenyl)-methoxy-methylene]propanedinitrile (0.76 mmol) and (4-methylthiazol-2-yl)hydrazine (0.91 mmol) gave, after purification, the titled compound (0.32 mmol) as a yellow solid. UPLC-MS (ES$^+$, Short acidic): 1.78 min, m/z 362.0 [M+2]$^+$ N-[[4-[5-Amino-4-cyano-1-(4-methylthiazol-2-yl)pyrazol-3-yl]phenyl]methyl]-2-methoxy-benzamide Following general procedure K, 5-amino-3-(4-bromophenyl)-1-(4-methylthiazol-2-yl)pyrazole-4-carbonitrile (86 mg, 0.24 mmol) and potassium trifluoro-[[(2-methoxybenzoyl)amino]methyl]boranuide (100 mg, 0.37 mmol) gave, after purification, the titled compound (0.08 mmol) as an orange solid. UPLC-MS (ES$^+$, Short acidic): 1.64 min, m/z 445.2 [M+H]$^+$ 5-Amino-3-[4-[[(2-methoxybenzoyl)amino]methyl]phenyl]-1-(4-methylthiazol-2-yl)pyrazole-4 carboxamide Following general procedure M, N-[[4-[5-amino-4-cyano-1-(4-methylthiazol-2-yl)pyrazol-3-yl]phenyl]methyl]-2-methoxy-benzamide (0.05 mmol) gave, after purification, the titled compound (0.02 mmol) as a yellow solid. UPLC-MS (ES$^+$, Short acidic): 1.34 min, m/z 463.1 [M+H]$^+$. UPLC-MS (ES$^+$, Long acidic): 3.01 min, m/z 463.1 [M+H]$^+$
$^1$H NMR (400 MHz, DMSO-d$_6$, δ): 8.80-8.72 (m, 1H), 7.77 (dd, J=7.8, 1.9 Hz, 1H), 7.52-7.47 (m, 1H), 7.44-7.35 (m, 4H), 7.30-7.29 (m, 1H), 7.17-7.15 (m, 1H), 6.38-6.35 (m, 1H), 5.97 (s, 2H), 4.59 (d, J=6.9 Hz, 2H), 3.91 (s, 3H), 2.14 (d, J=1.2 Hz, 3H)

Example 68: 5-amino-1-(4,4-difluorocyclohexyl)-3-[4-[[(2-methoxybenzoyl)amino]methyl]phenyl]pyrazole-4-carboxamide

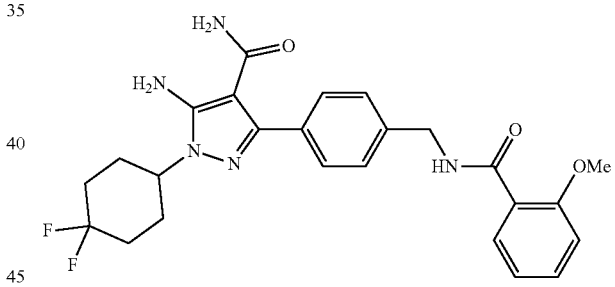

(4,4-Difluorocyclohexyl)hydrazine hydrochloride

To a solution of 4,4-difluorocyclohexanol (5.40 mmol) in toluene (20 mL) was added triphenylphosphine (8.10 mmol) and di-tert-butylazodicarboxylate (6.48 mmol) and the reaction mixture was stirred for 16 h at RT under nitrogen. The reaction mixture was concentrated. MeOH (30 mL) and then a hydrogen chloride solution (4 M in 1,4-dioxane, 10.8 mL, 43.19 mmol) was added and the mixture was stirred for 14 h at RT. After filtration the filtrate was concentrated and addition of EtOAc gave the titled compound (3.52 mmol) as a white solid. $^1$H NMR (400 MHz, DMSO-d$_6$, δ): 3.11-3.05 (m, 1H), 2.11-1.78 (m, 6H), 1.63-1.53 (m, 2H)

5-Amino-3-(4-bromophenyl)-1-(4,4-difluorocyclohexyl)pyrazole-4-carbonitrile

Following general procedure H at 85° C. for 2 h, 2-[(4-bromophenyl)-methoxy-methylene]propanedinitrile (133 mg, 0.51 mmol) and (4,4-difluorocyclohexyl)hydrazine hydrochloride (113 mg, 0.61 mmol) gave, after purification, the titled compound (114 mg, 0.30 mmol, 59% yield) as a white solid. UPLC-MS (ES$^+$, Short acidic): 2.01 min, m/z 383.0 [M+2]$^+$ N-[[4-[5-Amino-4-cyano-1-(4,4-difluorocyclohexyl) pyrazol-3-yl]phenyl]methyl]-2-methoxy-benzamide Following general procedure K, 5-amino-3-(4-bromophenyl)-1-(4,4-difluorocyclohexyl)pyrazole-4-carbonitrile (0.30 mmol) and potassium trifluoro-[[(2-methoxybenzoyl) amino]methyl]boranuide (0.45 mmol) gave, after purification, the titled compound (0.26 mmol) as an orange solid. UPLC-MS (ES$^+$, Short acidic): 1.79 min, m/z 466.1 [M+H]$^+$ 5-Amino-1-(4,4-difluorocyclohexyl)-3-[4-[[(2-methoxybenzoyl)amino]methyl]phenyl]pyrazole-4-carboxamide Following general procedure L, N-[[4-[5-amino-4-cyano-1-(4,4-difluorocyclohexyl)pyrazol-3-yl]phenyl]methyl]-2-methoxy-benzamide (160 mg, 0.34 mmol) gave, after purification, the titled compound (0.11 mmol) as a white solid. UPLC-MS (ES$^+$, Short acidic): 1.71 min, m/z 484.2 [M+H]$^+$ UPLC-MS (ES$^+$, Long acidic): 4.09 min, m/z 484.1 [M+H]$^+$ $^1$H NMR (400 MHz, DMSO-d$_6$, δ): 8.73 (t, J=6.1 Hz, 1H), 7.75 (dd, J=7.7, 1.8 Hz, 1H), 7.50-7.39 (m, 5H), 7.16-7.14 (m, 1H), 7.05-7.01 (m, 1H), 6.36 (s, 2H), 4.54 (d, J=6.1 Hz, 2H), 4.34-4.26 (m, 1H), 3.89 (s, 3H), 2.20-1.89 (m, 8H).

Example 69: 5-amino-1-cyclopentyl-3-[4-[[(2-methoxybenzoyl)amino]methyl]phenyl]-N-methyl-pyrazole-4-carboxamide

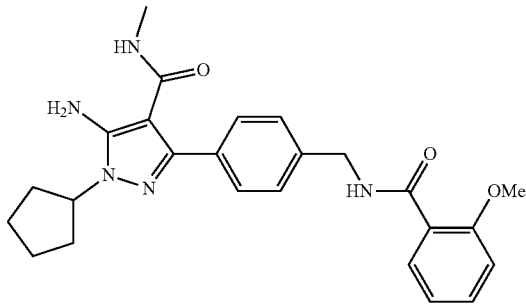 [SMILES: CNC(=O)c1c(-c2ccc(CNC(=O)c3ccccc3OC)cc2)nn(C2CCCC2)c1N]

5-Amino-1-cyclopentyl-3-[4-[[(2-methoxybenzoyl) amino]methyl]phenyl]pyrazole-4-carboxylic acid A mixture of ethyl 5-amino-1-cyclopentyl-3-[4-[[(2-methoxybenzoyl)amino]methyl]phenyl]pyrazole-4-carboxylate (0.22 mmol), sodium hydroxide (5 M in water, 1 mL, 5.00 mmol) and MeOH (3 mL) in THF (5 mL) was stirred at 80° C. for 48 h. The mixture was then cooled and MeOH was removed under reduced pressure. The residue was neutralized with hydrochloric acid (6 M) at 0° C. until a precipitate was observed. The aqueous layer was then extracted and, after concentration, gave crude titled compound (0.20 mmol) as a light brown solid. LC-MS (ES$^+$, Short acidic): 4.87 min, m/z 435.2 [M+H]$^+$ 5-Amino-1-cyclopentyl-3-[4-[[(2-methoxybenzoyl) amino]methyl]phenyl]-N-methyl-pyrazole-4-carboxamide 5-Amino-1-cyclopentyl-3-[4-[[(2-methoxybenzoyl) amino]methyl]phenyl]pyrazole-4-carboxylic acid (30 mg, 0.07 mmol) was dissolved in DMF (3 mL) under nitrogen. HATU (34 mg, 0.09 mmol) and N,N-diisopropylethylamine (36 μL, 0.21 mmol) were added at RT. The mixture was stirred for 45 min. Then methylamine (2 M in THF, 104 μL, 0.21 mmol) was added and the mixture was stirred for 48 h. After work-up and purification the titled compound (0.04 mmol) was obtained as white solid. UPLC-MS (ES$^+$, Short acidic): 1.80 min, m/z 448.2 [M+H]$^+$. UPLC-MS (ES$^+$, Long acidic): 4.21 min, m/z 448.2 [M+H]$^+$. $^1$H NMR (400 MHz, DMSO-d$_6$, δ): 8.72 (t, J=6.1 Hz, 1H), 7.76 (dd, J=7.7, 1.8 Hz, 1H), 7.51-7.45 (m, 3H), 7.39-7.37 (m, 2H), 7.17-7.15 (m, 1H), 7.07-7.03 (m, 1H), 6.18-6.11 (m, 1H), 6.11 (s, 2H), 4.64-4.57 (m, 1H), 4.54 (d, J=6.1 Hz, 2H), 3.91 (s, 3H), 2.59 (d, J=4.7 Hz, 3H), 2.03-1.76 (m, 6H), 1.64-1.56 (m, 2H).

Example 70: 5-amino-1-[3-(dimethylcarbamoyl) cyclohexyl]-3-[4-[[(2-methoxybenzoyl)amino] methyl]phenyl]pyrazole-4-carboxamide (Isomer 1)

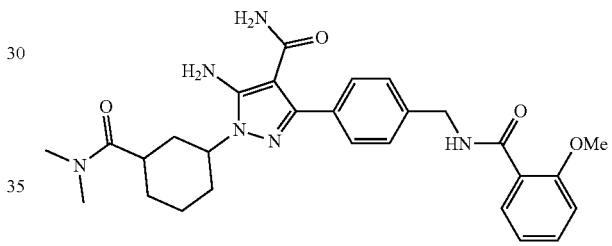

Lithium-3-[5-amino-4-carbamoyl-3-[4-[[(2-methoxybenzoyl)amino]methyl]phenyl]pyrazol-1-yl] cyclohexanecarboxylate (Isomer 1)

A suspension of lithium hydroxide (9 mg, 0.39 mmol) in a solution of ethyl 3-[5-amino-4-carbamoyl-3-[4-[[(2-methoxybenzoyl)amino]methyl]phenyl]pyrazol-1-yl]cyclohexanecarboxylate (isomer 1, 0.19 mmol) in THF (1.5 mL) and water (0.4 mL) was heated to 60° C. for 16 h. The reaction was concentrated to give crude titled compound (isomer 1, 0.19 mmol,) that was used immediately in the next step. UPLC-MS (ES$^+$, Short acidic): 1.60 min, m/z 492.1 [M+H]$^+$ 5-Amino-1-[3-(dimethylcarbamoyl)cyclohexyl]-3-[4-[[(2 methoxybenzoyl)amino]methyl]phenyl]pyrazole-4-carboxamide (Isomer 1)

Lithium-3-[5-amino-4-carbamoyl-3-[4-[[(2-methoxybenzoyl)amino]methyl]phenyl]pyrazol-1-yl]cyclohexanecarboxylate (isomer 1, 95 mg, 0.19 mmol), in THF (2 mL), with a dimethylamine solution (2 M in THF, 0.05 mL, 0.96 mmol) and a propylphosphonic anhydride solution (50 wt % in EtOAc, 0.34 mL, 0.57 mmol) was stirred at RT for 48 h. After work-up and purification the titled compound was obtained (isomer 1, 0.03 mmol). UPLC-MS (ES$^+$, Short acidic): 1.67 min, m/z 519.2 [M+H]$^+$ UPLC-MS (ES$^+$, Long acidic): 3.87 min, m/z 519.2 [M+H]$^+$ ¹H NMR (400 MHz, DMSO-d₆, δ): 8.74 (t, J=6.0 Hz, 1H), 7.76 (dd, J=7.6, 1.7 Hz, 1H), 7.51-7.38 (m, 5H), 7.16 (d, J=8.2 Hz, 1H), 7.08-7.01 (m, 1H), 6.24 (br s, 2H), 4.70-4.60 (m, 1H), 4.55 (d, J=6.1 Hz, 2H), 3.90 (s, 3H), 3.54-3.42 (m, 1H), 2.98 (s, 3H), 2.81 (s, 3H), 2.04-1.95 (m, 1H), 1.89-1.51 (m, 7H).

Example 71: 5-amino-3-[4-[[(2-methoxybenzoyl)amino]methyl]phenyl]-1-(2-oxaspiro[3.5]nonan-7-yl)pyrazole-4-carboxamide

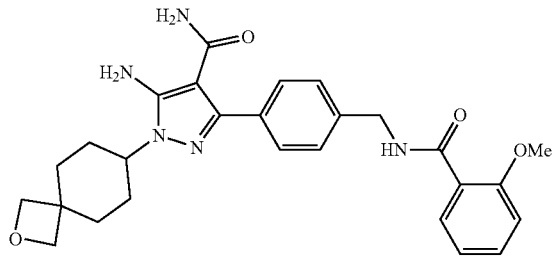 [SMILES: COc1ccccc1C(=O)NCc1ccc(-c2nn(C3CCC4(CC3)COC4)c(N)c2C(N)=O)cc1]

tert-Butyl N-(2-oxaspiro[3.5]nonan-7-ylideneamino)carbamate

Following general procedure E, 2-oxaspiro[3.5]nonan-7-one (120 mg, 0.86 mmol) and tert-butyl carbazate (136 mg, 1.03 mmol) gave crude, tert-butyl N-(2-oxaspiro[3.5]nonan-7-ylideneamino)carbamate (0.86 mmol) as a white solid. ¹H NMR (400 MHz, DMSO-d₆, δ): 9.58 (s, 1H), 4.33 (s, 4H), 2.28-2.25 (m, 2H), 2.16-2.13 (m, 2H), 1.88-1.85 (m, 2H), 1.81-1.78 (m, 2H), 1.43 (s, 9H).

5-Amino-3-(4-bromophenyl)-1-(2-oxaspiro[3.5]nonan-7-yl)pyrazole-4-carbonitrile tert-Butyl N-(2-oxaspiro[3.5]nonan-7-ylideneamino)carbamate (0.85 mmol) was dissolved in THF (10 mL) and a borane dimethyl sulfide complex solution (2 M in THF, 0.73 mL, 1.45 mmol) was added. The reaction was stirred at RT for 2 h. Volatiles were concentrated and the residue was dissolved in DCM (5 mL), followed by addition of TFA (0.88 mL, 4.27 mmol). The reaction mixture was stirred at 0° C. for 1 h and then at RT for 1 h. Volatiles were removed under reduced pressure and the residue was dissolved in EtOH (10 mL). 2-[(4-Bromophenyl)-methoxy-methylene]propanedinitrile (0.65 mmol) and triethylamine (3.23 mmol) were then added. The reaction mixture was heated to 80° C. for 3 h, then cooled to RT and concentrated. Purification gave the titled compound (0.30 mmol) as a yellow solid. UPLC-MS (ES⁺, Short acidic): 1.96 min, m/z 386.9 [M]⁺

N-[[4-[5-Amino-4-cyano-1-(2-oxaspiro[3.5]nonan-7-yl)pyrazol-3-yl]phenyl]methyl]-2-methoxy-benzamide Following general procedure K, 5-amino-3-(4-bromophenyl)-1-(2-oxaspiro[3.5]nonan-7-yl)pyrazole-4-carbonitrile (0.22 mmol) and potassium trifluoro-[[(2-methoxybenzoyl)amino]methyl]boranuide (0.31 mmol) gave, after purification, the titled compound (0.21 mmol) as a yellow solid. UPLC-MS (ES⁺, Short acidic): 1.78 min, 472.2 m/z [M+H]⁺

5-Amino-3-[4-[[(2-methoxybenzoyl)amino]methyl]phenyl]-1-(2-oxaspiro[3.5]nonan-7-yl)pyrazole-4-carboxamide General procedure L, N-[[4-[5-amino-4-cyano-1-(2-oxaspiro[3.5]nonan-7-yl)pyrazol-3-yl]phenyl]methyl]-2-methoxy-benzamide (0.24 mmol) gave, after purification, the titled compound (0.06 mmol) as a beige solid. UPLC-MS (ES⁺, Short acidic): 1.65 min, m/z 490.2 [M+H]⁺. UPLC-MS (ES⁺, Long acidic): 3.89 min, m/z 490.2 [M+H]⁺. ¹H NMR (400 MHz, DMSO-d₆, δ): 8.73 (t, J=6.1 Hz, 1H), 7.75 (dd, J=7.6, 1.8 Hz, 1H), 7.51-7.46 (m, 1H), 7.44-7.39 (m, 4H), 7.18-7.13 (m, 1H), 7.06-7.02 (m, 1H), 6.34 (s, 2H), 4.54 (d, J=6.7 Hz, 2H), 4.36 (s, 2H), 4.26 (s, 2H), 4.11-4.00 (m, 1H), 3.90 (s, 3H), 2.21-2.11 (m, 2H), 1.79-1.62 (m, 4H), 1.61-1.49 (m, 2H).

Example 72: 1-cyclopentyl-5-(isopropylamino)-3-[4-[[(2-methoxybenzoyl)amino]methyl]phenyl]pyrazole-4-carboxamide

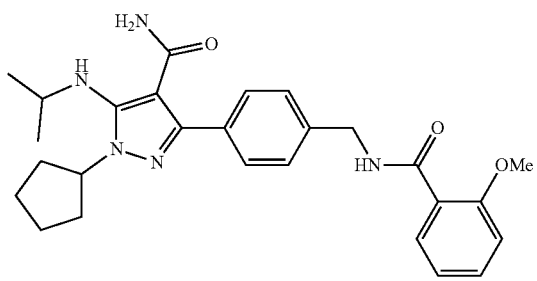 [SMILES: COc1ccccc1C(=O)NCc1ccc(-c2nn(C3CCCC3)c(NC(C)C)c2C(N)=O)cc1]

3-(4-Bromophenyl)-1-cyclopentyl-5-(isopropylamino)pyrazole-4-carbonitrile

The mixture of 5-amino-3-(4-bromophenyl)-1-cyclopentyl-pyrazole-4-carbonitrile (0.30 mmol), cesium carbonate (0.91 mmol) and 2-bromopropane (0.72 mmol) in DMF (10 mL) was heated to 50° C. for 16 h. After work-up and purification the titled compound was afforded (0.13 mmol) as a brown solid. UPLC-MS: (ES⁺, Short acidic): 2.45 min, m/z 375.0 [M+2]⁺

N-[[4-[4-Cyano-1-cyclopentyl-5-(isopropylamino)pyrazol-3-yl]phenyl]methyl]-2-methoxy-benzamide General procedure K, 3-(4-bromophenyl)-1-cyclopentyl-5-(isopropylamino)pyrazole-4-carbonitrile (0.13 mol) and potassium trifluoro-[[(2-methoxybenzoyl)amino]methyl]boranuide (0.18 mmol) gave, after purification, the titled compound (0.12 mmol) as a light brown solid. UPLC-MS: (ES⁺, Short acidic): 2.18 min, m/z 458.2 [M+H]⁺

1-Cyclopentyl-5-(isopropylamino)-3-[4-[[(2-methoxybenzoyl)amino]methyl]phenyl]pyrazole-4-carboxamide General procedure L, N-[[4-[4-cyano-1-cyclopentyl-5-(isopropylamino)pyrazol-3-yl]phenyl]methyl]-2-methoxy-benzamide (0.12 mmol) gave, after purification, the titled compound (0.05 mmol) as a white solid. UPLC-MS: (ES⁺, Long acidic): 4.99 min, m/z 476.2 [M+H]⁺. ¹H NMR (400 MHz, DMSO-d₆, δ): 8.71 (t, J=6.4 Hz, 1H), 7.76 (dd, J=8.0, 2.0 Hz, 1H), 7.54 (d, J=8.4 Hz, 2H), 7.51-7.46 (m, 1H), 7.36 (d, J=8.4 Hz, 2H), 7.17-7.15 (m, 1H), 7.07-7.01 (m, 1H), 5.29 (d, J=9.2 Hz, 1H), 4.78-4.70 (m, 1H), 4.53 (d, J=6.0 Hz, 2H), 3.90 (s, 3H), 3.48-3.36 (m, 1H), 2.06-1.79 (m, 6H), 1.69-1.59 (m, 2H), 1.11 (d, J=6.4 Hz, 6H).

Example 73: 1-cyclopentyl-5-(ethylamino)-3-[4-[[(2-methoxybenzoyl)amino]methyl]phenyl]pyrazole-4-carboxamide

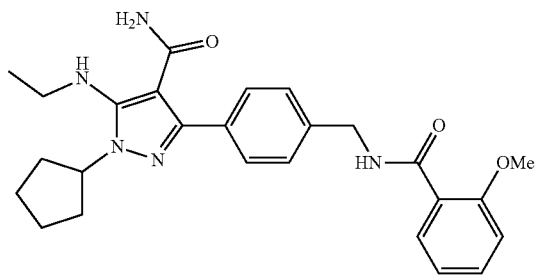 [SMILES: CCNc1c(C(N)=O)c(-c2ccc(CNC(=O)c3ccccc3OC)cc2)nn1C1CCCC1]

3-(4-Bromophenyl)-1-cyclopentyl-5-(ethylamino) pyrazole-4-carbonitrile

A mixture of 5-amino-3-(4-bromophenyl)-1-cyclopentyl-pyrazole-4-carbonitrile (0.30 mmol) and cesium carbonate (295 mg, 0.91 mmol) and iodoethane (0.36 mmol) in DMF (5 mL) was stirred at RT for 14 h. After work-up and purification the titled compound (0.15 mmol) was afforded as an off-white solid. UPLC-MS: (ES$^+$, Short acidic): 2.33 min, m/z 361.0 [M+2]$^+$ N-[[4-[4-Cyano-1-cyclopentyl-5-(ethylamino)pyrazol-3-yl]phenyl]methyl]-2-methoxy-benzamide General procedure K, 3-(4-bromophenyl)-1-cyclopentyl-5-(ethylamino)pyrazole-4-carbonitrile (0.15 mmol) and potassium trifluoro-[[(2-methoxybenzoyl)amino]methyl]boranuide (0.22 mmol) gave, after purification, the titled compound (0.14 mmol) as an off-white solid. UPLC-MS: (ES$^+$, Short acidic): 2.11 min, m/z 444.2 [M+H]$^+$ 1-Cyclopentyl-5-(ethylamino)-3-[4-[[(2-methoxy-benzoyl)amino]methyl]phenyl]pyrazole-4-carboxamide General procedure L, N-[[4-[4-cyano-1-cyclopentyl-5-(ethylamino)pyrazol-3-yl]phenyl]methyl]-2-methoxy-benzamide (0.14 mmol) gave, after purification, the titled compound (0.06 mmol) as a white solid. UPLC-MS (ES$^+$, Long acidic): 4.84 min, m/z 462.2 [M+H]$^+$. $^1$H NMR (400 MHz, DMSO-d$_6$, δ): 8.71 (t, J=6.3 Hz, 1H), 7.75 (dd, J=7.6, 1.8 Hz, 1H), 7.53 (d, J=8.3 Hz, 2H), 7.51-7.46 (m, 1H), 7.36 (d, J=8.4 Hz, 2H), 7.17-7.15 (m, 1H), 7.06-7.00 (m, 1H), 5.63 (t, J=6.4 Hz, 1H), 4.74-4.68 (m, 1H), 4.53 (d, J=6.1 Hz, 2H), 3.90 (s, 3H), 3.18-3.11 (m, 2H), 2.04-1.78 (m, 6H), 1.66-1.57 (m, 2H), 1.12 (t, J=7.1 Hz, 3H).

Example 74: Example 78: 4-[5-amino-4-carbamoyl-3-[4-[[(2-methoxybenzoyl)amino]methyl]phenyl]pyrazol-1-yl]cyclohexanecarboxylic acid

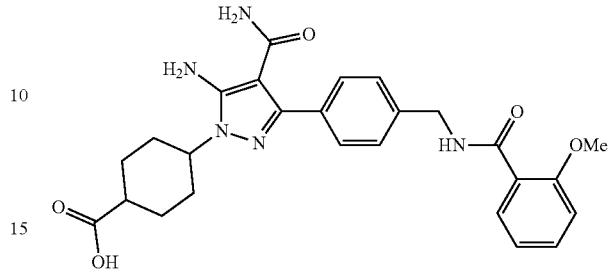

4-[5-Amino-4-carbamoyl-3-[4-[[(2-methoxybenzoyl)amino]methyl]phenyl]pyrazol-1-yl]cyclohexanecarboxylic acid Lithium hydroxide (6.16 mmol) was added to a solution of ethyl 4-[5-amino-4-carbamoyl-3-[4-[[(2-methoxybenzoyl)amino]methyl]phenyl]pyrazol-1-yl]cyclohexanecarboxylate (0.62 mmol) in THF (3 mL) and water (1 mL). The reaction mixture was stirred at 50° C. for 16 h and then cooled to RT. The reaction mixture was acidified to ~pH 2 with hydrochloric acid (1 M). Work-up and purification afforded an inseparable mixture of cis and trans titled compound (0.39 mmol) as a white solid. UPLC-MS (ES$^+$, Short acidic): 1.32 min, m/z 492.3 [M+H]$^+$. UPLC-MS (ES$^+$, Long acidic): 3.67 min, m/z 492.2 [M+H]$^+$. $^1$H NMR (400 MHz, DMSO-d$_6$, δ cis/trans mixture): 12.1 (br s, 1H), 8.73 (t, J=5.9 Hz, 1H), 7.76 (dd, J=7.6, 1.6 Hz, 1H), 7.52-7.38 (m, 5H), 7.16 (d, J=8.3 Hz, 1H), 7.08-7.01 (m, 1H), 6.40-6.25 (m, 2H), 4.55 (d, J=6.0 Hz, 2H), 4.17-4.04 (m, 1H), 3.90 (s, 3H), 2.64-2.10 (m, 1H), 2.07-1.94 (m, 2H), 1.93-1.39 (m, 6H).

Example 75: 5-amino-3-[4-[[(2-methoxybenzoyl)amino]methyl]phenyl]-1-[4-(methoxycarbamoyl)cyclohexyl]pyrazole-4-carboxamide

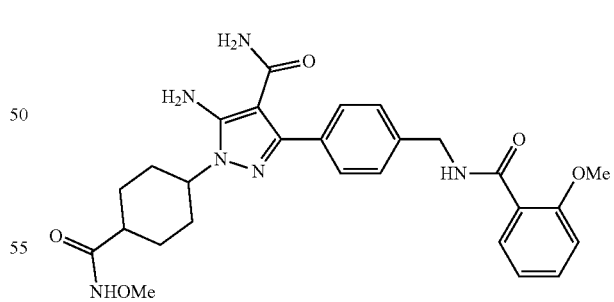

5-Amino-3-[4-[[(2-methoxybenzoyl)amino]methyl]phenyl]-1-[4 (methoxycarbamoyl)cyclohexyl]pyrazole-4-carboxamide A solution of propylphosphonic anhydride (50 wt % in EtOAc, 0.27 mmol), N,N-diisopropylethylamine (0.92 mmol), methoxyamine hydrochloride (0.22 mmol) and 4-[5-amino-4-carbamoyl-3-[4-[[(2-methoxybenzoyl)amino]

methyl]phenyl]pyrazol-1-yl]cyclohexanecarboxylic acid (0.18 mmol) in THF (1 mL) was stirred at 80° C. for 16 h, cooled to RT. Work up and purification gave the title compound (0.03 mmol) as a white solid. UPLC-MS (ES+, Short acidic): 1.53 min, m/z 521.2 [M+H]+. UPLC-MS (ES+, Long acidic): 3.58 min, m/z 521.2 [M+H]+. $^1$H NMR (400 MHz, DMSO-$d_6$, δ, cis/trans mixture): 11.02 (s, 0.45H), 10.95 (s, 0.55H), 8.78-8.70 (m, 1H), 7.79-7.73 (m, 1H), 7.52-7.38 (m, 5H), 7.16 (d, J=8.4 Hz, 1H), 7.08-7.01 (m, 1H), 6.36 (s, 0.90H), 6.30 (s, 1.10H), 4.55 (d, J=6.0 Hz, 2H), 4.18-4.05 (m, 1H), 3.90 (s, 3H), 3.60-3.54 (m, 3H), 2.33-2.24 (m, 0.45H), 2.12-1.92 (s, 2.55H), 1.92-1.49 (m, 6H).

Example 76: 5-amino-1-cyclopentyl-3-[3-fluoro-4-[[(5-fluoro-2-methoxy-benzoyl)amino]methyl]phenyl]pyrazole-4-carboxamide

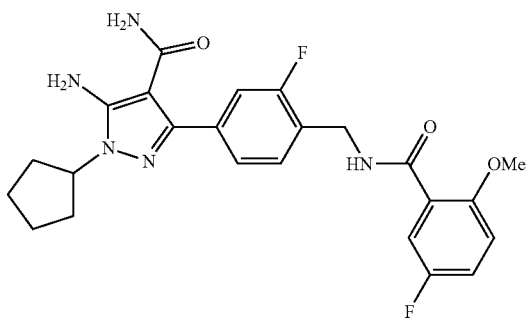

(4-Bromo-2-fluoro-phenyl)methanamine

4-Bromo-2-fluorobenzonitrile (5.00 mmol) in THF (30 mL) was cooled to 0° C. A borane tetrahydrofuran complex solution (1 M in THF, 15.0 mL) was added dropwise. The solution was stirred at 0° C. for 20 min before being brought up to RT and stirred for 16 h. MeOH was added dropwise (30 mL) and the solution was concentrated under reduced pressure. The residue was partitioned between an aqueous solution of NaOH (1 M) and EtOAc. The organic layer was worked up to give the titled compound (5.00 mmol) as a yellow oil. $^1$H NMR (400 MHz, CDCl$_3$, δ): 7.42-7.27 (m, 1H), 7.25-7.16 (m, 2H), 3.65 (t, J=6.6 Hz, 2H).

N-[(4-Bromo-2-fluoro-phenyl)methyl]-5-fluoro-2-methoxy-benzamide

A solution of (4-bromo-2-fluoro-phenyl)methanamine (5.00 mmol) in THF (8 mL) was added dropwise to a mixture of 5-fluoro-2-methoxybenzoic acid (1.03 g, 6.04 mmol), N,N-diisopropylethylamine (5.22 mL, 30.0 mmol) and a propylphosphonic anhydride solution (50 wt % in EtOAc, 4.46 mL, 7.50 mmol) in THF (17 mL). The reaction was heated at 80° C. for 4 h. Work-up and concentration afforded the title compound (3.18 mmol). UPLC-MS (ES+, Short acidic): 1.98 min, m/z 357.9 [M+2]+

5-Fluoro-N-[[2-fluoro-4-(4,4,5,5-tetramethyl-1,3,2-dioxaborolan-2-yl)phenyl]methyl]-2-methoxy-benzamide General procedure R, N-[(4-bromo-2-fluoro-phenyl)methyl]-5-fluoro-2-methoxy-benzamide (3.34 mmol) gave, after purification, the titled compound (3.30 mmol). UPLC-MS (ES+, Short acidic): 2.14 min, m/z 404.0 [M+H]+

N-[[4-(5-Amino-4-cyano-1H-pyrazol-3-yl)-2-fluoro-phenyl]methyl]-5-fluoro-2-methoxy-benzamide General procedure D, 5-fluoro-N-[[2-fluoro-4-(4,4,5,5-tetramethyl-1,3,2-dioxaborolan-2-yl)phenyl]methyl]-2-methoxy-benzamide (1.65 mmol) and 5-amino-3-bromo-1H-pyrazole-4-carbonitrile (1.34 mmol) gave, after purification, titled compound (0.78 mmol). UPLC-MS (ES+, Short acidic): 1.67 min, m/z 384.0 [M+H]+

N-[[4-(5-Amino-4-cyano-1-cyclopentyl-pyrazol-3-yl)-2-fluoro-phenyl]methyl]-5-fluoro-2-methoxy-benzamide Cesium carbonate (1.64 mmol), N-[[4-(5-amino-4-cyano-1H-pyrazol-3-yl)-2-fluoro-phenyl]methyl]-5-fluoro-2-methoxy-benzamide (1.27 mmol) and bromocyclopentane (1.39 mmol) in DMF (10 mL) was heated to 80° C. for 18 h. Work-up and purification gave the titled compound (0.21 mmol). UPLC-MS (ES+, Short acidic): 2.04 min, m/z 452.1 [M+H]+

5-Amino-1-cyclopentyl-3-[3-fluoro-4-[[(5-fluoro-2-methoxy-benzoyl)amino]methyl]phenyl]pyrazole-4-carboxamide General procedure L, N-[[4-(5-amino-4-cyano-1-cyclopentyl-pyrazol-3-yl)-2-fluoro-phenyl]methyl]-5-fluoro-2-methoxy-benzamide (0.11 mmol) afforded, after purification, titled compound (0.07 mmol). UPLC-MS (ES+, Short acidic): 1.93 min, m/z 470.1 [M+H]+ UPLC-MS (ES+, Long acidic): 5.12 min, m/z 470.1 [M+H]+. $^1$H NMR (400 MHz, DMSO-$d_6$, δ): 8.81 (t, J=5.9 Hz, 1H), 7.51 (dd, J=9.2, 3.3 Hz, 1H), 7.46-7.40 (m, 1H), 7.38-7.25 (m, 3H), 7.19 (dd, J=9.1, 4.3 Hz, 1H), 6.25 (s, 2H), 4.67-4.58 (m, 1H), 4.56 (d, J=5.9 Hz, 2H), 3.90 (s, 3H), 2.03-1.84 (m, 4H), 1.84-1.74 (m, 2H), 1.65-1.54 (m, 2H).

Example 77: 5-amino-3-[4-[[(2-methoxybenzoyl)amino]methyl]phenyl]-1-[2-methyltetrahydrofuran-3-yl]pyrazole-4-carboxamide (Isomer 1)

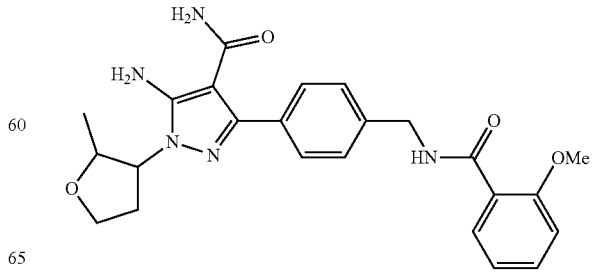

tert-Butyl N-[(2-methyltetrahydrofuran-3-ylidene)amino]carbamate tert-Butyl carbazate (11.99 mmol) and 2-methyltetrahydro-3-furanone (9.99 mmol) in EtOH (25 mL) was heated to reflux for 16 h, cooled and concentrated under reduced pressure. The residue was taken up with DCM, washed successively with water and a saturated solution of NaHCO$_3$, dried over sodium sulfate and concentrated under reduced pressure to afford the titled compound (9.99 mmol) as a white solid. $^1$H NMR (400 MHz, CDCl$_3$, δ): 7.22 (s, 1H), 4.39-4.31 (m, 1H), 4.27-4.19 (m, 1H), 3.97-3.88 (m, 1H), 2.53-2.46 (m, 2H), 1.54 (s, 9H), 1.44 (d, J=6.4 Hz, 3H).

(2-Methyltetrahydrofuran-3-yl)hydrazine

General procedures T and U, tert-butyl N-[(2-methyltetrahydrofuran-3-ylidene)amino]carbamate (9.99 mmol) gave, after purification by SPE SCX cartridge eluting with 1 M solution of NH$_3$ in MeOH, (2-methyltetrahydrofuran-3-yl)hydrazine (9.33 mmol). $^1$H NMR (400 MHz, CDCl$_3$, δ): 4.03-3.66 (m, 3H), 3.31-3.24 (m, 1H), 2.18-2.05 (m, 1H), 1.95-1.85 (m, 1H), 1.30-1.22 (m, 3H).

5-Amino-3-(4-bromophenyl)-1-(2-methyltetrahydrofuran-3-yl)pyrazole-4-carbonitrile General procedure H, 2-[(4-bromophenyl)-methoxymethylene]propanedinitrile (1.90 mmol) and (2-methyltetrahydrofuran-3-yl)hydrazine (2.28 mmol) gave, after purification, the titled compound as a mixture of inseparable diastereoisomers (600 mg, 1.73 mmol, 91% yield). UPLC-MS (ES$^+$, Short acidic, mixture of disastereoisomers): 2.02 min, m/z 349.0 [M+2]$^+$ and 2.07 min, m/z 349.0 [M+2]$^+$

N-[[4-[5-Amino-4-cyano-1-[2-methyltetrahydrofuran-3-yl]pyrazol-3-yl]phenyl]methyl]-2-methoxybenzamide General procedure K, 5-amino-3-(4-bromophenyl)-1-(2-methyltetrahydrofuran-3-yl)pyrazole-4-carbonitrile (0.86 mmol) and potassium trifluoro-[[(2-methoxybenzoyl)amino]methyl]boranuide (1.21 mmol) gave, after purification, the titled compound (isomer 1, 0.17 mmol) and (isomer 2, 0.32 mmol). UPLC-MS (ES$^+$, Short acidic, isomer 1): 1.98 min, m/z 432.1 [M+H]$^+$. UPLC-MS (ES$^+$, Short acidic, isomer 2): 1.96 min, m/z 432.1 [M+H]$^+$

5-Amino-3-[4-[[(2-methoxybenzoyl)amino]methyl]phenyl]-1-[2-methyltetrahydrofuran-3-yl]pyrazole-4-carboxamide (Isomer 1)

Following general procedure L, N-[[4-[5-amino-4-cyano-1-[2-methyltetrahydrofuran-3-yl]pyrazol-3-yl]phenyl]methyl]-2-methoxy-benzamide (isomer 1, 0.17 mmol) gave, after purification, the titled compound (isomer 1, 0.09 mmol). UPLC-MS (ES$^+$, Short acidic): 2.03 min, m/z 450.1 [M+H]$^+$. UPLC-MS (ES$^+$, Long acidic): 4.49 min, m/z 450.1 [M+H]$^+$. $^1$H NMR (400 MHz, DMSO-d$_6$, δ): 8.74 (t, J=6.3 Hz, 1H), 7.75 (dd, J=7.6, 1.7 Hz, 1H), 7.51-7.38 (m, 5H), 7.15 (d, J=8.5 Hz, 1H), 7.08-7.00 (m, 1H), 6.43 (br s, 2H), 4.55 (d, J=5.9 Hz, 2H), 4.51-4.44 (m, 1H), 4.08-4.02 (m, 1H), 3.95-3.90 (m, 2H), 3.90 (s, 3H), 2.38-2.18 (m, 2H), 1.21 (d, J=6.2 Hz, 3H).

Example 78: 5-chloro-1-cyclopentyl-3-[4-[[(2-methoxybenzoyl)amino]methyl]phenyl]pyrazole-4-carboxamide

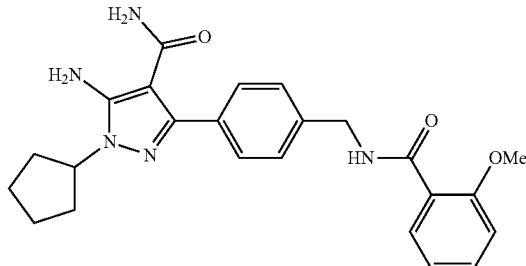

3-(4-Bromophenyl)-1H-pyrazol-5-ol

A solution of ethyl 3-(4-bromophenyl)-3-oxopropanoate (12.2 mmol) in EtOH (20 mL) and hydrazine hydrate solution (55-60% in water, 12.2 mmol) was stirred for 40 min at RT. The reaction mixture was then heated at reflux for 1 h, then cooled to RT and concentrated under reduced pressure to give the titled compound crude (12.2 mmol) as a white solid. UPLC-MS (ES$^+$, Short acidic): 1.57 min, m/z 240.6 [M+2]$^+$

3-(4-Bromophenyl)-5-chloro-1H-pyrazole-4-carbaldehyde

To phosphorus oxychloride (29.3 mmol) was added slowly under nitrogen at 0° C. anhydrous DMF (1.0 mL). The reaction mixture was then warmed to RT and stirred for 5 min then 3-(4-bromophenyl)-1H-pyrazol-5-ol (4.18 mmol) was added to the reaction mixture at 0° C. After the addition, the reaction mixture was heated at 85° C. for 24 h. The reaction mixture was cooled to RT and quenched with a saturated solution of potassium carbonate (20 mL), and extracted with EtOAc (3×20 mL). The combined organic layers were dried over sodium sulfate, filtered and concentrated under reduced pressure. Purification gave the titled compound (2.31 mmol) as an off-white solid. UPLC-MS (ES$^+$, Short acidic): 1.99 min, m/z 286.8 [M+H]$^+$

3-(4-Bromophenyl)-5-chloro-1-cyclopentyl-pyrazole-4-carbaldehyde

General procedure N, 3-(4-bromophenyl)-5-chloro-1H-pyrazole-4-carbaldehyde (2.31 mmol), cesium carbonate (4.62 mmol) and bromocyclopentane (3.47 mmol) gave, after purification, the titled compound (1.35 mmol) as a white solid. UPLC-MS (ES$^+$, Short acidic): 2.49 min, m/z 354.9 [M+H]$^+$

3-(4-Bromophenyl)-5-chloro-1-cyclopentyl-pyrazole-4-carboxylic acid

To a suspension of 3-(4-bromophenyl)-5-chloro-1-cyclopentyl-pyrazole-4-carbaldehyde (0.46 mmol) in water (5 mL) was added potassium permanganate (0.91 mmol) at RT. The reaction mixture was heated at 100° C. for 18 h and then cooled to RT, filtered through Celite® and washed with water and EtOAc. The two layers were separated and the aqueous layer was acidified to pH 1 with a 1 M solution of HCl. The aqueous layer was then extracted with EtOAc (3×20 mL). The combined organic layers were dried over sodium sulfate, and concentrated under reduced pressure to give a mixture the titled compound and 3-(4-bromophenyl)-5-chloro-1H-pyrazole-4-carboxylic acid (1:2 ratio) (0.86 mmol) which was used as such in the next step. UPLC-MS (ES+, Short acidic): 2.31 min, m/z 370.9 [M+H]+

3-(4-Bromophenyl)-5-chloro-1-cyclopentyl-pyrazole-4-carboxamide

A mixture 3-(4-bromophenyl)-5-chloro-1-cyclopentyl-pyrazole-4-carboxylic acid and 3-(4-bromophenyl)-5-chloro-1H-pyrazole-4-carboxylic acid (1:2 ratio) (0.86 mmol) in thionyl chloride (4.30 mmol) was heated at 80° C. for 1 h. The excess of thionyl chloride was removed under reduced pressure to afford a brown oil which was dissolved in anhydrous DCM (1.9 mL) under nitrogen at 0° C. with an ice bath. Ammonium hydroxide (30 wt % in water, 8.58 mmol) was added dropwise to the cooled reaction mixture and then it was stirred to RT for 16 h. The reaction mixture was then diluted in DCM and washed with water. The aqueous layer was extracted with DCM (×3) and the combined organic layers were dried over sodium sulfate, filtered off and concentrated under reduced pressure. Purification gave the titled compound (0.10 mmol) as a white solid. UPLC-MS (ES+, Short acidic): 2.24 min, m/z 369.9 [M+H]+

5-Chloro-1-cyclopentyl-3-[4-[[(2-methoxybenzoyl)amino]methyl]phenyl]pyrazole-4-carboxamide General procedure K, 3-(4-bromophenyl)-5-chloro-1-cyclopentyl-pyrazole-4-carboxamide (0.10 mmol) and potassium trifluoro-[[(2-methoxybenzoyl)amino]methyl]boranuide (29 mg, 0.11 mmol) gave, after purification, the titled compound (0.03 mmol) as an off-white solid. UPLC-MS (ES+, Short acidic): 2.23 min, m/z 453.0 [M]+. UPLC-MS (ES+, Long acidic): 6.07 min, m/z 453.1 [M]+. $^1$H NMR (400 MHz, DMSO-$d_6$, δ): 8.71 (t, J=6.0 Hz, 1H), 7.74 (dd, J=7.6, 1.8 Hz, 1H), 7.67 (br s, 1H), 7.63 (d, J=8.5 Hz, 2H), 7.53 (br s, 1H), 7.50-7.44 (m, 1H), 7.36 (d, J=8.4 Hz, 2H), 7.14 (d, J=7.8 Hz, 1H), 7.06-7.00 (m, 1H), 4.90-4.83 (m, 1H), 4.51 (d, J=6.2 Hz, 2H), 3.89 (s, 3H), 2.13-2.05 (m, 2H), 2.03-1.94 (m, 2H), 1.91-1.81 (m, 2H), 1.72-1.64 (m, 2H).

Example 79: 5-amino-1-cyclopentyl-3-[4-[1-[(2-methoxybenzoyl)amino]ethyl]phenyl]pyrazole-4-carboxamide

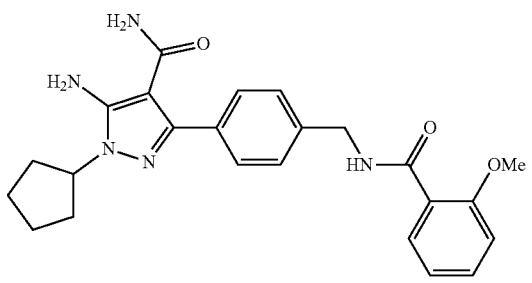

N-[1-(4-Bromophenyl)ethyl]-2-methoxy-benzamide

A solution of 4-bromo-α-methoxy-benzamide mmol) and N,N-diisopropylethylamine (9.85 mmol) in anhydous THF (30 mL) and 2-methoxybenzoyl chloride (7.22 mmol) at 0° C. was then allowed to return to RT and stirred for 15 h. The mixture was quenched with a saturated solution of ammonium chloride (40 mL), extracted with EtOAc (3×20 mL). The combined organic extracts were washed with water (2×30 mL), a saturated solution of brine (30 mL), dried over sodium sulfate, filtered and concentrated under reduced pressure. Further purification gave the titled compound (6.19 mmol) as a white solid. UPLC-MS (ES+, Short acidic): 1.96 min, m/z 336.1 [M+2]+

2-Methoxy-N-[1-[4-(4,4,5,5-tetramethyl-1,3,2-dioxaborolan-2-yl)phenyl]ethyl]benzamide General procedure J, N-[1-(4-bromophenyl)ethyl]-2-methoxy-benzamide (0.90 mmol) gave, after purification, the titled compound (0.87 mmol) as an orange oil. UPLC-MS (ES+, Short acidic): 2.12 min, m/z 382.1 [M+H]+

5-Amino-1-cyclopentyl-3-[4-[1-[(2-methoxybenzoyl)amino]ethyl]phenyl]pyrazole-4-carboxamide General procedure D, 5-amino-3-bromo-1-cyclopentyl-pyrazole-4-carboxamide (0.26 mmol) and 2-methoxy-N-[1-[4-(4,4,5,5-tetramethyl-1,3,2-dioxaborolan-2-yl)phenyl]ethyl]benzamide (0.26 mmol) gave, after purification, the titled compound (0.03 mmol) as a light brown solid. UPLC-MS (ES+, Short acidic): 2.47 min, m/z 448.2 [M+H]+. UPLC-MS (ES+, Long acidic): 5.82 min, m/z 448.2 [M+H]+. $^1$H NMR (400 MHz, DMSO-$d_6$, δ): 8.52 (d, J=8.0 Hz, 1H), 7.63 (dd, J=7.7, 1.8 Hz, 1H), 7.50-7.42 (m, 5H), 7.14 (d, J=7.8 Hz, 1H), 7.05-6.98 (m, 1H), 6.30 (br s, 2H), 5.22-5.12 (m, 1H), 4.65-4.55 (m, 1H), 3.90 (s, 3H), 2.02-1.84 (m, 4H), 1.84-1.70 (m, 2H), 1.64-1.51 (m, 2H), 1.48 (d, J=7.0 Hz, 3H)

Example 80: 5-amino-3-[4-[[(2-methoxybenzoyl)amino]methyl]phenyl]-1-tetrahydropyran-3-yl-pyrazole-4-carboxamide

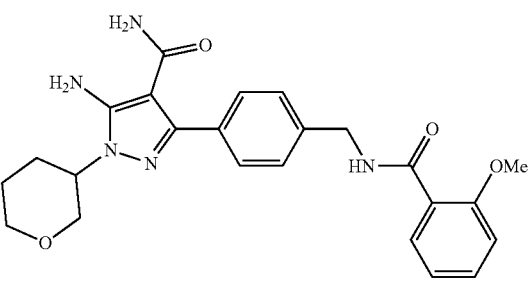 [SMILES: COc1ccccc1C(=O)NCc1ccc(-c2nn(C3CCCOC3)c(N)c2C(N)=O)cc1]

5-Amino-3-(4-bromophenyl)-1-tetrahydropyran-3-yl-pyrazole-4-carbonitrile

A modified general procedure H at RT, 2-[(4-bromophenyl)-methoxy-methylene]propanedinitrile (0.49 mmol) and tetrahydropyran-3-ylhydrazine hydrochloride (0.49 mmol) afforded, after purification, the titled compound (0.24 mmol) as a beige solid. UPLC-MS (ES+, Short acidic): 2.17 min, m/z 346.9 [M]+

N-[[4-(5-Amino-4-cyano-1-tetrahydropyran-3-yl-pyrazol-3-yl)phenyl]methyl]-2-methoxy-benzamide General procedure K, 5-amino-3-(4-bromophenyl)-1-tetrahydropyran-3-yl-pyrazole-4-carbonitrile (0.24 mmol) and potassium trifluoro-[[(2-methoxybenzoyl)amino]methyl]boranuide (0.27 mmol) afforded, after purification, the titled compound (0.24 mmol) as a yellow oil. UPLC-MS (ES⁺, Short acidic): 1.99 min, m/z 432.1 [M+H]⁺

5-Amino-3-[4-[[(2-methoxybenzoyl)amino]methyl]phenyl]-1-tetrahydropyran-3-yl-pyrazole-4-carboxamide General procedure M, N-[[4-(5-amino-4-cyano-1-tetrahydropyran-3-yl-pyrazol-3-yl)phenyl]methyl]-2-methoxybenzamide (0.21 mmol) afforded, after purification, the titled compound (0.04 mmol) as an off-white solid. UPLC-MS (ES⁺, Short acidic): 1.91 min, m/z 450.2 [M+H]⁺. UPLC-MS (ES⁺, Long acidic): 5.07 min, m/z 450.1 [M+H]⁺. ¹H NMR (400 MHz, DMSO-d₆, δ): 8.74 (t, J=6.1 Hz, 1H), 7.76 (dd, J=7.7, 1.7 Hz, 1H), 7.52-7.38 (m, 5H), 7.16 (d, J=8.2 Hz, 1H), 7.05 (m, 1H), 6.42 (s, 2H), 4.55 (d, J=6.1 Hz, 2H), 4.30-4.21 (m, 1H), 3.93-3.81 (m, 5H), 3.59-3.49 (m, 1H), 3.37-3.27 (m, 1H), 2.05-1.96 (m, 2H), 1.80-1.64 (m, 2H).

Example 81: 5-amino-1-(2,3-difluorophenyl)-3-[4-[[(2-methoxybenzoyl)amino]methyl]phenyl]pyrazole-4-carboxamide

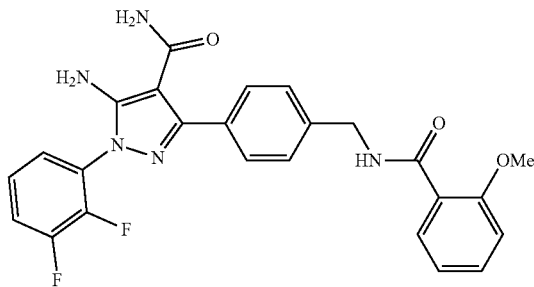 [SMILES: COc1ccccc1C(=O)NCc1ccc(-c2nn(-c3cccc(F)c3F)c(N)c2C(N)=O)cc1]

5-Amino-3-(4-bromophenyl)-1-(2,3-difluorophenyl)pyrazole-4-carbonitrile

Following general procedure H, 2-[(4-bromophenyl)-methoxy-methylene]propanedinitrile (0.38 mmol) and (2,3-difluorophenyl)hydrazine (0.46 mmol) afforded, after purification, the titled compound (0.29 mmol) as an orange solid. UPLC-MS (ES⁺, Short acidic): 2.08 min, m/z 376.9 [M+2]⁺

N-[[4-[5-Amino-4-cyano-1-(2,3-difluorophenyl)pyrazol-3-yl]phenyl]methyl]-2-methoxy-benzamide General procedure K, 5-amino-3-(4-bromophenyl)-1-(2,3-difluorophenyl)pyrazole-4-carbonitrile (0.29 mmol) and potassium trifluoro-[[(2-methoxybenzoyl)amino]methyl]boranuide (0.41 mmol) gave, after purification, the titled compound (0.14 mmol) as a grey solid. UPLC-MS (ES⁺, Short acidic): 1.89 min, m/z 460.1 [M+H]⁺

5-Amino-1-(2,3-difluorophenyl)-3-[4-[[(2-methoxybenzoyl)amino]methyl]phenyl]pyrazole-4-carboxamide General procedure M, N-[[4-[5-amino-4-cyano-1-(2,3-difluorophenyl)pyrazol-3-yl]phenyl]methyl]-2-methoxy-benzamide (0.14 mmol) afforded, after purification, the titled compound (0.03 mmol, 22% yield) as a white solid. UPLC-MS (ES⁺, Short acidic): 1.77 min, m/z 478.1 [M+H]⁺. UPLC-MS (ES⁺, Long acidic): 4.21 min, m/z 478.1 [M+H]⁺. ¹H NMR (400 MHz, DMSO-d₆, δ): 8.76 (t, J=6.0 Hz, 1H), 7.77 (dd, J=7.6, 1.6 Hz, 1H), 7.66-7.34 (m, 8H), 7.16 (d, J=8.4 Hz, 1H), 7.06-7.02 (m, 1H), 6.58 (s, 2H), 4.56 (d, J=6.4 Hz, 2H), 3.90 (s, 3H).

Example 82: 5-amino-3-[4-[[(2-methoxybenzoyl)amino]methyl]phenyl]-1-(2,2,5,5-tetramethyltetrahydrofuran-3-yl)pyrazole-4-carboxamide

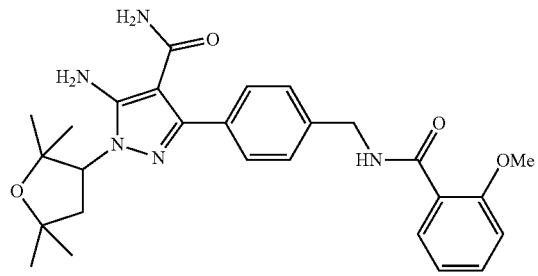 [SMILES: COc1ccccc1C(=O)NCc1ccc(-c2nn(C3CC(C)(C)OC3(C)C)c(N)c2C(N)=O)cc1]

tert-Butyl N-[(2,2,5,5-tetramethyltetrahydrofuran-3-ylidene)amino]carbamate

General procedure E, dihydro-2,2,5,5-tetramethyl-3(2H)-furanone (1.63 mmol) and tert-butyl carbazate (258 mg, 1.95 mmol) gave the titled compound crude (1.62 mmol) as a white solid. ¹H NMR (400 MHz, CDCl₃, δ): 7.11 (s, 1H), 2.47 (s, 2H), 1.51 (s, 9H), 1.42 (s, 6H), 1.34 (s, 6H).

5-Amino-3-(4-bromophenyl)-1-(2,2,5,5-tetramethyltetrahydrofuran-3-yl)pyrazole-4-carbonitrile tert-Butyl N-[(2,2,5,5-tetramethyltetrahydrofuran-3-ylidene)amino]carbamate (1.62 mmol) was dissolved in THF (10 mL) and a borane dimethyl sulfide complex solution (2 M in THF, 2.75 mmol) was added. The reaction mixture was stirred at RT for 2 h until TLC showed complete consumption of the starting material. Volatiles were removed under reduced pressure. The residue was taken up with DCM (5 mL) and TFA (8.10 mmol) was added and the mixture was stirred at RT for 1 h. The reaction mixture was then concentrated under reduced pressure. The residue was dissolved in EtOH (10 mL) and 2-[(4-bromophenyl)-methoxy-methylene]propanedinitrile (0.65 mmol) and triethylamine (3.23 mmol) were added. The reaction mixture was heated to 80° C. for 24 h. The solvent was removed under reduced pressure and the residue was purified to give the titled compound (0.23 mmol) as a solid. UPLC-MS (ES⁺, Short acidic): 2.33 min, m/z 389.0 [M]⁺

N-[[4-[5-Amino-4-cyano-1-(2,2,5,5-tetramethyltetrahydrofuran-3-yl)pyrazol-3-yl]phenyl]methyl]-2-methoxy-benzamide General procedure K, 5-amino-3-(4-bromophenyl)-1-(2,2,5,5-tetramethyltetrahydrofuran-3-yl)pyrazole-4-carbonitrile (0.23 mmol) and potassium trifluoro-[[(2-methoxybenzoyl)amino]methyl]boranuide (0.32 mmol) gave, after purification, the titled compound (0.19 mmol) as a yellow solid. UPLC-MS: (ES⁺, Short acidic): 2.09 min, m/z 474.2 [M+H]⁺

5-Amino-3-[4-[[(2-methoxybenzoyl)amino]methyl]phenyl]-1-(2,2,5,5-tetramethyltetrahydrofuran-3-yl)pyrazole-4-carboxamide General procedure L, N-[[4-[5-amino-4-cyano-1-(2,2,5,5-tetramethyltetrahydrofuran-3-yl)pyrazol-3-yl]phenyl]methyl]-2-methoxy-benzamide (0.19 mmol) gave, after purification, the titled compound (0.10 mmol) as a solid. UPLC-MS (ES⁺, Short acidic): 2.02 min, m/z 492.2 [M+H]⁺. UPLC-MS (ES⁺, Long acidic): 4.79 min, m/z 492.2 [M+H]⁺. ¹H NMR (400 MHz, DMSO-d₆, δ): 8.73 (t, J=6.2 Hz, 1H), 7.75 (dd, J=7.5, 1.7 Hz, 1H), 7.49-7.40 (m, 5H), 7.15 (d, J=8.6 Hz, 1H), 7.05-7.01 (m, 1H), 6.43 (s, 2H), 4.92-4.87 (m, 1H), 4.54 (d, J=6.1 Hz, 2H), 3.90 (s, 3H), 2.81-2.73 (m, 1H), 2.13-2.09 (m, 1H), 1.30 (s, 6H), 1.26 (s, 3H), 0.90 (s, 3H).

Example 83a: 5-amino-3-[4-[[(2-methoxybenzoyl)amino]methyl]phenyl]-1-[(3S)-tetrahydrofuran-3-yl]pyrazole-4-carboxamide

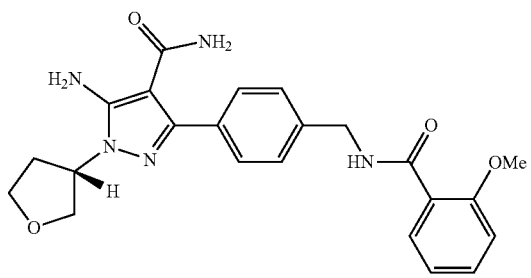 [SMILES: COc1ccccc1C(=O)NCc1ccc(-c2nn([C@H]3CCOC3)c(N)c2C(N)=O)cc1]

[(3S)-Tetrahydrofuran-3-yl]hydrazine hydrochloride

A solution of (3R)-tetrahydrofuran-3-ol (11.35 mmol) in toluene (20 mL), triphenylphosphine (17.0 mmol), and di-tert-butylazodicarboxylate (13.6 mmol) was stirred under nitrogen at RT for 48 h, then concentrated under reduced pressure and the residue redissolved in MeOH (50 mL). A hydrogen chloride solution (4 M in dioxane, 90.79 mmol) was added and the reaction mixture stirred at RT for 16 h. The reaction mixture was filtered and the filtrate concentrated under reduced pressure. The residue was recrystallized in EtOAc and MeOH to give the titled compound (7.32 mmol) as a beige solid. ¹H NMR (400 MHz, DMSO-d₆, δ): 3.81-3.72 (m, 3H), 3.69-3.62 (m, 2H), 2.07-1.98 (m, 1H), 1.96-1.88 (m, 1H).

N-[[4-[5-Amino-4-cyano-1-[(3S)-tetrahydrofuran-3-yl]pyrazol-3-yl]phenyl]methyl]-2-methoxy-benzamide General procedure K, 5-amino-3-(4-bromophenyl)-1-[(3S)-tetrahydrofuran-3-yl]pyrazole-4-carbonitrile (0.39 mmol) and potassium trifluoro-[[(2-methoxybenzoyl)amino]methyl]boranuide (0.59 mmol) gave, after purification, the titled compound (0.35 mmol) as a light brown solid. UPLC-MS (ES⁺, Short acidic): 1.94 min, m/z 418.1 [M+H]⁺

5-Amino-3-[4-[[(2-methoxybenzoyl)amino]methyl]phenyl]-1-[(3S)-tetrahydrofuran-3-yl]pyrazole-4-carboxamide General procedure M, N-[[4-[5-amino-4-cyano-1-[(3S)-tetrahydrofuran-3-yl]pyrazol-3-yl]phenyl]methyl]-2-methoxy-benzamide (0.18 mmol) gave, after purification, the titled compound (0.08 mmol) as a pale yellow solid. UPLC-MS (ES⁺, Short acidic): 1.32 min, m/z 436.1 [M+H]⁺. UPLC-MS (ES⁺, Long acidic): 2.96 min, m/z 436.1 [M+H]⁺. ¹H NMR (400 MHz, DMSO-d₆, δ): 8.73 (t, J=6.1 Hz, 1H), 7.75 (dd, J=7.7, 1.7 Hz, 1H), 7.50-7.40 (m, 5H), 7.15 (d, J=7.7 Hz, 1H), 7.06-7.02 (m, 1H), 6.39 (s, 2H), 4.93-4.90 (m, 1H), 4.54 (d, J=6.0 Hz, 2H), 4.00-3.92 (m, 2H), 3.90 (s, 3H), 3.83-3.79 (m, 2H), 2.30-2.20 (m, 2H).

Example 83b: 5-amino-3-[4-[[(2-methoxybenzoyl)amino]methyl]phenyl]-1-[(3R)-tetrahydrofuran-3-yl]pyrazole-4-carboxamide

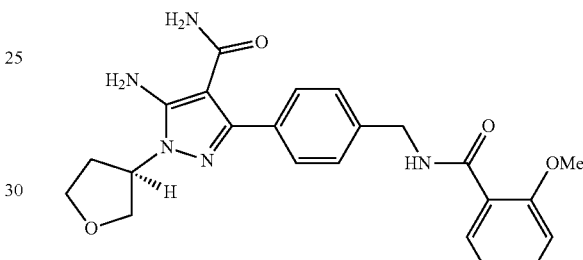

[(3R)-Tetrahydrofuran-3-yl]hydrazine hydrochloride

A solution of (S)-(−)-3-hydroxytetrahydrofuran (11.4 mmol) in toluene (20 mL), triphenylphosphine (17.0 mmol) and di-tert-butylazodicarboxylate (13.6 mmol) at 0° C. was stirred for 48 h at RT under nitrogen. Volatiles were removed under reduced pressure. MeOH (50 mL) and a hydrogen chloride solution (4 M in dioxane, 90.8 mmol) were then added. The reaction mixture was stirred for 16 h at RT, and then filtered. The filtrate was concentrated under reduced pressure. The residue was triturated with EtOAc to give the titled compound (5.4 mmol) as a white solid. ¹H NMR (400 MHz, DMSO-d₆, δ): 3.82-3.62 (m, 5H), 2.08-1.99 (m, 1H), 1.94-1.87 (m, 1H)

N-[[4-[5-Amino-4-cyano-1-[(3R)-tetrahydrofuran-3-yl]pyrazol-3-yl]phenyl]methyl]-2-methoxy-benzamide General procedure K, 5-amino-3-(4-bromophenyl)-1-[(3R)-tetrahydrofuran-3-yl]pyrazole-4-carbonitrile (0.27 mmol) and potassium trifluoro-[[(2-methoxybenzoyl)amino]methyl]boranuide (0.41 mmol) gave, after purification, the titled compound (0.27 mmol) as an beige solid. UPLC-MS (ES⁺, Short acidic): 1.50 min, m/z 418.1 [M+H]⁺

5-Amino-3-[4-[[(2-methoxybenzoyl)amino]methyl]phenyl]-1-[(3R)-tetrahydrofuran-3-yl]pyrazole-4-carboxamide General procedure M, N-[[4-[5-amino-4-cyano-1-[(3R)-tetrahydrofuran-3-yl]pyrazol-3-yl]phenyl]methyl]-2- methoxy-benzamide (0.30 mmol) gave, after purification, the titled compound (0.11 mmol) as a white solid. LC-MS (ES+, Short acidic): 3.94 min, m/z 436.1 [M+H]⁺. UPLC-MS (ES+, Long acidic): 2.96 min, m/z 436.1 [M+H]⁺. ¹H NMR (400 MHz, DMSO-d₆, δ): 8.73 (t, J=6.1 Hz, 1H), 7.75 (dd, J=7.7, 1.8 Hz, 1H), 7.50-7.39 (m, 5H), 7.16-7.14 (m, 1H), 7.06-7.01 (m, 1H), 6.39 (s, 2H), 4.96-4.90 (m, 1H), 4.54 (d, J=6.1 Hz, 2H), 4.01-3.92 (m, 2H), 3.90 (s, 3H), 3.82-3.77 (m, 2H), 2.28-2.23 (m, 2H).

Example 84: 5-amino-3-[4-[[(2-methoxybenzoyl)amino]methyl]phenyl]-1-[2-methyltetrahydrofuran-3-yl]pyrazole-4-carboxamide (Isomer 2)

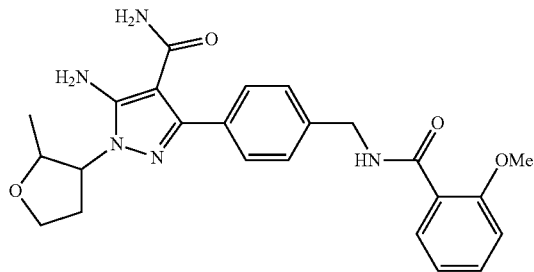 [SMILES: COc1ccccc1C(=O)NCc1ccc(-c2nn(C3CCOC3C)c(N)c2C(N)=O)cc1]

5-Amino-3-[4-[[(2-methoxybenzoyl)amino]methyl]phenyl]-1-[2-methyltetrahydrofuran-3-yl]pyrazole-4-carboxamide (Isomer 2)

General procedure M, N-[[4-[5-amino-4-cyano-1-[2-methyltetrahydrofuran-3-yl]pyrazol-3-yl]phenyl]methyl]-2-methoxy-benzamide (isomer 2, 0.32 mmol) gave, after purification, the titled compound (isomer 2, 0.07 mmol). UPLC-MS (ES⁺, Short acidic): 1.85 min, m/z 450.1 [M+H]⁺. UPLC-MS (ES⁺, Long acidic): 3.02 min, m/z 450.1 [M+H]⁺. ¹H NMR (400 MHz, DMSO-d₆, δ): 8.73 (t, J=6.0 Hz, 1H), 7.75 (dd, J=7.7, 1.7 Hz, 1H), 7.51-7.39 (m, 5H), 7.16 (d, J=8.2 Hz, 1H), 7.06-7.02 (m, 1H), 6.39 (br s, 2H), 4.88-4.80 (m, 1H), 4.55 (d, J=6.0 Hz, 2H), 4.14-4.05 (m, 1H), 4.05-3.96 (m, 1H), 3.90 (s, 3H), 3.64 (q, J=8.1 Hz, 1H), 2.54-2.44 (m, 1H), 2.41-2.31 (m, 1H), 0.83 (d, J=6.1 Hz, 3H).

Example 85: 5-amino-3-[4-[[(2-methoxybenzoyl)amino]methyl]phenyl]-1-(2-methyltetrahydropyran-4-yl)pyrazole-4-carboxamide

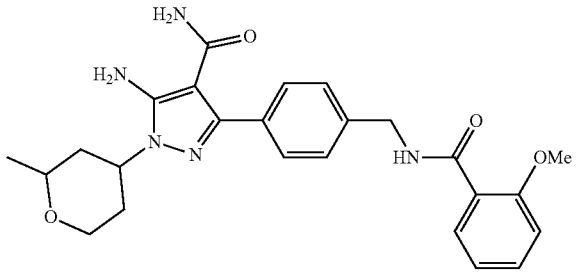 [SMILES: COc1ccccc1C(=O)NCc1ccc(-c2nn(C3CCOC(C)C3)c(N)c2C(N)=O)cc1]

tert-Butyl N-[(2-methyltetrahydropyran-4-ylidene)amino]carbamate

General procedure E, 2-methyldihydro-2H-pyran-4(3H)-one (2.03 mmol) and tert-butyl carbazate (2.23 mmol) gave the titled compound crude (2.04 mmol) as a pale yellow solid. ¹H NMR (400 MHz, CDCl₃, δ): 7.56 (s, 1H), 4.17-4.12 (m, 1H), 3.65-3.59 (m, 1H), 3.53-3.49 (m, 1H), 2.62-2.55 (m, 1H), 2.52-2.47 (m, 1H), 2.24-2.16 (m, 1H), 1.90-1.84 (m, 1H), 1.54 (s, 9H), 1.33-1.27 (m, 3H).

5-Amino-3-(4-bromophenyl)-1-(2-methyltetrahydropyran-4-yl)pyrazole-4-carbonitrile tert-Butyl N-[(2-methyltetrahydropyran-4-ylidene)amino]carbamate (2.03 mmol) in THF (10 mL) and a borane dimethyl sulfide complex solution (2 M in THF, 3.45 mmol) was stirred at RT for 2 h until TLC showed complete consumption of the starting material. Volatiles were removed under reduced pressure. The residue was dissolved in DCM (10 mL) and TFA (10.1 mmol) was added. The reaction mixture was stirred at RT for 1 h and then concentrated under reduced pressure. The residue was dissolved in EtOH (10 mL). 2-[(4-Bromophenyl)-methoxy-methylene]propanedinitrile (0.95 mmol) and triethylamine (4.75 mmol) were added. The reaction mixture was heated to 80° C. for 24 h, cooled and concentrated under reduced pressure. Further purification gave the titled compound (0.25 mmol mixture of diastereoisomers) as a beige solid. UPLC-MS: (ES⁺, Short acidic): 1.85 min, m/z 362.9 [M+2]⁺

N-[[4-[5-Amino-4-cyano-1-(2-methyltetrahydropyran-4-yl)pyrazol-3-yl]phenyl]methyl]-2-methoxybenzamide General procedure K, 5-amino-3-(4-bromophenyl)-1-(2-methyltetrahydropyran-4-yl)pyrazole-4-carbonitrile (0.23 mmol) and potassium trifluoro-[[(2-methoxybenzoyl)amino]methyl]boranuide (0.33 mmol) gave, after purification, the titled compound (0.22 mmol) as a yellow solid. UPLC-MS: (ES⁺, Short acidic): 1.58 min, m/z 446.1 [M+H]⁺

5-Amino-3-[4-[[(2-methoxybenzoyl)amino]methyl]phenyl]-1-(2-methyltetrahydropyran-4-yl)pyrazole-4-carboxamide Procedure L, N-[[4-[5-amino-4-cyano-1-(2-methyltetrahydropyran-4-yl)pyrazol-3-yl]phenyl]methyl]-2-methoxy-benzamide (100 mg, 0.22 mmol) gave, after purification, the titled compound (0.04 mmol) as a white solid. UPLC-MS: (ES⁺, Short acidic): 1.40 and 1.43 min, m/z 464.1 [M+H]⁺. UPLC-MS: (ES⁺, Long acidic): 3.12 and 3.20 min, m/z 464.1 [M+H]⁺. ¹H NMR (400 MHz, DMSO-d₆, δ, mixture of diastereoisomers): 8.74 (t, J=6.3 Hz, 1H), 7.76 (dd, J=7.6, 1.7 Hz, 1H), 7.51-7.41 (m, 5H), 7.16 (d, J=8.2 Hz, 1H), 7.07-7.03 (m, 1H), 6.38 (s, 2H), 4.55 (d, J=6.0 Hz, 2H), 4.42-4.34 (m, 1H), 3.98-3.95 (m, 1H), 3.91 (s, 3H), 3.55-3.44 (m, 2H), 1.92-1.82 (m, 2H), 1.77-1.62 (m, 2H), 1.16-1.12 (m, 3H).

Example 86: 5-amino-3-[4-[[(2-methoxybenzoyl)amino]methyl]phenyl]-1-(3-methyltetrahydropyran-4-yl)pyrazole-4-carboxamide

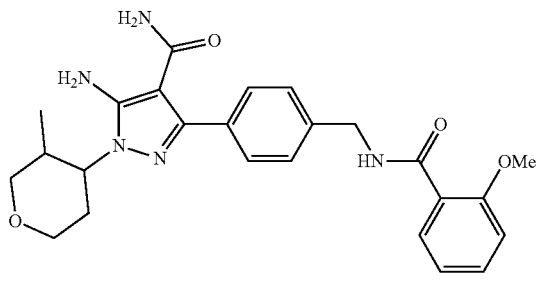 [SMILES: COc1ccccc1C(=O)NCc1ccc(-c2nn(C3CCOCC3C)c(N)c2C(N)=O)cc1]

tert-Butyl N-[(3-methyltetrahydropyran-4-ylidene)amino]carbamate

General procedure E, 3-methyldihydro-2H-pyran-4(3H)-one (1.75 mmol) and tert-butyl carbazate (1.93 mmol) gave the titled compound crude (1.69 mmol) as a white solid. $^1$H NMR (400 MHz, CDCl$_3$, δ): 7.52 (s, 1H), 3.94-3.90 (m, 1H), 3.89-3.84 (m, 1H), 3.75-3.69 (m, 1H), 3.49-3.44 (m, 1H), 2.69-2.61 (m, 1H), 2.52-2.46 (m 1H), 2.31-2.23 (m, 1H), 1.53 (s, 9H), 1.20 (d, J=6.9 Hz, 3H).

5-Amino-3-(4-bromophenyl)-1-(3-methyltetrahydropyran-4-yl)pyrazole-4-carbonitrile tert-Butyl N-[(3-methyltetrahydropyran-4-ylidene)amino]carbamate (1.69 mmol) dissolved in THF (10 mL) and a borane dimethyl sulfide complex solution (2 M in THF, 2.86 mmol) was stirred at RT for 2 h until TLC showed complete consumption of the starting material. Solvent was removed under reduced pressure. The residue was dissolved in DCM (7 mL) and TFA (8.43 mmol) was added. The reaction mixture was stirred at RT for 2 h and then concentrated under reduced pressure. The residue was dissolved in EtOH (10 mL) and 2-[(4-bromophenyl)-methoxy-methylene]propanedinitrile (1.37 mmol) and triethylamine (6.84 mmol) were added. The reaction mixture was heated to 80° C. for 24 h, cooled and concentrated under reduced pressure. Further purification gave the titled compound (1.15 mmol) as a white solid. UPLC-MS: (ES$^+$, Short acidic): 1.83 min and 1.86 min, m/z 362.9 [M+2]$^+$

N-[[4-[5-Amino-4-cyano-1-(3-methyltetrahydropyran-4-yl)pyrazol-3-yl]phenyl]methyl]-2-methoxy-benzamide General procedure K, 5-amino-3-(4-bromophenyl)-1-(3-methyltetrahydropyran-4-yl)pyrazole-4-carbonitrile (0.48 mmol) and potassium trifluoro-[[(2-methoxybenzoyl)amino]methyl]boranuide (0.71 mmol) gave, after purification, the titled compound (0.48 mmol) as a white solid. UPLC-MS: (ES$^+$, Short acidic): 1.59 min and 1.61 min, m/z 446.1 [M+H]$^+$

5-Amino-3-[4-[[(2-methoxybenzoyl)amino]methyl]phenyl]-1-(3-methyltetrahydropyran-4-yl)pyrazole-4-carboxamide General procedure L, N-[[4-[5-amino-4-cyano-1-(3-methyltetrahydropyran-4-yl)pyrazol-3-yl]phenyl]methyl]-2-methoxy-benzamide (0.14 mmol) gave, after purification, the titled compound (0.09 mmol) as a solid. UPLC-MS: (ES$^+$, Short acidic): 1.36 min, 1.38 min, m/z 464.1 [M+H]$^+$. UPLC-MS: (ES$^+$, Short acidic): 3.06 min, 3.13 min, m/z 464.1 [M+H]$^+$. $^1$H NMR (400 MHz, DMSO-d$_6$, δ) mixture of diastereoisomers): 8.74 (t, J=6.0 Hz, 1H), 7.76 (dd, J=7.6, 2.0 Hz, 1H), 7.51-7.41 (m, 5H), 7.15 (d, J=8.2 Hz, 1H), 7.07-7.03 (m, 1H), 6.40 (s, 2H), 4.55 (d, J=6.1 Hz, 2H), 4.52-4.47 (m, 1H), 4.06-4.01 (m, 1H), 3.91 (s, 3H), 3.72 (dd, J=11.3, 3.5 Hz, 1H), 3.58 (dd, J=11.2, 2.6 Hz, 1H), 3.51-3.41 (m, 1H), 2.36-2.29 (m, 1H), 2.17-2.14 (m, 1H), 1.71-1.66 (m, 1H), 0.80 (d, J=7.0 Hz, 3H).

Example 87: 1-cyclobutyl-3-[4-[[(2-methoxybenzoyl)amino]methyl]phenyl]-5-(methylamino)pyrazole-4-carboxamide

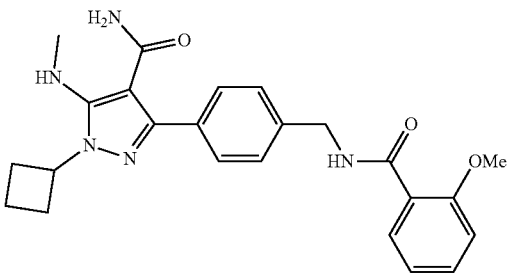 [SMILES: CNc1c(C(N)=O)c(-c2ccc(CNC(=O)c3ccccc3OC)cc2)nn1C1CCC1]

3-(4-Bromophenyl)-1-cyclobutyl-5-(methylamino)pyrazole-4-carbonitrile

5-Amino-3-(4-bromophenyl)-1-cyclobutyl-pyrazole-4-carbonitrile (0.28 mmol) dissolved in MeOH (2.8 mL), paraformaldehyde (0.85 mmol) and sodium methoxide (25 wt % in MeOH, 1.70 mmol) were heated at 70° C. for 1 h and then cooled to RT. Sodium borohydride (2.84 mmol) was added and the reaction mixture was stirred at RT for another 16 h. The reaction mixture was then carefully quenched with water. The aqueous layer was then extracted with DCM (×3). The combined organic layers were filtered over a hydrophobic frit and concentrated under reduced pressure. Further purification afforded the titled compound (0.23 mmol) as an off-white solid. UPLC-MS (ES$^+$, Short acidic): 2.25 min, m/z 331.0 [M]$^+$

N-[[4-[4-Cyano-1-cyclobutyl-5-(methylamino)pyrazol-3-yl]phenyl]methyl]-2-methoxy-benzamide General procedure K, 3-(4-bromophenyl)-1-cyclobutyl-5-(methylamino)pyrazole-4-carbonitrile (0.23 mmol) and potassium trifluoro-[[(2-methoxybenzoyl)amino]methyl]boranuide (0.25 mmol) gave, after purification, the titled compound (0.21 mmol) as a white powder. UPLC-MS (ES$^+$, Short acidic): 2.11 min, m/z 416.1 [M+H]$^+$

1-Cyclobutyl-3-[4-[[(2-methoxybenzoyl)amino]methyl]phenyl]-5-(methylamino)pyrazole-4-carboxamide General procedure L, N-[[4-[4-cyano-1-cyclobutyl-5-(methylamino)pyrazol-3-yl]phenyl]methyl]-2-methoxybenzamide (0.17 mmol) gave, after purification, the titled compound (0.09 mmol) as a white solid. UPLC-MS (ES+, Short acidic): 1.56 min, m/z 434.1 [M+H]+. UPLC-MS (ES+, Long acidic): 3.56 min, m/z 434.1 [M+H]+. 1H NMR (400 MHz, DMSO-d6, δ): 8.72 (t, J=6.0 Hz, 1H), 7.75 (dd, J=7.7, 1.7 Hz, 1H), 7.54 (d, J=8.2 Hz, 2H), 7.51-7.44 (m, 1H), 7.37 (d, J=8.2 Hz, 2H), 7.15 (d, J=8.2 Hz, 1H), 7.07 (br s, 1H), 7.07-7.00 (m, 1H), 6.36 (br s, 1H), 5.92 (q, J=5.6 Hz, 1H), 4.84-4.80 (m, 1H), 4.53 (d, J=6.0 Hz, 2H), 3.90 (s, 3H), 2.81 (d, J=5.4 Hz, 3H), 2.64-2.44 (m, 2H), 2.38-2.24 (m, 2H), 1.83-1.70 (m, 2H).

Example 88: 5-amino-1-cyclopentyl-3-[4-[[(5-fluoro-2-methoxy-benzoyl)amino]methyl]phenyl]pyrazole-4-carboxamide

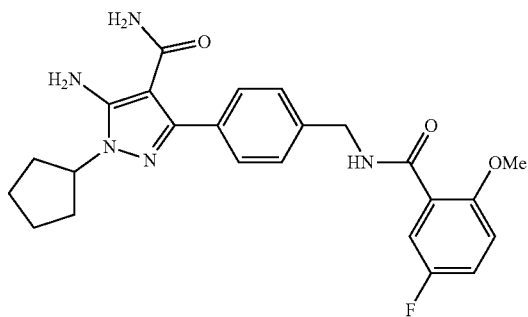

N-[[4-(5-Amino-4-cyano-1-cyclopentyl-pyrazol-3-yl)phenyl]methyl]-5-fluoro-2-methoxy-benzamide General procedure K, potassium trifluoro-[[(5-fluoro-2-methoxy-benzoyl)amino]methyl]boranuide (0.23 mmol) and 5-amino-3-(4-bromophenyl)-1-cyclopentyl-pyrazole-4-carbonitrile (0.17 mmol) gave, after purification, the titled compound (0.17 mmol) as an off-white solid. UPLC-MS (ES+, Short acidic): 1.77 min, m/z 434.1 [M+H]+

5-Amino-1-cyclopentyl-3-[4-[[(5-fluoro-2-methoxy-benzoyl)amino]methyl]phenyl]pyrazole-4-carboxamide General procedure M, N-[[4-(5-amino-4-cyano-1-cyclopentyl-pyrazol-3-yl)phenyl]methyl]-5-fluoro-2-methoxy-benzamide (0.17 mmol) afforded, after purification, the titled compound (0.10 mmol) as a white solid. UPLC-MS (ES+, Short acidic): 1.56 min, m/z 452.1 [M+H]+. UPLC-MS (ES+, Long acidic): 3.62 min, m/z 452.1 [M+H]+. 1H NMR (400 MHz, DMSO-d6, δ): 8.83 (t, J=6.0 Hz, 1H), 7.51 (dd, J=9.2, 3.3 Hz, 1H), 7.44 (d, J=8.2 Hz, 2H), 7.40 (d, J=8.2 Hz, 2H), 7.37-7.30 (m, 1H), 7.18 (dd, J=9.2, 4.3 Hz, 1H), 6.31 (s, 2H), 4.65-4.66 (m, 1H), 4.54 (d, J=6.1 Hz, 2H), 3.89 (s, 3H), 2.02-1.84 (m, 4H), 1.82-1.73 (m, 2H), 1.63-1.52 (m, 2H)

Example 89: 5-amino-1-(3,3-dimethyltetrahydropyran-4-yl)-3-[4-[[(2-methoxybenzoyl)amino]methyl]phenyl]pyrazole-4-carboxamide

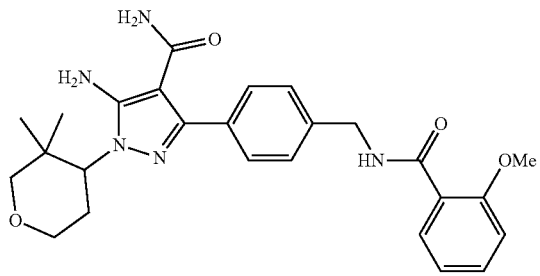 [SMILES: COc1ccccc1C(=O)NCc1ccc(-c2nn(C3CCOCC3(C)C)c(N)c2C(N)=O)cc1]

tert-Butyl N-[(3,3-dimethyltetrahydropyran-4-ylidene)amino]carbamate

General procedure E, 3,3-dimethyldihydro-2H-pyran-4(3H)-one (1.72 mmol) and tert-butyl carbazate (1.89 mmol) gave the titled compound (1.70 mmol) as a white solid. 1H NMR (400 MHz, CDCl3, δ): 7.46 (s, 1H), 3.77 (t, J=6.1 Hz, 2H), 3.46 (s, 2H), 2.36 (t, J=6.0 Hz, 2H), 1.50 (s, 9H), 1.19 (s, 6H).

[(3,3-Dimethyltetrahydropyran-4-yl)amino]ammonium; 2,2,2-trifluoroacetate tert-Butyl N-[(3,3-dimethyltetrahydropyran-4-ylidene)amino]carbamate (1.69 mol) dissolved in THF (10 mL) and a borane dimethyl sulfide complex solution (2 M in THF, 2.88 mmol) was stirred at RT for 2 h until TLC showed complete consumption of the starting material. Volatiles were removed under reduced pressure. The residue was dissolved in DCM (7 mL) and TFA (8.46 mmol) was added. The reaction mixture was stirred at RT for 2 h. The volatiles were then removed under reduced pressure to afford the titled compound crude (1.70 mmol). 1H NMR (400 MHz, DMSO-d6, δ): 3.93-3.89 (m, 1H), 3.33 (d, J=11.2 Hz, 1H), 3.29-3.22 (m, 1H), 3.01 (d, J=11.5 Hz, 1H), 2.71-2.67 (m, 1H), 1.88-1.84 (m, 1H), 1.53-1.43 (m, 1H), 0.88 (d, J=11.2 Hz, 6H).

(5-Amino-3-(4-bromophenyl)-1-(3,3-dimethyltetrahydropyran-4-yl)pyrazole-4-carbonitrile General procedure H, 2-[(4-bromophenyl)-methoxymethylene]propanedinitrile (0.76 mmol) and [(3,3-dimethyltetrahydropyran-4-yl)amino]ammonium; 2,2,2-trifluoroacetate (0.91 mmol) gave, after purification, the titled compound (0.72 mmol) as a white solid. UPLC-MS: (ES+, Short acidic): 1.91 min, m/z 376.9 [M+2]+

N-[[4-[5-Amino-4-cyano-1-(3,3-dimethyltetrahydropyran-4-yl)pyrazol-3-yl]phenyl]methyl]-2-methoxybenzamide General procedure K, 5-amino-3-(4-bromophenyl)-1-(3,3-dimethyltetrahydropyran-4-yl)pyrazole-4-carbonitrile (0.27 mmol) and potassium trifluoro-[[(2-methoxybenzoyl)amino]methyl]boranuide (0.40 mmol) gave, after purification, the titled compound (0.21 mmol) as a yellow solid. UPLC-MS: (ES+, Short acidic): 1.64 min, m/z 460.1 [M+H]+

5-Amino-1-(3,3-dimethyltetrahydropyran-4-yl)-3-[4-[[(2-methoxybenzoyl)amino]methyl]phenyl]pyrazole-4-carboxamide General procedure L, N-[[4-[5-amino-4-cyano-1-(3,3-dimethyltetrahydropyran-4-yl)pyrazol-3-yl]phenyl]methyl]-2-methoxy-benzamide (0.21 mmol) gave, after purification, the titled compound (0.13 mmol) as a solid. UPLC-MS: (ES+, Short acidic): 1.44 min, m/z 478.1 [M+H]+. UPLC-MS: (ES+, Long acidic): 3.30 min, m/z 478.2 [M+H]+. $^1$H NMR (400 MHz, DMSO-$d_6$, δ): 8.73 (t, J=6.1 Hz, 1H), 7.75 (dd, J=7.6, 1.7 Hz, 1H), 7.50-7.40 (m, 5H), 7.15 (d, J=8.3 Hz, 1H), 7.05-7.02 (m, 1H), 6.40 (s, 2H), 4.54 (d, J=6.5 Hz, 2H), 4.21 (dd, J=11.1, 4.0 Hz, 1H), 4.04-3.90 (m, 4H), 3.51-3.39 (m, 2H), 3.20 (d, J=11.1 Hz, 1H), 2.39-2.29 (m, 1H), 1.58-1.54 (m, 1H), 1.01 (s, 3H), 0.81 (s, 3H).

Example 90: 5-amino-3-[4-[[(2-methoxybenzoyl)amino]methyl]phenyl]-1-(2,2,6,6-tetramethyltetrahydropyran-4-yl)pyrazole-4-carboxamide

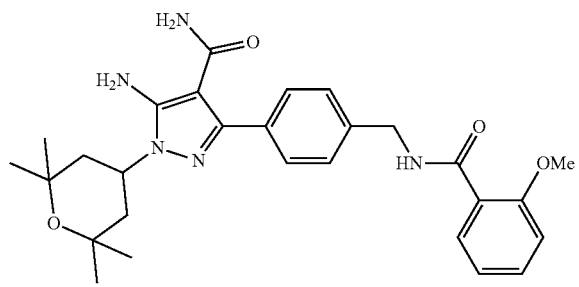 [SMILES: COc1ccccc1C(=O)NCc1ccc(-c2nn(C3CC(C)(C)OC(C)(C)C3)c(N)c2C(N)=O)cc1]

tert-Butyl N-[(2,2,6,6-tetramethyltetrahydropyran-4-ylidene)amino]carbamate

General procedure E, 2,2,6,6-tetramethyloxan-4-one (1.60 mmol) and tert-butyl carbazate (2.44 mmol) gave, after purification, the titled compound (1.44 mmol) as an off-white solid. $^1$H NMR (400 MHz, CDCl$_3$, δ): 7.47 (s, 1H), 2.52 (s, 2H), 2.25 (s, 2H), 1.51 (s, 9H), 1.29 (s, 6H), 1.23 (s, 6H).

5-Amino-3-(4-bromophenyl)-1-(2,2,6,6-tetramethyltetrahydropyran-4-yl)pyrazole-4-carbonitrile tert-Butyl N-[(2,2,6,6-tetramethyltetrahydropyran-4-ylidene)amino]carbamate (1.47 mmol) was dissolved in THF (15 mL) and a borane dimethyl sulfide complex solution (2 M in THF, 4.40 mmol) was added at 0° C. The reaction mixture was stirred at RT for 16 h. Volatiles were removed under reduced pressure. The residue was dissolved in DCM (5 mL) and TFA (36.10 mmol) was added. The reaction mixture was stirred at RT for 1 h and then concentrated under reduced pressure. The residue was dissolved in EtOH (10 mL) and 2-[(4-bromophenyl)-methoxy-methylene]propanedinitrile (0.76 mmol) and triethylamine (3.80 mmol) were added. The reaction mixture was heated to 80° C. for 16 h, cooled and concentrated under reduced pressure.

Further purification gave the titled compound (0.19 mmol) as a brown solid. UPLC-MS: (ES+, Short acidic): 2.09 min, m/z 405.0 [M+2]+

N-[[4-[5-Amino-4-cyano-1-(2,2,6,6-tetramethyltetrahydropyran-4-yl)pyrazol-3-yl]phenyl]methyl]-2-methoxy-benzamide General procedure K, 5-amino-3-(4-bromophenyl)-1-(2,2,6,6-tetramethyltetrahydropyran-4-yl)pyrazole-4-carbonitrile (0.19 mmol) and potassium trifluoro-[[(2-methoxybenzoyl)amino]methyl]boranuide (0.27 mmol) gave, after purification, the titled compound (0.08 mmol) as a yellow solid. UPLC-MS: (ES+, Short acidic): 1.78 min, m/z 488.1 [M+H]+

5-Amino-3-[4-[[(2-methoxybenzoyl)amino]methyl]phenyl]-1-(2,2,6,6-tetramethyltetrahydropyran-4-yl)pyrazole-4-carboxamide General procedure L, N-[[4-[5-amino-4-cyano-1-(2,2,6,6-tetramethyltetrahydropyran-4-yl)pyrazol-3-yl]phenyl]methyl]-2-methoxy-benzamide (0.08 mmol) gave, after purification, the titled compound (0.03 mmol) as a white solid. UPLC-MS: (ES+, Short acidic): 1.57 min, m/z 506.2 [M+H]+. UPLC-MS: (ES+, Long acidic): 3.63 min, m/z 506.2 [M+H]+. $^1$H NMR (400 MHz, DMSO-$d_6$, δ): 8.73 (t, J=6.1 Hz, 1H), 7.75 (dd, J=7.6, 1.7 Hz, 1H), 7.50-7.39 (m, 5H), 7.15 (d, J=7.9 Hz, 1H), 7.06-7.02 (m, 1H), 6.48 (s, 2H), 4.75-4.67 (m, 1H), 4.54 (d, J=6.2 Hz, 2H), 3.90 (s, 3H), 1.74 (d, J=7.8 Hz, 4H), 1.34 (s, 6H), 1.15 (s, 6H).

Example 91: 3-[4-[[(2-methoxybenzoyl)amino]methyl]phenyl]-5-(methylamino)-1-tetrahydropyran-4-yl-pyrazole-4-carboxamide

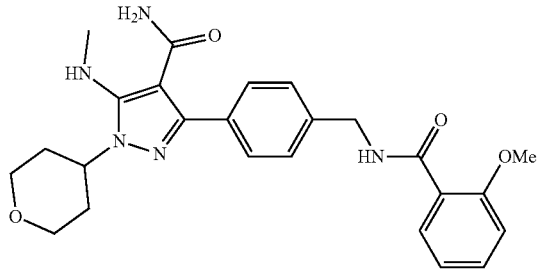 [SMILES: CNc1c(C(N)=O)c(-c2ccc(CNC(=O)c3ccccc3OC)cc2)nn1C1CCOCC1]

3-(4-Bromophenyl)-5-(methylamino)-1-tetrahydropyran-4-yl-pyrazole-4-carbonitrile 5-Amino-3-(4-bromophenyl)-1-tetrahydropyran-4-yl-pyrazole-4-carbonitrile (0.86 mmol) dissolved in MeOH (8 mL), paraformaldehyde (2.57 mmol) and sodium methoxide (25 wt % in MeOH, 5.15 mmol) were heated at 70° C. for 1 h, then allowed to cool back down to RT. Sodium borohydride (8.58 mmol) was added and the reaction was stirred at RT for 16 h, then carefully quenched with water. The aqueous layer was extracted with DCM (3×20 mL), and the combined organic layers were filtered over a hydrophobic frit, and concentrated under reduced pressure. Purification gave the titled compound (0.65 mmol) as a white solid. UPLC-MS (ES+, Short acidic): 1.80 min, m/z 362.9 [M+2]+

N-[[4-[4-Cyano-5-(methylamino)-1-tetrahydropyran-4-yl-pyrazol-3-yl]phenyl]methyl]-2-methoxy-benzamide General procedure K, 3-(4-bromophenyl)-5-(methylamino)-1-tetrahydropyran-4-yl-pyrazole-4-carbonitrile (0.65 mmol) and potassium trifluoro-[[(2-methoxybenzoyl)amino]methyl]boranuide (0.71 mmol) gave, after purification, the titled compound (0.44 mmol) as an off-white solid. UPLC-MS (ES+, Short acidic): 1.57 min, m/z 446.1 [M+H]+

3-[4-[[(2-Methoxybenzoyl)amino]methyl]phenyl]-5-(methylamino)-1-tetrahydropyran-4-yl-pyrazole-4-carboxamide General procedure L, N-[[4-[4-cyano-5-(methylamino)-1-tetrahydropyran-4-yl-pyrazol-3-yl]phenyl]methyl]-2-methoxy-benzamide (0.44 mmol) gave, after purification, the titled compound (0.04 mmol) as a white solid. UPLC-MS (ES+, Short acidic): 1.36 min, m/z 464.1 [M+H]+. UPLC-MS (ES+, Long acidic): 3.08 min, m/z 464.1 [M+H]+. $^1$H NMR (400 MHz, DMSO-$d_6$, δ): 8.71 (t, J=6.6 Hz, 1H), 7.76 (dd, J=7.7, 1.8 Hz, 1H), 7.54 (d, J=8.1 Hz, 2H), 7.48 (td, J=8.4, 1.8 Hz, 1H), 7.35 (d, J=8.2 Hz, 2H), 7.15 (d, J=8.3 Hz, 1H), 7.04 (td, J=8.1, 0.7 Hz, 1H), 6.7 (br s, 1H), 5.80 (q, J=5.2 Hz, 1H), 4.53 (d, J=6.0 Hz, 2H), 4.42-4.34 (m, 1H), 3.97 (dd, J=11.2, 3.8 Hz, 2H), 3.90 (s, 3H), 3.53-3.40 (m, 2H), 2.84 (d, J=5.6 Hz, 3H), 2.12-2.00 (m, 2H), 1.80-1.77 (m, 2H).

Example 92: 5-amino-1-cyclopentyl-3-[3-fluoro-4-[[(2-methoxy-5-methyl-benzoyl)amino]methyl]phenyl]pyrazole-4-carboxamide

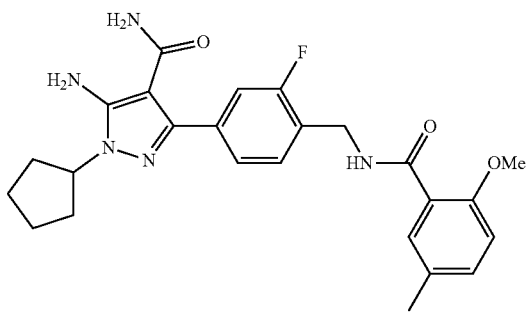 [SMILES: COc1ccc(C)cc1C(=O)NCc1ccc(-c2nn(C3CCCC3)c(N)c2C(N)=O)cc1F]

N-[(4-Bromo-2-fluoro-phenyl)methyl]-2-methoxy-5-methyl-benzamide

A solution of (4-bromo-2-fluoro-phenyl)methanamine (5.00 mmol) in THF (4 mL), a propylphosphonic anhydride solution (50 wt % in EtOAc, 7.50 mmol) in THF (6 mL), 2-methoxy-5-methylbenzoic acid (6.04 mmol), and N,N-diisopropylethylamine (8.88 mmol) was stirred at 80° C. for 18 h. The reaction was cooled to RT and partitioned between EtOAc and a saturated aqueous solution of NH$_4$Cl. The organic layer was washed with brine, dried over sodium sulfate, filtered and concentrated under reduced pressure. The residue was purified to give the titled compound (3.51 mmol). UPLC-MS (ES+, Short acidic): 2.05 min, m/z 353.9 [M+2]+

N-[[2-Fluoro-4-(4,4,5,5-tetramethyl-1,3,2-dioxaborolan-2-yl)phenyl]methyl]-2-methoxy-5-methyl-benzamide General procedure R, N-[(4-bromo-2-fluoro-phenyl)methyl]-2-methoxy-5-methyl-benzamide (3.51 mmol) gave, after purification, the titled compound (3.51 mmol). UPLC-MS (ES+, Short acidic): 2.18 min, m/z 400.1 [M+H]+

N-[[4-(5-Amino-4-cyano-1H-pyrazol-3-yl)-2-fluoro-phenyl]methyl]-2-methoxy-5-methyl-benzamide General procedure D, N-[[2-fluoro-4-(4,4,5,5-tetramethyl-1,3,2-dioxaborolan-2-yl)phenyl]methyl]-2-methoxy-5-methyl-benzamide (3.51 mmol) gave, after purification, the titled compound (1.03 mmol). UPLC-MS (ES+, Short acidic): 1.86 min, m/z 380.0 [M+H]+

N-[[4-(5-Amino-4-cyano-1-cyclopentyl-pyrazol-3-yl)-2-fluoro-phenyl]methyl]-2-methoxy-5-methyl-benzamide Cesium carbonate (1.34 mmol), N-[[4-(5-amino-4-cyano-1H-pyrazol-3-yl)-2-fluoro-phenyl]methyl]-2-methoxy-5-methyl-benzamide (1.03 mmol) and bromocyclopentane (1.13 mmol) in DMF (10 mL) were stirred at 80° C. for 3.5 h, then cooled to RT and partitioned between water and EtOAc. The organic layer was washed with brine, dried over sodium sulfate, filtered and concentrated under reduced pressure. Further purification gave the titled compound (0.07 mmol). UPLC-MS (ES+, Short acidic): 2.21 min, m/z 448.1 [M+H]+

5-Amino-1-cyclopentyl-3-[3-fluoro-4-[[(2-methoxy-5-methyl-benzoyl)amino]methyl]phenyl]pyrazole-4-carboxamide General procedure L, N-[[4-(5-amino-4-cyano-1-cyclopentyl-pyrazol-3-yl)-2-fluoro-phenyl]methyl]-2-methoxy-5-methyl-benzamide (0.07 mmol) gave, after purification, the titled compound (0.02 mmol, 24% yield). UPLC-MS (ES+, Short acidic): 2.10 min, m/z 466.2 [M+H]+. UPLC-MS (ES+, Long acidic): 3.88 min, m/z 466.1 [M+H]+. $^1$H NMR (400 MHz, DMSO-$d_6$, δ): 8.68 (t, J=6.0 Hz, 1H), 7.57 (d, J=2.3 Hz, 1H), 7.41 (t, J=7.9 Hz, 1H), 7.34-7.30 (dd, J=7.9, 1.5 Hz, 1H), 7.30-7.28 (m, 1H), 7.28-7.25 (m, 1H), 7.05 (d, J=8.5 Hz, 1H), 6.25 (s, 2H), 4.65-4.60 (m, 1H), 4.56 (d, J=6.0 Hz, 2H), 3.87 (s, 3H), 2.27 (s, 3H), 2.03-1.85 (m, 4H), 1.83-1.72 (m, 2H), 1.65-1.52 (m, 2H).

Example 93: 5-amino-1-cyclopentyl-3-[3-fluoro-4-[[(2-methoxybenzoyl)amino]methyl]phenyl]pyrazole-4-carboxamide

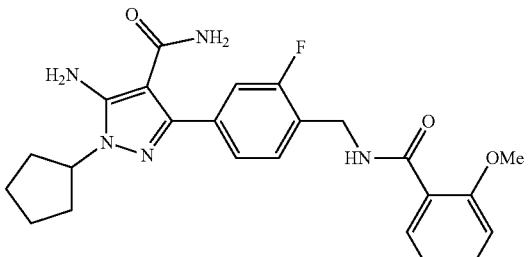

2-[(4-Bromo-3-fluoro-phenyl)-hydroxy-methylene]propanedinitrile

General procedure W, 4-bromo-3-fluorobenzoyl chloride (5.29 mmol) and malononitrile (0.37 mL, 5.81 mmol) gave the titled compound (5.15 mmol) as a pale brown solid. UPLC-MS (ES+, Short acidic): 1.32 min, m/z 266.9 [M]+

2-[(4-Bromo-3-fluoro-phenyl)-methoxy-methylene]propanedinitrile

General procedure X, 2-[(4-bromo-3-fluoro-phenyl)-hydroxy-methylene]propanedinitrile (5.11 mmol) and dimethyl sulfate (15.3 mmol) gave, after purification, the titled compound (1.62 mmol) as a white solid. $^1$H NMR (400 MHz, DMSO-$d_6$, δ): 8.06-8.02 (m, 1H), 7.86 (dd, J=9.1, 1.9 Hz, 1H), 7.54-7.52 (m, 1H), 3.92 (s, 3H).

5-Amino-3-(4-bromo-3-fluoro-phenyl)-1-cyclopentyl-pyrazole-4-carbonitrile

General procedure H, 2-[(4-bromo-3-fluoro-phenyl)-methoxy-methylene]propanedinitrile (200 mg, 0.71 mmol) and cyclopentylhydrazine hydrochloride (117 mg, 0.85 mmol) gave, after purification, the titled compound (0.48 mmol) as a white solid. UPLC-MS (ES+, Short acidic): 2.06 min, m/z 348.9 [M]+

N-[[4-(5-Amino-4-cyano-1-cyclopentyl-pyrazol-3-yl)-2-fluoro-phenyl]methyl]-2-methoxy-benzamide General procedure K, 5-amino-3-(4-bromo-3-fluoro-phenyl)-1-cyclopentyl-pyrazole-4-carbonitrile (0.46 mmol) and potassium trifluoro-[[(2-methoxybenzoyl)amino]methyl]boranuide (0.69 mmol) gave, after purification, the titled compound (0.19 mmol) as a pale brown solid. UPLC-MS (ES+, Short acidic): 1.80 min, m/z 434.1 [M+H]+

5-Amino-1-cyclopentyl-3-[3-fluoro-4-[[(2-methoxybenzoyl)amino]methyl]phenyl]pyrazole-4-carboxamide General procedure M, N-[[4-(5-amino-4-cyano-1-cyclopentyl-pyrazol-3-yl)-2-fluoro-phenyl]methyl]-2-methoxy-benzamide (0.18 mmol) gave, after purification, the titled compound (0.07 mmol) as a light brown solid. UPLC-MS (ES+, Short acidic): 1.58 min, m/z 452.1 [M+H]+. UPLC-MS (ES+, Long acidic): 3.66 min, m/z 452.1 [M+H]+. $^1$H NMR (400 MHz, DMSO-$d_6$, δ): 8.71 (t, J=6.1 Hz, 1H), 7.75 (dd, J=7.6, 1.8 Hz, 1H), 7.51-7.47 (m, 1H), 7.43 (t, J=7.7 Hz, 1H), 7.34-7.27 (m, 2H), 7.16 (d, J=8.2 Hz, 1H), 7.07-7.03 (m, 1H), 6.26 (s, 2H), 4.68-4.60 (m, 1H), 4.57 (d, J=6.0 Hz, 2H), 3.91 (s, 3H), 2.01-1.88 (m, 4H), 1.84-1.76 (m, 2H), 1.63-1.55 (m, 2H).

Example 94: 5-amino-1-[trans-4-hydroxytetrahydrofuran-3-yl]-3-[4-[[(2-methoxybenzoyl)amino]methyl]phenyl]pyrazole-4-carboxamide

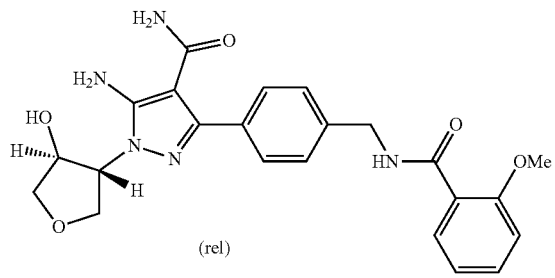 [SMILES: COc1ccccc1C(=O)NCc1ccc(-c2nn([C@@H]3COC[C@H]3O)c(N)c2C(N)=O)cc1]

trans-4-Hydrazinotetrahydrofuran-3-ol

To a solution of 3,6-dioxabicyclo[3.1.0]hexane (11.62 mmol) in EtOH (39 mL), cooled to 0° C., was added dropwise hydrazine hydrate (55-60% in water, 29.04 mmol). The reaction was stirred at RT for 10 min and then heated at 60° C. for 16 h. The reaction was concentrated under reduced pressure to give crude the titled compound (11.61 mmol). $^1$H NMR (400 MHz, DMSO-$d_6$, δ): 4.06-4.02 (m, 1H), 3.80-3.71 (m, 2H), 3.52-3.43 (m, 2H), 3.07-3.02 (m, 1H).

5-Amino-3-(4-bromophenyl)-1-[trans-4-hydroxytetrahydrofuran-3-yl]pyrazole-4-carbonitrile General procedure H, 2-[(4-bromophenyl)-methoxymethylene]propanedinitrile (5.7 mmol) and trans-4-hydrazinotetrahydrofuran-3-ol (6.97 mmol) gave, after purification, the titled compound (5.09 mmol). $^1$H NMR (400 MHz, DMSO-$d_6$, δ): 7.77-7.64 (m, 4H), 6.85 (m, 2H), 5.52 (d, J=4.1 Hz, 1H), 4.71-4.66 (m, 1H), 4.61-4.55 (m, 1H), 4.17-4.11 (m, 1H), 4.09-4.04 (m, 1H), 3.82-3.77 (m, 1H), 3.67-3.61 (m, 1H).

5-Amino-3-(4-bromophenyl)-1-[trans-4-[tert-butyl(dimethyl)silyl]oxytetrahydrofuran-3-yl]pyrazole-4-carbonitrile To a solution of 5-amino-3-(4-bromophenyl)-1-[trans-4-hydroxytetrahydrofuran-3-yl]pyrazole-4-carbonitrile (1.43 mmol) in DMF (7.2 mL) was added imidazole (3.44 mmol), and tert-butyl-chlorodimethylsilane (3.15 mmol). The reaction was heated at 50° C. for 16 h, cooled and then partitioned between water and EtOAc. The organic layer was washed with water, dried over sodium sulfate filtered and then concentrated under reduced pressure. Further purification gave the titled compound (0.54 mmol). UPLC-MS (ES+, Short acidic): 2.27 min, m/z 465.0 [M+2]+

N-[[4-[5-Amino-1-[trans-4-[tert-butyl(dimethyl)silyl]oxytetrahydrofuran-3-yl]-4-cyano-pyrazol-3-yl]phenyl]methyl]-2-methoxy-benzamide General procedure K, potassium trifluoro-[[(2-methoxybenzoyl)amino]methyl]boranuide (0.76 mmol) and 5-amino-3-(4-bromophenyl)-1-[trans-4-[tert-butyl(dimethyl)silyl]oxytetrahydrofuran-3-yl]pyrazole-4-carbonitrile (0.54 mmol) gave, after purification, the titled compound (0.39 mmol, 72% yield). UPLC-MS (ES+, Short acidic): 2.00 min, m/z 548.2 [M]+

5-Amino-1-[trans-4-hydroxytetrahydrofuran-3-yl]-3-[4-[[(2-methoxybenzoyl)amino]methyl]phenyl]pyrazole-4-carboxamide General procedure M, N-[[4-[5-amino-1-[trans-4-[tert-butyl(dimethyl)silyl]oxytetrahydrofuran-3-yl]-4-cyano-pyrazol-3-yl]phenyl]methyl]-2-methoxy-benzamide (0.23 mmol) gave, after purification, the titled compound (0.04 mmol). UPLC-MS (ES+, Long acidic): 2.74 min, m/z 452.1 [M+H]+. $^1$H NMR (400 MHz, DMSO-$d_6$, δ): 8.74 (t, J=6.1 Hz, 1H), 7.75 (dd, J=7.7, 1.8 Hz, 1H), 7.51-7.39 (m, 5H), 7.15 (d, J=8.3 Hz, 1H), 7.06-7.02 (m, 1H), 6.40 (br s, 2H), 5.46 (d, J=4.2 Hz, 1H), 4.69-4.62 (m, 1H), 4.57-4.51 (m, 3H), 4.15 (dd, J=9.0, 6.9 Hz, 1H), 4.00 (dd, J=9.3, 5.3 Hz, 1H), 3.90 (s, 3H), 3.81 (dd, J=9.2, 4.6 Hz, 1H), 3.62 (dd, J=9.1, 2.2 Hz, 1H).

Example 95: 5-amino-1-[3-fluorotetrahydropyran-4-yl]-3-[4-[[(2-methoxybenzoyl)amino]methyl]phenyl]pyrazole-4-carboxamide (Isomer 1)

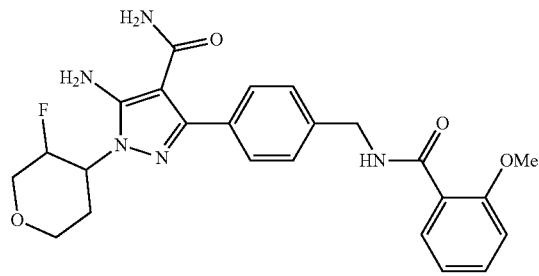

tert-Butyl N-[(3-fluorotetrahydropyran-4-ylidene)amino]carbamate

General procedure E, 3-fluorodihydro-2H-pyran-4(3H)-one (1.48 mmol) and tert-butyl carbazate (2.22 mmol) gave crude the titled compound (1.48 mmol). $^1$H NMR (400 MHz, CDCl$_3$, δ): 7.79 (s, 1H), 5.00 (d, J=47.8 Hz, 1H), 4.33 (d, J=13.7 Hz, 1H), 4.20-4.13 (m, 1H), 3.79-3.63 (m, 1H), 3.54-3.45 (m, 1H), 2.68-2.57 (m, 1H), 2.53-2.45 (m, 1H), 1.54 (s, 9H).

5-Amino-3-(4-bromophenyl)-1-(3-fluorotetrahydro-pyran-4-yl)pyrazole-4-carbonitrile General procedure O, tert-butyl N-[(3-fluorotetrahydro-pyran-4-ylidene)amino]carbamate (1.48 mmol) in THF (4.9 mL) and 2-[(4-bromophenyl)-methoxy-methylene]propane-dinitrile (0.99 mmol) gave, after purification, the titled compound (isomer 1, 0.50 mmol) and the titled compound (isomer 2, 0.22 mmol). UPLC-MS (ES+, Short acidic, isomer 1): 1.66 min, m/z 366.9 [M+2]+. UPLC-MS (ES+, Short acidic, isomer 2): 1.77 min, m/z 366.9 [M+2]+

N-[[4-[5-Amino-4-cyano-1-(3-fluorotetrahydropy-ran-4-yl)pyrazol-3-yl]phenyl]methyl]-2-methoxy-benzamide (Isomer 1)

General procedure K, potassium trifluoro-[[(2-methoxybenzoyl)amino]methyl]boranuide (0.70 mmol) and 5-amino-3-(4-bromophenyl)-1-(3-fluorotetrahydropyran-4-yl)pyrazole-4-carbonitrile (isomer 1, 0.50 mmol) gave, after purification, the titled compound (isomer 1, 0.40 mmol). UPLC-MS (ES+, Short acidic): 1.47 min, m/z 450.1 [M+H]+

5-Amino-1-[3-fluorotetrahydropyran-4-yl]-3-[4-[[(2-methoxybenzoyl)amino]methyl]phenyl]pyrazole-4-carboxamide (Isomer 1)

General procedure L, N-[[4-[5-amino-4-cyano-1-(3-fluorotetrahydropyran-4-yl)pyrazol-3-yl]phenyl]methyl]-2-methoxy-benzamide (isomer 1, 0.40 mmol) gave, after purification, the titled compound (isomer 1, 0.13 mmol) as a white solid. UPLC-MS (ES+, Long acidic): 2.92 min, m/z 468.1 [M+H]+. $^1$H NMR (400 MHz, DMSO-$d_6$, δ): 8.73 (t, J=6.2 Hz, 1H), 7.75 (dd, J=7.6, 1.7 Hz, 1H), 7.51-7.39 (m, 5H), 7.15 (d, J=8.1 Hz, 1H), 7.05-7.03 (m, 1H), 6.45 (br s, 2H), 4.94-4.74 (m, 1H), 4.62-4.48 (m, 3H), 4.09-3.98 (m, 2H), 3.90 (s, 3H), 3.72-3.44 (m, 2H), 2.63 (dd, J=13.0, 4.9 Hz, 1H), 1.81-1.71 (m, 1H).

Example 96: 5-amino-1-[3-fluorotetrahydropyran-4-yl]-3-[4-[[(2-methoxybenzoyl)amino]methyl]phenyl]pyrazole-4-carboxamide (Isomer 2)

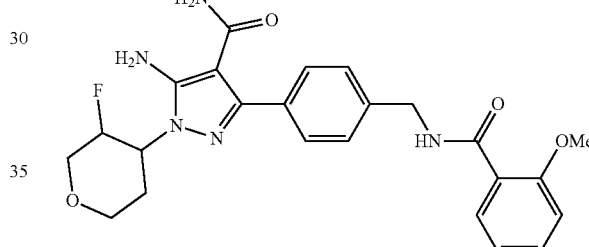

N-[[4-[5-Amino-4-cyano-1-(3-fluorotetrahydropy-ran-4-yl)pyrazol-3-yl]phenyl]methyl]-2-methoxy-benzamide (Isomer 2)

General procedure K, potassium trifluoro-[[(2-methoxybenzoyl)amino]methyl]boranuide (0.31 mmol) and 5-amino-3-(4-bromophenyl)-1-(3-fluorotetrahydropyran-4-yl)pyrazole-4-carbonitrile (isomer 2, 0.22 mmol) gave, after purification, the titled compound (isomer 2, 0.16 mmol, 72% yield). UPLC-MS (ES+, Short acidic): 1.54 min, m/z 450.1 [M+H]+

5-Amino-1-[3-fluorotetrahydropyran-4-yl]-3-[4-[[(2-methoxybenzoyl)amino]methyl]phenyl]pyrazole-4-carboxamide (Isomer 2)

General procedure L, N-[[4-[5-amino-4-cyano-1-(3-fluorotetrahydropyran-4-yl)pyrazol-3-yl]phenyl]methyl]-2-methoxy-benzamide (isomer 2, 0.16 mmol) gave after purification by flash column chromatography on silica gel eluting with 0-10% MeOH in DCM and further recrystallization from DCM, 5-amino-1-[3-fluorotetrahydropyran-4-yl]-3-[4-[[(2-methoxybenzoyl)amino]methyl]phenyl]pyrazole-4-carboxamide (isomer 2, 0.02 mmol). UPLC-MS (ES+, Long acidic): 3.09 min, m/z 468.1 [M+H]+. $^1$H NMR (400 MHz, DMSO-$d_6$, δ): 8.74 (t, J=6.1 Hz, 1H), 7.76 (dd, J=7.6, 1.6 Hz, 1H), 7.52-7.40 (m, 5H), 7.16 (d, J=8.2 Hz, 1H), 7.04 (t, J=7.7 Hz, 1H), 6.45 (br s, 2H), 5.03-4.82 (m, 1H), 4.65-4.52 (m, 3H), 4.18 (dd, J=10.6, 5.4 Hz, 1H), 3.97-3.91 (m, 1H), 3.91 (s, 3H), 3.49-3.38 (m, 1H), 3.33 (m, 1H), 2.09-1.91 (m, 2H).

Example 97: 3-[4-[[(2-methoxybenzoyl)amino]methyl]phenyl]-5-(methylamino)-1-tetrahydrofuran-3-yl-pyrazole-4-carboxamide

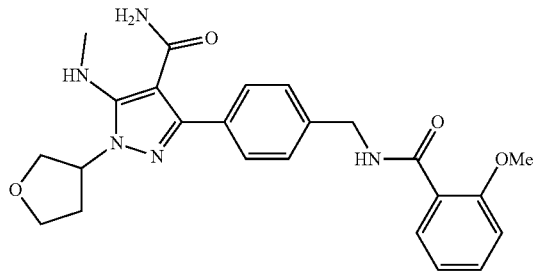 [SMILES: CNc1c(C(N)=O)c(-c2ccc(CNC(=O)c3ccccc3OC)cc2)nn1C1CCOC1]

3-(4-Bromophenyl)-5-(methylamino)-1-tetrahydrofuran-3-yl-pyrazole-4-carbonitrile Following general procedure W, 5-amino-3-(4-bromophenyl)-1-tetrahydrofuran-3-yl-pyrazole-4-carbonitrile (100 mg, 0.30 mmol) gave, after purification, the titled compound (64 mg, 0.18 mmol, 61% yield) as a white solid. UPLC-MS: (ES$^+$, Short acidic): 1.80 min, m/z 348.9 [M+2]$^+$ N-[[4-[4-Cyano-5-(methylamino)-1-tetrahydrofuran-3-yl-pyrazol-3-yl]phenyl]methyl]-2-methoxy-benzamide General procedure K, 3-(4-bromophenyl)-5-(methylamino)-1-tetrahydrofuran-3-yl-pyrazole-4-carbonitrile (0.18 mmol) and potassium trifluoro-[[(2-methoxybenzoyl)amino]methyl]boranuide (0.27 mmol) gave, after purification, the titled compound (0.18 mmol) as a yellow solid. UPLC-MS: (ES$^+$, Short acidic): 1.58 min, m/z 432.1 [M+H]$^+$ 3-[4-[[(2-Methoxybenzoyl)amino]methyl]phenyl]-5-(methylamino)-1-tetrahydrofuran-3-yl-pyrazole-4-carboxamide Following general procedure L, N-[[4-[4-cyano-5-(methylamino)-1-tetrahydrofuran-3-yl-pyrazol-3-yl]phenyl]methyl]-2-methoxy-benzamide (0.13 mmol) gave, after purification, the titled compound (0.03 mmol) as a white solid. UPLC-MS: (ES$^+$, Short acidic): 1.36 min, m/z 450.1 [M+H]$^+$. UPLC-MS: (ES$^+$, Long acidic): 3.08 min, m/z 450.1 [M+H]$^+$. $^1$H NMR (400 MHz, DMSO-d$_6$, δ): 8.73 (t, J=6.1 Hz, 1H), 7.75 (dd, J=7.6, 1.6 Hz, 1H), 7.54 (d, J=8.2 Hz, 2H), 7.51-7.44 (m, 1H), 7.36 (d, J=8.2 Hz, 2H), 7.15 (d, J=8.3 Hz, 1H), 7.06-7.02 (m, 1H), 5.92 (q, J=5.4 Hz, 1H), 5.04-4.95 (m, 1H), 4.53 (d, J=5.9 Hz, 2H), 4.07-3.95 (m, 2H), 3.90 (s, 3H), 3.88-3.79 (m, 2H), 2.85 (d, J=5.5 Hz, 3H), 2.33-2.24 (m, 2H).

Example 98: 5-amino-1-(3,4-difluorophenyl)-3-[4-[[(2-methoxybenzoyl)amino]methyl]phenyl]pyrazole-4-carboxamide

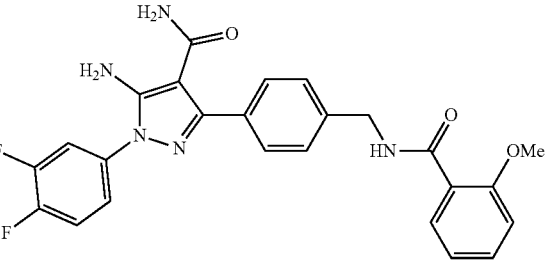

5-Amino-3-(4-bromophenyl)-1-(3,4-difluorophenyl)pyrazole-4-carbonitrile

General procedure H, 2-[(4-bromophenyl)-methoxymethylene]propanedinitrile (0.57 mmol) and (3,4-difluorophenyl)hydrazinium chloride (0.68 mmol) gave, after purification, the titled compound (0.30 mmol, 53% yield) as a white solid. UPLC-MS (ES$^+$, Short acidic): 1.96 min, m/z 376.9 [M+2]$^+$ N-[[4-[5-Amino-4-cyano-1-(3,4-difluorophenyl)pyrazol-3-yl]phenyl]methyl]-2-methoxy-benzamide General procedure K, 5-amino-3-(4-bromophenyl)-1-(3,4-difluorophenyl)pyrazole-4-carbonitrile (0.30 mmol) and potassium trifluoro-[[(2-methoxybenzoyl)amino]methyl]boranuide (0.46 mmol) gave, after purification, the titled compound (0.08 mmol) as a beige solid. UPLC-MS (ES$^+$, Short acidic): 1.71 min, m/z 460.1 [M+H]$^+$ 5-Amino-1-(3,4-difluorophenyl)-3-[4-[[(2-methoxybenzoyl)amino]methyl]phenyl]pyrazole-4-carboxamide General procedure M, N-[[4-[5-amino-4-cyano-1-(3,4-difluorophenyl)pyrazol-3-yl]phenyl]methyl]-2-methoxy-benzamide (0.08 mmol) gave, after purification, the titled compound (0.02 mmol) as an off-white solid. UPLC-MS (ES$^+$, Short acidic): 1.55 min, m/z 478.1 [M+H]$^+$. UPLC-MS (ES$^+$, Long acidic): 3.60 min, m/z 478.1 [M+H]$^+$. $^1$H NMR (400 MHz, DMSO-d$_6$, δ): 8.76 (t, J=6.1 Hz, 1H), 7.77-7.70 (m, 2H), 7.66-7.44 (m, 7H), 7.17-7.15 (m, 1H), 7.07-7.02 (m, 1H), 6.59 (s, 2H), 4.57 (d, J=6.0 Hz, 2H), 3.91 (s, 3H)

Example 99: 5-amino-3-[2-fluoro-4-[[(2-methoxybenzoyl)amino]methyl]phenyl]-1-tetrahydropyran-4-yl-pyrazole-4-carboxamide

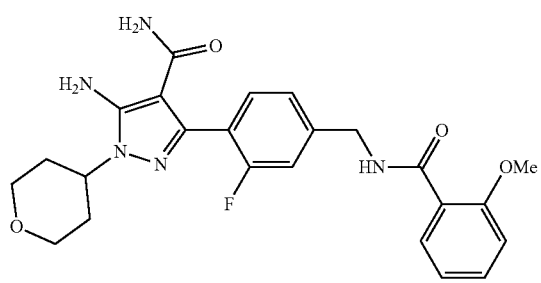 [SMILES: COc1ccccc1C(=O)NCc1ccc(-c2nn(C3CCOCC3)c(N)c2C(N)=O)c(F)c1]

2-[(4-Bromo-2-fluoro-phenyl)-hydroxy-methylene]propanedinitrile

General procedure W, 4-bromo-2-fluoro benzoyl chloride (14.1 mmol) and malononitrile (15.5 mmol) gave crude the titled compound (14.1 mmol). UPLC-MS (ES⁻, Short acidic): 1.21 min, m/z 266.7 [M]⁻

2-[(4-Bromo-2-fluoro-phenyl)-methoxy-methylene]propanedinitrile

General procedure X, 2-[(4-bromo-2-fluoro-phenyl)-hydroxy-methylene]propanedinitrile (14.6 mmol) gave, after purification, the titled compound (10.52 mmol) as a white solid. UPLC-MS (ES⁺, Short acidic): 1.68 min, m/z 280.8 [M]⁺

5-Amino-3-(4-bromo-2-fluoro-phenyl)-1-tetrahydro-pyran-4-yl-pyrazole-4-carbonitrile General procedure H, 2-[(4-bromo-2-fluoro-phenyl)-methoxy-methylene]propanedinitrile (0.92 mmol) and tetrahydropyran-4-ylhydrazine hydrochloride (1.11 mmol) afforded, after purification, the titled compound (0.82 mmol) as a colourless film. UPLC-MS (ES⁺, Short acidic): 1.65 min, m/z 366.9 [M+2]⁺

N-[[4-(5-Amino-4-cyano-1-tetrahydropyran-4-yl-pyrazol-3-yl)-3-fluoro-phenyl]methyl]-2-methoxy-benzamide General procedure K, potassium trifluoro-[[(2-methoxybenzoyl)amino]methyl]boranuide (0.74 mmol) and 5-amino-3-(4-bromo-2-fluoro-phenyl)-1-tetrahydropyran-4-yl-pyrazole-4-carbonitrile (0.49 mmol) gave, after purification, the titled compound (0.28 mmol) as an off-white solid. UPLC-MS (ES⁺, Short acidic): 1.48 min, m/z 450.1 [M+H]⁺

5-Amino-3-[2-fluoro-4-[[(2-methoxybenzoyl)amino]methyl]phenyl]-1-tetrahydropyran-4-yl-pyrazole-4-carboxamide Following general procedure M, N-[[4-(5-amino-4-cyano-1-tetrahydropyran-4-yl-pyrazol-3-yl)-3-fluoro-phenyl]methyl]-2-methoxy-benzamide (0.28 mmol) afforded, after purification, the titled compound (0.09 mmol) as a white solid. UPLC-MS (ES⁺, Short acidic): 1.31 min, m/z 468.1 [M+H]⁺. UPLC-MS (ES⁺, Long acidic): 2.96 min, m/z 468.1 [M+H]⁺. ¹H NMR (400 MHz, DMSO-d₆, δ): 8.79 (t, J=6.1 Hz, 1H), 7.73 (dd, J=7.7, 1.8 Hz, 1H), 7.51-7.47 (m, 1H), 7.40 (dd, J=8.2, 7.5 Hz, 1H), 7.27-7.22 (m, 2H), 7.16 (dd, J=8.3, 0.6 Hz, 1H), 7.07-7.03 (m, 1H), 6.34 (s, 2H), 4.55 (d, J=6.1 Hz, 2H), 4.41-4.31 (m, 1H), 3.99-3.92 (m, 2H), 3.90 (s, 3H), 3.46-3.38 (m, 2H), 2.02-1.89 (m, 2H), 1.82-1.73 (m, 2H).

Example 100: 5-amino-3-[2-fluoro-4-[[(2-methoxybenzoyl)amino]methyl]phenyl]-1-tetrahydrofuran-3-yl-pyrazole-4-carboxamide

5-Amino-3-(4-bromo-2-fluoro-phenyl)-1-tetrahydrofuran-3-yl-pyrazole-4-carbonitrile

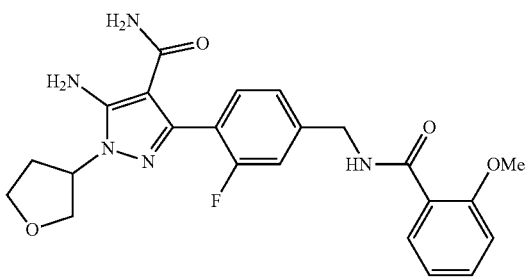 [SMILES: COc1ccccc1C(=O)NCc1ccc(-c2nn(C3CCOC3)c(N)c2C(N)=O)c(F)c1]

General procedure H, 2-[(4-bromo-2-fluoro-phenyl)-methoxy-methylene]propanedinitrile (0.77 mmol) and tetrahydrofuran-3-ylhydrazine hydrochloride (0.92 mmol) gave, after purification, the titled compound (0.69 mmol) as a colourless film. UPLC-MS (ES⁺, Short acidic): 1.63 min, m/z 352.9 [M+2]⁺

N-[[4-(5-Amino-4-cyano-1-tetrahydrofuran-3-yl-pyrazol-3-yl)-3-fluoro-phenyl]methyl]-2-methoxy-benzamide General procedure K, potassium trifluoro-[[(2-methoxybenzoyl)amino]methyl]boranuide (0.48 mmol) and 5-amino-3-(4-bromo-2-fluoro-phenyl)-1-tetrahydrofuran-3-yl-pyrazole-4-carbonitrile (0.37 mmol) gave, after purification, the titled compound (0.23 mmol) as an off-white solid. UPLC-MS (ES⁺, Short acidic): 1.47 min, m/z 436.0 [M+H]⁺

5-Amino-3-[2-fluoro-4-[[(2-methoxybenzoyl)amino]methyl]phenyl]-1-tetrahydrofuran-3-yl-pyrazole-4-carboxamide Following general procedure M, N-[[4-(5-amino-4-cyano-1-tetrahydrofuran-3-yl-pyrazol-3-yl)-3-fluoro-phenyl]methyl]-2-methoxy-benzamide (98 mg, 0.23 mmol) afforded, after purification, the titled compound (42 mg, 0.09 mmol, 41% yield) as a white solid. UPLC-MS (ES⁺, Short acidic): 1.31 min, m/z 454.1 [M+H]⁺. UPLC-MS (ES⁺, Long acidic): 2.96 min, m/z 454.1 M+H]⁺. ¹H NMR (400 MHz, DMSO-d₆, δ): 8.78 (t, J=6.0 Hz, 1H), 7.73 (dd, J=7.7, 1.8 Hz, 1H), 7.51-7.47 (m, 1H), 7.40 (dd, J=8.1, 7.6 Hz, 1H), 7.27-7.22 (m, 2H), 7.18-7.13 (m, 1H), 7.06-7.04 (m, 1H), 6.36 (s, 2H), 4.98-4.90 (m, 1H), 4.55 (d, J=6.1 Hz, 2H), 4.01-3.91 (m, 2H), 3.90 (s, 3H), 3.82-3.75 (m, 2H), 2.29-2.20 (m, 2H)

Example 101: 5-amino-1-cyclopentyl-3-[4-[[(2-methoxybenzoyl)amino]methyl]-2-methyl-phenyl]pyrazole-4-carboxamide

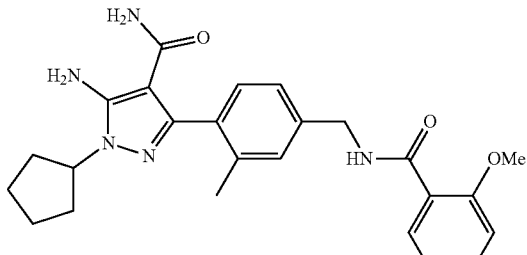

(4-Bromo-3-methyl-phenyl)methanamine

A solution of 4-bromo-3-methylbenzonitrile (5.10 mmol) in THF (30 mL) and a borane dimethyl sulfide complex solution (2 M in THF, 15.30 mmol) was stirred at 0° C. for 30 min before being warmed to RT and stirred for 18 h. The reaction was quenched with MeOH (30 mL) and was concentrated under reduced pressure. The residue was partitioned between EtOAc and a 1 M aqueous solution of NaOH. The organic layer was washed with brine, dried over sodium sulfate, filtered and concentrated under reduced pressure to afford crude the titled compound (5.10 mmol). $^1$H NMR (400 MHz, CDCl$_3$, δ): 7.43-7.50 (m, 1H), 7.21-7.15 (m, 1H), 6.95-7.03 (m, 1H), 3.80 (s, 2H), 2.39 (s, 3H).

N-[(4-Bromo-3-methyl-phenyl)methyl]-2-methoxy-benzamide (4-Bromo-3-methyl-phenyl)methanamine (5.10 mmol) dissolved in THF (20 mL) and N,N-diisopropylethylamine (15.29 mmol) was cooled to 0° C. before addition of 2-methoxybenzoyl chloride (5.61 mmol) and then stirred at 0° C. for 20 min. The reaction was warmed to RT and stirred for 66 h. The reaction was quenched with a saturated aqueous solution of NH$_4$Cl and concentrated under reduced pressure. The residue was extracted with EtOAc and washed with brine. The organic layer was dried over sodium sulfate, filtered and concentrated under reduced pressure. Purification gave the titled compound (5.10 mmol). UPLC-MS (ES$^+$, Short acidic): 2.01 min, m/z 335.9 [M+2]$^+$

2-Methoxy-N-[[3-methyl-4-(4,4,5,5-tetramethyl-1,3,2-dioxaborolan-2-yl)phenyl]methyl]benzamide General procedure R, N-[(4-bromo-3-methyl-phenyl)methyl]-2-methoxy-benzamide (5.1 mmol) gave, after purification, the titled compound (3.82 mmol). UPLC-MS (ES$^+$, Short acidic): 2.15 min, m/z 382.1 [M+H]$^+$

3-Amino-5-bromo-1H-pyrazole-4-carbonitrile

A solution of 3-amino-4-cyanopyrazole (46.25 mmol) in MeCN (180 mL) and N-bromosuccinimide (60.1 mmol) at 0° C. was warmed up to RT and stirred for 16 h. The reaction was concentrated under reduced pressure and the residue was purified to give the titled compound (22.4 mmol). UPLC-MS (ES$^+$, Short acidic): 0.98 min, m/z 188.8 [M+2]$^+$

5-Amino-3-bromo-1-cyclopentyl-pyrazole-4-carbonitrile

Cesium carbonate (33.6 mmol), 3-amino-5-bromo-1H-pyrazole-4-carbonitrile (22.4 mmol) and bromocyclopentane (2.64 mL, 24.6 mmol) in MeCN (170 mL) was stirred at 80° C. for 19 h, then cooled to RT and partitioned between water and EtOAc. The organic layer was washed with brine, dried over sodium sulfate, filtered and concentrated under reduced pressure. Purification gave the titled compound (1.00 g, 3.92 mmol, 18% yield). UPLC-MS (ES$^+$, Short acidic): 1.58 min, m/z 256.9 [M+2]$^+$

5-Amino-3-bromo-1-cyclopentyl-pyrazole-4-carboxamide

General procedure M, 5-amino-3-bromo-1-cyclopentyl-pyrazole-4-carbonitrile (3.92 mmol) gave, after purification, the titled compound (2.87 mmol). UPLC-MS (ES$^+$, Short acidic): 1.32 min, m/z 274.8 [M+2]$^+$

5-Amino-1-cyclopentyl-3-[4-[[(2-methoxybenzoyl)amino]methyl]-2-methyl-phenyl]pyrazole-4-carboxamide A mixture of potassium carbonate (2.40 mmol), 2-methoxy-N-[[3-methyl-4-(4,4,5,5-tetramethyl-1,3,2-dioxaborolan-2-yl)phenyl]methyl]benzamide (0.60 mmol) and 5-amino-3-bromo-1-cyclopentyl-pyrazole-4-carboxamide (0.57 mmol) in EtOH (3 mL) and water (0.6 mL) was purged and degassed with nitrogen. [1,1'-bis(di-tert-butylphosphino)ferrocene]dichloropalladium(II) (0.12 mmol) was added. The solution was sealed and heated to 120° C. for 1 h in the microwave. The reaction was then filtered through a pad of Celite® and washed with DCM, then concentrated under reduced pressure. Purification gave the titled compound (0.06 mmol). UPLC-MS (ES$^+$, Short acidic): 1.55 min, m/z 448.1 [M+H]$^+$. UPLC-MS (ES$^+$, Long acidic): 3.59 min, m/z 448.2 [M+H]$^+$. $^1$H NMR (400 MHz, DMSO-d$_6$, δ): 8.71 (t, J=6.1 Hz, 1H), 7.74 (dd, J=7.5, 1.9 Hz, 1H), 7.50-7.45 (m, 1H), 7.29 (s, 1H), 7.27-7.19 (m, 2H), 7.15 (d, J=8.6 Hz, 1H), 7.03 (td, J=7.5, 1.0 Hz, 1H), 6.37 (s, 2H), 4.66-4.58 (m, 1H), 4.52 (d, J=6.1 Hz, 2H), 3.89 (s, 3H), 2.13 (s, 3H), 2.01-1.92 (m, 2H), 1.92-1.82 (m, 2H), 1.81-1.71 (m, 2H), 1.63-1.52 (m, 2H).

Example 102: 5-amino-3-[2-fluoro-4-[[(2-methoxybenzoyl)amino]methyl]phenyl]-1-tetrahydropyran-3-yl-pyrazole-4-carboxamide

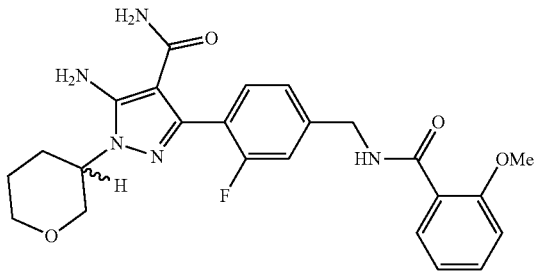 [SMILES: COc1ccccc1C(=O)NCc1ccc(-c2nn(C3CCCOC3)c(N)c2C(N)=O)c(F)c1]

5-Amino-3-(4-bromo-2-fluoro-phenyl)-1-tetrahydropyran-3-yl-pyrazole-4-carbonitrile General procedure H, 2-[(4-bromo-2-fluoro-phenyl)-methoxy-methylene]propanedinitrile (0.82 mmol) and tetrahydropyran-3-ylhydrazine hydrochloride (0.99 mmol) gave, after purification, the titled compound (0.42 mmol) as an off-white solid. UPLC-MS (ES+, Short acidic): 1.54 min, m/z 366.9 [M+2]+

N-[[4-(5-Amino-4-cyano-1-tetrahydropyran-3-yl-pyrazol-3-yl)-3-fluoro-phenyl]methyl]-2-methoxy-benzamide General procedure K, potassium trifluoro-[[(2-methoxybenzoyl)amino]methyl]boranuide (0.63 mmol) and 5-amino-3-(4-bromo-2-fluoro-phenyl)-1-tetrahydropyran-3-yl-pyrazole-4-carbonitrile (0.42 mmol) gave, after purification, the titled compound (0.16 mmol) as an off-white solid. UPLC-MS (ES+, Short acidic): 1.54 min, m/z 450.0 [M+H]+

5-Amino-3-[2-fluoro-4-[[(2-methoxybenzoyl)amino]methyl]phenyl]-1-tetrahydropyran-3-yl-pyrazole-4-carboxamide General procedure M, N-[[4-(5-amino-4-cyano-1-tetrahydropyran-3-yl-pyrazol-3-yl)-3-fluoro-phenyl]methyl]-2-methoxy-benzamide (0.28 mmol) afforded, after purification, the titled compound (0.03 mmol, 11% yield) as a white solid. UPLC-MS (ES+, Short acidic): 1.37 min, m/z 468.1 [M+H]+. UPLC-MS (ES+, Long acidic): 3.12 min, m/z 468.1 M+H]+. $^1$H NMR (400 MHz, DMSO-$d_6$, δ): 8.78 (t, J=6.1 Hz, 1H), 7.73 (dd, J=7.6, 1.7 Hz, 1H), 7.51-7.46 (m, 1H), 7.40 (dd, J=8.2, 7.5 Hz, 1H), 7.27-7.21 (m, 2H), 7.16 (dd, J=8.3, 0.6 Hz, 1H), 7.04 (td, J=7.5, 1.0 Hz, 1H), 6.37 (s, 2H), 4.55 (d, J=6.1 Hz, 2H), 4.32-4.22 (m, 1H), 3.90 (s, 3H), 3.89-3.80 (m, 2H), 3.52 (dd, J=10.5 Hz, 1H), 3.35-3.25 (m, 1H), 2.02-1.94 (m, 2H), 1.77-1.61 (m, 2H)

Example 103: 5-amino-1-(2-fluorocyclopentyl)-3-[4-[[(2-methoxybenzoyl)amino]methyl]phenyl]pyrazole-4-carboxamide

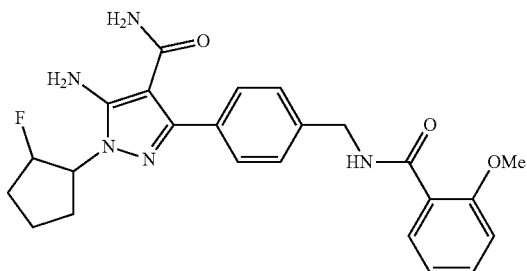

tert-Butyl N-[(2-fluorocyclopentylidene)amino]carbamate

A solution of N-fluorobenzenesulfonimide (1.85 mmol) and 1-(trimethylsiloxy)cyclopentene (1.69 mmol) in THF (8 mL) at RT was stirred at RT for 5 h, then tert-butyl carbazate (1.69 mmol) was added. The reaction was stirred at RT for an additional 16 h, then concentrated under reduced pressure. Further purification gave the titled compound (1.20 mmol) as an off-white solid. UPLC-MS (ES+, Short acidic): 1.41 min, m/z 217 [M+H]+

5-Amino-3-(4-bromophenyl)-1-(2-fluorocyclopentyl)pyrazole-4-carbonitrile

General procedure O at RT, tert-butyl N-[(2-fluorocyclopentylidene)amino]carbamate (1.20 mmol) and 2-[(4-brom-ophenyl)-methoxy-methylene]propanedinitrile (0.80 mmol) gave, after purification, the titled compound (0.24 mmol) as an off-white solid. UPLC-MS (ES+, Short acidic): 1.89 min, m/z 350.9 [M+2]+

N-[[4-[5-Amino-4-cyano-1-(2-fluorocyclopentyl)pyrazol-3-yl]phenyl]methyl]-2-methoxy-benzamide General procedure K, 5-amino-3-(4-bromophenyl)-1-(2-fluorocyclopentyl)pyrazole-4-carbonitrile (0.24 mmol) and potassium trifluoro-[[(2-methoxybenzoyl)amino]methyl]boranuide (0.28 mmol) gave, after purification, the titled compound (0.24 mmol) as a white solid. UPLC-MS (ES+, Short acidic): 1.65 min, m/z 434.0 [M+H]+

5-Amino-1-(2-fluorocyclopentyl)-3-[4-[[(2-methoxybenzoyl)amino]methyl]phenyl]pyrazole-4-carboxamide General procedure M, N-[[4-[5-amino-4-cyano-1-(2-fluorocyclopentyl)pyrazol-3-yl]phenyl]methyl]-2-methoxy-benzamide (0.24 mmol) gave, after purification, the titled compound (0.09 mmol) as a white solid. UPLC-MS (ES+, Short acidic): 1.44 min, m/z 452.1 [M+H]+. UPLC-MS (ES+, Long acidic): 3.38 min, m/z 452.1 [M+H]+. $^1$H NMR (400 MHz, DMSO-$d_6$, δ): 8.74 (t, J=6.1 Hz, 1H), 7.76 (dd, J=7.7, 1.7 Hz, 1H), 7.52-7.38 (m, 5H), 7.16 (d, J=8.3 Hz, 1H), 7.08-7.01 (m, 1H), 6.39 (s, 2H), 5.27-5.07 (m, 1H), 4.60-4.45 (m, 3H), 3.90 (s, 3H), 2.65-2.41 (m, 1H), 2.09-1.83 (m, 4H), 1.76-1.55 (m, 1H).

Example 104: 5-amino-1-(2,6-dimethyltetrahydropyran-4-yl)-3-[4-[[(2-methoxybenzoyl)amino]methyl]phenyl]pyrazole-4-carboxamide

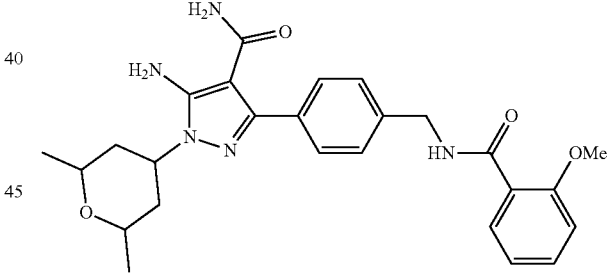

tert-Butyl N-[(2,6-dimethyltetrahydropyran-4-ylidene)amino]carbamate

Following general procedure E, 2,6-dimethyloxan-4-one (200 mg, 1.56 mmol) and tert-butyl carbazate (217 mg, 1.64 mmol) gave, after purification, the titled compound (0.88 mmol) as an off-white solid. $^1$H NMR (400 MHz, CDCl$_3$, δ): 7.52 (s, 1H), 3.69-3.61 (m, 1H), 3.59-3.51 (m, 1H), 2.59-2.50 (m, 2H), 2.13-2.07 (m, 1H), 1.82-1.75 (m, 1H), 1.53 (s, 9H), 1.33 (d, J=6.0 Hz, 3H), 1.28 (d, J=5.9 Hz, 3H)

5-Amino-3-(4-bromophenyl)-1-(2,6-dimethyltetrahydropyran-4-yl)pyrazole-4-carbonitrile General procedure O, tert-Butyl N-[(2,6-dimethyltetrahydropyran-4-ylidene)amino]carbamate (0.88 mmol) and 2-[(4-bromophenyl)-methoxy-methylene]propanedinitrile (0.76 mmol) gave, after purification, the titled compound (0.29 mmol) as a brown solid. UPLC-MS: (ES+, Short acidic): 1.91 min, m/z 376.9 [M+2]+

N-[[4-[5-Amino-4-cyano-1-(2,6-dimethyltetrahydropyran-4-yl)pyrazol-3-yl]phenyl]methyl]-2-methoxybenzamide General procedure K, 5-amino-3-(4-bromophenyl)-1-(2,6-dimethyltetrahydropyran-4-yl)pyrazole-4-carbonitrile (0.29 mmol) and potassium trifluoro-[[(2-methoxybenzoyl)amino]methyl]boranuide (0.61 mmol) gave, after purification, the titled compound (0.25 mmol) as a brown solid. UPLC-MS: (ES+, Short acidic): 1.63 min, m/z 460.1 [M+H]+

5-Amino-1-(2,6-dimethyltetrahydropyran-4-yl)-3-[4-[[(2-methoxybenzoyl)amino]methyl]phenyl]pyrazole-4-carboxamide General procedure L, N-[[4-[5-amino-4-cyano-1-(2,6-dimethyltetrahydropyran-4-yl)pyrazol-3-yl]phenyl]methyl]-2-methoxy-benzamide (0.25 mmol) gave, after purification, the titled compound (0.02 mmol) as an off-white solid. UPLC-MS: (ES+, Short acidic): 1.42 min, m/z 478.2 [M+H]+. UPLC-MS: (ES+, Short acidic): 3.26 min, m/z 478.2 [M+H]+. $^1$H NMR (400 MHz, DMSO-d$_6$, δ): 8.73 (t, J=6.2 Hz, 1H), 7.75 (dd, J=7.6, 1.7 Hz, 1H), 7.50-7.39 (m, 5H), 7.15 (d, J=8.3 Hz, 1H), 7.06-7.02 (m, 1H), 6.36 (s, 2H), 4.54 (d, J=6.1 Hz, 2H), 4.43-4.35 (m, 1H), 3.90 (s, 3H), 3.59-3.52 (m, 2H), 1.83-1.79 (m, 2H), 1.62-1.53 (m, 2H), 1.14 (d, J=6.1 Hz, 6H)

Example 105: 5-amino-3-[2-fluoro-4-[[(5-fluoro-2-methoxy-benzoyl)amino]methyl]phenyl]-1-tetrahydrofuran-3-yl-pyrazole-4-carboxamide

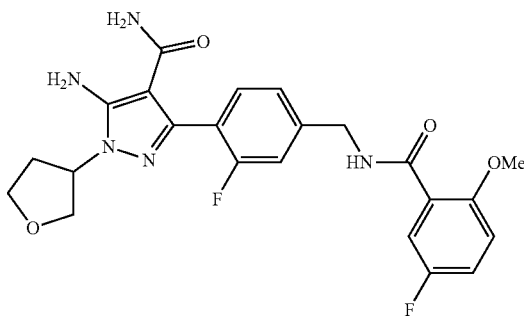 [SMILES: COc1ccc(F)cc1C(=O)NCc1ccc(-c2nn(C3CCOC3)c(N)c2C(N)=O)c(F)c1]

N-[[4-(5-Amino-4-cyano-1-tetrahydrofuran-3-yl-pyrazol-3-yl)-3-fluoro-phenyl]methyl]-5-fluoro-2-methoxy-benzamide General procedure K, 5-amino-3-(4-bromo-2-fluoro-phenyl)-1-tetrahydrofuran-3-yl-pyrazole-4-carbonitrile (0.31 mmol) and potassium trifluoro-[[(5-fluoro-2-methoxy-benzoyl)amino]methyl]boranuide (0.34 mmol) afforded, after purification, the titled compound (0.33 mmol) as a yellow oil. UPLC-MS (ES+, Short acidic): 1.52 min, m/z 454.1 [M+H]+

5-Amino-3-[2-fluoro-4-[[(5-fluoro-2-methoxy-benzoyl)amino]methyl]phenyl]-1-tetrahydrofuran-3-yl-pyrazole-4-carboxamide General procedure M, N-[[4-(5-amino-4-cyano-1-tetrahydrofuran-3-yl-pyrazol-3-yl)-3-fluoro-phenyl]methyl]-5-fluoro-2-methoxy-benzamide (0.33 mmol) gave, after purification, the titled compound (0.06 mmol) as a white solid. UPLC-MS (ES+, Short acidic): 1.36 min, m/z 472.1 [M+H]+. UPLC-MS (ES+, Long acidic): 3.08 min, m/z 472.0 [M+H]+. $^1$H NMR (400 MHz, DMSO-d$_6$, δ): 8.89 (t, J=6.1 Hz, 1H), 7.50 (dd, J=9.2, 3.3 Hz, 1H), 7.43-7.32 (m, 2H), 7.26-7.18 (m, 3H), 6.37 (s, 2H), 4.98-4.91 (m, 1H), 4.56 (d, J=6.1 Hz, 2H), 4.01-3.92 (m, 2H), 3.90 (s, 3H), 3.82-3.77 (m, 2H), 2.30-2.21 (m, 2H).

Example 106: 5-amino-3-[2-fluoro-4-[[(5-fluoro-2-methoxy-benzoyl)amino]methyl]phenyl]-1-tetrahydropyran-4-yl-pyrazole-4-carboxamide

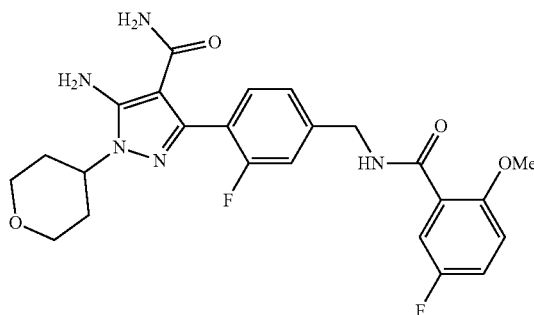

N-[[4-(5-Amino-4-cyano-1-tetrahydropyran-4-yl-pyrazol-3-yl)-3-fluoro-phenyl]methyl]-5-fluoro-2 methoxy-benzamide General procedure K, 5-amino-3-(4-bromo-2-fluoro-phenyl)-1-tetrahydropyran-4-yl-pyrazole-4-carbonitrile (0.30 mmol) and potassium trifluoro-[[(5-fluoro-2-methoxy-benzoyl)amino]methyl]boranuide (0.33 mmol) afforded, after purification, the titled compound (0.31 mmol) as a yellow oil. UPLC-MS (ES+, Short acidic): 1.53 min, m/z 468.1 [M+H]+

5-Amino-3-[2-fluoro-4-[[(5-fluoro-2-methoxy-benzoyl)amino]methyl]phenyl]-1-tetrahydropyran-4-yl-pyrazole-4-carboxamide General procedure M, N-[[4-(5-amino-4-cyano-1-tetrahydropyran-4-yl-pyrazol-3-yl)-3-fluoro-phenyl]methyl]-5-fluoro-2-methoxy-benzamide (0.31 mmol) afforded, after purification, the titled compound (0.10 mmol) as a white solid. UPLC-MS (ES+, Short acidic): 1.36 min, m/z 486.1 [M+H]+. UPLC-MS (ES+, Long acidic): 3.08 min, m/z 486.1 [M+H]+. $^1$H NMR (400 MHz, DMSO-d$_6$, δ): 8.89 (t, J=6.1 Hz, 1H), 7.50 (dd, J=9.2, 3.3 Hz 1H), 7.43-7.32 (m, 2H), 7.26-7.18 (m, 3H), 6.35 (s, 2H), 4.56 (d, J=6.1 Hz, 2H), 4.41-4.34 (m, 1H), 3.99-3.95 (m, 2H), 3.91 (s, 3H), 3.48-3.36 (m, 2H), 2.01-1.91 (m, 2H), 1.80-1.70 (m, 2H).

Example 107: 5-amino-3-[2-fluoro-4-[[(5-fluoro-2-methoxy-benzoyl)amino]methyl]phenyl]-1-tetrahydropyran-3-yl-pyrazole-4-carboxamide

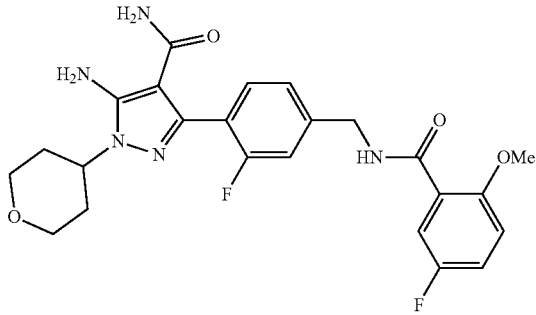 [SMILES: COc1ccc(F)cc1C(=O)NCc1ccc(-c2nn(C3CCOCC3)c(N)c2C(N)=O)c(F)c1]

N-[[4-(5-Amino-4-cyano-1-tetrahydropyran-3-yl-pyrazol-3-yl)-3-fluoro-phenyl]methyl]-5-fluoro-2-methoxy-benzamide General procedure K, 5-amino-3-(4-bromo-2-fluoro-phenyl)-1-tetrahydropyran-3-yl-pyrazole-4-carbonitrile (0.19 mmol) and potassium trifluoro-[[(5-fluoro-2-methoxy-benzoyl)amino]methyl]boranuide (0.28 mmol) afforded, after purification, the titled compound (0.21 mmol, assumed quantitative yield) as a yellow oil. UPLC-MS (ES+, Short acidic): 1.59 min, m/z 468.1 [M+H]+

5-Amino-3-[2-fluoro-4-[[(5-fluoro-2-methoxy-benzoyl)amino]methyl]phenyl]-1-tetrahydropyran-3-yl-pyrazole-4-carboxamide General procedure M, N-[[4-(5-amino-4-cyano-1-tetrahydropyran-3-yl-pyrazol-3-yl)-3-fluoro-phenyl]methyl]-5-fluoro-2-methoxy-benzamide (0.21 mmol) afforded, after purification, the titled compound (0.06 mmol) as a yellow solid. UPLC-MS (ES+, Short acidic): 1.42 min, m/z 486.1 [M+H]+. UPLC-MS (ES+, Long acidic): 3.24 min, m/z 486.1 [M+H]+. 1H NMR (400 MHz, DMSO-$d_6$, δ): 8.89 (t, J=6.1 Hz, 1H), 7.50 (dd, J=9.1, 3.3 Hz, 1H), 7.42-7.32 (m, 2H), 7.26-7.18 (m, 3H), 6.38 (s, 2H), 4.56 (d, J=6.1 Hz, 2H), 4.32-4.24 (m, 1H), 3.91 (s, 3H), 3.87-3.83 (m, 2H), 3.31 (m, 2H), 2.02-1.96 (m, 2H), 1.76-1.66 (m, 2H).

Example 108: 5-(difluoromethyl)-3-[4-[[(2-methoxybenzoyl)amino]methyl]phenyl]-1-tetrahydropyran-4-yl-pyrazole-4-carboxamide

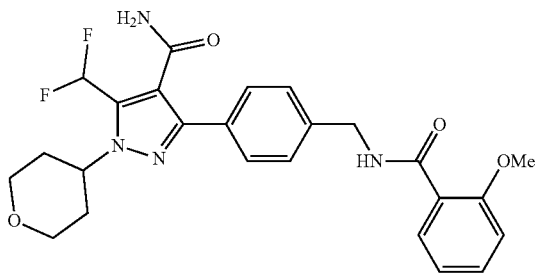 [SMILES: COc1ccccc1C(=O)NCc1ccc(-c2nn(C3CCOCC3)c(C(F)F)c2C(N)=O)cc1]

Ethyl-4,4-difluoro-2-(methoxymethylene)-3-oxo-butanoate

A solution of anhydrous trimethyl orthoformate (15.3 mmol) and ethyl 4,4-difluoro-3-oxobutanoate (7.64 mmol) in acetic anhydride (3 mL) was heated at 90° C. for 16 h under Dean-Stark conditions, cooled and concentrated under reduced pressure to afford crude the titled compound (7.30 mmol) as a brown oil. 1H NMR (400 MHz, CDCl3, δ, mixture of isomers): 7.81 (s, 0.5H), 7.79 (s, 0.5H), 6.58-6.22 (m, 1H), 4.39-4.25 (m, 2H), 4.15 (s, 1.5H), 4.12 (s, 1.5H), 1.38-1.31 (m, 3H).

Ethyl 5-(difluoromethyl)-1H-pyrazole-4-carboxylate

A solution of ethyl-4,4-difluoro-2-(methoxymethylene)-3-oxo-butanoate (2.40 mmol) in MeOH (8 mL) and hydrazine hydrate (55-60% in water, 2.40 mmol) was stirred at RT for 16 h. Then all volatiles were removed under reduced pressure. The residue was diluted in EtOAc. The layers were partitioned and the organic layer was washed successively with water (×2) then brine, dried over sodium sulfate, filtered and concentrated under reduced pressure to afford crude the titled compound (1.81 mmol, 75% yield) as a yellow oil. UPLC-MS (ES+, Short acidic): 1.25 min, m/z 190.9 [M+H]+

Ethyl 3-bromo-5-(difluoromethyl)-1H-pyrazole-4-carboxylate

N-Bromosuccinimide (2.36 mmol) was added portionwise to a solution of ethyl 5-(difluoromethyl)-1H-pyrazole-4-carboxylate (1.81 mmol) in MeCN (6 mL). The resulting mixture was then stirred at 80° C. for 72 h. Then the solvent was removed under reduced pressure. The crude product was purified to give the titled compound (1.38 mmol) as a yellow oil. UPLC-MS (ES+, Short acidic): 1.43 min, m/z 268.8 [M]+

Ethyl 3-bromo-5-(difluoromethyl)-1-tetrahydropyran-4-yl-pyrazole-4-carboxylate

4-Bromotetrahydro-2H-pyran (0.17 mL, 1.51 mmol) was added to a suspension of potassium carbonate (1.51 mmol) and ethyl 3-bromo-5-(difluoromethyl)-1H-pyrazole-4-carboxylate (1.38 mmol) in MeCN (2.7 mL). The reaction mixture was heated at 90° C. for 16 h then partitioned between water and DCM. The aqueous layer was extracted with DCM (×3), and the combined organic phases were filtered over a hydrophobic frit and concentrated under reduced pressure. Further purification gave the titled compound (0.50 mmol), which contained traces of the other regioisomer, as an off-white solid. UPLC-MS (ES+, Short acidic): 1.67 min, m/z 354.9 [M+2]+ and 1.78 min, m/z 352.9 [M]+

3-Bromo-5-(difluoromethyl)-1-tetrahydropyran-4-yl-pyrazole-4-carboxylic acid

An aqueous solution of NaOH (1 M, 0.85 mmol) was added to a solution of ethyl 3-bromo-5-(difluoromethyl)-1-tetrahydropyran-4-yl-pyrazole-4-carboxylate (0.28 mmol) in THF (1.3 mL). The reaction mixture was heated at 50° C. for 16 h, cooled to RT, acidified to ~pH 1 with hydrochloric acid (1 M), and then extracted with DCM (×3). The combined organic layers were filtered over a hydrophobic frit and concentrated under reduced pressure. Purification gave the titled compound (0.10 mmol) as a white solid. UPLC-MS (ES+, Short acidic): 1.37 min, m/z 326.9 [M+2]+

3-Bromo-5-(difluoromethyl)-1-tetrahydropyran-4-yl-pyrazole-4-carboxamide

A drop of DMF was added to a solution of oxalyl chloride (0.02 mL, 0.25 mmol) and 3-bromo-5-(difluoromethyl)-1-tetrahydropyran-4-yl-pyrazole-4-carboxylic acid (0.10 mmol) in DCM (1 mL) at RT. The reaction mixture was stirred at RT for 1 h then cooled to 0° C., and ammonium hydroxide (28 wt % in water, 1.01 mmol) was added carefully. The reaction mixture was stirred at RT for 20 min, then partitioned between water and DCM. The aqueous layer was extracted with DCM (×3) and the combined organic layers were filtered over a hydrophobic frit and concentrated under reduced pressure. Purification gave the titled compound (0.08 mmol) as a white solid. UPLC-MS (ES+, Short acidic): 1.25 min, m/z 325.9 [M+2]+

5-(Difluoromethyl)-3-[4-[[(2-methoxybenzoyl)amino]methyl]phenyl]-1-tetrahydropyran-4-yl-pyrazole-4-carboxamide General procedure C, [4-[[(2-methoxybenzoyl)amino]methyl]phenyl]boronic acid (0.12 mmol) and 3-bromo-5-(difluoromethyl)-1-tetrahydropyran-4-yl-pyrazole-4-carboxamide (0.08 mmol) gave, after purification, the titled compound (0.05 mmol) as a white solid. UPLC-MS (ES+, Short acidic): 1.49 min, m/z 485.1 [M+H]+. UPLC-MS (ES+, Long acidic): 3.42 min, m/z 485.1 [M+H]+. $^1$H NMR (400 MHz, DMSO-$d_6$, δ): 8.73 (t, J=6.1 Hz, 1H), 7.76 (dd, J=7.6, 1.8 Hz, 1H), 7.70-7.61 (m, 3H), 7.58 (br s, 1H), 7.52-7.45 (m, 1H), 7.40 (d, J=8.4 Hz, 2H), 7.34 (t, J=52.3 Hz, 1H), 7.16 (d, J=7.9 Hz, 1H), 7.08-7.01 (m, 1H), 4.67-4.56 (m, 1H), 4.54 (d, J=6.1 Hz, 2H), 4.05-3.96 (m, 2H), 3.91 (s, 3H), 3.55-3.45 (m, 2H), 2.26-2.10 (m, 2H), 1.95-1.82 (m, 2H).

Example 109: 5-amino-3-[3-fluoro-4-[[(2-methoxybenzoyl)amino]methyl]phenyl]-1-tetrahydrofuran-3-yl-pyrazole-4-carboxamide

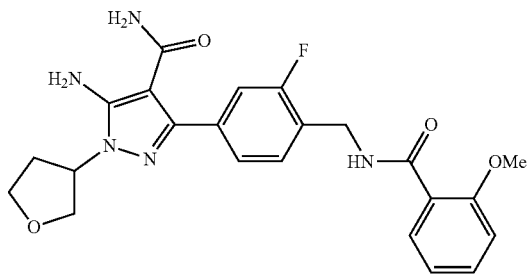

tert-Butyl N-[tetrahydrofuran-3-ylideneamino]carbamate

General procedure E, dihydro(3(2H)-furanone (0.15 mL, 1.95 mmol) and tert-butyl carbazate (2.35 mmol) gave crude the titled compound (2.02 mmol) as a white solid. $^1$H NMR (400 MHz, CDCl$_3$, δ): 7.23 (s, 1H), 4.35-4.34 (m, 2H), 4.09 (t, J=6.9 Hz, 2H), 2.50-2.46 (m, 2H), 1.52 (s, 9H).

5-Amino-3-(4-bromo-3-fluoro-phenyl)-1-tetrahydrofuran-3-yl-pyrazole-4-carbonitrile To a solution of tert-butyl N-[tetrahydrofuran-3-ylideneamino]carbamate (0.25 mmol) in THF (5 mL) was added a borane dimethyl sulfide complex solution (2 M in THF, 0.42 mmol). The reaction mixture was stirred at RT for 1 h then concentrated under reduced pressure. A hydrogen chloride solution in MeOH (1.25 M, 8.74 mmol) was added to the residue and the reaction mixture was heated under reflux for 16 h. The mixture was cooled to RT, and concentrated under reduced pressure. The residue was taken up with EtOH (10 mL) and 2-[(4-bromo-3-fluoro-phenyl)-methoxy-methylene]propanedinitrile (0.71 mmol) and triethylamine (0.50 mL, 3.56 mmol) were added. The reaction mixture was heated at reflux for 3 h, cooled, and filtered. The solid was washed with EtOH and EtOAc. The filtrate was evaporated to dryness and the obtained solid washed with EtOAc. The combined solids afforded the titled compound (0.71 mmol) as an off-white solid. UPLC-MS: (ES+, Short acidic): 1.72 min, m/z 352.9 [M+2]+

N-[[4-(5-Amino-4-cyano-1-tetrahydrofuran-3-yl-pyrazol-3-yl)-2-fluoro-phenyl]methyl]-2-methoxybenzamide General procedure K, 5-amino-3-(4-bromo-3-fluoro-phenyl)-1-tetrahydrofuran-3-yl-pyrazole-4-carbonitrile (0.68 mmol) and potassium trifluoro-[[(2-methoxybenzoyl)amino]methyl]boranuide (0.96 mmol) gave, after purification, the titled compound (0.47 mmol) as a yellow solid. UPLC-MS: (ES+, Short acidic): 1.54 min, m/z 436.1 [M+H]+

5-Amino-3-[3-fluoro-4-[[(2-methoxybenzoyl)amino]methyl]phenyl]-1-tetrahydrofuran-3-yl-pyrazole-4-carboxamide A modified general procedure L for 96 h, N-[[4-(5-amino-4-cyano-1-tetrahydrofuran-3-yl-pyrazol-3-yl)-2-fluoro-phenyl]methyl]-2-methoxy-benzamide (0.23 mmol) gave, after purification, the titled compound (80 mg, 0.18 mmol, 77% yield) as a white solid. UPLC-MS: (ES+, Short acidic): 1.35 min, m/z 454.1 [M+H]+. UPLC-MS: (ES+, Long acidic): 3.07 min, m/z 454.0 [M+H]+. $^1$H NMR (400 MHz, DMSO-$d_6$, δ): 8.17 (t, J=5.9 Hz, 1H), 7.75 (d, J=7.7, 1.7 Hz, 1H), 7.51-7.41 (m, 2H), 7.34-7.28 (m, 2H), 7.16 (d, J=8.3 Hz, 1H), 7.06-7.02 (m, 1H), 6.34 (s, 2H), 4.96-4.91 (m, 1H), 4.57 (d, J=5.9 Hz, 2H), 4.00-3.93 (m, 2H), 3.90 (s, 3H), 3.83-3.78 (m, 2H), 2.28-2.23 (m, 2H).

Example 110: 3-[4-[[(2-methoxybenzoyl)amino]methyl]phenyl]-5-(methylamino)-1-(3-pyridyl)pyrazole-4-carboxamide

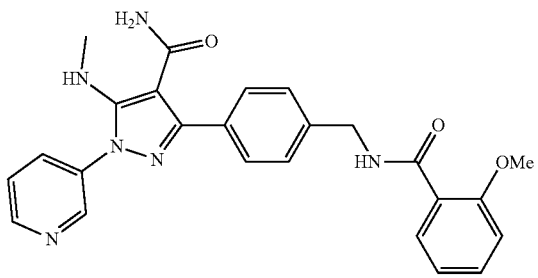 [SMILES: CNc1c(C(N)=O)c(-c2ccc(CNC(=O)c3ccccc3OC)cc2)nn1-c1cccnc1]

3-(4-Bromophenyl)-5-(methylamino)-1-(3-pyridyl)pyrazole-4-carbonitrile

A solution of 5-amino-3-(4-bromophenyl)-1-(3-pyridyl)pyrazole-4-carbonitrile (0.53 mmol) in MeOH (8 mL), paraformaldehyde (1.59 mmol) and sodium methoxide (3.17 mmol) was heated at 70° C. for 1 h. Then, it was cooled back down to RT. Sodium borohydride (5.29 mmol) was added and the reaction mixture was stirred at RT for 16 h. It was then carefully quenched with water and the aqueous layer was extracted with chloroform (3×20 mL). The combined organic layers were filtered over a hydrophobic frit and concentrated under reduced pressure. Purification gave the titled compound (0.56 mmol) as an off-white solid. UPLC-MS (ES+, Short acidic): 1.71 min, m/z 355.9 [M+2]+

N-[[4-[4-Cyano-5-(methylamino)-1-(3-pyridyl)pyrazol-3-yl]phenyl]methyl]-2-methoxy-benzamide General procedure K, 3-(4-bromophenyl)-5-(methylamino)-1-(3-pyridyl)pyrazole-4-carbonitrile (0.56 mmol) and potassium trifluoro-[[(2-methoxybenzoyl)amino]methyl]boranuide (0.62 mmol) gave, after purification, the titled compound (0.08 mmol) as an off-white solid. LC-MS (ES+, Short acidic): 4.71 min, m/z 439.2 [M+H]+

3-[4-[[(2-Methoxybenzoyl)amino]methyl]phenyl]-5-(methylamino)-1-(3-pyridyl)pyrazole-4-carboxamide General procedure L, N-[[4-[4-cyano-5-(methylamino)-1-(3-pyridyl)pyrazol-3-yl]phenyl]methyl]-2-methoxy-benzamide (0.11 mmol) gave, after purification, the titled compound (0.05 mmol) as an off-white solid. UPLC-MS (ES−, Short acidic): 1.32 min, m/z 455.0 [M−H]−. UPLC-MS (ES+, Long acidic): 2.98 min, m/z 457.1 [M+H]+. $^1$H NMR (400 MHz, DMSO-d$_6$, δ): 8.84-8.83 (m, 1H), 8.75 (t, J=6.2 Hz, 1H), 8.63 (dd, J=4.8, 1.5 Hz, 1H), 8.05-8.02 (m, 1H), 7.76 (dd, J=7.7, 1.7 Hz, 1H), 7.62-7.56 (m, 3H), 7.51-7.46 (m, 1H), 7.42 (d, J=8.4 Hz, 2H), 7.1 (d, J=7.8 Hz, 1H), 7.04 (td, J=7.5, 1.7 Hz, 1H), 6.60 (br s, 1H), 4.56 (d, J=6.1 Hz, 2H), 3.90 (s, 3H), 2.58 (s, 3H).

Example 111: 5-amino-3-[4-[[(2-methoxybenzoyl)amino]methyl]phenyl]-1-[2-(trifluoromethyl)tetrahydropyran-4-yl]pyrazole-4-carboxamide

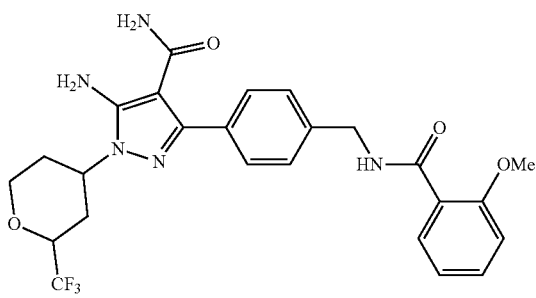 [SMILES: COc1ccccc1C(=O)NCc1ccc(-c2nn(C3CCOC(C(F)(F)F)C3)c(N)c2C(N)=O)cc1]

tert-Butyl N-[[2-(trifluoromethyl)tetrahydropyran-4-ylidene]amino]carbamate

A solution of 2-(trifluoromethyl)oxan-4-one (1.51 mmol) in MeOH (15 mL) and tert-butyl carbazate (1.59 mmol) was stirred for 14 h at RT. The reaction mixture was then quenched with a saturated aqueous solution of NH$_4$Cl and extracted with DCM (×3). The combined organic layers were dried over sodium sulfate, filtered and concentrated under reduced pressure. Further purification gave the titled compound (1.29 mmol) as a yellow solid. UPLC-MS (ES+, Short acidic): 1.50 min, m/z 283.0 [M+H]+ tert-Butyl N-[[2-(trifluoromethyl)tetrahydropyran-4-yl]amino]carbamate

To a solution of tert-butyl N-[[2-(trifluoromethyl)tetrahydropyran-4-ylidene]amino]carbamate (1.25 mmol) in THF (6 mL) was added a borane tetrahydrofuran complex solution (1.0 M in THF, 2.5 mmol) at 0° C. Afterwards, the reaction mixture was stirred for 14 h at RT. Subsequently, the reaction mixture was quenched with MeOH (2 mL). Then water was added and the aqueous phase was extracted with DCM (×3). The combined organic phases were dried over sodium sulfate, filtered and concentrated under reduced pressure to give the titled compound (1.17 mmol) as a yellow oil. UPLC-MS (ES+, Short acidic): 1.50 min, m/z 301.0 [M+H]+

5-Amino-3-(4-bromophenyl)-1-[2-(trifluoromethyl)tetrahydropyran-4-yl]pyrazole-4-carbonitrile A hydrogen chloride solution (4 M in dioxane, 14.5 mmol) was added to tert-butyl N-[[2-(trifluoromethyl)tetrahydropyran-4-yl]amino]carbamate (1.45 mmol). Afterwards, the mixture was stirred for 15 h at RT. A precipitate was formed and was collected. The filtrate was concentrated under reduced pressure to give crude [2-(trifluoromethyl)tetrahydropyran-4-yl]hydrazine hydrochloride (250 mg, 1.13 mmol, 79%) as a dark orange gum. Then following general procedure H at 85° C., [2-(trifluoromethyl)tetrahydropyran-4-yl]hydrazine hydrochloride (1.13 mmol) and 2-[(4-bromophenyl)-methoxy-methylene]propanedinitrile (0.57 mmol) gave, after purification, the titled compound (0.19 mmol) as an orange gum. UPLC-MS (ES+, Short acidic): 1.99 min, m/z 416.9 [M+2]+

N-[[4-[5-Amino-4-cyano-1-[2-(trifluoromethyl)tetrahydropyran-4-yl]pyrazol-3-yl]phenyl]methyl]-2-methoxy-benzamide General procedure K, 5-amino-3-(4-bromophenyl)-1-[2-(trifluoromethyl)tetrahydropyran-4-yl]pyrazole-4-carbonitrile (0.18 mmol) and potassium trifluoro-[[(2-methoxybenzoyl)amino]methyl]boranuide (0.27 mmol) gave, after purification, the titled compound (0.09 mmol) as an orange gum. UPLC-MS (ES+, Short acidic): 1.72 min, m/z 500.1 [M+H]+

5-Amino-3-[4-[[(2-methoxybenzoyl)amino]methyl]phenyl]-1-[2-(trifluoromethyl)tetrahydropyran-4-yl]pyrazole-4-carboxamide General procedure M, N-[[4-[5-amino-4-cyano-1-[2-(trifluoromethyl)tetrahydropyran-4-yl]pyrazol-3-yl]phenyl]methyl]-2-methoxy-benzamide (58 mg, 0.12 mmol) gave, after purification, the titled compound (0.02 mmol) as a white solid. UPLC-MS (ES+, Short acidic): 1.55 min, m/z 518.1 [M+H]+. UPLC-MS (ES+, Long acidic): 3.60 min, m/z 518.0 [M+H]+. $^1$H NMR (400 MHz, DMSO-d$_6$, δ): 8.74 (t, J=6.1 Hz, 1H), 7.76 (dd, J=7.7, 1.8 Hz, 1H), 7.51-7.41 (m, 5H), 7.17-7.15 (m, 1H), 7.06-7.04 (m, 1H), 6.41 (s, 2H), 4.55 (d, J=6.1 Hz, 2H), 4.54-4.48 (m, 1H), 4.18-4.13 (m, 2H), 3.91 (s, 3H), 3.67-3.60 (m, 1H), 2.08-1.85 (m, 4H)

Example 112: 5-(difluoromethyl)-3-[4-[[(2-methoxybenzoyl)amino]methyl]phenyl]-1-[(3S)-tetrahydrofuran-3-yl]pyrazole-4-carboxamide

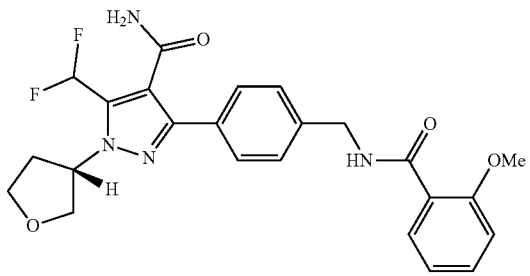 [SMILES: COc1ccccc1C(=O)NCc1ccc(-c2nn([C@H]3CCOC3)c(C(F)F)c2C(N)=O)cc1]

Ethyl 3-bromo-5-(difluoromethyl)-1-[(3S)-tetrahydrofuran-3-yl]pyrazole-4-carboxylate Diisopropyl azodicarboxylate (1.12 mmol) was added to a solution of (R)-(−)-3-hydroxytetrahydrofuran (1.12 mmol), triphenylphosphine (1.12 mmol) and ethyl 3-bromo-5-(difluoromethyl)-1H-pyrazole-4-carboxylate (0.74 mmol) in THF (3.5 mL). The mixture was stirred for 1 h at RT and then concentrated under reduced pressure. Further purification gave (isomer 2). UPLC-MS (ES+, Short acidic: isomer 1): 1.73 min, m/z 340.9 [M+2]+. UPLC-MS (ES+, Short acidic: isomer 2): 1.63 min, m/z 340.9 [M+2]+

3-Bromo-5-(difluoromethyl)-1-[(3S)-tetrahydrofuran-3-yl]pyrazole-4-carboxylic acid Sodium hydroxide (1 M in water, 0.95 mmol) was added to a solution of ethyl 3-bromo-5-(difluoromethyl)-1-[(3S)-tetrahydrofuran-3-yl]pyrazole-4-carboxylate (0.32 mmol) in THF (1.3 mL). The mixture was then heated to 50° C. for 16 h, cooled to RT, acidified to ~pH 1 with HCl (1 M in water). The layers were partitioned. The aqueous layer was extracted with DCM (×3). The combined organic extracts were filtered over a hydrophobic frit and concentrated under reduced pressure to afford crude the titled compound (0.32 mmol) as an off-white solid which was used directly in the next step. UPLC-MS (ES+, Short acidic): 1.31 min, m/z 312.8 [M+2]+

3-Bromo-5-(difluoromethyl)-1-[(3S)-tetrahydrofuran-3-yl]pyrazole-4-carboxamide

A drop of DMF was added to a solution of oxalyl chloride (0.48 mmol) and 3-bromo-5-(difluoromethyl)-1-[(3S)-tetrahydrofuran-3-yl]pyrazole-4-carboxylic acid (0.32 mmol) in DCM (3 mL) at RT. The mixture was allowed to stir at RT for 1 h, cooled to 0° C. and then ammonium hydroxide (28 wt % in water, 1.90 mmol) was added carefully. The reaction mixture was allowed to stir at RT for 10 min. The mixture was diluted with water and DCM and the layers were partitioned. The aqueous layer was extracted with DCM (×3) and the combined organic extracts were filtered over a hydrophobic frit and concentrated under reduced pressure. Purification gave the titled compound (0.27 mmol) as a white solid. UPLC-MS (ES+, Short acidic): 1.18 min, m/z 311.8 [M+2]+

5-(Difluoromethyl)-3-[4-[[(2-methoxybenzoyl)amino]methyl]phenyl]-1-[(3S)-tetrahydrofuran-3-yl]pyrazole-4-carboxamide General procedure C, [4-[[(2-methoxybenzoyl)amino]methyl]phenyl]boronic acid (0.15 mmol) and 3-bromo-5-(difluoromethyl)-1-[(3S)-tetrahydrofuran-3-yl]pyrazole-4-carboxamide (0.10 mmol) gave, after purification, the titled compound (0.05 mmol) as a white solid. UPLC-MS (ES+, Short acidic): 1.47 min, m/z 471.0 [M+H]+. UPLC-MS (ES+, Long acidic): 3.36 min, m/z 471.1 [M+H]+. $^1$H NMR (400 MHz, DMSO-$d_6$, δ): 8.73 (t, J=6.1 Hz, 1H), 7.75 (dd, J=7.7, 1.9 Hz, 1H), 7.68-7.61 (m, 3H), 7.60 (br s, 1H), 7.52-7.45 (m, 1H), 7.40 (d, J=8.4 Hz, 2H), 7.33 (t, J=53.6 Hz, 1H), 7.16 (d, J=7.8 Hz, 1H), 7.08-7.01 (m, 1H), 5.28-5.19 (m, 1H), 4.53 (d, J=6.1 Hz, 2H), 4.14-4.03 (m, 2H), 3.94-3.83 (m, 5H), 2.48-2.31 (m, 2H).

Example 113: 5-amino-3-[4-[[(5-fluoro-2-methoxybenzoyl)amino]methyl]phenyl]-1-tetrahydropyran-3-yl-pyrazole-4-carboxamide

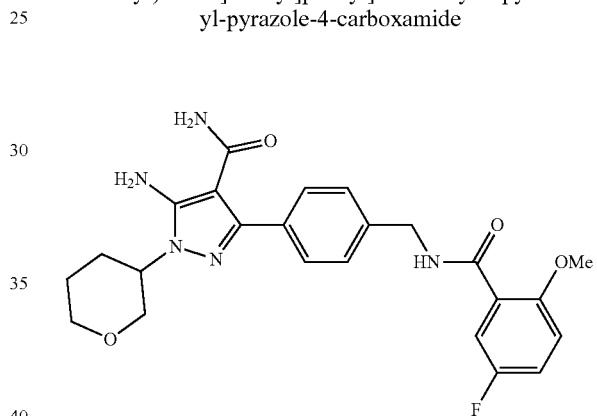

N-[[4-(5-Amino-4-cyano-1-tetrahydropyran-3-yl-pyrazol-3-yl)phenyl]methyl]-5-fluoro-2-methoxy-benzamide General procedure K, potassium trifluoro-[[(5-fluoro-2-methoxy-benzoyl)amino]methyl]boranuide (0.19 mmol) and 5-amino-3-(4-bromophenyl)-1-tetrahydropyran-3-yl-pyrazole-4-carbonitrile (0.14 mmol) gave, after purification, the titled compound (0.06 mmol) as a brown solid. UPLC-MS (ES+, Short acidic): 1.60 min, m/z 450 [M+H]+

5-Amino-3-[4-[[(5-fluoro-2-methoxy-benzoyl)amino]methyl]phenyl]-1-tetrahydropyran-3-yl-pyrazole-4-carboxamide General procedure M, N-[[4-(5-amino-4-cyano-1-tetrahydropyran-3-yl-pyrazol-3-yl)phenyl]methyl]-5-fluoro-2-methoxy-benzamide (0.06 mmol) gave, after purification, the titled compound (0.03 mmol) as a white solid. UPLC-MS (ES+, Short acidic): 1.41 min, m/z 468.1 [M+H]+. UPLC-MS (ES+, Long acidic): 3.22 min, m/z 468.1 [M+H]+. $^1$H NMR (400 MHz, DMSO-$d_6$, δ): 8.83 (t, J=6.2 Hz, 1H), 7.51 (dd, J=9.2, 3.3 Hz, 1H), 7.45 (d, J=8.4 Hz, 2H), 7.41 (d, J=8.4 Hz, 2H), 7.34 (m, 1H), 7.19 (m, 1H), 6.42 (s, 2H), 4.55 (d, J=6.1 Hz, 2H), 4.30-4.19 (m, 1H), 3.90

(s, 3H), 3.88-3.80 (m, 2H), 3.54 (t, J=10.5 Hz, 1H), 3.36-3.26 (m, 1H), 2.06-1.95 (m, 2H), 1.79-1.59 (m, 2H).

Example 114: 5-amino-3-[4-[[(5-fluoro-2-methoxy-benzoyl)amino]methyl]phenyl]-1-tetrahydrofuran-3-yl-pyrazole-4-carboxamide

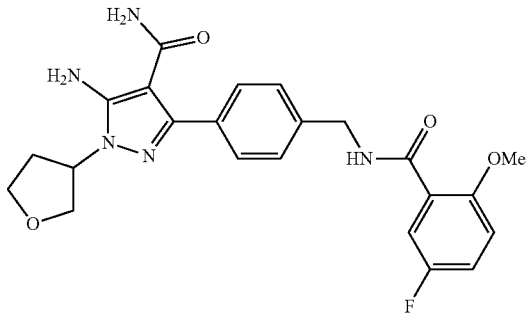 [SMILES: COc1ccc(F)cc1C(=O)NCc1ccc(-c2nn(C3CCOC3)c(N)c2C(N)=O)cc1]

5-Amino-3-(4-bromophenyl)-1-tetrahydrofuran-3-yl-pyrazole-4-carbonitrile

General procedure H, 2-[(4-bromophenyl)-methoxy-methylene]propanedinitrile (0.57 mmol), and tetrahydrofuran-3-ylhydrazine hydrochloride (0.68 mmol) gave, after purification, the titled compound (0.40 mmol) as an off-white solid. UPLC-MS (ES+, Short acidic): 1.68 min, m/z 334.9 [M+2]+

N-[[4-(5-Amino-4-cyano-1-tetrahydrofuran-3-yl-pyrazol-3-yl)phenyl]methyl]-5-fluoro-2-methoxy-benzamide General procedure K, potassium trifluoro-[[(5-fluoro-2-methoxy-benzoyl)amino]methyl]boranuide (0.23 mmol) and 5-amino-3-(4-bromophenyl)-1-tetrahydrofuran-3-yl-pyrazole-4-carbonitrile (0.18 mmol) gave, after purification, the titled compound (0.09 mmol) as an off-white solid. UPLC-MS (ES+, Short acidic): 1.53 min, m/z 436 [M+H]+

5-Amino-3-[4-[[(5-fluoro-2-methoxy-benzoyl)amino]methyl]phenyl]-1-tetrahydrofuran-3-yl-pyrazole-4-carboxamide General procedure M, N-[[4-(5-amino-4-cyano-1-tetrahydrofuran-3-yl-pyrazol-3-yl)phenyl]methyl]-5-fluoro-2-methoxy-benzamide (0.09 mmol) gave, after purification, the titled compound (0.07 mmol) as a white solid. UPLC-MS (ES+, Short acidic): 1.35 min, m/z 454.1 [M+H]+. UPLC-MS (ES+, Long acidic): 3.06 min, m/z 454.1 [M+H]+. $^1$H NMR (400 MHz, DMSO-$d_6$, δ): 8.84 (t, J=6.0 Hz, 1H), 7.52 (dd, J=9.2, 3.3 Hz, 1H), 7.46 (d, J=8.2 Hz, 2H), 7.41 (d, J=8.3 Hz, 2H), 7.38-7.30 (m, 1H), 7.19 (dd, J=9.1, 4.3 Hz, 1H), 6.40 (s, 2H), 4.99-4.89 (m, 1H), 4.55 (d, J=6.0 Hz, 2H), 4.03-3.92 (m, 2H), 3.90 (s, 3H), 3.85-3.76 (m, 2H), 2.30-2.21 (m, 2H).

Example 115: 5-amino-3-[4-[[(5-fluoro-2-methoxy-benzoyl)amino]methyl]phenyl]-1-tetrahydropyran-4-yl-pyrazole-4-carboxamide

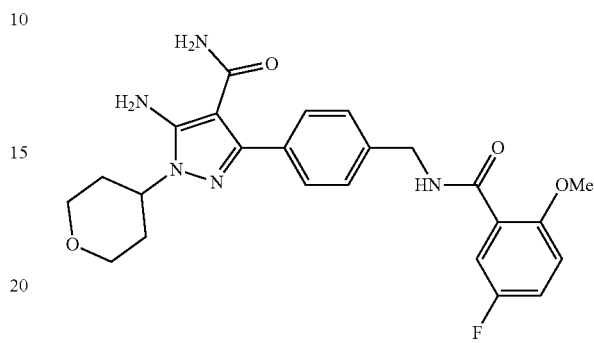

5-Amino-3-(4-bromophenyl)-1-tetrahydropyran-4-yl-pyrazole-4-carbonitrile

Following general procedure H, 2-[(4-bromophenyl)-methoxy-methylene]propanedinitrile (1.39 g, 5.29 mmol) and tetrahydropyran-4-ylhydrazine hydrochloride (1.00 g, 6.35 mmol) gave, after purification, the titled compound (4.78 mmol) as an off-white solid. LC-MS (ES+, Short acidic): 5.64 min, m/z 347.0 [M]+

N-[[4-(5-Amino-4-cyano-1-tetrahydropyran-4-yl-pyrazol-3-yl)phenyl]methyl]-5-fluoro-2-methoxy-benzamide General Procedure K, 5-amino-3-(4-bromophenyl)-1-tetrahydropyran-4-yl-pyrazole-4-carbonitrile (4.78 mmol) and potassium trifluoro-[[(5-fluoro-2-methoxy-benzoyl)amino]methyl]boranuide (9.56 mmol) gave, after purification, the titled compound (1.98 mmol) as a yellow solid. UPLC-MS (ES+, Short acidic): 1.60 min, m/z 450.1 [M+H]+

5-Amino-3-[4-[[(5-fluoro-2-methoxy-benzoyl)amino]methyl]phenyl]-1-tetrahydropyran-4-yl-pyrazole-4-carboxamide General procedure M, N-[[4-(5-amino-4-cyano-1-tetrahydropyran-4-yl-pyrazol-3-yl)phenyl]methyl]-5-fluoro-2-methoxy-benzamide (1.98 mmol) gave, after purification, the titled compound carboxamide (1.46 mmol) as a beige solid. UPLC-MS (ES+, Short acidic): 1.40 min, m/z 468.1 [M+H]+. UPLC-MS (ES+, Long acidic): 3.14 min, m/z 468.1 [M+H]+. $^1$H NMR (400 MHz, DMSO-$d_6$, δ): 8.84 (t, J=6.1 Hz, 1H), 7.52 (dd, J=9.2, 3.3 Hz, 1H), 7.46 (d, J=8.3 Hz, 2H), 7.41 (d, J=8.4 Hz, 2H), 7.38-7.30 (m, 1H), 7.19 (dd, J=9.1, 4.3 Hz, 1H), 6.38 (s, 2H), 4.55 (d, J=6.1 Hz, 2H), 4.42-4.27 (m, 1H), 4.01-3.93 (m, 2H), 3.90 (s, 3H), 3.48-3.37 (m, 2H), 2.05-1.91 (m, 2H), 1.82-1.72 (m, 2H).

Example 116: 5-amino-3-[3-fluoro-4-[[(2-methoxybenzoyl)amino]methyl]phenyl]-1-tetrahydropyran-4-yl-pyrazole-4-carboxamide

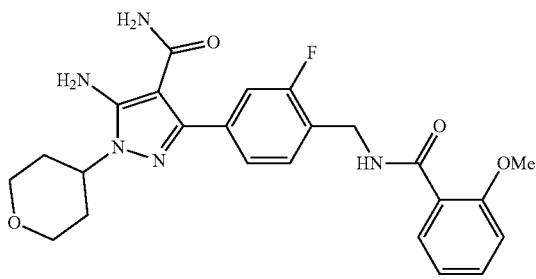 [SMILES: COc1ccccc1C(=O)NCc1ccc(-c2nn(C3CCOCC3)c(N)c2C(N)=O)cc1F]

5-Amino-3-(4-bromo-3-fluoro-phenyl)-1-tetrahydropyran-4-yl-pyrazole-4-carbonitrile General procedure H, 2-[(4-bromo-3-fluoro-phenyl)-methoxy-methylene]propanedinitrile (0.88 mmol), and tetrahydropyran-4-ylhydrazine hydrochloride (1.05 mmol) gave, after purification, the titled compound (0.60 mmol) as an off-white solid. UPLC-MS (ES$^+$, Short acidic): 1.76 min, m/z 366.9 [M+2]$^+$

N-[[4-(5-Amino-4-cyano-1-tetrahydropyran-4-yl-pyrazol-3-yl)-2-fluoro-phenyl]methyl]-2-methoxy-benzamide General procedure K, 5-amino-3-(4-bromo-3-fluoro-phenyl)-1-tetrahydropyran-4-yl-pyrazole-4-carbonitrile (0.60 mmol) and potassium trifluoro-[[(2-methoxybenzoyl)amino]methyl]boranuide (1.27 mmol) gave, after purification, the titled compound (0.49 mmol) as a brown solid. UPLC-MS (ES$^+$, Short acidic): 1.56 min, m/z 450.1 [M+H]$^+$

5-Amino-3-[3-fluoro-4-[[(2-methoxybenzoyl)amino]methyl]phenyl]-1-tetrahydropyran-4-yl-pyrazole-4-carboxamide General procedure M, N-[[4-(5-amino-4-cyano-1-tetrahydropyran-4-yl-pyrazol-3-yl)-2-fluoro-phenyl]methyl]-2-methoxy-benzamide (0.26 mol) gave, after purification, the titled compound (0.10 mmol) as an off-white solid. UPLC-MS (ES$^+$, Short acidic): 1.35 min, m/z 468.0 [M+H]$^+$. UPLC-MS (ES$^+$, Long acidic): 3.08 min, m/z 468.1 [M+H]$^+$. $^1$H NMR (400 MHz, DMSO-d$_6$, δ): 8.72 (t, J=5.9 Hz, 1H), 7.75 (dd, J=7.6, 1.6 Hz, 1H), 7.51-7.42 (m, 2H), 7.34-7.23 (m, 2H), 7.16 (d, J=8.3 Hz, 1H), 7.06-7.02 (m, 1H), 6.32 (s, 2H), 4.57 (d, J=6.1 Hz, 2H), 4.40-4.33 (m, 1H), 3.99-3.95 (m, 2H), 3.91 (s, 3H), 3.46-3.39 (m, 2H), 2.03-1.93 (m, 2H), 1.79-1.75 (m, 2H).

Example 117: 5-amino-3-[3-fluoro-4-[[(2-methoxybenzoyl)amino]methyl]phenyl]-1-tetrahydropyran-3-yl-pyrazole-4-carboxamide

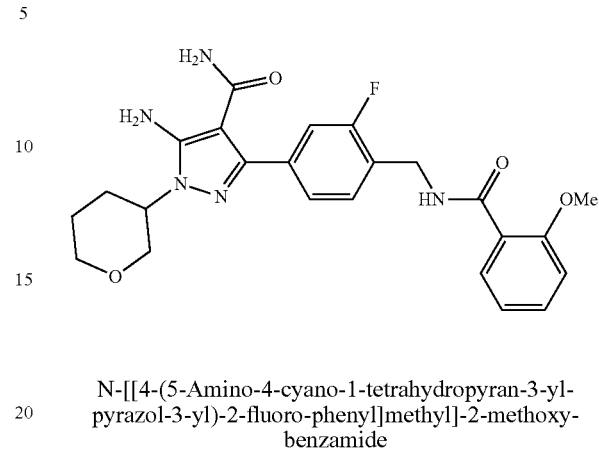

N-[[4-(5-Amino-4-cyano-1-tetrahydropyran-3-yl-pyrazol-3-yl)-2-fluoro-phenyl]methyl]-2-methoxy-benzamide General K, 5-amino-3-(4-bromo-3-fluoro-phenyl)-1-tetrahydropyran-3-yl-pyrazole-4-carbonitrile (0.20 mmol) and potassium trifluoro-[[(2-methoxybenzoyl)amino]methyl]boranuide (0.43 mmol) gave, after purification, the titled compound (0.16 mmol) as a brown solid. UPLC-MS (ES$^+$, Short acidic): 1.62 min, m/z 450.0 [M+H]$^+$

5-Amino-3-[3-fluoro-4-[[(2-methoxybenzoyl)amino]methyl]phenyl]-1-tetrahydropyran-3-yl-pyrazole-4-carboxamide General procedure M, N-[[4-(5-amino-4-cyano-1-tetrahydropyran-3-yl-pyrazol-3-yl)-2-fluoro-phenyl]methyl]-2-methoxy-benzamide (0.16 mmol) gave, after purification, the titled compound (0.09 mmol) as an off-white solid. UPLC-MS (ES$^+$, Short acidic): 1.42 min, m/z 468.0 [M+H]$^+$. UPLC-MS (ES$^+$, Long acidic): 3.24 min, m/z 468.0 [M+H]$^+$. $^1$H NMR (400 MHz, DMSO-d$_6$, δ): 8.72 (t, J=5.9 Hz, 1H), 7.75 (dd, J=7.5, 1.8 Hz, 1H), 7.51-7.41 (m, 2H), 7.33-7.26 (m, 2H), 7.16 (d, J=8.2 Hz, 1H), 7.06-7.02 (m, 1H), 6.35 (s, 2H), 4.57 (d, J=6.0 Hz, 2H), 4.30-4.22 (m, 1H), 3.91 (s, 3H), 3.89-3.83 (m, 2H), 3.54 (t, J=10.5 Hz, 1H), 3.39-3.26 (m, 1H), 2.03-1.98 (m, 2H), 1.77-1.65 (m, 2H).

Example 118: 5-amino-1-cyclopentyl-3-[4-fluoro-3-[[(2-methoxybenzoyl)amino]methyl]phenyl]pyrazole-4-carboxamide

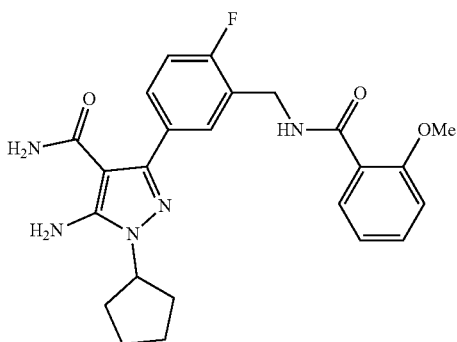 [SMILES: COc1ccccc1C(=O)NCc1cc(-c2nn(C3CCCC3)c(N)c2C(N)=O)ccc1F]

N-[(5-Bromo-2-fluoro-phenyl)methyl]-2-methoxy-benzamide

To a solution of 5-bromo-2-fluorobenzonitrile (2.50 mmol) in THF (15 mL), cooled at 0° C., was added dropwise a borane tetrahydrofuran complex solution (1 M in THF, 7.5 mL, 7.50 mmol). The reaction was stirred at 0° C. for 20 min and then at RT for 16 h. The reaction mixture was quenched with MeOH dropwise (15 mL) and the solution was concentrated under reduced pressure. The oil was then partitioned between an aqueous solution of NaOH (1 M) and EtOAc. The organic layer was washed with brine, dried over sodium sulfate, filtered and concentrated under reduced pressure to give crude (5-bromo-2-fluoro-phenyl)methanamine (629 mg) as a colourless oil. The oil was taken up with THF (10 mL) and cooled to 0° C. 2-Methoxybenzoyl chloride (2.75 mmol) and N,N-diisopropylethylamine (7.50 mmol) were then added sequentially. The reaction mixture was stirred for 20 min at 0° C. and then allowed to stir at RT for 16 h. The mixture was quenched with a saturated aqueous solution of NH$_4$Cl and the organics were removed under reduced pressure. The residue was then extracted with EtOAc. The organic layer was washed with brine, dried over sodium sulfate, filtered and concentrated under reduced pressure. The residue was then purified to give the titled compound (1.30 mmol) as a colourless oil. UPLC-MS (ES$^+$, Short acidic): 1.75 min, m/z 339.9 [M+2]$^+$

N-[[2-Fluoro-5-(4,4,5,5-tetramethyl-1,3,2-dioxaborolan-2-yl)phenyl]methyl]-2-methoxy-benzamide General procedure R, N-[(5-bromo-2-fluoro-phenyl)methyl]-2-methoxy-benzamide (1.30 mmol) gave, after purification, the titled compound (1.26 mmol) as a white solid. UPLC-MS (ES$^+$, Short acidic): 1.92 min, m/z 386.0 [M+H]$^+$

5-Amino-1-cyclopentyl-3-[4-fluoro-3-[[(2-methoxy-benzoyl)amino]methyl]phenyl]pyrazole-4-carboxamide General procedure D, N-[[2-fluoro-5-(4,4,5,5-tetramethyl-1,3,2-dioxaborolan-2-yl)phenyl]methyl]-2-methoxy-benzamide (0.65 mmol) and 5-amino-3-bromo-1-cyclopentyl-pyrazole-4-carboxamide (0.62 mmol) gave, after purification, the titled compound (0.05 mmol) as a white solid. UPLC-MS (ES$^+$, Short acidic): 1.56 min, m/z 452.1.0 [M+H]$^+$. UPLC-MS (ES$^+$, Long acidic): 3.59 min, m/z 452.0 [M+H]$^+$. $^1$H NMR (400 MHz, DMSO-d$_6$, δ): 8.71 (t, J=5.9 Hz, 1H), 7.69 (dd, J=7.6, 1.8 Hz, 1H), 7.52 (dd, J=7.5, 2.1 Hz, 1H), 7.46-7.44 (m, 1H), 7.42-7.36 (m, 1H), 7.26 (dd, J=10.0, 8.5 Hz, 1H), 7.15-7.11 (m, 1H), 7.04-6.99 (m, 1H), 6.31 (s, 2H), 4.64-4.54 (m, 3H), 3.84 (s, 3H), 1.98-1.90 (m, 2H), 1.90-1.81 (m, 2H), 1.81-1.69 (m, 2H), 1.61-1.50 (m, 2H).

Example 119: 5-amino-3-[3-fluoro-4-[[(5-fluoro-2-methoxy-benzoyl)amino]methyl]phenyl]-1-tetrahydrofuran-3-yl-pyrazole-4-carboxamide

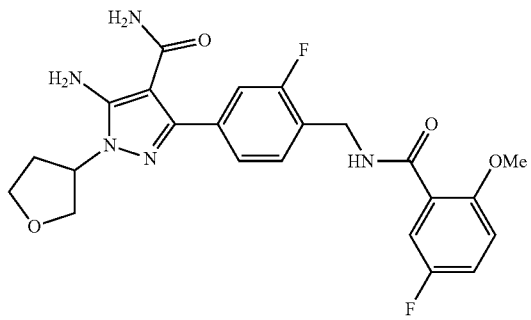

5-Amino-3-(4-bromo-3-fluoro-phenyl)-1-tetrahydrofuran-3-yl-pyrazole-4-carbonitrile General procedure H, 2-[(4-bromo-3-fluoro-phenyl)-methoxy-methylene]propanedinitrile (150 mg, 0.53 mmol), and tetrahydrofuran-3-ylhydrazine hydrochloride (0.64 mmol) gave, after purification, the titled compound (0.53 mmol) as an off-white solid. UPLC-MS (ES$^+$, Short acidic): 1.72 min, m/z 352.8 [M+2]$^+$

N-[[4-(5-Amino-4-cyano-1-tetrahydrofuran-3-yl-pyrazol-3-yl)-2-fluoro-phenyl]methyl]-5-fluoro-2-methoxy-benzamide General procedure K, 5-amino-3-(4-bromo-3-fluoro-phenyl)-1-tetrahydrofuran-3-yl-pyrazole-4-carbonitrile (0.23 mmol) and potassium trifluoro-[[(5-fluoro-2-methoxy-benzoyl)amino]methyl]boranuide (0.32 mmol) gave, after purification, the titled compound (0.20 mmol) as a yellow solid. UPLC-MS (ES$^+$, Short acidic): 1.59 min, m/z 454.0 [M+H]$^+$

5-Amino-3-[3-fluoro-4-[[(5-fluoro-2-methoxy-benzoyl)amino]methyl]phenyl]-1-tetrahydrofuran-3-yl-pyrazole-4-carboxamide General procedure L, N-[[4-(5-amino-4-cyano-1-tetrahydrofuran-3-yl-pyrazol-3-yl)-2-fluoro-phenyl]methyl]-5-fluoro-2-methoxy-benzamide (0.20 mmol) gave, after purification, the titled compound (0.16 mmol) as a beige solid. UPLC-MS (ES$^+$, Short acidic): 1.40 min, m/z 494.0 [M+Na]$^+$. UPLC-MS (ES$^+$, Long acidic): 3.20 min, m/z 472.0 [M+H]$^+$. $^1$H NMR (400 MHz, DMSO-d$_6$, δ): 8.82 (t, J=6.1 Hz, 1H), 7.50 (dd, J=9.2, 3.3 Hz, 1H), 7.43 (t, J=8.0 Hz, 1H), 7.37-7.28 (m, 3H), 7.19 (dd, J=9.1, 4.3 Hz, 1H), 6.34 (s, 2H), 4.97-4.91 (m, 1H), 4.56 (d, J=5.9 Hz, 2H), 4.01-3.93 (m, 2H), 3.90 (s, 3H), 3.83-3.78 (m, 2H), 2.28-2.23 (m, 2H).

Example 120: 5-amino-3-[4-[[(5-fluoro-2-methoxy-benzoyl)amino]methyl]phenyl]-1-(2,2,2-trifluoro-1-methyl-ethyl)pyrazole-4-carboxamide

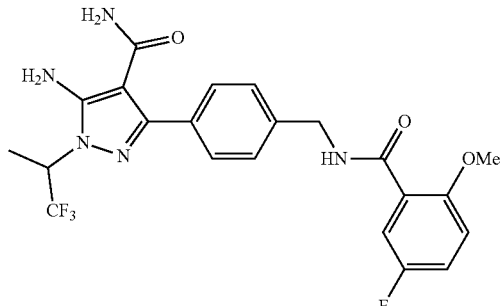

N-[(2,2,2-Trifluoro-1-methyl-ethylidene)amino]benzamide

General procedure S, benzhydrazide (49.9 mmol) and 1,1,1-trifluoroacetone (74.9 mmol) gave, after washing, the titled compound as a white solid. UPLC-MS (ES+, Short acidic): 1.45 min, m/z 230.9 [M+H]+

N'-(2,2,2-Trifluoro-1-methyl-ethyl)benzohydrazide

To a solution of N-[(2,2,2-trifluoro-1-methyl-ethylidene)amino]benzamide (21.7 mmol) in THF (50 mL), cooled at 0° C., was added dropwise borane tetrahydrofuran complex solution (1 M in THF, 43.44 mmol). The reaction was allowed to return to RT and stirred for 14 h. The reaction was cooled to 0° C., quenched with MeOH (20 mL) and then allowed to return to RT. The mixture was evaporated and DCM (75 mL) was added. The slurry was filtered to remove insoluble material. The organic layer was washed with saturated ammonium chloride (50 mL), dried over magnesium sulfate, filtered and concentrated under reduced pressure. Pet. Ether (50 mL) was added to the yellow oil resulting in a solid crashing out. The solvent was reduced by 50% and the slurry cooled in an ice bath and filtered. The solid was washed with Pet. Ether (25 mL) to give the titled compound as a white solid. UPLC-MS (ES+, Short acidic): 1.41 min, m/z 232.9 [M+H]+

(2,2,2-Trifluoro-1-methyl-ethyl)hydrazine hydrochloride

Following general procedure U, N'-(2,2,2-trifluoro-1-methyl-ethyl)benzohydrazide (4.0 g, 17.2 mmol), gave (2,2,2-trifluoro-1-methyl-ethyl)hydrazine hydrochloride (1.7 g, 10.3 mmol, 60% yield) as white solid. $^1$H NMR (400 MHz, DMSO-$d_6$, δ): 9.65 (br s, 2H), 5.97 (br s, 1H), 3.87-3.80 (m, 1H), 1.28 (d, J=6.8 Hz, 3H).

5-Amino-3-(4-bromophenyl)-1-(2,2,2-trifluoro-1-methyl-ethyl)pyrazole-4-carbonitrile To a solution of 2-[(4-bromophenyl)-methoxy-methylene]propanedinitrile (7.98 mmol) in EtOH (50 mL) was added triethylamine (31.9 mmol). After 10 min stirring, (2,2,2-trifluoro-1-methyl-ethyl)hydrazine hydrochloride (12.0 mmol) was added. The reaction mixture was heated to 80° C. for 14 h, cooled and concentrated under reduced pressure. Further purification gave the titled compound (7.24 mmol) as an off-white solid. UPLC-MS (ES+, Short acidic): 1.91 min, m/z 360.9 [M+2]+

N-[[4-[5-Amino-4-cyano-1-(2,2,2-trifluoro-1-methyl-ethyl)pyrazol-3-yl]phenyl]methyl]-5-fluoro-2-methoxy-benzamide General procedure K, potassium trifluoro-[[(5-fluoro-2-methoxy-benzoyl)amino]methyl]boranuide (4.26 mmol), and 5-amino-3-(4-bromophenyl)-1-(2,2,2-trifluoro-1-methyl-ethyl)pyrazole-4-carbonitrile (2.51 mmol) gave, after purification, the titled compound (2.17 mmol) as an off-white solid. UPLC-MS (ES+, Short acidic): 1.71 min, 462.0 [M+H]+

5-Amino-3-[4-[[(5-fluoro-2-methoxy-benzoyl)amino]methyl]phenyl]-1-(2,2,2-trifluoro-1-methyl-ethyl)pyrazole-4-carboxamide General procedure M, N-[[4-[5-amino-4-cyano-1-(2,2,2-trifluoro-1-methyl-ethyl)pyrazol-3-yl]phenyl]methyl]-5-fluoro-2-methoxy-benzamide (0.83 mmol) gave, after purification, the titled compound (0.42 mmol) as a white solid. UPLC-MS (ES+, Short acidic): 1.55 min, m/z 480.1 [M+H]+. UPLC-MS (ES+, Long acidic): 3.57 min, m/z 480.1 [M+H]+. $^1$H NMR (400 MHz, DMSO-$d_6$, δ): 8.84 (t, J=6.1 Hz, 1H), 7.52 (dd, J=9.2, 3.3 Hz, 1H), 7.48-7.41 (m, 4H), 7.37-7.32 (m, 1H), 7.19 (dd, J=9.1, 4.3 Hz, 1H), 6.67 (s, 2H), 5.35-5.24 (m, 1H), 4.56 (d, J=6.0 Hz, 2H), 3.90 (s, 3H), 1.62 (d, J=6.9 Hz, 3H).

Example 121: 5-amino-3-[4-[[(2-methoxybenzoyl)amino]methyl]phenyl]-1-(2,2,2-trifluoro-1-methyl-ethyl)pyrazole-4-carboxamide

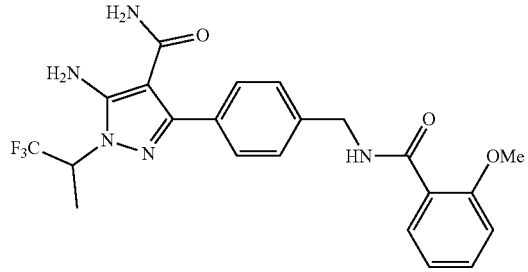 [SMILES: COc1ccccc1C(=O)NCc1ccc(-c2nn(C(C)C(F)(F)F)c(N)c2C(N)=O)cc1]

N-[[4-[5-Amino-4-cyano-1-(2,2,2-trifluoro-1-methyl-ethyl)pyrazol-3-yl]phenyl]methyl]-2-methoxy-benzamide General procedure K, 5-amino-3-(4-bromophenyl)-1-(2,2,2-trifluoro-1-methyl-ethyl)pyrazole-4-carbonitrile (0.92 mmol) and potassium trifluoro-[[(2-methoxybenzoyl)amino]methyl]boranuide (1.39 mmol) gave, after purification, the titled compound (0.41 mmol) as an off-white solid. UPLC-MS (ES+, Short acidic): 1.66 min, m/z 444.0 [M+H]+

5-Amino-3-[4-[[(2-methoxybenzoyl)amino]methyl]phenyl]-1-(2,2,2-trifluoro-1-methyl-ethyl)pyrazole-4-carboxamide Following general procedure M, N-[[4-[5-amino-4-cyano-1-(2,2,2-trifluoro-1-methyl-ethyl)pyrazol-3-yl]phenyl]methyl]-2-methoxy-benzamide (0.40 mmol) gave, after purification, the titled compound (0.182 mmol) as a white solid. UPLC-MS (ES⁺, Short acidic): 1.48 min, m/z 462.0 [M+H]⁺. UPLC-MS (ES⁺, Long acidic): 3.42 min, m/z 461.9 [M+H]⁺. ¹H NMR (400 MHz, DMSO-d₆, δ): 8.74 (t, J=6.2 Hz, 1H), 7.76 (dd, J=7.6, 1.8 Hz, 1H), 7.51-7.42 (m, 5H), 7.16 (d, J=7.8 Hz, 1H), 7.04 (td, J=7.5, 1.0 Hz, 1H), 6.67 (br s, 2H), 5.33-5.26 (m, 1H), 4.56 (d, J=6.1 Hz, 2H), 3.90 (s, 3H), 1.62 (d, J=6.8 Hz, 3H).

Example 122: 5-amino-3-[4-[[(5-fluoro-2-methoxy-benzoyl)amino]methyl]phenyl]-1-(2,2,2-trifluoro-ethyl)pyrazole-4-carboxamide

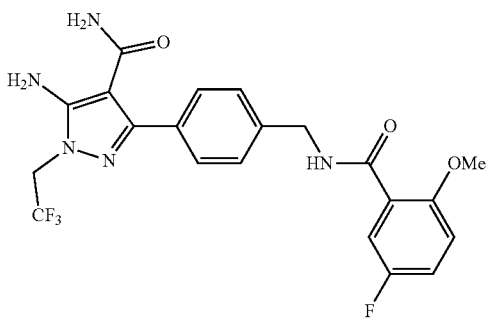 [SMILES: COc1ccc(F)cc1C(=O)NCc1ccc(-c2nn(CC(F)(F)F)c(N)c2C(N)=O)cc1]

5-Amino-3-(4-bromophenyl)-1-(2,2,2-trifluoroethyl)pyrazole-4-carbonitrile

A solution of triethylamine (380.13 mmol) and 2-[(4-bromophenyl)-methoxy-methylene]propanedinitrile (25.0 g, 95.03 mmol) in EtOH (600 mL) was left to stir for 10 min before adding 2,2,2-trifluoroethyl hydrazine (70 wt % in water, 142.54 mmol) in one aliquot to almost immediately give a clear orange solution and an exotherm from 22-29° C. over 2-3 min. The resulting mixture was then heated to reflux for 5 h. Once the reaction has reached completion, the reaction mixture was concentrated under reduced pressure to give an orange solid. Further purification gave the titled compound (25.3 g, 73.31 mmol, 77% yield) as a pale yellow solid. UPLC-MS (ES⁺, Short acidic): 1.78 min, m/z 346.8 [M+2]⁺

N-[[4-[5-Amino-4-cyano-1-(2,2,2-trifluoroethyl)pyrazol-3-yl]phenyl]methyl]-5-fluoro-2-methoxy-benzamide A mixture of 5-amino-3-(4-bromophenyl)-1-(2,2,2-trifluoroethyl)pyrazole-4-carbonitrile (29.0 mmol), potassium trifluoro-[[(5-fluoro-2-methoxy-benzoyl)amino]methyl]boranuide (58.03 mmol), cesium carbonate (86.92 mmol), 2-dicyclohexylphosphino-2',4',6'-triisopropylbiphenyl (2.03 mmol), THF (120 mL) and water (60 mL) at RT was degassed under vacuum and flushed with nitrogen three times. Then palladium (II) acetate (1.01 mmol) was added and the mixture was degassed again. The reaction mixture was heated to reflux for 2 h, cooled and diluted with water (100 mL) and EtOAc (200 mL), filtered over Celite® and separated. The aqueous layer was extracted with EtOAc (100 mL) and the combined organic extracts were washed with water before drying over magnesium sulfate. Further purification gave a solid which was further purified using a formation of a slurry in hot THF and EtOAc (100 mL, 1:1) and precipitated with Pet. Ether and stirred until cold. The product was filtered off and washed with Pet. Ether to give the titled compound (24.7 mmol). UPLC-MS (ES⁺, Short acidic): 1.61 min, m/z 448.0 [M+H]⁺

5-Amino-3-[4-[[(5-fluoro-2-methoxy-benzoyl)amino]methyl]phenyl]-1-(2,2,2-trifluoroethyl)pyrazole-4-carboxamide N-[[4-[5-amino-4-cyano-1-(2,2,2-trifluoroethyl)pyrazol-3-yl]phenyl]methyl]-5-fluoro-2-methoxy-benzamide (30.40 mmol) was added a solution of sulfuric acid (304 mmol) and TFA (912 mmol) to give a light brown solution. The reaction mixture was heated to 58° C. for 5 h, cooled and slowly poured onto an ice-cooled solution of sodium bicarbonate (153.2 g, 1824 mmol) in water (750 mL) and then extracted with EtOAc (3×250 mL). The combined organic extracts were washed with brine, dried over magnesium sulfate, filtered and concentrated under reduced pressure. Further purification gave the titled compound (28.4 mmol). UPLC-MS (ES⁻, Short acidic): 1.44 min, m/z 463.7 [M−H]⁻. UPLC-MS (ES⁺, Long acidic): 3.31 min, m/z 465.9 [M+H]⁺. ¹H NMR (400 MHz, DMSO-d₆, δ): 8.85 (t, J=6.0 Hz, 1H), 7.52 (dd, J=9.2, 3.3 Hz, 1H), 7.47 (d, J=8.2 Hz, 2H), 7.42 (d, J=8.2 Hz, 2H), 7.38-7.32 (m, 1H), 7.19 (dd, J=9.2, 4.3 Hz, 1H), 6.68 (s, 2H), 4.94 (q, J=9.0 Hz, 2H), 4.56 (d, J=6.1 Hz, 2H), 3.90 (s, 3H).

Example 123: 5-amino-3-[3-fluoro-4-[[(5-fluoro-2-methoxy-benzoyl)amino]methyl]phenyl]-1-tetrahydropyran-4-yl-pyrazole-4-carboxamide

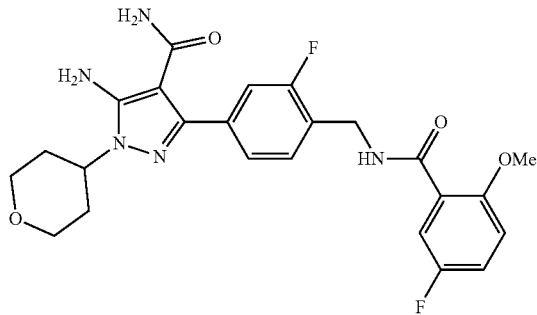 [SMILES: COc1ccc(F)cc1C(=O)NCc1ccc(-c2nn(C3CCOCC3)c(N)c2C(N)=O)cc1F]

N-[[4-(5-Amino-4-cyano-1-tetrahydropyran-4-yl-pyrazol-3-yl)-2-fluoro-phenyl]methyl]-5-fluoro-2-methoxy-benzamide General procedure K, 5-amino-3-(4-bromo-3-fluoro-phenyl)-1-tetrahydropyran-4-yl-pyrazole-4-carbonitrile (0.22 mmol) and potassium trifluoro-[[(5-fluoro-2-methoxy-benzoyl)amino]methyl]boranuide (0.31 mmol) gave, after purification, the titled compound (0.22 mmol, assumed quantitative yield) as a yellow solid. UPLC-MS (ES⁺, Short acidic): 1.61 min, m/z 468.0 [M+H]⁺

5-Amino-3-[3-fluoro-4-[[(5-fluoro-2-methoxy-benzoyl)amino]methyl]phenyl]-1-tetrahydropyran-4-yl-pyrazole-4-carboxamide General procedure L, N-[[4-(5-amino-4-cyano-1-tetrahydropyran-4-yl-pyrazol-3-yl)-2-fluoro-phenyl]methyl]-5-fluoro-2-methoxy-benzamide (0.22 mmol) gave, after purification, the titled compound (0.15 mmol) as a beige solid. UPLC-MS (ES+, Short acidic): 1.40 min, m/z 507.9 [M+Na]+. UPLC-MS (ES+, Long acidic): 3.20 min, m/z 486.1 [M+H]+. $^1$H NMR (400 MHz, DMSO-d$_6$, δ): 8.81 (t, J=6.1 Hz, 1H), 7.51 (dd, J=9.3, 3.4 Hz, 1H), 7.46-7.39 (m, 1H), 7.37-7.27 (m, 3H), 7.19 (dd, J=9.2, 4.3 Hz, 1H), 6.32 (s, 2H), 4.57 (d, J=5.9 Hz, 2H), 4.40-4.32 (m, 1H), 3.96 (dd, J=11.5, 3.4 Hz, 2H), 3.90 (s, 3H), 3.47-3.37 (m, 2H), 2.03-1.96 (m, 2H), 1.79-1.75 (m, 2H).

Example 124: 5-amino-3-[2-fluoro-4-[[(2-methoxy-benzoyl)amino]methyl]phenyl]-1-(2,2,2-trifluoro-ethyl)pyrazole-4-carboxamide

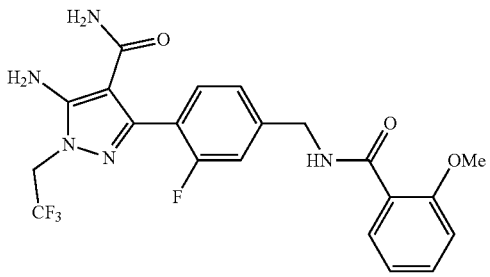 [SMILES: COc1ccccc1C(=O)NCc1ccc(-c2nn(CC(F)(F)F)c(N)c2C(N)=O)c(F)c1]

5-Amino-3-(4-bromo-2-fluoro-phenyl)-1-(2,2,2-trifluoroethyl)pyrazole-4-carbonitrile General procedure H, 2-[(4-bromo-2-fluoro-phenyl)-methoxy-methylene]propanedinitrile (0.73 mmol) and 2,2,2-trifluoroethyl hydrazine (70 wt % in water, 0.87 mmol) gave, after purification, the titled compound (0.47 mmol) as an off-white solid. UPLC-MS (ES+, Short acidic): 1.72 min, m/z 362.8 [M]+

N-[[4-[5-Amino-4-cyano-1-(2,2,2-trifluoroethyl)pyrazol-3-yl]-3-fluoro-phenyl]methyl]-2-methoxy-benzamide General procedure K, 5-amino-3-(4-bromo-2-fluoro-phenyl)-1-(2,2,2-trifluoroethyl)pyrazole-4-carbonitrile (0.23 mmol), and potassium trifluoro-[[(2-methoxybenzoyl)amino]methyl]boranuide (0.34 mmol) gave, after purification, the titled compound (0.21 mmol) as a yellow solid. UPLC-MS (ES+, Short acidic): 1.56 min, m/z 448.0 [M+H]+

5-Amino-3-[2-fluoro-4-[[(2-methoxybenzoyl)amino]methyl]phenyl]-1-(2,2,2-trifluoroethyl)pyrazole-4-carboxamide Following general procedure L, N-[[4-[5-amino-4-cyano-1-(2,2,2-trifluoroethyl)pyrazol-3-yl]-3-fluoro-phenyl]methyl]-2-methoxy-benzamide (0.21 mmol) gave, after purification, the titled compound (0.15 mmol) as a beige solid. UPLC-MS (ES+, Short acidic): 1.41 min, m/z 488.0 [M+Na]+. UPLC-MS (ES+, Long acidic): 3.22 min, m/z 466.0 [M+H]+. $^1$H NMR (400 MHz, DMSO-d$_6$, δ): 8.79 (t, J=6.1 Hz, 1H), 7.73 (dd, J=7.5, 1.8 Hz, 1H), 7.50-7.46 (m, 1H), 7.45-7.38 (m, 1H), 7.27-7.24 (m, 2H), 7.16 (d, J=8.1 Hz, 1H), 7.06-7.02 (m, 1H), 6.64 (s, 2H), 4.99-4.93 (m, 2H), 4.56 (d, J=5.9 Hz, 2H), 3.91 (s, 3H).

Example 125: 5-amino-3-[2-fluoro-4-[[(5-fluoro-2-methoxy-benzoyl)amino]methyl]phenyl]-1-(2,2,2-trifluoroethyl)pyrazole-4-carboxamide

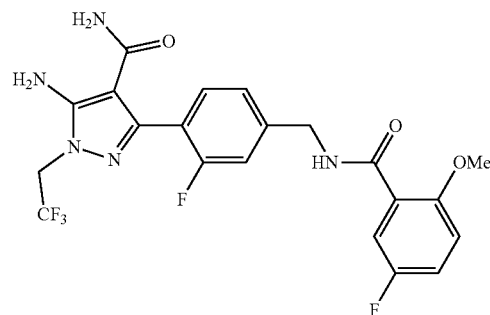 [SMILES: COc1ccc(F)cc1C(=O)NCc1ccc(-c2nn(CC(F)(F)F)c(N)c2C(N)=O)c(F)c1]

N-[[4-[5-Amino-4-cyano-1-(2,2,2-trifluoroethyl)pyrazol-3-yl]-3-fluoro-phenyl]methyl]-5-fluoro-2-methoxy-benzamide General procedure K, 5-amino-3-(4-bromo-2-fluoro-phenyl)-1-(2,2,2-trifluoroethyl)pyrazole-4-carbonitrile (0.23 mmol) and potassium trifluoro-[[(5-fluoro-2-methoxy-benzoyl)amino]methyl]boranuide (0.33 mmol) gave, after purification, the titled compound (0.20 mmol) as a yellow solid. UPLC-MS (ES+, Short acidic): 1.61 min, m/z 466.1 [M+H]+

5-Amino-3-[2-fluoro-4-[[(5-fluoro-2-methoxy-benzoyl)amino]methyl]phenyl]-1-(2,2,2-trifluoroethyl)pyrazole-4-carboxamide General procedure L, N-[[4-[5-amino-4-cyano-1-(2,2,2-trifluoroethyl)pyrazol-3-yl]-3-fluoro-phenyl]methyl]-5-fluoro-2-methoxy-benzamide (0.20 mmol) gave, after purification, the titled compound (0.12 mmol) as a beige solid. UPLC-MS (ES+, Short acidic): 1.46 min, m/z 506.0 [M+Na]+. UPLC-MS (ES+, Long acidic): 3.34 min, m/z 484.0 [M+H]+. $^1$H NMR (400 MHz, DMSO-d$_6$, δ): 8.89 (t, J=6.1 Hz, 1H), 7.50 (dd, J=9.2, 3.5 Hz, 1H), 7.45-7.38 (m, 1H), 7.37-7.32 (m, 1H), 7.25 (d, J=9.2 Hz, 2H), 7.19 (dd, J=9.1, 4.2 Hz, 1H), 6.64 (s, 2H), 4.99-4.93 (m, 2H), 4.56 (d, J=6.1 Hz, 2H), 3.90 (s, 3H).

Example 126: 5-amino-1-(2,2-difluoro-1-methyl-ethyl)-3-[4-[[(2-methoxybenzoyl)amino]methyl]phenyl]pyrazole-4-carboxamide

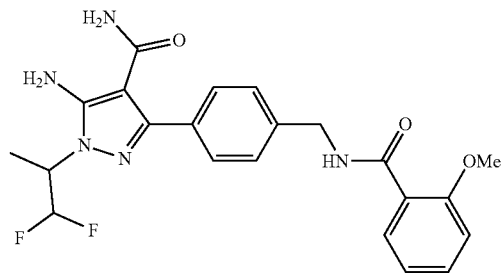 [SMILES: COc1ccccc1C(=O)NCc1ccc(-c2nn(C(C)C(F)F)c(N)c2C(N)=O)cc1]

tert-Butyl N-[(2,2-difluoro-1-methyl-ethylidene)amino]carbamate

A modified general procedure E at 60° C., tert-butyl carbazate (1.51 mmol) and 1,1-difluoro-propan-2-one (1.82 mmol) gave crude the titled compound (1.51 mmol) as a white solid. UPLC-MS (ES$^-$, Short acidic): 1.45 min, m/z 206.8 [M–H]$^-$

5-Amino-3-(4-bromophenyl)-1-(2,2-difluoro-1-methyl-ethyl)pyrazole-4-carbonitrile General procedure O at RT, tert-butyl N-[(2,2-difluoro-1-methyl-ethylidene)amino]carbamate (0.58 mmol) and 2-[(4-bromophenyl)-methoxy-methylene]propanedinitrile (0.46 mmol) gave, after purification, the titled compound (0.43 mmol) as a white solid. UPLC-MS (ES$^+$, Short acidic): 1.83 min, m/z 340.6 [M]$^+$

N-[[4-[5-Amino-4-cyano-1-(2,2-difluoro-1-methyl-ethyl)pyrazol-3-yl]phenyl]methyl]-2-methoxy-benzamide General procedure K, 5-amino-3-(4-bromophenyl)-1-(2,2-difluoro-1-methyl-ethyl)pyrazole-4-carbonitrile (0.15 mmol) and potassium trifluoro-[[(2-methoxybenzoyl)amino]methyl]boranuide (0.22 mmol) gave, after purification, the titled compound (0.08 mmol) as a white solid. UPLC-MS (ES$^+$, Short acidic): 1.60 min, m/z 426.0 [M+H]$^+$

5-Amino-1-(2,2-difluoro-1-methyl-ethyl)-3-[4-[[(2-methoxybenzoyl)amino]methyl]phenyl]pyrazole-4-carboxamide General procedure M, N-[[4-[5-amino-4-cyano-1-(2,2-difluoro-1-methyl-ethyl)pyrazol-3-yl]phenyl]methyl]-2-methoxy-benzamide (0.08 mmol) gave, after purification, the titled compound (0.04 mmol) as a white solid. UPLC-MS (ES$^+$, Short acidic): 1.43 min, m/z 444.1 [M+H]$^+$. UPLC-MS (ES$^+$, Long acidic): 3.25 min, m/z 444.1 [M+H]$^+$. $^1$H NMR (400 MHz, DMSO-d$_6$, δ): 8.73 (t, J=6.1 Hz, 1H), 7.74 (dd, J=7.6, 1.8 Hz, 1H), 7.51-7.38 (m, 5H), 7.15 (d, J=8.3 Hz, 1H), 7.07-7.00 (m, 1H), 6.53 (s, 2H), 6.21 (dt, J=55.7, 5.3 Hz, 1H), 4.85-4.70 (m, 1H), 4.54 (d, J=6.2 Hz, 2H), 3.89 (s, 3H), 1.44 (d, J=6.7 Hz, 3H).

Example 127: 5-amino-3-[3-fluoro-4-[[(5-fluoro-2-methoxy-benzoyl)amino]methyl]phenyl]-1-tetrahydropyran-3-yl-pyrazole-4-carboxamide

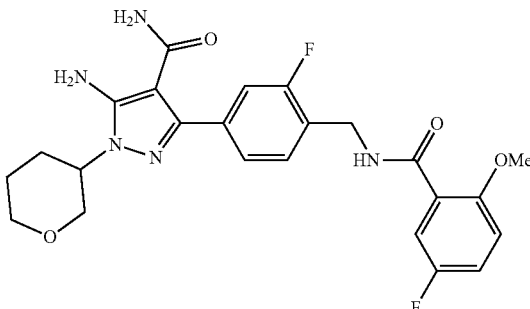

5-Amino-3-(4-bromo-3-fluoro-phenyl)-1-tetrahydropyran-3-yl-pyrazole-4-carbonitrile General procedure H, tetrahydropyran-3-ylhydrazine hydrochloride (0.77 mmol) and 2-[(4-bromo-3-fluoro-phenyl)-methoxy-methylene]propanedinitrile (0.64 mmol) gave, after purification, the titled compound (0.20 mmol) as an off-white solid. UPLC-MS (ES$^+$, Short acidic): 1.85 min, m/z 366.9 [M+2]$^+$

N-[[4-(5-Amino-4-cyano-1-tetrahydropyran-3-yl-pyrazol-3-yl)-2-fluoro-phenyl]methyl]-5-fluoro-2-methoxy-benzamide General procedure K, 5-amino-3-(4-bromo-3-fluoro-phenyl)-1-tetrahydropyran-3-yl-pyrazole-4-carbonitrile (0.18 mmol) and potassium trifluoro-[[(5-fluoro-2-methoxy-benzoyl)amino]methyl]boranuide (106 mg, 0.37 mmol) gave, after purification, the titled compound (54 mg, 0.12 mmol, 66% yield) as a brown solid. UPLC-MS (ES$^+$, Short acidic): 1.68 min, m/z 468.0 [M+H]$^+$

5-Amino-3-[3-fluoro-4-[[(5-fluoro-2-methoxy-benzoyl)amino]methyl]phenyl]-1-tetrahydropyran-3-yl-pyrazole-4-carboxamide Following general procedure M, N-[[4-(5-amino-4-cyano-1-tetrahydropyran-3-yl-pyrazol-3-yl)-2-fluoro-phenyl]methyl]-5-fluoro-2-methoxy-benzamide (54 mg, 0.12 mmol) gave, after purification, the titled compound (20 mg, 0.04 mmol, 36% yield) as an off-white solid. UPLC-MS (ES$^+$, Short acidic): 1.47 min, m/z 485.9 [M+H]$^+$. UPLC-MS (ES$^+$, Long acidic): 3.37 min, m/z 486.1 [M+H]$^+$. $^1$H NMR (400 MHz, DMSO-d$_6$, δ): 8.81 (t, J=6.0 Hz, 1H), 7.50 (dd, J=9.2, 3.3 Hz, 1H), 7.44-7.40 (m, 1H), 7.37-7.26 (m, 3H), 7.19 (dd, J=9.3, 4.3 Hz, 1H), 6.35 (s, 2H), 4.56 (d, J=6.0 Hz, 2H), 4.30-4.22 (m, 1H), 3.90 (s, 3H), 3.87-3.82 (m, 2H), 3.58-3.48 (m, 1H), 3.37-3.27 (m, 1H), 2.03-1.98 (m, 2H), 1.77-1.65 (m, 2H).

Example 128: 5-amino-3-[3-fluoro-4-[[(5-fluoro-2-methoxy-benzoyl)amino]methyl]phenyl]-1-(2,2,2-trifluoroethyl)pyrazole-4-carboxamide

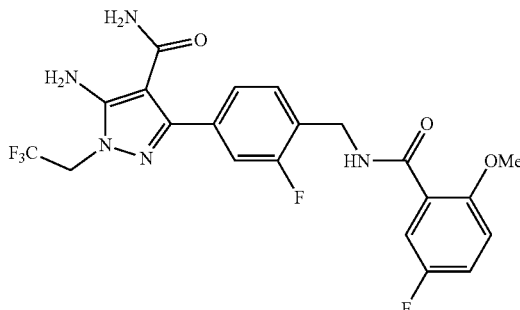

5-Amino-3-(4-bromo-3-fluoro-phenyl)-1-(2,2,2-trifluoroethyl)pyrazole-4-carbonitrile Following general procedure H, 2-[(4-bromo-3-fluoro-phenyl)-methoxy-methylene]propanedinitrile (500 mg, 1.78 mmol) and 2,2,2-trifluoroethyl hydrazine (70 wt % in water, 31 μL, 2.13 mmol) gave, after purification by flash column chromatography on silica gel eluting with 0-10% MeOH in DCM, 5-amino-3-(4-bromo-3-fluoro-phenyl)-1-(2,2,2-trifluoroethyl)pyrazole-4-carbonitrile (132 mg, 0.36 mmol, 20% yield) as a brown solid. UPLC-MS (ES+, Short acidic): 1.82 min, m/z 362.7 [M]+

N-[[4-[5-Amino-4-cyano-1-(2,2,2-trifluoroethyl)pyrazol-3-yl]-2-fluoro-phenyl]methyl]-5-fluoro-2-methoxy-benzamide General procedure K, 5-amino-3-(4-bromo-3-fluoro-phenyl)-1-(2,2,2-trifluoroethyl)pyrazole-4-carbonitrile (0.18 mmol) and potassium trifluoro-[[(5-fluoro-2-methoxy-benzoyl)amino]methyl]boranuide (0.27 mmol) gave, after purification, the titled compound (0.12 mmol) as a pale orange solid. UPLC-MS (ES+, Short acidic): 1.68 min, m/z 465.9 [M+H]+.

5-Amino-3-[3-fluoro-4-[[(5-fluoro-2-methoxy-benzoyl)amino]methyl]phenyl]-1-(2,2,2-trifluoroethyl)pyrazole-4-carboxamide General procedure M, N-[[4-[5-amino-4-cyano-1-(2,2,2-trifluoroethyl)pyrazol-3-yl]-2-fluoro-phenyl]methyl]-5-fluoro-2-methoxy-benzamide (0.12 mmol) gave, after purification, the titled compound (22 mg, 0.05 mmol, 39% yield) as a light brown solid. UPLC-MS (ES+, Short acidic): 1.50 min, m/z 484.1 [M+H]+. UPLC-MS (ES+, Long acidic): 3.44 min, m/z 484.0 [M+H]+. $^1$H NMR (400 MHz, DMSO-$d_6$, δ): 8.82 (t, J=5.9 Hz, 1H), 7.51 (dd, J=9.7, 3.7 Hz, 1H), 7.47-7.40 (m, 1H), 7.37-7.27 (m, 3H), 7.19 (dd, J=9.1, 4.3 Hz, 1H), 6.63 (s, 2H), 4.95 (q, J=9.3 Hz, 2H), 4.57 (d, J=6.5 Hz, 2H), 3.90 (s, 3H).

Example 129: 5-amino-3-[3-fluoro-4-[[(2-methoxybenzoyl)amino]methyl]phenyl]-1-(2,2,2-trifluoroethyl)pyrazole-4-carboxamide

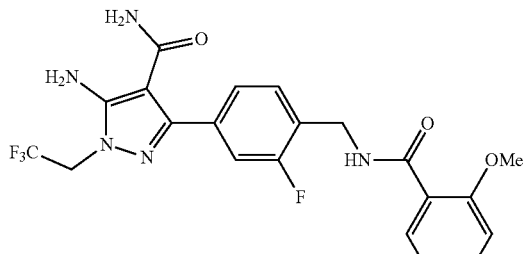

N-[[4-[5-Amino-4-cyano-1-(2,2,2-trifluoroethyl)pyrazol-3-yl]-2-fluoro-phenyl]methyl]-2-methoxy-benzamide General procedure K, 5-amino-3-(4-bromo-3-fluoro-phenyl)-1-(2,2,2-trifluoroethyl)pyrazole-4-carbonitrile (0.18 mmol) and potassium trifluoro-[[(2-methoxybenzoyl)amino]methyl]boranuide (0.27 mmol) gave, after purification, the titled compound (0.07 mmol) as a pale brown solid. UPLC-MS (ES+, Short acidic): 1.63 min, m/z 448.0 [M+H]+

5-Amino-3-[3-fluoro-4-[[(2-methoxybenzoyl)amino]methyl]phenyl]-1-(2,2,2-trifluoroethyl)pyrazole-4-carboxamide Following general procedure M, N-[[4-[5-amino-4-cyano-1-(2,2,2-trifluoroethyl)pyrazol-3-yl]-2-fluoro-phenyl]methyl]-2-methoxy-benzamide (27 mg, 0.06 mmol) gave, after purification, the titled compound (0.03 mmol, 54% yield) as a light brown solid. UPLC-MS (ES+, Short acidic): 1.45 min, m/z 466.1 [M+H]+. UPLC-MS (ES+, Long acidic): 3.32 min, m/z 466.1 [M+H]+. $^1$H NMR (400 MHz, DMSO-$d_6$, δ): 8.73 (t, J=6.1 Hz, 1H), 7.75 (dd, J=7.7, 1.8 Hz, 1H), 7.51-7.42 (m, 2H), 7.35-7.28 (m, 2H), 7.16 (d, J=7.7 Hz, 1H), 7.07-7.01 (m, 1H), 6.61 (s, 2H), 5.00-4.90 (m, 2H), 4.57 (d, J=6.0 Hz, 2H), 3.90 (s, 3H).

Example 130: 5-amino-1-cyclopentyl-3-[2-fluoro-4-[[(2-methoxybenzoyl)amino]methyl]phenyl]pyrazole-4-carboxamide

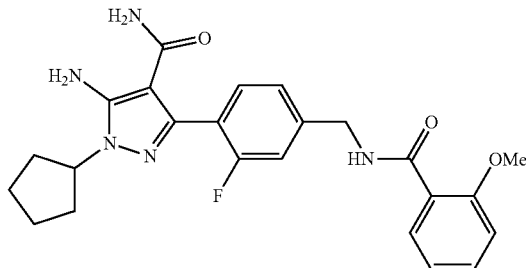

5-Amino-3-(4-bromo-2-fluoro-phenyl)-1-cyclopentyl-pyrazole-4-carbonitrile

Following general procedure H, 2-[(4-bromo-2-fluoro-phenyl)-methoxy-methylene]propanedinitrile (0.71 mmol) and cyclopentylhydrazine hydrochloride (0.85 mmol) afforded, after purification, the titled compound (0.37 mmol) as a yellow gum. UPLC-MS (ES+, Short acidic): 1.95 min, m/z 350.8 [M+2]+

N-[[4-(5-Amino-4-cyano-1-cyclopentyl-pyrazol-3-yl)-3-fluoro-phenyl]methyl]-2-methoxy-benzamide General procedure K, 5-amino-3-(4-bromo-2-fluoro-phenyl)-1-cyclopentyl-pyrazole-4-carbonitrile (0.37 mmol) and potassium trifluoro-[[(2-methoxybenzoyl)amino]methyl]boranuide (0.41 mmol) afforded, after purification, the titled compound (0.32 mmol) as a yellow solid. UPLC-MS (ES+, Short acidic): 1.70 min, m/z 434.1 [M+H]+

5-Amino-1-cyclopentyl-3-[2-fluoro-4-[[(2-methoxybenzoyl)amino]methyl]phenyl]pyrazole-4-carboxamide General procedure M, N-[[4-(5-amino-4-cyano-1-cyclopentyl-pyrazol-3-yl)-3-fluoro-phenyl]methyl]-2-methoxy-benzamide (0.32 mmol) afforded, after purification, the titled compound (0.07 mmol) as a white solid. UPLC-MS (ES+, Short acidic): 1.53 min, m/z 452.1 [M+H]+. UPLC-MS (ES+, Long acidic): 3.52 min, m/z 452.1 [M+H]+. $^1$H NMR (400 MHz, DMSO-$d_6$, δ): 8.79 (t, J=6.0 Hz, 1H), 7.74 (dd, J=7.7, 1.8 Hz, 1H), 7.52-7.46 (m, 1H), 7.43-7.37 (m, 1H), 7.26-7.21 (m, 2H), 7.19-7.14 (m, 1H), 7.04 (td, J=11.2, 0.9 Hz, 1H), 6.29 (s, 2H), 4.66-4.59 (m, 1H), 4.56 (d, J=6.1 Hz, 2H), 3.91 (s, 3H), 2.02-1.73 (m, 6H), 1.64-1.56 (m, 2H).

Example 131: 5-amino-1-(1-cyclopropylethyl)-3-[4-[[(2-methoxybenzoyl)amino]methyl]phenyl]pyrazole-4-carboxamide

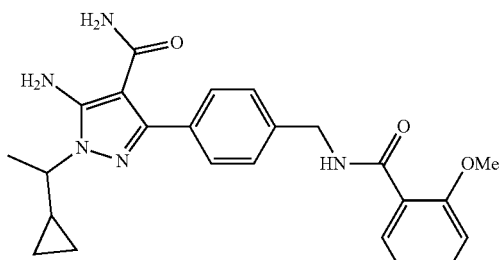

tert-Butyl N-[1-cyclopropylethylideneamino]carbamate

Following general procedure E, cyclopropyl methyl ketone (0.60 mL, 6.06 mmol), and tert-butyl carbazate (880 mg, 6.66 mmol) gave the titled compound (6.06 mmol) as a white solid. $^1$H NMR (400 MHz, CDCl$_3$, δ): 7.35 (br s, 1H), 1.80-1.71 (m, 1H), 1.63 (s, 3H), 1.50 (s, 9H), 0.77 (s, 2H), 0.75 (s, 2H).

5-Amino-3-(4-bromophenyl)-1-(1-cyclopropylethyl)pyrazole-4-carbonitrile

To a solution of tert-butyl N-[1-cyclopropylethylideneamino]carbamate (6.05 mmol) in THF (20 mL) was added a borane dimethyl sulfide complex solution (2 M in THF, 10.3 mmol). The reaction was stirred at RT for 2 h and then the volatiles were removed under reduced pressure. The residue was taken up with MeOH (20 mL) and concentrated hydrochloric acid (30.3 mmol) was added. Then the reaction mixture was stirred at RT for 16 h and concentrated under reduced pressure. The residue was taken up with EtOH (10 mL) followed by addition of 2-[(4-bromophenyl)-methoxymethylene]propanedinitrile (100 mg, 0.38 mmol) and triethylamine (1.9 mmol). The reaction mixture was heated to reflux and stirred for 16 h. All volatiles were then removed under reduced pressure and the residue was purified to give the titled compound (0.33 mmol) as an off-white solid. UPLC-MS (ES$^+$, Short acidic): 1.95 min, m/z 332.9 [M+2]$^+$ N-[[4-[5-Amino-4-cyano-1-(1-cyclopropylethyl)pyrazol-3-yl]phenyl]methyl]-2-methoxy-benzamide General procedure K, 5-amino-3-(4-bromophenyl)-1-(1-cyclopropylethyl)pyrazole-4-carbonitrile (0.33 mmol), and potassium trifluoro-[[(2-methoxybenzoyl)amino]methyl]boranuide (0.48 mmol) gave, after purification, the titled compound (0.12 mmol) as a yellow solid. UPLC-MS (ES$^+$, Short acidic): 1.67 min, m/z 416.1 [M+H]$^+$ 5-Amino-1-(1-cyclopropylethyl)-3-[4-[[(2-methoxybenzoyl)amino]methyl]phenyl]pyrazole-4-carboxamide General procedure L, N-[[4-[5-amino-4-cyano-1-(1-cyclopropylethyl)pyrazol-3-yl]phenyl]methyl]-2-methoxy-benzamide (0.12 mmol) gave, after purification, the titled compound (0.06 mmol) as a solid. UPLC-MS (ES$^+$, Short acidic): 1.47 min, m/z 434.1 [M+H]$^+$. UPLC-MS (ES$^+$, Long acidic): 3.35 min, m/z 434.1 [M+H]$^+$. $^1$H NMR (400 MHz, DMSO-d$_6$, δ): 8.73 (t, J=6.4 Hz, 1H), 7.75 (dd, J=7.7, 1.7 Hz, 1H), 7.50-7.40 (m, 5H), 7.15 (d, J=8.2 Hz, 1H), 7.06-7.02 (m, 1H), 6.26 (s, 2H), 4.54 (d, J=6.2 Hz, 2H), 3.90 (s, 3H), 3.71-3.64 (m, 1H), 1.41 (d, J=6.6 Hz, 3H), 1.33-1.23 (m, 1H), 0.58-0.51 (m, 1H), 0.40-0.34 (m, 2H), 0.28-0.22 (m, 1H).

Example 132: 5-amino-3-[3,5-difluoro-4-[[(2-methoxybenzoyl)amino]methyl]phenyl]-1-tetrahydropyran-4-yl-pyrazole-4-carboxamide

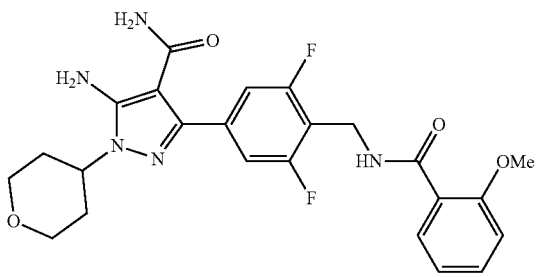 [SMILES: COc1ccccc1C(=O)NCc1c(F)cc(-c2nn(C3CCOCC3)c(N)c2C(N)=O)cc1F]

5-Amino-3-(4-chloro-3,5-difluoro-phenyl)-1-tetrahydropyran-4-yl-pyrazole-4-carbonitrile Following a modified general procedure H at RT, 2-[(4-chloro-3,5-difluoro-phenyl)-methoxy-methylene]propanedinitrile (0.98 mmol) and tetrahydropyran-4-ylhydrazine hydrochloride (1.18 mmol) gave crude the titled compound (0.98 mmol). UPLC-MS (ES$^+$, Short acidic): 1.82 min, m/z 339.0 [M]$^+$ N-[[4-(5-Amino-4-cyano-1-tetrahydropyran-4-yl-pyrazol-3-yl)-2,6-difluoro-phenyl]methyl]-2-methoxy-benzamide General procedure K, potassium trifluoro-[[(2-methoxybenzoyl)amino]methyl]boranuide (1.09 mmol) and 5-amino-3-(4-chloro-3,5-difluoro-phenyl)-1-tetrahydropyran-4-yl-pyrazole-4-carbonitrile (0.49 mmol) gave, after purification, the titled compound (0.13 mmol). UPLC-MS (ES$^+$, Short acidic): 1.62 min, m/z 468.1 [M+H]$^+$ 5-Amino-3-[3,5-difluoro-4-[[(2-methoxybenzoyl)amino]methyl]phenyl]-1-tetrahydropyran-4-yl-pyrazole-4-carboxamide Following general method L, N-[[4-(5-amino-4-cyano-1-tetrahydropyran-4-yl-pyrazol-3-yl)-2,6-difluoro-phenyl]methyl]-2-methoxy-benzamide (0.13 mmol) gave, after purification, the titled compound (0.01 mmol) as a white solid. UPLC-MS (ES$^+$, Short acidic): 1.40 min, m/z 486.1 [M+H]$^+$. UPLC-MS (ES$^+$, Long acidic): 3.18 min, m/z 486.1 [M+H]$^+$. $^1$H NMR (400 MHz, DMSO-d$_6$, δ): 8.57 (t, J=5.5 Hz, 1H), 7.73 (dd, J=7.8, 1.8 Hz, 1H), 7.51-7.44 (m, 1H), 7.26-7.19 (m, 2H), 7.14 (d, J=8.5 Hz, 1H), 7.05-7.01 (m, 1H), 6.27 (br s, 2H), 4.58 (d, J=5.6 Hz, 2H), 4.43-4.32 (m, 1H), 4.00-3.93 (m, 2H), 3.88 (s, 3H), 3.43 (t, J=11.9 Hz, 2H), 2.04-1.94 (m, 2H), 1.79-1.75 (m, 2H).

Example 133: 5-amino-3-[3,5-difluoro-4-[[(5-fluoro-2-methoxy-benzoyl)amino]methyl]phenyl]-1-tetrahydropyran-4-yl-pyrazole-4-carboxamide

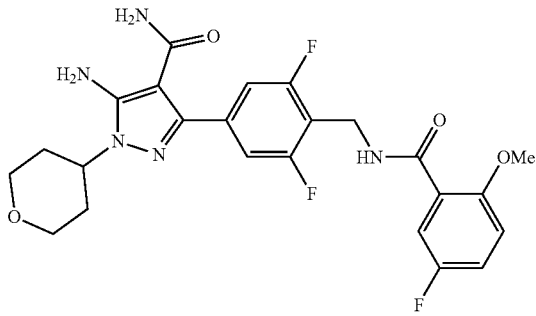 [SMILES: COc1ccc(F)cc1C(=O)NCc1c(F)cc(-c2nn(C3CCOCC3)c(N)c2C(N)=O)cc1F]

N-[[4-(5-Amino-4-cyano-1-tetrahydropyran-4-yl-pyrazol-3-yl)-2,6-difluoro-phenyl]methyl]-5-fluoro-2-methoxy-benzamide General procedure K, potassium trifluoro-[[(5-fluoro-2-methoxy-benzoyl)amino]methyl]boranuide (0.99 mmol) and 5-amino-3-(4-chloro-3,5-difluoro-phenyl)-1-tetrahydropyran-4-yl-pyrazole-4-carbonitrile (0.49 mmol) gave crude the titled compound (0.49 mmol). UPLC-MS (ES+, Short acidic): 1.67 min, m/z 486.0 [M+H]+

5-Amino-3-[3,5-difluoro-4-[[(5-fluoro-2-methoxy-benzoyl)amino]methyl]phenyl]-1-tetrahydropyran-4-yl-pyrazole-4-carboxamide General procedure M, N-[[4-(5-amino-4-cyano-1-tetrahydropyran-4-yl-pyrazol-3-yl)-2,6-difluoro-phenyl]methyl]-5-fluoro-2-methoxy-benzamide (0.49 mmol) gave, after purification, the titled compound (0.09 mmol) as a white solid. UPLC-MS (ES+, Short acidic): 1.45 min, m/z 504.1 [M+H]+. UPLC-MS (ES+, Long acidic): 3.31 min, m/z 504.1 [M+H]+. $^1$H NMR (400 MHz, DMSO-$d_6$, δ): 8.67 (t, J=5.6 Hz, 1H), 7.48 (dd, J=9.0, 3.3 Hz, 1H), 7.36-7.30 (m, 1H), 7.26-7.13 (m, 3H), 6.27 (br s, 2H), 4.58 (d, J=5.5 Hz, 2H), 4.43-4.33 (m, 1H), 3.99-3.94 (m, 2H), 3.87 (s, 3H), 3.43 (t, J=11.1 Hz, 2H), 2.03-1.93 (m, 2H), 1.79-1.74 (m, 2H).

Example 134: 5-amino-1-cyclopentyl-3-[6-[[(2-methoxybenzoyl)amino]methyl]-3-pyridyl]pyrazole-4-carboxamide

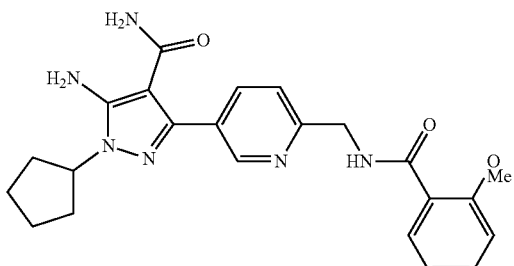

N-[(5-Bromo-2-pyridyl)methyl]-2-methoxy-benzamide

To a solution of (5-bromo-2-pyridyl)methanamine (1.60 mmol) in DMF (4 mL), at 0° C., was added N,N-diisopropylethylamine (4.81 mmol). After 10 min of stirring, 2-methoxybenzoyl chloride (3.21 mmol) was added slowly. The reaction mixture was warmed to RT and stirred under nitrogen for 18 h. The mixture was quenched with saturated aqueous sodium bicarbonate solution and diluted with EtOAc. The layers were partitioned and the aqueous layer was extracted with EtOAc. The combined organic extracts were washed with brine, dried over sodium sulfate and concentrated under reduced pressure. Further purification gave the titled compound (0.92 mmol) as a pale yellow oil. UPLC-MS (ES+, Short acidic): 1.53 min, m/z 322.8 [M+2]+

[6-[[(2-Methoxybenzoyl)amino]methyl]-3-pyridyl]boronic acid

To a solution of N-[(5-bromo-2-pyridyl)methyl]-2-methoxy-benzamide (240 mg, 0.75 mmol) in THF (10 mL), at −78° C., was slowly added triisopropylborate (0.35 mL, 1.50 mmol). A solution of n-butyllithium (2.5 M in hexane, 0.90 mL, 2.24 mmol) was added dropwise and the mixture was stirred at −78° C. for 1 h, and then allowed to return to −20° C. for 1.5 h. The reaction mixture was quenched with hydrochloric acid (2 M), neutralized with saturated aqueous sodium bicarbonate solution and partitioned with EtOAc. The aqueous layer was extracted with EtOAc. The combined organic extracts were filtered over a hydrophobic frit and concentrated under reduced pressure to give the titled compound (0.86 mmol), which was used as such in the next step. UPLC-MS (ES+, Short acidic): 0.99 min, m/z 287.0 [M+H]+

5-Amino-1-cyclopentyl-3-[6-[[(2-methoxybenzoyl)amino]methyl]-3-pyridyl]pyrazole-4-carboxamide Following general procedure D, [6-[[(2-methoxybenzoyl)amino]methyl]-3-pyridyl]boronic acid (0.86 mmol) and 5-amino-3-bromo-1-cyclopentyl-pyrazole-4-carboxamide (0.43 mmol) gave, after purification, the titled compound (0.09 mmol) as a light brown solid. UPLC-MS (ES+, Short acidic): 1.36 min, m/z 435.1 [M+H]+. UPLC-MS (ES+, Long acidic): 3.07 min, m/z 435.1 [M+H]+. $^1$H NMR (400 MHz, DMSO-$d_6$, δ): 8.99 (t, J=6.1 Hz, 1H), 8.64 (m, 1H), 7.88 (dd, J=8.1, 2.2 Hz, 1H), 7.84 (dd, J=7.7, 1.8 Hz, 1H), 7.50-7.47 (m, 1H), 7.42 (d, J=8.5 Hz, 1H), 7.18 (dd, J=8.6, 0.9 Hz, 1H), 7.01 (td, J=7.6, 1.2 Hz, 1H), 6.23 (s, 2H), 4.68-4.59 (m, 3H), 3.95 (s, 3H), 2.02-1.86 (m, 4H), 1.85-1.76 (m, 2H), 1.65-1.55 (m, 2H).

Example 135: 5-amino-1-(2-hydroxy-1-methyl-ethyl)-3-[4-[[(2-methoxybenzoyl)amino]methyl]phenyl]pyrazole-4-carboxamide

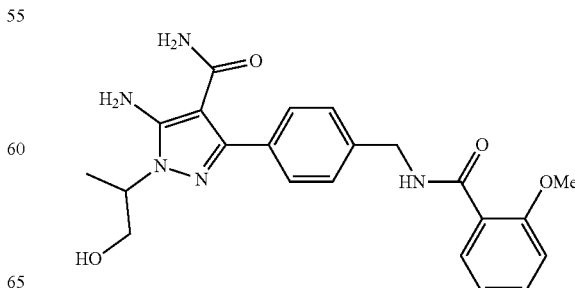

tert-Butyl N-[(2-hydroxy-1-methyl-ethylidene)amino]carbamate

General procedure E, tert-butyl carbazate (7.57 mmol) and hydroxyacetone (9.08 mmol) gave the titled compound (7.57 mmol) as a yellow oil. UPLC-MS (ES⁺, Short acidic): 1.07 min, m/z 188.9 [M+H]⁺

5-Amino-3-(4-bromophenyl)-1-(2-hydroxy-1-methyl-ethyl)pyrazole-4-carbonitrile General procedure O, tert-butyl N-[(2-hydroxy-1-methyl-ethylidene)amino]carbamate (7.39 mmol) and 2-[(4-bromophenyl)-methoxy-methylene]propanedinitrile (0.76 mmol), gave after purification, the titled compound (0.28 mmol) as an off-white solid. UPLC (ES⁺, Short acidic): 1.59 min, 322.9 m/z [M+2]⁺

N-[[4-[5-Amino-4-cyano-1-(2-hydroxy-1-methyl-ethyl)pyrazol-3-yl]phenyl]methyl]-2-methoxy-benzamide General procedure K, potassium trifluoro-[[(2-methoxy-benzoyl)amino]methyl]boranuide (0.72 mmol), and 5-amino-3-(4-bromophenyl)-1-(2-hydroxy-1-methyl-ethyl)pyrazole-4-carbonitrile (0.28 mmol) gave, after purification, the titled compound (0.22 mmol) as an orange solid.

UPLC-MS (ES⁺, Short acidic): 1.42 min, 406.1 m/z [M+H]⁺

5-Amino-1-(2-hydroxy-1-methyl-ethyl)-3-[4-[[(2-methoxybenzoyl)amino]methyl]phenyl]pyrazole-4-carboxamide General procedure M, N-[[4-[5-amino-4-cyano-1-(2-hydroxy-1-methyl-ethyl)pyrazol-3-yl]phenyl]methyl]-2-methoxy-benzamide (0.22 mmol) gave, after purification, the titled compound (0.07 mmol) as a pale brown solid. UPLC-MS (ES⁺, Short acidic): 1.25 min, 424.1 m/z [M+H]⁺. UPLC-MS (ES⁺, Long acidic): 2.78 min, 424.1 m/z [M+H]⁺. ¹H NMR (400 MHz, DMSO-d₆, δ): 8.74 (t, J=6.0 Hz, 1H), 7.76 (dd, J=7.6, 1.7 Hz, 1H), 7.50-7.40 (m, 5H), 7.16 (d, J=8.3 Hz, 1H), 7.06-7.02 (m, 1H), 6.24 (s, 2H), 4.89 (t, J=5.4 Hz, 1H), 4.55 (d, J=5.9 Hz, 2H), 4.36-4.27 (m, 1H), 3.90 (s, 3H), 3.70-3.62 (m, 2H), 1.29 (d, J=6.7 Hz, 3H).

Example 136: 5-amino-1-cyclopentyl-3-[2-fluoro-4-[[(5-fluoro-2-methoxy-benzoyl)amino]methyl]phenyl]pyrazole-4-carboxamide

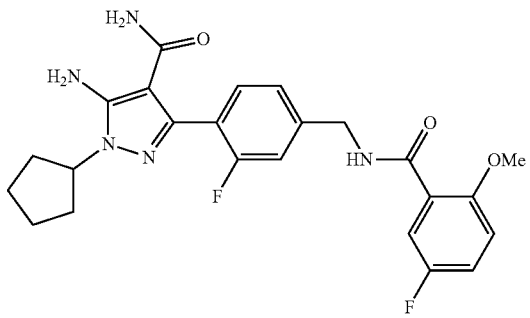 [SMILES: COc1ccc(F)cc1C(=O)NCc1ccc(-c2nn(C3CCCC3)c(N)c2C(N)=O)c(F)c1]

N-[[4-(5-Amino-4-cyano-1-cyclopentyl-pyrazol-3-yl)-3-fluoro-phenyl]methyl]-5-fluoro-2-methoxy-benzamide General procedure K, 5-amino-3-(4-bromo-2-fluoro-phenyl)-1-cyclopentyl-pyrazole-4-carbonitrile (0.28 mmol) and potassium trifluoro-[[(5-fluoro-2-methoxy-benzoyl)amino]methyl]boranuide (89 mg, 0.31 mmol) afforded, after purification, the titled compound (126 mg, 0.28 mmol, 99%) as a yellow solid. UPLC-MS (ES⁺, Short acidic): 1.75 min, m/z 452.1 [M+H]⁺

5-Amino-1-cyclopentyl-3-[2-fluoro-4-[[(5-fluoro-2-methoxy-benzoyl)amino]methyl]phenyl]pyrazole-4-carboxamide Following general procedure M, N-[[4-(5-amino-4-cyano-1-cyclopentyl-pyrazol-3-yl)-3-fluoro-phenyl]methyl]-5-fluoro-2-methoxy-benzamide (133 mg, 0.29 mmol) afforded, after purification, the titled compound (66 mg, 0.14 mmol, 47% yield) as a white solid. UPLC-MS (ES⁺, Short acidic): 1.58 min, m/z 470.1 [M+H]⁺. UPLC-MS (ES⁺, Long acidic): 3.63 min, m/z 470.1 [M+H]⁺. ¹H NMR (400 MHz, DMSO-d₆, δ): 8.88 (t, J=6.0 Hz, 1H), 7.50 (dd, J=7.6, 1.7 Hz, 1H), 7.42-7.32 (m, 2H), 7.25-7.17 (m, 3H), 6.28 (s, 2H), 4.66-4.59 (m, 1H), 4.55 (d, J=6.0 Hz, 2H), 3.91 (s, 3H), 2.03-1.73 (m, 6H), 1.63-1.53 (m, 2H).

Example 137: 5-amino-1-cyclopentyl-3-[2,5-difluoro-4-[[(5-fluoro-2-methoxy-benzoyl)amino]methyl]phenyl]pyrazole-4-carboxamide

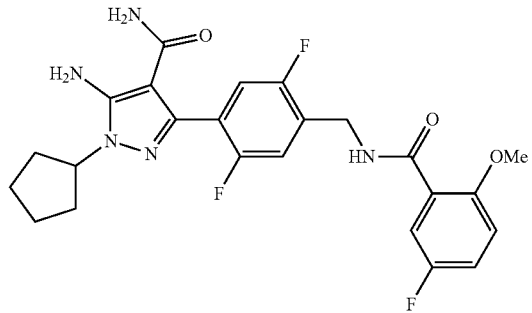 [SMILES: COc1ccc(F)cc1C(=O)NCc1cc(F)c(-c2nn(C3CCCC3)c(N)c2C(N)=O)cc1F]

N-[[4-(5-Amino-4-cyano-1-cyclopentyl-pyrazol-3-yl)-2,5-difluoro-phenyl]methyl]-5-fluoro-2-methoxy-benzamide General procedure K, 5-amino-3-(4-chloro-2,5-difluoro-phenyl)-1-cyclopentyl-pyrazole-4-carbonitrile (0.39 mmol) and potassium trifluoro-[[(5-fluoro-2-methoxy-benzoyl)amino]methyl]boranuide (0.58 mmol) gave, after recrystallization from MeOH, the titled compound (0.23 mmol). UPLC-MS (ES⁺, Short acidic): 1.83 min, m/z 470.1 [M+H]⁺

5-Amino-1-cyclopentyl-3-[2,5-difluoro-4-[[(5-fluoro-2-methoxy-benzoyl)amino]methyl]phenyl]pyrazole-4-carboxamide General procedure M, N-[[4-(5-amino-4-cyano-1-cyclopentyl-pyrazol-3-yl)-2,5-difluoro-phenyl]methyl]-5-fluoro-2-methoxy-benzamide (0.22 mmol) gave, after purification, the titled compound (0.13 mmol) as a pale brown solid.

UPLC-MS (ES+, Short acidic): 1.66 min, m/z 488.2 [M+H]+. UPLC-MS (ES+, Long acidic): 3.80 min, m/z 488.2 [M+H]+. ¹H NMR (400 MHz, DMSO-d₆, δ): 8.86 (t, J=6.0 Hz, 1H), 7.49 (dd, J=9.2, 3.3 Hz, 1H), 7.37-7.32 (m, 1H), 7.27-7.17 (m, 3H), 6.23 (s, 2H), 4.66-4.58 (m, 1H), 4.55 (d, J=6.9 Hz, 2H), 3.90 (s, 3H), 2.02-1.92 (m, 2H), 1.91-1.83 (m, 2H), 1.82-1.72 (m, 2H), 1.63-1.52 (m, 2H).

Example 138: 5-amino-1-cyclopentyl-3-[3,5-difluoro-4-[[(2-methoxybenzoyl)amino]methyl]phenyl]pyrazole-4-carboxamide

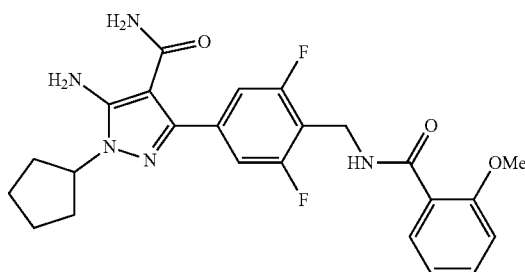

5-Amino-3-(4-chloro-3,5-difluoro-phenyl)-1-cyclopentyl-pyrazole-4-carbonitrile

A modified general procedure H at RT, cyclopentylhydrazine hydrochloride (0.47 mmol) and 2-[(4-chloro-3,5-difluoro-phenyl)-methoxy-methylene]propanedinitrile (0.39 mmol) gave, after purification, the titled compound (0.31 mmol) as an off-white solid. UPLC-MS (ES+, Short acidic): 2.13 min, m/z 323.0[M]+

N-[[4-(5-Amino-4-cyano-1-cyclopentyl-pyrazol-3-yl)-2,6-difluoro-phenyl]methyl]-2-methoxy-benzamide General procedure K, 5-amino-3-(4-chloro-3,5-difluoro-phenyl)-1-cyclopentyl-pyrazole-4-carbonitrile (0.16 mmol) and potassium trifluoro-[[(2-methoxybenzoyl)amino]methyl]boranuide (0.31 mmol) gave, after purification, the titled compound (0.11 mmol) as a white solid. UPLC-MS (ES+, Short acidic): 1.86 min, m/z 452.1 [M+H]+

5-Amino-1-cyclopentyl-3-[3,5-difluoro-4-[[(2-methoxybenzoyl)amino]methyl]phenyl]pyrazole-4-carboxamide General procedure M, N-[[4-(5-amino-4-cyano-1-cyclopentyl-pyrazol-3-yl)-2,6-difluoro-phenyl]methyl]-2-methoxy-benzamide (0.11 mmol) gave, after purification, the titled compound (0.08 mmol) as a white solid. UPLC-MS (ES+, Short acidic): 1.64 min, m/z 470.1 [M+H]+. UPLC-MS (ES+, Long acidic): 3.80 min, m/z 470.1 [M+H]+. ¹H NMR (400 MHz, DMSO-d₆, δ): 8.56 (t, J=5.5 Hz, 1H), 7.73 (dd, J=7.7, 1.7 Hz, 1H), 7.50-7.43 (m, 1H), 7.25-7.17 (m, 2H), 7.13 (d, J=8.3 Hz, 1H), 7.05-6.99 (m, 1H), 6.20 (s, 2H), 4.68-4.54 (m, 3H), 3.87 (s, 3H), 2.05-1.73 (m, 6H), 1.65-1.51 (m, 2H).

Example 139: 5-amino-1-cyclopentyl-3-[3,5-difluoro-4-[[(5-fluoro-2-methoxy-benzoyl)amino]methyl]phenyl]pyrazole-4-carboxamide

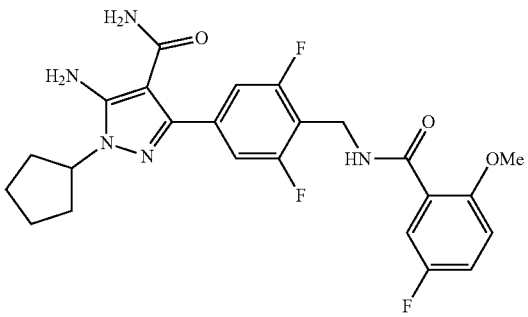 [SMILES: COc1ccc(F)cc1C(=O)NCc1c(F)cc(-c2nn(C3CCCC3)c(N)c2C(N)=O)cc1F]

N-[[4-(5-Amino-4-cyano-1-cyclopentyl-pyrazol-3-yl)-2,6-difluoro-phenyl]methyl]-5-fluoro-2-methoxy-benzamide General procedure K, 5-amino-3-(4-chloro-3,5-difluoro-phenyl)-1-cyclopentyl-pyrazole-4-carbonitrile (0.16 mmol) and potassium trifluoro-[[(5-fluoro-2-methoxy-benzoyl)amino]methyl]boranuide (0.39 mmol) gave, after purification, the titled compound (20 mg, 0.04 mmol, 27% yield) as an off-white solid. UPLC-MS (ES+, Short acidic): 1.91 min, m/z 470.1 [M+H]+

5-Amino-1-cyclopentyl-3-[3,5-difluoro-4-[[(5-fluoro-2-methoxy-benzoyl)amino]methyl]phenyl]pyrazole-4-carboxamide General procedure M, N-[[4-(5-amino-4-cyano-1-cyclopentyl-pyrazol-3-yl)-2,6-difluoro-phenyl]methyl]-5-fluoro-2-methoxy-benzamide (0.04 mmol) gave, after purification, the titled compound (0.03 mmol) as a white solid. UPLC-MS (ES+, Short acidic): 1.69 min, m/z 488.1 [M+H]+. UPLC-MS (ES+, Long acidic): 3.92 min, m/z 488.1 [M+H]+. ¹H NMR (400 MHz, DMSO-d₆, δ): 8.66 (t, J=5.6 Hz, 1H), 7.47 (dd, J=9.2, 3.3 Hz, 1H), 7.37-7.28 (m, 1H), 7.25-7.12 (m, 3H), 6.20 (s, 2H), 4.67-4.52 (m, 3H), 3.86 (s, 3H), 2.05-1.73 (m, 6H), 1.65-1.52 (m, 2H).

Example 140: 5-amino-1-cyclopentyl-3-[2,6-difluoro-4-[[(2-methoxybenzoyl)amino]methyl]phenyl]pyrazole-4-carboxamide

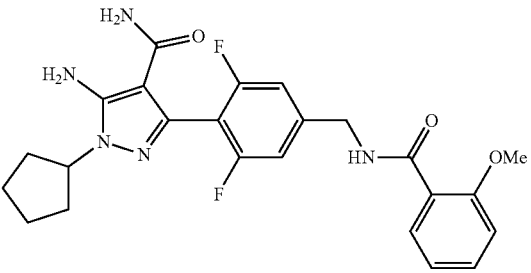 [SMILES: COc1ccccc1C(=O)NCc1cc(F)c(-c2nn(C3CCCC3)c(N)c2C(N)=O)c(F)c1]

5-Amino-3-(4-bromo-2,6-difluoro-phenyl)-1H-pyrazole-4-carbonitrile

General procedure H in the absence of triethylamine, hydrazine hydrate (55-60% in water, 1.43 mmol) and 2-[(4-bromo-2,6-difluoro-phenyl)-methoxy-methylene]propanedinitrile (1.19 mmol) gave crude the titled compound (1.17 mmol) as a pale yellow solid. UPLC-MS (ES+, Short acidic): 1.42 min, m/z 300.8 [M+2]+

5-Amino-3-(4-bromo-2,6-difluoro-phenyl)-1-cyclopentyl-pyrazole-4-carbonitrile Following general procedure N, 5-amino-3-(4-bromo-2,6-difluoro-phenyl)-1H-pyrazole-4-carbonitrile (350 mg, 1.17 mmol) and bromocyclopentane (1.76 mmol) gave, after purification, a mixture of 5-amino-3-(4-bromo-2,6-difluoro-phenyl)-1-cyclopentyl-pyrazole-4-carbonitrile and the titled compound (3:2 ratio) (0.80 mmol) as a white solid. UPLC-MS (ES+, Short acidic): 1.86 and 1.92 min, m/z 368.9 [M+2]+

N-[[4-(5-Amino-4-cyano-1-cyclopentyl-pyrazol-3-yl)-3,5-difluoro-phenyl]methyl]-2-methoxy-benzamide General procedure K, a mixture of 5-amino-3-(4-bromo-2,6-difluoro-phenyl)-1-cyclopentyl-pyrazole-4-carbonitrile and 3-amino-5-(4-bromo-2,6-difluoro-phenyl)-1-cyclopentyl-pyrazole-4-carbonitrile (0.33 mmol) and potassium trifluoro-[[(2-methoxybenzoyl)amino]methyl]boranuide (0.36 mmol) gave, after purification, the titled compound (0.12 mmol) as an off-white solid. UPLC-MS (ES+, Short acidic): 1.72 min, m/z 452.1 [M+H]+

5-Amino-1-cyclopentyl-3-[2,6-difluoro-4-[[(2-methoxybenzoyl)amino]methyl]phenyl]pyrazole-4-carboxamide General procedure L, N-[[4-(5-amino-4-cyano-1-cyclopentyl-pyrazol-3-yl)-3,5-difluoro-phenyl]methyl]-2-methoxy-benzamide (0.12 mmol) gave, after purification the titled compound (0.03 mmol) as a white solid. UPLC-MS (ES+, Short acidic): 1.56 min, m/z 470.1 [M+H]+. UPLC-MS (ES+, Long acidic): 3.60 min, m/z 470.2 [M+H]+. 1H NMR (400 MHz, DMSO-d6, δ): 8.81 (t, J=6.2 Hz, 1H), 7.72 (dd, J=7.6, 1.9 Hz, 1H), 7.52-7.45 (m, 1H), 7.17-7.13 (m, 3H), 7.06-7.00 (m, 1H), 6.28 (br s, 2H), 4.67-4.60 (m, 1H), 4.55 (d, J=6.1 Hz, 2H), 3.90 (s, 3H), 2.03-1.92 (m, 2H), 1.90-1.72 (m, 4H), 1.62-1.52 (m, 2H).

Example 141: 5-amino-3-[2,3-difluoro-4-[[(2-methoxybenzoyl)amino]methyl]phenyl]-1-tetrahydropyran-4-yl-pyrazole-4-carboxamide

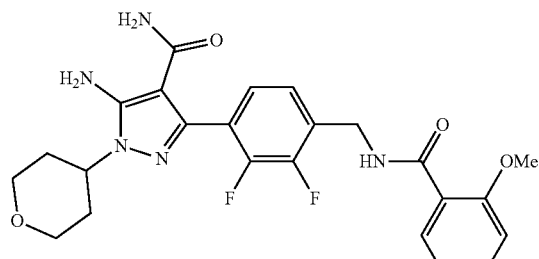

5-Amino-3-(4-chloro-2,3-difluoro-phenyl)-1-tetrahydropyran-4-yl-pyrazole-4-carbonitrile Following general procedure H, 2-[(4-chloro-2,3-difluoro-phenyl)-methoxy-methylene]propanedinitrile (200 mg, 0.79 mmol) and tetrahydropyran-4-ylhydrazine hydrochloride (144 mg, 0.94 mmol) gave, after purification the titled compound (0.65 mmol). UPLC-MS (ES+, Short acidic): 1.68 min, m/z 339.0 [M]+

N-[[4-(5-Amino-4-cyano-1-tetrahydropyran-4-yl-pyrazol-3-yl)-2,3-difluoro-phenyl]methyl]-2-methoxy-benzamide General procedure K, 5-amino-3-(4-chloro-2,3-difluoro-phenyl)-1-tetrahydropyran-4-yl-pyrazole-4-carbonitrile (0.32 mmol) and potassium trifluoro-[[(2-methoxybenzoyl)amino]methyl]boranuide (0.65 mmol) gave, after purification the titled compound (0.24 mmol) as a yellow solid. UPLC-MS (ES+, Short acidic): 1.55 min, m/z 468.1 [M+H]+

5-Amino-3-[2,3-difluoro-4-[[(2-methoxybenzoyl)amino]methyl]phenyl]-1-tetrahydropyran-4-yl-pyrazole-4-carboxamide Following general procedure M, N-[[4-(5-amino-4-cyano-1-tetrahydropyran-4-yl-pyrazol-3-yl)-2,3-difluoro-phenyl]methyl]-2-methoxy-benzamide (112 mg, 0.24 mmol) gave, after purification the titled compound (78 mg, 0.16 mmol, 67% yield) as an off-white solid. UPLC-MS (ES+, Short acidic): 1.40 min, m/z 486.1 [M+H]+. UPLC-MS (ES+, Long acidic): 3.12 min, m/z 486.2 [M+H]+. 1H NMR (400 MHz, DMSO-d6, δ): 8.77 (t, J=6.0 Hz, 1H), 7.78-7.72 (m, 1H), 7.53-7.45 (m, 1H), 7.29-7.19 (m, 2H), 7.16 (d, J=7.8 Hz, 1H), 7.07-7.01 (m, 1H), 6.31 (s, 2H), 4.60 (d, J=6.0 Hz, 2H), 4.43-4.32 (m, 1H), 4.00-3.93 (m, 2H), 3.91 (s, 3H), 3.45-3.39 (m, 2H), 2.01-1.90 (m, 2H), 1.82-1.73 (m, 2H).

Example 142: 5-amino-3-[2,3-difluoro-4-[[(5-fluoro-2-methoxy-benzoyl)amino]methyl]phenyl]-1-tetrahydropyran-4-yl-pyrazole-4-carboxamide

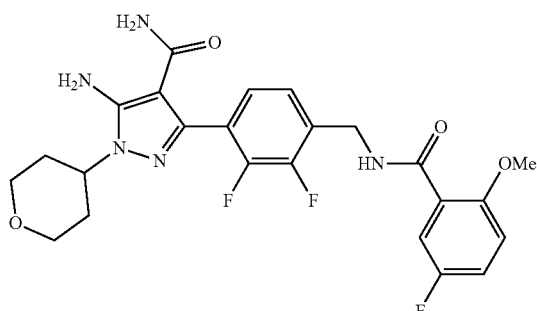

N-[[4-(5-Amino-4-cyano-1-tetrahydropyran-4-yl-pyrazol-3-yl)-2,3-difluoro-phenyl]methyl]-5-fluoro-2-methoxy-benzamide Following general procedure K, 5-amino-3-(4-chloro-2,3-difluoro-phenyl)-1-tetrahydropyran-4-yl-pyrazole-4-carbonitrile (106 mg, 0.31 mmol) and potassium trifluoro-[[(5-fluoro-2-methoxy-benzoyl)amino]methyl]boranuide (181 mg, 0.63 mmol) gave, after purification the titled compound (124 mg, 0.26 mmol, 82% yield) as a yellow solid. UPLC-MS (ES$^+$, Short acidic): 1.60 min, m/z 486.1 [M+H]$^+$ 5-Amino-3-[2,3-difluoro-4-[[(5-fluoro-2-methoxybenzoyl)amino]methyl]phenyl]-1-tetrahydropyran-4-yl-pyrazole-4-carboxamide General procedure M, N-[[4-(5-amino-4-cyano-1-tetrahydropyran-4-yl-pyrazol-3-yl)-2,3-difluoro-phenyl]methyl]-5-fluoro-2-methoxy-benzamide (0.25 mmol) gave, after purification the titled compound (0.12 mmol) as an off-white solid. UPLC-MS (ES$^+$, Short acidic): 1.44 min, m/z 504.1 [M+H]$^+$. UPLC-MS (ES$^+$, Long acidic): 3.24 min, m/z 504.1 [M+H]$^+$. $^1$H NMR (400 MHz, DMSO-d$_6$, δ): 8.87 (t, J=6.0 Hz, 1H), 7.51 (dd, J=9.2, 3.3 Hz, 1H), 7.38-7.33 (m, 1H), 7.24-7.18 (m, 3H), 6.31 (s, 2H), 4.60 (d, J=6.2 Hz, 2H), 4.42-4.34 (m, 1H), 3.98-3.94 (m, 2H), 3.90 (s, 3H), 3.46-3.39 (m, 2H), 2.00-1.90 (m, 2H), 1.78-1.76 (m, 2H).

Example 143: 5-amino-3-[4-[[(2-methoxybenzoyl)amino]methyl]phenyl]-1-(2-methoxy-1-methyl-ethyl)pyrazole-4-carboxamide

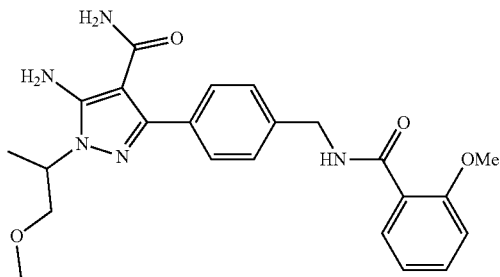 [SMILES: COCC(C)n1nc(-c2ccc(CNC(=O)c3ccccc3OC)cc2)c(C(N)=O)c1N]

tert-Butyl N-[(2-methoxy-1-methyl-ethylidene)amino]carbamate

General procedure E, tert-butyl carbazate (3.78 mmol) and methoxyacetone (2.27 mmol) gave, the titled compound (2.27 mmol) as a yellow oil. UPLC-MS (ES$^+$, Short acidic): 1.36 min, m/z 202.9 [M+H]$^+$ 5-Amino-3-(4-bromophenyl)-1-(2-methoxy-1-methyl-ethyl)pyrazole-4-carbonitrile Following general procedure O, tert-butyl N-[(2-methoxy-1-methyl-ethylidene)amino]carbamate (830 mg, 4.11 mmol), and 2-[(4-bromophenyl)-methoxy-methylene]propanedinitrile (0.76 mmol) gave, after purification the titled compound (0.18 mmol). UPLC-MS (Short acidic): 1.82 min, 337 m/z [M+2]$^+$ N-[[4-[5-Amino-4-cyano-1-(2-methoxy-1-methyl-ethyl)pyrazol-3-yl]phenyl]methyl]-2-methoxy-benzamide General procedure K, potassium trifluoro-[[(2-methoxybenzoyl)amino]methyl]boranuide (0.31 mmol), and 5-amino-3-(4-bromophenyl)-1-(2-methoxy-1-methyl-ethyl)pyrazole-4-carbonitrile (0.18 mmol) gave, after purification the titled compound (0.13 mmol) as an off-white solid. UPLC-MS (ES$^+$, Short acidic): 1.57 min, 420.1 m/z [M+H]$^+$ 5-Amino-3-[4-[[(2-methoxybenzoyl)amino]methyl]phenyl]-1-(2-methoxy-1-methyl-ethyl)pyrazole-4-carboxamide General procedure M, N-[[4-[5-amino-4-cyano-1-(2-methoxy-1-methyl-ethyl)pyrazol-3-yl]phenyl]methyl]-2-methoxy-benzamide (0.13 mmol) gave, after purification the titled compound (0.03 mmol) as a white solid. UPLC-MS (ES$^+$, Short acidic): 1.38 min, 438.1 m/z [M+H]$^+$. UPLC-MS (ES$^+$, Long acidic): 3.10 min, 438.1 m/z [M+H]$^+$. $^1$H NMR (400 MHz, DMSO-d$_6$, δ): 8.73 (t, J=6.1 Hz, 1H), 7.75 (dd, J=7.6, 1.7 Hz, 1H), 7.51-7.38 (m, 5H), 7.15 (d, J=8.2 Hz, 1H), 7.04 (t, J=7.4 Hz, 1H), 6.31 (s, 2H), 4.54 (d, J=6.0 Hz, 2H), 4.48-4.51 (m, 1H), 3.90 (s, 3H), 3.69-3.62 (m, 1H), 3.49 (dd, J=9.8, 5.4 Hz, 1H), 3.23 (s, 3H), 1.28 (d, J=6.6 Hz, 3H).

Example 144: 5-amino-1-(4,4-difluoropyrrolidin-3-yl)-3-[4-[[(2-methoxybenzoyl)amino]methyl]phenyl]pyrazole-4-carboxamide

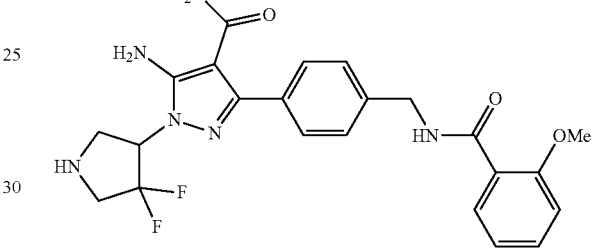

2,2-Difluorovinyl 4-methylbenzenesulfonate

A solution of 2,2,2-trifluoroethyl tosylate (33.4 mmol) in anhydrous THF (111 mL), at −78° C., and n-butyllithium solution (11 M in hexane, 66.9 mmol) was stirred at −78° C. for 20 min, then quenched with a mixture of water (20 mL) and THF (20 mL) whilst maintaining internal temperature at −60° C., then warmed to RT and extracted with EtOAc. The combined organic extracts were washed with a saturated solution of brine, dried over sodium sulfate, filtered and concentrated under reduced pressure. Purification gave the titled compound (26.9 mmol) as a colourless oil.
$^1$H NMR (400 MHz, DMSO-d$_6$, δ): 7.86 (d, J=8.4 Hz, 2H), 7.54 (d, J=8.6 Hz, 2H), 6.85 (dd, J=15.6, 3.9 Hz, 1H), 2.45 (s, 3H).

(1-Benzyl-4,4-difluoro-pyrrolidin-3-yl) 4-methylbenzenesulfonate

A mixture of 2,2-difluorovinyl 4-methylbenzenesulfonate (26.6 mmol), and N-(methoxymethyl)-N-(trimethylsilylmethyl)benzylamine (106 mmol), under nitrogen, was heated to 130° C. for 5 min. Trifluoroacetic acid (2.66 mmol) was added dropwise and stirred for 30 min at 130° C., cooled to RT, concentrated under reduced pressure and triethylamine (2.66 mmol) was added. The residue was then purified to give the titled compound (23.0 mmol) as a light yellow oil. UPLC-MS (ES$^+$, Short acidic): 1.98 min, m/z 368.0 [M+H]$^+$ 1-Benzyl-4,4-difluoro-pyrrolidin-3-ol Magnesium turnings (1.7 g, 64.6 mmol) were added to a solution of (1-benzyl-4,4-difluoro-pyrrolidin-3-yl) 4-methylbenzenesulfonate (12.9 mmol) in MeOH (40 mL), under nitrogen, at 0° C. The reaction was stirred at RT for 1 h, water (4 mL) was added slowly followed by hydrochloric acid (5 M, 20 mL). The volatiles were removed under reduced pressure, basified with aqueous KOH to pH 8 and extracted with DCM (×3). The organic extracts were combined, dried over a hydrophobic frit, and concentrated under reduced pressure. The residue was diluted with EtOAc and stirred at RT for 16 h, filtered and concentrated under reduced pressure. The resulting residue was purified to give the titled compound (9.15 mmol) as yellow oil. $^1$H NMR (400 MHz, DMSO-d$_6$, δ): 7.39-7.23 (m, 5H), 5.69 (d, J=5.8 Hz, 1H), 4.13-4.01 (m, 1H), 3.66-3.53 (m, 2H), 3.15-3.00 (m, 2H), 2.73-2.59 (m, 1H), 2.32-2.26 (m, 1H).

tert-Butyl 3,3-difluoro-4-hydroxy-pyrrolidine-1-carboxylate

Under an atmosphere of nitrogen, to a solution of 1-benzyl-4,4-difluoro-pyrrolidin-3-ol (6.78 mmol) in EtOH (60 mL) was added di-tert-butyl dicarbonate (8.14 mmol) followed by palladium hydroxide (20 wt % on carbon, 1.14 mmol). The reaction was flushed with hydrogen several times, and stirred at RT for 16 h. The reaction was then filtered over a pad of Celite® and the filtrate concentrated under reduced pressure. Further purification gave the titled compound (4.95 mmol) as yellow oil. $^1$H NMR (400 MHz, DMSO-d$_6$, δ): 6.08 (d, J=5.2 Hz, 1H), 4.20 (s, 1H), 3.66-3.55 (m, 3H), 3.22-3.20 (m, 1H), 1.41 (s, 9H).

tert-Butyl 3,3-difluoro-4-(trifluoromethylsulfonyloxy)pyrrolidine-1-carboxylate

To a solution of tert-butyl 3,3-difluoro-4-hydroxy-pyrrolidine-1-carboxylate (3.04 mmol) in anhydrous DCM (20 mL), at −20° C. and under nitrogen, was added dropwise trifluoromethanesulfonic anhydride (1 M in DCM, 7.57 mmol). The reaction was stirred at −20 to −10° C. for 40 min, quenched with aqueous citric acid (0.5 M), basified with saturated aqueous sodium bicarbonate solution to achieve pH of approximately 4.5 and extracted with DCM. The organic extracts were combined, dried over a hydrophobic frit and concentrated under reduced pressure to give crude the titled compound (2.51 mmol) as brown oil. $^1$H NMR (400 MHz, DMSO-d$_6$, δ): 5.98-5.93 (m, 1H), 3.97-3.68 (m, 3H), 3.71-3.67 (m, 1H), 1.43 (s, 9H).

5-Amino-3-(4-bromophenyl)-1H-pyrazole-4-carbonitrile

General procedure H, 2-[(4-bromophenyl)-methoxymethylene]propanedinitrile (0.76 mmol) and hydrazine hydrate (55-60% in water, 1.9 mmol) without triethylamine gave, after purification the titled compound (0.69 mmol) as a white solid. UPLC-MS (ES$^+$, Short acidic): 1.44 min, m/z 265.9 [M+2]$^+$ tert-Butyl 4-[5-amino-3-(4-bromophenyl)-4-cyano-pyrazol-1-yl]-3,3-difluoro-pyrrolidine-1-carboxylate A solution of tert-butyl 3,3-difluoro-4-(trifluoromethylsulfonyloxy)pyrrolidine-1-carboxylate (578 mg, 1.59 mmol), 5-amino-3-(4-bromophenyl)-1H-pyrazole-4-carbonitrile (300 mg, 1.14 mmol) and cesium carbonate (743 mg, 2.28 mmol) in DMF (12 mL) was heated to 90° C. for 2.5 h. The reaction was cooled to RT, diluted with water and extracted with EtOAc. The combined organic extracts were dried over sodium sulfate, filtered and concentrated under reduced pressure. Purification gave the titled compound (105 mg, 0.22 mmol) as orange solid. UPLC-MS (ES$^+$, Short acidic): 2.06 min, m/z 468.0 [M]$^+$ tert-Butyl 4-[5-amino-4-cyano-3-[4-[[(2-methoxybenzoyl)amino]methyl]phenyl]pyrazol-1-yl]-3,3-difluoro-pyrrolidine-1-carboxylate General procedure K, tert-butyl 4-[5-amino-3-(4-bromophenyl)-4-cyano-pyrazol-1-yl]-3,3-difluoro-pyrrolidine-1-carboxylate (0.22 mmol) and potassium trifluoro-[[(2-methoxybenzoyl)amino]methyl]boranuide (0.37 mmol) gave, after purification the titled compound (0.15 mmol) as a white solid. UPLC-MS (ES$^+$, Short acidic): 1.82 min, m/z 553.2 [M+H]$^+$ 5-Amino-1-(4,4-difluoropyrrolidin-3-yl)-3-[4-[[(2-methoxybenzoyl)amino]methyl]phenyl]pyrazole-4-carboxamide General procedure M, tert-butyl 4-[5-amino-4-cyano-3-[4-[[(2-methoxybenzoyl)amino]methyl]phenyl]pyrazol-1-yl]-3,3-difluoro-pyrrolidine-1-carboxylate (80 mg, 0.14 mmol) gave, after purification the titled compound (20 mg, 0.04 mmol, 29% yield) as light yellow solid. UPLC-MS (ES$^+$, Short acidic): 1.14 min, m/z 471.1 [M+H]$^+$. UPLC-MS (ES$^+$, Long acidic): 2.42 min, m/z 471.2 [M+H]$^+$. $^1$H NMR (400 MHz, DMSO-d$_6$, δ): 8.73 (t, J=6.0 Hz, 1H), 7.74 (dd, J=7.6, 1.7 Hz, 1H), 7.50-7.40 (m, 5H), 7.15 (d, J=8.3 Hz, 1H), 7.05-7.01 (m, 1H), 6.54 (br s, 2H), 5.04-4.96 (m, 1H), 4.54 (d, J=6.1 Hz, 2H), 3.90 (s, 3H), 3.54-3.45 (m, 2H), 3.26-3.07 (m, 2H).

Example 145: 5-amino-3-[4-[[(2-methoxybenzoyl)amino]methyl]phenyl]-1-[1-(3-pyridyl)ethyl]pyrazole-4-carboxamide

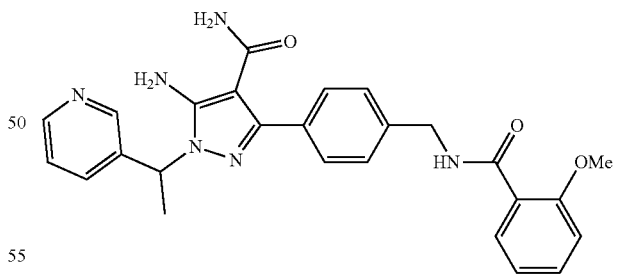

1-(3-Pyridyl)ethanol

Under an atmosphere of nitrogen, bromo(methyl)magnesium (2.7 M in diethyl ether, 0.31 mmol) and a solution of 3-pyridinecarboxaldehyde (1.60 mmol) in THF (3.2 mL) at −78° C. was stirred at RT for 1 h, quenched with MeOH and concentrated under reduced pressure. Purification gave the titled compound (1.47 mmol) as a clear oil. $^1$H NMR (400

MHz, CDCl₃, δ): 8.65-8.58 (m, 1H), 8.56-8.50 (m, 1H), 7.80-7.75 (m, 1H), 7.35-7.29 (m, 1H), 4.99 (q, J=6.5 Hz, 1H), 1.56 (d, J=6.5 Hz, 3H)

3-Acetylpyridine

Pyridine (0.04 mL, 0.49 mmol) was added to a solution of pyridinium chlorochromate (2.20 mmol) and 1-(3-pyridyl)ethanol (1.47 mmol) in DCM (3 mL) at 0° C. The reaction was left to stir at RT for 2 h, with DCM and the black residue obtained was washed with more DCM (×3). The combined organics were then passed through a pad of Celite® and the solvent removed under reduced pressure to afford crude 3-acetylpyridine (0.66 mmol) as a dark oil which was used directly in the next step. ¹H NMR (400 MHz, CDCl₃, δ): 9.27-9.15 (m, 1H), 8.88-8.76 (m, 1H), 8.29 (d, J=7.8 Hz, 1H), 7.53-7.44 (m, 1H), 2.68 (s, 3H)

tert-Butyl N-[1-(3-pyridyl)ethylideneamino]carbamate

Following general procedure E, 3-acetylpyridine (0.66 mmol) gave, after purification the titled compound (97 mg, 0.41 mmol) as a white solid. UPLC-MS (ES⁺, Short acidic): 1.05 min, m/z 236.0 [M+H]⁺

5-Amino-3-(4-bromophenyl)-1-[i-(3-pyridyl)ethyl]pyrazole-4-carbonitrile

A modified general procedure O at RT, tert-butyl N-[1-(3-pyridyl)ethylideneamino]carbamate (97 mg, 0.41 mmol) and 2-[(4-bromophenyl)-methoxy-methylene]propanedinitrile (0.34 mmol) gave, after purification the titled compound (0.33 mmol) as a white solid. UPLC-MS (ES⁺, Short acidic): 1.55 min, m/z 369.9 [M+2]⁺

N-[[4-[5-Amino-4-cyano-1-[1-(3-pyridyl)ethyl]pyrazol-3-yl]phenyl]methyl]-2-methoxy-benzamide General procedure K, 5-amino-3-(4-bromophenyl)-1-[1-(3-pyridyl)ethyl]pyrazole-4-carbonitrile (0.22 mmol) and potassium trifluoro-[[(2-methoxybenzoyl)amino]methyl]boranuide (0.54 mmol) gave, after purification the titled compound (0.16 mmol) as a white solid. UPLC-MS (ES⁺, Short acidic): 1.37 min, m/z 453.2 [M+H]⁺

5-Amino-3-[4-[[(2-methoxybenzoyl)amino]methyl]phenyl]-1-[1-(3-pyridyl)ethyl]pyrazole-4-carboxamide General procedure M, N-[[4-[5-amino-4-cyano-1-[1-(3-pyridyl)ethyl]pyrazol-3-yl]phenyl]methyl]-2-methoxy-benzamide (0.16 mmol) gave, after purification the titled compound (47 mg, 0.10 mmol, 62% yield) as a light yellow solid. UPLC-MS (ES⁺, Short acidic): 1.20 min, m/z 471.1 [M+H]⁺. UPLC-MS (ES⁺, Long acidic): 2.62 min, m/z 471.3 [M+H]⁺. ¹H NMR (400 MHz, DMSO-d₆, δ): 8.73 (t, J=6.1 Hz, 1H), 8.53 (d, J=1.6 Hz, 1H), 8.47 (dd, J=4.7, 1.4 Hz, 1H), 7.75 (dd, J=7.6, 1.6 Hz, 1H), 7.72-7.66 (m, 1H), 7.51-7.34 (m, 6H), 7.15 (d, J=8.3 Hz, 1H), 7.07-7.00 (m, 1H), 6.47 (br s, 2H), 5.66 (q, J=6.9 Hz, 1H), 4.54 (d, J=6.0 Hz, 2H), 3.90 (s, 3H), 1.76 (d, J=6.9 Hz, 3H)

Example 146: 5-amino-3-[2,5-difluoro-4-[[(5-fluoro-2-methoxy-benzoyl)amino]methyl]phenyl]-1-tetrahydropyran-4-yl-pyrazole-4-carboxamide

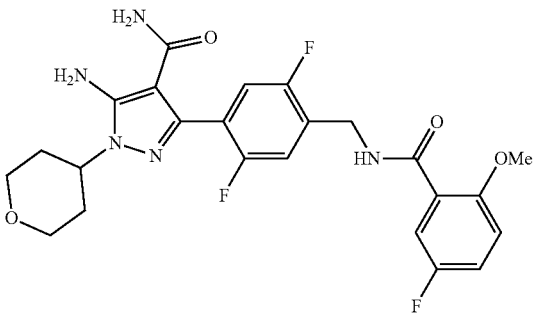 [SMILES: COc1ccc(F)cc1C(=O)NCc1cc(F)c(-c2nn(C3CCOCC3)c(N)c2C(N)=O)cc1F]

5-Amino-3-[2,5-difluoro-4-[[(5-fluoro-2-methoxy-benzoyl)amino]methyl]phenyl]-1-tetrahydropyran-4-yl-pyrazole-4-carboxamide General procedures K and M, 5-amino-3-(4-chloro-2,5-difluoro-phenyl)-1-tetrahydropyran-4-yl-pyrazole-4-carbonitrile (0.38 mmol) and potassium trifluoro-[[(5-fluoro-2-methoxy-benzoyl)amino]methyl]boranuide (0.77 mmol) gave, after purification the titled compound (43 mg, 0.09 mmol, 24% yield). UPLC-MS (ES⁺, Short acidic): 1.42 min, m/z 504.1 [M+H]⁺. UPLC-MS (ES⁺, Long acidic): 3.24 min, m/z 504.2 [M+H]⁺. ¹H NMR (400 MHz, DMSO-d₆, δ): 8.86 (t, J=6.0 Hz, 1H), 7.49 (dd, J=9.1, 3.3 Hz, 1H), 7.38-7.31 (m, 1H), 7.28-7.22 (m, 2H), 7.20 (dd, J=9.1, 4.3 Hz, 1H), 6.28 (s, 2H), 4.56 (d, J=6.0 Hz, 2H), 4.42-4.33 (m, 1H), 3.96 (dd, J=11.9, 4.1 Hz, 2H), 3.90 (s, 3H), 3.42 (t, J=12.0 Hz, 2H), 2.01-1.96 (m, 2H), 1.77 (d, J=12.0 Hz, 2H).

Example 147: 5-amino-1-(5,5-dimethyltetrahydrofuran-3-yl)-3-[4-[[(2-methoxybenzoyl)amino]methyl]phenyl]pyrazole-4-carboxamide

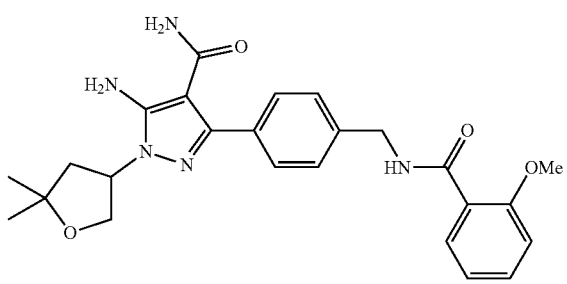 [SMILES: COc1ccccc1C(=O)NCc1ccc(-c2nn(C3COC(C)(C)C3)c(N)c2C(N)=O)cc1]

2-Methylpent-4-en-2-ol

Anhydrous acetone (136.19 mmol) was added dropwise to an allylmagnesium bromide solution (1 M in diethyl ether, 272.4 mmol) at 0° C. After stirring at 0° C. for 15 min, the reaction mixture was stirred at RT for 2 h. A saturated solution of $NH_4Cl$ was added to partition the layers. The aqueous layer was extracted with diethyl ether, washed with water and a saturated solution of brine, dried over sodium sulfate and all volatiles were carefully removed under reduced pressure to afford 2-methylpent-4-en-2-ol (49.64 mmol) as a colourless oil. $^1$H NMR (400 MHz, $CDCl_3$, δ): 5.98-5.83 (m, 1H), 5.23-5.09 (m, 2H), 2.26 (d, J=7.6 Hz, 2H), 1.29-1.26 (m, 1H), 1.25 (s, 6H)

4-Methylpentane-1,2,4-triol

2-Methylpent-4-en-2-ol (20.0 mmol) was dissolved in tert-butanol (88 mL) and water (88 mL) and AD-mix-beta (16 g) was added. The reaction mixture was stirred at RT for 72 h. EtOAc (25 mL) and sodium sulfite (12 g) were added, the reaction was stirred for 1 h until clear separation of the two phases. The aqueous phase was extracted with EtOAc, dried over sodium sulfate and all volatiles removed under reduced pressure to afford crude 4-methylpentane-1,2,4-triol (8.34 mmol) as a colourless oil. $^1$H NMR (400 MHz, $CDCl_3$, δ): 4.19-4.07 (m, 1H), 3.75-3.60 (m, 2H), 3.55-3.44 (m, 1H), 2.41 (br s, 1H), 2.16-2.00 (m, 1H), 1.78 (dd, J=14.5, 10.8 Hz, 1H), 1.50 (dd, J=14.5, 2.3 Hz, 1H), 1.37 (s, 3H), 1.33 (s, 3H).

5,5-Dimethyltetrahydrofuran-3-ol

4-Methylpentane-1,2,4-triol (8.35 mmol) was dissolved in DCM (40 mL), the reaction mixture was purged with nitrogen, then p-toluenesulfonyl chloride (12.52 mmol) and triethylamine (25.04 mmol) were added. The reaction mixture was heated to reflux and stirred for 48 h. A saturated solution of $NH_4Cl$ was added to partition the layers, the organic layer was extracted with DCM, washed with a saturated solution of brine, dried over sodium sulfate and all volatiles were removed under reduced pressure. Purification by flash column chromatography on silica gel eluting with 0-100% EtOAc in heptane to afford 5,5-dimethyltetrahydrofuran-3-ol (3.56 mmol) as a colourless oil. $^1$H NMR (400 MHz, $CDCl_3$, δ): 4.57-4.46 (m, 1H), 3.97 (dd, J=9.9, 4.5 Hz, 1H), 3.82 (ddd, J=9.9, 2.5, 1.2 Hz, 1H), 2.04 (dd, J=13.5, 6.5 Hz, 1H), 1.82 (ddd, J=13.5, 2.5, 1.2 Hz, 1H), 1.78-1.69 (m, 1H), 1.41 (s, 3H), 1.25 (s, 3H)

5,5-Dimethyltetrahydrofuran-3-one

To a solution of 5,5-dimethyltetrahydrofuran-3-ol (1.93 mmol) in DCM (10 mL) was added dess martin periodinane (2.12 mmol) at RT under nitrogen atmosphere and then allowed to stir for 72 h. The mixture was quenched with a saturated solution of sodium thiosulfate and then a saturated solution of $NaHCO_3$. Phases were separated and organic phase was dried over sodium sulfate and filtered. The solvent was concentrated under reduced pressure to afford crude the titled compound (1.93 mmol) which was used immediately in the next step. $^1$H NMR (400 MHz, $CDCl_3$, δ): 4.06 (s, 2H), 2.38 (s, 2H), 1.42 (s, 6H).

tert-Butyl N-[(5,5-dimethyltetrahydrofuran-3-ylidene)amino]carbamate

General procedure E, tert-butyl carbazate (1.97 mmol) and 5,5-dimethyltetrahydrofuran-3-one (1.93 mmol) gave crude the titled compound (mixture of isomers, 1.93 mmol) as a yellow oil. $^1$H NMR (400 MHz, $CDCl_3$, δ, isomer 1 and isomer 2): isomer 1: 5.94 (s, 1H), 4.49-4.45 (m, 2H), 2.36-2.30 (m, 2H), 1.48 (s, 9H), 1.36 (s, 6H) and isomer 2: 5.94 (s, 1H), 4.38-4.32 (m, 2H), 2.64-2.58 (m, 2H), 1.48 (s, 9H), 1.33 (s, 6H)

5-Amino-3-(4-bromophenyl)-1-(5,5-dimethyltetrahydrofuran-3-yl)pyrazole-4-carbonitrile To a solution of tert-Butyl N-[(5,5-dimethyltetrahydrofuran-3-ylidene)amino]carbamate (1.93 mmol) in THF (10 mL) was added a borane dimethyl sulfide complex solution (2 M in THF, 3.43 mmol). The reaction was stirred at RT for 1 h and was concentrated under reduced pressure. The residue was taken up with MeOH (10 mL) and hydrochloric acid (12 M, 20.15 mmol) then heated to reflux for 14 h, cooled and concentrated under reduced pressure. The residue was taken up with EtOH (10 mL), followed by addition of 2-[(4-bromophenyl)-methoxy-methylene]propanedinitrile (0.38 mmol) and triethylamine (1.9 mmol), and heated to reflux for 16 h. The solvent was evaporated under reduced pressure and the residue was purified by flask column chromatography on silica gel eluting with 0-100% EtOAc in heptane to give the titled compound (0.12 mmol) as a yellow oil. UPLC-MS (ES$^-$, Short acidic): 1.86 min, m/z 360.9 [M]$^+$

N-[[4-[5-Amino-4-cyano-1-(5,5-dimethyltetrahydrofuran-3-yl)pyrazol-3-yl]phenyl]methyl]-2-methoxybenzamide General procedure K, 5-amino-3-(4-bromophenyl)-1-(5,5-dimethyltetrahydrofuran-3-yl)pyrazole-4-carbonitrile (0.14 mmol), and potassium trifluoro-[[(2-methoxybenzoyl)amino]methyl]boranuide (0.19 mmol) gave, after purification by flash column chromatography on silica gel eluting with 20-100% EtOAc in heptane, the titled compound (0.1 mmol) as a pale yellow solid. UPLC-MS (ES$^+$, Short acidic): 1.62 min, m/z 446.0 [M+H]$^+$

5-Amino-1-(5,5-dimethyltetrahydrofuran-3-yl)-3-[4-[[(2-methoxybenzoyl)amino]methyl]phenyl]pyrazole-4-carboxamide General procedure L, N-[[4-[5-amino-4-cyano-1-(5,5-dimethyltetrahydrofuran-3-yl)pyrazol-3-yl]phenyl]methyl]-2-methoxy-benzamide (0.10 mmol) gave, after purification the titled compound (0.03 mmol) as a beige solid. UPL-CMS (ES$^+$, Short acidic): 1.44 min, m/z 464.1 [M+H]$^+$. UPLC-MS (ES$^+$, Long acidic): 3.32 min, m/z 464.2 [M+H]$^+$. $^1$H NMR (400 MHz, DMSO-$d_6$): 8.66 (t, J=6.0 Hz, 1H), 7.68 (dd, J=7.6, 1.7 Hz, 1H), 7.42-7.33 (m, 5H), 7.07 (d, J=8.3 Hz, 1H), 6.96 (t, J=7.1 Hz, 1H), 6.34 (s, 2H), 4.99-4.92 (m, 1H), 4.45 (d, J=6.1 Hz, 2H), 3.98 (t, J=8.1 Hz, 1H), 3.82 (s, 3H), 3.80-3.78 (m, 1H), 2.10 (dd, J=3.5, 2.6 Hz, 2H), 1.24 (s, 3H), 1.16 (s, 3H).

Example 148: 5-amino-3-[2,5-difluoro-4-[[(2-methoxybenzoyl)amino]methyl]phenyl]-1-tetrahydropyran-4-yl-pyrazole-4-carboxamide

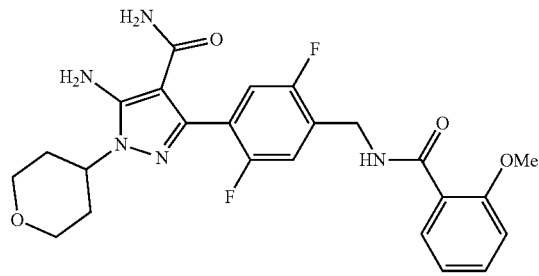 [SMILES: COc1ccccc1C(=O)NCc1cc(F)c(-c2nn(C3CCOCC3)c(N)c2C(N)=O)cc1F]

5-Amino-3-(4-chloro-2,5-difluoro-phenyl)-1-tetrahydropyran-4-yl-pyrazole-4-carbonitrile General procedure H, 2-[(4-chloro-2,5-difluoro-phenyl)-methoxy-methylene]propanedinitrile (1.57 mmol) gave, after purification by flash chromatography on silica gel eluting with 15-75% EtOAc in heptane, the titled compound (0.77 mmol) as a solid. UPLC-MS (ES$^+$, Short acidic): 1.68 min, m/z 339.0 [M]$^+$

N-[[4-(5-Amino-4-cyano-1-tetrahydropyran-4-yl-pyrazol-3-yl)-2,5-difluoro-phenyl]methyl]-2-methoxy-benzamide General procedure K, 5-amino-3-(4-chloro-2,5-difluoro-phenyl)-1-tetrahydropyran-4-yl-pyrazole-4-carbonitrile (130 mg, 0.38 mmol) and potassium trifluoro-[[(2-methoxybenzoyl)amino]methyl]boranuide (208 mg, 0.77 mmol) gave crude the titled compound (136 mg, 0.29 mmol, 76% yield) as a solid, which was used without further purification. UPLC-MS (ES$^+$, Short acidic): 1.56 min, m/z 468.1 [M+H]$^+$

5-Amino-3-[2,5-difluoro-4-[[(2-methoxybenzoyl)amino]methyl]phenyl]-1-tetrahydropyran-4-yl-pyrazole-4-carboxamide Following general procedure L, N-[[4-(5-amino-4-cyano-1-tetrahydropyran-4-yl-pyrazol-3-yl)-2,5-difluoro-phenyl]methyl]-2-methoxy-benzamide (136 mg, 0.29 mmol) gave, after purification, the titled compound (0.04 mmol) as a solid. UPLC-MS (ES$^+$, Short acidic): 1.37 min, m/z 486.1 [M+H]$^+$. UPLC-MS (ES$^+$, Long acidic): 3.12 min, m/z 486.2 [M+H]$^+$. $^1$H NMR (400 MHz, DMSO-d$_6$, δ): 8.77 (t, J=6.0 Hz, 1H), 7.72 (dd, J=7.6, 1.8 Hz, 1H), 7.51-7-47 (m, 1H), 7.28-7.22 (m, 2H), 7.18-7.15 (m, 1H), 7.04 (td, J=7.6, 0.9 Hz, 1H), 6.28 (s, 2H), 4.56 (d, J=6.0 Hz, 2H), 4.42-4.34 (m, 1H), 3.96 (dd, J=11.5, 4.1 Hz, 2H), 3.91 (s, 3H), 3.45-3.39 (m, 2H), 2.01-1.91 (m, 2H), 1.80-1.75 (m, 2H).

Example 149: 5-amino-3-[2,5-difluoro-4-[[(5-fluoro-2-methoxy-benzoyl)amino]methyl]phenyl]-1-tetrahydropyran-3-yl-pyrazole-4-carboxamide

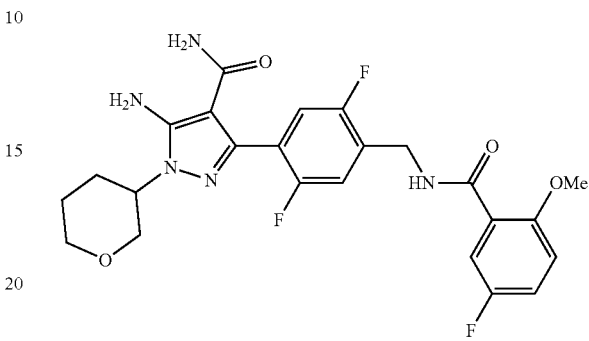

5-Amino-3-(4-chloro-2,5-difluoro-phenyl)-1-tetrahydropyran-3-yl-pyrazole-4-carbonitrile General procedure H, 2-[(4-chloro-2,5-difluoro-phenyl)-methoxy-methylene]propanedinitrile (0.79 mmol) and tetrahydropyran-3-ylhydrazine hydrochloride (240 mg, 1.57 mmol) gave after purification the titled compound (0.34 mmol) as a yellow solid. UPLC-MS (ES$^+$, Short acidic): 1.78 min, m/z 339.0 [M]$^+$

N-[[4-(5-Amino-4-cyano-1-tetrahydropyran-3-yl-pyrazol-3-yl)-2,5-difluoro-phenyl]methyl]-5-fluoro-2-methoxy-benzamide General procedure K, 5-amino-3-(4-chloro-2,5-difluoro-phenyl)-1-tetrahydropyran-3-yl-pyrazole-4-carbonitrile (0.16 mmol) and potassium trifluoro-[[(5-fluoro-2-methoxybenzoyl)amino]methyl]boranuide (0.32 mmol) gave the titled compound (0.16 mmol) as a white solid. UPLC-MS (ES$^+$, Short acidic): 1.68 min, m/z 486.1 [M+H]$^+$

5-Amino-3-[2,5-difluoro-4-[[(5-fluoro-2-methoxy-benzoyl)amino]methyl]phenyl]-1-tetrahydropyran-3-yl-pyrazole-4-carboxamide General procedure M, N-[[4-(5-amino-4-cyano-1-tetrahydropyran-3-yl-pyrazol-3-yl)-2,5-difluoro-phenyl]methyl]-5-fluoro-2-methoxy-benzamide (0.16 mmol) gave after purification the titled compound (0.05 mmol) as an off-white solid. UPLC-MS (ES$^+$, Short acidic): 1.50 min, m/z 504.1 [M+H]$^+$. UPLC-MS (ES$^+$, Long acidic): 3.43 min, m/z 504.2 [M+H]$^+$. $^1$H NMR (400 MHz, DMSO-d$_6$, δ): 8.86 (t, J=6.0 Hz, 1H), 7.48 (dd, J=9.1, 3.3 Hz, 1H), 7.39-7.31 (m, 1H), 7.28-7.16 (m, 3H), 6.31 (s, 2H), 4.55 (d, J=6.0 Hz, 2H), 4.33-4.21 (m, 1H), 3.92-3.73 (m, 5H), 3.52 (t, J=10.5 Hz, 1H), 3.35-3.26 (m, 1H), 2.03-1.94 (m, 2H), 1.79-1.58 (m, 2H).

Example 150: 5-amino-3-[4-[[(2-methoxybenzoyl)amino]methyl]phenyl]-1-sec-butyl-pyrazole-4-carboxamide

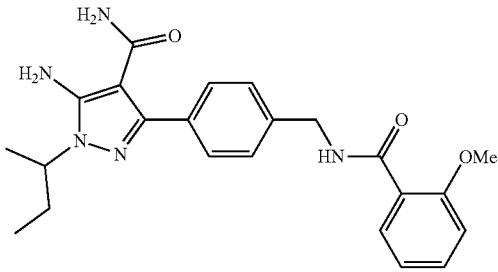 [SMILES: CCC(C)n1nc(-c2ccc(CNC(=O)c3ccccc3OC)cc2)c(C(N)=O)c1N]

tert-Butyl N-[1-methylpropylideneamino]carbamate

Following general procedure E, tert-butyl carbazate (7.57 mmol), and 2-butanone (9.08 mmol) gave the titled compound (7.57 mmol) as a yellow oil. UPLC-MS (ES+, Short acidic): 1.36 min, m/z 186.9 [M+H]+

5-Amino-3-(4-bromophenyl)-1-sec-butyl-pyrazole-4-carbonitrile

General procedure O, tert-butyl N-[1-methylpropylideneamino]carbazate (7.39 mmol), and 2-[(4-bromophenyl)-methoxy-methylene]propanedinitrile (0.76 mmol) gave, after purification, the titled compound (0.38 mmol) as an off-white solid. UPLC (ES+, Short acidic): 1.95 min, 321.0 m/z [M+2]+

N-[[4-(5-Amino-4-cyano-1-sec-butyl-pyrazol-3-yl)phenyl]methyl]-2-methoxy-benzamide General procedure K, potassium trifluoro-[[(2-methoxybenzoyl)amino]methyl]boranuide (0.69 mmol), and 5-amino-3-(4-bromophenyl)-1-sec-butyl-pyrazole-4-carbonitrile (0.40 mmol) gave, after purification, the titled compound (0.26 mmol) as an off-white solid. UPLC-MS (ES+, Short acidic): 1.66 min, 404.1 m/z [M+H]+

5-Amino-3-[4-[[(2-methoxybenzoyl)amino]methyl]phenyl]-1-sec-butyl-pyrazole-4-carboxamide General procedure M, N-[[4-(5-amino-4-cyano-1-sec-butyl-pyrazol-3-yl)phenyl]methyl]-2-methoxy-benzamide (0.06 mmol) gave, after purification the titled compound (0.04 mmol) as a white solid. UPLC-MS (ES+, Short acidic): 1.49 min, 422.2 m/z [M+H]+. UPLC-MS (ES+, Long acidic): 3.34 min, 422.2 m/z [M+H]+. $^1$H NMR (400 MHz, DMSO-$d_6$, δ): 8.73 (t, J=6.0 Hz, 1H), 7.75 (dd, J=7.6, 1.7 Hz, 1H), 7.51-7.45 (m, 5H), 7.15 (d, J=8.3 Hz, 1H), 7.04 (t, J=7.5 Hz, 1H), 6.31 (s, 2H), 4.54 (d, J=6.0 Hz, 2H), 4.28-4.16 (m, 1H), 3.90 (s, 3H), 1.88-1.72 (m, 1H), 1.72-1.56 (m, 1H), 1.31 (d, J=6.5 Hz, 3H), 0.76 (t, J=7.3 Hz, 3H).

Example 151: 5-amino-3-[2,5-difluoro-4-[[(2-methoxybenzoyl)amino]methyl]phenyl]-1-tetrahydropyran-3-yl-pyrazole-4-carboxamide

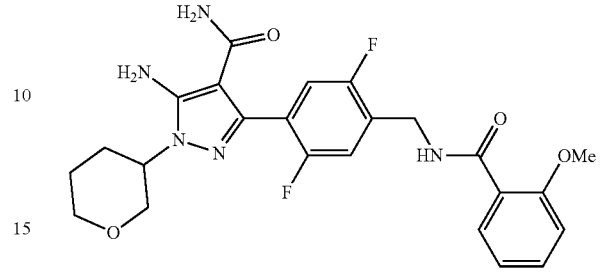

N-[[4-(5-Amino-4-cyano-1-tetrahydropyran-3-yl-pyrazol-3-yl)-2,5-difluoro-phenyl]methyl]-2-methoxy-benzamide Following general procedure K, 5-amino-3-(4-chloro-2,5-difluoro-phenyl)-1-tetrahydropyran-3-yl-pyrazole-4-carbonitrile (0.16 mmol) and potassium trifluoro-[[(2-methoxybenzoyl)amino]methyl]boranuide (0.32 mmol) gave, after purification, titled compound (0.15 mmol, 93% yield) as a yellow solid. UPLC-MS: (ES+, Short acidic): 1.63 min, m/z 468.1 [M+H]+

5-Amino-3-[2,5-difluoro-4-[[(2-methoxybenzoyl)amino]methyl]phenyl]-1-tetrahydropyran-3-yl-pyrazole-4-carboxamide Following general procedure M, N-[[4-(5-amino-4-cyano-1-tetrahydropyran-3-yl-pyrazol-3-yl)-2,5-difluoro-phenyl]methyl]-2-methoxy-benzamide (65 mg, 0.14 mmol) gave, after purification, titled compound (10 mg, 0.02 mmol, 15% yield) as an off-white solid. UPLC-MS: (ES+, Short acidic): 1.49 min, m/z 486.1 [M+H]+ UPLC-MS: (ES+, Long acidic): 3.32 min, m/z 468.1 [M+H]+
$^1$H NMR (400 MHz, DMSO-$d_6$, δ): 8.77 (t, J=5.9 Hz, 1H), 7.71 (dd, J=7.7, 1.7 Hz, 1H), 7.51-7.47 (m, 1H), 7.26-7.22 (m, 2H), 7.16 (d, J=8.3 Hz, 1H), 7.06-7.02 (m, 1H), 6.32 (s, 2H), 4.55 (d, J=6.0 Hz, 2H), 4.31-4.24 (m, 1H), 3.91-3.81 (m, 5H), 3.55-3.50 (m, 1H), 3.37-3.26 (m, 1H), 2.02-1.96 (m, 2H), 1.76-1.64 (m, 2H).

Example 152: 5-amino-3-[2,5-difluoro-4-[[(2-methoxybenzoyl)amino]methyl]phenyl]-1-tetrahydrofuran-3-yl-pyrazole-4-carboxamide

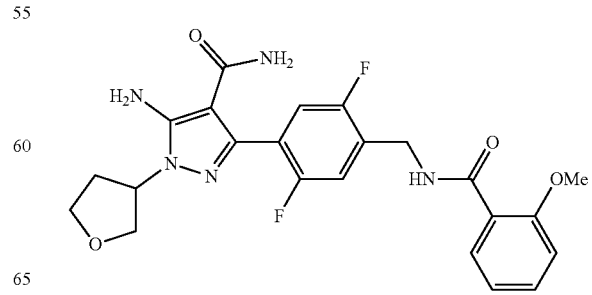

5-Amino-3-(4-chloro-2,5-difluoro-phenyl)-1-tetrahydrofuran-3-yl-pyrazole-4-carbonitrile Following general procedure H, 2-[(4-chloro-2,5-difluoro-phenyl)-methoxy-methylene]propanedinitrile (250 mg, 0.98 mmol) and tetrahydrofuran-3-ylhydrazine hydrochloride (163 mg, 1.18 mmol) gave, after purification, titled compound (70 mg, 0.22 mmol). UPLC-MS (ES+, Short acidic): 1.66 min, m/z 325.0 [M]+

N-[[4-(5-Amino-4-cyano-1-tetrahydrofuran-3-yl-pyrazol-3-yl)-2,5-difluoro-phenyl]methyl]-2-methoxy-benzamide Following general procedure K, 5-amino-3-(4-chloro-2,5-difluoro-phenyl)-1-tetrahydrofuran-3-yl-pyrazole-4-carbonitrile (70 mg, 0.22 mmol) and potassium trifluoro-[[(2-methoxybenzoyl)amino]methyl]boranuide (117 mg, 0.43 mmol) gave, after purification, titled compound (0.14 mmol, 63% yield) as a white solid. UPLC-MS (ES+, Short acidic): 1.58 min, m/z 454.1 [M+H]+

5-Amino-3-[2,5-difluoro-4-[[(2-methoxybenzoyl)amino]methyl]phenyl]-1-tetrahydrofuran-3-yl-pyrazole-4-carboxamide Following general procedure M, N-[[4-(5-amino-4-cyano-1-tetrahydrofuran-3-yl-pyrazol-3-yl)-2,5-difluoro-phenyl]methyl]-2-methoxy-benzamide (60 mg, 0.13 mmol) gave, after purification, titled compound (18 mg, 0.04 mmol, 29% yield) as a solid. UPLC-MS (ES+, Short acidic): 1.46 min, m/z 472.1 [M+H]+ UPLC-MS (ES+, Long acidic): 3.16 min, m/z 472.1 [M+H]+

$^1$H NMR (400 MHz, DMSO-$d_6$, δ): 8.77 (t, J=6.1 Hz, 1H), 7.72 (dd, J=7.6, 1.7 Hz, 1H), 7.51-7.47 (m, 1H), 7.29-7.22 (m, 2H), 7.16 (d, J=8.3 Hz, 1H), 7.06-7.02 (m, 1H), 6.30 (s, 2H), 4.98-4.91 (m, 1H), 4.55 (d, J=6.0 Hz, 2H), 4.01-3.92 (m, 2H), 3.91 (s, 3H), 3.83-3.76 (m, 2H), 2.30-2.20 (m, 2H).

Example 153: 5-amino-3-[2,5-difluoro-4-[[(5-fluoro-2-methoxy-benzoyl)amino]methyl]phenyl]-1-tetrahydrofuran-3-yl-pyrazole-4-carboxamide

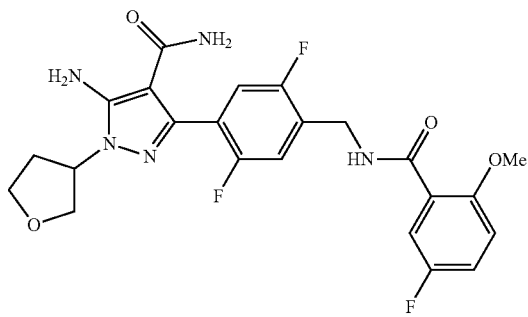 [SMILES: COc1ccc(F)cc1C(=O)NCc1cc(F)c(-c2nn(C3CCOC3)c(N)c2C(N)=O)cc1F]

N-[[4-(5-Amino-4-cyano-1-tetrahydrofuran-3-yl-pyrazol-3-yl)-2,5-difluoro-phenyl]methyl]-5-fluoro-2-methoxy-benzamide Following general procedure K, 5-amino-3-(4-chloro-2,5-difluoro-phenyl)-1-tetrahydrofuran-3-yl-pyrazole-4-carbonitrile (60 mg, 0.18 mmol) and potassium trifluoro-[[(5-fluoro-2-methoxy-benzoyl)amino]methyl]boranuide (134 mg, 0.46 mmol) gave, after purification, titled compound (40 mg, 0.08 mmol, 46% yield) as a white solid. UPLC-MS (ES+, Short acidic): 1.63 min, m/z 472.1 [M+H]+

5-Amino-3-[2,5-difluoro-4-[[(5-fluoro-2-methoxy-benzoyl)amino]methyl]phenyl]-1-tetrahydrofuran-3-yl-pyrazole-4-carboxamide Following general procedure M, N-[[4-(5-amino-4-cyano-1-tetrahydrofuran-3-yl-pyrazol-3-yl)-2,5-difluoro-phenyl]methyl]-5-fluoro-2-methoxy-benzamide (39 mg, 0.08 mmol) gave, after purification, titled compound (18 mg, 0.04 mmol, 43% yield). UPLC-MS (ES+, Short acidic): 1.51 min, m/z 490.1 [M+H]+ UPLC-MS (ES+, Long acidic): 3.29 min, m/z 490.1 [M+H]+

$^1$H NMR (400 MHz, DMSO-$d_6$, δ): 8.86 (t, J=6.3 Hz, 1H), 7.49 (dd, J=9.1, 3.3 Hz, 1H), 7.38-7.31 (m, 1H), 7.29-7.17 (m, 3H), 6.30 (s, 2H), 4.98-4.91 (m, 1H), 4.55 (d, J=5.9 Hz, 2H), 4.01-3.92 (m, 2H), 3.90 (s, 3H), 3.84-3.76 (m, 2H), 2.30-2.21 (m, 2H).

Example 154: 5-amino-1-cyclopentyl-3-[2,3-difluoro-4-[[(5-fluoro-2-methoxy-benzoyl)amino]methyl]phenyl]pyrazole-4-carboxamide

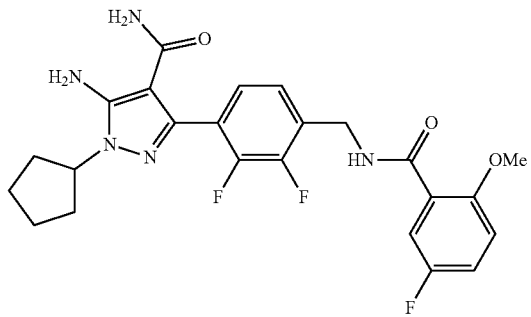 [SMILES: COc1ccc(F)cc1C(=O)NCc1ccc(-c2nn(C3CCCC3)c(N)c2C(N)=O)c(F)c1F]

5-Amino-3-(4-chloro-2,3-difluoro-phenyl)-1-cyclopentyl-pyrazole-4-carbonitrile Following general procedure H, 2-[(4-chloro-2,3-difluoro-phenyl)-methoxy-methylene]propanedinitrile (250 mg, 0.98 mmol) and cyclopentylhydrazine hydrochloride (174 mg, 1.28 mmol) gave, after purification, titled compound (173 mg, 0.54 mmol, 55% yield) as a white solid.

UPLC-MS (ES+, Short acidic): 1.97 min, m/z 322.9 [M]+

N-[[4-(5-Amino-4-cyano-1-cyclopentyl-pyrazol-3-yl)-2,3-difluoro-phenyl]methyl]-5-fluoro-2-methoxy-benzamide Following general procedure K, 5-amino-3-(4-chloro-2,3-difluoro-phenyl)-1-cyclopentyl-pyrazole-4-carbonitrile (79 mg, 0.25 mmol) and potassium trifluoro-[[(5-fluoro-2-methoxy-benzoyl)amino]methyl]boranuide (120 mg, 0.42 mmol) gave, after purification, titled compound (91 mg, 0.19 mmol, 79% yield) as an white solid.

UPLC-MS (ES+, Short acidic): 1.81 min, m/z 470.1 [M+H]+

5-Amino-1-cyclopentyl-3-[2,3-difluoro-4-[[(5-fluoro-2-methoxy-benzoyl)amino]methyl]phenyl]pyrazole-4-carboxamide Following general procedure M, N-[[4-(5-amino-4-cyano-1-cyclopentyl-pyrazol-3-yl)-2,3-difluoro-phenyl]methyl]-5-fluoro-2-methoxy-benzamide (90 mg, 0.19 mmol) gave, after purification, titled compound (65 mg, 0.13 mmol, 70% yield) as white solid. UPLC-MS (ES$^+$, Short acidic): 1.66 min, m/z 488.2 [M+H]$^+$ UPLC-MS (ES$^+$, Long acidic): 3.86 min, m/z 488.2 [M+H]$^+$ $^1$H NMR (400 MHz, DMSO-d$_6$, δ): 8.87 (t, J=6.0 Hz, 1H), 7.51 (dd, J=9.2, 3.3 Hz, 1H), 7.38-7.33 (m, 1H), 7.25-7.18 (m, 3H), 6.26 (br s, 2H), 4.67-4.59 (m, 1H), 4.60 (d, J=5.9 Hz, 2H), 3.90 (s, 3H), 2.01-1.94 (m, 2H), 1.92-1.83 (m, 2H), 1.82-1.73 (m, 2H), 1.63-1.56 (m, 2H).

Example 155: 5-amino-1-cyclopentyl-3-[2,3-difluoro-4-[[(2-methoxybenzoyl)amino]methyl]phenyl]pyrazole-4-carboxamide

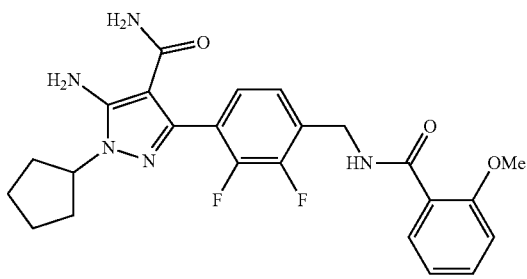 [SMILES: COc1ccccc1C(=O)NCc1ccc(-c2nn(C3CCCC3)c(N)c2C(N)=O)c(F)c1F]

N-[[4-(5-Amino-4-cyano-1-cyclopentyl-pyrazol-3-yl)-2,3-difluoro-phenyl]methyl]-2-methoxy-benzamide Following general procedure K, 5-amino-3-(4-chloro-2,3-difluoro-phenyl)-1-cyclopentyl-pyrazole-4-carbonitrile (86 mg, 0.27 mmol) and potassium trifluoro-[[(2-methoxybenzoyl)amino]methyl]boranuide (123 mg, 0.45 mmol) gave, after purification, titled compound (111 mg, 0.25 mmol, 92% yield) as an white solid.

UPLC-MS (ES$^-$, Short acidic): 1.77 min, m/z 450.1 [M–H]$^-$

5-Amino-1-cyclopentyl-3-[2,3-difluoro-4-[[(2-methoxybenzoyl)amino]methyl]phenyl]pyrazole-4-carboxamide Following general procedure M, N-[[4-(5-amino-4-cyano-1-cyclopentyl-pyrazol-3-yl)-2,3-difluoro-phenyl]methyl]-2-methoxy-benzamide (110 mg, 0.24 mmol) gave, after purification, titled compound (74 mg, 0.16 mmol, 65% yield) as white solid. UPLC-MS (ES$^+$, Short acidic): 1.65 min, m/z 470.2 [M+H]$^+$ UPLC-MS (ES$^+$, Long acidic): 3.75 min, m/z 470.2 [M+H]$^+$ $^1$H NMR (400 MHz, DMSO-d$_6$, δ): 8.77 (t, J=6.0 Hz, 1H), 7.75 (dd, J=7.6, 1.7 Hz, 1H), 7.52-7.49 (m, 1H), 7.26-7.20 (m, 2H), 7.17 (d, J=8.2 Hz, 1H), 7.06-7.03 (m, 1H), 6.26 (br s, 2H), 4.67-4.60 (m, 1H), 4.60 (d, J=6.0 Hz, 2H), 3.91 (s, 3H), 2.03-1.93 (m, 2H), 1.92-1.83 (m, 2H), 1.82-1.73 (m, 2H), 1.63-1.54 (m, 2H).

Example 156: 5-amino-1-cyclopentyl-3-[2,5-difluoro-4-[[(2-methoxybenzoyl)amino]methyl]phenyl]pyrazole-4-carboxamide

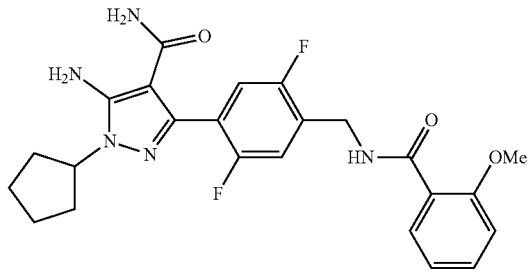 [SMILES: COc1ccccc1C(=O)NCc1cc(F)c(-c2nn(C3CCCC3)c(N)c2C(N)=O)cc1F]

5-Amino-3-(4-chloro-2,5-difluoro-phenyl)-1-cyclopentyl-pyrazole-4-carbonitrile Following general procedure H, 2-[(4-chloro-2,5-difluoro-phenyl)-methoxy-methylene]propanedinitrile (250 mg, 0.98 mmol) and cyclopentylhydrazine hydrochloride (161 mg, 1.18 mmol) gave, after purification, titled compound (250 mg, 0.77 mmol, 79% yield) UPLC-MS (ES$^+$, Short acidic) 1.98 min, m/z 323.0 [M]$^+$

N-[[4-(5-amino-4-cyano-1-cyclopentyl-pyrazol-3-yl)-2,5-difluoro-phenyl]methyl]-2-methoxy-benzamide Following general procedure K, 5-amino-3-(4-chloro-2,5-difluoro-phenyl)-1-cyclopentyl-pyrazole-4-carbonitrile (125 mg, 0.39 mmol) and potassium trifluoro-[[(2-methoxybenzoyl)amino]methyl]boranuide (158 mg, 0.58 mmol) gave, after purification, titled compound (75 mg, 0.17 mmol, 43% yield) as a white solid. UPLC-MS (ES$^+$, Short acidic) 1.78 min, m/z 452.1 [M+H]$^+$

5-Amino-1-cyclopentyl-3-[2,5-difluoro-4-[[(2-methoxybenzoyl)amino]methyl]phenyl]pyrazole-4-carboxamide Following general procedure M, N-[[4-(5-amino-4-cyano-1-cyclopentyl-pyrazol-3-yl)-2,5-difluoro-phenyl]methyl]-2-methoxy-benzamide (135 mg, 0.30 mmol) gave, after purification by flash column chromatography on silica gel eluting with 50-100% EtOAc in heptane and then by SCX-SPE cartridge, 5-amino-1-cyclopentyl-3-[2,5-difluoro-4-[[(2-methoxybenzoyl)amino]methyl]phenyl]pyrazole-4-carboxamide (63 mg, 0.13 mmol, 45% yield) as a light brown solid. UPLC-MS (ES$^+$, Short acidic): 1.65 min, m/z 470.2 [M+H]$^+$ UPLC-MS (ES$^+$, Long acidic): 3.78 min, m/z 470.1 [M+H]$^+$ $^1$H NMR (400 MHz, DMSO-d$_6$, δ): 8.77 (t, J=6.0 Hz, 1H), 7.72 (dd, J=7.7, 1.7 Hz, 1H), 7.51-7.47 (m, 1H), 7.27-7.22 (m, 2H), 7.17 (d, J=8.3 Hz, 1H), 7.06-7.02 (m, 1H), 6.22 (s, 2H), 4.67-4.57 (m, 1H), 4.55 (d, J=6.0 Hz, 2H), 3.91 (s, 3H), 2.03-1.83 (m, 4H), 1.79-1.77 (m, 2H), 1.60-1.57 (m, 2H).

Example 157: 5-amino-3-[2,3-difluoro-4-[[(2-methoxybenzoyl)amino]methyl]phenyl]-1-tetrahydropyran-3-yl-pyrazole-4-carboxamide

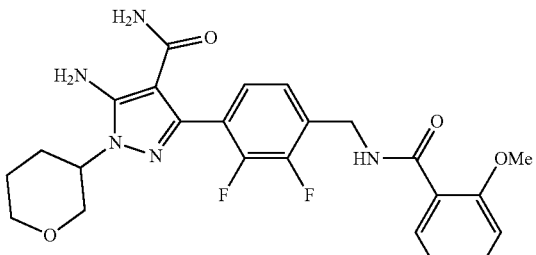

Tetrahydropyran-3-ylhydrazine hydrochloride

To a solution of 3-hydroxytetrahydropyrane (1.8 mL, 19.58 mmol) in toluene (30 mL), under nitrogen, was added triphenylphosphine (7.7 g, 29.37 mmol) and di-tert-butylazodicarboxylate (5.4 g, 23.50 mmol). The reaction mixture was stirred at RT for 60 h. The reaction mixture was concentrated then suspended in MeOH (55 mL), followed by addition of a hydrogen chloride solution (4 M in dioxane, 39.17 mL, 156.7 mmol). The reaction mixture was stirred at RT for 16 h, filtered, and the filtrate was concentrated under reduced pressure. EtOAc was then added to the resulting residue followed by filtration. The solid collected was washed with EtOAc to afford titled compound (2.99 g, 19.58 mmol, assumed quantitative yield) as a yellow solid.

$^1$H NMR (400 MHz, DMSO-$d_6$, δ): 3.91-3.82 (m, 1H), 3.76-3.58 (m, 1H), 3.45-3.29 (m, 2H), 3.04-2.94 (m, 1H), 2.00-1.90 (m, 1H), 1.77-1.65 (m, 1H), 1.62-1.37 (m, 2H).

N-[[4-(5-Amino-4-cyano-1-tetrahydropyran-3-yl-pyrazol-3-yl)-2,3-difluoro-phenyl]methyl]-2-methoxy-benzamide Following general procedure K, 5-amino-3-(4-chloro-2,3-difluoro-phenyl)-1-tetrahydropyran-3-yl-pyrazole-4-carbonitrile (50 mg, 0.15 mmol) and potassium trifluoro-[[(2-methoxybenzoyl)amino]methyl]boranuide (81 mg, 0.30 mmol) afforded crude titled compound (0.15 mmol) as a yellow solid. UPLC-MS (ES$^+$, Short acidic): 1.63 min, m/z 468.1 [M+H]$^+$ 5-Amino-3-[2,3-difluoro-4-[[(2-methoxybenzoyl)amino]methyl]phenyl]-1-tetrahydropyran-3-yl-pyrazole-4-carboxamide Following general procedure M, N-[[4-(5-amino-4-cyano-1-tetrahydropyran-3-yl-pyrazol-3-yl)-2,3-difluoro-phenyl]methyl]-2-methoxy-benzamide (98 mg, 0.21 mmol) afforded, after purification by flash column chromatography on silica gel eluting with 0-5% MeOH in DCM, titled compound (13 mg, 0.02 mmol, 12% yield) as a pale yellow solid. UPLC-MS (ES$^+$, Short acidic): 1.50 min, m/z 486.1 [M+H]$^+$ UPLC-MS (ES$^+$, Long acidic): 3.41 min, m/z 486.1 [M+H]$^+$ $^1$H NMR (400 MHz, DMSO-$d_6$, δ): 8.78 (t, J=6.0 Hz, 1H), 7.75 (dd, J=7.6, 1.7 Hz, 1H), 7.52-7.47 (m, 1H), 7.26-7.16 (m, 3H), 7.07-7.03 (m, 1H), 6.35 (s, 2H), 4.60 (d, J=5.9 Hz, 2H), 4.32-4.25 (m, 1H), 3.91-3.83 (m, 5H), 3.52 (t, J=10.5 Hz, 1H), 3.32-3.28 (m, 1H), 2.04-1.93 (m, 2H), 1.77-1.65 (m, 2H).

Example 158: 5-amino-3-[3,5-difluoro-4-[[(5-fluoro-2-methoxy-benzoyl)amino]methyl]phenyl]-1-tetrahydropyran-3-yl-pyrazole-4-carboxamide

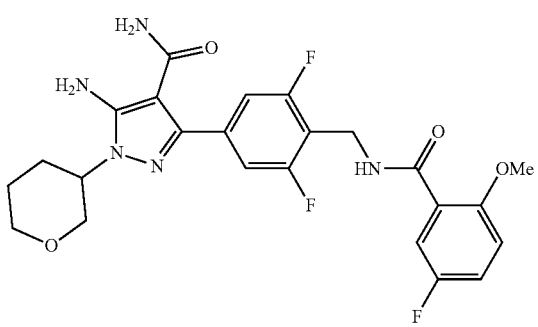 [SMILES: COc1ccc(F)cc1C(=O)NCc1c(F)cc(-c2nn(C3CCCOC3)c(N)c2C(N)=O)cc1F]

5-Amino-3-(4-chloro-3,5-difluoro-phenyl)-1-tetrahydropyran-3-yl-pyrazole-4-carbonitrile Following general procedure H, 2-[(4-chloro-3,5-difluoro-phenyl)-methoxy-methylene]propanedinitrile (166 mg, 0.65 mmol), and tetrahydropyran-3-ylhydrazine hydrochloride (150 mg, 0.98 mmol) afforded, after purification, titled compound (32 mg, 0.09 mmol, 14% yield) as a yellow solid. UPLC-MS (ES$^+$, Short acidic): 1.94 min, m/z 339.0 [M]$^+$ N-[[4-(5-Amino-4-cyano-1-tetrahydropyran-3-yl-pyrazol-3-yl)-2,6-difluoro-phenyl]methyl]-5-fluoro-2-methoxy-benzamide Following general procedure K, 5-amino-3-(4-chloro-3,5-difluoro-phenyl)-1-tetrahydropyran-3-yl-pyrazole-4-carbonitrile (0.09 mmol) and potassium trifluoro-[[(5-fluoro-2-methoxy-benzoyl)amino]methyl]boranuide (0.23 mmol) afforded, after purification, titled compound (0.10 mmol) as a yellow solid. UPLC-MS (ES$^+$, Short acidic): 1.78 min, m/z 486.1 [M+H]$^+$ 5-Amino-3-[3,5-difluoro-4-[[(5-fluoro-2-methoxy-benzoyl)amino]methyl]phenyl]-1-tetrahydropyran-3-yl-pyrazole-4-carboxamide Following general procedure M, N-[[4-(5-amino-4-cyano-1-tetrahydropyran-3-yl-pyrazol-3-yl)-2,6-difluoro-phenyl]methyl]-5-fluoro-2-methoxy-benzamide (47 mg, 0.10 mmol) afforded, after purification, titled compound (22 mg, 0.04 mmol, 39% yield) as a white solid. UPLC-MS (ES$^+$, Short acidic): 1.58 min, m/z 504.1 [M+H]$^+$ UPLC-MS (ES$^+$, Long acidic): 3.63 min, m/z 504.1 [M+H]$^+$ $^1$H NMR (400 MHz, DMSO-$d_6$, δ): 8.66 (t, J=6.0 Hz, 1H), 7.47 (dd, J=9.2, 3.3 Hz, 1H), 7.36-7.31 (m, 1H), 7.22-7.16 (m, 3H), 6.30 (s, 2H), 4.60 (d, J=5.5 Hz, 2H), 4.31-4.24 (m, 1H), 3.87-3.85 (m, 5H), 3.54 (t, J=10.5 Hz, 1H), 3.39-3.25 (m, 1H), 2.04-1.98 (m, 2H), 1.78-1.63 (m, 2H).

Example 159: 5-amino-3-[2,3-difluoro-4-[[(5-fluoro-2-methoxy-benzoyl)amino]methyl]phenyl]-1-tetrahydropyran-3-yl-pyrazole-4-carboxamide

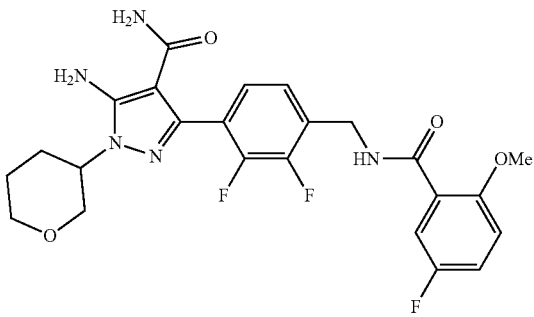

5-Amino-3-(4-chloro-2,3-difluoro-phenyl)-1-tetrahydropyran-3-yl-pyrazole-4-carbonitrile Following general procedure H, 2-[(4-chloro-2,3-difluoro-phenyl)-methoxy-methylene]propanedinitrile (150 mg, 0.59 mmol) and tetrahydropyran-3-ylhydrazine hydrochloride (225 mg, 1.47 mmol) afforded, after purification, titled compound (60 mg, 0.18 mmol, 30% yield) as a brown solid. UPLC-MS (ES$^+$, Short acidic): 1.79 min, m/z 339.0 [M]$^+$

N-[[4-(5-Amino-4-cyano-1-tetrahydropyran-3-yl-pyrazol-3-yl)-2,3-difluoro-phenyl]methyl]-5-fluoro-2-methoxy-benzamide Following general procedure K, 5-amino-3-(4-chloro-2,3-difluoro-phenyl)-1-tetrahydropyran-3-yl-pyrazole-4-carbonitrile (0.18 mmol) and potassium trifluoro-[[(5-fluoro-2-methoxy-benzoyl)amino]methyl]boranuide (0.53 mmol) afforded, after purification, titled compound (0.22 mmol, assumed quantitative yield) as a yellow solid. UPLC-MS (ES$^+$, Short acidic): 1.69 min, m/z 486.1 [M+H]$^+$

5-Amino-3-[2,3-difluoro-4-[[(5-fluoro-2-methoxy-benzoyl)amino]methyl]phenyl]-1-tetrahydropyran-3-yl-pyrazole-4-carboxamide Following general procedure M, N-[[4-(5-amino-4-cyano-1-tetrahydropyran-3-yl-pyrazol-3-yl)-2,3-difluoro-phenyl]methyl]-5-fluoro-2-methoxy-benzamide (108 mg, 0.22 mmol) afforded, after purification, titled compound (25 mg, 0.04 mmol, 20% yield) as a white solid. UPLC-MS (ES$^+$, Short acidic): 1.54 min, m/z 504.1 [M+H]$^+$ UPLC-MS (ES$^+$, Long acidic): 3.54 min, m/z 504.1 [M+H]$^+$ $^1$H NMR (400 MHz, DMSO-d$_6$, δ): 8.87 (t, J=6.0 Hz, 1H), 7.51 (dd, J=9.2, 3.3 Hz, 1H), 7.39-7.33 (m, 1H), 7.26-7.18 (m, 3H), 6.35 (s, 2H), 4.60 (d, J=5.9 Hz, 2H), 4.33-4.26 (m, 1H), 3.90-3.84 (m, 5H), 3.52 (t, J=10.5 Hz, 1H), 3.32-3.28 (m, 1H), 2.00-1.96 (m, 2H), 1.77-1.61 (m, 2H).

Example 160: 5-amino-1-(4,4-difluoropyrrolidin-3-yl)-3-[3-fluoro-4-[[(2-methoxybenzoyl)amino]methyl]phenyl]pyrazole-4-carboxamide

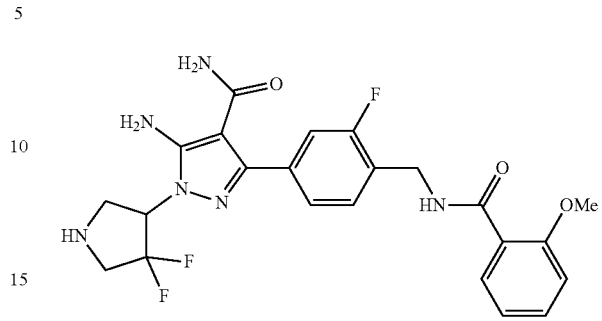

5-Amino-3-(4-bromo-3-fluoro-phenyl)-1H-pyrazole-4-carbonitrile

To a solution of 2-[(4-bromo-3-fluoro-phenyl)-methoxy-methylene]propanedinitrile (2.23 g, 7.94 mmol) in EtOH (90 mL) was added hydrazine hydrate (55-60% in water, 2.71 mL, 27.8 mmol). The reaction mixture was heated at 90° C. for 1 h. The reaction was cooled to RT and, the solvent was removed under reduced pressure to afford crude titled compound (1.88 g, 6.70 mmol, 84% yield) as a yellow solid.
UPLC-MS (ES$^+$, Short acidic): 1.57 min, m/z 282.9 [M+2]$^+$ tert-Butyl 4-[5-amino-3-(4-bromo-3-fluoro-phenyl)-4-cyano-pyrazol-1-yl]-3,3-difluoro-pyrrolidine-1-carboxylate tert-Butyl 3,3-difluoro-4-(trifluoromethylsulfonyloxy)pyrrolidine-1-carboxylate (626 mg, 1.73 mmol), 5-amino-3-(4-bromo-3-fluoro-phenyl)-1H-pyrazole-4-carbonitrile (370 mg, 1.32 mmol) and cesium carbonate (858 mg, 2.63 mmol) were suspended in DMF (8 mL) and heated at 90° C. for 2.5 h. The reaction was cooled to RT and diluted with water. Work up and purification gave titled compound (0.22 mmol, 16% yield) as a beige solid. UPLC-MS (ES$^+$, Short acidic): 2.11 min, m/z 488.0 [M+2]$^+$ tert-Butyl 4-[5-amino-4-cyano-3-[3-fluoro-4-[[(2-methoxybenzoyl)amino]methyl]phenyl]pyrazol-1-yl]-3,3-difluoro-pyrrolidine-1-carboxylate Following general procedure K, tert-butyl 4-[5-amino-3-(4-bromo-3-fluoro-phenyl)-4-cyano-pyrazol-1-yl]-3,3-difluoro-pyrrolidine-1-carboxylate (120 mg, 0.25 mmol), and potassium trifluoro-[[(2-methoxybenzoyl)amino]methyl]boranuide (114 mg, 0.42 mmol) gave, after purification, titled compound (102 mg, 0.17 mmol) as light yellow solid. UPLC-MS (ES$^+$, Short acidic): 1.91 min, m/z 571.2 [M+H]$^+$

5-Amino-1-(4,4-difluoropyrrolidin-3-yl)-3-[3-fluoro-4-[[(2-methoxybenzoyl)amino]methyl]phenyl]pyrazole-4-carboxamide Following general procedure M, tert-butyl 4-[5-amino-4-cyano-3-[3-fluoro-4-[[(2-methoxybenzoyl)amino]methyl]phenyl]pyrazol-1-yl]-3,3-difluoro-pyrrolidine-1-carboxylate (96 mg, 0.17 mmol) gave, after purification, titled compound (57 mg, 0.12 mmol, 69% yield) as white solid.

UPLC-MS (ES+, Short acidic): 1.24 min, m/z 489.1 [M+H]+
UPLC-MS (ES+, Long acidic): 2.56 min, m/z 489.1 [M+H]+
$^1$H NMR (400 MHz, DMSO-$d_6$, δ): 8.73 (t, J=6.0 Hz, 1H), 7.76 (dd, J=7.7, 1.7 Hz, 1H), 7.51-7.43 (m, 2H), 7.36-7.30 (m, 2H), 7.17 (d, J=8.3 Hz, 1H), 7.07-7.03 (m, 1H), 6.48 (br s, 2H), 5.04-4.97 (m, 1H), 4.58 (d, J=6.0 Hz, 2H), 3.91 (s, 3H), 3.54-3.44 (m, 2H), 3.24-3.08 (m, 2H).

Example 161: 5-amino-3-[4-[[(5-fluoro-2-methoxy-benzoyl)amino]methyl]phenyl]-1-(1-tetrahydropyran-4-ylethyl)pyrazole-4-carboxamide

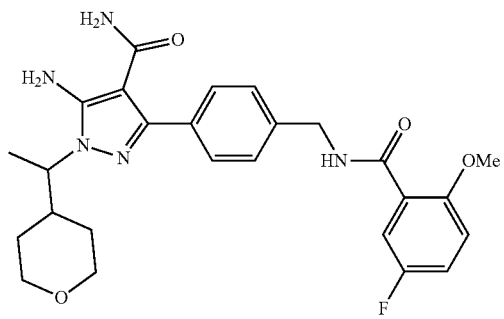 [SMILES: COc1ccc(F)cc1C(=O)NCc1ccc(-c2nn(C(C)C3CCOCC3)c(N)c2C(N)=O)cc1]

1-Tetrahydropyran-4-ylethanone hydrazone

To a solution of 1-tetrahydro-2H-pyran-4-ylethanone (166 mg, 1.30 mmol) in MeOH (7.5 mL) hydrazine hydrate (55-60% in water, 0.90 mL, 17.61 mmol) was added. The reaction mixture was heated to reflux for 16 h, cooled and concentrated under reduced pressure to give crude 1-tetrahydropyran-4-ylethanone hydrazone (171 mg, 1.20 mmol, 93% yield) as a colourless oil. $^1$H NMR (400 MHz, CDCl$_3$, δ): 4.92 (s, 2H), 4.03-3.98 (m, 2H), 3.45-3.40 (m, 2H), 2.38-2.30 (m, 1H), 1.73 (s, 3H), 1.65-1.63 (m, 4H).

5-Amino-3-(4-bromophenyl)-1-(1-tetrahydropyran-4-ylethyl)pyrazole-4-carbonitrile A borane tetrahydrofuran complex solution (1 M in THF, 3.00 mL, 3.00 mmol) was added to a solution of 1-tetrahydropyran-4-ylethanone hydrazone (171 mg, 1.20 mmol) in THF (7 mL) at 0° C. The reaction mixture was stirred at RT for 16 h and concentrated under reduced pressure. The residue was taken up with EtOH (10 mL) and 2-[(4-bromophenyl)-methoxy-methylene]propanedinitrile (200 mg, 0.76 mmol) was added. The reaction mixture was heated to reflux for 16 h to give titled compound (60 mg, 0.16 mmol, 21% yield) as a brown oil.
UPLC-MS: (ES+, Short acidic): 1.90 min, m/z 377.0 [M+2]+

N-[[4-[5-Amino-4-cyano-1-(1-tetrahydropyran-4-ylethyl)pyrazol-3-yl]phenyl]methyl]-5-fluoro-2-methoxy-benzamide Following general procedure K, 5-amino-3-(4-bromophenyl)-1-(1-tetrahydropyran-4-ylethyl)pyrazole-4-carbonitrile (0.16 mmol) and potassium trifluoro-[[(5-fluoro-2-methoxy-benzoyl)amino]methyl]boranuide (0.80 mmol) gave, after purification, titled compound (0.16 mmol,) as an yellow oil.
UPLC-MS: (ES+, Short acidic): 1.67 min, m/z 478.1 [M+H]+

5-Amino-3-[4-[[(5-fluoro-2-methoxy-benzoyl)amino]methyl]phenyl]-1-(1-tetrahydropyran-4-yl-ethyl)pyrazole-4-carboxamide Following general procedure L, N-[[4-[5-amino-4-cyano-1-(1-tetrahydropyran-4-ylethyl)pyrazol-3-yl]phenyl]methyl]-5-fluoro-2-methoxy-benzamide (76 mg, 0.16 mmol) gave, after purification, titled compound (10 mg, 0.02 mmol, 13% yield) as an off-white solid.
UPLC-MS: (ES+, Short acidic): 1.51 min, m/z 496.2 [M+H]+ UPLC-MS: (ES+, Long acidic): 3.28 min, m/z 496.2 [M+H]+
$^1$H NMR (400 MHz, DMSO-$d_6$, δ): 8.82 (t, J=6.0 Hz, 1H), 7.50 (dd, J=9.2, 3.1 Hz, 1H), 7.45-7.39 (m, 4H), 7.36-7.31 (m, 1H), 7.18 (dd, J=9.0, 4.3 Hz, 1H), 6.34 (s, 2H), 4.54 (d, J=5.9 Hz, 2H), 4.10-4.03 (m, 1H), 3.93-3.83 (m, 4H), 3.82-3.74 (m, 1H), 3.29-3.22 (m, 1H), 3.19-3.12 (m, 1H), 2.03-1.90 (m, 1H), 1.71-1.65 (m, 1H), 1.37 (d, J=6.5 Hz, 3H), 1.28-1.16 (m, 2H), 1.07-1.03 (m, 1H).

Example 162: 5-amino-3-[4-[[(5-fluoro-2-methoxy-benzoyl)amino]methyl]phenyl]-1-[(3S)-tetrahydro-furan-3-yl]pyrazole-4-carboxamide

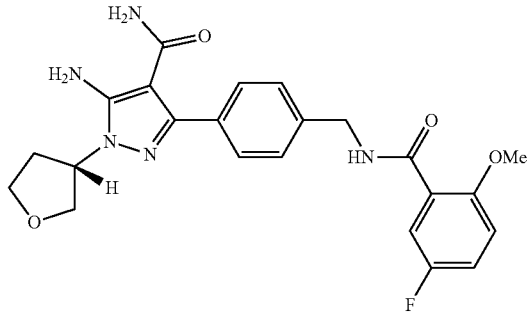 [SMILES: COc1ccc(F)cc1C(=O)NCc1ccc(-c2nn([C@H]3CCOC3)c(N)c2C(N)=O)cc1]

5-Amino-3-(4-bromophenyl)-1-[(3S)-tetrahydro-furan-3-yl]pyrazole-4-carbonitrile

Following a modified general procedure H at RT, 2-[(4-bromophenyl)-methoxy-methylene]propanedinitrile (2 mmol) and [(3S)-tetrahydrofuran-3-yl]hydrazine hydrochloride (3.65 mmol) gave crude titled compound (2 mmol).
UPLC-MS (ES+, Short acidic): 1.75 min, m/z 335.0 [M+2]+

N-[[4-[5-Amino-4-cyano-1-[(3S-tetrahydrofuran-3-yl]pyrazol-3-yl]phenyl]methyl]-5-fluoro-2-methoxy-benzamide Following general procedure K, potassium trifluoro-[[(5-fluoro-2-methoxy-benzoyl)amino]methyl]boranuide (1229 mg, 4.25 mmol) and 5-amino-3-(4-bromophenyl)-1-[(3S)-tetrahydrofuran-3-yl]pyrazole-4-carbonitrile (644 mg, 1.93 mmol) gave crude titled compound (840 mg, 1.93 mmol, assumed quantitative yield). LC-MS (ES+, Short acidic): 1.59 min, m/z 436.1 [M+H]+

5-Amino-3-[4-[[(5-fluoro-2-methoxy-benzoyl)amino]methyl]phenyl]-1-[(3S)-tetrahydrofuran-3-yl]pyrazole-4-carboxamide Following general procedure M, N-[[4-[5-amino-4-cyano-1-[(3S)-tetrahydrofuran-3-yl]pyrazol-3-yl]phenyl]

methyl]-5-fluoro-2-methoxy-benzamide (840 mg, 1.93 mmol) gave, after purification, titled compound (293 mg, 0.65 mmol, 34% yield) as a white solid. UPLC-MS (ES+, Long acidic): 3.09 min, m/z 454.1 [M+H]+

¹H NMR (400 MHz, DMSO-d₆, δ): 8.83 (t, J=6.2 Hz, 1H), 7.51 (dd, J=9.2, 3.3 Hz, 1H), 7.47-7.39 (m, 4H), 7.37.7.31 (m, 1H), 7.22-7.16 (m, 1H), 6.39 (br s, 2H), 4.97-4.89 (m, 1H), 4.54 (d, J=6.1 Hz, 2H), 4.02-3.91 (m, 2H), 3.89 (s, 3H), 3.83-3.77 (m, 2H), 2.31-2.21 (m, 2H).

Example 163a: 5-amino-3-[4-[[(5-fluoro-2-methoxy-benzoyl)amino]methyl]phenyl]-1-(2,2,2-trifluoro-1-methyl-ethyl)pyrazole-4-carboxamide—Isomer 1 and Example 163b—Isomer 2

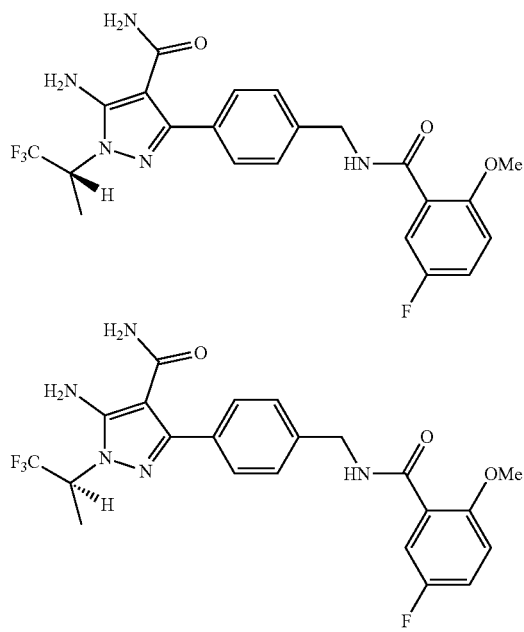

5-Amino-3-[4-[[(5-fluoro-2-methoxy-benzoyl)amino] methyl]phenyl]-1-(2,2,2-trifluoro-1-methyl-ethyl)pyrazole-4-carboxamide (150 mg, 0.31 mmol) was purified by preparative SFC (SFC-B) to give, after evaporation and lyophilization, 5-amino-3-[4-[[(5-fluoro-2-methoxy-benzoyl)amino]methyl]phenyl]-1-(2,2,2-trifluoro-1-methyl-ethyl)pyrazole-4-carboxamide (isomer 1, 44 mg, 0.09 mmol, 29% yield) and 5-amino-3-[4-[[(5-fluoro-2-methoxy-benzoyl)amino]methyl]phenyl]-1-(2,2,2-trifluoro-1-methyl-ethyl)pyrazole-4-carboxamide (isomer 2, 48 mg, 0.10 mmol, 32% yield) as white solids. UPLC-MS (ES+, Short acidic, Isomer 1): 1.53 min, m/z 480.1 [M+H]+ UPLC-MS (ES+, Long acidic, Isomer 1): 3.55 min, m/z 480.1 [M+H]+ SFC (SFC-A, Isomer 1): 1.95 min ¹H NMR (DMSO-d₆, δ, Isomer 1): 8.83 (t, J=6.1 Hz, 1H), 7.51 (dd, J=9.3, 3.3 Hz, 1H), 7.48-7.39 (m, 4H), 7.33 (ddd, J=9.0, 7.9, 3.3 Hz, 1H), 7.18 (dd, J=9.0, 4.3 Hz, 1H), 6.67 (s, 2H), 5.35-5.22 (m, 1H), 4.55 (d, J=6.1 Hz, 2H), 3.89 (s, 3H), 1.61 (d, J=6.7 Hz, 3H)

UPLC-MS (ES+, Short acidic, Isomer 2): 1.53 min, m/z 480.1 [M+H]+ UPLC-MS (ES+, Long acidic, Isomer 2): 3.55 min, m/z 480.1 [M+H]+ SFC (SFC-A, Isomer 2): 2.26 min ¹H NMR (DMSO-d₆, δ, Isomer 2): 8.84 (t, J=6.1 Hz, 1H), 7.52 (dd, J=9.3, 3.3 Hz, 1H), 7.49-7.40 (m, 4H), 7.38-7.31 (m, 1H), 7.19 (dd, J=9.0, 4.3 Hz, 1H), 6.68 (s, 2H), 5.34-5.24 (m, 1H), 4.56 (d, J=6.1 Hz, 2H), 3.90 (s, 3H), 1.62 (d, J=6.7 Hz, 3H)

Example 164: 5-amino-3-[4-[[(5-fluoro-2-methoxy-benzoyl)amino]methyl]phenyl]-1-[(3R)-tetrahydro-furan-3-yl]pyrazole-4-carboxamide

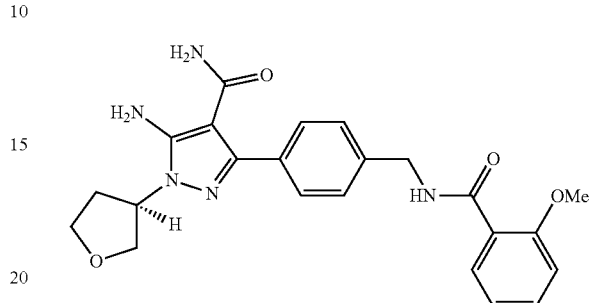

5-Amino-3-(4-bromophenyl)-1-[(3R)-tetrahydro-furan-3-yl]pyrazole-4-carbonitrile

Following general procedure H, 2-[(4-bromophenyl)-methoxy-methylene]propanedinitrile (300 mg, 1.14 mmol), and [(3R)-tetrahydrofuran-3-yl]hydrazine hydrochloride (190 mg, 1.37 mmol) gave, after purification, titled compound (210 mg, 0.63 mmol, 55% yield).

UPLC (ES+, Short acidic): 1.77 min, m/z 335.0 [M+2]+

N-[[4-[5-Amino-4-cyano-1-[(3R)-tetrahydrofuran-3-yl]pyrazol-3-yl]phenyl]methyl]-5-fluoro-2-methoxy-benzamide Following general procedure K, potassium trifluoro-[[(5-fluoro-2-methoxy-benzoyl)amino]methyl]boranuide (334 mg, 1.15 mmol), and 5-amino-3-(4-bromophenyl)-1-[(3R)-tetrahydrofuran-3-yl]pyrazole-4-carbonitrile (150 mg, 0.45 mmol) gave, after purification, titled compound (48 mg, 0.11 mmol, 25% yield) as a pale yellow solid.

UPLC-MS (ES+, Short acidic): 1.63 min, m/z 436.1 [M+H]+

5-Amino-3-[4-[[(5-fluoro-2-methoxy-benzoyl) amino]methyl]phenyl]-1-[(3R)-tetrahydrofuran-3-yl] pyrazole-4-carboxamide Following general procedure M, N-[[4-[5-amino-4-cyano-1-[(3R)-tetrahydrofuran-3-yl]pyrazol-3-yl]phenyl] methyl]-5-fluoro-2-methoxy-benzamide (48 mg, 0.11 mmol) gave, after purification, titled compound (25 mg, 0.05 mmol, 50% yield) as a white solid. UPLC-MS (ES+, Short acidic): 1.45 min, 454.1 m/z [M+H]+ UPLC-MS (ES+, Long acidic): 3.08 min, 454.1 m/z [M+H]+ ¹H NMR (400 MHz, DMSO-d₆, δ): 8.84 (t, J=6.1 Hz, 1H), 7.51 (dd, J=9.2, 3.3 Hz, 1H), 7.46 (d, J=8.2 Hz, 2H), 7.41 (d, J=8.2 Hz, 2H), 7.39-7.30 (m, 1H), 7.19 (dd, J=9.1, 4.3 Hz, 1H), 6.40 (s, 2H), 4.98-4.89 (m, 1H), 4.55 (d, J=6.1 Hz, 2H), 4.03-3.92 (m, 2H), 3.90 (s, 3H), 3.85-3.76 (m, 2H), 2.30-2.22 (m, 2H).

Example 165: 5-amino-3-[2,3-difluoro-4-[[(5-fluoro-2-methoxy-benzoyl)amino]methyl]phenyl]-1-(2,2,2-trifluoro-1-methyl-ethyl)pyrazole-4-carboxamide

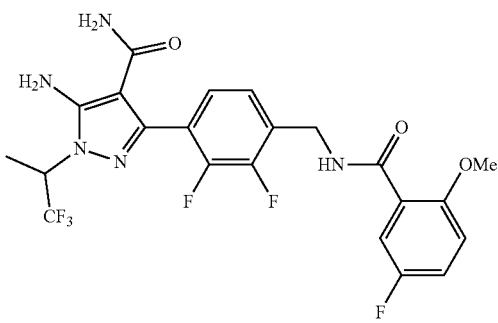 [SMILES: COc1ccc(F)cc1C(=O)NCc1ccc(-c2nn(C(C)C(F)(F)F)c(N)c2C(N)=O)c(F)c1F]

5-Amino-3-(4-bromo-2,3-difluoro-phenyl)-1-(2,2,2-trifluoro-1-methyl-ethyl)pyrazole-4-carbonitrile Following general procedure H, 2-[(4-bromo-2,3-difluoro-phenyl)-methoxy-methylene]propanedinitrile (140 mg, 0.47 mmol), and (2,2,2-trifluoro-1-methyl-ethyl)hydrazine hydrochloride (100 mg, 0.61 mmol) gave after purification, titled compound (129 mg, 0.33 mmol, 70% yield) as white solid.

UPLC-MS (ES$^+$, Short acidic): 1.86 min, m/z 397.0 [M+2]$^+$

N-[[4-[5-Amino-4-cyano-1-(2,2,2-trifluoro-1-methyl-ethyl)pyrazol-3-yl]-2,3-difluoro-phenyl]methyl]-5-fluoro-2-methoxy-benzamide Following general procedure K, 5-amino-3-(4-bromo-2,3-difluoro-phenyl)-1-(2,2,2-trifluoro-1-methyl-ethyl)pyrazole-4-carbonitrile (124 mg, 0.31 mmol), and potassium trifluoro-[[(5-fluoro-2-methoxy-benzoyl)amino]methyl]boranuide (154 mg, 0.53 mmol) gave, after purification by flash column chromatography on silica gel eluting with 0-10% MeOH in DCM, N-[[4-[5-amino-4-cyano-1-(2,2,2-trifluoro-1-methyl-ethyl)pyrazol-3-yl]-2,3-difluoro-phenyl]methyl]-5-fluoro-2-methoxy-benzamide (120 mg, 0.24 mmol, 77% yield) as a light yellow solid.

UPLC-MS (ES$^+$, Short acidic): 1.75 min, m/z 498.1 [M+H]$^+$

5-Amino-3-[2,3-difluoro-4-[[(5-fluoro-2-methoxy-benzoyl)amino]methyl]phenyl]-1-(2,2,2-trifluoro-1-methyl-ethyl)pyrazole-4-carboxamide Following general procedure M, N-[[4-[5-amino-4-cyano-1-(2,2,2-trifluoro-1-methyl-ethyl)pyrazol-3-yl]-2,3-difluoro-phenyl]methyl]-5-fluoro-2-methoxy-benzamide (110 mg, 0.22 mmol) gave, after purification by flash column chromatography on silica gel eluting with 0-10% MeOH in DCM, 5-amino-3-[2,3-difluoro-4-[[(5-fluoro-2-methoxy-benzoyl)amino]methyl]phenyl]-1-(2,2,2-trifluoro-1-methyl-ethyl)pyrazole-4-carboxamide (73 mg, 0.14 mmol, 64% yield) as a white solid.

UPLC-MS (ES$^+$, Short acidic): 1.62 min, m/z 516.1 [M+H]$^+$

UPLC-MS (ES$^+$, Long acidic): 3.80 min, m/z 516.1 [M+H]$^+$ $^1$H NMR (400 MHz, DMSO-d$_6$, δ): 8.88 (t, J=5.9 Hz, 1H), 7.51 (dd, J=9.2, 3.3 Hz, 1H), 7.38-7.33 (m, 1H), 7.28-7.18 (m, 3H), 6.61 (s, 2H), 5.36-5.27 (m, 1H), 4.61 (d, J=5.9 Hz, 2H), 3.90 (s, 3H), 1.61 (d, J=6.7 Hz, 3H)

Example 166: 5-amino-1-(4,4-difluoro-1-methyl-pyrrolidin-3-yl)-3-[3-fluoro-4-[[(2-methoxybenzoyl)amino]methyl]phenyl]pyrazole-4-carboxamide

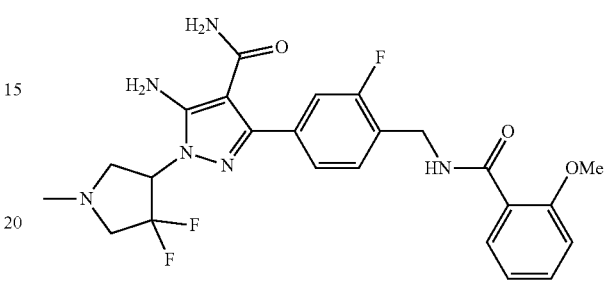

5-Amino-1-(4,4-difluoro-1-methyl-pyrrolidin-3-yl)-3-[3-fluoro-4-[[(2-methoxybenzoyl)amino]methyl]phenyl]pyrazole-4-carboxamide 5-Amino-1-(4,4-difluoropyrrolidin-3-yl)-3-[3-fluoro-4-[[(2-methoxybenzoyl)amino]methyl]phenyl]pyrazole-4-carboxamide (11 mg, 0.02 mmol) and cesium carbonate (15 mg, 0.05 mmol) were suspended in DMF (2 mL). The mixture was cooled to −10° C., purged with nitrogen, and a 0.2 M solution of iodomethane in DMF (0.1 mL, 0.02 mmol) was then added. The reaction was allowed to warm to RT and stirred for 16 h. Work up and purification gave titled compound (4 mg, 0.01 mmol, 35% yield) as light yellow solid. UPLC-MS (ES$^+$, Short acidic): 1.25 min, m/z 503.2 [M+H]$^+$ UPLC-MS (ES$^+$, Long acidic): 2.73 min, m/z 503.2 [M+H]$^+$ $^1$H NMR (400 MHz, DMSO-d$_6$, δ): 8.73 (t, J=6.0 Hz, 1H), 7.76 (dd, J=7.7, 1.7 Hz, 1H), 7.51-7.43 (m, 2H), 7.34-7.27 (m, 2H), 7.17 (d, J=8.4 Hz, 1H), 7.06-7.02 (m, 1H), 6.51 (s, 2H), 5.25-5.16 (m, 1H), 4.58 (d, J=6.0 Hz, 2H), 3.91 (s, 3H), 3.29-3.17 (m, 3H), 2.91-2.70 (m, 1H), 2.36 (s, 3H).

Example 167: 5-amino-1-(4,4-difluoro-1-methyl-pyrrolidin-3-yl)-3-[4-[[(2-methoxybenzoyl)amino]methyl]phenyl]pyrazole-4-carboxamide

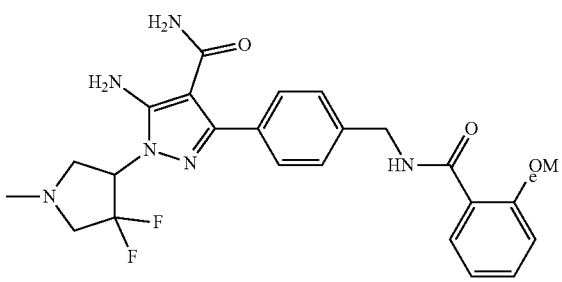 [SMILES: COc1ccccc1C(=O)NCc1ccc(-c2nn(C3CN(C)CC3(F)F)c(N)c2C(N)=O)cc1]

5-Amino-1-(4,4-difluoro-1-methyl-pyrrolidin-3-yl)-3-[4-[[(2-methoxybenzoyl)amino]methyl]phenyl]pyrazole-4-carboxamide 5-Amino-1-(4,4-difluoropyrrolidin-3-yl)-3-[4-[[(2-methoxybenzoyl)amino]methyl]phenyl]pyrazole-4-carboxamide (40 mg, 0.09 mmol) and cesium carbonate (55 mg, 0.17 mmol) were suspended in DMF (3 mL). The mixture was cooled to −15° C. purged with nitrogen, and a solution of iodomethane (0.9 M in THF, 0.2 mL, 0.18 mmol) was then added dropwise. The reaction was allowed to warm to RT and stirred for 16 h. Work up and purification gave titled compound (5 mg, 0.01 mmol, 12% yield) was obtained as white solid. UPLC-MS (ES+, Short acidic): 1.19 min, m/z 485.2 [M+H]+ UPLC-MS (ES+, Long acidic): 2.62 min, m/z 485.2 [M+H]+

$^1$H NMR (400 MHz, DMSO-$d_6$, δ): 8.73 (t, J=6.0 Hz, 1H), 7.74 (dd, J=7.6, 1.7 Hz, 1H), 7.49-7.40 (m, 5H), 7.15 (d, J=8.3 Hz, 1H), 7.05-7.01 (m, 1H), 6.56 (s, 2H), 5.22-5.13 (m, 1H), 4.54 (d, J=6.0 Hz, 2H), 3.89 (s, 3H), 3.28-3.15 (m, 3H), 2.86-2.73 (m, 1H), 2.34 (s, 3H).

Example 168: 5-amino-3-[2,5-difluoro-4-[[(5-fluoro-2-methoxy-benzoyl)amino]methyl]phenyl]-1-(2,2,2-trifluoro-1-methyl-ethyl)pyrazole-4-carboxamide

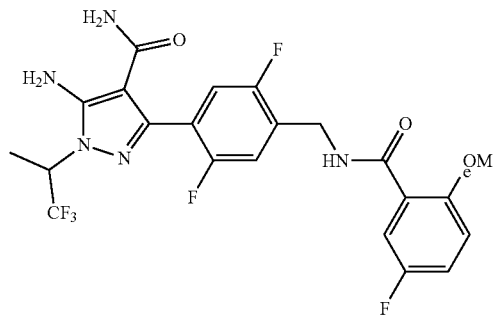 [SMILES: COc1ccc(F)cc1C(=O)NCc1cc(F)c(-c2nn(C(C)C(F)(F)F)c(N)c2C(N)=O)cc1F]

5-Amino-3-(4-chloro-2,5-difluoro-phenyl)-1-(2,2,2-trifluoro-1-methyl-ethyl)pyrazole-4-carbonitrile Following general procedure H, (2,2,2-trifluoro-1-methyl-ethyl)hydrazine hydrochloride (96 mg, 0.58 mmol) and 2-[(4-chloro-2,5-difluoro-phenyl)-methoxy-methylene]propanedinitrile (114 mg, 0.45 mmol) gave crude 5 titled compound (156 mg, 0.44 mmol, assumed quantative yield). UPLC-MS (ES+, Short acidic): 1.99 min, m/z 351.0 [M]+

N-[[4-[5-Amino-4-cyano-1-(2,2,2-trifluoro-1-methyl-ethyl)pyrazol-3-yl]-2,5-difluoro-phenyl]methyl]-5-fluoro-2-methoxy-benzamide Following general procedure K, potassium trifluoro-[[(5-fluoro-2-methoxy-benzoyl)amino]methyl]boranuide (257 mg, 0.89 mmol) and 5-amino-3-(4-chloro-2,5-difluoro-phenyl)-1-(2,2,2-trifluoro-1-methyl-ethyl)pyrazole-4-carbonitrile (156 mg, 0.44 mmol) gave, titled compound (221 mg, 0.44 mmol, 98% yield). UPLC-MS (ES+, Short acidic): 1.76 min, m/z 498.1 [M+H]+

5-Amino-3-[2,5-difluoro-4-[[(5-fluoro-2-methoxy-benzoyl)amino]methyl]phenyl]-1-(2,2,2-trifluoro-1-methyl-ethyl)pyrazole-4-carboxamide Following general procedure M, N-[[4-[5-amino-4-cyano-1-(2,2,2-trifluoro-1-methyl-ethyl)pyrazol-3-yl]-2,5-difluoro-phenyl]methyl]-5-fluoro-2-methoxy-benzamide (221 mg, 0.44 mmol) gave, after purification titled compound (0.10 mmol). UPLC-MS (ES+, Long acidic): 3.77 min, m/z 516.1 [M+H]+

$^1$H NMR (400 MHz, DMSO-$d_6$, δ): 8.87 (t, J=6.1 Hz, 1H), 7.49 (dd, J=9.2, 3.3 Hz, 1H), 7.38-7.31 (m, 1H), 7.29-7.22 (m, 3H), 6.57 (br s, 2H), 5.36-5.27 (m, 1H), 4.56 (d, J=5.9 Hz, 2H), 3.90 (s, 3H), 1.60 (d, J=7.0 Hz, 3H).

Example 169: 5-amino-1-(4,4-difluoropyrrolidin-3-yl)-3-[4-[[(5-fluoro-2-methoxy-benzoyl)amino]methyl]phenyl]pyrazole-4-carboxamide

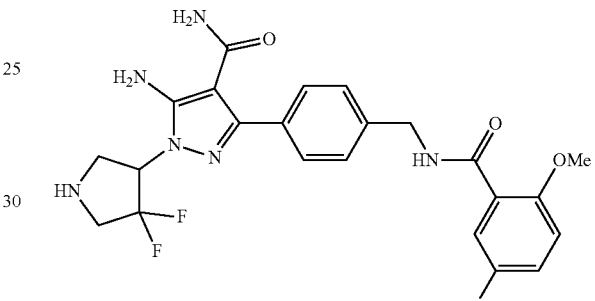

tert-Butyl 4-[5-amino-4-cyano-3-[4-[[(5-fluoro-2-methoxy-benzoyl)amino]methyl]phenyl]pyrazol-1-yl]-3,3-difluoro-pyrrolidine-1-carboxylate Following general procedure K, potassium trifluoro-[[(5-fluoro-2-methoxy-benzoyl)amino]methyl]boranuide (128 mg, 0.44 mmol) and tert-butyl 4-[5-amino-3-(4-bromophenyl)-4-cyano-pyrazol-1-yl]-3,3-difluoro-pyrrolidine-1-carboxylate (81 mg, 0.17 mmol) gave, after purification, titled compound (50 mg, 0.09 mmol, 51% yield) as a pale yellow solid. UPLC-MS (ES−, Short acidic): 1.86 min, 569.2 m/z [M−H]−

5-Amino-1-(4,4-difluoropyrrolidin-3-yl)-3-[4-[[(5-fluoro-2-methoxy-benzoyl)amino]methyl]phenyl]pyrazole-4-carboxamide Following general procedure M, tert-butyl 4-[5-amino-4-cyano-3-[4-[[(5-fluoro-2-methoxy-benzoyl)amino]methyl]phenyl]pyrazol-1-yl]-3,3-difluoro-pyrrolidine-1-carboxylate (50 mg, 0.09 mmol) gave, after purification, titled compound (13 mg, 0.05 mmol) as a white solid. UPLC-MS (ES+, Short acidic): 1.20 min, 489.1 m/z [M+H]+ UPLC-MS (ES+, Long acidic): 2.61 min, 489.2 m/z [M+H]+ $^1$H NMR (400 MHz, DMSO-$d_6$, δ): 8.84 (t, J=6.0 Hz, 1H), 7.51 (dd, J=9.2, 3.3 Hz, 1H), 7.47 (d, J=8.3 Hz, 2H), 7.42 (d, J=8.3 Hz, 2H), 7.38-7.30 (m, 1H), 7.19 (dd, J=9.1, 4.3 Hz, 1H), 6.54 (s, 2H), 5.08-4.94 (m, 1H), 4.55 (d, J=6.1 Hz, 2H), 3.90 (s, 3H), 3.59-3.43 (m, 2H), 3.26-3.07 (m, 2H).

Example 170: 5-amino-3-[4-[[(2-methoxybenzoyl)amino]methyl]phenyl]-1-[1-(trifluoromethyl)propyl]pyrazole-4-carboxamide

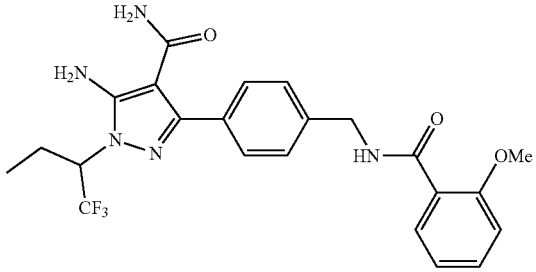 [SMILES: CCC(n1nc(-c2ccc(CNC(=O)c3ccccc3OC)cc2)c(C(N)=O)c1N)C(F)(F)F]

N-[1-(Trifluoromethyl)propylideneamino]benzamide

Following general procedure S, 1,1,1-trifluoro-2-butanone (0.45 mL, 3.30 mmol) and benzhydrazide (2.20 mmol) afforded crude titled compound (487 mg, 2.0 mmol, 91% yield) as a white solid. UPLC-MS (ES+, Short acidic): 1.70 min, m/z 245.0 [M+H]+

N'-[1-(Trifluoromethyl)propyl]benzohydrazide

Following general procedure T, N-[1-(trifluoromethyl)propylideneamino]benzamide (487 mg, 2.0 mmol) afforded crude titled compound (487 mg, 1.98 mmol) as a white solid. UPLC-MS (ES+, Short acidic): 1.56 min, m/z 247.0 [M+H]+

1-(Trifluoromethyl)propylhydrazine hydrochloride

Following general procedure U, N'-[1-(trifluoromethyl)propyl]benzohydrazide (487 mg, 1.98 mmol) afforded crude titled compound (1.98 mmol, assumed quantitative yield) as a white solid.

$^1$H NMR (400 MHz, DMSO-$d_6$, δ): 3.64-3.59 (m, 1H), 1.76-1.53 (m, 2H), 1.02 (t, J=7.4 Hz, 3H).

5-Amino-3-(4-bromophenyl)-1-[1-(trifluoromethyl)propyl]pyrazole-4-carbonitrile

Following a modified general procedure H at RT, 2-[(4-bromophenyl)-methoxy-methylene]propanedinitrile (100 mg, 0.38 mmol) and 1-(trifluoromethyl)propylhydrazine hydrochloride (102 mg, 0.57 mmol) afforded, after purification, titled compound (135 mg, 0.36 mmol, 95% yield) as a white solid. UPLC-MS (ES+, Short acidic): 2.03 min, m/z 373.0 [M]+

N-[[4-[5-Amino-4-cyano-1-[1-(trifluoromethyl)propyl]pyrazol-3-yl]phenyl]methyl]-2-methoxy-benzamide Following general procedure K, 5-amino-3-(4-bromophenyl)-1-[1-(trifluoromethyl)propyl]pyrazole-4-carbonitrile (135 mg, 0.36 mmol) and potassium trifluoro-[[(2-methoxybenzoyl)amino]methyl]boranuide (196 mg, 0.72 mmol) afforded, after purification, titled compound (219 mg, 0.48 mmol) as a yellow gum. UPLC-MS (ES+, Short acidic): 1.78 min, m/z 458.1 [M+H]+

5-Amino-3-[4-[[(2-methoxybenzoyl)amino]methyl]phenyl]-1-[1-(trifluoromethyl)propyl]pyrazole-4-carboxamide Following general procedure M, N-[[4-[5-amino-4-cyano-1-[1-(trifluoromethyl)propyl]pyrazol-3-yl]phenyl]methyl]-2-methoxy-benzamide (219 mg, 0.48 mmol) afforded, after purification, titled compound (77 mg, 0.16 mmol, 34% yield) as a white solid. UPLC-MS (ES+, Short acidic): 1.62 min, m/z 476.1 [M+H]+ UPLC-MS (ES+, Long acidic): 3.69 min, m/z 476.1 [M+H]+

$^1$H NMR (400 MHz, DMSO-$d_6$, δ): 8.73 (t, J=6.1 Hz, 1H), 7.74 (dd, J=7.7, 1.7 Hz, 1H), 7.49-7.39 (m, 5H), 7.14 (d, J=8.2 Hz, 1H), 7.06-7.00 (m, 1H), 6.69 (s, 2H), 5.12-5.00 (m, 1H), 4.54 (d, J=6.1 Hz, 2H), 3.89 (s, 3H), 2.27-2.16 (m, 1H), 1.99-1.88 (m, 1H), 0.79 (t, J=7.3 Hz, 3H).

Example 171: 5-amino-3-[4-[[(2-methoxybenzoyl)amino]methyl]phenyl]-1-[2-methyl-1-(trifluoromethyl)propyl]pyrazole-4-carboxamide

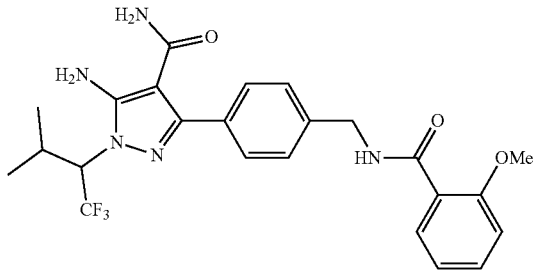 [SMILES: COc1ccccc1C(=O)NCc1ccc(-c2nn(C(C(C)C)C(F)(F)F)c(N)c2C(N)=O)cc1]

N-[[2-Methyl-1-(trifluoromethyl)propylidene]amino]benzamide

Following general procedure S, 1,1,1-trifluoro-3-methyl-2-butanone (3.31 mmol) and benzhydrazide (2.20 mmol) afforded titled compound (1.30 mmol) as a white solid. UPLC-MS (ES+, Short acidic): 1.69 min, m/z 259.0 [M+H]+

N'-[2-Methyl-1-(trifluoromethyl)propyl]benzohydrazide

Following general procedure T, N-[[2-methyl-1-(trifluoromethyl)propylidene]amino]benzamide (335 mg, 1.30 mmol) afforded titled compound (341 mg, 1.31 mmol, quantitative yield) as a crude white solid. UPLC-MS (ES+, Short acidic): 1.66 min, m/z 261.0 [M+H]+

[2-Methyl-1-(trifluoromethyl)propyl]hydrazine hydrochloride

Following general procedure U, N'-[2-methyl-1-(trifluoromethyl)propyl]benzohydrazide (341 mg, 1.31 mmol) afforded crude titled compound (243 mg, 1.26 mmol) as a white solid. $^1$H NMR (400 MHz, DMSO-$d_6$, δ): 3.63-3.52 (m, 1H), 2.14-2.04 (m, 1H), 1.04 (d, J=6.9 Hz, 3H), 0.97 (d, J=6.9 Hz, 3H).

5-Amino-3-(4-bromophenyl)-1-[2-methyl-1-(trifluoromethyl)propyl]pyrazole-4-carbonitrile Following a modified general procedure H at RT, 2-[(4-bromophenyl)-methoxy-methylene]propanedinitrile (100 mg, 0.38 mmol) and [2-methyl-1-(trifluoromethyl)propyl] hydrazine hydrochloride (110 mg, 0.57 mmol) afforded, after purification, titled compound (99 mg, 0.26 mmol, 67% yield) as a white solid. UPLC-MS (ES+, Short acidic): 2.10 min, m/z 387.0 [M]+

N-[[4-[5-Amino-4-cyano-1-[2-methyl-1-(trifluoromethyl)propyl]pyrazol-3-yl]phenyl]methyl]-2-methoxy-benzamide Following general procedure K, 5-amino-3-(4-bromophenyl)-1-[2-methyl-1-(trifluoromethyl)propyl]pyrazole-4-carbonitrile (99 mg, 0.26 mmol) and potassium trifluoro-[[(2-methoxybenzoyl)amino]methyl]boranuide (139 mg, 0.51 mmol) afforded, after purification, titled compound (179 mg, 0.38 mmol, assumed quantitative yield) as a yellow gum. UPLC-MS (ES+, Short acidic): 1.82 min, m/z 472.1 [M+H]+

5-Amino-3-[4-[[(2-methoxybenzoyl)amino]methyl]phenyl]-1-[2-methyl-1-(trifluoromethyl)propyl]pyrazole-4-carboxamide Following general procedure M, N-[[4-[5-amino-4-cyano-1-[2-methyl-1-(trifluoromethyl)propyl]pyrazol-3-yl]phenyl]methyl]-2-methoxy-benzamide (179 mg, 0.38 mmol) afforded, after purification, titled compound (66 mg, 0.12 mmol, 32% yield) as a white solid. UPLC-MS (ES+, Short acidic): 1.69 min, m/z 490.2 [M+H]+ UPLC-MS (ES+, Long acidic): 3.89 min, m/z 490.2 [M+H]+ $^1$H NMR (400 MHz, DMSO-$d_6$, δ): 8.72 (t, J=6.0 Hz, 1H), 7.74 (dd, J=7.7, 1.7 Hz, 1H), 7.49-7.39 (m, 5H), 7.14 (d, J=8.2 Hz, 1H), 7.05-7.00 (m, 1H), 6.68 (s, 2H), 4.90-4.80 (m, 1H), 4.54 (d, J=6.0 Hz, 2H), 3.89 (s, 3H), 2.61-2.50 (m, 1H), 1.09 (d, J=6.4 Hz, 3H), 0.77 (d, J=6.6 Hz, 3H).

Example 172: 5-amino-3-[4-[[(5-fluoro-2-methoxy-benzoyl)amino]methyl]phenyl]-1-(1-tetrahydrofuran-3-ylethyl)pyrazole-4-carboxamide

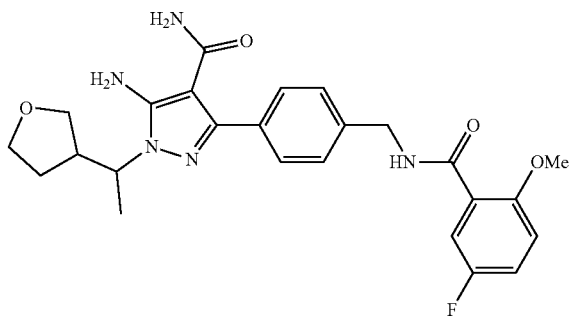 [SMILES: COc1ccc(F)cc1C(=O)NCc1ccc(-c2nn(C(C)C3CCOC3)c(N)c2C(N)=O)cc1]

N-Methoxy-N-methyl-tetrahydrofuran-3-carboxamide

A solution of tetrahydro-3-furoic acid (0.25 mL, 2.61 mmol), triethylamine (0.7 mL, 5.23 mmol), a propylphosphonic anhydride solution (50 wt % in EtOAc, 2.3 mL, 3.92 mmol) and N,O-dimethylhydroxylamine hydrochloride (382 mg, 3.92 mmol) in DCM (10 mL) was stirred for 16 h at RT to give (after work up) titled compound (416 mg, 2.61 mmol, assumed quantitative yield) as a colourless oil. $^1$H NMR (400 MHz, CDCl$_3$, δ): 4.10-4.03 (m, 1H), 3.95-3.78 (m, 3H), 3.72 (s, 3H), 3.50-3.37 (m, 3H), 3.22 (s, 3H) 2.30-2.19 (m, 1H), 2.15-2.03 (m, 1H)

1-Tetrahydrofuran-3-ylethanone

To a solution of N-methoxy-N-methyl-tetrahydrofuran-3-carboxamide (276 mg, 1.73 mmol) in THF (8 mL), at 0° C., was added bromo(methyl)magnesium (3.4 M in 2-MeTHF, 0.7 mL, 2.25 mmol). The reaction mixture was stirred at RT for 16 h. The reaction mixture was quenched with HCl (1 M in water), the residue was diluted with diethyl ether, washed with water, dried over sodium sulfate and concentrated under reduced pressure to afford crude 1-tetrahydrofuran-3-ylethanone (127 mg, 1.11 mmol, 64% yield) as a clear oil. $^1$H NMR (400 MHz, CDCl$_3$, δ): 4.00-3.70 (m, 4H), 3.27-3.18 (m, 1H), 2.23 (s, 3H), 2.17-2.09 (m, 2H).

tert-Butyl N-[1-tetrahydrofuran-3-ylethylideneamino]carbamate

Following general procedure E, 1-tetrahydrofuran-3-ylethanone (127 mg, 1.11 mmol) gave, after purification by flash column chromatographyon silica gel eluting with 0-100% EtOAc in heptane, titled compound (0.60 mmol) as a white solid. UPLC-MS (ES+, Short acidic): 1.26 min, m/z 229.0 [M+H]+

5-Amino-3-(4-bromophenyl)-1-(1-tetrahydrofuran-3-ylethyl)pyrazole-4-carbonitrile Following a modified general procedure O at RT, tert-butyl N-[1-tetrahydrofuran-3-ylethylideneamino]carbamate (0.38 mmol) and 2-[(4-bromophenyl)-methoxy-methylene] propanedinitrile (95 mg, 0.36 mmol) gave, after purification by reverse-phase chromatography eluting with isocratic 30% MeCN in water containing 0.1% formic acid, titled compound (33 mg, 0.09 mmol, 26% yield) as an off-white powder. UPLC-MS (ES+, Short acidic): 1.81 min, m/z 361.0 [M]+

N-[[4-[5-Amino-4-cyano-1-(1-tetrahydrofuran-3-ylethyl)pyrazol-3-yl]phenyl]methyl]-5-fluoro-2-methoxy-benzamide Following general procedure K, 5-amino-3-(4-bromophenyl)-1-(1-tetrahydrofuran-3-ylethyl)pyrazole-4-carbonitrile (33 mg, 0.09 mmol) and potassium trifluoro-[[(5-fluoro-2-methoxy-benzoyl)amino]methyl]boranuide (59 mg, 0.20 mmol) gave, after purification by flash column chromatography on silica gel eluting with 0-100% EtOAc in heptane, titled compound (37 mg, 0.08 mmol, 87% yield) as an off-white powder. UPLC-MS (ES+, Short acidic): 1.62 min, m/z 464.1 [M+H]+

5-Amino-3-[4-[[(5-fluoro-2-methoxy-benzoyl)amino]methyl]phenyl]-1-(1-tetrahydrofuran-3-ylethyl)pyrazole-4-carboxamide Following general procedure M, N-[[4-[5-amino-4-cyano-1-(1-tetrahydrofuran-3-ylethyl)pyrazol-3-yl]phenyl] methyl]-5-fluoro-2-methoxy-benzamide (37 mg, 0.08 mmol) gave, after purification by flash column chromatography on silica gel eluting with 2-5% MeOH in DCM, an inseparable diastereoisomeric mixture of 5-amino-3-[4-[[(5-fluoro-2-methoxy-benzoyl)amino]methyl]phenyl]-1-(1-tetrahydrofuran-3-ylethyl)pyrazole-4-carboxamide (12 mg, 0.02 mmol, 30% yield) as a white solid. UPLC-MS (ES+, Short acidic): 1.43 min, m/z 482.2 [M+H]+ UPLC-MS (ES+, Long acidic): 3.24 min, m/z 482.2 [M+H]+, 3.28 min, m/z 482.2 [M+H]+

$^1$H NMR (400 MHz, DMSO-d$_6$, δ, mixture of diastereoisomers): 8.83 (t, J=6.0 Hz, 1H), 7.51 (dd, J=9.2, 3.3 Hz, 1H), 7.48-7.43 (m, 2H), 7.41 (d, J=8.2 Hz, 2H), 7.37-7.30 (m, 1H), 7.18 (dd, J=9.1, 4.3 Hz, 1H), 6.38 (s, 1.34H), 6.36 (s, 0.66H), 4.54 (d, J=6.0 Hz, 2H), 4.30-4.18 (m, 1H), 3.89 (s, 3H), 3.86-3.40 (m, 3.67H), 3.28-3.30 (m, 0.33H), 2.82-2.63 (m, 1H), 2.10-1.91 (m, 0.33H), 1.76-1.54 (m, 1H), 1.54-1.40 (m, 0.67H), 1.34 (d, J=6.5 Hz, 1H), 1.29 (d, J=6.5 Hz, 2H).

Example 173: 5-amino-1-(2,2-difluoro-1-methyl-ethyl)-3-[4-[[(5-fluoro-2-methoxy-benzoyl)amino]methyl]phenyl]pyrazole-4-carboxamide

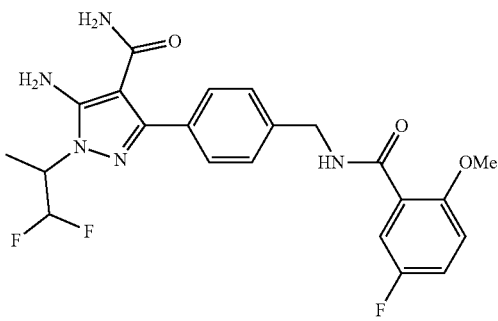 [SMILES: COc1ccc(F)cc1C(=O)NCc1ccc(-c2nn(C(C)C(F)F)c(N)c2C(N)=O)cc1]

N-[[4-[5-Amino-4-cyano-1-(2,2-difluoro-1-methyl-ethyl)pyrazol-3-yl]phenyl]methyl]-5-fluoro-2-methoxy-benzamide Following general procedure K, 5-amino-3-(4-bromophenyl)-1-(2,2-difluoro-1-methyl-ethyl)pyrazole-4-carbonitrile (91 mg, 0.27 mmol) and potassium trifluoro-[[(5-fluoro-2-methoxy-benzoyl)amino]methyl]boranuide (170 mg, 0.59 mmol) gave, after purification, titled compound (119 mg, 0.27 mmol, assumed quantitative yield) as an off-white powder. UPLC-MS (ES$^+$, Short acidic): 1.70 min, m/z 444.1 [M+H]$^+$ 5-Amino-1-(2,2-difluoro-1-methyl-ethyl)-3-[4-[[(5-fluoro-2-methoxy-benzoyl)amino]methyl]phenyl]pyrazole-4-carboxamide Following general procedure M, N-[[4-[5-amino-4-cyano-1-(2,2-difluoro-1-methyl-ethyl)pyrazol-3-yl]phenyl]methyl]-5-fluoro-2-methoxy-benzamide (119 mg, 0.27 mmol) gave, after purification, titled compound (85 mg, 0.18 mmol, 69% yield) as a white solid. UPLC-MS (ES$^+$, Short acidic): 1.53 min, m/z 462.2 [M+H]$^+$ UPLC-MS (ES$^+$, Long acidic): 3.49 min, m/z 462.1 [M+H]$^+$ $^1$H NMR (400 MHz, DMSO-d$_6$, δ): 8.83 (t, J=6.1 Hz, 1H), 7.51 (dd, J=9.2, 3.3 Hz, 1H), 7.46 (d, J=8.2 Hz, 2H), 7.41 (d, J=8.2 Hz, 2H), 7.38-7.30 (m, 1H), 7.18 (dd, J=9.1, 4.3 Hz, 1H), 6.53 (s, 2H), 6.21 (dt, J=55.8, 5.4 Hz, 1H), 4.85-4.70 (m, 1H), 4.55 (d, J=6.0 Hz, 2H), 3.89 (s, 3H), 1.44 (d, J=6.7 Hz, 3H).

Example 174: 5-amino-3-[4-[[(5-fluoro-2-methoxy-benzoyl)amino]methyl]phenyl]-1-(3,3,3-trifluoropropyl)pyrazole-4-carboxamide

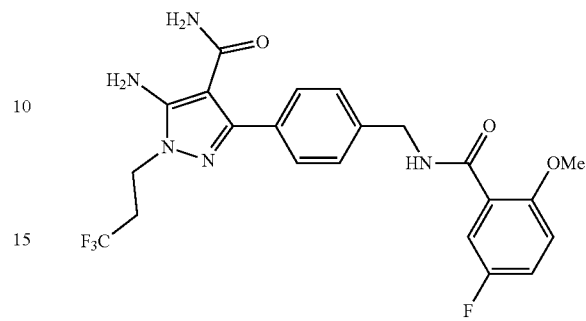

N-[3,3,3-Trifluoropropylideneamino]benzamide

Following general procedure S, 3,3,3-trifluoropropanal (0.15 mL, 1.78 mmol) gave a cis-trans mixture of N-[3,3,3-trifluoropropylideneamino]benzamide (290 mg, 1.26 mmol) as an off-white solid. UPLC-MS (ES$^+$, Short acidic): 1.32 min, m/z 230.9 [M+H]$^+$ N'-(3,3,3-Trifluoropropyl)benzohydrazide Following general procedure T, N-[3,3,3-trifluoropropylideneamino]benzamide (290 mg, 1.26 mmol) gave crude N'-(3,3,3-trifluoropropyl)benzohydrazide (201 mg, 0.87 mmol, 69% yield) as an off-white solid. UPLC-MS (ES$^+$, Short acidic): 1.37 min, m/z 233.1[M+H]$^+$ 3,3,3-Trifluoropropylhydrazine hydrochloride Following general procedure U, N'-(3,3,3-trifluoropropyl)benzohydrazide (201 mg, 0.87 mmol) gave crude 3,3,3-trifluoropropylhydrazine hydrochloride (140 mg, 0.85 mmol, assumed quantitative yield) as a white solid. $^1$H NMR (400 MHz, DMSO-d$_6$, δ): 3.07 (t, J=14.9 Hz, 2H), 2.58-2.56 (m, 2H).

5-Amino-3-(4-bromophenyl)-1-(3,3,3-trifluoropropyl)pyrazole-4-carbonitrile

Following general procedure H, 3,3,3-trifluoropropylhydrazine hydrochloride (140 mg, 0.85 mmol), and 2-[(4-bromophenyl)-methoxy-methylene]propanedinitrile (224 mg, 0.85 mmol) gave, after purification by flash column chromatography on silica gel eluting with 0-80% EtOAc in heptane, titled compound (227 mg, 0.63 mmol) as an off-white solid. UPLC-MS (ES$^+$, Short acidic): 1.91 min, m/z 361.0 [M+2]$^+$ N-[[4-[5-Amino-4-cyano-1-(3,3,3-trifluoropropyl)pyrazol-3-yl]phenyl]methyl]-5-fluoro-2-methoxy-benzamide Following general procedure K, 5-amino-3-(4-bromophenyl)-1-(3,3,3-trifluoropropyl)pyrazole-4-carbonitrile (227 mg, 0.63 mmol), and potassium trifluoro-[[(5-fluoro-2-methoxy-benzoyl)amino]methyl]boranuide (909 mg, 3.15 mmol) gave, after purification, titled compound (270 mg, 0.59 mmol). UPLC-MS (ES+, Short acidic): 1.74 min, m/z 462.1 [M+H]+

5-Amino-3-[4-[[(5-fluoro-2-methoxy-benzoyl)amino]methyl]phenyl]-1-(3,3,3-trifluoropropyl)pyrazole-4-carboxamide Following general procedure M, N-[[4-[5-amino-4-cyano-1-(3,3,3-trifluoropropyl)pyrazol-3-yl]phenyl]methyl]-5-fluoro-2-methoxy-benzamide (270 mg, 0.59 mmol) gave, after purification by flash column chromatography on silica gel eluting with 0-100% EtOAc in heptane, titled compound (66 mg, 0.14 mmol, 24% yield) as an off-white solid. UPLC-MS (ES+, Short acidic): 1.48 min, m/z 480.1 [M+H]+

UPLC-MS (ES+, Long acidic): 3.42 min, m/z 480.1 [M+H]+

$^1$H NMR (400 MHz, DMSO-$d_6$, δ): 8.83 (t, J=6.4 Hz, 1H), 7.50 (dd, J=9.2, 3.6 Hz, 1H), 7.44 (d, J=8.4 Hz, 2H), 7.39 (d, J=8.4 Hz, 2H), 7.36-7.28 (m, 1H), 7.17 (dd, J=9.2, 4.4 Hz, 1H), 6.45 (s, 2H), 4.53 (d, J=6.1 Hz, 2H), 4.18 (t, J=7.2 Hz, 2H), 3.87 (s, 3H), 2.83-2.69 (m, 2H).

Example 175: 5-amino-3-[4-[[(5-fluoro-2-methoxy-benzoyl)amino]methyl]phenyl]-1-(2,2,2-trifluoro-1-tetrahydrofuran-3-yl-ethyl)pyrazole-4-carboxamide

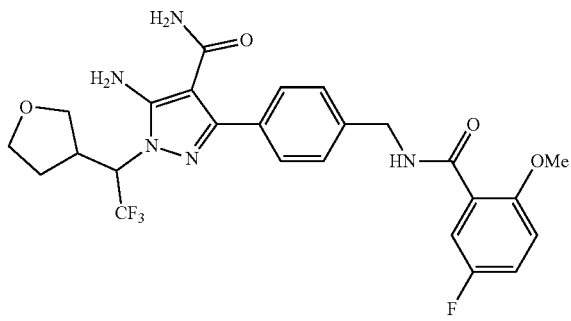 [SMILES: COc1ccc(F)cc1C(=O)NCc1ccc(-c2nn(C(C3CCOC3)C(F)(F)F)c(N)c2C(N)=O)cc1]

Benzyl tetrahydrofuran-3-carboxylate

A solution of tetrahydro-3-furoic acid (0.25 mL, 2.61 mmol), potassium carbonate (433 mg, 3.14 mmol) and benzyl bromide (0.3 mL, 2.74 mmol) in MeCN (5.5 mL) was stirred at RT for 16 h. Work up and purification afforded titled compound (398 mg, 1.93 mmol, 74% yield) as a colourless oil.

$^1$H NMR (400 MHz, CDCl$_3$, δ): 7.43-7.32 (m, 5H), 5.17 (s, 2H), 4.04-3.80 (m, 4H), 3.21-3.11 (m, 1H), 2.30-2.10 (m, 2H)

tert-Butyl N-[(2,2,2-trifluoro-1-tetrahydrofuran-3-yl-ethylidene)amino]carbamate To a solution of benzyl tetrahydrofuran-3-carboxylate (398 mg, 1.93 mmol) in THF (3.8 mL), at 0° C., was added trimethyl(trifluoromethyl)silane (0.34 mL, 2.32 mmol) and tetrabutylammonium fluoride (1 M in THF, 0.48 mL, 0.48 mmol). The reaction mixture was stirred at RT for 16 h, then tert-butyl carbazate (255 mg, 1.93 mmol) and acetic acid (3.8 mL) were added. The mixture was heated to 90° C. for 3 h and cooled to RT. Work up and purification afforded titled compound (409 mg, 1.45 mmol, 75% yield) as a clear oil. UPLC-MS (ES−, Short acidic): 1.79 min, m/z 281.0 [M−H]−

5-Amino-3-(4-bromophenyl)-1-(2,2,2-trifluoro-1-tetrahydrofuran-3-yl-ethyl)pyrazole-4-carbonitrile Following general procedure O, tert-butyl N-[(2,2,2-trifluoro-1-tetrahydrofuran-3-yl-ethylidene)amino]carbamate (409 mg, 1.45 mmol) and 2-[(4-bromophenyl)-methoxymethylene]propanedinitrile (120 mg, 0.46 mmol) gave, after purification by flash column chromatography on silica gel eluting with 0-55% EtOAc in heptane, 5-amino-3-(4-bromophenyl)-1-(2,2,2-trifluoro-1-tetrahydrofuran-3-yl-ethyl)pyrazole-4-carbonitrile (98 mg, 0.24 mmol, 52% yield) as a white powder.

UPLC-MS (ES+, Short acidic): 1.89 min, m/z 414.9 [M]+

N-[[4-[5-Amino-4-cyano-1-(2,2,2-trifluoro-1-tetrahydrofuran-3-yl-ethyl)pyrazol-3-yl]phenyl]methyl]-5-fluoro-2-methoxy-benzamide Following general procedure K, 5-amino-3-(4-bromophenyl)-1-(2,2,2-trifluoro-1-tetrahydrofuran-3-yl-ethyl)pyrazole-4-carbonitrile (98 mg, 0.24 mmol) and potassium trifluoro-[[(5-fluoro-2-methoxy-benzoyl)amino]methyl]boranuide (149 mg, 0.52 mmol) gave, after purification, titled compound (115 mg, 0.22 mmol) as an off-white powder. UPLC-MS (ES+, Short acidic): 1.68 min, m/z 518.1 [M+H]+

5-Amino-3-[4-[[(5-fluoro-2-methoxy-benzoyl)amino]methyl]phenyl]-1-(2,2,2-trifluoro-1-tetrahydrofuran-3-yl-ethyl)pyrazole-4-carboxamide Following general procedure M, N-[[4-[5-amino-4-cyano-1-(2,2,2-trifluoro-1-tetrahydrofuran-3-yl-ethyl)pyrazol-3-yl]phenyl]methyl]-5-fluoro-2-methoxy-benzamide (115 mg, 0.22 mmol) gave, after purification, titled compound (15 mg, 0.03 mmol, 13% yield) as a white solid.

UPLC-MS (ES+, Short acidic): 1.51 min, m/z 536.2 [M+H]+, 1.53 min, m/z 536.2 [M+H]+

UPLC-MS (ES+, Long acidic): 3.51 min, m/z 536.1 [M+H]+, 3.56 min, m/z 536.1 [M+H]+

$^1$H NMR (400 MHz, DMSO-$d_6$, δ, mixture of diastereoisomers): 8.82 (t, J=5.9 Hz, 1H), 7.52-7.43 (m, 3H), 7.41 (d, J=7.9 Hz, 2H), 7.36-7.28 (m, 1H), 7.17 (dd, J=9.1, 4.3 Hz, 1H), 6.73 (s, 0.66H), 6.71 (s, 1.34), 5.26-5.12 (m, 1H), 4.53 (d, J=6.0 Hz, 2H), 3.94-3.82 (m, 4H), 3.76-3.67 (m, 1H), 3.65-3.57 (m, 1H), 3.57-3.50 (m, 0.33H), 3.25-3.03 (m, 1.67H), 2.18-2.04 (m, 0.67H), 1.86-1.71 (m, 1H), 1.54-1.40 (m, 0.33H)

Example 176: 5-amino-3-[4-[[(5-fluoro-2-methoxy-benzoyl)amino]methyl]phenyl]-1-(3,3,3-trifluoro-2-methyl-propyl)pyrazole-4-carboxamide

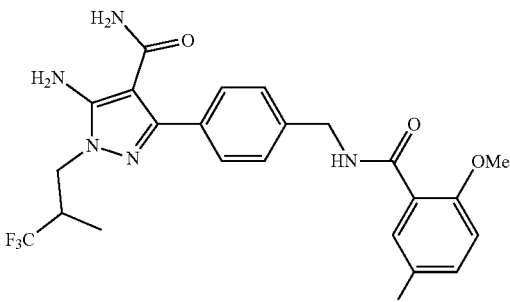

N-[(3,3,3-Trifluoro-2-methyl-propylidene)amino]benzamide

Following general procedure S, 3,3,3-trifluoro-2-methyl-propanal (200 mg, 1.59 mmol), gave after purification by flash column chromatography on silica gel eluting with 0-100% EtOAc in heptane N-[(3,3,3-trifluoro-2-methyl-propylidene)amino]benzamide (164 mg, 0.67 mmol, 42% yield) as a mixture of diastereoisomers. UPLC-MS (ES+, Short acidic): 1.45 min, m/z 245.0 [M+H]+

N'-(3,3,3-Trifluoro-2-methyl-propyl)benzohydrazide

Following general procedure T, N-[(3,3,3-trifluoro-2-methyl-propylidene)amino]benzamide (164 mg, 0.67 mmol) gave crude N-(3,3,3-trifluoro-2-methyl-propyl)benzohydrazide (160 mg, 0.65 mmol) as a white solid. UPLC-MS (ES+, Short acidic): 1.51 min, m/z 247.1 [M+H]+

(3,3,3-Trifluoro-2-methyl-propyl)hydrazine hydrochloride

Following general procedure U, N-(3,3,3-trifluoro-2-methyl-propyl)benzohydrazide (160 mg, 0.65 mmol) gave (3,3,3-trifluoro-2-methyl-propyl)hydrazine hydrochloride (0.65 mmol) as a white solid.
$^1$H NMR (400 MHz, DMSO-$d_6$, δ): 3.17-3.14 (m, 1H), 2.82-2.76 (m, 2H), 1.10 (d, J=6.5 Hz, 3H)

5-Amino-3-(4-bromophenyl)-1-(3,3,3-trifluoro-2-methyl-propyl)pyrazole-4-carbonitrile General procedure H, (3,3,3-trifluoro-2-methyl-propyl)hydrazine hydrochloride (0.65 mmol), and 2-[(4-bromophenyl)-methoxy-methylene]propanedinitrile (0.65 mmol) gave, after purification, the titled compound (0.34 mmol) as an off-white solid. UPLC-MS (ES+, Short acidic): 2.01 min, m/z 375.0 [M+2]+

N-[[4-[5-Amino-4-cyano-1-(3,3,3-trifluoro-2-methyl-propyl)pyrazol-3-yl]phenyl]methyl]-5-fluoro-2-methoxy-benzamide Following general procedure K, 5-amino-3-(4-bromophenyl)-1-(3,3,3-trifluoro-2-methyl-propyl)pyrazole-4-carbonitrile (130 mg, 0.34 mmol), and potassium trifluoro-[[(5-fluoro-2-methoxy-benzoyl)amino]methyl]boranuide (490 mg, 1.71 mmol) gave, after purification, the titled compound (0.26 mmol) as an off-white solid. UPLC-MS (ES+, Short acidic): 1.81 min, m/z 476.1 [M+H]+

5-Amino-3-[4-[[(5-fluoro-2-methoxy-benzoyl)amino]methyl]phenyl]-1-(3,3,3-trifluoro-2-methyl-propyl)pyrazole-4-carboxamide Following general procedure M, N-[[4-[5-amino-4-cyano-1-(3,3,3-trifluoro-2-methyl-propyl)pyrazol-3-yl]phenyl]methyl]-5-fluoro-2-methoxy-benzamide (127 mg, 0.27 mmol) gave, after purification, titled compound (31 mg, 0.06 mmol, 23% yield) as a pale yellow solid. UPLC-MS (ES+, Short acidic): 1.55 min, m/z 494.1 [M+H]+ UPLC-MS (ES+, Long acidic): 3.61 min, m/z 494.1 [M+H]+
$^1$H NMR (400 MHz, DMSO-$d_6$, δ): 8.83 (t, J=6.0 Hz, 1H), 7.49 (dd, J=9.2, 3.2 Hz, 1H), 7.44 (d, J=8.4 Hz, 2H), 7.39 (d, J=8.4 Hz, 2H), 7.36-7.28 (m, 1H), 7.17 (dd, J=9.2, 4.4 Hz, 1H), 6.47 (s, 2H), 4.53 (d, J=6.0 Hz, 2H), 4.16 (dd, J=14.2, 9.6 Hz, 1H), 4.05 (dd, J=14.2, 8.8 Hz, 1H), 3.87 (s, 3H), 3.06-2.92 (m, 1H), 1.02 (d, J=6.8 Hz, 3H).

Example 177: 5-amino-3-[3-fluoro-4-[[(5-fluoro-2-methoxy-benzoyl)amino]methyl]phenyl]-1-(2,2,2-trifluoro-1-methyl-ethyl)pyrazole-4-carboxamide

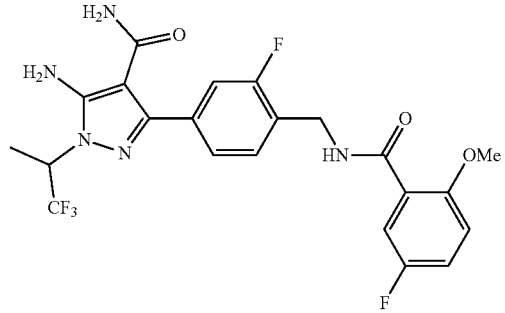 [SMILES: COc1ccc(F)cc1C(=O)NCc1ccc(-c2nn(C(C)C(F)(F)F)c(N)c2C(N)=O)cc1F]

5-Amino-3-(4-bromo-3-fluoro-phenyl)-1-(2,2,2-trifluoro-1-methyl-ethyl)pyrazole-4-carbonitrile Following general procedure H, 2-[(4-bromo-3-fluoro-phenyl)-methoxy-methylene]propanedinitrile (130 mg, 0.46 mmol) and (2,2,2-trifluoro-1-methyl-ethyl)hydrazine hydrochloride (100 mg, 0.61 mmol) afforded, after purification, titled compound (153 mg, 0.41 mmol, 88% yield) as white solid. UPLC-MS (ES+, Short acidic): 2.01 min, m/z 378.9 [M+2]+

N-[[4-[5-Amino-4-cyano-1-(2,2,2-trifluoro-1-methyl-ethyl)pyrazol-3-yl]-2-fluoro-phenyl]methyl]-5-fluoro-2-methoxy-benzamide Following general procedure K, 5-amino-3-(4-bromo-3-fluoro-phenyl)-1-(2,2,2-trifluoro-1-methyl-ethyl)pyrazole-4-carbonitrile (147 mg, 0.39 mmol) and potassium trifluoro-[[(5-fluoro-2-methoxy-benzoyl)amino]methyl]boranuide (225 mg, 0.78 mmol) gave crude titled compound (0.39 mmol) as a light yellow solid. UPLC-MS (ES+, Short acidic): 1.86 min, m/z 480.0 [M+H]+

5-Amino-3-[3-fluoro-4-[[(5-fluoro-2-methoxy-benzoyl)amino]methyl]phenyl]-1-(2,2,2-trifluoro-1-methyl-ethyl)pyrazole-4-carboxamide Following general procedure M, N-[[4-[5-amino-4-cyano-1-(2,2,2-trifluoro-1-methyl-ethyl)pyrazol-3-yl]-2-fluoro-phenyl]methyl]-5-fluoro-2-methoxy-benzamide (230 mg, 0.48 mmol) gave, after purification, titled compound (73 mg, 0.15 mmol, 31% yield) as a pale yellow solid. UPLC-MS (ES+, Short acidic): 1.58 min, m/z 498.1 [M+H]$^+$
UPLC-MS (ES+, Long acidic): 3.69 min, m/z 498.1 [M+H]$^+$
$^1$H NMR (400 MHz, DMSO-d$_6$, δ): 8.82 (t, J=6.0 Hz, 1H), 7.49 (dd, J=9.2, 3.2 Hz, 1H), 7.45-7.26 (m, 4H), 7.18 (dd, J=9.1, 4.3 Hz, 1H), 6.60 (s, 2H), 5.34-5.23 (m, 1H), 4.56 (d, J=6.0 Hz, 2H), 3.88 (s, 3H), 1.60 (d, J=6.9 Hz, 3H).

Example 178: 5-Amino-3-[4-[[(5-fluoro-2-methoxy-benzoyl)amino]methyl]phenyl]-1-(2,2,2-trifluoro-1-phenyl-ethyl)pyrazole-4-carboxamide

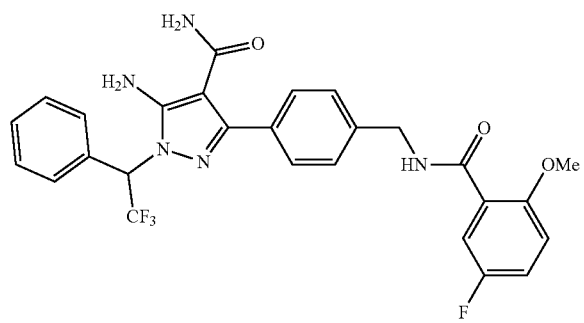 [SMILES: COc1ccc(F)cc1C(=O)NCc1ccc(-c2nn(C(c3ccccc3)C(F)(F)F)c(N)c2C(N)=O)cc1]

N-[(2,2,2-Trifluoro-1-phenyl-ethylidene)amino]benzamide

Following general procedure S, 2,2,2-trifluoroacetophenone (33.0 mmol) and benzhydrazide (22.0 mmol) gave, after purification, titled compound (3.44 mmol) as a white solid. UPLC-MS (ES+, Short acidic): 1.82 min, m/z 293.0 [M+H]$^+$

N-(2,2,2-Trifluoro-1-phenyl-ethyl)benzohydrazide

Following general procedure T, N-[(2,2,2-trifluoro-1-phenyl-ethylidene)amino]benzamide (997 mg, 3.41 mmol) in THF (15 mL) gave N'-(2,2,2-trifluoro-1-phenyl-ethyl)benzohydrazide (1.01 g, 3.43 mmol) as a yellow solid. UPLC-MS (ES$^+$, Short acidic): 1.77 min, m/z 295.0 [M+H]$^+$

(2,2,2-Trifluoro-1-phenyl-ethyl)hydrazine hydrochloride

Following general procedure U, N'-(2,2,2-trifluoro-1-phenyl-ethyl)benzohydrazide (996 mg, 3.38 mmol) gave titled compound (628 mg, 2.77 mmol) as a white solid. $^1$H NMR (400 MHz, DMSO-d$_6$, δ): 9.67 (s, 3H), 7.53-7.46 (m, 5H), 6.63 (d, J=6.4 Hz, 1H), 5.10-5.02 (m, 1H)

5-Amino-3-(4-bromophenyl)-1-(2,2,2-trifluoro-1-phenyl-ethyl)pyrazole-4-carbonitrile Following general procedure H, 2-[(4-bromophenyl)-methoxy-methylene]propanedinitrile (200 mg, 0.76 mmol) and (2,2,2-trifluoro-1-phenyl-ethyl)hydrazine hydrochloride (621 mg, 0.96 mmol) afforded, after purification, titled compound (266 mg, 0.63 mmol, 83% yield) was obtained as white solid. UPLC-MS (ES$^+$, Short acidic): 2.06 min, m/z 422.9 [M+2]$^+$

N-[[4-[5-Amino-4-cyano-1-(2,2,2-trifluoro-1-phenyl-ethyl)pyrazol-3-yl]phenyl]methyl]-5-fluoro-2-methoxy-benzamide Following general procedure K, 5-amino-3-(4-bromophenyl)-1-(2,2,2-trifluoro-1-phenyl-ethyl)pyrazole-4-carbonitrile (261 mg, 0.62 mmol) and potassium trifluoro-[[(5-fluoro-2-methoxy-benzoyl)amino]methyl]boranuide (358 mg, 1.24 mmol) gave, after purification, titled compound (73 mg, 0.14 mmol, 23% yield) as a white solid. UPLC-MS (ES+, Short acidic): 1.85 min, m/z 524.1 [M+H]$^+$

5-Amino-3-[4-[[(5-fluoro-2-methoxy-benzoyl)amino]methyl]phenyl]-1-(2,2,2-trifluoro-1-phenyl-ethyl)pyrazole-4-carboxamide Following general procedure M, N-[[4-[5-amino-4-cyano-1-(2,2,2-trifluoro-1-phenyl-ethyl)pyrazol-3-yl]phenyl]methyl]-5-fluoro-2-methoxy-benzamide (71 mg, 0.14 mmol) gave, after purification, titled compound (62 mg, 0.12 mmol, 84% yield) as a white solid. UPLC-MS (ES+, Short acidic): 1.71 min, m/z 542.1 [M+H]$^+$ UPLC-MS (ES+, Long acidic): 4.06 min, m/z 542.1 [M+H]$^+$
$^1$H NMR (400 MHz, DMSO-d$_6$, δ): 8.85 (t, J=6.1 Hz, 1H), 7.72-7.70 (m, 2H), 7.52-7.41 (m, 8H), 7.35-7.30 (m, 1H), 7.19-7.16 (m, 1H), 6.79 (s, 2H), 6.51-6.45 (m, 1H), 4.54 (d, J=6.0 Hz, 2H), 3.88 (s, 3H).

Example 179: 5-amino-3-[2-fluoro-4-[[(5-fluoro-2-methoxy-benzoyl)amino]methyl]phenyl]-1-(2,2,2-trifluoro-1-methyl-ethyl)pyrazole-4-carboxamide

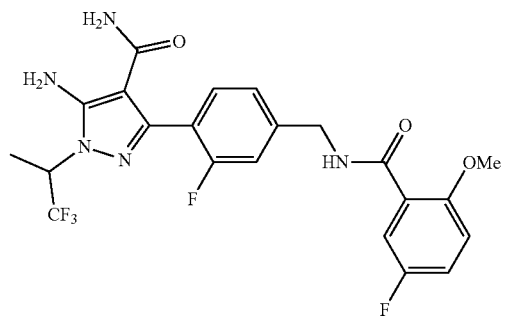 [SMILES: COc1ccc(F)cc1C(=O)NCc1ccc(-c2nn(C(C)C(F)(F)F)c(N)c2C(N)=O)c(F)c1]

5-Amino-3-(4-bromo-2-fluoro-phenyl)-1-(2,2,2-trifluoro-1-methyl-ethyl)pyrazole-4-carbonitrile Following general procedure H at RT, 2-[(4-bromo-2-fluoro-phenyl)-methoxy-methylene]propanedinitrile (100 mg, 0.38 mmol) and (2,2,2-trifluoro-1-methyl-ethyl)hydrazine hydrochloride (88 mg, 0.53 mmol) afforded, after purification, titled compound (120 mg, 0.32 mmol, 84% yield) as a white solid. UPLC-MS (ES$^+$, Short acidic): 1.84 min, m/z 378.9 [M+2]$^+$

N-[[4-[5-Amino-4-cyano-1-(2,2,2-trifluoro-1-methyl-ethyl)pyrazol-3-yl]-3-fluoro-phenyl]methyl]-5-fluoro-2-methoxy-benzamide Following general procedure K, 5-amino-3-(4-bromo-2-fluoro-phenyl)-1-(2,2,2-trifluoro-1-methyl-ethyl)pyrazole-4-carbonitrile (120 mg, 0.32 mmol) and potassium trifluoro-[[(5-fluoro-2-methoxy-benzoyl)amino]methyl]boranuide (184 mg, 0.64 mmol) afforded, after purification, titled compound (126 mg, 0.26 mmol, 83% yield) as a yellow solid. UPLC-MS (ES+, Short acidic): 1.69 min, m/z 480.0 [M+H]+

5-Amino-3-[2-fluoro-4-[[(5-fluoro-2-methoxy-benzoyl)amino]methyl]phenyl]-1-(2,2,2-trifluoro-1-methyl-ethyl)pyrazole-4-carboxamide Following general procedure M, N-[[4-[5-amino-4-cyano-1-(2,2,2-trifluoro-1-methyl-ethyl)pyrazol-3-yl]-3-fluoro-phenyl]methyl]-5-fluoro-2-methoxy-benzamide (126 mg, 0.26 mmol) afforded, after purification, titled compound (97 mg, 0.17 mmol, 66% yield) as a white solid. UPLC-MS (ES+, Short acidic): 1.54 min, m/z 498.1 [M+H]+ UPLC-MS (ES+, Long acidic): 3.56 min, m/z 498.1 [M+H]+

$^1$H NMR (400 MHz, DMSO-$d_6$, δ): 8.88 (t, J=6.1 Hz, 1H), 7.48 (dd, J=9.1, 3.2 Hz, 1H), 7.41-7.30 (m, 2H), 7.27-7.21 (m, 2H), 7.20-7.16 (m, 1H), 6.62 (s, 2H), 5.34-5.24 (m, 1H), 4.54 (d, J=6.1 Hz, 2H), 3.88 (s, 3H), 1.58 (d, J=6.8 Hz, 3H).

Example 180: 5-amino-3-[4-[[(5-fluoro-2-methoxy-benzoyl)amino]methyl]phenyl]-1-[2-methyl-1-(trifluoromethyl)propyl]pyrazole-4-carboxamide

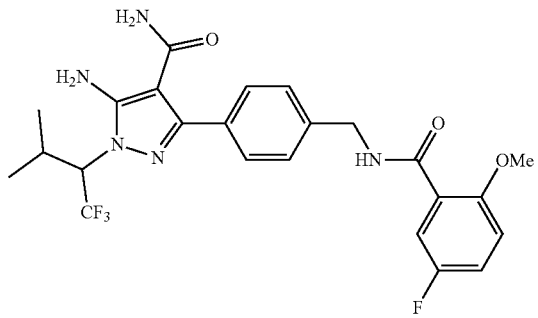 [SMILES: COc1ccc(F)cc1C(=O)NCc1ccc(-c2nn(C(C(C)C)C(F)(F)F)c(N)c2C(N)=O)cc1]

N-[[4-[5-Amino-4-cyano-1-[2-methyl-1-(trifluoromethyl)propyl]pyrazol-3-yl]phenyl]methyl]-5-fluoro-2-methoxy-benzamide Following general procedure K, 5-amino-3-(4-bromophenyl)-1-[2-methyl-1-(trifluoromethyl)propyl]pyrazole-4-carbonitrile (102 mg, 0.26 mmol) and potassium trifluoro-[[(5-fluoro-2-methoxy-benzoyl)amino]methyl]boranuide (152 mg, 0.53 mmol) afforded, after purification, titled compound (69 mg, 0.14 mmol, 54% yield) as a yellow gum. UPLC-MS (ES+, Short acidic): 1.89 min, m/z 490.1 [M+H]+

5-Amino-3-[4-[[(5-fluoro-2-methoxy-benzoyl)amino]methyl]phenyl]-1-[2-methyl-1-(trifluoromethyl)propyl]pyrazole-4-carboxamide Following general procedure M, N-[[4-[5-amino-4-cyano-1-[2-methyl-1-(trifluoromethyl)propyl]pyrazol-3-yl]phenyl]methyl]-5-fluoro-2-methoxy-benzamide (69 mg, 0.14 mmol) afforded, after purification, titled compound (22 mg, 0.04 mmol, 31% yield) as a white solid. UPLC-MS (ES+, Short acidic): 1.66 min, m/z 508.1 [M+H]+ UPLC-MS (ES+, Long acidic): 3.91 min, m/z 508.1 [M+H]+

$^1$H NMR (400 MHz, DMSO-$d_6$, δ): 8.82 (t, J=6.0 Hz, 1H), 7.53-7.39 (m, 5H), 7.36-7.29 (m, 1H), 7.20-7.15 (m, 1H), 6.68 (s, 2H), 4.90-4.80 (m, 1H), 4.53 (d, J=6.0 Hz, 2H), 3.88 (s, 3H), 2.61-2.52 (m, 1H), 1.09 (d, J=6.4 Hz, 3H), 0.77 (d, J=6.6 Hz, 3H).

Example 181: 5-amino-3-[4-[[(5-fluoro-2-methoxy-benzoyl)amino]methyl]phenyl]-1-[1-(trifluoromethyl)propyl]pyrazole-4-carboxamide

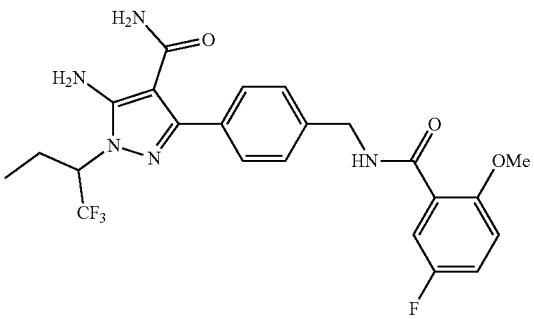 [SMILES: CCC(n1nc(-c2ccc(CNC(=O)c3cc(F)ccc3OC)cc2)c(C(N)=O)c1N)C(F)(F)F]

N-[[4-[5-Amino-4-cyano-1-[1-(trifluoromethyl)propyl]pyrazol-3-yl]phenyl]methyl]-5-fluoro-2-methoxy-benzamide Following general procedure K, 5-amino-3-(4-bromophenyl)-1-[1-(trifluoromethyl)propyl]pyrazole-4-carbonitrile (123 mg, 0.33 mmol) and potassium trifluoro-[[(5-fluoro-2-methoxy-benzoyl)amino]methyl]boranuide (190 mg, 0.66 mmol) afforded, after purification, titled compound (101 mg, 0.21 mmol, 65% yield) as a yellow gum. UPLC-MS (ES+, Short acidic): 1.83 min, m/z 476.1 [M+H]+

5-Amino-3-[4-[[(5-fluoro-2-methoxy-benzoyl)amino]methyl]phenyl]-1-[1-(trifluoromethyl)propyl]pyrazole-4-carboxamide Following general procedure M, N-[[4-[5-amino-4-cyano-1-[1-(trifluoromethyl)propyl]pyrazol-3-yl]phenyl]methyl]-5-fluoro-2-methoxy-benzamide (101 mg, 0.21 mmol) afforded, after purification, titled compound (32 mg, 0.06 mmol, 28% yield) as a white solid. UPLC-MS (ES+, Short acidic): 1.59 min, m/z 494.1 [M+H]+ UPLC-MS (ES+, Long acidic): 3.71 min, m/z 494.1 [M+H]+

$^1$H NMR (400 MHz, DMSO-$d_6$, δ): 8.82 (t, J=6.0 Hz, 1H), 7.53-7.38 (m, 5H), 7.37-7.27 (m, 1H), 7.20-7.14 (m, 1H), 6.69 (s, 2H), 5.12-5.00 (m, 1H), 4.53 (d, J=6.0 Hz, 2H), 3.88 (s, 3H), 2.28-2.14 (m, 1H), 2.01-1.87 (m, 1H), 0.79 (t, J=7.3 Hz, 3H).

Example 182: 5-amino-3-[2,3-difluoro-4-[[(5-fluoro-2-methoxy-benzoyl)amino]methyl]phenyl]-1-tetrahydrofuran-3-yl-pyrazole-4-carboxamide

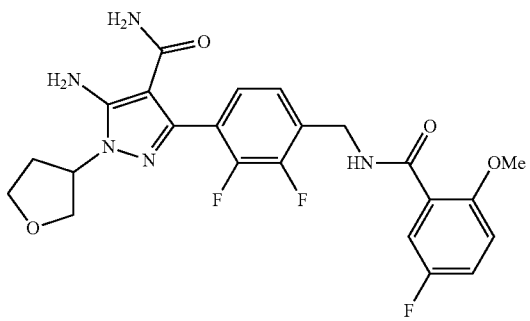

Tetrahydrofuran-3-ylhydrazine hydrochloride

To a solution of 3-hydroxytetrahydrofuran (2.8 mL, 34.0 mmol) in toluene (40 mL), under nitrogen, was added triphenylphosphine (13.4 g, 51.1 mmol) and di-tert-butylazodicarboxylate (9.4 g, 40.9 mmol). The reaction mixture was stirred at RT for 60 h. The reaction mixture was concentrated then suspended in MeOH (100 mL), followed by addition of a hydrogen chloride solution (4 M in dioxane, 68.1 mL, 272.4 mmol). The reaction mixture was stirred at RT for 16 h, filtered, and the filtrate was concentrated under reduced pressure. EtOAc was then added to the residue, filtered and washed with EtOAc to afford crude titled compound (6.7 g, 48.1 mmol) as a yellow solid. $^1$H NMR (400 MHz, DMSO-$d_6$, δ): 3.91-3.61 (m, 5H), 2.12-1.86 (m, 2H).

5-Amino-3-(4-chloro-2,3-difluoro-phenyl)-1-tetrahydrofuran-3-yl-pyrazole-4-carbonitrile A modified general procedure H at RT, 2-[(4-chloro-2,3-difluoro-phenyl)-methoxy-methylene]propanedinitrile (0.59 mmol) and tetrahydrofuran-3-ylhydrazine hydrochloride (0.88 mmol) afforded, after purification, the titled compound (0.18 mmol) as a yellow gum. UPLC-MS (ES$^+$, Short acidic): 1.73 min, m/z 325.0 [M]$^+$

N-[[4-(5-Amino-4-cyano-1-tetrahydrofuran-3-yl-pyrazol-3-yl)-2,3-difluoro-phenyl]methyl]-5-fluoro-2-methoxy-benzamide Following general procedure K, 5-amino-3-(4-chloro-2,3-difluoro-phenyl)-1-tetrahydrofuran-3-yl-pyrazole-4-carbonitrile (60 mg, 0.18 mmol) and potassium trifluoro-[[(5-fluoro-2-methoxy-benzoyl)amino]methyl]boranuide (159 mg, 0.55 mmol) afforded, after purification, the titled compound (0.18 mmol) as a yellow gum. UPLC-MS (ES$^+$, Short acidic): 1.69 min, m/z 472.1 [M+H]$^+$

5-Amino-3-[2,3-difluoro-4-[[(5-fluoro-2-methoxy-benzoyl)amino]methyl]phenyl]-1-tetrahydrofuran-3-yl-pyrazole-4-carboxamide Following general procedure M, N-[[4-(5-amino-4-cyano-1-tetrahydrofuran-3-yl-pyrazol-3-yl)-2,3-difluoro-phenyl]methyl]-5-fluoro-2-methoxy-benzamide (94 mg, 0.20 mmol) afforded, after purification, the titled compound (26 mg, 0.05 mmol, 24% yield) as a yellow solid. UPLC-MS (ES$^+$, Short acidic): 1.41 min, m/z 490.1 [M+H]$^+$ UPLC-MS (ES$^+$, Long acidic): 3.23 min, m/z 490.1 [M+H]$^+$ $^1$H NMR (400 MHz, DMSO-$d_6$, δ): 8.86 (t, J=6.0 Hz, 1H), 7.51-7.47 (m, 1H), 7.38-7.30 (m, 1H), 7.25-7.15 (m, 3H), 6.32 (s, 2H), 4.97-4.90 (m, 1H), 4.58 (d, J=6.0 Hz, 2H), 4.00-3.86 (m, 5H), 3.81-3.75 (m, 2H), 2.28-2.18 (m, 2H).

Example 183: 5-amino-3-[4-[[(5-fluoro-2-methoxy-benzoyl)amino]methyl]phenyl]-1-[(3R)-tetrahydro-pyran-3-yl]pyrazole-4-carboxamide

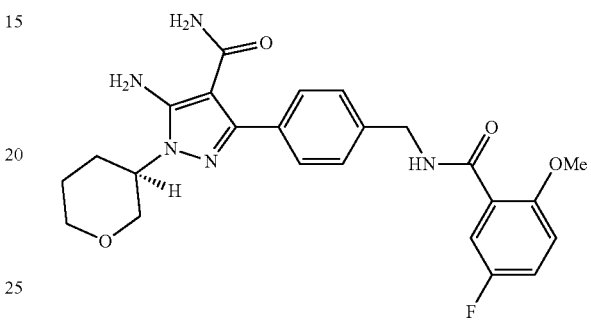

[(3R)-Tetrahydropyran-3-yl]hydrazine

To a solution of (S)-tetrahydro-2H-pyran-3-ol (0.46 mL, 4.9 mmol) in toluene (9 mL) was added triphenylphosphine (1.93 g, 7.34 mmol) and di-tert-butylazodicarboxylate (1.35 g, 5.87 mmol). The reaction mixture was stirred at RT under nitrogen for 16 h. The reaction mixture was concentrated and MeOH (21 mL) was added followed by a hydrogen chloride solution (4 M in dioxane, 9.8 mL, 39.17 mmol). The reaction mixture was stirred at RT for 16 h. The reaction mixture was then filtered and the filtrate was concentrated under reduced pressure. The resulting residue was then recrystalised from EtOAc, purified by SCX column eluting with NH$_3$ (7 M solution in MeOH), and concentrated under reduced pressure to give crude [(3R)-tetrahydropyran-3-yl]hydrazine (0.09 g, 0.77 mmol, 16% yield) as a yellow oil.

$^1$H NMR (400 MHz, DMSO-$d_6$, δ): 3.90-3.82 (m, 1H), 3.71-3.61 (m, 1H), 3.34-3.22 (m, 1H), 3.13-3.04 (m, 1H), 2.65-2.50 (m, 1H), 1.90-1.77 (m, 1H), 1.69-1.55 (m, 1H), 1.51-1.35 (m, 1H), 1.33-1.20 (m, 1H).

5-Amino-3-(4-bromophenyl)-1-[(3R)-tetrahydropyran-3-yl]pyrazole-4-carbonitrile Following general procedure H, 2-[(4-bromophenyl)-methoxy-methylene]propanedinitrile (166 mg, 0.63 mmol), and [(3R)-tetrahydropyran-3-yl]hydrazine (88 mg, 0.76 mmol) gave, after purification, titled compound (110 mg, 0.32 mmol, 42% yield). UPLC-MS (ES$^+$, Short acidic): 1.76 min, 347.0 m/z [M]$^+$

N-[[4-[5-Amino-4-cyano-1-[(3R)-tetrahydropyran-3-yl]pyrazol-3-yl]phenyl]methyl]-5-fluoro-2-methoxy-benzamide Following general procedure K, potassium trifluoro-[[(5-fluoro-2-methoxy-benzoyl)amino]methyl]boranuide (210 mg, 0.73 mmol), and 5-amino-3-(4-bromophenyl)-1-[(3R)-tetrahydropyran-3-yl]pyrazole-4-carbonitrile (150 mg, 0.43 mmol) gave, after purification, titled compound (0.25 mmol) as an off-white solid. UPLC-MS (ES⁺, Short acidic): 1.60 min, 450.1 m/z [M+H]⁺

5-Amino-3-[4-[[(5-fluoro-2-methoxy-benzoyl)amino]methyl]phenyl]-1-[(3R)-tetrahydropyran-3-yl]pyrazole-4-carboxamide Following general procedure M, N-[[4-[5-amino-4-cyano-1-[(3R)-tetrahydropyran-3-yl]pyrazol-3-yl]phenyl]methyl]-5-fluoro-2-methoxy-benzamide (112 mg, 0.25 mmol) gave, after purification, titled compound (29 mg, 0.06 mmol, 25% yield) as a white solid. UPLC-MS (ES+, Short acidic): 1.39 min, 468.1 m/z [M+H]⁺ UPLC-MS (ES+, Long acidic): 3.19 min, 468.1 m/z [M+H]⁺

$^1$H NMR (400 MHz, DMSO-$d_6$, δ): 8.84 (t, J=6.1 Hz, 1H), 7.52 (dd, J=9.2, 3.3 Hz, 1H), 7.46 (d, J=8.1 Hz, 2H), 7.41 (d, J=8.2 Hz, 2H), 7.38-7.30 (m, 1H), 7.19 (dd, J=9.1, 4.3 Hz, 1H), 6.22 (s, 2H), 4.55 (d, J=6.1 Hz, 2H), 4.22-4.14 (m, 1H), 4.00-3.96 (m, 2H), 3.90 (s, 3H), 3.83-3.76 (m, 1H), 3.67-3.60 (m, 1H), 1.99-1.87 (m, 1H), 1.87-1.74 (m, 2H), 1.74-1.61 (m, 1H).

Example 184: 5-amino-3-[4-[[(5-fluoro-2-methoxy-benzoyl)amino]methyl]phenyl]-1-(2,2,2-trifluoro-1-tetrahydropyran-4-yl-ethyl)pyrazole-4-carboxamide

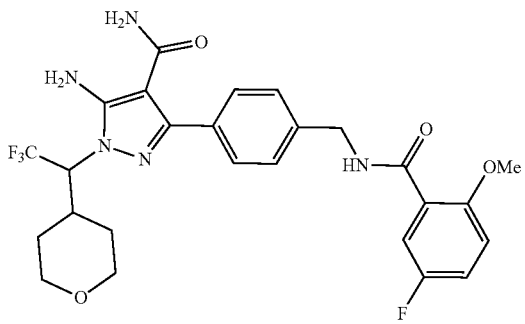 [SMILES: COc1ccc(F)cc1C(=O)NCc1ccc(-c2nn(C(C3CCOCC3)C(F)(F)F)c(N)c2C(N)=O)cc1]

N-[(2,2,2-Trifluoro-1-tetrahydropyran-4-yl-ethylidene)amino]benzamide

A mixture of magnesium (1.2 g, 45.4 mmol) and iodine (23 mg, 0.09 mmol) in THF (7 mL) was heated to 60° C. Following activation, the mixture was cooled to RT and a solution 4-bromotetrahydro-2H-pyran (1.02 mL, 9.09 mmol) in THF (2 mL) was added dropwise. The mixture was heated to reflux for 1 h, and then cooled to RT. The preformed reagent was then added to a solution of N-methoxy-N-methyltrifluoroacetamide (0.82 mL, 6.82 mmol) in THF (2 mL) at 0° C. The reaction mixture was stirred at 0° C. for 1 h, quenched with saturated aqueous solution of NH₄Cl and partitioned with diethyl ether. The aqueous layer was extracted with Et₂O. The combined organic layers were dried over sodium sulfate, filtered and Et₂O was removed under reduced pressure to give a THF solution of 2,2,2-trifluoro-1-tetrahydropyran-4-yl-ethanone (assumed quantitative yield). Following general procedure S, the previously prepared solution of benzohydrazide and 2,2,2-trifluoro-1-tetrahydropyran-4-yl-ethanone (0.15 mL, 9.09 mmol) gave, after 48 h and further purification by flash column chromatography on silica gel eluting with 0-100% EtOAc in heptane, N-[(2,2,2-trifluoro-1-tetrahydropyran-4-yl-ethylidene)amino]benzamide (300 mg, 1.00 mmol, 11% yield).

UPLC-MS (ES⁺, Short acidic): 1.60 min, m/z 301.0 [M+H]⁺

N'-(2,2,2-Trifluoro-1-tetrahydropyran-4-yl-ethyl)benzohydrazide

Following general procedure T, N-[(2,2,2-trifluoro-1-tetrahydropyran-4-yl-ethylidene)amino]benzamide (403 mg, 1.34 mmol) gave, after purification, titled compound (168 mg, 0.56 mmol, 41% yield). UPLC-MS (ES⁺, Short acidic): 1.56 min, m/z 303.0 [M+H]⁺

(2,2,2-Trifluoro-1-tetrahydropyran-4-yl-ethyl)hydrazine hydrochloride

Following procedure U, N'-(2,2,2-trifluoro-1-tetrahydropyran-4-yl-ethyl)benzohydrazide (168 mg, 0.56 mmol) gave, after 48 h, (titled compound (85 mg, 0.36 mmol, 65% yield) as a white solid. $^1$H NMR (400 MHz, DMSO-$d_6$, δ): 3.91-3.83 (m, 2H), 3.72-3.61 (m, 1H), 3.35-3.22 (m, 2H), 2.07-1.95 (m, 1H), 1.67-1.52 (m, 3H), 1.50-1.36 (m, 1H).

5-Amino-3-(4-bromophenyl)-1-(2,2,2-trifluoro-1-tetrahydropyran-4-yl-ethyl)pyrazole-4-carbonitrile Following a modified general procedure H at RT, 2-[(4-bromophenyl)-methoxy-methylene]propanedinitrile (80 mg, 0.30 mmol) and (2,2,2-trifluoro-1-tetrahydropyran-4-yl-ethyl)hydrazine hydrochloride (85 mg, 0.36 mmol) afforded crude titled compound (146 mg, 0.34 mmol, assumed quantitative yield).

UPLC-MS (ES⁺, Short acidic) 1.93 min, m/z 428.9 [M]⁺

N-[[4-[5-Amino-4-cyano-1-(2,2,2-trifluoro-1-tetrahydropyran-4-yl-ethyl)pyrazol-3-yl]phenyl]methyl]-5-fluoro-2-methoxy-benzamide Following general procedure K, 5-amino-3-(4-bromophenyl)-1-(2,2,2-trifluoro-1-tetrahydropyran-4-yl-ethyl)pyrazole-4-carbonitrile (130 mg, 0.30 mmol) and potassium trifluoro-[[(5-fluoro-2-methoxy-benzoyl)amino]methyl]boranuide (193 mg, 0.67 mmol) gave crude titled compound (160 mg, 0.30 mmol, quantitative yield).

UPLC-MS (ES⁺, Short acidic): 1.71 min, m/z 532.2 [M+H]⁺

5-Amino-3-[4-[[(5-fluoro-2-methoxy-benzoyl)amino]methyl]phenyl]-1-(2,2,2-trifluoro-1-tetrahydropyran-4-yl-ethyl)pyrazole-4-carboxamide Following general procedure M, N-[[4-[5-amino-4-cyano-1-(2,2,2-trifluoro-1-tetrahydropyran-4-yl-ethyl)pyrazol-3-yl]phenyl]methyl]-5-fluoro-2-methoxy-benzamide (160 mg, 0.30 mmol) afforded, after purification by flash column chromatography on silica gel eluting with 0-6% MeOH in DCM and further purification by mass directed semi-preparative HPLC, titled compound (0.02 mmol). UPLC-MS (ES⁺, Short acidic): 1.55 min, m/z 550.2 [M+H]⁺ UPLC-MS (ES⁺, Long acidic): 3.61 min, m/z 550.2 [M+H]⁺

$^1$H NMR (400 MHz, DMSO-$d_6$, δ): 8.83 (t, J=6.1 Hz, 1H), 7.51 (dd, J=9.2, 3.3 Hz, 1H), 7.48-7.40 (m, 4H), 7.37-7.30 (m, 1H), 7.19 (dd, J=9.2, 4.3 Hz, 1H), 6.71 (br s, 2H), 5.06-4.98 (m, 1H), 4.55 (d, J=6.1 Hz, 2H), 3.89 (s, 3H), 3.89-3.77 (m, 2H), 3.37-3.22 (m, 2H), 2.68-2.42 (m, 1H), 1.81-1.17 (m, 1H), 1.54-1.43 (m, 1H), 1.34-1.21 (m, 1H), 1.10-1.01 (m, 1H).

Example 185: 5-amino-1-cyclopentyl-3-[4-[2-hydroxy-1-[(2-methoxybenzoyl)amino]ethyl]-3-methyl-phenyl]pyrazole-4-carboxamide

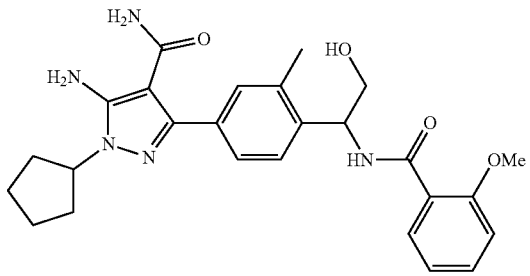 [SMILES: COc1ccccc1C(=O)NC(CO)c1ccc(-c2nn(C3CCCC3)c(N)c2C(N)=O)cc1C]

2-Bromo-1-(4-bromo-2-methyl-phenyl)ethanone

To a solution of 1-(4-bromo-2-methylphenyl)ethanone (2.0 g, 9.39 mmol) in MeCN (40 mL) was added N-bromosuccinimide (1.7 g, 9.57 mmol) and p-toluenesulfonic acid monohydrate (1.8 g, 9.39 mmol). The reaction was stirred at 50° C. for 18 h, concentrated and after work-up afforded the titled compound (9.39 mmol). UPLC-MS (ES$^+$, Short acidic): 1.91 min, m/z 292.8 [M+H]$^+$ 1-(4-Bromo-2-methyl-phenyl)-2-hydroxy-ethanone To a solution of 2-bromo-1-(4-bromo-2-methyl-phenyl) ethanone (9.4 mmol) in MeOH (30 mL) was added cesium formate hydrate (28.2 mmol) and the solution was stirred at 80° C. for 4 h. Following work-up the titled compound was afforded (10.3 mmol). UPLC-MS (ES$^+$, Short acidic): 1.53 min, m/z 230.8 [M+2]$^+$ 1-(4-Bromo-2-methyl-phenyl)-2-[tert-butyl(dimethyl)silyl]oxy-ethanone To a solution of 1-(4-bromo-2-methyl-phenyl)-2-hydroxy-ethanone (2.15 g, 9.39 mmol) in DCM (30 mL) was added imidazole (959 mg, 14.1 mmol). The solution was cooled to 0° C. followed by dropwise addition of tert-butylchlorodimethylsilane (2.00 mL, 14.1 mmol) in DCM (10 mL). The solution was then stirred at 0° C. for 30 min then stirred at RT for 18 h. Work up and purification afforded titled compound (2.22 g, 6.47 mmol) as a colourless oil. UPLC-MS (ES$^+$, Short acidic): 2.43 min, m/z 345.0 [M+2]$^+$ 1-(4-Bromo-2-methyl-phenyl)-2-[tert-butyl(dimethyl)silyl]oxy-ethanol Sodium borohydride (32.3 mmol) was added to a solution of 1-(4-bromo-2-methyl-phenyl)-2-[tert-butyl(dimethyl)silyl]oxy-ethanone (6.47 mmol) in MeOH (20 mL) at 0° C. The reaction was stirred at 0° C. for 1 h then stirred at RT for 3.5 h. Work up and purification gave titled compound (6.26 mmol).
$^1$H NMR (400 MHz, CDCl$_3$, δ): 7.40-7.38 (m, 1H), 7.33-7.36 (m, 1H), 7.28-7.29 (m, 1H), 4.89-4.95 (m, 1H), 3.75-3.68 (m, 1H), 3.50-3.40 (m, 1H), 2.33-2.27 (m, 3H), 0.92 (s, 9H), 0.07 (s, 6H).

2-[1-(4-Bromo-2-methyl-phenyl)-2-[tert-butyl(dimethyl)silyl]oxy-ethyl]isoindoline-1,3-dione Phthalimide (1.06 g, 7.20 mmol) and triphenylphosphine (1.89 g, 7.20 mmol) was added to 1-(4-bromo-2-methyl-phenyl)-2-[tert-butyl(dimethyl)silyl]oxy-ethanol (2.16 g, 6.26 mmol) in THF (10 mL) at 0° C. A solution of diisopropyl azodicarboxylate (1.4 mL, 7.20 mmol) in THF (10 mL) was added dropwise to the reaction. The reaction was stirred at 0° C. for 30 min then stirred at RT for 66 h. Work up and purification by flash column chromatography on silica gel eluting with 0-20% EtOAc in heptane afforded 2-[1-(4-bromo-2-methyl-phenyl)-2-[tert-butyl(dimethyl)silyl]oxy-ethyl]isoindoline-1,3-dione (1.55 g, 3.26 mmol, 52% yield) as a yellow oil, and 2-[2-(4-bromo-2-methyl-phenyl)-2-[tert-butyl(dimethyl)silyl]oxy-ethyl]isoindoline-1,3-dione (901 mg, 1.90 mmol, 30% yield) as a white solid.

2-[1-(4-Bromo-2-methyl-phenyl)-2-[tert-butyl(dimethyl)silyl]oxy-ethyl]isoindoline-1,3-dione UPLC-MS (ES$^-$, Short acidic): 2.50 min, m/z 476.0 [M+2]$^+$ 2-[2-(4-Bromo-2-methyl-phenyl)-2-[tert-butyl(dimethyl)silyl]oxy-ethyl]isoindoline-1,3-dione UPLC-MS (ES$^+$, Short acidic): 2.48 min, m/z 476.1 [M+2]$^+$ 2-[1-(4-Bromo-2-methyl-phenyl)-2-[tert-butyl(dimethyl)silyl]oxy-ethyl]isoindoline-1,3-dione Hydrazine hydrate (55-60% in water, 0.26 mL, 5.27 mmol) was added dropwise to a solution of 2-[1-(4-bromo-2-methyl-phenyl)-2-[tert-butyl(dimethyl)silyl]oxy-ethyl] isoindoline-1,3-dione (500 mg, 1.05 mmol) in EtOH (5 mL). The reaction was heated to 80° C. for 1.5 h, cooled to RT and filtered. The filtrate was concentrated under reduced pressure and purification by SCX eluting with 1 M NH$_3$ in MeOH afforded titled compound (243 mg, 0.70 mmol, 67% yield).
$^1$H NMR (400 MHz, DMSO-d$_6$, δ): 7.43 (d, J=8.1 Hz, 1H), 7.31-7.36 (m, 2H), 4.11 (dd, J=6.9, 5.6 Hz, 1H), 3.44-3.56 (m, 2H), 2.29 (s, 3H), 0.81 (s, 9H), −0.05 (s, 3H), −0.06 (s, 3H), N-[1-(4-bromo-2-methyl-phenyl)-2-[tert-butyl(dimethyl)silyl]oxy-ethyl]-2-methoxy-benzamide To a solution of 1-(4-bromo-2-methyl-phenyl)-2-[tert-butyl(dimethyl)silyl]oxy-ethanamine (0.710 mmol) in THF (3 mL) was added N,N-diisopropylethylamine (2.12 mmol). 2-Methoxybenzoyl chloride (0.78 mmol) was added to the reaction at 0° C. The reaction was stirred at 0° C. for 20 min then stirred at RT for 66 h and quenched with saturated aqueous solution of NH$_4$Cl. Work-up and purification afforded titled compound (0.38 mmol). UPLC-MS (ES$^+$, Short acidic): 2.44 min, m/z 480.1 [M+2]$^+$ N-[2-[tert-Butyl(dimethyl)silyl]oxy-1-[2-methyl-4-(4,4,5,5-tetramethyl-1,3,2-dioxaborolan-2-yl)phenyl]ethyl]-2-methoxy-benzamide Following general procedure R, N-[1-(4-bromo-2-methyl-phenyl)-2-[tert-butyl(dimethyl)silyl]oxy-ethyl]-2- methoxy-benzamide (183 mg, 0.38 mmol) gave, after purification, the titled compound (146 mg, 0.28 mmol, 73% yield).

UPLC-MS (ES+, Short acidic): 2.51 min, m/z 526.3 [M+H]+

5-Amino-3-[4-[2-[tert-butyl(dimethyl)silyl]oxy-1-[(2-methoxybenzoyl)amino]ethyl]-3-methyl-phenyl]-1-cyclopentyl-pyrazole-4-carboxamide Following general procedure D, N-[2-[tert-butyl(dimethyl)silyl]oxy-1-[2-methyl-4-(4,4,5,5-tetramethyl-1,3,2-dioxaborolan-2-yl)phenyl]ethyl]-2-methoxy-benzamide (150 mg, 0.29 mmol) and 5-amino-3-bromo-1-cyclopentyl-pyrazole-4-carboxamide (74 mg, 0.27 mmol) afforded, following further purification, the titled compound (0.27 mmol). UPLC-MS (ES+, Short acidic): 2.25 min, m/z 592.3 [M+H]+

5-Amino-1-cyclopentyl-3-[4-[2-hydroxy-1-[(2-methoxybenzoyl)amino]ethyl]-3-methyl-phenyl]pyrazole-4-carboxamide A tetrabutylammonium fluoride solution (1 M in THF, 84 µL, 0.291 mmol) was added dropwise to a solution of 5-amino-3-[4-[2-[tert-butyl(dimethyl)silyl]oxy-1-[(2-methoxybenzoyl)amino]ethyl]-3-methyl-phenyl]-1-cyclopentyl-pyrazole-4-carboxamide (0.27 mmol) in THF (1.5 mL) at 0° C. The reaction was stirred at 0° C. for 3 h then partitioned between DCM and water. The organic layer was washed with brine, dried over sodium sulfate, filtered and concentrated under reduced pressure. Further purification by flash column chromatography on silica gel eluting with 0-5% MeOH in DCM followed by mass-directed semi-preparative HPLC afforded titled compound (0.06 mmol). UPLC-MS (ES+, Short acidic): 1.42 min, m/z 478.1 [M+H]+
UPLC-MS (ES+, Long acidic): 3.29 min, m/z 478.2 [M+H]+
1H NMR (400 MHz, DMSO-d6, δ): 8.69 (d, J=7.6 Hz, 1H), 7.73 (dd, J=7.6, 1.9 Hz, 1H), 7.52-7.46 (m, 1H), 7.42-7.39 (m, 1H), 7.30-7.25 (m, 2H), 7.18 (d, J=8.4 Hz, 1H), 7.08-7.01 (m, 1H), 6.33 (s, 2H), 5.32-5.23 (m, 1H), 5.03 (t, J=5.5 Hz, 1H), 4.65-4.55 (m, 1H), 3.95 (s, 3H), 3.71-3.58 (m, 2H), 2.45 (s, 3H), 2.01-1.84 (m, 4H), 1.83-1.72 (m, 2H), 1.63-1.52 (m, 2H).

Example 186: 5-amino-1-(3,3-difluoro-4-piperidyl)-3-[4-[[(5-fluoro-2-methoxy-benzoyl)amino]methyl]phenyl]pyrazole-4-carboxamide

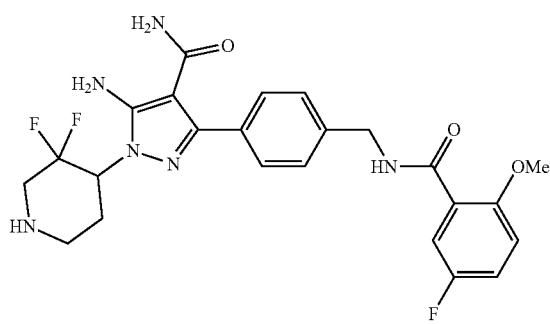 [SMILES: COc1ccc(F)cc1C(=O)NCc1ccc(-c2nn(C3CCNCC3(F)F)c(N)c2C(N)=O)cc1]

tert-Butyl 3,3-difluoro-4-oxo-piperidine-1-carboxylate

Di-tert-butyl dicarbonate (1.19 g, 5.44 mmol) was added to a solution of 1-benzyl-3,3-difluoropiperidin-4-one (995 mg, 4.42 mmol) in EtOH (60 mL) under nitrogen. Palladium hydroxide (Pd 20% on carbon, 148 mg, 1.05 mmol) was added and the system was evacuated and flushed with hydrogen several times. The mixture was stirred at RT for 20 h under hydrogen. The residual hydrogen was removed and the mixture was filtered over Celite®, and washed with EtOH. Purification gave titled compound (810 mg, 3.44 mmol, 78% yield) as a white solid.
1H NMR (400 MHz, DMSO-d6, δ): 3.66-3.52 (m, 2H), 3.39-3.33 (m, 2H), 1.69-1.64 (m, 2H), 1.38 (s, 9H)

tert-Butyl 4-(benzoylhydrazono)-3,3-difluoro-piperidine-1-carboxylate

Following general procedure S, tert-butyl 3,3-difluoro-4-oxo-piperidine-1-carboxylate (650 mg, 2.76 mmol) in toluene (2 mL) and benzhydrazide (300 mg, 2.20 mmol) gave, after purification, titled compound (2.00 mmol) as a white solid. UPLC-MS (ES+, Short acidic): 1.63 min, m/z 354.1 [M+H]+ tert-Butyl 4-(2-benzoylhydrazino)-3,3-difluoro-piperidine-1-carboxylate

Following general procedure T, tert-butyl 4-(benzoylhydrazono)-3,3-difluoro-piperidine-1-carboxylate (250 mg, 0.71 mmol) gave crude b titled compound (265 mg, 0.75 mmol, assumed quantitative yield) as colourless oil. UPLC-MS (ES+, Short acidic): 1.62 min, m/z 356.1 [M+H]+

(3,3-Difluoro-4-piperidyl)hydrazine dihydrochloride

Following general procedure U, tert-butyl 4-(2-benzoylhydrazino)-3,3-difluoro-piperidine-1-carboxylate (0.73 mmol) gave, after washing with hot EtOAc, the titled compound as a pale yellow solid.
1H NMR (400 MHz, DMSO-d6, δ): 5.97 (m, 1H), 3.68-3.45 (m, 3H), 3.23-3.17 (m, 1H), 3.10-3.01 (m, 1H), 2.27-2.20 (m, 1H), 1.90-1.80 (m, 1H).

5-Amino-3-(4-bromophenyl)-1-(3,3-difluoro-4-piperidyl)pyrazole-4-carbonitrile Following general procedure H, 2-[(4-bromophenyl)methoxy-methylene]propanedinitrile (160 mg, 0.61 mmol) and (3,3-difluoro-4-piperidyl)hydrazine dihydrochloride (170 mg, 0.76 mmol) were stirred for 2 h at 85° C. Work-up and purification afforded the titled compound (126 mg, 0.33 mmol, 54% yield) as a red solid. UPLC-MS (ES+, Short acidic): 1.29 min, m/z 383.9 [M+2]+

N-[[4-[5-Amino-4-cyano-1-(3,3-difluoro-4-piperidyl)pyrazol-3-yl]phenyl]methyl]-5-fluoro-2-methoxy-benzamide Following general procedure K, 5-amino-3-(4-bromophenyl)-1-(3,3-difluoro-4-piperidyl)pyrazole-4-carbonitrile (121 mg, 0.32 mmol) and potassium trifluoro-[[(5-fluoro-2-methoxy-benzoyl)amino]methyl]boranuide (158 mg, 0.55 mmol) gave, after purification, the titled compound (99 mg, 0.20 mmol, 65% yield) as a yellow solid. UPLC-MS (ES+, Short acidic): 1.29 min, m/z 485.1 [M+H]+

5-Amino-1-(3,3-difluoro-4-piperidyl)-3-[4-[[(5-fluoro-2-methoxy-benzoyl)amino]methyl]phenyl]pyrazole-4-carboxamide Following general procedure M, N-[[4-[5-amino-4-cyano-1-(3,3-difluoro-4-piperidyl)pyrazol-3-yl]phenyl]

methyl]-5-fluoro-2-methoxy-benzamide (89 mg, 0.18 mmol) gave, after purification, the titled compound (64 mg, 0.13 mmol, 69% yield) as a light yellow solid. UPLC-MS (ES+, Short acidic): 1.16 min, m/z 503.2 [M+H]+ UPLC-MS (ES+, Long acidic): 2.54 min, m/z 503.1 [M+H]+

$^1$H NMR (400 MHz, DMSO-d$_6$, δ): 8.84 (t, J=6.0 Hz, 1H), 7.52 (dd, J=9.2, 3.3 Hz, 1H), 7.48-7.41 (m, 4H), 7.37-7.32 (m, 1H), 7.19 (dd, J=9.2, 4.3 Hz, 1H), 6.42 (s, 2H), 4.86-4.75 (m, 1H), 4.56 (d, J=6.0 Hz, 2H), 3.90 (s, 3H), 3.30-3.21 (m, 1H), 3.14-3.11 (m, 1H), 2.99-2.88 (m, 1H), 2.69-2.64 (m, 1H), 2.43-2.36 (m, 1H), 1.95-1.89 (m, 1H).

Example 187: 5-amino-1-cyclopentyl-3-[4-[1-hydroxy-2-[(2-methoxybenzoyl)amino]ethyl]-3-methyl-phenyl]pyrazole-4-carboxamide

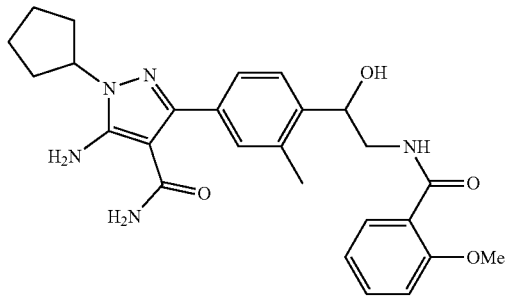 [SMILES: COc1ccccc1C(=O)NCC(O)c1ccc(-c2nn(C3CCCC3)c(N)c2C(N)=O)cc1C]

2-(4-Bromo-2-methyl-phenyl)-2-[tert-butyl(dimethyl)silyl]oxy-ethanamine

Hydrazine hydrate (55-60% in water, 0.26 mL, 5.27 mmol) was added dropwise to a solution of 2-[2-(4-bromo-2-methyl-phenyl)-2-[tert-butyl(dimethyl)silyl]oxy-ethyl]isoindoline-1,3-dione (500 mg, 1.05 mmol) in EtOH (5 mL). The reaction was heated to 80° C. for 1.5 h, cooled to RT, filtered and concentrated under reduced pressure to crude titled compound (324 mg, 0.94 mmol, 89% yield).

$^1$H NMR (400 MHz, DMSO-d$_6$, δ): 7.39-7.33 (m, 2H), 7.28 (d, J=8.3 Hz, 1H), 4.73 (dd, J=7.5, 3.9 Hz, 1H), 2.59 (dd, J=13.0, 3.9 Hz, 1H), 2.51-2.40 (m, 1H), 2.28 (s, 3H), 0.84 (s, 9H), 0.04 (s, 3H), −0.13 (s, 3H).

N-[2-(4-Bromo-2-methyl-phenyl)-2-[tert-butyl(dimethyl)silyl]oxy-ethyl]-2-methoxy-benzamide To a solution of 2-(4-bromo-2-methyl-phenyl)-2-[tert-butyl(dimethyl)silyl]oxy-ethanamine (324 mg, 0.94 mmol) in THF (5 mL) was added N,N-diisopropylethylamine (0.5 mL, 2.82 mmol). The reaction mixture was cooled down to 0° C. followed by addition of 2-methoxybenzoyl chloride (0.15 mL, 1.04 mmol). The reaction was stirred at 0° C. for 20 min then stirred at RT for 66 h. Work up and purification afforded the titled compound (0.61 mmol). UPLC-MS (ES+, Short acidic): 2.47 min, m/z 480.1 [M+2]+

N-[2-[tert-Butyl(dimethyl)silyl]oxy-2-[2-methyl-4-(4,4,5,5-tetramethyl-1,3,2-dioxaborolan-2-yl)phenyl]ethyl]-2-methoxy-benzamide Following general procedure R, N-[2-(4-bromo-2-methyl-phenyl)-2-[tert-butyl(dimethyl)silyl]oxy-ethyl]-2-methoxy-benzamide (293 mg, 0.61 mmol) afforded, following purification, titled compound (286 mg, 0.54 mmol, 89% yield). UPLC-MS (ES+, Short acidic): 2.51 min, m/z 526.3 [M+H]+

5-Amino-3-[4-[1-[tert-butyl(dimethyl)silyl]oxy-2-[(2-methoxybenzoyl)amino]ethyl]-3-methyl-phenyl]-1-cyclopentyl-pyrazole-4-carboxamide Following general procedure D, N-[2-[tert-butyl(dimethyl)silyl]oxy-2-[2-methyl-4-(4,4,5,5-tetramethyl-1,3,2-dioxaborolan-2-yl)phenyl]ethyl]-2-methoxy-benzamide (0.54 mmol) afforded, after purification, titled compound (0.43 mmol, 77% yield). UPLC-MS (ES+, Short acidic): 2.24 min, m/z 592.3 [M+H]+

5-Amino-1-cyclopentyl-3-[4-[1-hydroxy-2-[(2-methoxybenzoyl)amino]ethyl]-3-methyl-phenyl]pyrazole-4-carboxamide A tetrabutylammonium fluoride solution (1 M in THF, 0.14 mL, 0.480 mmol) was added dropwise to a solution of 5-amino-3-[4-[1-[tert-butyl(dimethyl)silyl]oxy-2-[(2-methoxybenzoyl)amino]ethyl]-3-methyl-phenyl]-1-cyclopentyl-pyrazole-4-carboxamide (256 mg, 0.43 mmol) in THF (2 mL) at 0° C. The reaction was stirred for 3 h before being allowed to warm to RT and partitioned between DCM and water. Work-up and purification afforded titled compound (103 mg, 0.22 mmol, 50% yield). UPLC-MS (ES+, Short acidic): 1.46 min, m/z 478.1 [M+H]+ UPLC-MS (ES+, Long acidic): 3.39 min, m/z 478.2 [M+H]+

$^1$H NMR (400 MHz, DMSO-d$_6$, δ): 8.34 (t, J=5.7 Hz, 1H), 7.86 (dd, J=7.8, 1.7 Hz, 1H), 7.57 (d, J=8.0 Hz, 1H), 7.52-7.45 (m, 1H), 7.31 (d, J=8.0 Hz, 1H), 7.25 (s, 1H), 7.15 (d, J=8.3 Hz, 1H), 7.05 (t, J=7.3 Hz, 1H), 6.33 (s, 2H), 5.55 (d, J=4.3 Hz, 1H), 5.03-4.96 (m, 1H), 4.65-4.55 (m, 1H), 3.89 (s, 3H), 3.69-3.60 (m, 1H), 3.31-3.23 (m, 1H), 2.38 (s, 3H), 2.02-1.84 (m, 4H), 1.84-1.72 (m, 2H), 1.64-1.52 (m, 2H).

Example 188: 5-amino-1-(1-cyclopropyl-2,2,2-trifluoro-ethyl)-3-[4-[[(5-fluoro-2-methoxy-benzoyl)amino]methyl]phenyl]pyrazole-4-carboxamide

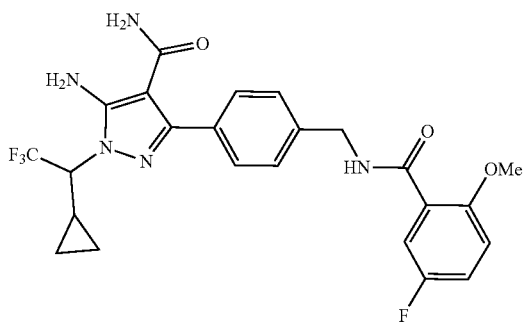 [SMILES: COc1ccc(F)cc1C(=O)NCc1ccc(-c2nn(C(C3CC3)C(F)(F)F)c(N)c2C(N)=O)cc1]

N-[2,2,2-Trifluoroethylideneamino]benzamide

To a solution of 2,2,2-trifluoro-1-methoxy-ethanol (0.74 mL, 7.69 mmol) in EtOH (26 mL) was added benzhydrazide (1.26 g, 9.23 mmol) and molecular sieve. The reaction mixture was heated to 80° C. for 16 h. Filtration through a pad of Celite® and purification gave the titled compound (1.16 g, 5.35 mmol, 70% yield) as a white solid. UPLC-MS (ES+, Short acidic): 1.39 min, m/z 216.9 [M+H]+

N'-(1-Cyclopropyl-2,2,2-trifluoro-ethyl)benzohydrazide

To a solution of N-[2,2,2-trifluoroethylideneamino]benzamide (2.31 mmol) in THF (15 mL) at 0° C. was added a cyclopropylmagnesium bromide solution (0.5 M in THF, 10 mL). The reaction was stirred at RT for 16 h. Additional cyclopropylmagnesium bromide solution (0.5 M in THF, 10 mL) was added and the reaction was stirred for another 5 h. The reaction was quenched with a saturated aqueous solution of NH$_4$Cl and extracted with EtOAc. Work-up and purification afforded titled compound (508 mg, 1.97 mmol, 85% yield) as a yellow oil. LC-MS (ES+, Short acidic): 5.17 min, m/z 259.2 [M+H]+

(1-Cyclopropyl-2,2,2-trifluoro-ethyl)hydrazine hydrochloride

To a solution of hydrochloric acid (12 M in water, 5.0 mL, 60 mmol) was added N-(1-cyclopropyl-2,2,2-trifluoro-ethyl)benzohydrazide (507 mg, 1.96 mmol). The reaction mixture was stirred at 80° C. for 16 h. The volatiles were removed under reduced pressure and the residue taken up in EtOAc. The solid was filtered and washed with EtOAc to give crude (1-cyclopropyl-2,2,2-trifluoro-ethyl)hydrazine hydrochloride (149 mg, 0.78 mmol, 40% yield) as a brown solid.

$^1$H NMR (400 MHz, CDCl$_3$, δ): 3.09-3.02 (m, 1H), 0.94-0.85 (m, 1H), 0.71-0.59 (m, 3H), 0.47-0.40 (m, 1H).

5-Amino-3-(4-bromophenyl)-1-(1-cyclopropyl-2,2,2-trifluoro-ethyl)pyrazole-4-carbonitrile Modified general procedure H at RT, 2-[(4-bromophenyl)-methoxy-methylene]propanedinitrile (0.57 mmol) and (1-cyclopropyl-2,2,2-trifluoro-ethyl)hydrazine hydrochloride (0.78 mmol) gave, after purification, titled compound (0.21 mmol) as a white solid. UPLC-MS (ES+, Short acidic): 1.99 min, m/z 386.9 [M+2]+

N-[[4-[5-Amino-4-cyano-1-(1-cyclopropyl-2,2,2-trifluoro-ethyl)pyrazol-3-yl]phenyl]methyl]-5-fluoro-2-methoxy-benzamide General procedure K, 5-amino-3-(4-bromophenyl)-1-(1-cyclopropyl-2,2,2-trifluoro-ethyl)pyrazole-4-carbonitrile (50 mg, 0.13 mmol) and potassium trifluoro-[[(5-fluoro-2-methoxy-benzoyl)amino]methyl]boranuide (83 mg, 0.29 mmol) gave, after purification, the titled compound (40 mg, 0.08 mmol, 63% yield) as a beige solid. LC-MS (ES+, Short acidic): 5.79 min, m/z 488.1 [M+H]+

5-Amino-1-(1-cyclopropyl-2,2,2-trifluoro-ethyl)-3-[4-[[(5-fluoro-2-methoxy-benzoyl)amino]methyl]phenyl]pyrazole-4-carboxamide Following general procedure M, N-[[4-[5-amino-4-cyano-1-(1-cyclopropyl-2,2,2-trifluoro-ethyl)pyrazol-3-yl]phenyl]methyl]-5-fluoro-2-methoxy-benzamide (40 mg, 0.08 mmol) gave, after purification by flash column chromatography on silica gel eluting with 0-20% MeOH in DCM, 5-amino-1-(1-cyclopropyl-2,2,2-trifluoro-ethyl)-3-[4-[[(5-fluoro-2-methoxy-benzoyl)amino]methyl]phenyl]pyrazole-4-carboxamide (31 mg, 0.06 mmol, 76% yield) as a beige solid.

UPLC-MS (ES+, Short acidic): 1.61 min, m/z 528.2 [M+Na]+

UPLC-MS (ES+, Long acidic): 3.76 min, m/z 506.1 [M+H]+

$^1$H NMR (400 MHz, DMSO-d$_6$, δ): 8.83 (t, J=6.0 Hz, 1H), 7.50 (dd, J=9.2, 3.3 Hz, 1H), 7.48 (d, J=8.3 Hz, 2H), 7.42 (d, J=8.3 Hz, 2H), 7.36-7.31 (m, 1H), 7.18 (dd, J=9.2, 4.2 Hz, 1H), 6.57 (s, 2H), 4.55 (d, J=6.0 Hz, 2H), 4.52-4.46 (m, 1H), 3.89 (s, 3H), 1.70-1.60 (m, 1H), 0.86-0.76 (m, 1H), 0.62-0.52 (m, 2H), 0.41-0.32 (m, 1H).

Example 189: 5-amino-3-[4-[[(5-fluoro-2-methoxy-benzoyl)amino]methyl]phenyl]-1-(2,2,2-trifluoro-1,1-dimethyl-ethyl)pyrazole-4-carboxamide

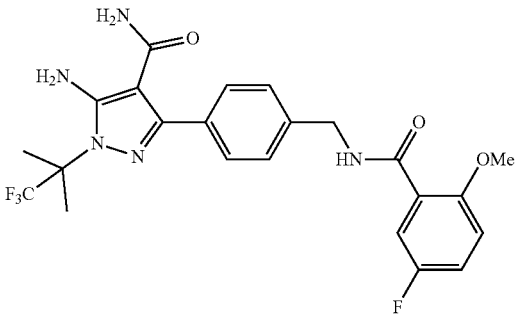 [SMILES: COc1ccc(F)cc1C(=O)NCc1ccc(-c2nn(C(C)(C)C(F)(F)F)c(N)c2C(N)=O)cc1]

N-(Isopropylideneamino)benzamide

Following general procedure S, anhydrous acetone (0.19 mL, 2.58 mmol) gave, without further purification, N-(isopropylideneamino)benzamide (450 mg, 2.55 mmol, 99% yield) as an off-white solid. UPLC-MS (ES+, Short acidic): 1.06 min, m/z 177.0 [M+H]+

N'-(2,2,2-Trifluoro-1,1-dimethyl-ethyl)benzohydrazide

Following general procedure Y, N-(isopropylideneamino)benzamide (450 mg, 2.55 mmol) gave, after purification by flash column chromatography on silica gel eluting with 0-100% EtOAc in heptane, N'-(2,2,2-trifluoro-1,1-dimethyl-ethyl)benzohydrazide (277 mg, 1.12 mmol, 44% yield) as an off-white solid.

UPLC-MS (ES+, Short acidic): 1.50 min, m/z 247.0 [M+H]+

(2,2,2-Trifluoro-1,1-dimethyl-ethyl)hydrazine hydrochloride

Following general procedure U, N'-(2,2,2-trifluoro-1,1-dimethyl-ethyl)benzohydrazide (1.12 mmol) gave, without further purification, (2,2,2-trifluoro-1,1-dimethyl-ethyl)hydrazine hydrochloride (1.43 mmol) as an off-white solid. $^1$H NMR (400 MHz, MeOD-d$_4$, δ): 1.42 (s, 6H)

5-Amino-3-(4-bromophenyl)-1-(2,2,2-trifluoro-1,1-dimethyl-ethyl)pyrazole-4-carbonitrile Following general procedure H, (2,2,2-trifluoro-1,1-dimethyl-ethyl)hydrazine hydrochloride (200 mg, 1.12 mmol)

and 2-[(4-bromophenyl)-methoxy-methylene]propanedinitrile (295 mg, 1.12 mmol) gave, crude 5-amino-3-(4-bromophenyl)-1-(2,2,2-trifluoro-1,1-dimethyl-ethyl)pyrazole-4-carbonitrile (316 mg, 0.85 mmol, 76% yield) as a yellow solid.

UPLC-MS (ES+, Short acidic): 2.02 min, m/z 375.0 [M+2]+

N-[[4-[5-Amino-4-cyano-1-(2,2,2-trifluoro-1,1-dimethyl-ethyl)pyrazol-3-yl]phenyl]methyl]-5-fluoro-2-methoxy-benzamide Following general procedure K, 5-amino-3-(4-bromophenyl)-1-(2,2,2-trifluoro-1,1-dimethyl-ethyl)pyrazole-4-carbonitrile (216 mg, 0.58 mmol) and potassium trifluoro-[[(5-fluoro-2-methoxy-benzoyl)amino]methyl]boranuide (833 mg, 2.88 mmol) gave, after purification, titled compound (250 mg, 0.52 mmol, 91% yield) as an off-white solid. UPLC-MS (ES+, Short acidic): 1.80 min, m/z 476.1 [M+H]+

5-Amino-3-[4-[[(5-fluoro-2-methoxy-benzoyl)amino]methyl]phenyl]-1-(2,2,2-trifluoro-1,1-dimethyl-ethyl)pyrazole-4-carboxamide Following general procedure M, N-[[4-[5-amino-4-cyano-1-(2,2,2-trifluoro-1,1-dimethyl-ethyl)pyrazol-3-yl]phenyl]methyl]-5-fluoro-2-methoxy-benzamide (250 mg, 0.53 mmol) gave, after purification by flash column chromatography on silica gel eluting with 0-100% EtOAc in heptane, followed by SPE SCX cartridge eluting with MeOH, titled compound (0.28 mmol, 53% yield) as a white solid. UPLC-MS (ES+, Short acidic): 1.64 min, m/z 494.1 [M+H]+

UPLC-MS (ES+, Long acidic): 3.85 min, m/z 494.2 [M+H]+

$^1$H NMR (400 MHz, DMSO-$d_6$, δ): 8.85 (t, J=6.0 Hz, 1H), 7.52 (dd, J=9.3, 3.4 Hz, 1H), 7.48-7.41 (m, 4H), 7.38-7.31 (m, 1H), 7.19 (dd, J=9.2, 4.3 Hz, 1H), 6.51 (br s, 2H), 4.56 (d, J=6.1 Hz, 2H), 3.90 (s, 3H), 1.88 (s, 6H).

Example 190: 5-Amino-3-[4-[[(5-fluoro-2-methoxy-benzoyl)amino]methyl]phenyl]-1-[4-(trifluoromethyl)tetrahydropyran-4-yl]pyrazole-4-carboxamide

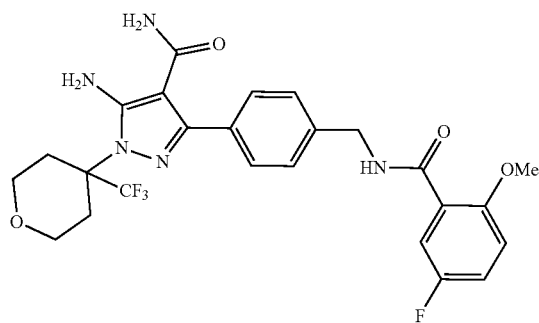 [SMILES: COc1ccc(F)cc1C(=O)NCc1ccc(-c2nn(C3(C(F)(F)F)CCOCC3)c(N)c2C(N)=O)cc1]

N-(Tetrahydropyran-4-ylideneamino)benzamide

Benzhydrazide (633 mg, 4.65 mmol) was added to a solution of tetrahydro-4H-pyran-4-one (0.4 mL, 4.65 mmol) in MeOH (9 mL). The reaction mixture was stirred at RT for 16 h and concentrated under reduced pressure. Purification afforded titled compound (920 mg, 4.22 mmol, 91% yield) as a white solid. UPLC-MS (ES+, Short acidic): 1.05 min, m/z 218.9 [M+H]+

N'-[4-(Trifluoromethyl)tetrahydropyran-4-yl]benzohydrazide

Following general procedure Y in DCM (9 mL), N-(tetrahydropyran-4-ylideneamino)benzamide (250 mg, 1.15 mmol) gave, after purification, titled compound (329 mg, 1.14 mmol, quantitative) as a white solid.

UPLC-MS (ES+, Short acidic): 1.40 min, m/z 289.0 [M+H]+

[4-(Trifluoromethyl)tetrahydropyran-4-yl]hydrazine hydrochloride

Following general procedure U, N'-[4-(trifluoromethyl)tetrahydropyran-4-yl]benzohydrazide (329 mg, 1.14 mmol) gave crude titled compound (252 mg, 1.14 mmol, assumed quantitative) as a clear oil. $^1$H NMR (400 MHz, DMSO-$d_6$, δ): 3.77-3.68 (m, 2H), 3.66-3.55 (m, 2H), 1.87-1.72 (m, 4H)

5-Amino-3-(4-bromophenyl)-1-[4-(trifluoromethyl)tetrahydropyran-4-yl]pyrazole-4-carbonitrile Following general procedure H at 80° C., [4-(trifluoromethyl)tetrahydropyran-4-yl]hydrazine hydrochloride (252 mg, 1.14 mmol) and 2-[(4-bromophenyl)-methoxy-methylene]propanedinitrile (250 mg, 0.95 mmol) gave, after purification, titled compound (122 mg, 0.29 mmol, 31% yield) as off-white solid. UPLC-MS (ES+, Short acidic): 1.95 min, m/z 415.0 [M]+

N-[[4-[5-amino-4-cyano-1-[4-(trifluoromethyl)tetrahydropyran-4-yl]pyrazol-3-yl]phenyl]methyl]-5-fluoro-2-methoxy-benzamide Following general procedure K, 5-amino-3-(4-bromophenyl)-1-[4-(trifluoromethyl)tetrahydropyran-4-yl]pyrazole-4-carbonitrile (50 mg, 0.12 mmol) and potassium trifluoro-[[(5-fluoro-2-methoxy-benzoyl)amino]methyl]boranuide (52 mg, 0.18 mmol) gave, after purification, titled compound (62 mg, 0.12 mmol) as an off-white powder. UPLC-MS (ES+, Short acidic): 1.74 min, m/z 518.2 [M+H]+

5-Amino-3-[4-[[(5-fluoro-2-methoxy-benzoyl)amino]methyl]phenyl]-1-[4-(trifluoromethyl)tetrahydropyran-4-yl]pyrazole-4-carboxamide Following general procedure M, N-[[4-[5-amino-4-cyano-1-[4-(trifluoromethyl)tetrahydropyran-4-yl]pyrazol-3-yl]phenyl]methyl]-5-fluoro-2-methoxy-benzamide (62 mg, 0.12 mmol) gave, after purification by reverse phase column chromatography eluting with 0-45% MeCN in water with 0.1% formic acid additive and flash column chromatography on silica gel eluting with 0-7% MeOH in DCM, titled compound (5 mg, 0.01 mmol, 8% yield) as an off-white solid. UPLC-MS (ES+, Short acidic): 1.59 min, m/z 536.2 [M+H]+ UPLC-MS (ES+, Long acidic): 3.72 min, m/z 536.2 [M+H]+

$^1$H NMR (400 MHz, DMSO-$d_6$, δ): 8.85 (t, J=6.0 Hz, 1H), 7.51 (dd, J=9.2, 3.3 Hz, 1H), 7.49-7.41 (m, 4H), 7.38-7.31 (m, 1H), 7.19 (dd, J=9.1, 4.3 Hz, 1H), 6.57 (s, 2H), 4.55 (d, J=6.0 Hz, 2H), 3.95-3.86 (m, 5H), 3.32-3.24 (m, 2H), 3.02-2.93 (m, 2H), 2.07-1.95 (m, 2H)

Example 191: 5-amino-1-(3,3-difluoro-1-methyl-4-piperidyl)-3-[4-[[(5-fluoro-2-methoxy-benzoyl)amino]methyl]phenyl]pyrazole-4-carboxamide

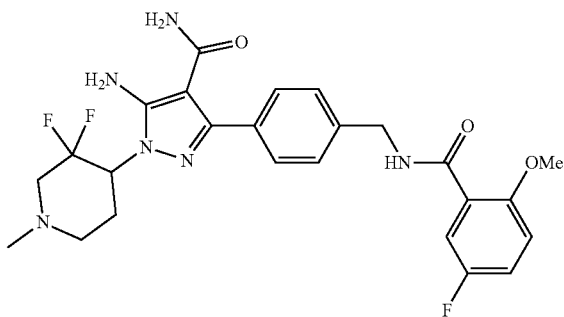 [SMILES: COc1ccc(F)cc1C(=O)NCc1ccc(-c2nn(C3CCN(C)CC3(F)F)c(N)c2C(N)=O)cc1]

5-Amino-1-(3,3-difluoro-1-methyl-4-piperidyl)-3-[4-[[(5-fluoro-2-methoxy-benzoyl)amino]methyl]phenyl]pyrazole-4-carboxamide 5-Amino-1-(3,3-difluoro-4-piperidyl)-3-[4-[[(5-fluoro-2-methoxy-benzoyl)amino]methyl]phenyl]pyrazole-4-carboxamide (36 mg, 0.07 mmol) and cesium carbonate (47 mg, 0.14 mmol) were suspended in DMF (2 mL). The mixture was cooled to 0° C. and a solution of iodomethane (0.9 M in DMF, 0.1 mL, 0.09 mmol) was added dropwise. The mixture was stirred at RT for 16 h. Work up and purification afforded titled compound (20 mg, 0.04 mmol, 54% yield) as a white solid. UPLC-MS (ES$^+$, Short acidic): 1.18 min, m/z 517.2 [M+H]$^+$ UPLC-MS (ES$^+$, Long acidic): 2.56 min, m/z 517.2 [M+H]$^+$ $^1$H NMR (400 MHz, DMSO-d$_6$, δ): 8.84 (t, J=6.0 Hz, 1H), 7.52 (dd, J=9.2, 3.4 Hz, 1H), 7.47-7.41 (m, 4H), 7.37-7.32 (m, 1H), 7.19 (dd, J=9.1, 4.3 Hz, 1H), 6.44 (s, 2H), 4.74-4.63 (m, 1H), 4.55 (d, J=6.0 Hz, 2H), 3.90 (s, 3H), 3.17-3.10 (m, 1H), 2.96-2.93 (m, 1H), 2.47-2.38 (m, 2H), 2.29 (s, 3H), 2.22-2.16 (m, 1H), 1.94-1.88 (m, 1H).

Example 192: 5-amino-1-(1-cyclohexyl-2,2,2-trifluoro-ethyl)-3-[4-[[(5-fluoro-2-methoxy-benzoyl)amino]methyl]phenyl]pyrazole-4-carboxamide

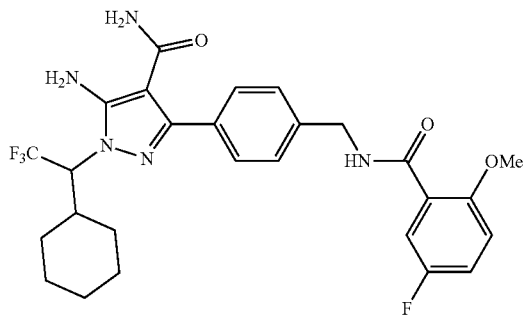 [SMILES: COc1ccc(F)cc1C(=O)NCc1ccc(-c2nn(C(C3CCCCC3)C(F)(F)F)c(N)c2C(N)=O)cc1]

N-[(1-Cyclohexyl-2,2,2-trifluoro-ethylidene)amino]benzamide

Following general procedure S, 1-cyclohexyl-2,2,2-trifluoro-ethanone (5.55 mmol) gave, after purification, titled compound (1.11 mmol,). UPLC-MS (ES$^+$, Short acidic): 1.92 min, m/z 299.0 [M+H]$^+$

N'-(1-Cyclohexyl-2,2,2-trifluoro-ethyl)benzohydrazide

General procedure T N-[(1-cyclohexyl-2,2,2-trifluoro-ethylidene)amino]benzamide (1.11 mmol) gave titled compound (0.64 mmol) as colorless oil. UPLC-MS (ES$^+$, Short acidic): 1.89 min, m/z 301.0 [M+H]$^+$

(1-Cyclohexyl-2,2,2-trifluoro-ethyl)hydrazine hydrochloride

Following general procedure U, N'-(1-cyclohexyl-2,2,2-trifluoro-ethyl)benzohydrazide (0.64 mmol) gave, without further purification, titled compound (0.42 mmol) as a white solid. $^1$H NMR (400 MHz, DMSO-d$_6$, δ): 5.97 (s, 1H), 1.79-1.66 (m, 5H), 1.65-1.57 (m, 1H), 1.37-1.04 (m, 5H)

5-Amino-3-(4-bromophenyl)-1-(1-cyclohexyl-2,2,2-trifluoro-ethyl)pyrazole-4-carbonitrile Following general procedure H, 2-[(4-bromophenyl)-methoxy-methylene]propanedinitrile (0.42 mmol) and (1-cyclohexyl-2,2,2-trifluoro-ethyl)hydrazine hydrochloride (0.42 mmol) gave titled compound (0.42 mmol) as an orange oil. UPLC-MS (ES$^+$, Short acidic): 2.25 min, m/z 429.0 [M+2]$^+$

N-[[4-[5-Amino-4-cyano-1-(1-cyclohexyl-2,2,2-trifluoro-ethyl)pyrazol-3-yl]phenyl]methyl]-5-fluoro-2-methoxy-benzamide Following general procedure K, potassium trifluoro-[[(5-fluoro-2-methoxy-benzoyl)amino]methyl] boranuide (365 mg, 1.26 mmol) and 5-amino-3-(4-bromophenyl)-1-(1-cyclohexyl-2,2,2-trifluoro-ethyl) pyrazole-4-carbonitrile (180 mg, 0.42 mmol) gave titled compound (223 mg, 0.42 mmol). UPLC-MS (ES$^+$, Short acidic): 1.99 min, m/z 530.2 [M+H]$^+$

5-Amino-1-(1-cyclohexyl-2,2,2-trifluoro-ethyl)-3-[4-[[(5-fluoro-2-methoxy-benzoyl)amino]methyl]phenyl]pyrazole-4-carboxamide Following general procedure M, N-[[4-[5-amino-4-cyano-1-(1-cyclohexyl-2,2,2-trifluoro-ethyl)pyrazol-3-yl]phenyl]methyl]-5-fluoro-2-methoxy-benzamide (223 mg, 0.42 mmol) gave, after purification, titled compound (72 mg, 0.13 mmol, 31% yield) as a white solid. UPLC-MS (ES$^+$, Short acidic): 1.83 min, m/z 548.3 [M+H]$^+$ UPLC-MS (ES$^+$, Long acidic): 4.33 min, m/z 548.3 [M+H]$^+$ $^1$H NMR (400 MHz, DMSO-d$_6$, δ): 8.83 (t, J=6.1 Hz, 1H), 7.51 (dd, J=9.3, 3.3 Hz, 1H), 7.47-7.40 (m, 4H), 7.37-7.30 (m, 1H), 7.18 (dd, J=9.1, 4.4 Hz, 1H), 6.69 (br s, 2H), 4.99-4.88 (m, 1H), 4.54 (d, J=6.2 Hz, 2H), 3.89 (s, 3H), 2.39-2.25 (m, 1H), 1.93-1.85 (m, 1H), 1.79-1.71 (m, 1H), 1.66-1.56 (m, 2H), 1.36-1.11 (m, 5H), 1.04-0.93 (m, 1H).

Example 193: 5-Amino-1-[1-(difluoromethyl)-3-hydroxy-propyl]-3-[4-[[(5-fluoro-2-methoxy-benzoyl)amino]methyl]phenyl]pyrazole-4-carboxamide

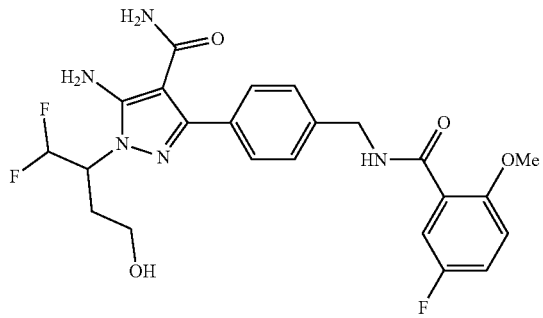 [SMILES: COc1ccc(F)cc1C(=O)NCc1ccc(-c2nn(C(CCO)C(F)F)c(N)c2C(N)=O)cc1]

Ethyl 3-(tert-butoxycarbonylhydrazono)-4,4-difluoro-butanoate

Following general procedure E at 60° C., tert-butyl carbazate (505 mg, 3.82 mmol) and ethyl 4,4-difluoro-3-oxobutanoate (0.5 mL, 3.82 mmol) gave, after purification, titled compound (983 mg, 3.51 mmol, 92% yield) as an off-white solid. UPLC-MS (ES⁻, Short acidic): 1.61 min, m/z 279.0 [M−H]⁻ tert-Butyl N-[[1-(difluoromethyl)-3-hydroxy-propyl]amino]carbamate

To a solution of ethyl 3-(tert-butoxycarbonylhydrazono)-4,4-difluoro-butanoate (200 mg, 0.71 mmol) in THF (1.4 mL) was added borane tetrahydrofuran complex (1 M in THF, 3.6 mL, 3.60 mmol) at 0° C. The reaction mixture was stirred for 2 h at RT. MeOH (3.6 mL) was then added carefully and the mixture was then concentrated to afford crude titled compound (171 mg, 0.71 mmol) as a brown oil.

UPLC-MS (ES⁻, Short acidic): 1.24 min, m/z 239.1 [M−H]⁻

5-Amino-3-(4-bromophenyl)-1-[1-(difluoromethyl)-3-hydroxy-propyl]pyrazole-4-carbonitrile A hydrogen chloride solution (4 M in dioxane, 1.78 mL, 7.14 mmol) was added to tert-butyl N-[[1-(difluoromethyl)-3-hydroxy-propyl]amino]carbamate (171 mg, 0.71 mmol). After 1 h stirring at RT, the mixture was concentrated under reduced pressure. The residue was taken up with EtOH (2.2 mL) and 2-[(4-bromophenyl)-methoxy-methylene]propanedinitrile (150 mg, 0.57 mmol) was then added, followed by triethylamine (0.2 mL, 1.43 mmol). The reaction mixture was heated to 80° C. for 30 min, cooled to RT and concentrated under reduced pressure. Purification afforded titled compound (143 mg, 0.39 mmol, 68% yield) as an off-white solid. UPLC-MS (ES⁺, Short acidic): 1.67 min, m/z 373.0 [M+2]⁺

N-[[4-[5-Amino-4-cyano-1-[1-(difluoromethyl)-3-hydroxy-propyl]pyrazol-3-yl]phenyl]methyl]-5-fluoro-2-methoxy-benzamide Following general procedure K, 5-amino-3-(4-bromophenyl)-1-[1-(difluoromethyl)-3-hydroxy-propyl]pyrazole-4-carbonitrile (50 mg, 0.13 mmol) and potassium trifluoro-[[(5-fluoro-2-methoxy-benzoyl)amino]methyl]boranuide (58 mg, 0.20 mmol) gave, after purification, titled compound (0.10 mmol) as an off-white powder. UPLC-MS (ES⁺, Short acidic): 1.54 min, m/z 474.2 [M+H]⁺

5-Amino-1-[1-(difluoromethyl)-3-hydroxy-propyl]-3-[4-[[(5-fluoro-2-methoxy-benzoyl)amino]methyl]phenyl]pyrazole-4-carboxamide Following general procedure M, N-[[4-[5-amino-4-cyano-1-[1-(difluoromethyl)-3-hydroxy-propyl]pyrazol-3-yl]phenyl]methyl]-5-fluoro-2-methoxy-benzamide (46 mg, 0.10 mmol) gave, after purification, titled compound (22 mg, 0.05 mmol, 47% yield) as a white solid. UPLC-MS (ES⁺, Short acidic): 1.38 min, m/z 492.2 [M+H]⁺ UPLC-MS (ES⁺, Long acidic): 3.14 min, m/z 492.2 [M+H]⁺

¹H NMR (400 MHz, DMSO-$d_6$, δ): 8.84 (t, J=5.9 Hz, 1H), 7.51 (dd, J=9.2, 3.3 Hz, 1H), 7.49-7.39 (m, 4H), 7.38-7.30 (m, 1H), 7.19 (dd, J=9.1, 4.3 Hz, 1H), 6.51 (s, 2H), 6.25 (dt, J=55.5, 4.9 Hz, 1H), 4.84-4.66 (m, 2H), 4.55 (d, J=6.1 Hz, 2H), 3.90 (s, 3H), 3.48-3.36 (m, 1H), 3.28-3.15 (m, 1H), 2.28-2.13 (m, 1H), 2.06-1.87 (m, 1H)

Example 194: 5-amino-1-[2,2-dimethyl-1-(trifluoromethyl)propyl]-3-[4-[[(5-fluoro-2-methoxy-benzoyl)amino]methyl]phenyl]pyrazole-4-carboxamide

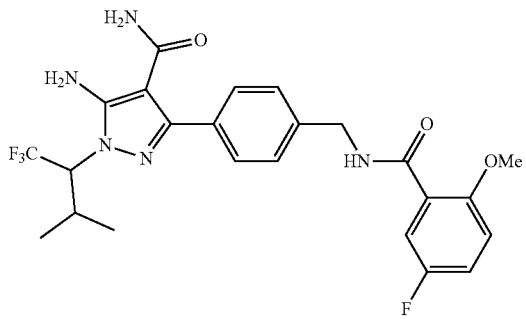 [SMILES: COc1ccc(F)cc1C(=O)NCc1ccc(-c2nn(C(C(C)C)C(F)(F)F)c(N)c2C(N)=O)cc1]

N-(2,2-Dimethylproplideneamino)benzamide

Following general procedure S, benzhydrazide (300 mg, 2.20 mmol) and pivalaldehyde (0.40 mL, 3.31 mmol) afforded, after purification, titled compound (407 mg, 1.99 mmol, 90% yield) as a white solid. UPLC-MS (ES⁺, Short acidic): 1.40 min, m/z 205.0 [M+H]⁺

N-[2,2-Dimethyl-1-(trifluoromethyl)propyl]benzohydrazide

Following general procedure Y, N-(2,2-dimethylpropylideneamino)benzamide (407 mg, 1.99 mmol) afforded, after purification, titled compound (492 mg, 1.79 mmol, 90% yield) as a white solid. UPLC-MS (ES⁺, Short acidic): 1.74 min, m/z 275.0 [M+H]⁺

[2,2-Dimethyl-1-(trifluoromethyl)propyl]hydrazine hydrochloride

Following general procedure U, N'-[2,2-dimethyl-1-(trifluoromethyl)propyl]benzohydrazide (492 mg, 1.79 mmol) afforded crude titled compound (371 mg, 1.79 mmol, assumed quantitative yield) as a white solid. ¹H NMR (400 MHz, DMSO-d₆, δ): 6.09-5.98 (m, 1H), 1.04 (s, 9H).

5-Amino-3-(4-bromophenyl)-1-[2,2-dimethyl-1-(trifluoromethyl)propyl]pyrazole-4-carbonitrile Following general procedure H, 2-[(4-bromophenyl)-methoxy-methylene]propanedinitrile (100 mg, 0.38 mmol) and [2,2-dimethyl-1-(trifluoromethyl)propyl]hydrazine hydrochloride (118 mg, 0.57 mmol) afforded crude titled compound (152 mg, 0.38 mmol, assumed quantitative yield) as a yellow solid. UPLC-MS (ES⁺, Short acidic): 2.16 min, m/z 403.0 [M+2]⁺

N-[[4-[5-Amino-4-cyano-1-[2,2-dimethyl-1-(trifluoromethyl)propyl]pyrazol-3-yl]phenyl]methyl]-5-fluoro-2-methoxy-benzamide Following general procedure K, 5-amino-3-(4-bromophenyl)-1-[2,2-dimethyl-1-(trifluoromethyl)propyl] pyrazole-4-carbonitrile (168 mg, 0.42 mmol) and potassium trifluoro-[[(5-fluoro-2-methoxy-benzoyl) amino]methyl]boranuide (243 mg, 0.84 mmol) afforded, after purification, titled compound (208 mg, 0.41 mmol, 98% yield) as a yellow gum. UPLC-MS (ES⁺, Short acidic): 1.90 min, m/z 504.1 [M+H]⁺

5-Amino-1-[2,2-dimethyl-1-(trifluoromethyl)propyl]-3-[4-[[(5-fluoro-2-methoxy-benzoyl)amino]methyl]phenyl]pyrazole-4-carboxamide Following general procedure M, N-[[4-[5-amino-4-cyano-1-[2,2-dimethyl-1-(trifluoromethyl)propyl]pyrazol-3-yl]phenyl]methyl]-5-fluoro-2-methoxy-benzamide (208 mg, 0.41 mmol) afforded, after purification, (54 mg, 0.09 mmol, 22% yield) as a white solid.
UPLC-MS (ES⁺, Short acidic): 1.77 min, m/z 522.2 [M+H]⁺ UPLC-MS (ES⁺, Long acidic): 4.19 min, m/z 522.2 [M+H]⁺
¹H NMR (400 MHz, DMSO-d₆, δ): 8.84 (t, J=6.0 Hz, 1H), 7.51 (dd, J=9.2, 3.3 Hz, 1H), 7.5-7.4 (m, 4H), 7.38-7.30 (m, 1H), 7.22-7.16 (m, 1H), 6.76 (s, 2H), 5.03-4.94 (m, 1H), 4.55 (d, J=6.1 Hz, 2H), 3.89 (s, 3H), 1.11 (s, 9H).

Example 195: 5-amino-1-ethyl-3-[4-[[(5-fluoro-2-methoxy-benzoyl)amino]methyl]phenyl]pyrazole-4-carboxamide

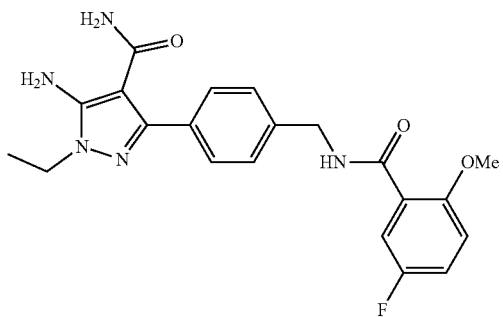 [SMILES: CCn1nc(-c2ccc(CNC(=O)c3cc(F)ccc3OC)cc2)c(C(N)=O)c1N]

5-Amino-3-(4-bromophenyl)-1-ethyl-pyrazole-4-carbonitrile

Following general procedure H, 2-[(4-bromophenyl)-methoxy-methylene]propanedinitrile (263 mg, 1.0 mmol) and ethylhydrazine oxalate (150 mg, 1.0 mmol) gave titled compound (210 mg, 0.7 mmol, 72% yield) as a yellow solid. UPLC-MS (ES⁺, Short acidic): 1.69 min, m/z 292.9 [M+2]⁺

N-[[4-(5-Amino-4-cyano-1-ethyl-pyrazol-3-yl)phenyl]methyl]-5-fluoro-2-methoxy-benzamide Following general procedure K, 5-amino-3-(4-bromophenyl)-1-ethyl-pyrazole-4-carbonitrile (0.21 g, 0.72 mmol), and potassium trifluoro-[[(5-fluoro-2-methoxy-benzoyl) amino]methyl]boranuide (1.04 g, 3.59 mmol) gave, after purification, titled compound (0.28 g, 0.71 mmol, 99% yield) as an off-white solid. UPLC-MS (ES⁺, Short acidic): 1.53 min, m/z 394.2 [M+H]⁺

5-Amino-1-ethyl-3-[4-[[(5-fluoro-2-methoxy-benzoyl)amino]methyl]phenyl]pyrazole-4-carboxamide Following general procedure M, N-[[4-(5-amino-4-cyano-1-ethyl-pyrazol-3-yl)phenyl]methyl]-5-fluoro-2-methoxy-benzamide (207 mg, 0.53 mmol) gave, after purification by flash column chromatography on silica gel eluting with 0-100% EtOAc in heptane, followed by further purification by SPE SCX cartridge eluting with MeOH, titled compound (96 mg, 0.23 mmol, 44% yield) as a white solid. UPLC-MS (ES⁺, Short acidic): 1.34 min, m/z 412.2 [M+H]⁺ UPLC-MS (ES⁺, Long acidic): 3.04 min, m/z 412.2 [M+H]⁺
¹H NMR (400 MHz, DMSO-d₆, δ): 8.84 (t, J=6.3 Hz, 1H), 7.52 (dd, J=9.0, 3.2 Hz, 1H), 7.46 (d, J=8.2 Hz, 2H), 7.41 (d, J=8.2 Hz, 2H), 7.38-7.31 (m, 1H), 7.19 (dd, J=9.2, 4.2 Hz, 1H), 6.32 (br s, 2H), 4.55 (d, J=6.1 Hz, 2H), 3.95 (q, J=7.2 Hz, 2H), 3.90 (s, 3H), 1.26 (t, J=7.1 Hz, 3H).

Example 196: 5-Amino-1-(1-cyclopentyl-2,2,2-trifluoro-ethyl)-3-[4-[[(5-fluoro-2-methoxy-benzoyl)amino]methyl]phenyl]pyrazole-4-carboxamide

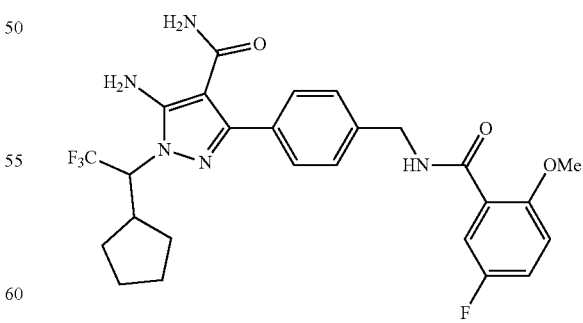

N-[Cyclopentylmethyleneamino]benzamide

To a solution of benzhydrazide (300 mg, 2.20 mmol) in toluene (4.40 mL) was added cyclopentane carbaldehyde (0.25 mL, 3.31 mmol). The reaction mixture was heated to 110° C. for 16 h, cooled to RT and poured into water (20 mL). Work up afforded crude titled compound (420 mg, 1.94 mmol, 88% yield) as a yellow solid. UPLC-MS (ES⁺, Short acidic): 1.42 min, m/z 217.0 [M+H]⁺

N'-(1-Cyclopentyl-2,2,2-trifluoro-ethyl)benzohydrazide

Following general procedure Y, N-[cyclopentylmethyleneamino]benzamide (420 mg, 1.94 mmol) and trimethyl (trifluoromethyl)silane (0.57 mL, 3.88 mmol) afforded N'-(1-cyclopentyl-2,2,2-trifluoro-ethyl)benzohydrazide (556 mg, 1.94 mmol). UPLC-MS (ES⁺, Short acidic): 1.81 min, m/z 287.0 [M+H]⁺

(1-Cyclopentyl-2,2,2-trifluoro-ethyl)hydrazine hydrochloride

Following general procedure U, N'-(1-Cyclopentyl-2,2,2-trifluoro-ethyl)benzohydrazide (1.94 mmol) gave (1-cyclopentyl-2,2,2-trifluoro-ethyl)hydrazine hydrochloride (1.83 mmol) as an off-white solid. ¹H NMR (400 MHz, CDCl₃, δ): 3.81-3.69 (m, 1H), 2.07-2.01 (m, 1H), 1.85-1.70 (m, 2H), 1.64-1.57 (m, 2H), 1.52-1.40 (m, 4H)

5-Amino-3-(4-bromophenyl)-1-(1-cyclopentyl-2,2,2-trifluoro-ethyl)pyrazole-4-carbonitrile Following general procedure H, 2-[(4-bromophenyl)-methoxy-methylene]propanedinitrile (0.70 mmol) and (1-cyclopentyl-2,2,2-trifluoro-ethyl)hydrazine hydrochloride (0.84 mmol) afforded, after purification, titled compound (0.12 mmol) as a yellow oil. UPLC (ES⁺, Short acidic): 2.91 min, m/z 415.0 [M+2]⁺

N-[[4-[5-Amino-4-cyano-1-(1-cyclopentyl-2,2,2-trifluoro-ethyl)pyrazol-3-yl]phenyl]methyl]-5-fluoro-2-methoxy-benzamide Following general procedure K, potassium trifluoro-[[(5-fluoro-2-methoxy-benzoyl)amino]methyl]boranuide (108 mg, 0.37 mmol) and 5-amino-3-(4-bromophenyl)-1-(1-cyclopentyl-2,2,2-trifluoro-ethyl)pyrazole-4-carbonitrile (91 mg, 0.22 mmol) afforded, after purification, titled compound (112 mg, 0.22 mmol, 98% yield) as an off-white solid. LC-MS (ES⁺, Short Acidic): 5.58 min, m/z 516.1 [M+H]⁺

5-Amino-1-(1-cyclopentyl-2,2,2-trifluoro-ethyl)-3-[4-[[(5-fluoro-2-methoxy-benzoyl)amino]methyl]phenyl]pyrazole-4-carboxamide Following general procedure M, N-[[4-[5-amino-4-cyano-1-(1-cyclopentyl-2,2,2-trifluoro-ethyl)pyrazol-3-yl]phenyl]methyl]-5-fluoro-2-methoxy-benzamide (112 mg, 0.22 mmol) afforded, after purification, titled compound (18 mg, 0.03 mmol, 15%) as a white solid. UPLC-MS (ES⁺, Short acidic): 1.71 min, m/z 534.2 [M+H]⁺ UPLC-MS (ES⁺, Long acidic): 4.17 min, m/z 534.2 [M+H]⁺
¹H NMR (400 MHz, DMSO-d₆, δ): 8.84 (t, J=6.0 Hz, 1H), 7.51 (dd, J=9.2, 3.3 Hz, 1H), 7.48-7.39 (m, 4H), 7.38-7.30 (m, 1H), 7.19 (dd, J=9.1, 4.3 Hz, 1H), 6.71 (s, 2H), 5.05-4.93 (m, 1H), 4.55 (d, J=6.1 Hz, 2H), 3.90 (s, 3H), 2.79-2.69 (m, 1H), 1.94-1.81 (m, 1H), 1.80-1.32 (m, 6H), 1.22-1.08 (m, 1H)

Example 197: 5-amino-1-(4,4-difluoro-1-isopropyl-pyrrolidin-3-yl)-3-[4-[[(5-fluoro-2-methoxy-benzoyl)amino]methyl]phenyl]pyrazole-4-carboxamide

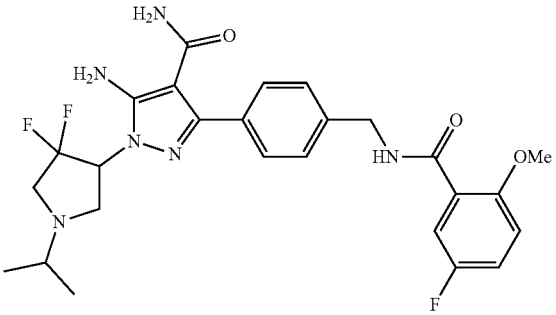 [SMILES: COc1ccc(F)cc1C(=O)NCc1ccc(-c2nn(C3CN(C(C)C)CC3(F)F)c(N)c2C(N)=O)cc1]

4,4-Difluoro-1-isopropyl-pyrrolidin-3-ol

A mixture of 4,4-difluoropyrrolidin-3-ol (300 mg, 2.44 mmol), acetone (0.27 mL, 3.66 mmol) and glacial acetic acid (0.21 mL, 3.66 mmol) in THF (9.8 mL) was stirred for 30 min at RT. Sodium diacetoxy(acetyl)boranuide (716 mg, 3.66 mmol) was then added and the reaction was stirred for 3 h at RT. The reaction mixture was diluted with a saturated solution of sodium bicarbonate and following work up and purification afforded titled compound (178 mg, 1.08 mmol, 44% yield) as a yellow oil.
¹H NMR (400 MHz, CDCl₃, δ): 4.25-4.18 (m, 1H), 3.10-3.00 (m, 3H), 2.70-2.65 (m, 1H), 2.59-2.49 (m, 1H), 1.05 (d, J=6.4 Hz, 3H), 1.04 (d, J=6.4 Hz, 3H)

5-Amino-3-(4-bromophenyl)-1-(4,4-difluoro-1-isopropyl-pyrrolidin-3-yl)pyrazole-4-carbonitrile A solution of 4,4-difluoro-1-isopropyl-pyrrolidin-3-ol (178 mg, 1.08 mmol) in anhydrous DCM (20 mL) was cooled to −20° C. and purged with nitrogen. Trifluoromethanesulfonic anhydride (1 M in DCM, 2.69 mL, 2.69 mmol) was added and the reaction mixture was stirred for 40 min, before being quenched with water. Work up afforded crude (4,4-difluoro-1-isopropyl-pyrrolidin-3-yl) trifluoromethanesulfonate (31.08 mmol) as a red oil. Following general procedure N, the crude compound and 5-amino-3-(4-bromophenyl)-1H-pyrazole-4-carbonitrile (1.06 mmol) afforded, after purification, titled compound (0.31 mmol) as a pale yellow oil. UPLC-MS (ES⁺, Short acidic): 1.61 min, m/z 412.0 [M+2]⁺

N-[[4-[5-Amino-4-cyano-1-(4,4-difluoro-1-isopropyl-pyrrolidin-3-yl)pyrazol-3-yl]phenyl]methyl]-5-fluoro-2-methoxy-benzamide Following general procedure K, potassium trifluoro-[[(5-fluoro-2-methoxy-benzoyl)amino]methyl]boranuide (155 mg, 0.54 mmol) and 5-amino-3-(4-bromophenyl)-1-(4,4-difluoro-1-isopropyl-pyrrolidin-3-yl)pyrazole-4-carbonitrile (129 mg, 0.32 mmol) afforded, after purification, titled compound (88 mg, 0.17 mmol, 54% yield) as a yellow oil. UPLC-MS (ES⁻, Short Acidic): 1.48 min, m/z 511.2 [M−H]⁻

5-Amino-1-(4,4-difluoro-1-isopropyl-pyrrolidin-3-yl)-3-[4-[[(5-fluoro-2-methoxy-benzoyl)amino]methyl]phenyl]pyrazole-4-carboxamide Following general procedure M, N-[[4-[5-amino-4-cyano-1-(4,4-difluoro-1-isopropyl-pyrrolidin-3-yl)pyrazol- 3-yl]phenyl]methyl]-5-fluoro-2-methoxy-benzamide (88 mg, 0.17 mmol) afforded, after purification, titled compound (35 mg, 0.07 mmol, 38%) as an off-white solid. UPLC-MS (ES⁺, Short Acidic): 1.30 min, m/z 531.3 [M+H]⁺ UPLC-MS (ES⁺, Long Acidic): 2.83 min, m/z 531.4 [M+H]′″

¹H NMR (400 MHz, DMSO-d₆, δ): 8.86 (t, J=6.1 Hz, 1H), 7.51 (dd, J=9.2, 3.3 Hz, 1H), 7.46-7.41 (m, 4H), 7.37-7.33 (m, 1H), 7.19 (dd, J=9.1, 4.3 Hz, 1H), 6.62 (s, 2H), 5.21-5.14 (m, 1H), 4.55 (d, J=6.1, 2H), 3.90 (s, 3H), 3.26-3.17 (m, 2H), 2.98-2.89 (m, 1H), 2.62-2.57 (m, 1H), 2.53-2.40 (m, 1H), 1.06-1.03 (m, 6H)

Example 198: -amino-1-(1-ethyl-4,4-difluoro-pyrrolidin-3-yl)-3-[4-[[(5-fluoro-2-methoxy-benzoyl)amino]methyl]phenyl]pyrazole-4-carboxamide

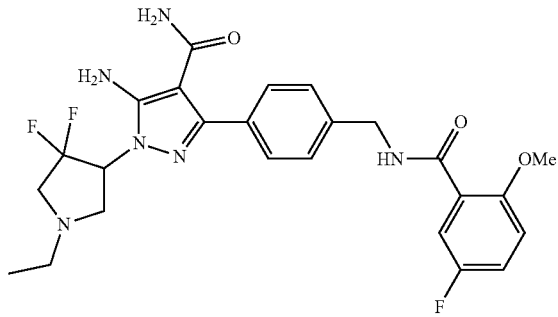 [SMILES: CCN1CC(n2nc(-c3ccc(CNC(=O)c4cc(F)ccc4OC)cc3)c(C(N)=O)c2N)C(F)(F)C1]

1-Ethyl-4,4-difluoro-pyrrolidin-3-ol

A mixture of 4,4-difluoropyrrolidin-3-ol dihydrochloride (1.02 mmol), acetaldehyde (1.53 mmol), glacial acetic acid (1.53 mmol) in THF (6.5 mL) was stirred for 1 h at RT. Sodium diacetoxy(acetyl)boranuide (1.53 mmol) was then added and the reaction was stirred for 3 h. Work up and purification afforded titled compound (94 mg, 0.62 mmol, 61% yield) as a yellow oil. ¹H NMR (400 MHz, CDCl₃, δ): 4.25-4.18 (m, 1H), 3.07-2.91 (m, 3H), 2.64-2.60 (m, 1H), 2.53 (q, J=7.2 Hz, 2H), 1.10 (t, J=7.2 Hz, 3H)

(1-Ethyl-4,4-difluoro-pyrrolidin-3-yl) trifluoromethanesulfonate

A solution of 1-ethyl-4,4-difluoro-pyrrolidin-3-ol (94 mg, 0.62 mmol) in anhydrous DCM (20 mL), was cooled to −20° C. and purged with nitrogen. Trifluoromethanesulfonic anhydride (1 M in DCM, 1.55 mL, 1.55 mmol) was then added. The reaction mixture was stirred for 40 min at the same temperature. Work up afforded crude titled compound (94 mg, 0.33 mmol, 53% yield) as a red oil.

¹H NMR (400 MHz, CDCl₃, δ): 5.08-5.03 (m, 1H), 3.25-3.21 (m, 1H), 3.10-3.04 (m, 1H), 2.98-2.87 (m, 1H), 2.83-2.78 (m, 1H), 2.52 (q, J=7.2 Hz, 2H), 1.04 (t, J=7.2 Hz, 3H)

5-Amino-3-(4-bromophenyl)-1-(1-ethyl-4,4-difluoro-pyrrolidin-3-yl)pyrazole-4-carbonitrile Following general procedure N, (1-ethyl-4,4-difluoro-pyrrolidin-3-yl) trifluoromethanesulfonate (93 mg, 0.33 mmol) and 5-amino-3-(4-bromophenyl)-1H-pyrazole-4-carbonitrile (72 mg, 0.27 mmol) afforded, after purification, titled compound (60 mg, 0.15 mmol, 55% yield) as a yellow solid. UPLC-MS (ES⁺, Short acidic): 1.52 min, m/z 398.0 [M+2]⁺

N-[[4-[5-Amino-4-cyano-1-(1-ethyl-4,4-difluoro-pyrrolidin-3-yl)pyrazol-3-yl]phenyl]methyl]-5-fluoro-2-methoxy-benzamide Following general procedure K, potassium trifluoro-[[(5-fluoro-2-methoxy-benzoyl)amino]methyl] boranuide (74 mg, 0.26 mmol) and 5-amino-3-(4-bromophenyl)-1-(1-ethyl-4,4-difluoro-pyrrolidin-3-yl)pyrazole-4-carbonitrile (60 mg, 0.15 mmol) afforded, after purification, titled compound (30 mg, 0.06 mmol, 39% yield) as a colourless oil. UPLC-MS (ES⁻, Short acidic): 1.42 min, 497.2 m/z [M−H]⁻

5-Amino-1-(1-ethyl-4,4-difluoro-pyrrolidin-3-yl)-3-[4-[[(5-fluoro-2-methoxy-benzoyl)amino]methyl]phenyl]pyrazole-4-carboxamide Following general procedure M, N-[[4-[5-amino-4-cyano-1-(1-ethyl-4,4-difluoro-pyrrolidin-3-yl)pyrazol-3-yl]phenyl]methyl]-5-fluoro-2-methoxy-benzamide (29 mg, 0.06 mmol) afforded, after purification, titled compound (5 mg, 0.01 mmol, 16% yield) as an off-white solid. UPLC-MS (ES⁺, Short Acidic): 1.26 min, m/z 517.2 [M+H]⁺ UPLC-MS (ES⁺, Long Acidic): 2.74 min, m/z 517.2 [M+H]⁺

¹H NMR (500 MHz, DMSO-d₆, δ): 8.86 (t, J=6.0 Hz, 1H), 7.51 (dd, J=9.2, 3.3 Hz, 1H), 7.46-7.41 (m, 4H), 7.37-7.33 (m, 1H), 7.19 (dd, 9.1, 4.2 Hz, 1H), 6.60 (s, 2H), 5.22-5.15 (m, 1H), 4.55 (d, J=6.1 Hz, 2H), 3.89 (s, 3H), 3.30-3.15 (m, 2H), 2.91-2.77 (m, 1H), 2.69-2.36 (m, 3H), 1.05 (t, J=7.2 Hz, 3H).

Example 199: 5-amino-1-(4,4-difluoro-1-methyl-pyrrolidin-3-yl)-3-[4-[[(5-fluoro-2-methoxy-benzoyl)amino]methyl]phenyl]pyrazole-4-carboxamide

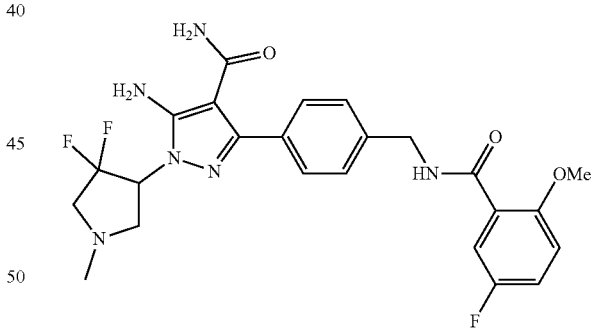

4,4-Difluoro-1-methyl-pyrrolidin-3-ol

Paraformaldehyde (64 mg, 1.33 mmol) and sodium hydroxide (53 mg, 1.33 mmol) were suspended in THF (12 mL) and stirred for 20 min. 4,4-Difluoropyrrolidin-3-ol dihydrochloride (520 mg, 2.65 mmol) and formic acid (0.25 mL, 6.63 mmol) were then added and the reaction was heated to reflux for 2 h. The mixture was cooled to 0° C., diluted with NaOH (10 N, 1 mL) and extracted with diethyl ether (×2). The combined organic layers were dried over a hydrophobic frit and concentrated under reduced pressure to give 4,4-difluoro-1-methyl-pyrrolidin-3-ol (269 mg, 1.96 mmol, 74% yield) as a pale yellow oil.

¹H NMR (400 MHz, CDCl₃, δ): 4.27-4.17 (m, 1H), 3.05-3.01 (m, 1H), 3.00-2.91 (m, 2H), 2.63-2.59 (m, 1H), 2.38 (s, 3H).

(4,4-Difluoro-1-methyl-pyrrolidin-3-yl) trifluoromethanesulfonate 4,4-Difluoro-1-methyl-pyrrolidin-3-ol (268 mg, 1.95 mmol) was dissolved in anhydrous DCM (20 mL) in a 3-neck flask. The solution was cooled to −20° C. and flushed with nitrogen (×3). Trifluoromethanesulfonic anhydride (1 M in DCM, 4.87 mL, 4.87 mmol) was slowly added. The mixture was stirred at −20−−10° C. for 40 min. Work up afforded titled compound (429 mg, 1.60 mmol, 81% yield) as a red oil which was used without further purification.

¹H NMR (400 MHz, CDCl₃, δ): 5.07-5.02 (m, 1H), 3.19-3.15 (m, 1H), 3.03-2.88 (m, 2H), 2.80-2.77 (m, 1H), 2.34 (s, 3H)

5-Amino-3-(4-bromophenyl)-1-(4,4-difluoro-1-methyl-pyrrolidin-3-yl)pyrazole-4-carbonitrile Following general procedure N, (4,4-difluoro-1-methyl-pyrrolidin-3-yl) trifluoromethanesulfonate (235 mg, 0.87 mmol) and 5-amino-3-(4-bromophenyl)-1H-pyrazole-4-carbonitrile (276 mg, 1.05 mmol) afforded, after purification, titled compound (177 mg, 0.46 mmol, 53% yield) as a pale yellow solid.

UPLC-MS (ES⁺, Short acidic): 1.49 min, m/z 383.8 [M+H]⁺

N-[[4-[5-Amino-4-cyano-1-(4,4-difluoro-1-methyl-pyrrolidin-3-yl)pyrazol-3-yl]phenyl]methyl]-5-fluoro-2-methoxy-benzamide Following general procedure K, potassium trifluoro-[[(5-fluoro-2-methoxy-benzoyl)amino]methyl]boranuide (228_mg, 0.79 mmol) and 5-amino-3-(4-bromophenyl)-1-(4,4-difluoro-1-methyl-pyrrolidin-3-yl)pyrazole-4-carbonitrile (177 mg, 0.46 mmol) afforded, after purification, titled compound (0.06 mmol) as a yellow oil. UPLC-MS (ES⁺, Short acidic): 1.41 min, m/z 485.2 [M+H]⁺

5-Amino-1-(4,4-difluoro-1-methyl-pyrrolidin-3-yl)-3-[4-[[(5-fluoro-2-methoxy-benzoyl)amino]methyl]phenyl]pyrazole-4-carboxamide Following general procedure M, N-[[4-[5-amino-4-cyano-1-(4,4-difluoro-1-methyl-pyrrolidin-3-yl)pyrazol-3-yl]phenyl]methyl]-5-fluoro-2-methoxy-benzamide (31 mg, 0.06 mmol) afforded, after purification, titled compound (6 mg, 0.01 mmol, 19% yield) as an off white solid. UPLC-MS (ES⁺, Short acidic): 1.23 min, m/z 503.3 [M+H]⁺ UPLC-MS (ES⁺, Long acidic): 2.70 min, m/z 503.2 [M+H]⁺

¹H NMR (500 MHz, DMSO, d₆, δ): 8.84 (t, J=6.1 Hz, 1H), 7.52 (dd, J=9.2, 3.3 Hz, 1H), 7.46-7.41 (m, 4H), 7.37-7.32 (m, 1H), 7.19 (dd, J=9.1, 4.3 Hz, 1H), 6.58 (br s, 2H), 5.21-5.17 (m, 1H), 4.55 (d, J=6.1 Hz, 2H), 3.90 (s, 3H), 3.34-3.15 (m, 2H), 2.91-2.73 (m, 1H), 2.61-2.42 (m, 1H), 2.36 (s, 3H)

Example 200: 5-amino-1-(4,4-difluorotetrahydro-furan-3-yl)-3-[4-[[(5-fluoro-2-methoxy-benzoyl)amino]methyl]phenyl]pyrazole-4-carboxamide

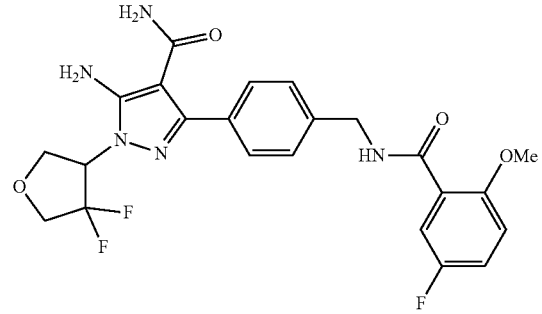 [SMILES: COc1ccc(F)cc1C(=O)NCc1ccc(-c2nn(C3COCC3(F)F)c(N)c2C(N)=O)cc1]

5-Amino-3-(4-bromophenyl)-1-(4,4-difluorotetrahydrofuran-3-yl)pyrazole-4-carbonitrile To a solution of 4,4-difluorotetrahydrofuran-3-ol (215 mg, 1.73 mmol) and pyridine (0.70 mL, 8.66 mmol) in dry DCM (1 mL), at −15° C. under nitrogen, was added dropwise a solution trifluoromethanesulfonic anhydride in DCM (1 M, 4.30 mL, 4.30 mmol). The reaction was stirred between −15 and −5° C. for 60 min, quenched with water. Work up gave 5-amino-3-(4-bromophenyl)-1H-pyrazole-4-carbonitrile. The crude material (90 mg, 0.34 mmol) and cesium carbonate (223 mg, 0.68 mmol) in DMF (3 mL) were heated to 90° C. for 16 h. Work up and purification afforded titled compound (63 mg, 0.14 mmol, 40% yield) as a white solid. UPLC-MS (ES⁺, Short acidic): 1.83 min, m/z 369.0 [M]⁺

N-[[4-[5-Amino-4-cyano-1-(4,4-difluorotetrahydro-furan-3-yl)pyrazol-3-yl]phenyl]methyl]-5-fluoro-2-methoxy-benzamide Following general procedure K, 5-amino-3-(4-bromophenyl)-1-(4,4-difluorotetrahydrofuran-3-yl)pyrazole-4-carbonitrile (63 mg, 0.17 mmol) and potassium trifluoro-[[(5-fluoro-2-methoxy-benzoyl)amino]methyl]boranuide (94 mg, 0.33 mmol) gave, after purification, titled compound (66 mg, 0.12 mmol, 68% yield) as a white solid. UPLC-MS (ES⁺, Short acidic): 1.67 min, m/z 471.1 [M+H]⁺

5-Amino-1-(4,4-difluorotetrahydrofuran-3-yl)-3-[4-[[(5-fluoro-2-methoxy-benzoyl)amino]methyl]phenyl]pyrazole-4-carboxamide Following general procedure M, N-[[4-[5-amino-4-cyano-1-(4,4-difluorotetrahydrofuran-3-yl)pyrazol-3-yl]phenyl]methyl]-5-fluoro-2-methoxy-benzamide (62 mg, 0.13 mmol) gave, after purification, titled compound (25 mg, 0.05 mmol, 39% yield) as a light yellow solid. UPLC-MS (ES⁺, Short acidic): 1.50 min, m/z 490.2 [M+H]⁺ UPLC-MS (ES⁺, Long acidic): 3.39 min, m/z 490.2 [M+H]⁺

¹H NMR (500 MHz, DMSO-d₆, δ): 8.84 (t, J=6.1 Hz, 1H), 7.52 (dd, J=9.2, 3.4 Hz, 1H), 7.48-7.42 (m, 4H), 7.37-7.32 (m, 1H), 7.19 (dd, J=9.2, 4.3 Hz, 1H), 6.60 (br s, 2H), 5.37-5.30 (m, 1H), 4.55 (d, J=6.1 Hz, 2H), 4.47-4.41 (m, 2H), 4.16-4.10 (m, 1H), 4.05-3.96 (m, 1H), 3.90 (s, 3H).

Example 201: $BTK^{WT}$ Binding Affinity $BTK^{WT}$ binding affinity of each compound tested was determined using a time-resolved fluorescence resonance energy transfer (TR-FRET) methodology. 2.5 nM Recombinant $BTK^{WT}$ kinase, varying concentrations of inhibitor, 2 nM LanthaScreen™ Eu anti-His Antibody and 15 nM Kinase Tracer 236 was incubated in 1× LanthaScreen™ Kinase Buffer A for 5 h. Recombinant BTK kinase and all LanthaScreen™ components were purchased from Invitrogen. Measurements were performed in a reaction volume of 30 µL using half-area 96-well assay plates. The TR-FRET signal was read on a plate reader with an excitation wavelength of 340 nm and detection wavelengths of 615 and 665 nm. Binding affinity was determined for each compound by measuring TR-FRET signal at various concentrations of compound and plotting the relative fluorescence units against the inhibitor concentration to estimate the $IC_{50}$ from log[Inhibitor] vs response using the Variable Slope model in Graphpad prism from Graphpad software (San Diego, Calif.).

Results of the $BTK^{WT}$ Binding Affinity are shown below in Table 4

Table 4 shows the $BTK^{WT}$ Binding affinity, as determined by the assay described above, for compounds of formula (I), categorised based on the BTK $IC_{50}$ value of the compound as "A", "B", "C", "D" and "E".

$IC_{50}$: A≤10 nM; 10 nM<B≤100 nM; 100 nM<C≤1 µM; 1 µM<D≤10 µM; E>10 µM

Example 202: $BTK^{C481S}$ Binding Affinity $BTK^{C481S}$ binding affinity of each compound tested was determined using a time-resolved fluorescence resonance energy transfer (TR-FRET) methodology. 5 nM Recombinant $BTK^{WT}$ kinase, varying concentrations of inhibitor, 2 nM LanthaScreen™ Eu anti-His Antibody and 30 nM Kinase Tracer 236 was incubated in 1× LanthaScreen™ Kinase Buffer A for 5 h. Recombinant $BTK^{C481S}$ kinase was purchased from SignalChem and all LanthaScreen™ components were purchased from Invitrogen. Measurements were performed in a reaction volume of 30 µL using half-area 96-well assay plates. The TR-FRET signal was read on a plate reader with an excitation wavelength of 340 nm and detection wavelengths of 615 and 665 nm. Binding affinity was determined for each compound by measuring TR-FRET signal at various concentrations of compound and plotting the relative fluorescence units against the inhibitor concentration to estimate the $IC_{50}$ from log[Inhibitor] vs response using the Variable Slope model in Graphpad prism from Graphpad software (San Diego, Calif.).

Table 4 shows the $BTK^{C481S}$ Binding affinity, as determined by the assay described above, for compounds of formula (I), categorised based on the BTK $IC_{50}$ value of the compound as "A", "B", "C", "D" and "E".

$IC_{50}$: A≤10 nM; 10 nM<B≤100 nM; 100 nM<C≤1 µM; 1 µM<D≤10 µM; E>10 µM

Example 203: EGFR Binding Affinity

EGFR binding affinity was determined using a time-resolved fluorescence resonance energy transfer (TR-FRET) methodology. 2.5 nM Recombinant EGFR, varying concentrations of inhibitor, 2 nM LanthaScreen™ Eu anti-GST Antibody and 3 nM Kinase Tracer 199 was incubated in 1× LanthaScreen™ Kinase Buffer A for 5 h. Recombinant EGFR and all LanthaScreen™ components were purchased from Invitrogen. Measurements were performed in a reaction volume of 30 µL using half-area 96-well assay plates. The TR-FRET signal was read on a plate reader with an excitation wavelength of 340 nm and detection wavelengths of 615 and 665 nm. Binding affinity was determined for each compound by measuring TR-FRET signal at various concentrations of compound and plotting the relative fluorescence units against the inhibitor concentration to estimate the $IC_{50}$ from log[Inhibitor] vs response using the Variable Slope model in Graphpad prism from Graphpad software (San Diego, Calif.).

Table 4 shows the EGFR Binding Affinity, as determined by the assay described above, for compounds of formula (I), categorised based on the EGFR $IC_{50}$ value of the compound as "A", "B" "C", "D" and "E".

$IC_{50}$: A≤10 nM; 10 nM<B≤100 nM; 100 nM<C≤1 µM; 1 µM<D≤10 µM; E>10 µM

Example 204: OCI-Ly10 Anti-Proliferative Activity

Compounds were assayed for effects on the growth of OCI-Ly10 human DLBCL cells that are dependent on NFκB signalling. OCI-Ly10 cells were grown in suspension in T225 flasks, centrifuged and re-suspended in 2.5% FBS containing media. Cells were then plated at $7.5 \times 10^3$ cells per well in 96-well plates in varying concentrations of compound and incubated for 72 h at 37° C. An additional plate of cells to be used as the Day 0 read was seeded without compound addition, Resazurin was added to each well, incubated for 5 h and the fluorescence measured at 590 nm. After 72 h of compound treatment, Resazurin was added to each well of the compound treated plates, incubated for 5 h and the fluorescence measured at 590 nm. The $IC_{50}$ was then calculated by subtracting the average Day 0 value from each well value from the treated plates, each treatment was then calculated as a percentage of the DMSO control and the percentages plotted against the inhibitor concentration to estimate the $IC_{50}$ from log[Inhibitor] vs response using the Variable Slope model in Graphpad prism from Graphpad software (San Diego, Calif.).

Table 4 shows the OCI-Ly10 anti-proliferative activity, as determined by the assay described above, for compounds of formula (I), categorised based on the OCI-Ly10 $IC_{50}$ value of the compound as "A", "B", "C", "D" and "E".

$IC_{50}$: A≤10 nM; 10 nM<B≤100 nM; 100 nM<C≤1 µM; 1 µM<D≤10 µM; E>10 µM

TABLE 4

| Example | LanthaScreen Binding BTK WT | LanthaScreen Binding BTK C481S | LanthaScreen Binding EGFR | Proliferation Assay OCI-Ly10- 20% FBS |
|---|---|---|---|---|
| 200 | A | A | D | B |
| 199 | A | A | D | B |
| 198 | A | A | D | B |
| 197 | A | A | D | B |
| 196 | B | B | D | C |
| 195 | A | A | D | B |
| 194 | B | B | D | C |
| 193 | B | A | D | C |
| 192 | B | B | D | C |
| 191 | A | A | D | B |
| 190 | C | B | D | D |
| 189 | A | A | D | B |
| 188 | A | A | D | ND |
| 187 | C | C | D | C |
| 186 | A | A | D | B |
| 185 | D | D | D | ND |

TABLE 4-continued

| Example | LanthaScreen Binding BTK WT | LanthaScreen Binding BTK C481S | LanthaScreen Binding EGFR | Proliferation Assay OCI-Ly10- 20% FBS |
|---|---|---|---|---|
| 184 | B | A | E | A |
| 183 | A | A | D | C |
| 182 | B | A | D | C |
| 181 | A | A | D | B |
| 180 | A | A | D | B |
| 179 | A | A | D | B |
| 178 | B | A | D | B |
| 177 | A | A | D | B |
| 176 | A | A | D | B |
| 175 | B | B | D | C |
| 174 | A | A | D | B |
| 173 | A | A | D | B |
| 172 | A | A | D | C |
| 171 | B | A | D | C |
| 170 | B | A | D | C |
| 169 | A | A | D | B |
| 168 | B | A | D | B |
| 167 | A | A | D | B |
| 166 | B | A | D | B |
| 165 | B | A | D | B |
| 164 | A | A | D | B |
| 163b | A | A | D | B |
| 163a | A | A | D | A |
| 162 | A | A | D | B |
| 161 | B | A | E | C |
| 160 | B | A | D | C |
| 159 | A | A | E | B |
| 158 | B | B | E | C |
| 157 | A | A | E | B |
| 156 | A | A | E | B |
| 155 | A | A | D | B |
| 154 | A | A | E | B |
| 153 | B | A | E | C |
| 152 | B | B | E | C |
| 151 | A | A | D | C |
| 150 | A | A | D | B |
| 149 | A | A | E | B |
| 148 | B | A | E | C |
| 147 | A | A | D | B |
| 146 | A | A | E | C |
| 145 | B | B | E | C |
| 144 | A | A | C | C |
| 143 | B | A | E | C |
| 142 | A | A | D | C |
| 141 | B | A | E | C |
| 140 | A | A | E | C |
| 139 | B | A | E | C |
| 138 | B | B | E | C |
| 137 | A | A | D | B |
| 136 | A | A | D | B |
| 135 | B | A | E | D |
| 134 | B | B | E | D |
| 133 | C | B | E | ND |
| 132 | C | B | E | ND |
| 131 | A | A | C | B |
| 130 | A | A | D | B |
| 129 | A | A | D | C |
| 128 | A | A | D | B |
| 127 | A | A | D | B |
| 126 | B | A | D | C |
| 125 | B | A | E | C |
| 124 | B | B | D | C |
| 123 | A | A | D | C |
| 122 | A | A | D | B |
| 121 | A | A | C | B |
| 120 | A | A | D | B |
| 119 | A | A | D | B |
| 118 | C | B | D | D |
| 117 | A | A | D | B |
| 116 | B | A | D | C |
| 115 | A | A | D | B |
| 114 | A | A | D | B |
| 113 | A | A | D | B |
| 112 | C | C | E | E |
| 111 | A | A | C | C |
| 110 | B | B | D | D |
| 109 | A | A | D | C |
| 108 | B | B | E | D |
| 107 | A | A | E | B |
| 106 | A | A | E | C |
| 105 | B | A | D | C |
| 104 | B | A | D | C |
| 103 | A | A | D | B |
| 102 | A | A | E | C |
| 101 | B | A | E | C |
| 100 | B | A | E | C |
| 99 | B | A | E | C |
| 98 | A | A | D | C |
| 97 | B | A | D | D |
| 96 | A | A | D | B |
| 95 | B | A | D | C |
| 94 | B | A | D | D |
| 93 | A | A | C | B |
| 92 | A | A | E | B |
| 91 | B | A | D | C |
| 90 | B | A | D | C |
| 89 | B | B | D | D |
| 88 | A | A | C | A |
| 87 | A | A | C | C |
| 86 | A | A | C | C |
| 85 | A | A | C | B |
| 84 | B | A | D | D |
| 83b | A | A | D | B |
| 83a | A | A | D | C |
| 82 | B | B | D | D |
| 81 | A | A | C | B |
| 80 | A | A | C | B |
| 79 | C | C | D | D |
| 78 | B | B | E | D |
| 77 | A | A | C | B |
| 76 | A | A | C | B |
| 75 | A | A | C | C |
| 74 | A | A | C | D |
| 73 | A | A | C | B |
| 72 | B | A | D | C |
| 71 | A | A | C | B |
| 70 | A | A | C | B |
| 69 | E | ND | ND | ND |
| 68 | A | A | C | B |
| 67 | C | ND | ND | ND |
| 66 | B | A | D | D |
| 65 | A | A | C | B |
| 64 | A | A | C | B |
| 63 | A | A | C | B |
| 62 | A | A | C | B |
| 61 | A | A | C | B |
| 60 | A | A | C | B |
| 59 | A | A | D | B |
| 58 | A | A | D | B |
| 57b | A | A | C | C |
| 57a | A | A | C | B |
| 56 | C | C | ND | D |
| 55 | A | A | C | B |
| 54 | B | A | D | C |
| 53 | A | A | C | B |
| 52 | A | A | C | B |
| 51 | A | A | C | B |
| 50 | A | A | C | B |
| 49 | A | A | C | B |
| 48 | A | A | C | C |
| 47 | B | A | D | C |
| 46 | A | A | C | B |
| 45 | A | A | D | B |
| 44 | A | A | C | B |
| 43 | A | A | C | B |
| 42 | E | ND | E | ND |
| 41 | A | A | C | B |
| 40 | A | A | C | B |
| 39 | A | A | C | B |
| 38 | E | D | E | E |

TABLE 4-continued

| Example | LanthaScreen Binding BTK WT | LanthaScreen Binding BTK C481S | LanthaScreen Binding EGFR | Proliferation Assay OCI-Ly10-20% FBS |
|---|---|---|---|---|
| 37 | A | A | C | B |
| 36 | A | A | D | B |
| 35 | A | A | D | B |
| 34b | A | A | D | B |
| 34a | A | A | C | B |
| 33 | A | A | C | B |
| 32 | A | A | C | B |
| 31 | B | B | E | D |
| 30 | B | B | E | C |
| 29 | A | A | D | C |
| 28 | A | A | C | B |
| 27 | A | A | C | B |
| 26 | A | A | B | A |
| 25 | B | A | D | E |
| 24 | B | B | D | C |
| 23 | A | A | C | B |
| 22 | A | A | D | B |
| 21 | A | A | C | C |
| 20 | A | A | C | B |
| 19 | A | A | C | B |
| 18 | A | A | C | A |
| 18 | A | A | C | B |
| 17 | A | A | C | B |
| 16 | B | A | D | C |
| 15 | A | A | D | B |
| 14 | B | B | D | C |
| 13 | A | A | D | C |
| 12 | C | C | E | D |
| 11 | B | B | D | D |
| 10 | B | B | D | C |
| 9 | B | B | D | C |
| 8 | C | B | E | C |
| 7 | C | B | E | C |
| 6 | B | A | E | C |
| 5 | A | A | C | B |
| 4 | A | A | C | A |
| 3 | A | A | C | B |
| 2 | A | A | ND | C |
| 1 | A | A | C | A |

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

The invention claimed is:

1. A compound according to formula (I) or pharmaceutically acceptable salts thereof:

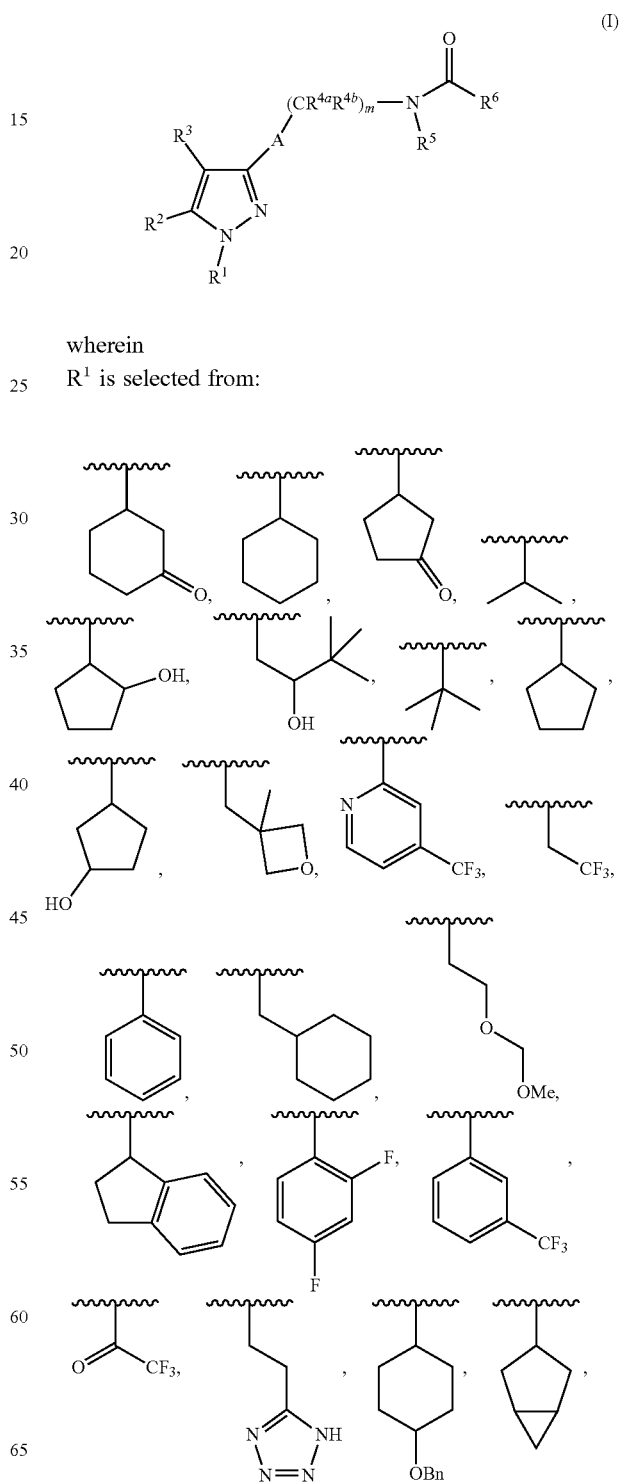

wherein $R^1$ is selected from:

-continued

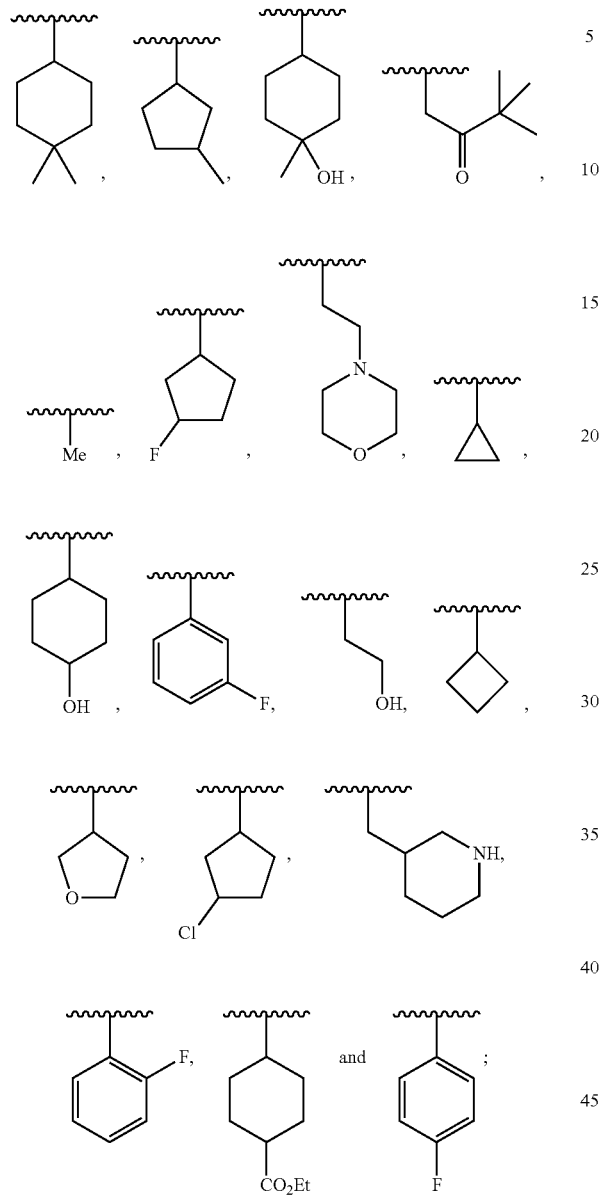

R² represents a group selected from: halo, C₁₋₈ alkyl, C₁₋₈ haloalkyl and —NR^C R^D,
  wherein R^C and R^D are, at each occurrence, independently selected from: H and C₁₋₄ alkyl;
R³ represents —C(O)NH₂, —C(O)NHMe, —CH₂OH, CH(OH)CH₃, —CF₃, or —CHF₂;
R^{4a} and R^{4b} are H;
R⁵ is H;
R⁶ is methoxyphenyl or methoxyfluorophenyl;
A is unsubstituted phenyl or phenyl substituted by one or two R⁷, wherein R⁷ is selected from: fluoro, methyl, methoxy, and —CH₂OH; and
m is 1.

2. The compound according to claim 1 wherein the compound is of the formula:

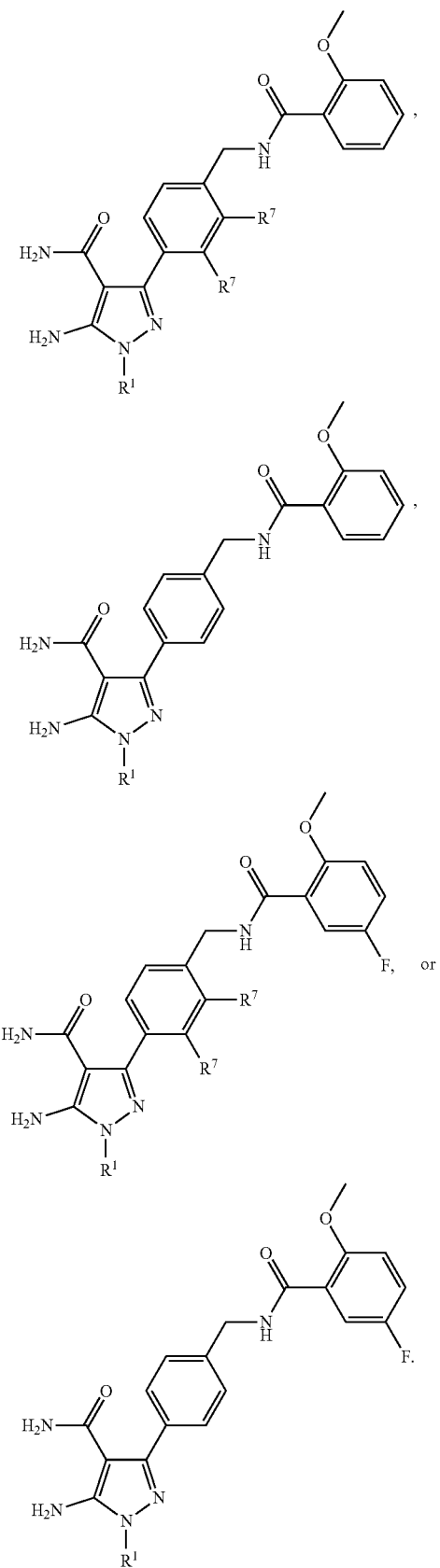

or a pharmaceutically acceptable salt thereof.

3. The compound according to claim 2, wherein the compound is of the formula:

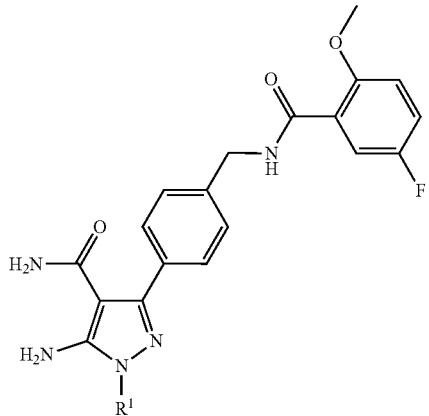

or a pharmaceutically acceptable salt thereof.

4. The compound according to claim 3 wherein $R^1$ is:

or a pharmaceutically acceptable salt thereof.

5. The compound according to claim 3 wherein $R^1$ is:

6. A compound of the formula:

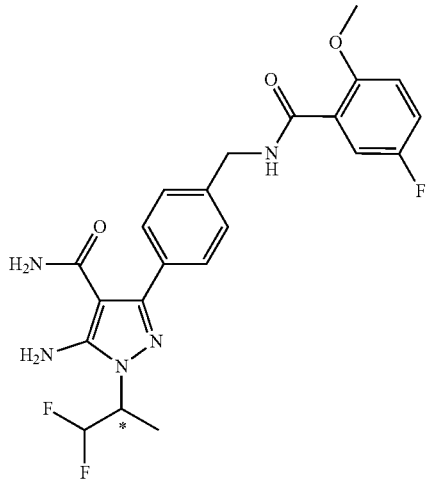 [SMILES: COc1ccc(F)cc1C(=O)NCc1ccc(-c2nn(C(C)C(F)F)c(N)c2C(N)=O)cc1]

wherein * indicates a chiral center, or a pharmaceutically acceptable salt thereof.

7. The compound according to claim 6 wherein the chiral center * is in an (S)-configuration.

8. A pharmaceutical composition, wherein the pharmaceutical composition comprises a compound according to formula (I) or pharmaceutically acceptable salts thereof:

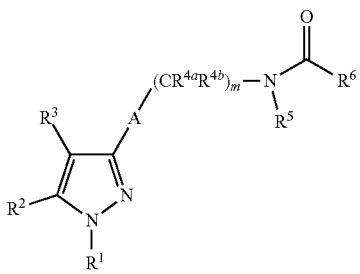

wherein $R^1$ is selected from:

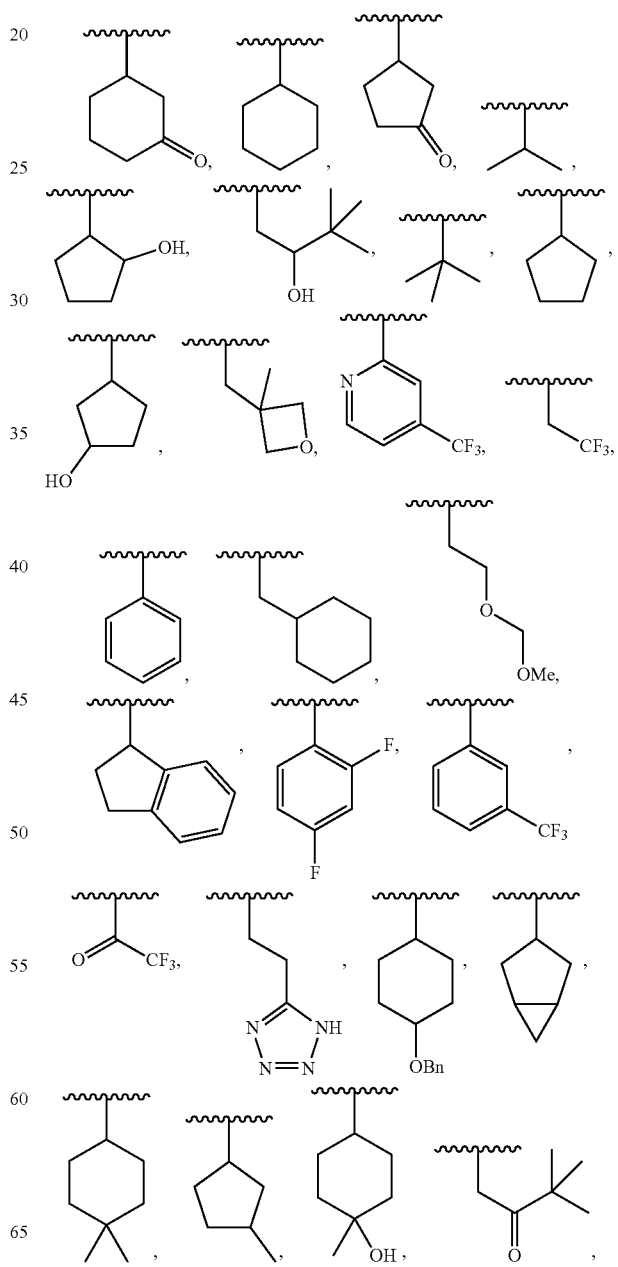

-continued

[structures shown: cyclopentyl-Me, cyclopentyl-F, morpholinyl-propyl, cyclopropyl, cyclohexyl-OH, meta-fluorophenyl, propyl-OH, cyclobutyl, tetrahydrofuranyl, chlorocyclopentyl, piperidinyl-NH, ortho-fluorophenyl, cyclohexyl-CO₂Et, and para-fluorophenyl]

$R^2$ represents a group selected from: halo, $C_{1-8}$ alkyl, $C_{1-8}$ haloalkyl and $-NR^CR^D$, wherein $R^C$ and $R^D$ are, at each occurence, independently selected from: H and $C_{1-4}$ alkyl;

$R^3$ represents $-C(O)NH_2$, $-C(O)NHMe$, $-CH_2OH$, $CH(OH)CH_3$, $-CF_3$, or $-CHF_2$;

$R^{4a}$ and $R^{4b}$ are H;

$R^5$ is H;

$R^6$ is methoxyphenyl or methoxyfluorophenyl;

A is unsubstituted phenyl or phenyl substituted by one or two $R^7$, wherein $R^7$ is selected from: fluoro, methyl, methoxy, and $-CH_2OH$; and m is 1;

and pharmaceutically acceptable excipients.

9. A pharmaceutical composition, wherein the pharmaceutical composition comprises a compound of the formula:

[chemical structure]

wherein $R^1$ is

[isobutyl structure];

or a pharmaceutically acceptable salt thereof, and pharmaceutically acceptable excipients.

10. A pharmaceutical composition, wherein the pharmaceutical composition comprises a compound of the formula:

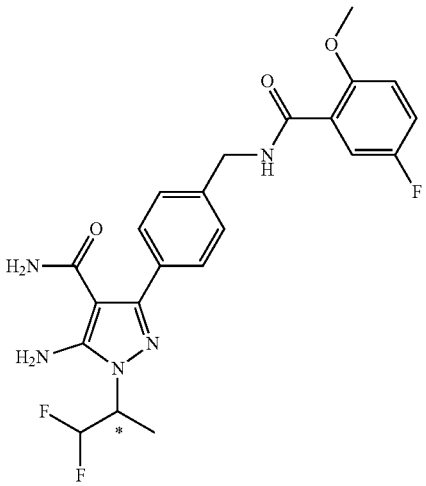

wherein * indicates a chiral center, or a pharmaceutically acceptable salt thereof and pharmaceutically acceptable excipients.

11. A pharmaceutical composition, wherein the pharmaceutical composition comprises a compound of the formula:

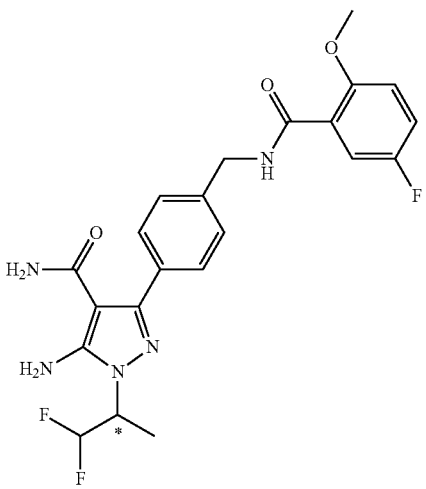

wherein * indicates a chiral center wherein the chiral center * is in an (S)—configuration, or a pharmaceutically acceptable salt thereof and pharmaceutically acceptable excipients.

12. A method of treating a condition which is modulated by BTK in a patient in need thereof comprising administering to the patient a compound according to formula (I) or a pharmaceutically acceptable salt thereof:

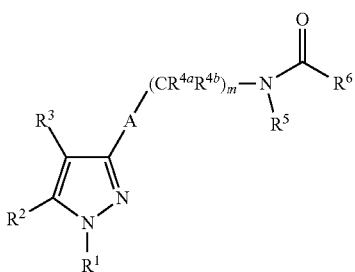

wherein
R¹ is selected from:

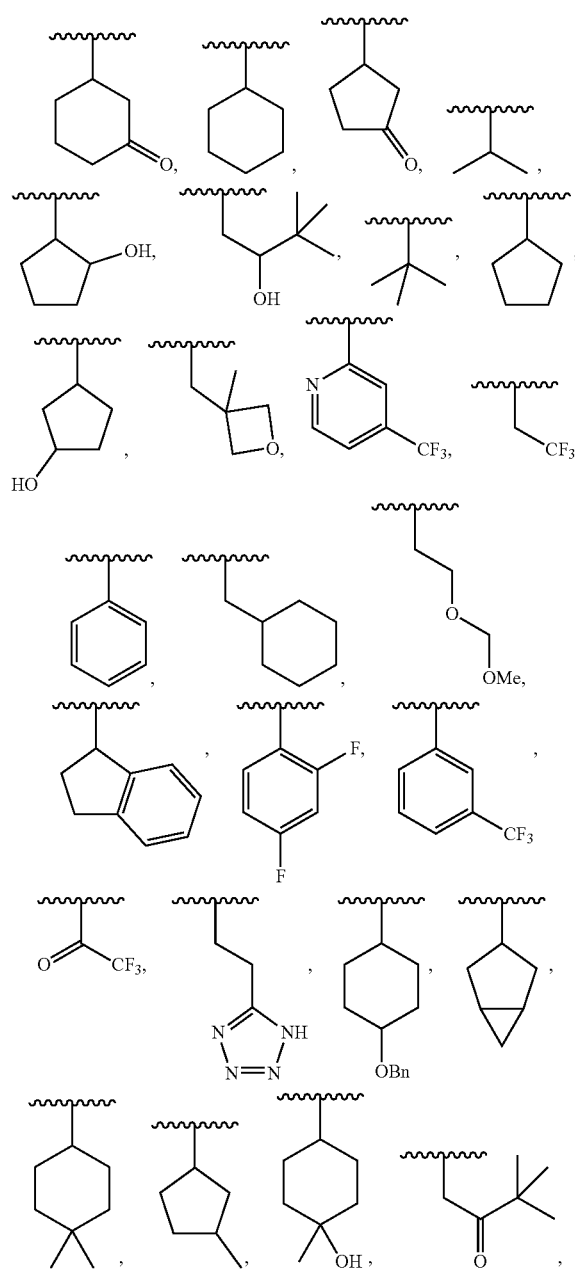

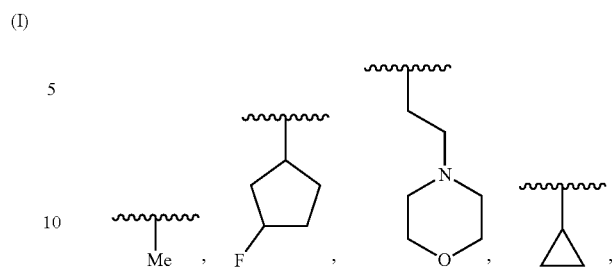

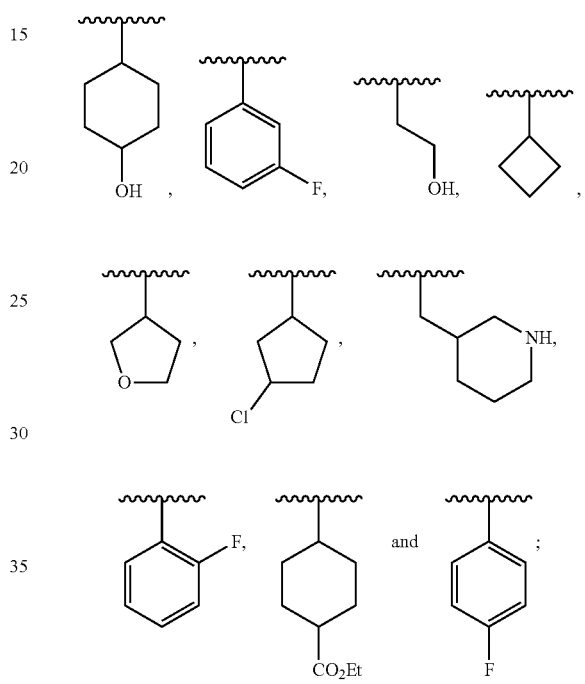

R² represents a group selected from: halo, $C_{1-8}$ alkyl, $C_{1-8}$ haloalkyl and —$NR^CR^D$,
wherein $R^C$ and $R^D$ are, at each occurrence, independently selected from: H and $C_{1-4}$ alkyl;
R³ represents —C(O)NH₂, —C(O)NHMe, —CH₂OH, CH(OH)CH₃, —CF₃, or —CHF₂;
$R^{4a}$ and $R^{4b}$ are H;
R⁵ is H;
R⁶ is methoxyphenyl or methoxyfluorophenyl;
A is unsubstituted phenyl or phenyl substituted by one or two R⁷, wherein R⁷ is selected from: fluoro, methyl, methoxy, and —CH₂OH; and
m is 1.

13. The method according to claim 12 wherein the condition modulated by BTK is cancer, lymphoma, leukemia, autoimmune diseases, inflammatory disorders, heteroimmune conditions, or fibrosis.

14. The method according to claim 13 wherein the condition modulated by BTK is selected from B-cell malignancy, B-cell lymphoma, diffuse large B cell lymphoma, chronic lymphocytic leukemia, non-Hodgkin lymphoma, ABC-DLBCL, mantle cell lymphoma, follicular lymphoma, hairy cell leukemia, B-cell non-Hodgkin lymphoma, Waldenstrom's macroglobulinemia, multiple myeloma, bone cancer, bone metastasis, arthritis, multiple sclerosis, osteoporosis, irritable bowel syndrome, inflammatory bowel disease, Crohn's disease, Sjögren's syndrome, and lupus.

15. The method according to claim 13 wherein the condition modulated by BTK is selected from arthritis, multiple sclerosis, osteoporosis, irritable bowel syndrome, inflammatory bowel disease, Crohn's disease, and lupus.

16. A method of treating a condition which is modulated by BTK in a patient in need thereof comprising administering to the patient a compound of the formula:

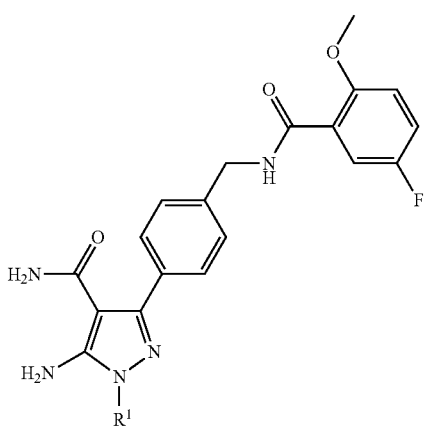

wherein $R^1$ is

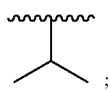

or a pharmaceutically acceptable salt thereof.

17. The method according to claim 16 wherein the condition modulated by BTK is cancer, lymphoma, leukemia, autoimmune diseases, inflammatory disorders, heteroimmune conditions, or fibrosis.

18. The method according to claim 17 wherein the condition modulated by BTK is selected from B-cell malignancy, B-cell lymphoma, diffuse large B cell lymphoma, chronic lymphocytic leukemia, non-Hodgkin lymphoma, ABC-DLBCL, mantle cell lymphoma, follicular lymphoma, hairy cell leukemia, B-cell non-Hodgkin lymphoma, Waldenstrom's macroglobulinemia, multiple myeloma, bone cancer, bone metastasis, arthritis, multiple sclerosis, osteoporosis, irritable bowel syndrome, inflammatory bowel disease, Crohn's disease, Sjogren's syndrome, and lupus.

19. The method according to claim 17 wherein the condition modulated by BTK is selected from arthritis, multiple sclerosis, osteoporosis, irritable bowel syndrome, inflammatory bowel disease, Crohn's disease, and lupus.

20. A method of treating a condition which is modulated by BTK in a patient in need thereof comprising administering to the patient a compound of the formula:

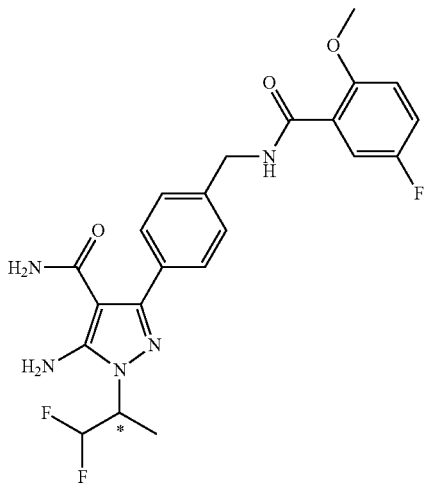 [SMILES: COc1ccc(F)cc1C(=O)NCc1ccc(-c2nn(C(C)C(F)F)c(N)c2C(N)=O)cc1]

wherein * indicates a chiral center, or a pharmaceutically acceptable salt thereof.

21. The method according to claim 20 wherein the condition modulated by BTK is cancer, lymphoma, leukemia, autoimmune diseases, inflammatory disorders, heteroimmune conditions, or fibrosis.

22. The method according to claim 21 wherein the condition modulated by BTK is selected from B-cell malignancy, B-cell lymphoma, diffuse large B cell lymphoma, chronic lymphocytic leukemia, non-Hodgkin lymphoma, ABC-DLBCL, mantle cell lymphoma, follicular lymphoma, hairy cell leukemia, B-cell non-Hodgkin lymphoma, Waldenstrom's macroglobulinemia, multiple myeloma, bone cancer, bone metastasis, arthritis, multiple sclerosis, osteoporosis, irritable bowel syndrome, inflammatory bowel disease, Crohn's disease, Sjogren's syndrome, and lupus.

23. The method according to claim 21 wherein the condition modulated by BTK is selected from arthritis, multiple sclerosis, osteoporosis, irritable bowel syndrome, inflammatory bowel disease, Crohn's disease, and lupus.

24. A method of treating a condition which is modulated by BTK in a patient in need thereof comprising administering to the patient a compound of the formula:

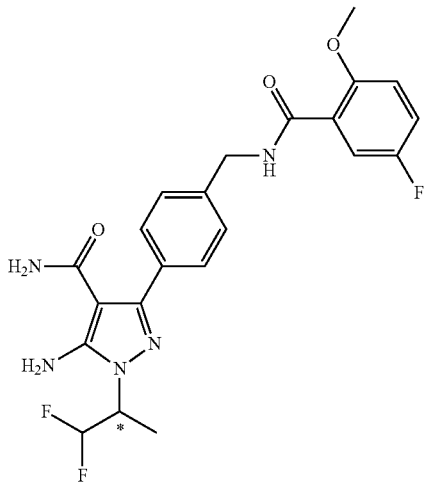 [SMILES: COc1ccc(F)cc1C(=O)NCc1ccc(-c2nn(C(C)C(F)F)c(N)c2C(N)=O)cc1]

wherein * indicates a chiral center wherein the chiral center * is in an (S)—configuration, or a pharmaceutically acceptable salt thereof.

25. The method according to claim 24 wherein the condition modulated by BTK is cancer, lymphoma, leukemia, autoimmune diseases, inflammatory disorders, heteroimmune conditions, or fibrosis.

26. The method according to claim 25 wherein the condition modulated by BTK is selected from B-cell malignancy, B-cell lymphoma, diffuse large B cell lymphoma, chronic lymphocytic leukemia, non-Hodgkin lymphoma, ABC-DLBCL, mantle cell lymphoma, follicular lymphoma, hairy cell leukemia, B-cell non-Hodgkin lymphoma, Waldenstrom's macroglobulinemia, multiple myeloma, bone cancer, bone metastasis, arthritis, multiple sclerosis, osteoporosis, irritable bowel syndrome, inflammatory bowel disease, Crohn's disease, Sjogren's syndrome, and lupus.

27. The method according to claim 25 wherein the condition modulated by BTK is selected from arthritis, multiple sclerosis, osteoporosis, irritable bowel syndrome, inflammatory bowel disease, Crohn's disease, and lupus.

\* \* \* \* \*

UNITED STATES PATENT AND TRADEMARK OFFICE
CERTIFICATE OF CORRECTION

PATENT NO. : 11,826,351 B2
APPLICATION NO. : 17/525350
DATED : November 28, 2023
INVENTOR(S) : Nicolas Guisot It is certified that error appears in the above-identified patent and that said Letters Patent is hereby corrected as shown below:

In the Claims

Column 361, Line 34: Claim 8, "occurence" should read --occurrence--

Signed and Sealed this
Twenty-sixth Day of March, 2024

Katherine Kelly Vidal
*Director of the United States Patent and Trademark Office*